US012338273B2

(12) United States Patent
Kumar et al.

(10) Patent No.: US 12,338,273 B2
(45) **Date of Patent: *Jun. 24, 2025**

(54) SINGLE-ARM TYPE I AND TYPE II RECEPTOR FUSION PROTEINS AND USES THEREOF

(71) Applicant: Accerelon Pharma Inc., Cambridge, MA (US)

(72) Inventors: Ravindra Kumar, Cambridge, MA (US); Asya Grinberg, Cambridge, MA (US); Dianne Sako, Cambridge, MA (US)

(73) Assignee: Accerelon Pharma Inc., Cambridge, MA (US)

( * ) Notice: Subject to any disclaimer, the term of this patent is extended or adjusted under 35 U.S.C. 154(b) by 401 days.

This patent is subject to a terminal disclaimer.

(21) Appl. No.: 17/523,226

(22) Filed: Nov. 10, 2021

(65) Prior Publication Data

US 2022/0315642 A1 Oct. 6, 2022

Related U.S. Application Data

(62) Division of application No. 16/423,593, filed on May 28, 2019, now Pat. No. 11,208,460, which is a division of application No. 15/092,600, filed on Apr. 6, 2016, now Pat. No. 10,358,476.

(60) Provisional application No. 62/259,422, filed on Nov. 24, 2015, provisional application No. 62/143,579, filed on Apr. 6, 2015.

(51) Int. Cl.
*C07K 14/71* (2006.01)
*A61K 38/00* (2006.01)

(52) U.S. Cl.
CPC .............. *C07K 14/71* (2013.01); *A61K 38/00* (2013.01); *C07K 2319/30* (2013.01)

(58) Field of Classification Search
None
See application file for complete search history.

(56) References Cited

U.S. PATENT DOCUMENTS

| | | | |
|---|---|---|---|
| 5,731,168 | A | 3/1998 | Carter et al. |
| 5,932,448 | A | 8/1999 | Tso et al. |
| 7,183,076 | B2 | 2/2007 | Arathoon et al. |
| 7,612,041 | B2 | 11/2009 | Knopf et al. |
| 7,709,605 | B2 | 5/2010 | Knopf et al. |
| 7,820,620 | B2 | 10/2010 | Vale et al. |
| 7,842,663 | B2 | 11/2010 | Knopf et al. |
| 8,252,900 | B2 | 8/2012 | Knopf et al. |
| 8,338,377 | B2 | 12/2012 | Seehra |
| 8,361,957 | B2 | 1/2013 | Seehra et al. |
| 8,410,043 | B2 | 4/2013 | Sun et al. |
| 8,592,562 | B2 | 11/2013 | Kannan et al. |
| 8,703,927 | B2 | 4/2014 | Seehra et al. |
| 8,734,760 | B2 | 5/2014 | O'Connor-McCourt et al. |
| 9,181,533 | B2 | 11/2015 | Seehra et al. |
| 9,611,306 | B2 | 4/2017 | Hinck et al. |
| 9,809,638 | B2 | 11/2017 | Sun et al. |
| 9,975,934 | B2 | 5/2018 | Kumar et al. |
| 2010/0168020 | A1 | 7/2010 | Sun et al. |
| 2010/0330657 | A1 | 12/2010 | Miyazono et al. |
| 2011/0236309 | A1 | 9/2011 | O'Connor-McCourt et al. |
| 2012/0247863 | A1 | 10/2012 | Lamoine et al. |
| 2012/0302737 | A1 | 11/2012 | Christensen et al. |
| 2016/0289292 | A1 | 10/2016 | Kumar et al. |
| 2016/0297867 | A1 | 10/2016 | Kumar et al. |
| 2016/0298093 | A1 | 10/2016 | Kumar et al. |
| 2017/0306027 | A1 | 10/2017 | Knopf et al. |
| 2018/0008672 | A1 | 1/2018 | Chalothorn et al. |
| 2018/0072791 | A1 | 3/2018 | Sun et al. |

(Continued)

FOREIGN PATENT DOCUMENTS

| | | | |
|---|---|---|---|
| EP | 3101029 | A1 | 12/2016 |
| JP | 2010518009 | A | 5/2010 |

(Continued)

OTHER PUBLICATIONS

Allendorph, George P. et al., Structure of the ternary signaling complex of a TGF-β superfamily member, PNAS, 2006, 7643-7648, 103(20).
Andersson, Olov et al., Growth differentiation factor 11 signals through the transforming growth factor-β receptor ALK5 to regionalize the anterior-posterior axis, EMBO Reports, 2006, 831-837, 7(8).
Andersson, Olov et al., Growth/differentiation factor 3 signals through ALK7 and regulates accumulation of adipose tissue and diet-induced obesity, PNAS, 2008, 7252-7256, 105(2).
Ashmore, C.R. et al., Comparative aspects of muscle fiber types in fetuses of the normal and "double-muscled" cattle, Growth, 1974, 501-506, 38(4).

(Continued)

*Primary Examiner* — Ruixiang Li
(74) *Attorney, Agent, or Firm* — Eric Greenwald; John C. Todaro

(57) ABSTRACT

In certain aspects, the disclosure provides soluble single-arm heteromeric polypeptide complexes comprising an extracellular domain of a type I serine/threonine kinase receptor of the TGF-beta family or an extracellular domain of a type II serine/threonine kinase receptor of the TGF-beta family. In some embodiments, the disclosure provides soluble single-arm polypeptide complexes comprising an extracellular domain of a type II receptor selected from: ActRIIA, ActRIIB, TGFBRII, BMPRII, and MISRII. In some embodiments, the disclosure provides soluble single-arm polypeptide complexes comprising an extracellular domain of a type I receptor selected from: ALK1, ALK2, ALK3, ALK4, ALK5, ALK6, and ALK7. Optionally the soluble complex is a heterodimer. In certain aspects, such soluble polypeptide complexes may be used for the treatment or prevention of various TGF-beta associated conditions, including without limitation diseases and disorders associated with, for example, cancer, muscle, bone, fat, red blood cells, metabolism, fibrosis and other tissues that are affected by one or more ligands of the TGF-beta superfamily.

15 Claims, 8 Drawing Sheets

Specification includes a Sequence Listing.

(56) References Cited

U.S. PATENT DOCUMENTS

| | | | |
|---|---|---|---|
| 2018/0111991 A1 | 4/2018 | Miller et al. |
| 2018/0148491 A1 | 5/2018 | Han et al. |
| 2018/0163187 A1 | 6/2018 | Kumar et al. |
| 2019/0100570 A1 | 4/2019 | Kumar et al. |

FOREIGN PATENT DOCUMENTS

| | | | |
|---|---|---|---|
| JP | 2011526626 | A | 10/2011 |
| JP | 2012529294 | A | 11/2012 |
| JP | 2013510090 | A | 3/2013 |
| WO | 1984001106 | A1 | 3/1984 |
| WO | 1993011162 | A1 | 6/1993 |
| WO | 2000043781 | A2 | 7/2000 |
| WO | 2004039948 | A2 | 5/2004 |
| WO | 2005028433 | A2 | 3/2005 |
| WO | 2005028517 | A2 | 3/2005 |
| WO | 2005047336 | A1 | 5/2005 |
| WO | 2006012627 | A2 | 2/2006 |
| WO | 2007147901 | A1 | 12/2007 |
| WO | 2008057461 | A2 | 5/2008 |
| WO | 2008097541 | A2 | 8/2008 |
| WO | 2009089004 | A1 | 7/2009 |
| WO | 2009134428 | A2 | 11/2009 |
| WO | 2009158033 | A2 | 12/2009 |
| WO | 2010062383 | A2 | 6/2010 |
| WO | 2010151426 | A1 | 12/2010 |
| WO | 2011034605 | A2 | 3/2011 |
| WO | 2011045497 | A1 | 4/2011 |
| WO | 2011056497 | A1 | 5/2011 |
| WO | 2011056896 | A1 | 5/2011 |
| WO | 2011117329 | A1 | 9/2011 |
| WO | 2013000234 | A1 | 1/2013 |
| WO | 2015027082 | A1 | 2/2015 |
| WO | 2016205370 | A1 | 12/2016 |
| WO | 2017037634 | A1 | 3/2017 |
| WO | 2018009624 | A1 | 1/2018 |
| WO | 2018075747 | A1 | 4/2018 |

OTHER PUBLICATIONS

Attisano, Liiana et al., Novel Activin Receptors: Distinct Genes and Alternative mRNA Splicing Generate a Repertoire of Serine/Threonine Kinase Receptors, Cell, 1992, 97-108, 68.
Berasi, Stephen P. et al., Divergent activities of osteogenic BMP2, and tenogenic BMP12 and BMP13 Independent of receptor binding affinities, Growth Factors, 2011, 128-139, 29:4.
Bogdanovich, Sasha et al., Functional improvement of dystrophic muscle by myostatin blockade, Nature, 2002, 418-421, 420.
Brown, Peter D. et al., Physicochemical Activation of Recombinant Latent Transforming Growth Factor-beta's 1, 2, and 3, Growth Factors, 1990, 35-43, 3:1.
Cheng, Li et al., Transforming Growth Factor-β1 (TGF-β1) Induces Mouse Precartilaginous Stem Cell Proliferation through TGF-β Receptor II (TGFRII)-Akt-β-Catenin Signaling, Int. J. Mol. Sci., 2014, 12665-12676, 14.
Chiu, Chi-Sung et al., Increased Muscle Force Production and Bone Mineral Density in ActRIIB-Fc-Treated Mature Rodents, J Gerontol A Biol Sci Med Sci, 2013, 1181-1192, 68(10).
Clouthier, David E. et al., Hepatic Fibrosis, Glomerulosclerosis, and a Lipodystrophy-like Syndrome in PEPCK-TGF-β1 Transgenic Mice, J. Clin. Invest., 1997, 2697-2713, 100.
Cunha, Sara I. et al., ALK1 as an emerging target for antiangiogenic therapy of cancer, Blood, 2011, 6999-7006, 117(26).
Davis, Jonathan H. et al., SEEDbodies: fusion proteins based on strand-exchange engineered domain (SEED) CH3 heterodimers in an Fc analogue platform for asymmetric binders or immunofusions and bispecific antibodies, rotein Engineering, Design & Selection, 2010, 195-202, 23:4.
De Silva, Tanya et al., Nodal promotes glioblastoma cell growth, Frontiers in Endocrinology, 2012, 1-6, 3:59.
Del Re, Elisabetta et al., Reconstitution and Analysis of Soluble Inhibin and Activin Receptor Complexes in a Cell-free System, The Journal of Biological Chemistry, 2004, 53126-53135, vol. 279, No. 51.
Demirhan, O. et al., A homozygous BMPR1B mutation causes a new subtype of acromesomelic chondrodysplasia with genital anomalies, J Med Genet, 2005, 314-317, 42.
Depaolo, Louis V. et al., Follistatin and Activin: A Potential Intrinsic Regulatory System within Diverse Tissues, Proceedings of the Society for Experimental Biology and Medicine, 1991, 500-512, 198:1.
Di Clemente, Nathalie et al., Processing of Anti-Mullerian Hormone Regulates Receptor Activation by a Mechanism Distinct from TGF-β, Mol Endocrinol, 2010, 2193-2206, 24(11).
Dyson, Steven et al., Activin signalling has a necessary function in Xenopus early development, Current Biology, 1997, 81-84, 7.
Fukuda, Toru et al., Constitutively Activated ALK2 and Increased SMAD1/5 Cooperatively Induce Bone Morphogenetic Protein Signaling in Fibrodysplasia Ossificans Progressiva, The Journal of Biological Chemistry, 2009, 7149-7156, vol. 284, No. 11.
Gamer, Laura W. et al., A Novel BMP Expressed in Developing Mouse Limb, Spinal Cord, and Tail Bud Is a Potent Mesoderm Inducer in Xenopus Embryos, Developmental Biology, 1999, 222-232, 208.
Gamer, Laura W. et al., Gdf11 Is a Negative Regulator of Chondrogenesis and Myogenesis in the Developing Chick Limb, Developmental Biology, 2001, 407-420, 229.
Gibco, Recombinant Human Activin A Receptor, Type 1B (ACVR1B), Life Technologies Corporation, 2011, 1-2, Manual.
Gonzalez-Cadavid, Nestor F. et al., Organization of the human myostatin gene and expression in healthy men and HIV-infected men with muscle wasting, Proc. Natl. Acad. Sci. USA, 1998, 14938-14943, 95.
Goumans, Marie-Jose et al., Activin Receptor-like Kinase (ALK)1 Is an Antagonistic Mediator of Lateral TGFβ/ALK5 Signaling, Molecular Cell, 2003, 817-828, 12.
Greenwald, Jason et al., Three-finger toxin fold for the extracellular ligand-binding domain of the type II activin receptor serine kinase, Nature Structural Biology, 1999, 18-22, 6.
Grobet, Luc et al., A deletion in the bovine myostatin gene causes the double-muscled phenotype in cattle, nature genetics, 1997, 71-74, 17.
Gunasekaran, Kannan et al., Enhancing Antibody Fc Heterodimer Formation through Electrostatic Steering Effects, The Journal of Biological Chemistry, 2010, 19637-19646, 285(25).
Hilden, Kristiina et al., Expression of Type II Activin Receptor Genes During Differentiation of Human K562 Cells and cDNA Cloning of the Human Type IIB Activin Receptor, Blood, 1994, 2163-2170, 83(8).
Hinck, Andrew P., Structural studies of the TGF-βs and their receptors—insights into evolution of the TGF-β superfamily, FEBS Letters, 2012, 1860-1870, 586.
Huang, Chichi, Receptor-Fc fusion therapeutics, traps, and Mimetibody technology, Current Opinion in Biotechnology, 2009, 692-699, 20.
Kabat, Heavy Constant Chains Ch3 Region, Sequences of Proteins of Immunological Interest, 1991, 688-696, 91 (3242).
Kambadur, Ravi et al., Mutations in myostatin (GDF8) in Double-Muscled Belgian Blue and Piedmontese Cattle, Genome Research, 1997, 910-915, 7.
Kamiya, Nobuhiro et al., BMP signaling negatively regulates bone mass through sclerostin by inhibiting the canonical Wnt pathway, Development, 2008, 3801-3811, 135.
Kamiya, Nobuhiro et al., Disruption of BMP Signaling in Osteoblasts Through Type IA Receptor (BMPRIA) Increases Bone Mass, J Bone Miner Res, 2008, 2007-2017, 23(12).
Kaplan, Frederick S. et al., Fibrodysplasia ossificans progressiva: a blueprint for metamorphosis, Ann. N.Y. Acad. Sci., 2011, 5-10, 1237.
Kemaladewi, Dwi U. et al., Targeting TGF-β Signaling by Antisense Oligonucleotide-mediated Knockdown of TGF-β Type I Receptor, Molecular Therapy—Nucleic Acids, 2014, 1-8, 3, e156.
Klein, Christian et al., Progress in overcoming the chain association issue in bispecific heterodimeric IgG antibodies, mAbs, 2012, 653-663, 4(6).

(56) References Cited

OTHER PUBLICATIONS

Komesli, Sylviane et al., Chimeric extracellular domain of type II transforming growth factor (TGF)-3 receptor fused to the Fc region of human immunoglobulin as a TGF-β antagonist, Eur. J. Biochem., 1998, 505-513, 254.
Koncarevic, A. et al., A Soluble Activin Receptor Type IIB Prevents the Effects of Androgen Deprivation on Body Composition and Bone Health, Endocrinology, 2010, 4289-4300, 151(1).
Konrad, Lutz et al., Alternative splicing of TGF-betas and their high-affinity receptors TβRI, TβRII and TβRIII (betaglycan) reveal new variants in human prostatic cells, BMC Genomics, 2007, 1-13, 8:318.
Kubiczkova, Lenka et al., TGF-β—an excellent servant but a bad master, Journal of Translational Medicine, 2012, 1-24, 10:183.
Larsson, Jonas et al., Abnormal angiogenesis but intact hematopoietic potential in TGF-β type I receptor-deficient mice, The EMBO Journal, 2001, 1663-1673, 20(7).
Lavery, Karen et al., BMP-2/4 and BMP-6/7 Differentially Utilize Cell Surface Receptors to Induce Osteoblastic Differentiation of Human Bone Marrow-derived Mesenchymal Stem Cells, The Journal of Biological Chemistry, 2008, 20948-20958, 283(30).
Li, Ming O. et al., Transforming Growth Factor-β Controls Development, Homeostasis, and Tolerance of T Cells by Regulatory T Cell-Dependent and -Independent Mechanisms, Immunity, 2006, 455-471, 25.
Lin, S Jack et al., The structural basis of TGF-β, bone morphogenetic protein, and activin ligand binding, Reproduction, 2006, 179-190, 132.
Maci'as-Silva, Marina et al., Specific Activation of Smad1 Signaling Pathways by the BMP7 Type I Receptor, ALK2, The Journal of Biological Chemistry, 1998, 25628-25636, vol. 273, No. 40.
Maeshima, Akito et al., Follistatin, an Activin Antagonist, Ameliorates Renal Interstitial Fibrosis in a Rat Model of Unilateral Ureteral Obstruction, BioMed Research International, 2014, 1-10, Article ID 376191.
Massagué, Joan, How Cells Read TGF-β Signals, Nature Reviews Molecular Cell Biology, 2000, 169-178, 1 (3).
McPherron, Alexandra C. et al., Double muscling in cattle due to mutations in the myostatin gene, Proc. Natl. Acad. Sci. USA, 1997, 12457-12461, 94.
McPherron, Alexandra C. et al., Regulation of anterior/posterior patterning of the axial skeleton by growth/differentiation factor 11, nature genetics, 1999, 260-264, 22.
McPherron, Alexandra C. et al., Regulation of skeletal muscle mass in mice by a new TGF-β superfamily member, Nature, 1997, 83-90, 387.
Merchant, A. Margaret et al., An efficient route to human bispecific IgG, Nature Biotechnology, 1998, 677-681, 16.
Mishina, Yuji et al., Multiple Roles for Activin-Like Kinase-2 Signaling during Mouse Embryogenesis, Developmental Biology, 1999, 314-326, 213.
Mitchell, Dianne et al., ALK1-Fc Inhibits Multiple Mediators of Angiogenesis and Suppresses Tumor Growth, Mol Cancer Ther, 2010, 379-388, 9(2).
Miyazono, Kohei et al., Latent High Molecular Weight Complex of Transforming Growth Factor β1, The Journal of Biological Chemistry, 1988, 6407-6415, 263(13).
Nakashima, Misako et al., Expression of growth/differentiation factor 11, a new member of the BMP/TGFβ superfamily during mouse embryogenesis, Mechanisms of Development, 1999, 185-189, 80.
Pack, Peter et al., Improved bivalent miniantbodies, with identical avidity as whole antibodies, produced by high cell density fermentation of *Escherichia coli*, Bio/Technology, 1993, 1271-1277, 11.
Pack, Peter et al., Miniantibodies: Use of Amphipathic Helices to Produce Functional, Flexibly Linked Dimeric Fv Fragments with High Avidity in *Escherichia coli*, Biochemistry, 1992, 1579-1584, 31(6).
Pistilli, Emidio E. et al., Targeting the Activin Type IIB Receptor to Improve Muscle Mass and Function in the mdx Mouse Model of Duchenne Muscular Dystrophy, The American Journal of Pathology, 2011, 1287-1297, vol. 178, No. 3.
Qin, Tai et al., A novel highly potent trivalent TGF-β receptor trap inhibits early-stage tumorigenesis and tumor cell invasion in murine Pten-deficient prostate glands, Oncotarget, 2016, 86087-86102, 7(52).
Rider, Christopher C. et al., Bone morphogenetic protein and growth differentiation factor cytokine families and their protein antagonists, Biochem. J., 2010, 1-12 + Supplementary Online Data 3 pp. 429.
Ridgway, John B.B. et al., 'Knobs-into-holes' engineering of antibody CH3 domains for heavy chain heterodimerization, Protein Engineering, 1996, 617-621, 9(7).
Roberts, Heather J. et al., Identification of Novel Isoforms of Activin Receptor-Like Kinase 7 (ALK7) Generated by Alternative Splicing and Expression of ALK7 and Its Ligand, Nodal, in Human Placenta, Biology of Reproduction, 2003, 1719-1726, 68.
Rosenzweig, Bradley L. et al., Cloning and characterization of a human type II receptor for bone morphogenetic proteins, Proc. Natl. Acad. Sci. USA, 1995, 7632-7636, 92.
Sako, Dianne et al., Characterization of the Ligand Binding Functionality of the Extracellular Domain of Activin Receptor Type IIB, Journal of Biological Chemistry, 2010, 21037-21048, 285(27).
Schuelke, Markus et al., Myostatin Mutation Associated with Gross Muscle Hypertrophy in a Child, N Engl J Med, 2004, 2682-2688, 350.
Spiess, Christoph et al., Bispecific antibodies with natural architecture produced by co-culture of bacteria expressing two distinct half-antibodies, Nature Biotechnology, 2013, 753-758, 31(8).
Supplementary Partial European Search Report for EP16777227 dated Sep. 19, 2018, 5 pages.
Swatland, H. J. et al., Fetal development of the double muscled condition in cattle, Journal of Animal Science, 1974, 752-757, 38(4).
Ten Dijke, Peter, et al., Activin receptor-like kinases: a novel subclass of cell-surface receptors with predicted serine/threonine kinase activity, Oncogene, 1993, 2879-2887, 8(10).
Thompson, Thomas B. et al., Structures of an ActRIIB: activin A complex reveal a novel binding mode for TGF-β ligand: receptor interactions, The EMBO Journal, 2003, 1555-1566, 22(7).
Tsuchida, Kunihiro et al., Signal Transduction Pathway through Activin Receptors as a Therapeutic Target of Musculoskeletal Diseases and Cancer, Endocrine Journal, 2008, 11-21, 55(1).
Wakefield, Lalage M. et al., Latent Transforming Growth Factor-β from Human Platelets, The Journal of Biological Chemistry, 1988, 7646-7654, 263(16).
Weiss, Alexander et al., The TGFbeta Superfamily Signaling Pathway, Developmental Biology, 2013, 47-63, 2.
Woodruff, Teresa K., Regulation of Cellular and System Function by Activin, Biochemical Pharmacology, 1998, 953-963, 55.
Wranik, Bernd J. et al., LUZ-Y, a Novel Platform for the Mammalian Cell Production of Full-length IgG-bispecific Antibodies, The Journal of Biological Chemistry, 2012, 43331-43339, vol. 287, No. 52.
Wu, Hsiao-Huei et al., Autoregulation of Neurogenesis by GDF11, Neuron, 2003, 197-207, 37.
Yi, Soyun E. et al., The type I BMP receptor BMPRIB is required for chondrogenesis in the mouse limb, Development, 2000, 621-630, 127.
Zec, Ivana et al., Anti-Müllerian hormone: A unique biochemical marker of gonadal development and fertility in humans, Biochemia Medica, 2011, 219-230, 21(3).
Zimmers, Teresa A. et al., Induction of Cachexia in Mice by Systemically Administered Myostatin, Science, 2002, 1486-1488, 296.
Zwaagstra, John C. et al., Engineering and Therapeutic Application of Single-Chain Bivalent TGF-β Family Traps, Mol Cancer Ther, 2012, 1477-1487, 11(7).

```
ActRIIa    ILGRSETQEC LFFNANWEKD RTNQTGVEPC YGDKDKRRHC FATWKNISGS
ActRIIb    GRGEAETREC IYYNANWELE RTNQSGLERC EGEQDKRLHC YASWRNSSGT

           IEIVKQGCWL DDINCYDRTD CVEKKDSPEV YFCCCEGNMC NEKFSYFPEM
           IELVKKGCWL DDFNCYDRQE CVATEENPQV YFCCCEGNFC NERFTHLPEA

           EVTQPTSNPV TPKPP
           GGPEVTYEPP PTAPT
```

FIGURE 3

```
IgG1    -------THTCPPCPAPELLGGPSVFLFPPKPKDTLMISRTPEVTCVVVDVSHEDPEVKF 53
IgG4    ---ESKYGPPCPSCPAPEFLGGPSVFLFPPKPKDTLMISRTPEVTCVVVDVSQEDPEVQF 57
IgG2    --------VECPPCPAPPVAG-PSVFLFPPKPKDTLMISRTPEVTCVVVDVSHEDPEVQF 51
IgG3    EPKSCDTPPPCPRCPAPELLGGPSVFLFPPKPKDTLMISRTPEVTCVVVDVSHEDPEVQF 60
                  ** ****  . * ******************************:*****:*

IgG1    NWYVDGVEVHNAKTKPREEQYNSTYRVVSVLTVLHQDWLNGKEYKCKVSNKALPAPIEKT 113
IgG4    NWYVDGVEVHNAKTKPREEQFNSTYRVVSVLTVLHQDWLNGKEYKCKVSNKGLPSSIEKT 117
IgG2    NWYVDGVEVHNAKTKPREEQFNSTFRVVSVLTVVHQDWLNGKEYKCKVSNKGLPAPIEKT 111
IgG3    KWYVDGVEVHNAKTKPREEQYNSTFRVVSVLTVLHQDWLNGKEYKCKVSNKALPAPIEKT 120
        :*******************:***:********:*****************.**:.****

IgG1    ISKAKGQPREPQVYTLPPSREEMTKNQVSLTCLVKGFYPSDIAVEWESNGQPENNYKTTP 173
IgG4    ISKAKGQPREPQVYTLPPSQEEMTKNQVSLTCLVKGFYPSDIAVEWESNGQPENNYKTTP 177
IgG2    ISKTKGQPREPQVYTLPPSREEMTKNQVSLTCLVKGFYPSDIAVEWESNGQPENNYKTTP 171
IgG3    ISKTKGQPREPQVYTLPPSREEMTKNQVSLTCLVKGFYPSDIAVEWESSGQPENNYNTTP 180
        ***:***************:****************************.*******:***

IgG1    PVLDSDGSFFLYSKLTVDKSRWQQGNVFSCSVMHEALHNHYTQKSLSLSPGK 225
IgG4    PVLDSDGSFFLYSRLTVDKSRWQEGNVFSCSVMHEALHNHYTQKSLSLSLGK 229
IgG2    PMLDSDGSFFLYSKLTVDKSRWQQGNVFSCSVMHEALHNHYTQKSLSLSPGK 223
IgG3    PMLDSDGSFFLYSKLTVDKSRWQQGNIFSCSVMHEALHNRFTQKSLSLSPGK 232
        *:***********:*********:**:************::******** **
```

FIGURE 5

SINGLE-ARM TYPE I AND TYPE II RECEPTOR FUSION PROTEINS AND USES THEREOF

CROSS-REFERENCE TO RELATED APPLICATIONS

This application is a divisional of U.S. application Ser. No. 16/423,593, filed May 28, 2019 (now allowed), which is a divisional application of U.S. application Ser. No. 15/092,600, filed Apr. 6, 2016 (now U.S. Pat. No. 10,358,476), which claims the benefit of priority to U.S. Provisional Application Ser. No. 62/143,579, filed Apr. 6, 2015, and 62/259,422, filed Nov. 24, 2015. The disclosures of the foregoing applications are hereby incorporated by reference in their entirety.

SEQUENCE LISTING

The instant application contains a Sequence Listing which has been submitted in ASCII format via EFS-Web and is hereby incorporated by reference in its entirety. Said ASCII copy, created on Nov. 9, 2021, is named 1848179-0002-110-103_Seq.txt and is 443,762 bytes in size.

BACKGROUND OF THE INVENTION

The transforming growth factor-beta (TGF-beta) superfamily contains a variety of growth factors that share common sequence elements and structural motifs. These proteins are known to exert biological effects on a large variety of cell types in both vertebrates and invertebrates. Members of the superfamily perform important functions during embryonic development in pattern formation and tissue specification and can influence a variety of differentiation processes, including adipogenesis, myogenesis, chondrogenesis, cardiogenesis, hematopoiesis, neurogenesis, and epithelial cell differentiation. The superfamily is divided into two general phylogenetic clades: the more recently evolved members of the superfamily, which includes TGF-betas, activins, and nodal and the clade of more distantly related proteins of the superfamily, which includes a number of BMPs and GDFs. Hinck (2012) FEBS Letters 586:1860-1870. TGF-beta superfamily members have diverse, often complementary biological effects. By manipulating the activity of a member of the TGF-beta superfamily, it is often possible to cause significant physiological changes in an organism. For example, the Piedmontese and Belgian Blue cattle breeds carry a loss-of-function mutation in the GDF8 (also called myostatin) gene that causes a marked increase in muscle mass. Grobet et al. (1997) Nat Genet., 17(1):71-4. Furthermore, in humans, inactive alleles of GDF8 are associated with increased muscle mass and, reportedly, exceptional strength. Schuelke et al. (2004) N Engl J Med, 350:2682-8.

Changes in muscle, bone, fat, red blood cells, and other tissues may be achieved by enhancing or inhibiting signaling (e.g., SMAD 1, 2, 3, 5, and/or 8) that is mediated by ligands of the TGF-beta superfamily. Thus, there is a need for agents that regulate the activity of various ligands of the TGF-beta superfamily.

SUMMARY OF THE INVENTION

In part, the disclosure provides heteromultimeric complexes comprising a single TGF-beta superfamily type I or type II serine/threonine kinase receptor polypeptide (e.g., an ALK1, ALK2, ALK3, ALK4, ALK5, ALK6, ALK7, ActRIIA, ActRIIB, TGFBRII, BMPRII, or MISRII polypeptide), including fragments and variants thereof. These constructs may be referred to herein as "single-arm" polypeptide complexes. Optionally, single-arm polypeptide complexes disclosed herein (e.g., a single-arm ActRIIB polypeptide complex, such as an ActRIIB-Fc:Fc heterodimer) have different ligand-binding specificities/profiles compared to a corresponding homodimeric complex (e.g., an ActRIIB homodimer, such as an ActRIIB-Fc:ActRIIB-Fc). Novel properties are exhibited by heteromultimeric polypeptide complexes comprising a single domain of a TGF-beta superfamily type I or type II serine/threonine kinase receptor polypeptide, as shown by Examples herein.

Heteromultimeric structures include, for example, heterodimers, heterotrimers, and higher order complexes. Preferably, TGF-beta superfamily type I and type II receptor polypeptides as described herein comprise a ligand-binding domain of the receptor, for example, an extracellular domain of a TGF-beta superfamily type I or type II receptor. Accordingly, in certain aspects, protein complexes described herein comprise an extracellular domain of a type II TGF-beta superfamily receptor selected from: ActRIIA, ActRIIB, TGFBRII, BMPRII, and MISRII, as well as truncations and variants thereof, or an extracellular domain of a type I TGF-beta superfamily receptor selected from: ALK1, ALK2, ALK3, ALK4, ALK5, ALK6, and ALK7, as well as truncations and variants thereof. Preferably, TGF-beta superfamily type I and type II polypeptides as described herein, as well as protein complexes comprising the same, are soluble. In certain aspects, heteromultimer complexes of the disclosure bind to one or more TGF-beta superfamily ligands (e.g., BMP2, BMP2/7, BMP3, BMP4, BMP4/7, BMP5, BMP6, BMP7, BMP8a, BMP8b, BMP9, BMP10, GDF3, GDF5, GDF6/BMP13, GDF7, GDF8, GDF9b/BMP15, GDF11/BMP11, GDF15/MIC1, TGF-β1, TGF-β2, TGF-β3, activin A, activin B, activin C, activin E, activin AB, activin AC, activin AE, activin BC, activin BE, nodal, glial cell-derived neurotrophic factor (GDNF), neurturin, artemin, persephin, Müllerian-inhibiting substance (MIS), and Lefty). Optionally, protein complexes of the disclosure bind to one or more of these ligands with a $K_D$ of less than or equal to $10^{-8}$, $10^{-9}$, $10^{-10}$, $10^{-11}$, or $10^{-12}$. In general, heteromultimer complexes of the disclosure antagonize (inhibit) one or more activities of at least one TGF-beta superfamily ligand, and such alterations in activity may be measured using various assays known in the art, including, for example, a cell-based assay as described herein. Preferably, protein complexes of the disclosure exhibit a serum half-life of at least 4, 6, 12, 24, 36, 48, or 72 hours in a mammal (e.g., a mouse or a human). Optionally, protein complexes of the disclosure may exhibit a serum half-life of at least 6, 8, 10, 12, 14, 20, 25, or 30 days in a mammal (e.g., a mouse or a human).

In certain aspects, protein complexes described herein comprise a first polypeptide covalently or non-covalently associated with a second polypeptide wherein the first polypeptide comprises the amino acid sequence of a TGF-beta superfamily type I or type II receptor polypeptide and the amino acid sequence of a first member of an interaction pair and the second polypeptide comprises a second member of the interaction pair and does not contain an amino acid sequence of a TGF-beta superfamily type I or type II receptor polypeptide. Optionally, the second polypeptide comprises, in addition to the second member of the interaction pair, a further polypeptide sequence that is not a TGF-beta superfamily type I or type II receptor polypeptide and may optionally comprise not more than 5, 10, 15, 20, 30, 40, 50, 100, 200, 300, 400 or 500 amino acids. Optionally, the TGF-beta superfamily type I or type II receptor polypeptide is connected directly to the first member of the interaction pair, or an intervening sequence, such as a linker, may be positioned between the amino acid sequence of the TGF-beta superfamily type I or type II receptor polypeptide and the amino acid sequence of the first member of the interaction pair. Examples of linkers include, but are not limited to, the sequences TGGG (SEQ ID NO: 62), TGGGG (SEQ ID NO: 60), SGGGG (SEQ ID NO: 61), GGGGS (SEQ ID NO: 510), and GGG (SEQ ID NO: 58).

Interaction pairs described herein are designed to promote dimerization or form higher order multimers. In some embodiments, the interaction pair may be any two polypeptide sequences that interact to form a complex, particularly a heterodimeric complex although operative embodiments may also employ an interaction pair that forms a homodimeric complex. The first and second members of the interaction pair may be an asymmetric pair, meaning that the members of the pair preferentially associate with each other rather than self-associate. Accordingly, first and second members of an asymmetric interaction pair may associate to form a heterodimeric complex. Alternatively, the interaction pair may be unguided, meaning that the members of the pair may associate with each other or self-associate without substantial preference and thus may have the same or different amino acid sequences. Accordingly, first and second members of an unguided interaction pair may associate to form a homodimer complex or a heterodimeric complex. Optionally, the first member of the interaction pair (e.g., an asymmetric pair or an unguided interaction pair) associates covalently with the second member of the interaction pair. Optionally, the first member of the interaction pair (e.g., an asymmetric pair or an unguided interaction pair) associates non-covalently with the second member of the interaction pair.

Traditional Fc fusion proteins and antibodies are examples of unguided interaction pairs, whereas a variety of engineered Fc domains have been designed as asymmetric interaction pairs. Therefore, a first member and/or a second member of an interaction pair described herein may comprise a constant domain of an immunoglobulin, including, for example, the Fc portion of an immunoglobulin. Optionally, a first member of an interaction pair may comprise an amino acid sequence that is derived from an Fc domain of an IgG1, IgG2, IgG3, or IgG4 immunoglobulin. For example, the first member of an interaction pair may comprise, consist essentially of, or consist of an amino acid sequence that is at least 80%, 85%, 90%, 91%, 92%, 93%, 94%, 95%, 96%, 97%, 98%, 99% or 100% identical to any one of SEQ ID NOs: 200-214. Optionally, a second member of an interaction pair may comprise an amino acid sequence that is derived from an Fc domain of an IgG1, IgG2, IgG3, or IgG4. For example, the second member of an interaction pair may comprise, consist essentially of, or consist of an amino acid sequence that is at least 80%, 85%, 90%, 91%, 92%, 93%, 94%, 95%, 96%, 97%, 98%, 99% or 100% identical to any one of SEQ ID NOs: 200-214. In some embodiments, a first member and a second member of an interaction pair comprise Fc domains derived from the same immunoglobulin class and subtype. In other embodiments, a first member and a second member of an interaction pair comprise Fc domains derived from different immunoglobulin classes or subtypes. Optionally, a first member and/or a second member of an interaction pair (e.g., an asymmetric pair or an unguided interaction pair) comprise a modified constant domain of an immunoglobulin, including, for example, a modified Fc portion of an immunoglobulin. For example, protein complexes of the disclosure may comprise a first Fc portion of an IgG comprising an amino acid sequence that is at least 80%, 85%, 90%, 91%, 92%, 93%, 94%, 95%, 96%, 97%, 98%, or 99% identical to an amino acid sequence selected from the group: SEQ ID NOs: 200-214 and a second Fc portion of an IgG, which may be the same or different from the amino acid sequence of the first modified Fc portion of the IgG, comprising an amino acid sequence that is at least 80%, 85%, 90%, 91%, 92%, 93%, 94%, 95%, 96%, 97%, 98%, or 99% identical to an amino acid sequence selected from the group: SEQ ID NOs: 200-214.

In some embodiments, the disclosure provides heteromeric polypeptide complexes comprising a single type I or type II TGF-beta superfamily receptor polypeptide, wherein the TGF-beta superfamily receptor polypeptide is derived from an ActRIIA receptor. For example, ActRIIA polypeptides may comprise, consist essentially of, or consist of an amino acid sequence that is at least 70%, 80%, 85%, 90%, 95%, 97%, 98%, 99% or 100% identical to an ActRIIA sequence disclosed herein (e.g., SEQ ID NOs: 9, 10, 11, 101, 103, 401, and 402). Optionally, ActRIIA polypeptides may comprise, consist essentially of, or consist of an amino acid sequence that is at least 70%, 80%, 85%, 90%, 95%, 97%, 98%, 99% or 100% identical to a polypeptide that a) begins at any one of amino acids of 21-30 (e.g., amino acid residues 21, 22, 23, 24, 25, 26, 27, 28, 29, or 30) SEQ ID NO: 9, and b) ends at any one of amino acids 110-135 (e.g., 110, 111, 112, 113, 114, 115, 116, 117, 118, 119, 120, 121, 122, 123, 124, 125, 126, 127, 128, 129, 130, 131, 132, 133, 134 or 135) of SEQ ID NO: 9. Optionally, ActRIIA polypeptides of the disclosure may be fusion proteins that further comprise one or more portions (domains) that are heterologous to ActRIIA. For example, an ActRIIA polypeptide may be fused to a heterologous polypeptide that comprises a multimerization domain, optionally with a linker domain positioned between the ActRIIA polypeptide and the heterologous polypeptide (e.g., SEQ ID NOs: 101, 103, 401, and 402). In some embodiments, multimerization domains described herein comprise one component of an interaction pair. Heteromeric complexes that comprise an ActRIIA polypeptide do not comprise another type I or type II TGF-beta superfamily receptor polypeptide but may contain additional polypeptides that are not type I or type II TGF-beta superfamily receptor polypeptides.

In some embodiments, the disclosure provides heteromeric polypeptide complexes comprising a type I or type II TGF-beta superfamily receptor polypeptide, wherein the TGF-beta superfamily receptor polypeptide is derived from an ActRIIB receptor. For example, ActRIIB polypeptides may comprise, consist essentially of, or consist of an amino acid sequence that is at least 70%, 80%, 85%, 90%, 95%, 97%, 98%, 99% or 100% identical to an ActRIIB sequence disclosed herein (e.g., SEQ ID NOs: 1, 2, 3, 4, 5, 6, 104, 106, 403, and 404). Optionally, ActRIIB polypeptides may comprise, consist essentially of, or consist of an amino acid sequence that is at least 70%, 80%, 85%, 90%, 95%, 97%, 98%, 99% or 100% identical to a polypeptide that a) begins at any one of amino acids of 20-29 (e.g., amino acid residues 20, 21, 22, 23, 24, 25, 26, 27, 28, or 29) SEQ ID NO: 1, and b) ends at any one of amino acids 109-134 (e.g., amino acid residues 109, 110, 111, 112, 113, 114, 115, 116, 117, 118, 119, 120, 121, 122, 123, 124, 125, 126, 127, 128, 129, 130, 131, 132, 133, or 134 of SEQ ID NO: 1. Optionally, ActRIIB polypeptides of the disclosure may be fusion proteins that further comprise one or more portions (domains) that are heterologous to ActRIIB For example, an ActRIIB polypeptide may be fused to a heterologous polypeptide that comprises a multimerization domain, optionally with a linker domain positioned between the ActRIIB polypeptide and the heterologous polypeptide (e.g., SEQ ID NOs: 104, 106, 403, and 404). In some embodiments, multimerization domains described herein comprise one component of an interaction pair. Heteromeric complexes that comprise an ActRIIB polypeptide do not comprise another type I or type II TGF-beta superfamily receptor polypeptide but may contain additional polypeptides that are not type I or type II TGF-beta superfamily receptor polypeptides.

In some embodiments, the disclosure provides heteromeric polypeptide complexes comprising a type I or type II TGF-beta superfamily receptor polypeptide, wherein the TGF-beta superfamily receptor polypeptide is derived from a TGFBRII receptor. For example, TGFBRII polypeptides may comprise, consist essentially of, or consist of an amino acid sequence that is at least 70%, 80%, 85%, 90%, 95%, 97%, 98%, 99% or 100% identical to an TGFBRII sequence disclosed herein (e.g., SEQ ID NOs: 42, 43, 67, 68, 113, 115, 409, and 410). Optionally, TGFBRII polypeptides may comprise, consist essentially of, or consist of an amino acid sequence that is at least 70%, 80%, 85%, 90%, 95%, 97%, 98%, 99% or 100% identical to a polypeptide that a) begins at any one of amino acids of 23, 24, 25, 26, 27, 28, 29, 30, 31, 32, 33, 34, 35, 36, 37, 38, 39, 40, 41, 42, 43, 44, 45, 46, 47, 48, 49, 50 or 51 of SEQ ID NO: 42, and b) ends at any one of amino acids 143, 144, 145, 146, 147, 148, 149, 150, 151, 152, 153, 154, 155, 156, 157, 158, 159, 160, 161, 162, 163, 164, 165 or 166 of SEQ ID NO: 42. Optionally, TGFBRII polypeptides may comprise, consist essentially of, or consist of an amino acid sequence that is at least 70%, 80%, 85%, 90%, 95%, 97%, 98%, 99% or 100% identical to a polypeptide that a) begins at any one of amino acids of 23, 24, 25, 26, 27, 28, 29, 30, 31, 32, 33, 34, 35, 36, 37, 38, 39, 40, 41, 42, 43 or 44 of SEQ ID NO: 67, and b) ends at any one of amino acids 163, 164, 165, 166, 167, 168, 169, 170, 171, 172, 173, 174, 175, 176, 177, 178, 179, 180, 181, 182, 183, 184, 185, 186, 187, 188, 189, 190 or 191 of SEQ ID NO: 67. Optionally, TGFBRII polypeptides of the disclosure may be fusion proteins that further comprise one or more portions (domains) that are heterologous to TGFBRII. For example, a TGFBRII polypeptide may be fused to a heterologous polypeptide that comprises a multimerization domain, optionally with a linker domain positioned between the TGFBRII polypeptide and the heterologous polypeptide (e.g., SEQ ID NOs: 113, 115, 409, and 410). In some embodiments, multimerization domains described herein comprise one component of an interaction pair. Heteromeric complexes that comprise a TGFBRII polypeptide do not comprise another type I or type II TGF-beta superfamily receptor polypeptide but may contain additional polypeptides that are not type I or type II TGF-beta superfamily receptor polypeptides.

In some embodiments, the disclosure provides heteromeric polypeptide complexes comprising a type I or type II TGF-beta superfamily receptor polypeptide, wherein the TGF-beta superfamily receptor polypeptide is derived from a BMPRII receptor. For example, BMPRII polypeptides may comprise, consist essentially of, or consist of an amino acid sequence that is at least 70%, 80%, 85%, 90%, 95%, 97%, 98%, 99% or 100% identical to a BMPRII sequence disclosed herein (e.g., SEQ ID NOs: 46, 47, 71, 72, 107, 109, 405, and 406). Optionally, BMPRII polypeptides may comprise, consist essentially of, or consist of an amino acid sequence that is at least 70%, 80%, 85%, 90%, 95%, 97%, 98%, 99% or 100% identical to a polypeptide that a) begins at any one of amino acids of 27-34 (e.g., amino acid residues 27, 28, 29, 30, 31, 32, 33, and 34) SEQ ID NO: 46 or 71, and b) ends at any one of amino acids 123-150 (e.g., amino acid residues 123, 124, 125, 126, 127, 128, 129, 130, 131, 132, 133, 134, 135, 136, 137, 138, 139, 140, 141, 142, 143, 144, 145, 146, 147, 148, 149, and 150) of SEQ ID NO: 46 or 71. Optionally, BMPRII polypeptides of the disclosure may be fusion proteins that further comprise one or more portions (domains) that are heterologous to BMPRII. For example, a BMPRII polypeptide may be fused to a heterologous polypeptide that comprises a multimerization domain, optionally with a linker domain positioned between the BMPRII polypeptide and the heterologous polypeptide (e.g., SEQ ID NOs: 107, 109, 405, and 406). Heteromeric complexes that comprise a BMPRII polypeptide do not comprise another type I or type II TGF-beta superfamily receptor polypeptide but may contain additional polypeptides that are not type I or type II TGF-beta superfamily receptor polypeptides.

In some embodiments, the disclosure provides heteromeric polypeptide complexes comprising a type I or type II TGF-beta superfamily receptor polypeptide, wherein the TGF-beta superfamily receptor polypeptide is derived from an MISRII receptor. For example, MISRII polypeptides may comprise, consist essentially of, or consist of an amino acid sequence that is at least 70%, 80%, 85%, 90%, 95%, 97%, 98%, 99% or 100% identical to an MISRII sequence disclosed herein (e.g., SEQ ID NOs: 50, 51, 75, 76, 79, 80, 110, 112, 407, and 408). Optionally, MISRII polypeptides may comprise, consist essentially of, or consist of an amino acid sequence that is at least 70%, 80%, 85%, 90%, 95%, 97%, 98%, 99% or 100% identical to a polypeptide that a) begins at any one of amino acids of 17-24 (e.g., amino acid residues 17, 18, 19, 20, 21, 22, 23, and 24) SEQ ID NO: 50, 75, or 79, and b) ends at any one of amino acids 116-149 (e.g., amino acid residues 116, 117, 118, 119, 120, 121, 122 123, 124, 125, 126, 127, 128, 129, 130, 131, 132, 133, 134, 135, 136, 137, 138, 139, 140, 141, 142, 143, 144, 145, 146, 147, 148, and 149) of SEQ ID NO: 50, 75, or 79. Optionally, MISRII polypeptides of the disclosure may be fusion proteins that further comprise one or more portions (domains) that are heterologous to MISRII. For example, an MISRII polypeptide may be fused to a heterologous polypeptide that comprises a multimerization domain, optionally with a linker domain positioned between the MISRII polypeptide and the heterologous polypeptide (e.g., SEQ ID NOs: 110, 112, 407, and 408). In some embodiments, multimerization domains described herein comprise one component of an interaction pair. Heteromeric complexes that comprise an MISRII polypeptide do not comprise another type I or type II TGF-beta superfamily receptor polypeptide but may contain additional polypeptides that are not type I or type II TGF-beta superfamily receptor polypeptides.

In some embodiments, the disclosure provides heteromeric polypeptide complexes comprising a type I or type II TGF-beta superfamily receptor polypeptide, wherein the TGF-beta superfamily receptor polypeptide is derived from an ALK1 receptor. For example, ALK1 polypeptides may comprise, consist essentially of, or consist of an amino acid sequence that is at least 70%, 80%, 85%, 90%, 95%, 97%, 98%, 99% or 100% identical to an ALK1 sequence disclosed herein (e.g., SEQ ID NOs: 14, 15, 116, 118, 411, and 412). Optionally, ALK1 polypeptides may comprise, consist essentially of, or consist of an amino acid sequence that is at least 70%, 80%, 85%, 90%, 95%, 97%, 98%, 99% or 100% identical to a polypeptide that a) begins at any one of amino acids of 22-34 (e.g., amino acid residues 22, 23, 24, 25, 26, 27, 28, 29, 30, 31, 32, 33, and 34) SEQ ID NO: 14, and b) ends at any one of amino acids 95-118 (e.g., amino acid residues 95, 96, 97, 98, 99, 100, 101, 102, 103, 104, 105, 106, 107, 108, 109, 110, 111, 112, 113, 114, 115, 116, 117, and 118) of SEQ ID NO: 14. Optionally, ALK1 polypeptides of the disclosure may be fusion proteins that further comprise one or more portions (domains) that are heterologous to ALK1. For example, an ALK1 polypeptide may be fused to a heterologous polypeptide that comprises a multimerization domain, optionally with a linker domain positioned between the ALK1 polypeptide and the heterologous polypeptide (e.g., SEQ ID NOs: 116, 118, 411, and 412). Heteromeric complexes that comprise an ALK1 polypeptide do not comprise another type I or type II TGF-beta superfamily receptor polypeptide but may contain additional polypeptides that are not type I or type II TGF-beta superfamily receptor polypeptides.

In some embodiments, the disclosure provides heteromeric polypeptide complexes comprising a type I or type II TGF-beta superfamily receptor polypeptide, wherein the TGF-beta superfamily receptor polypeptide is derived from an ALK2 receptor. For example, ALK2 polypeptides may comprise, consist essentially of, or consist of an amino acid sequence that is at least 70%, 80%, 85%, 90%, 95%, 97%, 98%, 99% or 100% identical to an ALK2 sequence disclosed herein (e.g., SEQ ID NOs: 18, 19, 119, 121, 413, and 414). Optionally, ALK2 polypeptides may comprise, consist essentially of, or consist of an amino acid sequence that is at least 70%, 80%, 85%, 90%, 95%, 97%, 98%, 99% or 100% identical to a polypeptide that a) begins at any one of amino acids of 21-35 (e.g., amino acid residues 21, 22, 23, 24, 25, 26, 27, 28, 29, 30, 31, 32, 33, 34, and 35) SEQ ID NO: 18, and b) ends at any one of amino acids 99-123 (e.g., amino acid residues 99, 100, 101, 102, 103, 104, 105, 106, 107, 108, 109, 110, 111, 112, 113, 114, 115, 116, 117, 118, 119, 120, 121, 122, and 123) of SEQ ID NO: 18. Optionally, ALK2 polypeptides of the disclosure may be fusion proteins that further comprise one or more portions (domains) that are heterologous to ALK2. For example, an ALK2 polypeptide may be fused to a heterologous polypeptide that comprises a multimerization domain, optionally with a linker domain positioned between the ALK2 polypeptide and the heterologous polypeptide (e.g., SEQ ID NOs: 119, 121, 413, and 414). Heteromeric complexes that comprise an ALK2 polypeptide do not comprise another type I or type II TGF-beta superfamily receptor polypeptide but may contain additional polypeptides that are not type I or type II TGF-beta superfamily receptor polypeptides.

In some embodiments, the disclosure provides heteromeric polypeptide complexes comprising a type I or type II TGF-beta superfamily receptor polypeptide, wherein the TGF-beta superfamily receptor polypeptide is derived from an ALK3 receptor. For example, ALK3 polypeptides may comprise, consist essentially of, or consist of an amino acid sequence that is at least 70%, 80%, 85%, 90%, 95%, 97%, 98%, 99% or 100% identical to an ALK3 sequence disclosed herein (e.g., SEQ ID NOs: 22, 23, 122, 124, 415, and 416). Optionally, ALK3 polypeptides may comprise, consist essentially of, or consist of an amino acid sequence that is at least 70%, 80%, 85%, 90%, 95%, 97%, 98%, 99% or 100% identical to a polypeptide that a) begins at any one of amino acids of 24-61 (e.g., amino acid residues 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, and 61) SEQ ID NO: 22, and b) ends at any one of amino acids 130-152 (e.g., amino acid residues 130, 131, 132, 133, 134, 135, 136, 137, 138, 139, 140, 141, 142, 143, 144, 145, 146, 147, 148, 149, 150, 151, and 152) of SEQ ID NO: 22. Optionally, ALK3 polypeptides of the disclosure may be fusion proteins that further comprise one or more portions (domains) that are heterologous to ALK3. For example, an ALK3 polypeptide may be fused to a heterologous polypeptide that comprises a multimerization domain, optionally with a linker domain positioned between the ALK3 polypeptide and the heterologous polypeptide (e.g., SEQ ID NOs: 122, 124, 415, and 416). Heteromeric complexes that comprise an ALK3 polypeptide do not comprise another type I or type II TGF-beta superfamily receptor polypeptide but may contain additional polypeptides that are not type I or type II TGF-beta superfamily receptor polypeptides.

In some embodiments, the disclosure provides heteromeric polypeptide complexes comprising a type I or type II TGF-beta superfamily receptor polypeptide, wherein the TGF-beta superfamily receptor polypeptide is derived from an ALK4 receptor. For example, ALK4 polypeptides may comprise, consist essentially of, or consist of an amino acid sequence that is at least 70%, 80%, 85%, 90%, 95%, 97%, 98%, 99% or 100% identical to an ALK4 sequence disclosed herein (e.g., SEQ ID NOs: 26, 27, 83, 84, 125, 127, 417, and 418). Optionally, ALK4 polypeptides may comprise, consist essentially of, or consist of an amino acid sequence that is at least 70%, 80%, 85%, 90%, 95%, 97%, 98%, 99% or 100% identical to a polypeptide that a) begins at any one of amino acids of 23-34 (e.g., amino acid residues 23, 24, 25, 26, 27, 28, 29, 30, 31, 32, 33, 34) SEQ ID NO: 26 or 83, and b) ends at any one of amino acids 101-126 (e.g., amino acid residues 101, 102, 103, 104, 105, 106, 107, 108, 109, 110, 111, 112, 113, 114, 115, 116, 117, 118, 119, 120, 121, 122, 123, 124, 125, and 126) of SEQ ID NO: 26 or 83. Optionally, ALK4 polypeptides of the disclosure may be fusion proteins that further comprise one or more portions (domains) that are heterologous to ALK4. For example, an ALK4 polypeptide may be fused to a heterologous polypeptide that comprises a multimerization domain, optionally with a linker domain positioned between the ALK4 polypeptide and the heterologous polypeptide (e.g., SEQ ID NOs: 125, 127, 417, and 418). Heteromeric complexes that comprise an ALK4 polypeptide do not comprise another type I or type II TGF-beta superfamily receptor polypeptide but may contain additional polypeptides that are not type I or type II TGF-beta superfamily receptor polypeptides.

In some embodiments, the disclosure provides heteromeric polypeptide complexes comprising a type I or type II TGF-beta superfamily receptor polypeptide, wherein the TGF-beta superfamily receptor polypeptide is derived from an ALK5 receptor. For example, ALK5 polypeptides may comprise, consist essentially of, or consist of an amino acid sequence that is at least 70%, 80%, 85%, 90%, 95%, 97%, 98%, 99% or 100% identical to an ALK5 sequence disclosed herein (e.g., SEQ ID NOs: 30, 31, 87, 88, 128, 130, 419, and 420). Optionally, ALK5 polypeptides may comprise, consist essentially of, or consist of an amino acid sequence that is at least 70%, 80%, 85%, 90%, 95%, 97%, 98%, 99% or 100% identical to a polypeptide that a) begins at any one of amino acids of 25-36 (e.g., amino acid residues 25, 26, 27, 28, 29, 30, 31, 32, 33, 34, 35, and 36) SEQ ID NO: 30 or 87, and b) ends at any one of amino acids 106-126 (e.g., amino acid residues 106, 107, 108, 109, 110, 111, 112, 113, 114, 115, 116, 117, 118, 119, 120, 121, 122, 123, 124, 125, and 126) of SEQ ID NO: 30 or 87. Optionally, ALK5 polypeptides of the disclosure may be fusion proteins that further comprise one or more portions (domains) that are heterologous to ALK5. For example, an ALK5 polypeptide may be fused to a heterologous polypeptide that comprises a multimerization domain, optionally with a linker domain positioned between the ALK5 polypeptide and the heterologous polypeptide (e.g., SEQ ID NOs: 128, 130, 419, and 420). Heteromeric complexes that comprise an ALK5 polypeptide do not comprise another type I or type II TGF-beta superfamily receptor polypeptide but may contain additional polypeptides that are not type I or type II TGF-beta superfamily receptor polypeptides.

In some embodiments, the disclosure provides heteromeric polypeptide complexes comprising a type I or type II TGF-beta superfamily receptor polypeptide, wherein the TGF-beta superfamily receptor polypeptide is derived from an ALK6 receptor. For example, ALK6 polypeptides may comprise, consist essentially of, or consist of an amino acid sequence that is at least 70%, 80%, 85%, 90%, 95%, 97%, 98%, 99% or 100% identical to an ALK6 sequence disclosed herein (e.g., SEQ ID NOs: 34, 35, 91, 92, 131, 133, 421, and 422). Optionally, ALK6 polypeptides may comprise, consist essentially of, or consist of an amino acid sequence that is at least 70%, 80%, 85%, 90%, 95%, 97%, 98%, 99% or 100% identical to a polypeptide that a) begins at any one of amino acids of 14-32 (e.g., amino acid residues 14, 15, 16, 17, 18, 19, 20, 21, 22, 23, 24, 25, 26, 27, 28, 29, 30, 31, and 32) SEQ ID NO: 34, and b) ends at any one of amino acids 102-126 (e.g., amino acid residues 102, 103, 104, 105, 106, 107, 108, 109, 110, 111, 112, 113, 114, 115, 116, 117, 118, 119, 120, 121, 122, 123, 124, 125, and 126) of SEQ ID NO: 34. Optionally, ALK6 polypeptides may comprise, consist essentially of, or consist of an amino acid sequence that is at least 70%, 80%, 85%, 90%, 95%, 97%, 98%, 99% or 100% identical to a polypeptide that a) begins at any one of amino acids of 26-62 (e.g., amino acid residues 26, 27, 28, 29, 30, 31, 32, 33, 34, 35, 36, 37, 38, 39, 40, 41, 42, 43, 44, 45, 46, 47, 48, 49, 50, 52, 53, 54, 55, 56, 57, 58, 59, 60, 61, and 62) SEQ ID NO: 91, and b) ends at any one of amino acids 132-156 (e.g., amino acid residues 132, 133, 134, 135, 136, 137, 138, 139, 140, 141, 142, 143, 144, 145, 146, 147, 148, 149, 150, 151, 152, 153, 154, 155, and 156) of SEQ ID NO: 91. Optionally, ALK6 polypeptides of the disclosure may be fusion proteins that further comprise one or more portions (domains) that are heterologous to ALK6. For example, an ALK6 polypeptide may be fused to a heterologous polypeptide that comprises a multimerization domain, optionally with a linker domain positioned between the ALK6 polypeptide and the heterologous polypeptide (e.g., SEQ ID NOs: 131, 133, 421, and 422). Heteromeric complexes that comprise an ALK6 polypeptide do not comprise another type I or type II TGF-beta superfamily receptor polypeptide but may contain additional polypeptides that are not type I or type II TGF-beta superfamily receptor polypeptides.

In some embodiments, the disclosure provides heteromeric polypeptide complexes comprising a type I or type II TGF-beta superfamily receptor polypeptide, wherein the TGF-beta superfamily receptor polypeptide is derived from an ALK7 receptor. For example, ALK7 polypeptides may comprise, consist essentially of, or consist of an amino acid sequence that is at least 70%, 80%, 85%, 90%, 95%, 97%, 98%, 99% or 100% identical to an ALK7 sequence disclosed herein (e.g., SEQ ID NOs: 38, 39, 134, 136, 301, 302, 305, 306, 309, 310, 313, 423, and 424). Optionally, ALK7 polypeptides may comprise, consist essentially of, or consist of an amino acid sequence that is at least 70%, 80%, 85%, 90%, 95%, 97%, 98%, 99% or 100% identical to a polypeptide that begins at any one of amino acids 21-28 of SEQ ID NO: 38 (e.g., amino acids 21, 22, 23, 24, 25, 26, 27, or 28) and ends at any one of amino acids 92-113 of SEQ ID NO: 38 (e.g., amino acids 92, 93, 94, 95, 96, 97, 98, 99, 100, 101, 102, 103, 104, 105, 106, 107, 108, 109, 110, 111, 112, or 113 of SEQ ID NO: 38). Optionally, ALK7 polypeptides of the disclosure may be fusion proteins that further comprise one or more portions (domains) that are heterologous to ALK7. For example, an ALK7 polypeptide may be fused to a heterologous polypeptide that comprises a multimerization domain, optionally with a linker domain positioned between the ALK7 polypeptide and the heterologous polypeptide (e.g., SEQ ID NOs: 134, 136, 423, and 424). Heteromeric complexes that comprise an ALK7 polypeptide do not comprise another type I or type II TGF-beta superfamily receptor polypeptide but may contain additional polypeptides that are not type I or type II TGF-beta superfamily receptor polypeptides.

In some embodiments, the TGF-beta superfamily type I and/or type II receptor polypeptides disclosed herein comprise one or more modified amino acid residues selected from: a glycosylated amino acid, a PEGylated amino acid, a farnesylated amino acid, an acetylated amino acid, a biotinylated amino acid, an amino acid conjugated to a lipid moiety, and an amino acid conjugated to an organic derivatizing agent. In some embodiments, the TGF-beta superfamily type I and/or type II polypeptides described herein are glycosylated and have a glycosylation pattern obtainable from the expression of the polypeptides in a mammalian cell, including, for example, a CHO cell.

In certain aspects the disclosure provides nucleic acids encoding any of the TGF-beta superfamily type I and/or type II polypeptides described herein, including any fusion proteins comprising members of an interaction pair. Nucleic acids disclosed herein may be operably linked to a promoter for expression, and the disclosure further provides cells transformed with such recombinant polynucleotides. Preferably the cell is a mammalian cell such as a COS cell or a CHO cell.

In certain aspects, the disclosure provides methods for making any of the TGF-beta superfamily type I and/or type II polypeptides described herein as well as protein complexes comprising such a polypeptide. Such a method may include expressing any of the nucleic acids disclosed herein in a suitable cell (e.g., CHO cell or a COS cell). Such a method may comprise: a) culturing a cell under conditions suitable for expression of a TGF-beta superfamily type I or type II polypeptides described herein, wherein said cell is transformed with a type I or type II polypeptide expression construct; and b) recovering the type I or type II polypeptides so expressed. TGF-beta superfamily type I and/or type II polypeptides described herein, as well as protein complexes of the same, may be recovered as crude, partially purified, or highly purified fractions using any of the well-known techniques for obtaining protein from cell cultures.

Any of the protein complexes described herein may be incorporated into a pharmaceutical preparation. Optionally, such pharmaceutical preparations are at least 80%, 85%, 90%, 95%, 97%, 98% or 99% pure with respect to other polypeptide components. Optionally, pharmaceutical preparations disclosed herein may comprise one or more additional active agents.

The disclosure further provides methods for use of the protein complexes and pharmaceutical preparations described herein for the treatment or prevention of various TGF-beta associated conditions, including without limitation diseases and disorders associated with, for example, cancer, muscle, bone, fat, red blood cells, metabolism, fibrosis and other tissues that are affected by one or more ligands of the TGF-beta superfamily.

BRIEF DESCRIPTION OF THE DRAWINGS

FIG. 3 shows an alignment of extracellular domains of human ActRIIA (SEQ ID NO: 500) and human ActRIIB (SEQ ID NO: 2) with the residues that are deduced herein, based on composite analysis of multiple ActRIIB and ActRIIA crystal structures, to directly contact ligand indicated with boxes.

FIG. 5 shows multiple sequence alignment of Fc domains from human IgG isotypes using Clustal 2.1. Hinge regions are indicated by dotted underline. Double underline indicates examples of positions engineered in IgG1 Fc to promote asymmetric chain pairing and the corresponding positions with respect to other isotypes IgG2, IgG3 and IgG4. FIG. 5 discloses SEQ ID NOs: 208, 212, 209, and 210, respectively, in order of appearance.

DETAILED DESCRIPTION OF THE INVENTION

1. Overview

Figure 1:
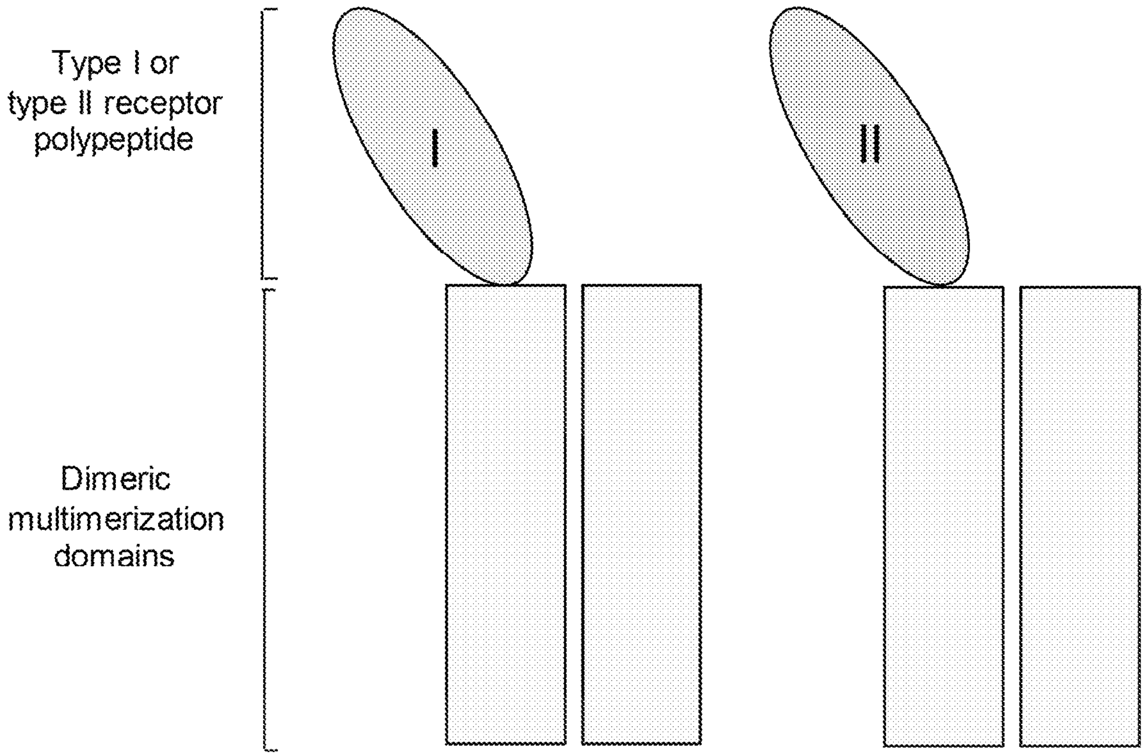
FIG. 1 shows schematic examples of single-arm heteromeric protein complexes comprising either a type I receptor polypeptide or a type II receptor polypeptide. Such complexes can be assembled covalently or noncovalently via a multimerization domain contained within each polypeptide chain. Two assembled multimerization domains constitute an interaction pair, which can be either guided or unguided.

In part, the present disclosure relates to single-arm heteromultimer complexes comprising an extracellular domain of a TGFβ superfamily type I receptor polypeptide or an extracellular domain of a TGFβ superfamily type II receptor polypeptide, methods of making such single-arm heteromultimer complexes, and uses thereof. As described herein, single-arm heteromultimer complexes may comprise an extracellular domain of a TGFβ superfamily type I receptor polypeptide selected from: ALK1, ALK2, ALK3, ALK4, ALK5, ALK6, and ALK7, or an extracellular domain of a TGFβ superfamily type II receptor polypeptide selected from: ActRIIA, ActRIIB, TGFBRII, BMPRII, and MISRII. In certain preferred embodiments, heteromultimer complexes of the disclosure have an altered profile of binding to TGFβ superfamily ligands relative to a corresponding homomultimer complex (e.g., an ActRIIB-Fc:Fc heterodimer compared to an ActRIIB-Fc:ActRIIB-Fc homodimer complex).

The TGF-β superfamily is comprised of over thirty secreted factors including TGF-betas, activins, nodals, bone morphogenetic proteins (BMPs), growth and differentiation factors (GDFs), and anti-Mullerian hormone (AMH). See, e.g., Weiss et al. (2013) Developmental Biology, 2(1): 47-63. Members of the superfamily, which are found in both vertebrates and invertebrates, are ubiquitously expressed in diverse tissues and function during the earliest stages of development throughout the lifetime of an animal. Indeed, TGF-β superfamily proteins are key mediators of stem cell self-renewal, gastrulation, differentiation, organ morphogenesis, and adult tissue homeostasis. Consistent with this ubiquitous activity, aberrant TGF-beta superfamily signaling is associated with a wide range of human pathologies including, for example, autoimmune disease, cardiovascular disease, fibrotic disease, and cancer.

Ligands of the TGF-beta superfamily share the same dimeric structure in which the central 3½ turn helix of one monomer packs against the concave surface formed by the beta-strands of the other monomer. The majority of TGF-beta family members are further stabilized by an intermolecular disulfide bond. This disulfide bonds traverses through a ring formed by two other disulfide bonds generating what has been termed a 'cysteine knot' motif. See, e.g., Lin et al., (2006) Reproduction 132: 179-190 and Hinck (2012) FEBS Letters 586: 1860-1870.

TGF-beta superfamily signaling is mediated by heteromeric complexes of type I and type II serine/threonine kinase receptors, which phosphorylate and activate downstream SMAD proteins (e.g., SMAD proteins 1, 2, 3, 5, and 8) upon ligand stimulation. See, e.g., Massagué (2000) Nat. Rev. Mol. Cell Biol. 1:169-178. These type I and type II receptors are transmembrane proteins, composed of a ligand-binding extracellular domain with cysteine-rich region, a transmembrane domain, and a cytoplasmic domain with predicted serine/threonine kinase specificity. In general, type I receptors mediate intracellular signaling while the type II receptors are required for binding TGF-beta superfamily ligands. Type I and II receptors form a stable complex after ligand binding, resulting in phosphorylation of type I receptors by type II receptors.

The TGF-beta family can be divided into two phylogenetic branches based on the type I receptors they bind and the Smad proteins they activate. One is the more recently evolved branch, which includes, e.g., the TGF-betas, activins, GDF8, GDF9, GDF11, BMP3 and nodal. The other branch comprises the more distantly related proteins of the superfamily and includes, e.g., BMP2, BMP4, BMP5, BMP6, BMP7, BMP8a, BMP8b, BMP9, BMP10, GDF1, GDF5, GDF6, and GDF7. See, e.g. Hinck (2012) FEBS Letters 586:1860-1870.

TGF-beta isoforms are the founding members of the TGF-beta superfamily, of which there are 3 known isoforms in mammals designated as TGF-beta1, TGF-beta2 and TGF-beta3. Mature bioactive TGF-beta ligands function as homodimers and predominantly signal through the type I receptor ALK5 but have also been found to signal through ALK1 in endothelial cells. See, e.g., Goumans et al. (2003) Mol Cell 12(4): 817-828. TGF-beta1 is the most abundant and ubiquitously expressed isoform. TGF-beta1 is known to have an important role in wound healing, and mice expressing a constitutively active TGF-beta1 transgene develop fibrosis. See e.g., Clouthier et al., (1997) J Clin. Invest. 100(11): 2697-2713. TGF-beta1 is also involved in T cell activation and maintenance of T regulatory cells. See, e.g., Li et al., (2006) Immunity 25(3): 455-471. TGF-beta2 expression was first described in human glioblastoma cells and occurs in neurons and astroglial cells of the embryonic nervous system. TGF-beta2 is also known to suppress interleukin-2-dependent growth of T lymphocytes. TGF-beta3 was initially isolated from a human rhabdomyosarcoma cell line and since has been found in lung adenocarcinoma and kidney carcinoma cell lines. TGF-beta3 is known to be important for palate and lung morphogenesis. See, e.g., Kubiczkova et al., (2012) Journal of Translational Medicine 10:183.

Activins are members of the TGF-beta superfamily that were initially discovered as regulators of follicle-stimulating hormone secretion, but subsequently various reproductive and non-reproductive roles have been characterized. Principal activin forms A, B, and AB are homo/heterodimers of two closely related β subunits ($\beta_A\beta_A$, $\beta_B\beta_B$, and $\beta_A\beta_B$, respectively). The human genome also encodes an activin C and an activin E, which are primarily expressed in the liver, and heterodimeric forms containing $\beta_C$ or $\beta_E$ are also known. In the TGF-beta superfamily, activins are unique and multifunctional factors that can stimulate hormone production in ovarian and placental cells, support neuronal cell survival, influence cell-cycle progress positively or negatively depending on cell type, and induce mesodermal differentiation at least in amphibian embryos. See, e.g., DePaolo et al. (1991) Proc Soc Ep Biol Med. 198:500-512; Dyson et al. (1997) Curr Biol. 7:81-84; and Woodruff (1998) Biochem Pharmacol. 55:953-963. In several tissues, activin signaling is antagonized by its related heterodimer, inhibin. For example, in the regulation of follicle-stimulating hormone (FSH) secretion from the pituitary, activin promotes FSH synthesis and secretion, while inhibin reduces FSH synthesis and secretion. Other proteins that may regulate activin bioactivity and/or bind to activin include follistatin (FS), follistatin-related protein (FSRP, also known as FLRG or FSTL3), and $\alpha_2$-macroglobulin.

As described herein, agents that bind to "activin A" are agents that specifically bind to the $\beta_A$ subunit, whether in the context of an isolated PA subunit or as a dimeric complex (e.g., a $\beta_A\beta_A$ homodimer or a $\beta_A\beta_B$ heterodimer). In the case of a heterodimer complex (e.g., a $\beta_A\beta_B$ heterodimer), agents that bind to "activin A" are specific for epitopes present within the $\beta_A$ subunit, but do not bind to epitopes present within the non-$\beta_A$ subunit of the complex (e.g., the $\beta_B$ subunit of the complex). Similarly, agents disclosed herein that antagonize (inhibit) "activin A" are agents that inhibit one or more activities as mediated by a $\beta_A$ subunit, whether in the context of an isolated $\beta_A$ subunit or as a dimeric complex (e.g., a $\beta_A\beta_A$ homodimer or a $\beta_A\beta_B$ heterodimer). In the case of $\beta_A\beta_B$ heterodimers, agents that inhibit "activin A" are agents that specifically inhibit one or more activities of the $\beta_A$ subunit but do not inhibit the activity of the non-$\beta_A$ subunit of the complex (e.g., the $\beta_B$ subunit of the complex). This principle applies also to agents that bind to and/or inhibit "activin B", "activin C", and "activin E". Agents disclosed herein that antagonize "activin AB" are agents that inhibit one or more activities as mediated by the PA subunit and one or more activities as mediated by the $R_B$ subunit.

The BMPs and GDFs together form a family of cysteine-knot cytokines sharing the characteristic fold of the TGF-beta superfamily. See, e.g., Rider et al. (2010) Biochem J., 429(1):1-12. This family includes, for example, BMP2, BMP4, BMP6, BMP7, BMP2a, BMP3, BMP3b (also known as GDF10), BMP4, BMP5, BMP6, BMP7, BMP8, BMP8a, BMP8b, BMP9 (also known as GDF2), BMP10, BMP11 (also known as GDF11), BMP12 (also known as GDF7), BMP13 (also known as GDF6), BMP14 (also known as GDF5), BMP15, GDF1, GDF3 (also known as VGR2), GDF8 (also known as myostatin), GDF9, GDF15, and decapentaplegic. Besides the ability to induce bone formation, which gave the BMPs their name, the BMP/GDFs display morphogenetic activities in the development of a wide range of tissues. BMP/GDF homo- and hetero-dimers interact with combinations of type I and type II receptor dimers to produce multiple possible signaling complexes, leading to the activation of one of two competing sets of SMAD transcription factors. BMP/GDFs have highly specific and localized functions. These are regulated in a number of ways, including the developmental restriction of BMP/GDF expression and through the secretion of several proteins that bind certain TGF-beta superfamily ligands with high affinity and thereby inhibit ligand activity. Curiously, some of these endogenous antagonists resemble TGF-beta superfamily ligands themselves.

Growth and differentiation factor-8 (GDF8) is also known as myostatin. GDF8 is a negative regulator of skeletal muscle mass and is highly expressed in developing and adult skeletal muscle. The GDF8 null mutation in transgenic mice is characterized by a marked hypertrophy and hyperplasia of skeletal muscle. See, e.g., McPherron et al., Nature (1997) 387:83-90. Similar increases in skeletal muscle mass are evident in naturally occurring mutations of GDF8 in cattle and, strikingly, in humans. See, e.g., Ashmore et al. (1974) Growth, 38:501-507; Swatland and Kieffer, J. Anim. Sci. (1994) 38:752-757; McPherron and Lee, Proc. Natl. Acad. Sci. USA (1997) 94:12457-12461; Kambadur et al., Genome Res. (1997) 7:910-915; and Schuelke et al. (2004) N Engl J Med, 350:2682-8. Studies have also shown that muscle wasting associated with HIV-infection in humans is accompanied by increases in GDF8 protein expression. See, e.g., Gonzalez-Cadavid et al., PNAS (1998) 95:14938-43. In addition, GDF8 can modulate the production of muscle-specific enzymes (e.g., creatine kinase) and modulate myoblast cell proliferation. See, e.g., International Patent Application Publication No. WO 00/43781). The GDF8 propeptide can noncovalently bind to the mature GDF8 domain dimer, inactivating its biological activity. See, e.g., Miyazono et al. (1988) J. Biol. Chem., 263: 6407-6415; Wakefield et al. (1988) J. Biol. Chem., 263; 7646-7654; and Brown et al. (1990) Growth Factors, 3: 35-43. Other proteins which bind to GDF8 or structurally related proteins and inhibit their biological activity include follistatin, and potentially, follistatin-related proteins. See, e.g., Gamer et al. (1999) Dev. Biol., 208: 222-232.

GDF11, also known as BMP11, is a secreted protein that is expressed in the tail bud, limb bud, maxillary and mandibular arches, and dorsal root ganglia during mouse development. See, e.g., McPherron et al. (1999) Nat. Genet., 22: 260-264; and Nakashima et al. (1999) Mech. Dev., 80: 185-189. GDF11 plays a unique role in patterning both mesodermal and neural tissues. See, e.g., Gamer et al. (1999) Dev Biol., 208:222-32. GDF11 was shown to be a negative regulator of chondrogenesis and myogenesis in developing chick limb. See, e.g., Gamer et al. (2001) Dev Biol., 229:407-20. The expression of GDF11 in muscle also suggests its role in regulating muscle growth in a similar way to GDF8. In addition, the expression of GDF11 in brain suggests that GDF11 may also possess activities that relate to the function of the nervous system. Interestingly, GDF11 was found to inhibit neurogenesis in the olfactory epithelium. See, e.g., Wu et al. (2003) Neuron., 37:197-207. Hence, GDF11 may have in vitro and in vivo applications in the treatment of diseases such as muscle diseases and neurodegenerative diseases (e.g., amyotrophic lateral sclerosis).

BMP7, also called osteogenic protein-1 (OP-1), is well known to induce cartilage and bone formation. In addition, BMP7 regulates a wide array of physiological processes. For example, BMP7 may be the osteoinductive factor responsible for the phenomenon of epithelial osteogenesis. It is also found that BMP7 plays a role in calcium regulation and bone homeostasis. Like activin, BMP7 binds to type II receptors, ActRIIA and ActRIIB However, BMP7 and activin recruit distinct type I receptors into heteromeric receptor complexes. The major BMP7 type I receptor observed was ALK2, while activin bound exclusively to ALK4 (ActRIIB) BMP7 and activin elicited distinct biological responses and activated different SMAD pathways. See, e.g., Macias-Silva et al. (1998) J Biol Chem. 273:25628-36.

Anti-Mullerian hormone (AMH), also known as Mullerian-inhibiting substance (MIS), is a TGF-beta family glycoprotein. One AMH-associated type II receptor has been identified and is designated as AMHRII, or alternatively MISRII. AMH induces regression of the Mullerian ducts in the human male embryo. AMH is expressed in reproductive age women and does not fluctuate with cycle or pregnancy, but was found to gradually decrease as both oocyte quantity and quality decrease, suggesting AMH could serve as a biomarker for ovarian physiology. See e.g. Zec et al., (2011) Biochemia Medica 21(3): 219-30.

Activin receptor-like kinase-1 (ALK1), the product of the ACVRL1 gene known alternatively as ACVRLK1, is a type I receptor whose expression is predominantly restricted to endothelial cells. See, e.g., OMIM entry 601284. ALK1 is activated by the binding of TGF-beta family ligands such as BMP9 and BMP10, and ALK1 signaling is critical in the regulation of both developmental and pathological blood vessel formation. ALK1 expression overlaps with sites of vasculogenesis and angiogenesis in early mouse development, and ALK1 knockout mice die around embryonic day 11.5 because of severe vascular abnormalities (see e.g., Cunha and Pietras (2011) Blood 117(26):6999-7006.) ALK1 expression has also been described in other cell types such as hepatic stellate cells and chondrocytes. Additionally, ALK1 along with activin receptor-like kinase-2 (ALK2) have been found to be important for BMP9-induced osteogenic signaling in mesenchymal stem cells. See e.g., Cunha and Pietras (2011) Blood 117(26):6999-7006.

ALK2, the product of the ACVR1 gene known alternatively as ActRIA or ACVRLK2, is a type I receptor that has been shown to bind activins and BMPs. ALK2 is critical for embryogenesis as ALK2 knockout mice die soon after gastrulation. See, e.g., Mishina et al. (1999) Dev Biol. 213: 314-326 and OMIM entry 102576. Constitutively active mutations in ALK2 are associated with fibrodysplasia ossificans progressiva (FOP), a rare genetic disorder that causes fibrous tissue, including muscle, tendon and ligament, to be ossified spontaneously or when damaged. An arginine-to-histidine mutation in position 206 of ALK2 is a naturally occurring mutation associated with FOP in humans. This mutation induces BMP-specific signaling via ALK2 without the binding of ligand. See, e.g., Fukuda et al., (2009) J Biol Chem. 284(11):7149-7156 and Kaplan et al., (2011) Ann N.Y. Acad Sci. 1237: 5-10.

Activin receptor-like kinase-3 (ALK3), the product of the BMPR1A gene known alternatively as ACVRLK3, is a type I receptor mediating effects of multiple ligands in the BMP family. Unlike several type I receptors with ubiquitous tissue expression, ALK3 displays a restricted pattern of expression consistent with more specialized functionality. See, e.g., ten Dijke (1993) Oncogene, 8: 2879-2887 and OMIM entry 601299. ALK3 is generally recognized as a high-affinity receptor for BMP2, BMP4, BMP7 and other members of the BMP family. BMP2 and BMP7 are potent stimulators of osteoblastic differentiation, and are now used clinically to induce bone formation in spine fusions and certain non-union fractures. ALK3 is regarded as a key receptor in mediating BMP2 and BMP4 signaling in osteoblasts. See, e.g., Lavery et al. (2008) J. Biol. Chem. 283: 20948-20958. A homozygous ALK3 knockout mouse dies early in embryogenesis (~day 9.5), however, adult mice carrying a conditional disruption of ALK3 in osteoblasts have been recently reported to exhibit increased bone mass, although the newly formed bone showed evidence of disorganization. See, e.g., Kamiya (2008) J. Bone Miner. Res., 23:2007-2017; and Kamiya (2008) Development 135: 3801-3811. This finding is in startling contrast to the effectiveness of BMP2 and BMP7 (ligands for ALK3) as bone building agents in clinical use.

Activin receptor-like kinase-4 (ALK4), the product of the ACVR1B gene alternatively known as ACVRLK4, is a type I receptor that transduces signaling for a number of TGF-beta family ligands including activins, nodal and GDFs. ALK4 mutations are associated with pancreatic cancer, and expression of dominant negative truncated ALK4 isoforms are highly expressed in human pituitary tumors. See, e.g., Tsuchida et al., (2008) Endocrine Journal 55(1):11-21 and OMIM entry 601300.

Activin receptor-like kinase-5 (ALK5), the product of the TGFBR1 gene, is widely expressed in most cell types. Several TGF-beta superfamily ligands, including TGF-betas, activin, and GDF-8, signal via ALK5 and activate downstream Smad 2 and Smad 3. Mice deficient in ALK5 exhibit severe defects in the vascular development of the yolk sac and placenta, lack circulating red blood cells, and die mid-gestation. It was found that these embryos had normal hematopoietic potential, but enhanced proliferation and improper migration of endothelial cells. Thus, ALK5-dependent signaling is important for angiogenesis, but not for the development of hematopoietic progenitor cells and functional hematopoiesis. See, e.g. Larsson et al., (2001) The EMBO Journal, 20(7): 1663-1673 and OMIM entry 190181. In endothelial cells, ALK5 acts cooperatively and opposite to ALK1 signaling. ALK5 inhibits cell migration and proliferation, notably the opposite effect of ALK1. See, e.g., Goumans et al. (2003) Mol Cell 12(4): 817-828. Additionally, ALK5 is believed to negatively regulate muscle growth. Knockdown of ALK5 in the muscle a mouse model of muscular dystrophy was found to decrease fibrosis and increase expression of genes associate with muscle growth. See, e.g. Kemaladewi et al., (2014) Mol Ther Nucleic Acids 3, e156.

Activin receptor-like kinase-6 (ALK6) is the product of the BMPR1B gene, whose deficiency is associated with chrondodysplasia and limb defects in both humans and mice. See, e.g., Demirhan et al., (2005) J Med Genet. 42:314-317. ALK6 is widely expressed throughout the developing skeleton, and is required for chondrogenesis in mice. See, e.g., Yi et al., (2000) Development 127:621-630 and OMIM entry 603248.

Activin receptor-like kinase-7 (ALK7) is the product of the ACVR1C gene. ALK7 null mice are viable, fertile, and display no skeletal or limb malformations. GDF3 signaling through ALK7 appears to play a role in insulin sensitivity and obesity. This is supported by results that ALK7 null mice show reduced fat accumulation and resistance to diet-induced obesity. See, e.g., Andersson et al., (2008) PNAS 105(20): 7252-7256. ALK7-mediated Nodal signaling has been implicated to have both tumor promoting and tumor suppressing effects in a variety of different cancer cell lines. See, e.g., De Silva et al., (2012) Frontiers in Endocrinology 3:59 and OMIM entry 608981.

As used herein the term "ActRII" refers to the family of type II activin receptors. This family includes both the activin receptor type IIA (ActRIIA), encoded by the ACVR2A gene, and the activin receptor type IIB (ActRIIB), encoded by the ACVR2B gene. ActRII receptors are TGF-beta superfamily type II receptors that bind a variety of TGF-beta superfamily ligands including activins, GDF8 (myostatin), GDF11, and a subset of BMPs, notably BMP6 and BMP7. ActRII receptors are implicated in a variety of biological disorders including muscle and neuromuscular disorders (e.g., muscular dystrophy, amyotrophic lateral sclerosis (ALS), and muscle atrophy), undesired bone/cartilage growth, adipose tissue disorders (e.g., obesity), metabolic disorders (e.g., type 2 diabetes), and neurodegenerative disorders. See, e.g., Tsuchida et al., (2008) Endocrine Journal 55(1):11-21, Knopf et al., U.S. Pat. No. 8,252,900, and OMIM entries 102581 and 602730.

Transforming growth factor beta receptor II (TGFBRII), encoded by the TGFBR2 gene, is a type II receptor that is known to bind TGF-beta ligands and activate downstream Smad 2 and Smad 3 effectors. See, e.g., Hinck (2012) FEBS Letters 586: 1860-1870 and OMIM entry 190182. TGF-beta signaling through TGFBRII is critical in T-cell proliferation, maintenance of T regulatory cells and proliferation of precartilaginous stem cells. See, e.g., Li et al., (2006) Immunity 25(3): 455-471 and Cheng et al., Int. J. Mol. Sci. 2014, 15, 12665-12676.

Bone morphogenetic protein receptor II (BMPRII), encoded by the BMPR2 gene, is a type II receptor that is known to bind BMP ligands including BMP7 and BMP4. Efficient ligand binding to BMPRII is dependent on the presence of the appropriate TGFBR type I receptors. See, e.g., Rosenzweig et al., (1995) PNAS 92:7632-7636. Mutations in BMPRII are associated with pulmonary hypertension in humans. See OMIM entry 600799.

Müllerian-inhibiting substance receptor II (MISRII), the product of the AMHR2 gene known alternatively as anti-Mullerian hormone type II receptor, is a type II TGF-beta superfamily receptor. MISRII binds the MIS ligand, but requires the presence of an appropriate type I receptor, such as ALK3 or ALK6, for signal transduction. See, e.g., Hinck (2012) FEBS Letters 586:1860-1870 and OMIM entry 600956. MISRII is involved in sex differentiation in humans and is required for Mullerian regression in the human male. AMH is expressed in reproductive-age women and does not fluctuate with cycle or pregnancy, but was found to gradual decrease as both oocyte quantity and quality decrease, suggesting AMH could serve as a biomarker of ovarian physiology. See, e.g., Zec et al., (2011) Biochemia Medica 21(3): 219-30 and OMIM entry 600956.

In certain aspects, the present disclosure relates to the use of single-arm heteromultimer complexes comprising an extracellular domain of a TGFβ superfamily type I receptor polypeptide (e.g., ALK1, ALK2, ALK3, ALK4, ALK5, ALK6, and ALK7) or an extracellular domain of a TGFβ superfamily type II receptor polypeptide (e.g., ActRIIA, ActRIIB, TGFBRII, BMPRII, and MISRII), preferably soluble heteromultimer complexes, to antagonize intracellular signaling transduction (e.g., Smad 2/3 and/or Smad 1/5/8 signaling) initiated by one or more TGFβ superfamily ligands (e.g., activin A, activin B, activin C, activin E, activin AB, activin AC, activin AE, activin BC, activin BE, Nodal, GDF8, GDF11, BMP6 and/or BMP7). As described herein, such antagonist single-arm heteromultimer complexes may be useful for the treatment or prevention of various TGF-beta associated conditions, including without limitation diseases and disorders associated with, for example, cancer, muscle, bone, fat, red blood cells, metabolism, fibrosis and other tissues that are affected by one or more ligands of the TGF-beta superfamily.

In particular, the data of the present disclosure demonstrates that single-arm heteromultimer complexes comprising an extracellular domain of a TGFβ superfamily type I receptor polypeptide or an extracellular domain of a TGFβ superfamily type II receptor polypeptide have different ligand selectivity profiles in comparison to their corresponding homomultimer complexes.

The terms used in this specification generally have their ordinary meanings in the art, within the context of this disclosure and in the specific context where each term is used. Certain terms are discussed below or elsewhere in the specification to provide additional guidance to the practitioner in describing the compositions and methods of the disclosure and how to make and use them. The scope or meaning of any use of a term will be apparent from the specific context in which it is used.

The terms "heteromer" or "heteromultimer" is a complex comprising at least a first polypeptide and a second polypeptide, wherein the second polypeptide differs in amino acid sequence from the first polypeptide by at least one amino acid residue. The heteromer can comprise a "heterodimer" formed by the first and second polypeptide or can form higher order structures where polypeptides in addition to the first and second polypeptide are present. Exemplary structures for the heteromultimer include heterodimers, heterotrimers, heterotetramers and further oligomeric structures. Heterodimers are designated herein as X:Y or equivalently as X-Y, where X represents a first polypeptide chain and Y represents a second polypeptide chain. Higher-order heteromers and oligomeric structures are designated herein in a corresponding manner. In certain embodiments a heteromultimer is recombinant (e.g., one or more polypeptide component may be a recombinant protein), isolated and/or purified.

"Homologous," in all its grammatical forms and spelling variations, refers to the relationship between two proteins that possess a "common evolutionary origin," including proteins from superfamilies in the same species of organism, as well as homologous proteins from different species of organism. Such proteins (and their encoding nucleic acids) have sequence homology, as reflected by their sequence similarity, whether in terms of percent identity or by the presence of specific residues or motifs and conserved positions. However, in common usage and in the instant application, the term "homologous," when modified with an adverb such as "highly," may refer to sequence similarity and may or may not relate to a common evolutionary origin.

The term "sequence similarity," in all its grammatical forms, refers to the degree of identity or correspondence between nucleic acid or amino acid sequences that may or may not share a common evolutionary origin.

"Percent (%) sequence identity" with respect to a reference polypeptide (or nucleotide) sequence is defined as the percentage of amino acid residues (or nucleic acids) in a candidate sequence that are identical to the amino acid residues (or nucleic acids) in the reference polypeptide (nucleotide) sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid (nucleic acid) sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX operating system, including digital UNIX V4.0D. All sequence comparison parameters are set by the ALIGN-2 program and do not vary.

As used herein "does not substantially bind to X" is intended to mean that an agent has a $K_D$ that is greater than about $10^{-7}$, $10^{-6}$, $10^{-5}$, $10^{-4}$ or greater (e.g., no detectable binding by the assay used to determine the $K_D$) for "X".

2. Heteromultimer Complexes Comprising Single-Arm TGFβ Superfamily Receptor Polypeptides In certain aspects, the disclosure concerns heteromultimer protein complexes comprising one or more single-arm TGF-beta superfamily type I or type II receptor polypeptides. In certain embodiments, the polypeptides disclosed herein may form protein complexes comprising a first polypeptide covalently or non-covalently associated with a second polypeptide, wherein the first polypeptide comprises the amino acid sequence of a type I or type II receptor polypeptide and the amino acid sequence of a first member of an interaction pair; and the second polypeptide comprises the amino acid sequence of a second member of the interaction pair, and wherein the second polypeptide does not comprise a type I or type II receptor polypeptide. The interaction pair may be any two polypeptide sequences that interact to form a complex, particularly a heterodimeric complex although operative embodiments may also employ an interaction pair that forms a homodimeric sequence. As described herein, one member of the interaction pair may be fused to a type I or type II receptor polypeptide, such as a polypeptide comprising an amino acid sequence that is at least 80%, 85%, 90%, 95%, 97%, 98%, 99% or 100% identical to the sequence of any of SEQ ID NOs: 1, 2, 3, 4, 5, 6, 9, 10, 11, 14, 15, 18, 19, 22, 23, 26, 27, 30, 31, 34, 35, 38, 39, 42, 43, 46, 47, 50, 51, 67, 68, 71, 72, 75, 76, 79, 80, 83, 84, 87, 88, 91, 92, 301, 302, 305, 306, 309, 310, and 313. Preferably, the interaction pair is selected to confer an improved serum half-life, or to act as an adapter on to which another moiety, such as a polyethylene glycol moiety, is attached to provide an improved serum half-life relative to the monomeric form of the type I or type II receptor polypeptide.

As shown herein, monomeric (single-arm) forms of TGF-beta superfamily type I or type II receptors can exhibit substantially altered ligand-binding selectivity compared to their corresponding homodimeric forms, but the monomeric forms tend to have a short serum residence time (half-life), which is undesirable in the therapeutic setting. A common mechanism for improving serum half-life is to express a polypeptide as a homodimeric fusion protein with a constant domain portion (e.g., an Fc portion) of an IgG. However, TGF-beta superfamily receptor polypeptides expressed as homodimeric proteins (e.g., in an Fc fusion construct) may not exhibit the same activity profile as the monomeric form. As demonstrated herein, the problem may be solved by fusing the monomeric form to a half-life extending moiety, and surprisingly, this can be readily achieved by expressing such proteins as an asymmetric heterodimeric fusion protein in which one member of an interaction pair is fused to a TGF-beta superfamily receptor polypeptide and another member of the interaction pair is fused to either no moiety or to a heterologous moiety, resulting in a novel ligand-binding profile coupled with an improvement in serum half-life conferred by the interaction pair.

In certain aspects, the present disclosure relates to single-arm heteromultimer complexes comprising at least one TGF-beta superfamily type I receptor polypeptide (e.g., ALK1, ALK2, ALK3, ALK4, ALK5, ALK6, and ALK7 as well as SEQ ID NOs: 14, 15, 18, 19, 22, 23, 26, 27, 30, 31, 34, 35, 38, 39, 83, 84, 87, 88, 91, 92, 301, 302, 305, 306, 309, 310, 313) or at least one TGF-beta superfamily type II receptor polypeptide (e.g., ActRIIA, ActRIIB, TGFBRII, BMPRII, and MISRII as well SEQ ID NOs: 1, 2, 3, 4, 5, 6, 9, 10, 11, 42, 43, 46, 47, 50, 51, 67, 68, 71, 72, 75, 76, 79, and 80), which are generally referred to herein as "single-arm heteromultimer complexes of the disclosure" or "TGF-beta superfamily receptor single-arm heteromultimer complexes". Preferably, single-arm heteromultimer complexes of the disclosure are soluble, e.g., a single-arm heteromultimer complex comprises a soluble portion of at least one TGFβ superfamily type I receptor polypeptide or a soluble portion of at least one TGFβ superfamily type II receptor polypeptide. In general, the extracellular domains of TGFβ superfamily type I and type II receptors correspond to a soluble portion of the type I or type II receptor. Therefore, in some embodiments, single-arm heteromultimer complexes of the disclosure comprise an extracellular domain of a TGFβ superfamily type I receptor polypeptide (e.g., one or more ALK1, ALK2, ALK3, ALK4, ALK5, ALK6, and/or ALK7 receptor extracellular domains) or an extracellular domain of a TGFβ superfamily type II receptor polypeptide (e.g., one or more ActRIIA, ActRIIB, TGFBRII, BMPRII, and/or MISRII receptor extracellular domains). Exemplary extracellular domains of ALK1, ALK2, ALK3, ALK4, ALK5, ALK6, ALK7, ActRIIA, ActRIIB, TGFBRII, BMPRII, and MISRII are disclosed herein and such sequences, as well as fragments, functional variants, and modified forms thereof, may be used in accordance with the inventions of the present disclosure (e.g., single-arm heteromultimer complexes compositions and uses thereof).

A defining structural motif known as a three-finger toxin fold is important for ligand binding by type I and type II receptors and is formed by 10, 12, or 14 conserved cysteine residues located at varying positions within the extracellular domain of each monomeric receptor. See, e.g., Greenwald et al. (1999) Nat Struct Biol 6:18-22; Hinck (2012) FEBS Lett 586:1860-1870. Any of the heteromeric complexes described herein may comprise such domain of a type I or type II receptor of the TGF-beta superfamily. The core ligand-binding domains of TGFβ superfamily receptors, as demarcated by the outermost of these conserved cysteines, correspond to positions 29-109 of SEQ ID NO: 1 (ActRIIB precursor); positions 30-110 of SEQ ID NO: 9 (ActRIIA precursor); positions 34-95 of SEQ ID NO: 14 (ALK1 precursor); positions 35-99 of SEQ ID NO: 18 (ALK2 precursor); positions 61-130 of SEQ ID NO: 22 (ALK3 precursor); positions 34-101 of SEQ ID NOs: 26 and 83 (ALK4 precursors); positions 36-106 of SEQ ID NOs: 30 and 87 (ALK 5 precursors); positions 32-102 of SEQ ID NO: 34 (ALK6 isoform B precursor); positions 28-92 of SEQ ID NOs: 38, 305, and 309 (ALK7 precursors); positions 51-143 of SEQ ID NO: 42 (TGFBRII isoform B precursor); positions 34-123 of SEQ ID NO: 46 and 71 (BMPRII precursors); positions 24-116 of SEQ ID NO: 50, 75, and 79 (MISRII precursors); positions 44-168 of SEQ ID NO: 67 (TGFBRII isoform A precursor); and positions 62-132 of SEQ ID NO: 91 (ALK6 isoform A precursor). The structurally less-ordered amino acids flanking these cysteine-demarcated core sequences can be truncated by 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, or 37 residues on either terminus without necessarily altering ligand binding. Exemplary extracellular domains for N-terminal and/or C-terminal truncation include SEQ ID NOs: 2, 3, 5, 6, 10, 11 15, 19, 23, 27, 31, 35, 39, 43, 47, 51, 68, 72, 76, 80, 84, 88, 92, 302, 306, 310, and 313.

In other preferred embodiments, single-arm heteromultimer complexes of the disclosure bind to and inhibit (antagonize) activity of one or more TGF-beta superfamily ligands including, but not limited to, BMP2, BMP2/7, BMP3, BMP4, BMP4/7, BMP5, BMP6, BMP7, BMP8a, BMP8b, BMP9, BMP10, GDF3, GDF5, GDF6/BMP13, GDF7, GDF8, GDF9b/BMP15, GDF11/BMP11, GDF15/MIC1, TGF-β1, TGF-β2, TGF-β3, activin A, activin B, activin C, activin E, activin AB, activin AC, activin AE, activin BC, activin BE, nodal, glial cell-derived neurotrophic factor (GDNF), neurturin, artemin, persephin, MIS, and Lefty. In particular, single-arm heteromultimer complexes of the disclosure may be used to antagonize intracellular signaling transduction (e.g., Smad 2/3 and/or Smad 1/5/8 signaling) initiated by one or more TGFβ superfamily ligands. As described herein, such antagonist heteromultimer complexes may be for the treatment or prevention of various TGF-beta associated conditions, including without limitation diseases and disorders associated with, for example, cancer, muscle, bone, fat, red blood cells, metabolism, fibrosis and other tissues that are affected by one or more ligands of the TGF-beta superfamily. In some embodiments, single-arm heteromultimer complexes of the disclosure have different ligand-binding profiles in comparison to their corresponding homomultimer complex (e.g., an ActRIIB-Fc:Fc heterodimer vs. a corresponding ActRIIB-Fc:ActRIIB-Fc or Fc:Fc homodimer). As described herein, single-arm heteromultimer complexes of the disclosure include, e.g., heterodimers, heterotrimers, heterotetramers and further oligomeric structures based on a single-arm unitary complex. In certain preferred embodiments, single-arm heteromultimer complexes of the disclosure are heterodimers.

As used herein, the term "ActRIIB" refers to a family of activin receptor type IIB (ActRIIB) proteins from any species and variants derived from such ActRIIB proteins by mutagenesis or other modification. Reference to ActRIIB herein is understood to be a reference to any one of the currently identified forms. Members of the ActRIIB family are generally transmembrane proteins, composed of a ligand-binding extracellular domain comprising a cysteine-rich region, a transmembrane domain, and a cytoplasmic domain with predicted serine/threonine kinase activity.

The term "ActRIIB polypeptide" includes polypeptides comprising any naturally occurring polypeptide of an ActRIIB family member as well as any variants thereof (including mutants, fragments, fusions, and peptidomimetic forms) that retain a useful activity. Examples of such variant ActRIIB polypeptides are provided throughout the present disclosure as well as in International Patent Application Publication No. WO 2006/012627, which is incorporated herein by reference in its entirety. Numbering of amino acids for all ActRIIB-related polypeptides described herein is based on the numbering of the human ActRIIB precursor protein sequence provided below (SEQ ID NO: 1), unless specifically designated otherwise.

The human ActRIIB precursor protein sequence is as follows:

(SEQ ID NO: 1)
```
1   MTAPWVALAL LWGSLCAGSG RGEAETRECI YYNANWELER TNQSGLERCE
51  GEQDKRLHCY ASWRNSSGTI ELVKKGCWLD DFNCYDRQEC VATEENPQVY
101 FCCCEGNFCN ERFTHLPEAG GPEVTYEPPP TAPTLLTVLA YSLLPIGGLS
151 LIVLLAFWMY RHRKPPYGHV DIHEDPGPPP PSPLVGLKPL QLLEIKARGR
201 FGCVWKAQLM NDFVAVKIFP LQDKQSWQSE REIFSTPGMK HENLLQFIAA
251 EKRGSNLEVE LWLITAFHDK GSLTDYLKGN IITWNELCHV AETMSRGLSY
301 LHEDVPWCRG EGHKPSIAHR DFKSKNVLLK SDLTAVLADF GLAVRFEPGK
351 PPGDTHGQVG TRRYMAPEVL EGAINFQRDA FLRIDMYAMG LVLWELVSRC
401 KAADGPVDEY MLPFEEEIGQ HPSLEELQEV VVHKKMRPTI KDHWLKHPGL
451 AQLCVTIEEC WDHDAEARLS AGCVEERVSL IRRSVNGTTS DCLVSLVTSV
501 TNVDLPPKES SI
```

The signal peptide is indicated with a single underline; the extracellular domain is indicated in bold font; and the potential, endogenous N-linked glycosylation sites are indicated with a double underline.

The processed extracellular ActRIIB polypeptide sequence is as follows:

(SEQ ID NO: 2)
```
GRGEAETRECIYYNANWELERTNQSGLERCEGEQDKRLHCYASWRNSSGTI
ELVKKGCWLDDFNCYDRQECVATEENPQVYFCCCEGNFCNERFTHLPEAGG
PEVTYEPPPTAPT.
```

In some embodiments, the protein may be produced with an "SGR . . . " sequence at the N-terminus. The C-terminal "tail" of the extracellular domain is indicated by a single underline. The sequence with the "tail" deleted (a 415 sequence) is as follows:

(SEQ ID NO: 3)
```
GRGEAETRECIYYNANWELERTNQSGLERCEGEQDKRLHCYASWRNSSGTI
ELVKKGCWLDDFNCYDRQECVATEENPQVYFCCCEGNFCNERFTHLPEA.
```

A form of ActRIIB with an alanine at position 64 of SEQ ID NO: 1 (A64) is also reported in the literature See, e.g., Hilden et al. (1994) Blood, 83(8): 2163-2170. Applicants have ascertained that an ActRIIB-Fc fusion protein comprising an extracellular domain of ActRIIB with the A64 substitution has a relatively low affinity for activin and GDF11. By contrast, the same ActRIIB-Fc fusion protein with an arginine at position 64 (R64) has an affinity for activin and GDF11 in the low nanomolar to high picomolar range. Therefore, sequences with an R64 are used as the "wild-type" reference sequence for human ActRIIB in this disclosure.

The form of ActRIIB with an alanine at position 64 is as follows:

(SEQ ID NO: 4)
```
1   MTAPWVALAL LWGSLCAGSG RGEAETRECI YYNANWELER TNQSGLERCE
51  GEQDKRLHCY ASWANSSGTI ELVKKGCWLD DFNCYDRQEC VATEENPQVY
101 FCCCEGNFCN ERFTHLPEAG GPEVTYEPPP TAPTLLTVLA YSLLPIGGLS
151 LIVLLAFWMY RHRKPPYGHV DIHEDPGPPP PSPLVGLKPL QLLEIKARGR
201 FGCVWKAQLM NDFVAVKIFP LQDKQSWQSE REIFSTPGMK HENLLQFIAA
251 EKRGSNLEVE LWLITAFHDK GSLTDYLKGN IITWNELCHV AETMSRGLSY
301 LHEDVPWCRG EGHKPSIAHR DFKSKNVLLK SDLTAVLADF GLAVRFEPGK
351 PPGDTHGQVG TRRYMAPEVL EGAINFQRDA FLRIDMYAMG LVLWELVSRC
401 KAADGPVDEY MLPFEEEIGQ HPSLEELQEV VVHKKMRPTI KDHWLKHPGL
451 AQLCVTIEEC WDHDAEARLS AGCVEERVSL IRRSVNGTTS DCLVSLVTSV
501 TNVDLPPKES SI
```

The signal peptide is indicated by single underline and the extracellular domain is indicated by bold font.

The processed extracellular ActRIIB polypeptide sequence of the alternative A64 form is as follows:

(SEQ ID NO: 5)
GRGEAETRECIYYNANWELERTNQSGLERCEGEQDKRLHCYASWANSSGTI

ELVKKGCWLDDFNCYDRQECVATEENPQVYFCCCEGNFCNERFTHLPEAGG

PEVTYEPPPTAPT

In some embodiments, the protein may be produced with an "SGR . . . " sequence at the N-terminus. The C-terminal "tail" of the extracellular domain is indicated by single underline. The sequence with the "tail" deleted (a Δ15 sequence) is as follows:

(SEQ ID NO: 6)
GRGEAETRECIYYNANWELERTNQSGLERCEGEQDKRLHCYASWANSSGTI

ELVKKGCWLDDFNCYDRQECVATEENPQVYFCCCEGNFCNERFTHLPEA

A nucleic acid sequence encoding the human ActRIIB precursor protein is shown below (SEQ ID NO: 7), consisting of nucleotides 25-1560 of Genbank Reference Sequence NM_001106.3, which encode amino acids 1-513 of the ActRIIB precursor. The sequence as shown provides an arginine at position 64 and may be modified to provide an alanine instead. The signal sequence is underlined.

(SEQ ID NO: 7)
```
1    ATGACGGCGC CCTGGGTGGC CCTCGCCCTC CTCTGGGGAT CGCTGTGCGC
51   CGGCTCTGGG CGTGGGGAGG CTGAGACACG GGAGTGCATC TACTACAACG
101  CCAACTGGGA GCTGGAGCGC ACCAACCAGA GCGGCCTGGA GCGCTGCGAA
151  GGCGAGCAGG ACAAGCGGCT GCACTGCTAC GCCTCCTGGC GCAACAGCTC
201  TGGCACCATC GAGCTCGTGA AGAAGGGCTG CTGGCTAGAT GACTTCAACT
251  GCTACGATAG GCAGGAGTGT GTGGCCACTG AGGAGAACCC CCAGGTGTAC
301  TTCTGCTGCT GTGAAGGCAA CTTCTGCAAC GAACGCTTCA CTCATTTGCC
351  AGAGGCTGGG GGCCCGGAAG TCACGTACGA GCCACCCCCG ACAGCCCCCA
401  CCCTGCTCAC GGTGCTGGCC TACTCACTGC TGCCCATCGG GGGCCTTTCC
451  CTCATCGTCC TGCTGGCCTT TTGGATGTAC CGGCATCGCA AGCCCCCCTA
501  CGGTCATGTG GACATCCATG AGGACCCTGG GCCTCCACCA CCATCCCCTC
551  TGGTGGGCCT GAAGCCACTG CAGCTGCTGG AGATCAAGGC TCGGGGGCGC
601  TTTGGCTGTG TCTGGAAGGC CCAGCTCATG AATGACTTTG TAGCTGTCAA
651  GATCTTCCCA CTCCAGGACA AGCAGTCGTG GCAGAGTGAA CGGGAGATCT
701  TCAGCACACC TGGCATGAAG CACGAGAACC TGCTACAGTT CATTGCTGCC
751  GAGAAGCGAG GCTCCAACCT CGAAGTAGAG CTGTGGCTCA TCACGGCCTT
801  CCATGACAAG GGCTCCCTCA CGGATTACCT CAAGGGGAAC ATCATCACAT
851  GGAACGAACT GTGTCATGTA GCAGAGACGA TGTCACGAGG CCTCTCATAC
901  CTGCATGAGG ATGTGCCCTG GTGCCGTGGC GAGGGCCACA AGCCGTCTAT
951  TGCCCACAGG GACTTTAAAA GTAAGAATGT ATTGCTGAAG AGCGACCTCA
1001 CAGCCGTGCT GGCTGACTTT GGCTTGGCTG TTCGATTTGA GCCAGGGAAA
1051 CCTCCAGGGG ACACCCACGG ACAGGTAGGC ACGAGACGGT ACATGGCTCC
1101 TGAGGTGCTC GAGGGAGCCA TCAACTTCCA GAGAGATGCC TTCCTGCGCA
1151 TTGACATGTA TGCCATGGGG TTGGTGCTGT GGGAGCTTGT GTCTCGCTGC
1201 AAGGCTGCAG ACGGACCCGT GGATGAGTAC ATGCTGCCCT TTGAGGAAGA
1251 GATTGGCCAG CACCCTTCGT TGGAGGAGCT GCAGGAGGTG GTGGTGCACA
1301 AGAAGATGAG GCCCACCATT AAAGATCACT GGTTGAAACA CCCGGGCCTG
1351 GCCCAGCTTT GTGTGACCAT CGAGGAGTGC TGGGACCATG ATGCAGAGGC
1401 TCGCTTGTCC GCGGGCTGTG TGGAGGAGCG GGTGTCCCTG ATTCGGAGGT
```

-continued

```
1451 CGGTCAACGG CACTACCTCG GACTGTCTCG TTTCCCTGGT GACCTCTGTC

1501 ACCAATGTGG ACCTGCCCCC TAAAGAGTCA AGCATC
```

A nucleic acid sequence encoding processed extracellular human ActRIIB polypeptide is as follows (SEQ ID NO: 8). The sequence as shown provides an arginine at position 64, and may be modified to provide an alanine instead.

```
                                          (SEQ ID NO: 8)
  1 GGGCGTGGGG AGGCTGAGAC ACGGGAGTGC ATCTACTACA ACGCCAACTG

 51 GGAGCTGGAG CGCACCAACC AGAGCGGCCT GGAGCGCTGC GAAGGCGAGC

101 AGGACAAGCG GCTGCACTGC TACGCCTCCT GGCGCAACAG CTCTGGCACC

151 ATCGAGCTCG TGAAGAAGGG CTGCTGGCTA GATGACTTCA ACTGCTACGA

201 TAGGCAGGAG TGTGTGGCCA CTGAGGAGAA CCCCCAGGTG TACTTCTGCT

251 GCTGTGAAGG CAACTTCTGC AACGAACGCT TCACTCATTT GCCAGAGGCT

301 GGGGGCCCGG AAGTCACGTA CGAGCCACCC CCGACAGCCC CCACC
```

Figure 4:
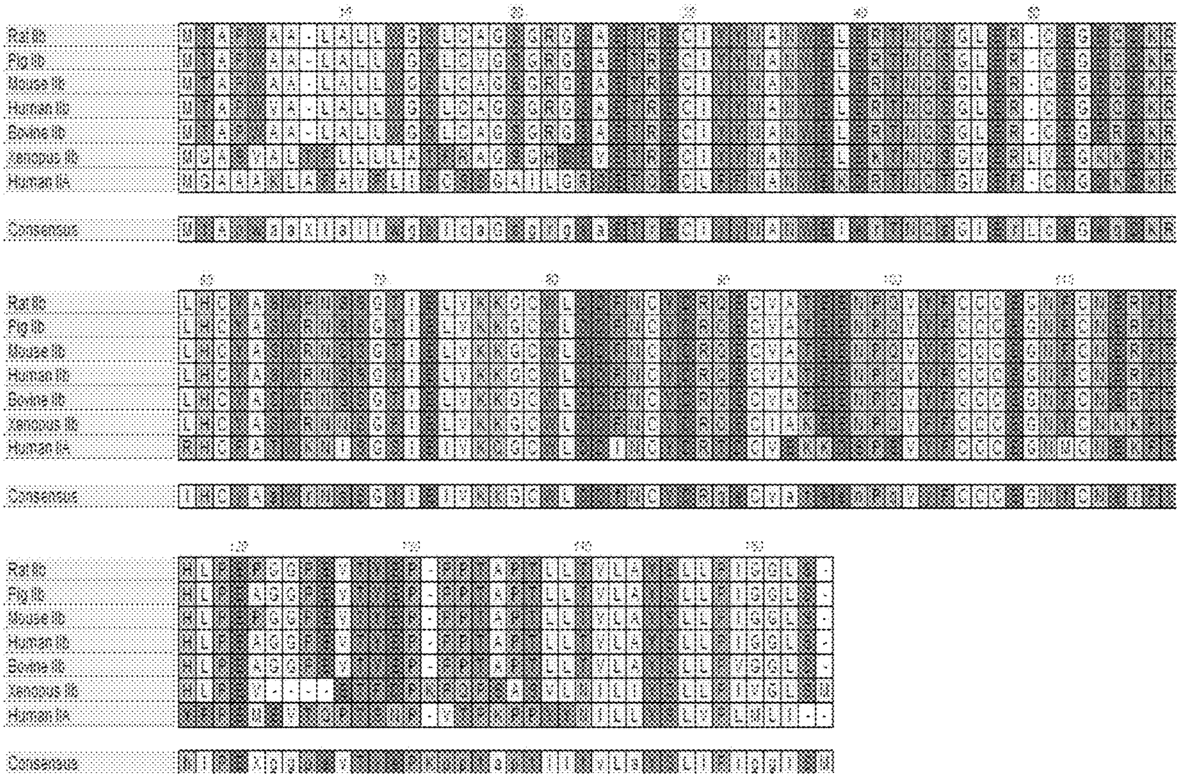
FIG. 4 shows a multiple sequence alignment of various vertebrate ActRIIB precursor proteins without their intracellular domains (SEQ ID NOs: 501, 502, 503, 504, 505, and 506, respectively) human ActRIIA precursor protein without its intracellular domain (SEQ ID NO: 507), and a consensus ActRII precursor protein (SEQ ID NO: 508).

An alignment of the amino acid sequences of human ActRIIB soluble extracellular domain and human ActRIIA soluble extracellular domain are illustrated in FIG. 3. This alignment indicates amino acid residues within both receptors that are believed to directly contact ActRII ligands. FIG. 4 depicts a multiple-sequence alignment of various vertebrate ActRIIB proteins and human ActRIIA. From these alignments is it possible to predict key amino acid positions within the ligand-binding domain that are important for normal ActRII-ligand binding activities as well as to predict amino acid positions that are likely to be tolerant to substitution without significantly altering normal ActRII-ligand binding activities. ActRII proteins have been characterized in the art in terms of structural and functional characteristics, particularly with respect to ligand binding. See, e.g., Attisano et al. (1992) Cell 68(1):97-108; Greenwald et al. (1999) Nature Structural Biology 6(1): 18-22; Allendorph et al. (2006) PNAS 103(20: 7643-7648; Thompson et al. (2003) The EMBO Journal 22(7): 1555-1566; as well as U.S. Pat. Nos. 7,709,605, 7,612,041, and 7,842,663.

For example, Attisano et al. showed that a deletion of the proline knot at the C-terminus of the extracellular domain of ActRIIB reduced the affinity of the receptor for activin. An ActRIIB-Fc fusion protein containing amino acids 20-119 of present SEQ ID NO: 1, "ActRIIB(20-119)-Fc", has reduced binding to GDF11 and activin relative to an ActRIIB(20-134)-Fc, which includes the proline knot region and the complete juxtamembrane domain (see, e.g., U.S. Pat. No. 7,842,663). However, an ActRIIB(20-129)-Fc protein retains similar but somewhat reduced activity relative to the wild-type, even though the proline knot region is disrupted. Thus, ActRIIB extracellular domains that stop at amino acid 134, 133, 132, 131, 130 and 129 (with respect to SEQ ID NO: 1) are all expected to be active, but constructs stopping at 134 or 133 may be most active. Similarly, mutations at any of residues 129-134 (with respect to SEQ ID NO: 1) are not expected to alter ligand-binding affinity by large margins. In support of this, it is known in the art that mutations of P129 and P130 (with respect to SEQ ID NO: 1) do not substantially decrease ligand binding. Therefore, an ActRIIB polypeptide of the present disclosure may end as early as amino acid 109 (the final cysteine), however, forms ending at or between 109 and 119 (e.g., 109, 110, 111, 112, 113, 114, 115, 116, 117, 118, or 119) are expected to have reduced ligand binding. Amino acid 119 (with respect to present SEQ ID NO:1) is poorly conserved and so is readily altered or truncated. ActRIIB polypeptides and ActRIIB-based GDF traps ending at 128 (with respect to SEQ ID NO: 1) or later should retain ligand-binding activity. ActRIIB polypeptides and ActRIIB-based GDF traps ending at or between 119 and 127 (e.g., 119, 120, 121, 122, 123, 124, 125, 126, or 127), with respect to SEQ ID NO: 1, will have an intermediate binding ability. Any of these forms may be desirable to use, depending on the clinical or experimental setting.

At the N-terminus of ActRIIB, it is expected that a protein beginning at amino acid 29 or before (with respect to SEQ ID NO: 1) will retain ligand-binding activity. Amino acid 29 represents the initial cysteine. An alanine-to-asparagine mutation at position 24 (with respect to SEQ ID NO: 1) introduces an N-linked glycosylation sequence without substantially affecting ligand binding. See, e.g., U.S. Pat. No. 7,842,663. This confirms that mutations in the region between the signal cleavage peptide and the cysteine cross-linked region, corresponding to amino acids 20-29, are well tolerated. In particular, ActRIIB polypeptides and ActRIIB-based GDF traps beginning at position 20, 21, 22, 23, and 24 (with respect to SEQ ID NO: 1) should retain general ligand-biding activity, and ActRIIB polypeptides and ActRIIB-based GDF traps beginning at positions 25, 26, 27, 28, and 29 (with respect to SEQ ID NO: 1) are also expected to retain ligand-biding activity. Data shown in, e.g., U.S. Pat. No. 7,842,663 demonstrates that, surprisingly, an ActRIIB construct beginning at 22, 23, 24, or 25 will have the most activity.

Taken together, an active portion (e.g., ligand-binding portion) of ActRIIB comprises amino acids 29-109 of SEQ ID NO: 1. Therefore ActRIIB polypeptides of the present disclosure may, for example, comprise an amino acid sequence that is at least 80%, 85%, 90%, 95%, 96%, 97%, 98%, 99%, or 100% identical to a portion of ActRIIB beginning at a residue corresponding to amino acids 20-29 (e.g., beginning at amino acid 20, 21, 22, 23, 24, 25, 26, 27, 28, or 29) of SEQ ID NO: 1 and ending at a position corresponding to amino acids 109-134 (e.g., ending at amino acid 109, 110, 111, 112, 113, 114, 115, 116, 117, 118, 119, 120, 121, 122, 123, 124, 125, 126, 127, 128, 129, 130, 131, 132, 133, or 134) of SEQ ID NO: 1. Other examples include polypeptides that begin at a position from 20-29 (e.g., position 20, 21, 22, 23, 24, 25, 26, 27, 28, or 29) or 21-29 (e.g., position 21, 22, 23, 24, 25, 26, 27, 28, or 29) and end at a position from 119-134 (e.g., 119, 120, 121, 122, 123, 124, 125, 126, 127, 128, 129, 130, 131, 132, 133, or 134), 119-133 (e.g., 119, 120, 121, 122, 123, 124, 125, 126, 127, 128, 129, 130, 131, 132, or 133), 129-134 (e.g., 129, 130, 131, 132, 133, or 134), or 129-133 (e.g., 129, 130, 131, 132, or 133) of SEQ ID NO: 1. Other examples include constructs that begin at a position from 20-24 (e.g., 20, 21, 22, 23, or 24), 21-24 (e.g., 21, 22, 23, or 24), or 22-25 (e.g., 22, 22, 23, or 25) and end at a position from 109-134 (e.g., 109, 110, 111, 112, 113, 114, 115, 116, 117, 118, 119, 120, 121, 122, 123, 124, 125, 126, 127, 128, 129, 130, 131, 132, 133, or 134), 119-134 (e.g., 119, 120, 121, 122, 123, 124, 125, 126, 127, 128, 129, 130, 131, 132, 133, or 134) or 129-134 (e.g., 129, 130, 131, 132, 133, or 134) of SEQ ID NO: 1. Variants within these ranges are also contemplated, particularly those having at least 80%, 85%, 90%, 95%, 96%, 97%, 98%, 99%, or 100% identity to the corresponding portion of SEQ ID NO: 1.

The disclosure includes the results of an analysis of composite ActRIIB structures, shown in FIG. 3, demonstrating that the ligand-binding pocket is defined, in part, by residues Y31, N33, N35, L38 through T41, E47, E50, Q53 through K55, L57, H58, Y60, S62, K74, W78 through N83, Y85, R87, A92, and E94 through F101. At these positions, it is expected that conservative mutations will be tolerated. R40 is a K in *Xenopus*, indicating that basic amino acids at this position will be tolerated. Q53 is R in bovine ActRIIB and K in *Xenopus* ActRIIB, and therefore amino acids including R, K, Q, N and H will be tolerated at this position. Thus, a general formula for an ActRIIB polypeptide of the disclosure is one that comprises an amino acid sequence that is at least 80%, 85%, 90%, 95%, 96%, 97%, 98%, 99%, or 100% identical to amino acids 29-109 of SEQ ID NO: 1, optionally beginning at a position ranging from 20-24 (e.g., 20, 21, 22, 23, or 24) or 22-25 (e.g., 22, 23, 24, or 25) and ending at a position ranging from 129-134 (e.g., 129, 130, 131, 132, 133, or 134), and comprising no more than 1, 2, 5, 10 or 15 conservative amino acid changes in the ligand-binding pocket, and zero, one or more non-conservative alterations at positions 40, 53, 55, 74, 79 and/or 82 in the ligand-binding pocket. Sites outside the binding pocket, at which variability may be particularly well tolerated, include the amino and carboxy termini of the extracellular domain (as noted above), and positions 42-46 and 65-73 (with respect to SEQ ID NO: 1). An asparagine-to-alanine alteration at position 65 (N65A) actually improves ligand binding in the A64 background, and is thus expected to have no detrimental effect on ligand binding in the R64 background. See, e.g., U.S. Pat. No. 7,842,663. This change probably eliminates glycosylation at N65 in the A64 background, thus demonstrating that a significant change in this region is likely to be tolerated. While an R64A change is poorly tolerated, R64K is well-tolerated, and thus another basic residue, such as H may be tolerated at position 64. See, e.g., U.S. Pat. No. 7,842,663.

ActRIIB is well-conserved across nearly all vertebrates, with large stretches of the extracellular domain conserved completely. Many of the ligands that bind to ActRIIB are also highly conserved. Accordingly, comparisons of ActRIIB sequences from various vertebrate organisms provide insights into residues that may be altered. Therefore, an active, human ActRIIB variant polypeptide useful in accordance with the presently disclosed methods may include one or more amino acids at corresponding positions from the sequence of another vertebrate ActRIIB, or may include a residue that is similar to that in the human or other vertebrate sequence. The following examples illustrate this approach to defining an active ActRIIB variant. L46 is a valine in *Xenopus* ActRIIB, and so this position may be altered, and optionally may be altered to another hydrophobic residue, such as V, I or F, or a non-polar residue such as A. E52 is a K in *Xenopus*, indicating that this site may be tolerant of a wide variety of changes, including polar residues, such as E, D, K, R, H, S, T, P, G, Y and probably A. T93 is a K in *Xenopus*, indicating that a wide structural variation is tolerated at this position, with polar residues favored, such as S, K, R, E, D, H, G, P, G and Y. F108 is a Y in *Xenopus*, and therefore Y or other hydrophobic group, such as I, V or L should be tolerated. E111 is K in *Xenopus*, indicating that charged residues will be tolerated at this position, including D, R, K and H, as well as Q and N. R112 is K in *Xenopus*, indicating that basic residues are tolerated at this position, including R and H. A at position 119 is relatively poorly conserved, and appears as P in rodents and V in *Xenopus*, thus essentially any amino acid should be tolerated at this position.

The variations described herein may be combined in various ways. Additionally, the results of the mutagenesis program described in the art indicate that there are amino acid positions in ActRIIB that are often beneficial to conserve. With respect to SEQ ID NO: 1, these include position 64 (basic amino acid), position 80 (acidic or hydrophobic amino acid), position 78 (hydrophobic, and particularly tryptophan), position 37 (acidic, and particularly aspartic or glutamic acid), position 56 (basic amino acid), position 60 (hydrophobic amino acid, particularly phenylalanine or tyrosine). Thus, in the ActRIIB polypeptides disclosed herein, the disclosure provides a framework of amino acids that may be conserved. Other positions that may be desirable to conserve are as follows: position 52 (acidic amino acid), position 55 (basic amino acid), position 81 (acidic), 98 (polar or charged, particularly E, D, R or K), all with respect to SEQ ID NO: 1.

In certain embodiments, the disclosure relates to single-arm heteromultimer complexes that comprise at least one ActRIIB polypeptide, which includes fragments, functional variants, and modified forms thereof. Preferably, ActRIIB polypeptides for use in accordance with inventions of the disclosure (e.g., single-arm heteromultimer complexes comprising an ActRIIB polypeptide and uses thereof) are soluble (e.g., an extracellular domain of ActRIIB) In other preferred embodiments, ActRIIB polypeptides for use in accordance with the inventions of the disclosure bind to and/or inhibit (antagonize) activity (e.g., induction of Smad 2/3 and/or Smad 1/5/8 signaling) of one or more TGF-beta superfamily ligands. In some embodiments, single-arm heteromultimer complexes of the disclosure comprise at least one ActRIIB polypeptide that comprises, consists, or consists essentially of an amino acid sequence that is at least 80%, 85%, 90%, 95%, 96%, 97%, 98%, 99%, or 100% identical to a portion of ActRIIB beginning at a residue corresponding to amino acids 20-29 (e.g., beginning at amino acid 20, 21, 22, 23, 24, 25, 26, 27, 28, or 29) of SEQ ID NO: 1 and ending at a position corresponding to amino acids 109-134 (e.g., ending at amino acid 109, 110, 111, 112, 113, 114, 115, 116, 117, 118, 119, 120, 121, 122, 123, 124, 125, 126, 127, 128, 129, 130, 131, 132, 133, or 134) of SEQ ID NO: 1. In some embodiments, single-arm heteromultimer complexes of the disclosure comprise at least one ActRIIB polypeptide that comprises, consists, or consists essentially of an amino acid sequence that is at least 80%, 85%, 90%, 95%, 96%, 97%, 98%, 99%, or 100% identical to a portion of ActRIIB beginning at a residue corresponding to amino acids 20-29 (e.g., beginning at amino acid 20, 21, 22, 23, 24, 25, 26, 27, 28, or 29) of SEQ ID NO: 1 and ending at a position corresponding to amino acids 109-134 (e.g., ending at amino acid 109, 110, 111, 112, 113, 114, 115, 116, 117, 118, 119, 120, 121, 122, 123, 124, 125, 126, 127, 128, 129, 130, 131, 132, 133, or 134) of SEQ ID NO: 1, wherein the position corresponding to L79 of SEQ ID NO: 1 is an acidic amino acid (i.e., a D or E amino acid residue). In certain preferred embodiments, single-arm heteromultimer complexes of the disclosure comprise at least one ActRIIB polypeptide that comprises, consists, or consists essentially of an amino acid sequence that is at least 80%, 85%, 90%, 95%, 96%, 97%, 98%, 99%, or 100% identical amino acids 29-109 of SEQ ID NO: 1. In other preferred embodiments, single-arm heteromultimer complexes of the disclosure comprise at least one ActRIIB polypeptide that comprises, consists, or consists essentially of an amino acid sequence that is at least 80%, 85%, 90%, 95%, 96%, 97%, 98%, 99%, or 100% identical amino acids 29-109 of SEQ ID NO: 1, wherein the position corresponding to L79 of SEQ ID NO: 1 is an acidic amino acid (i.e., a D or E amino acid residue). In some embodiments, single-arm heteromultimer complexes of the disclosure comprise at least one ActRIIB polypeptide that is at least 70%, 75%, 80%, 85%, 90%, 95%, 97%, 98%, or 99% identical to the amino acid sequence of any one of SEQ ID NOs: 1, 2, 3, 4, 5, 6, 104, 106, 403, or 404. In some embodiments, single-arm heteromultimer complexes of the disclosure comprise at least one ActRIIB polypeptide that is at least 70%, 75%, 80%, 85%, 90%, 95%, 97%, 98%, or 99% identical to the amino acid sequence of any one of SEQ ID NOs: 1, 2, 3, 4, 5, 6, 104, 106, 403, or 404, wherein the position corresponding to L79 of SEQ ID NO: 1 is an acidic amino acid (i.e., a D or E amino acid residue). In some embodiments, single-arm heteromultimer complexes of the disclosure comprise, consist, or consist essentially of at least one ActRIIB polypeptide that is at least 70%, 75%, 80%, 85%, 90%, 95%, 97%, 98%, or 99% identical to the amino acid sequence of any one of SEQ ID NOs: 1, 2, 3, 4, 5, 6, 104, 106, 403, or 404. In some embodiments, single-arm heteromultimer complexes of the disclosure comprise, consist, or consist essentially of at least one ActRIIB polypeptide that is at least 70%, 75%, 80%, 85%, 90%, 95%, 97%, 98%, or 99% identical to the amino acid sequence of any one of SEQ ID NOs: 1, 2, 3, 4, 5, 6, 104, 106, 403, or 404, wherein the position corresponding to L79 of SEQ ID NO: 1 is an acidic amino acid (i.e., a D or E amino acid residue).

In certain embodiments, the present disclosure relates to a protein complex comprising an ActRIIA polypeptide. As used herein, the term "ActRIIA" refers to a family of activin receptor type IIA (ActRIIA) proteins from any species and variants derived from such ActRIIA proteins by mutagenesis or other modification. Reference to ActRIIA herein is understood to be a reference to any one of the currently identified forms. Members of the ActRIIA family are generally transmembrane proteins, composed of a ligand-binding extracellular domain comprising a cysteine-rich region, a transmembrane domain, and a cytoplasmic domain with predicted serine/threonine kinase activity.

The term "ActRIIA polypeptide" includes polypeptides comprising any naturally occurring polypeptide of an ActRIIA family member as well as any variants thereof (including mutants, fragments, fusions, and peptidomimetic forms) that retain a useful activity. Examples of such variant ActRIIA polypeptides are provided throughout the present disclosure as well as in International Patent Application Publication No. WO 2006/012627, which is incorporated herein by reference in its entirety. Numbering of amino acids for all ActRIIA-related polypeptides described herein is based on the numbering of the human ActRIIA precursor protein sequence provided below (SEQ ID NO: 9), unless specifically designated otherwise.

The human ActRIIA precursor protein sequence is as follows:

(SEQ ID NO: 9)

```
1   MGAAAKLAFA VFLISCSSGA ILGRSETQEC LFFNANWEKD RTNQTGVEPC
51  YGDKDKRRHC FATWKNISGS IEIVKQGCWL DDINCYDRTD CVEKEDSPEV
101 YFCCCEGNMC NEKFSYFPEM EVTQPTSNPV TPKPPYYNIL LYSLVPLMLI
151 AGIVICAFWV YRHHKMAYPP VLVPTQDPGP PPPSPLLGLK PLQLLEVKAR
201 GRFGCVWKAQ LLNEYVAVKI FPIQDKQSWQ NEYEVYSLPG MKHENILQFI
251 GAEKRGTSVD VDLWLITAFH EKGSLSDFLK ANVVSWNELC HIAETMARGL
301 AYLHEDIPGL KDGHKPAISH RDIKSKNVLL KNNLTACIAD FGLALKFEAG
351 KSAGDTHGQV GTRRYMAPEV LEGAINFQRD AFLRIDMYAM GLVLWELASR
401 CTAADGPVDE YMLPFEEEIG QHPSLEDMQE VVVHKKKRPV LRDYWQKHAG
451 MAMLCETIEE CWDHDAEARL SAGCVGERIT QMQRLTNIIT TEDIVTVVTM
501 VTNVDFPPKE SSL
```

The signal peptide is indicated by a single underline; the extracellular domain is indicated in bold font; and the potential, endogenous N-linked glycosylation sites are indicated by a double underline.

The processed extracellular human ActRIIA polypeptide sequence is as follows:

(SEQ ID NO: 10)

```
ILGRSETQECLFFNANWEKDRTNQTGVEPCYGDKDKRRHCFATWKNISGS
IEIVKQGCWLDDINCYDRTDCVEKKDSPEVYFCCCEGNMCNEKFSYFPEM
EVTQPTSNPVTPKPP
```

The C-terminal "tail" of the extracellular domain is indicated by a single underline. The sequence with the "tail" deleted (a 415 sequence) is as follows:

(SEQ ID NO: 11)
ILGRSETQECLFFNANWEKDRTNQTGVEPCYGDKDKRRHCFATWKNISGS

IEIVKQGCWLDDINCYDRTDCVEKKDSPEVYFCCCEGNMCNEKFSYFPEM

A nucleic acid sequence encoding the human ActRIIA precursor protein is shown below (SEQ ID NO: 12), corresponding to nucleotides 159-1700 of Genbank Reference Sequence NM_001616.4. The signal sequence is underlined.

(SEQ ID NO: 12)
```
   1 ATGGGAGCTG CTGCAAAGTT GGCGTTTGCC GTCTTTCTTA TCTCCTGTTC
  51 TTCAGGTGCT ATACTTGGTA GATCAGAAAC TCAGGAGTGT CTTTTCTTTA
 101 ATGCTAATTG GGAAAAAGAC AGAACCAATC AAACTGGTGT TGAACCGTGT
 151 TATGGTGACA AAGATAAACG GCGGCATTGT TTTGCTACCT GGAAGAATAT
 201 TTCTGGTTCC ATTGAAATAG TGAAACAAGG TTGTTGGCTG GATGATATCA
 251 ACTGCTATGA CAGGACTGAT TGTGTAGAAA AAAAAGACAG CCCTGAAGTA
 301 TATTTTTGTT GCTGTGAGGG CAATATGTGT AATGAAAAGT TTTCTTATTT
 351 TCCGGAGATG GAAGTCACAC AGCCCACTTC AAATCCAGTT ACACCTAAGC
 401 CACCCTATTA CAACATCCTG CTCTATTCCT TGGTGCCACT TATGTTAATT
 451 GCGGGGATTG TCATTTGTGC ATTTTGGGTG TACAGGCATC ACAAGATGGC
 501 CTACCCTCCT GTACTTGTTC CAACTCAAGA CCCAGGACCA CCCCCACCTT
 551 CTCCATTACT AGGTTTGAAA CCACTGCAGT TATTAGAAGT GAAAGCAAGG
 601 GGAAGATTTG GTTGTGTCTG GAAAGCCCAG TTGCTTAACG AATATGTGGC
 651 TGTCAAAATA TTTCCAATAC AGGACAAACA GTCATGGCAA AATGAATACG
 701 AAGTCTACAG TTTGCCTGGA ATGAAGCATG AGAACATATT ACAGTTCATT
 751 GGTGCAGAAA AACGAGGCAC CAGTGTTGAT GTGGATCTTT GGCTGATCAC
 801 AGCATTTCAT GAAAAGGGTT CACTATCAGA CTTTCTTAAG GCTAATGTGG
 851 TCTCTTGGAA TGAACTGTGT CATATTGCAG AAACCATGGC TAGAGGATTG
 901 GCATATTTAC ATGAGGATAT ACCTGGCCTA AAAGATGGCC ACAAACCTGC
 951 CATATCTCAC AGGGACATCA AAAGTAAAAA TGTGCTGTTG AAAAACAACC
1001 TGACAGCTTG CATTGCTGAC TTTGGGTTGG CCTTAAAATT TGAGGCTGGC
1051 AAGTCTGCAG GCGATACCCA TGGACAGGTT GGTACCCGGA GGTACATGGC
1101 TCCAGAGGTA TTAGAGGGTG CTATAAACTT CCAAAGGGAT GCATTTTTGA
1151 GGATAGATAT GTATGCCATG GGATTAGTCC TATGGGAACT GGCTTCTCGC
1201 TGTACTGCTG CAGATGGACC TGTAGATGAA TACATGTTGC CATTTGAGGA
1251 GGAAATTGGC CAGCATCCAT CTCTTGAAGA CATGCAGGAA GTTGTTGTGC
1301 ATAAAAAAAA GAGGCCTGTT TTAAGAGATT ATTGGCAGAA ACATGCTGGA
1351 ATGGCAATGC TCTGTGAAAC CATTGAAGAA TGTTGGGATC ACGACGCAGA
1401 AGCCAGGTTA TCAGCTGGAT GTGTAGGTGA AAGAATTACC CAGATGCAGA
1451 GACTAACAAA TATTATTACC ACAGAGGACA TTGTAACAGT GGTCACAATG
1501 GTGACAAATG TTGACTTTCC TCCCAAAGAA TCTAGTCTA
```

-

The nucleic acid sequence encoding processed extracellular ActRIIA polypeptide is as follows:

(SEQ ID NO: 13)
```
 1 ATACTTGGTA GATCAGAAAC TCAGGAGTGT CTTTTCTTTA ATGCTAATTG
51 GGAAAAAGAC AGAACCAATC AAACTGGTGT TGAACCGTGT TATGGTGACA
```

-continued

```
101 AAGATAAACG GCGGCATTGT TTTGCTACCT GGAAGAATAT TTCTGGTTCC

151 ATTGAAATAG TGAAACAAGG TTGTTGGCTG GATGATATCA ACTGCTATGA

201 CAGGACTGAT TGTGTAGAAA AAAAAGACAG CCCTGAAGTA TATTTTTGTT

251 GCTGTGAGGG CAATATGTGT AATGAAAAGT TTTCTTATTT TCCGGAGATG

301 GAAGTCACAC AGCCCACTTC AAATCCAGTT ACACCTAAGC CACCC
```

A general formula for an active (e.g., ligand binding) ActRIIA polypeptide is one that comprises a polypeptide that starts at amino acid 30 and ends at amino acid 110 of SEQ ID NO: 9. Accordingly, ActRIIA polypeptides of the present disclosure may comprise a polypeptide that is at least 80%, 85%, 90%, 95%, 96%, 97%, 98%, 99%, or 100% identical to amino acids 30-110 of SEQ ID NO: 9. Optionally, ActRIIA polypeptides of the present disclosure comprise a polypeptide that is at least 80%, 85%, 90%, 95%, 96%, 97%, 98%, 99%, or 100% identical to amino acids amino acids 12-82 of SEQ ID NO: 9 optionally beginning at a position ranging from 1-5 (e.g., 1, 2, 3, 4, or 5) or 3-5 (e.g., 3, 4, or 5) and ending at a position ranging from 110-116 (e.g., 110, 111, 112, 113, 114, 115, or 116) or 110-115 (e.g., 110, 111, 112, 113, 114, or 115), respectively, and comprising no more than 1, 2, 5, 10 or 15 conservative amino acid changes in the ligand binding pocket, and zero, one or more non-conservative alterations at positions 40, 53, 55, 74, 79 and/or 82 in the ligand-binding pocket with respect to SEQ ID NO: 9.

In certain embodiments, the disclosure relates to single-arm heteromultimer complexes that comprise at least one ActRIIA polypeptide, which includes fragments, functional variants, and modified forms thereof. Preferably, ActRIIA polypeptides for use in accordance with inventions of the disclosure (e.g., single-arm heteromultimer complexes comprising an ActRIIA polypeptide and uses thereof) are soluble (e.g., an extracellular domain of ActRIIA). In other preferred embodiments, ActRIIA polypeptides for use in accordance with the inventions of the disclosure bind to and/or inhibit (antagonize) activity (e.g., induction of Smad 2/3 and/or Smad 1/5/8 signaling) of one or more TGF-beta superfamily ligands. In some embodiments, single-arm heteromultimer complexes of the disclosure comprise at least one ActRIIA polypeptide that is at least 70%, 75%, 80%, 85%, 90%, 95%, 97%, 98%, or 99% identical to the amino acid sequence of any one of SEQ ID NOs: 9, 10, 11, 101, 103, 401, or 402. In some embodiments, single-arm heteromultimer complexes of the disclosure comprise, consist, or consist essentially of at least one ActRIIA polypeptide that is at least 70%, 75%, 80%, 85%, 90%, 95%, 97%, 98%, or 99% identical to the amino acid sequence of any one of SEQ ID NOs: 9, 10, 11, 101, 103, 401, or 402.

In certain aspects, the present disclosure relates to protein complexes that comprise a TGFBRII polypeptide. As used herein, the term "TGFBRII" refers to a family of transforming growth factor-beta receptor II (TGFBRII) proteins from any species and variants derived from such proteins by mutagenesis or other modification. Reference to TGFBRII herein is understood to be a reference to any one of the currently identified forms. Members of the TGFBRII family are generally transmembrane proteins, composed of a ligand-binding extracellular domain with a cysteine-rich region, a transmembrane domain, and a cytoplasmic domain with predicted serine/threonine kinase activity.

The term "TGFBRII polypeptide" includes polypeptides comprising any naturally occurring polypeptide of a TGFBRII family member as well as any variants thereof (including mutants, fragments, fusions, and peptidomimetic forms) that retain a useful activity. Numbering of amino acids for all TGFBRII-related polypeptides described herein is based on the numbering of the human TGFBRII precursor protein sequence below (SEQ ID NO: 42), unless specifically designated otherwise.

The canonical human TGFBRII precursor protein sequence (NCBI Ref Seq NP_003233.4) is as follows:

(SEQ ID NO: 42)

```
  1 MGRGLLRGLW PLHIVLWTRI ASTIPPHVQK SVNNDMIVTD NNGAVKFPQL

 51 CKFCDVRFST CDNQKSCMSN CSITSICEKP QEVCVAVWRK NDENITLETV

101 CHDPKLPYHD FILEDAASPK CIMEEKKKPG ETFFMCSCSS DECNDNIIFS

151 EEYNTSNPDL LLVIFQVTGI SLLPPLGVAI SVIIIFYCYR VNRQQKLSST

201 WETGKTRKLM EFSEHCAIIL EDDRSDISST CANNINHNTE LLPIELDTLV

251 GKGRFAEVYK AKLKQNTSEQ FETVAVKIFP YEEYASWKTE KDIFSDINLK

301 HENILQFLTA EERKTELGKQ YWLITAFHAK GNLQEYLTRH VISWEDLRKL

351 GSSLARGIAH LHSDHTPCGR PKMPIVHRDL KSSNILVKND LTCCLCDFGL

401 SLRLDPTLSV DDLANSGQVG TARYMAPEVL ESRMNLENVE SFKQTDVYSM

451 ALVLWEMTSR CNAVGEVKDY EPPFGSKVRE HPCVESMKDN VLRDRGRPEI

501 PSFWLNHQGI QMVCETLTEC WDHDPEARLT AQCVAERFSE LEHLDRLSGR

551 SCSEEKIPED GSLNTTK
```

The signal peptide is indicated by a single underline and the extracellular domain is indicated in bold font.

The processed extracellular TGFBRII polypeptide sequence is as follows:

(SEQ ID NO: 43)
TIPPHVQKSVNNDMIVTDNNGAVKFPQLCKFCDVRFSTCDNQKSCMSNCSI

-continued

TSICEKPQEVCVAVWRKNDENITLETVCHDPKLPYHDFILEDAASPKCIMK

EKKKPGETFFMCSCSSDECNDNIIFSEEYNTSNPDLLLVIFQ

The nucleic acid sequence encoding TGFBRII precursor protein is shown below (SEQ ID NO:44), corresponding to nucleotides 383-2083 of Genbank Reference Sequence NM_003242.5. The signal sequence is underlined.

(SEQ ID NO: 44)
ATGGGTCGGGGGCTGCTCAGGGGCCTGTGGCCGCTGCACATCGTCCTGTGGACGCGTATCGCCA

GCACGATCCCACCGCACGTTCAGAAGTCGGTTAATAACGACATGATAGTCACTGACAACAACGG

TGCAGTCAAGTTTCCACAACTGTGTAAATTTTGTGATGTGAGATTTTCCACCTGTGACAACCAG

AAATCCTGCATGAGCAACTGCAGCATCACCTCCATCTGTGAGAAGCCACAGGAAGTCTGTGTGG

CTGTATGGAGAAAGAATGACGAGAACATAACACTAGAGACAGTTTGCCATGACCCCAAGCTCCC

CTACCATGACTTTATTCTGGAAGATGCTGCTTCTCCAAAGTGCATTATGAAGGAAAAAAAAAAG

CCTGGTGAGACTTTCTTCATGTGTTCCTGTAGCTCTGATGAGTGCAATGACAACATCATCTTCT

CAGAAGAATATAACACCAGCAATCCTGACTTGTTGCTAGTCATATTTCAAGTGACAGGCATCAG

CCTCCTGCCACCACTGGGAGTTGCCATATCTGTCATCATCATCTTCTACTGCTACCGCGTTAAC

CGGCAGCAGAAGCTGAGTTCAACCTGGGAAACCGGCAAGACGCGGAAGCTCATGGAGTTCAGCG

AGCACTGTGCCATCATCCTGGAAGATGACCGCTCTGACATCAGCTCCACGTGTGCCAACAACAT

CAACCACAACACAGAGCTGCTGCCCATTGAGCTGGACACCCTGGTGGGGAAAGGTCGCTTTGCT

GAGGTCTATAAGGCCAAGCTGAAGCAGAACACTTCAGAGCAGTTTGAGACAGTGGCAGTCAAGA

TCTTTCCCTATGAGGAGTATGCCTCTTGGAAGACAGAGAAGGACATCTTCTCAGACATCAATCT

GAAGCATGAGAACATACTCCAGTTCCTGACGGCTGAGGAGCGGAAGACGGAGTTGGGGAAACAA

TACTGGCTGATCACCGCCTTCCACGCCAAGGGCAACCTACAGGAGTACCTGACGCGGCATGTCA

TCAGCTGGGAGGACCTGCGCAAGCTGGGCAGCTCCCTCGCCCGGGGGATTGCTCACCTCCACAG

TGATCACACTCCATGTGGGAGGCCCAAGATGCCCATCGTGCACAGGGACCTCAAGAGCTCCAAT

ATCCTCGTGAAGAACGACCTAACCTGCTGCCTGTGTGACTTTGGGCTTTCCCTGCGTCTGGACC

CTACTCTGTCTGTGGATGACCTGGCTAACAGTGGGCAGGTGGGAACTGCAAGATACATGGCTCC

AGAAGTCCTAGAATCCAGGATGAATTTGGAGAATGTTGAGTCCTTCAAGCAGACCGATGTCTAC

TCCATGGCTCTGGTGCTCTGGGAAATGACATCTCGCTGTAATGCAGTGGGAGAAGTAAAAGATT

ATGAGCCTCCATTTGGTTCCAAGGTGCGGGAGCACCCCTGTGTCGAAAGCATGAAGGACAACGT

GTTGAGAGATCGAGGGCGACCAGAAATTCCCAGCTTCTGGCTCAACCACCAGGGCATCCAGATG

GTGTGTGAGACGTTGACTGAGTGCTGGGACCACGACCCAGAGGCCCGTCTCACAGCCCAGTGTG

TGGCAGAACGCTTCAGTGAGCTGGAGCATCTGGACAGGCTCTCGGGGAGGAGCTGCTCGGAGGA

GAAGATTCCTGAAGACGGCTCCCTAAACACTACCAAA

The nucleic acid sequence encoding processed extracellular TGFBRII polypeptide is as follows:

(SEQ ID NO: 45)
ACGATCCCACCGCACGTTCAGAAGTCGGTTAATAACGACATGATAGTCACTGACAACAACGGTG

CAGTCAAGTTTCCACAACTGTGTAAATTTTGTGATGTGAGATTTTCCACCTGTGACAACCAGAA

ATCCTGCATGAGCAACTGCAGCATCACCTCCATCTGTGAGAAGCCACAGGAAGTCTGTGTGGCT

GTATGGAGAAAGAATGACGAGAACATAACACTAGAGACAGTTTGCCATGACCCCAAGCTCCCCT

-continued

ACCATGACTTTATTCTGGAAGATGCTGCTTCTCCAAAGTGCATTATGAAGGAAAAAAAAAAGCC

TGGTGAGACTTTCTTCATGTGTTCCTGTAGCTCTGATGAGTGCAATGACAACATCATCTTCTCA

GAAGAATATAACACCAGCAATCCTGACTTGTTGCTAGTCATATTTCAA

An alternative isoform of TGFBRII, isoform A (NP_001020018.1), is as follows:

(SEQ ID NO: 67)

1 MGRGLLRGLW PLHIVLWTRI ASTIPPHVQK SDVEMEAQKD EIICPSCNRT

51 AHPLRHINND MIVTDNNGAV KFPQLCKFCD VRFSTCDNQK SCMSNCSITS

101 ICEKPQEVCV AVWRKNDENI TLETVCHDPK LPYHDFILED AASPKCIMEE

151 KKKPGETFFM CSCSSDECND NIIFSEEYNT SNPDLLLVIF QVTGISLLPP

201 LGVAISVIII FYCYRVNRQQ KLSSTWETGK TRKLMEFSEH CAIILEDDRS

251 DISSTCANNI NHNTELLPIE LDTLVGKGRF AEVYKAKLKQ NTSEQFETVA

301 VKIFPYEEYA SWKTEKDIFS DINLKHENIL QFLTAEERKT ELGKQYWLIT

351 AFHAKGNLQE YLTRHVISWE DLRKLGSSLA RGIAHLHSDH TPCGRPKMPI

401 VHRDLKSSNI LVKNDLTCCL CDFGLSLRLD PTLSVDDLAN SGQVGTARYM

451 APEVLESRMN LENVESFKQT DVYSMALVLW EMTSRCNAVG EVKDYEPPFG

501 SKVREHPCVE SMKDNVLRDR GRPEIPSFWL NHQGIQMVCE TLTECWDHDP

551 EARLTAQCVA ERFSELEHLD RLSGRSCSEE KIPEDGSLNT TK

The signal peptide is indicated by a single underline and the extracellular domain is indicated in bold font.

The processed extracellular TGFBRII polypeptide sequence (isoform A) is as follows:

(SEQ ID NO: 68)

TIPPHVQKSDVEMEAQKDEIICPSCNRTAHPLRHINNDMIVTDNNGAVKFP

QLCKFCDVRFSTCDNQKSCMSNCSITSICEKPQEVCVAVWRKNDENITLET

-continued

VCHDPKLPYHDFILEDAASPKCIMKEKKKPGETFFMCSCSSDECNDNIIFS

EEYNTSNPDLLLVIFQ

A nucleic acid sequence encoding the TGFBRII precursor protein (isoform A) is shown below (SEQ ID NO: 69), corresponding to nucleotides 383-2158 of Genbank Reference Sequence NM_001024847.2. The signal sequence is underlined.

(SEQ ID NO: 69)

ATGGGTCGGGGGCTGCTCAGGGGCCTGTGGCCGCTGCACATCGTCCTGTGGACGCGTATCGCCA

GCACGATCCCACCGCACGTTCAGAAGTCGGATGTGGAAATGGAGGCCCAGAAAGATGAAATCAT

CTGCCCCAGCTGTAATAGGACTGCCCATCCACTGAGACATATTAATAACGACATGATAGTCACT

GACAACAACGGTGCAGTCAAGTTTCCACAACTGTGTAAATTTTGTGATGTGAGATTTTCCACCT

GTGACAACCAGAAATCCTGCATGAGCAACTGCAGCATCACCTCCATCTGTGAGAAGCCACAGGA

AGTCTGTGTGGCTGTATGGAGAAAGAATGACGAGAACATAACACTAGAGACAGTTTGCCATGAC

CCCAAGCTCCCCTACCATGACTTTATTCTGGAAGATGCTGCTTCTCCAAAGTGCATTATGAAGG

AAAAAAAAAAGCCTGGTGAGACTTTCTTCATGTGTTCCTGTAGCTCTGATGAGTGCAATGACAA

CATCATCTTCTCAGAAGAATATAACACCAGCAATCCTGACTTGTTGCTAGTCATATTTCAAGTG

ACAGGCATCAGCCTCCTGCCACCACTGGGAGTTGCCATATCTGTCATCATCATCTTCTACTGCT

ACCGCGTTAACCGGCAGCAGAAGCTGAGTTCAACCTGGGAAACCGGCAAGACGCGGAAGCTCAT

GGAGTTCAGCGAGCACTGTGCCATCATCCTGGAAGATGACCGCTCTGACATCAGCTCCACGTGT

GCCAACAACATCAACCACAACACAGAGCTGCTGCCCATTGAGCTGGACACCCTGGTGGGGAAAG

GTCGCTTTGCTGAGGTCTATAAGGCCAAGCTGAAGCAGAACACTTCAGAGCAGTTTGAGACAGT

-continued

GGCAGTCAAGATCTTTCCCTATGAGGAGTATGCCTCTTGGAAGACAGAGAAGGACATCTTCTCA

GACATCAATCTGAAGCATGAGAACATACTCCAGTTCCTGACGGCTGAGGAGCGGAAGACGGAGT

TGGGGAAACAATACTGGCTGATCACCGCCTTCCACGCCAAGGGCAACCTACAGGAGTACCTGAC

GCGGCATGTCATCAGCTGGGAGGACCTGCGCAAGCTGGGCAGCTCCCTCGCCCGGGGGATTGCT

CACCTCCACAGTGATCACACTCCATGTGGGAGGCCCAAGATGCCCATCGTGCACAGGGACCTCA

AGAGCTCCAATATCCTCGTGAAGAACGACCTAACCTGCTGCCTGTGTGACTTTGGGCTTTCCCT

GCGTCTGGACCCTACTCTGTCTGTGGATGACCTGGCTAACAGTGGGCAGGTGGGAACTGCAAGA

TACATGGCTCCAGAAGTCCTAGAATCCAGGATGAATTTGGAGAATGTTGAGTCCTTCAAGCAGA

CCGATGTCTACTCCATGGCTCTGGTGCTCTGGGAAATGACATCTCGCTGTAATGCAGTGGGAGA

AGTAAAAGATTATGAGCCTCCATTTGGTTCCAAGGTGCGGGAGCACCCCTGTGTCGAAAGCATG

AAGGACAACGTGTTGAGAGATCGAGGGCGACCAGAAATTCCCAGCTTCTGGCTCAACCACCAGG

GCATCCAGATGGTGTGTGAGACGTTGACTGAGTGCTGGGACCACGACCCAGAGGCCCGTCTCAC

AGCCCAGTGTGTGGCAGAACGCTTCAGTGAGCTGGAGCATCTGGACAGGCTCTCGGGGAGGAGC

TGCTCGGAGGAGAAGATTCCTGAAGACGGCTCCCTAAACACTACCAAA

A nucleic acid sequence encoding the processed extracellular TGFBRII polypeptide (isoform A) is as follows:

(SEQ ID NO: 70)

ACGATCCCACCGCACGTTCAGAAGTCGGATGTGGAAATGGAGGCCCAGAAAGATGAAATCATCT

GCCCCAGCTGTAATAGGACTGCCCATCCACTGAGACATATTAATAACGACATGATAGTCACTGA

CAACAACGGTGCAGTCAAGTTTCCACAACTGTGTAAATTTTGTGATGTGAGATTTTCCACCTGT

GACAACCAGAAATCCTGCATGAGCAACTGCAGCATCACCTCCATCTGTGAGAAGCCACAGGAAG

TCTGTGTGGCTGTATGGAGAAAGAATGACGAGAACATAACACTAGAGACAGTTTGCCATGACCC

CAAGCTCCCCTACCATGACTTTATTCTGGAAGATGCTGCTTCTCCAAAGTGCATTATGAAGGAA

AAAAAAAAGCCTGGTGAGACTTTCTTCATGTGTTCCTGTAGCTCTGATGAGTGCAATGACAACA

TCATCTTCTCAGAAGAATATAACACCAGCAATCCTGACTTGTTGCTAGTCATATTTCAA.

Either of the foregoing TGFβRII isoforms (SEQ ID NOs: 42, 43, 67, and 68) could incorporate an insertion of 36 amino acids (SEQ ID NO: 95) between the pair of glutamate residues (positions 151 and 152 of SEQ ID NO: 42; positions 129 and 130 of SEQ ID NO: 43; positions 176 and 177 of SEQ ID NO: 67; or positions 154 and 155 of SEQ ID NO: 68) located near the C-terminus of the TGFβRII ECD, as occurs naturally in the TGFβRII isoform C (Konrad et al., BMC Genomics 8:318, 2007).

GRCKIRHIGS NNRLQRSTCQ NTGWESAHVM KTPGFR (SEQ ID NO: 95)

In certain embodiments, the disclosure relates to single-arm heteromultimer complexes that comprise at least one TGFBRII polypeptide, which includes fragments, functional variants, and modified forms thereof. Preferably, TGFBRII polypeptides for use in accordance with inventions of the disclosure (e.g., single-arm heteromultimer complexes comprising a TGFBRII polypeptide and uses thereof) are soluble (e.g., an extracellular domain of TGFBRII). In other preferred embodiments, TGFBRII polypeptides for use in accordance with the inventions of the disclosure bind to and/or inhibit (antagonize) activity (e.g., induction of Smad 2/3 and/or Smad 1/5/8 signaling) of one or more TGF-beta superfamily ligands. In some embodiments, single-arm heteromultimer complexes of the disclosure comprise at least one TGFBRII polypeptide that is at least 70%, 75%, 80%, 85%, 90%, 95%, 97%, 98%, or 99% identical to the amino acid sequence of SEQ ID NOs: 42, 43, 67, 68, 113, 115, 409, or 410. In some embodiments, single-arm heteromultimer complexes of the disclosure comprise at least one TGFBRII polypeptide that is at least 70%, 75%, 80%, 85%, 90%, 95%, 97%, 98%, or 99% identical to any of the amino acid sequences of SEQ ID NOs: 42, 43, 67, 68, 113, 115, 409, or 410, into which is inserted SEQ ID NO: 95 between the paired glutamate residues as described above. In some embodiments, single-arm heteromultimer complexes of the disclosure consist or consist essentially of at least one TGFBRII polypeptide that is at least 70%, 75%, 80%, 85%, 90%, 95%, 97%, 98%, or 99% identical to the amino acid sequence of SEQ ID NOs: 42, 43, 67, 68, 113, 115, 409, or 410.

In certain aspects, the present disclosure relates to protein complexes that comprise a BMPRII polypeptide. As used herein, the term "BMPRII" refers to a family of bone morphogenetic protein receptor type II (BMPRII) proteins from any species and variants derived from such BMPRII proteins by mutagenesis or other modification. Reference to BMPRII herein is understood to be a reference to any one of the currently identified forms. Members of the BMPRII family are generally transmembrane proteins, composed of a ligand-binding extracellular domain with a cysteine-rich region, a transmembrane domain, and a cytoplasmic domain with predicted serine/threonine kinase activity.

The term "BMPRII polypeptide" includes polypeptides comprising any naturally occurring polypeptide of a BMPRII family member as well as any variants thereof (including mutants, fragments, fusions, and peptidomimetic forms) that retain a useful activity. Numbering of amino acids for all BMPRII-related polypeptides described herein is based on the numbering of the human BMPRII precursor protein sequence below (SEQ ID NO: 46), unless specifically designated otherwise.

The canonical human BMPRII precursor protein sequence (NCBI Ref Seq NP_001195.2) is as follows:

(SEQ ID NO: 46)

1 MTSSLQRPWR VPWLPWTILL VSTAAASQNQ ERLCAFKDPY QQDLGIGESR

51 ISHENGTILC SKGSTCYGLW EKSKGDINLV KQGCWSHIGD PQECHYEECV

101 VTTTPPSIQN GTYRFCCCST DLCNVNFTEN FPPPDTTPLS PPHSFNRDET

151 IIIALASVSV LAVLIVALCF GYRMLTGDRK QGLHSMNMME AAASEPSLDL

201 DNLKLLELIG RGRYGAVYKG SLDERPVAVK VFSFANRQNF INEKNIYRVP

251 LMEHDNIARF IVGDERVTAD GRMEYLLVME YYPNGSLCKY LSLHTSDWVS

301 SCRLAHSVTR GLAYLHTELP RGDHYKPAIS HRDLNSRNVL VKNDGTCVIS

351 DFGLSMRLTG NRLVRPGEED NAAISEVGTI RYMAPEVLEG AVNLRDCESA

401 LKQVDMYALG LIYWEIFMRC TDLFPGESVP EYQMAFQTEV GNHPTFEDMQ

451 VLVSREKQRP KFPEAWKENS LAVRSLKETI EDCWDQDAEA RLTAQCAEER

501 MAELMMIWER NKSVSPTVNP MSTAMQNERN LSHNRRVPKI GPYPDYSSSS

551 YIEDSIHHTD SIVKNISSEH SMSSTPLTIG EKNRNSINYE RQQAQARIPS

601 PETSVTSLST NTTTTNTTGL TPSTGMTTIS EMPYPDETNL HTTNVAQSIG

651 PTPVCLQLTE EDLETNKLDP KEVDKNLKES SDENLMEHSL KQFSGPDPLS

701 STSSSLLYPL IKLAVEATGQ QDFTQTANGQ ACLIPDVLPT QIYPLPKQQN

751 LPKRPTSLPL NTKNSTKEPR LKFGSKHKSN LKQVETGVAK MNTINAAEPH

801 VVTVTMNGVA GRNHSVNSHA ATTQYANGTV LSGQTTNIVT HRAQEMLQNQ

851 FIGEDTRLNI NSSPDEHEPL LRREQQAGHD EGVLDRLVDR RERPLEGGRT

901 NSNNNNSNPC SEQDVLAQGV PSTAADPGPS KPRRAQRPNS LDLSATNVLD

951 GSSIQIGEST QDGKSGSGEK IKKRVKTPYS LKRWRPSTWV ISTESLDCEV

1001 NNNGSNRAVH SKSSTAVYLA EGGTATTMVS KDIGMNCL

The signal peptide is indicated by a single underline and the extracellular domain is indicated in bold font.

The processed extracellular BMPRII polypeptide sequence is as follows:

(SEQ ID NO: 47)

SQNQERLCAFKDPYQQDLGIGESRISHENGTILCSKGSTCYGLWEKSKGDI

NLVKQGCWSHIGDPQECHYEECVVTTTPPSIQNGTYRFCCCSTDLCNVNFT

ENFPPPDTTPLSPPHSFNRDET

A nucleic acid sequence encoding BMPRII precursor protein is shown below (SEQ ID NO: 48), as follows nucleotides 1149-4262 of Genbank Reference Sequence NM_001204.6. The signal sequence is underlined.

(SEQ ID NO: 48)

ATGACTTCCTCGCTGCAGCGGCCCTGGCGGGTGCCCTGGCTACCATGGAC

CATCCTGCTGGTCAGCACTGCGGCTGCTTCGCAGAATCAAGAACGGCTAT

GTGCGTTTAAAGATCCGTATCAGCAAGACCTTGGGATAGGTGAGAGTAGA

ATCTCTCATGAAAATGGGACAATATTATGCTCGAAAGGTAGCACCTGCTA

TGGCCTTTGGGAGAAATCAAAAGGGGACATAAATCTTGTAAAACAAGGAT

GTTGGTCTCACATTGGAGATCCCCAAGAGTGTCACTATGAAGAATGTGTA

GTAACTACCACTCCTCCCTCAATTCAGAATGGAACATACCGTTTCTGCTG

-continued

TTGTAGCACAGATTTATGTAATGTCAACTTTACTGAGAATTTTCCACCTC

CTGACACAACACCACTCAGTCCACCTCATTCATTTAACCGAGATGAGACA

ATAATCATTGCTTTGGCATCAGTCTCTGTATTAGCTGTTTTGATAGTTGC

CTTATGCTTTGGATACAGAATGTTGACAGGAGACCGTAAACAAGGTCTTC

ACAGTATGAACATGATGGAGGCAGCAGCATCCGAACCCTCTCTTGATCTA

GATAATCTGAAACTGTTGGAGCTGATTGGCCGAGGTCGATATGGAGCAGT

ATATAAAGGCTCCTTGGATGAGCGTCCAGTTGCTGTAAAAGTGTTTTCCT

TTGCAAACCGTCAGAATTTTATCAACGAAAAGAACATTTACAGAGTGCCT

-continued

```
TTGATGGAACATGACAACATTGCCCGCTTTATAGTTGGAGATGAGAGAGT
CACTGCAGATGGACGCATGGAATATTTGCTTGTGATGGAGTACTATCCCA
ATGGATCTTTATGCAAGTATTTAAGTCTCCACACAAGTGACTGGGTAAGC
TCTTGCCGTCTTGCTCATTCTGTTACTAGAGGACTGGCTTATCTTCACAC
AGAATTACCACGAGGAGATCATTATAAACCTGCAATTTCCCATCGAGATT
TAAACAGCAGAAATGTCCTAGTGAAAAATGATGGAACCTGTGTTATTAGT
GACTTTGGACTGTCCATGAGGCTGACTGGAAATAGACTGGTGCGCCCAGG
GGAGGAAGATAATGCAGCCATAAGCGAGGTTGGCACTATCAGATATATGG
CACCAGAAGTGCTAGAAGGAGCTGTGAACTTGAGGGACTGTGAATCAGCT
TTGAAACAAGTAGACATGTATGCTCTTGGACTAATCTATTGGGAGATATT
TATGAGATGTACAGACCTCTTCCCAGGGGAATCCGTACCAGAGTACCAGA
TGGCTTTTCAGACAGAGGTTGGAAACCATCCCACTTTTGAGGATATGCAG
GTTCTCGTGTCTAGGGAAAAACAGAGACCCAAGTTCCCAGAAGCCTGGAA
AGAAAATAGCCTGGCAGTGAGGTCACTCAAGGAGACAATCGAAGACTGTT
GGGACCAGGATGCAGAGGCTCGGCTTACTGCACAGTGTGCTGAGGAAAGG
ATGGCTGAACTTATGATGATTTGGGAAAGAAACAAATCTGTGAGCCCAAC
AGTCAATCCAATGTCTACTGCTATGCAGAATGAACGCAACCTGTCACATA
ATAGGCGTGTGCCAAAAATTGGTCCTTATCCAGATTATTCTTCCTCCTCA
TACATTGAAGACTCTATCCATCATACTGACAGCATCGTGAAGAATATTTC
CTCTGAGCATTCTATGTCCAGCACACCTTTGACTATAGGGGAAAAAAACC
GAAATTCAATTAACTATGAACGACAGCAAGCACAAGCTCGAATCCCCAGC
CCTGAAACAAGTGTCACCAGCCTCTCCACCAACACAACAACCACAAACAC
CACAGGACTCACGCCAAGTACTGGCATGACTACTATATCTGAGATGCCAT
ACCCAGATGAAACAAATCTGCATACCACAAATGTTGCACAGTCAATTGGG
CCAACCCCTGTCTGCTTACAGCTGACAGAAGAAGACTTGGAAACCAACAA
GCTAGACCCAAAAGAAGTTGATAAGAACCTCAAGGAAAGCTCTGATGAGA
ATCTCATGGAGCACTCTCTTAAACAGTTCAGTGGCCCAGACCCACTGAGC
AGTACTAGTTCTAGCTTGCTTTACCCACTCATAAAACTTGCAGTAGAAGC
AACTGGACAGCAGGACTTCACACAGACTGCAAATGGCCAAGCATGTTTGA
TTCCTGATGTTCTGCCTACTCAGATCTATCCTCTCCCCAAGCAGCAGAAC
CTTCCCAAGAGACCTACTAGTTTGCCTTTGAACACCAAAAATTCAACAAA
AGAGCCCCGGCTAAAATTTGGCAGCAAGCACAAATCAAACTTGAAACAAG
TCGAAACTGGAGTTGCCAAGATGAATACAATCAATGCAGCAGAACCTCAT
GTGGTGACAGTCACCATGAATGGTGTGGCAGGTAGAAACCACAGTGTTAA
CTCCCATGCTGCCACAACCCAATATGCCAATGGGACAGTACTATCTGGCC
AAACAACCAACATAGTGACACATAGGGCCCAAGAAATGTTGCAGAATCAG
TTTATTGGTGAGGACACCCGGCTGAATATTAATTCCAGTCCTGATGAGCA
TGAGCCTTTACTGAGACGAGAGCAACAAGCTGGCCATGATGAAGGTGTTC
TGGATCGTCTTGTGGACAGGAGGGAACGGCCACTAGAAGGTGGCCGAACT
AATTCCAATAACAACAACAGCAATCCATGTTCAGAACAAGATGTTCTTGC
ACAGGGTGTTCCAAGCACAGCAGCAGATCCTGGGCCATCAAAGCCCAGAA
GAGCACAGAGGCCTAATTCTCTGGATCTTTCAGCCACAAATGTCCTGGAT
GGCAGCAGTATACAGATAGGTGAGTCAACACAAGATGGCAAATCAGGATC
AGGTGAAAAGATCAAGAAACGTGTGAAAACTCCCTATTCTCTTAAGCGGT
GGCGCCCCTCCACCTGGGTCATCTCCACTGAATCGCTGGACTGTGAAGTC
AACAATAATGGCAGTAACAGGGCAGTTCATTCCAAATCCAGCACTGCTGT
TTACCTTGCAGAAGGAGGCACTGCTACAACCATGGTGTCTAAAGATATAG
GAATGAACTGTCTG
```

The nucleic acid sequence encoding the extracellular BMPRII polypeptide is as follows:

(SEQ ID NO: 49)

```
TCGCAGAATCAAGAACGGCTATGTGCGTTTAAAGATCCGTATCAGCAAGA
CCTTGGGATAGGTGAGAGTAGAATCTCTCATGAAAATGGGACAATATTAT
GCTCGAAAGGTAGCACCTGCTATGGCCTTTGGGAGAAATCAAAAGGGGAC
ATAAATCTTGTAAAACAAGGATGTTGGTCTCACATTGGAGATCCCCAAGA
GTGTCACTATGAAGAATGTGTAGTAACTACCACTCCTCCCTCAATTCAGA
ATGGAACATACCGTTTCTGCTGTTGTAGCACAGATTTATGTAATGTCAAC
TTTACTGAGAATTTTCCACCTCCTGACACAACACCACTCAGTCCACCTCA
TTCATTTAACCGAGATGAGACA
```

An alternative isoform of BMPRII, isoform 2 (GenBank: AAA86519.1) is as follows:

(SEQ ID NO: 71)

1 MTSSLQRPWR VPWLPWTILL VSTAAASQNQ ERLCAFKDPY QQDLGIGESR

51 ISHENGTILC SKGSTCYGLW EKSKGDINLV KQGCWSHIGD PQECHYEECV

101 VTTTPPSIQN GTYRFCCCST DLCNVNFTEN FPPPDTTPLS PPHSFNRDET

-continued

```
151 IIIALASVSV LAVLIVALCF GYRMLTGDRK QGLHSMNMME AAASEPSLDL

201 DNLKLLELIG RGRYGAVYKG SLDERPVAVK VFSFANRQNF INEKNIYRVP

251 LMEHDNIARF IVGDERVTAD GRMEYLLVME YYPNGSLCKY LSLHTSDWVS

301 SCRLAHSVTR GLAYLHTELP RGDHYKPAIS HRDLNSRNVL VKNDGTCVIS

351 DFGLSMRLTG NRLVRPGEED NAAISEVGTI RYMAPEVLEG AVNLRDCESA

401 LKQVDMYALG LIYWEIFMRC TDLFPGESVP EYQMAFQTEV GNHPTFEDMQ

451 VLVSREKQRP KFPEAWKENS LAVRSLKETI EDCWDQDAEA RLTAQCAEER

501 MAELMMIWER NKSVSPTVNP MSTAMQNERR
```

The signal peptide is indicated by a single underline and the extracellular domain is indicated in bold font.

The processed extracellular BMPRII polypeptide sequence (isoform 2) is as follows:

(SEQ ID NO: 72)

SQNQERLCAFKDPYQQDLGIGESRISHENGTILCSKGSTCYGLWEKSKGD

INLVKQGCWSHIGDPQECHYEECVVTTTPPSIQNGTYRFCCCSTDLCNVN

FTENFPPPDTTPLSPPHSFNRDET

A nucleic acid sequence encoding human BMPRII precursor protein (isoform 2) is shown below (SEQ ID NO: 73), corresponding to nucleotides 163-1752 of Genbank Reference Sequence U25110.1. The signal sequence is underlined.

(SEQ ID NO: 73)

ATGACTTCCTCGCTGCAGCGGCCCTGGCGGGTGCCCTGGCTACCATGGAC

CATCCTGCTGGTCAGCACTGCGGCTGCTTCGCAGAATCAAGAACGGCTAT

GTGCGTTTAAAGATCCGTATCAGCAAGACCTTGGGATAGGTGAGAGTAGA

ATCTCTCATGAAAATGGGACAATATTATGCTCGAAAGGTAGCACCTGCTA

TGGCCTTTGGGAGAAATCAAAAGGGGACATAAATCTTGTAAAACAAGGAT

GTTGGTCTCACATTGGAGATCCCCAAGAGTGTCACTATGAAGAATGTGTA

GTAACTACCACTCCTCCCTCAATTCAGAATGGAACATACCGTTTCTGCTG

TTGTAGCACAGATTTATGTAATGTCAACTTTACTGAGAATTTTCCACCTC

CTGACACAACACCACTCAGTCCACCTCATTCATTTAACCGAGATGAGACA

ATAATCATTGCTTTGGCATCAGTCTCTGTATTAGCTGTTTTGATAGTTGC

CTTATGCTTTGGATACAGAATGTTGACAGGAGACCGTAAACAAGGTCTTC

ACAGTATGAACATGATGGAGGCAGCAGCATCCGAACCCTCTCTTGATCTA

GATAATCTGAAACTGTTGGAGCTGATTGGCCGAGGTCGATATGGAGCAGT

ATATAAAGGCTCCTTGGATGAGCGTCCAGTTGCTGTAAAAGTGTTTTCCT

TTGCAAACCGTCAGAATTTTATCAACGAAAAGAACATTTACAGAGTGCCT

TTGATGGAACATGACAACATTGCCCGCTTTATAGTTGGAGATGAGAGAGT

CACTGCAGATGGACGCATGGAATATTTGCTTGTGATGGAGTACTATCCCA

ATGGATCTTTATGCAAGTATTTAAGTCTCCACACAAGTGACTGGGTAAGC

TCTTGCCGTCTTGCTCATTCTGTTACTAGAGGACTGGCTTATCTTCACAC

AGAATTACCACGAGGAGATCATTATAAACCTGCAATTTCCCATCGAGATT

-continued

TAAACAGCAGAAATGTCCTAGTGAAAAATGATGGAACCTGTGTTATTAGT

GACTTTGGACTGTCCATGAGGCTGACTGGAAATAGACTGGTGCGCCCAGG

GGAGGAAGATAATGCAGCCATAAGCGAGGTTGGCACTATCAGATATATGG

CACCAGAAGTGCTAGAAGGAGCTGTGAACTTGAGGGACTGTGAATCAGCT

TTGAAACAAGTAGACATGTATGCTCTTGGACTAATCTATTGGGAGATATT

TATGAGATGTACAGACCTCTTCCCAGGGGAATCCGTACCAGAGTACCAGA

TGGCTTTTCAGACAGAGGTTGGAAACCATCCCACTTTTGAGGATATGCAG

GTTCTCGTGTCTAGGGAAAAACAGAGACCCAAGTTCCCAGAAGCCTGGAA

AGAAAATAGCCTGGCAGTGAGGTCACTCAAGGAGACAATCGAAGACTGTT

GGGACCAGGATGCAGAGGCTCGGCTTACTGCACAGTGTGCTGAGGAAAGG

ATGGCTGAACTTATGATGATTTGGGAAAGAAACAAATCTGTGAGCCCAAC

AGTCAATCCAATGTCTACTGCTATGCAGAATGAACGTAGG

A nucleic acid sequence encoding an extracellular BMPRII polypeptide (isoform 2) is as follows:

(SEQ ID NO: 74)

TCGCAGAATCAAGAACGGCTATGTGCGTTTAAAGATCCGTATCAGCAAGA

CCTTGGGATAGGTGAGAGTAGAATCTCTCATGAAAATGGGACAATATTAT

GCTCGAAAGGTAGCACCTGCTATGGCCTTTGGGAGAAATCAAAAGGGGAC

ATAAATCTTGTAAAACAAGGATGTTGGTCTCACATTGGAGATCCCCAAGA

GTGTCACTATGAAGAATGTGTAGTAACTACCACTCCTCCCTCAATTCAGA

ATGGAACATACCGTTTCTGCTGTTGTAGCACAGATTTATGTAATGTCAAC

TTTACTGAGAATTTTCCACCTCCTGACACAACACCACTCAGTCCACCTCA

TTCATTTAACCGAGATGAGACA

In certain embodiments, the disclosure relates to single-arm heteromultimer complexes that comprise at least one BMPRII polypeptide, which includes fragments, functional variants, and modified forms thereof. Preferably, BMPRII polypeptides for use in accordance with inventions of the disclosure (e.g., single-arm heteromultimer complexes comprising a BMPRII polypeptide and uses thereof) are soluble (e.g., an extracellular domain of BMPRII). In other preferred embodiments, BMPRII polypeptides for use in accordance with the inventions of the disclosure bind to and/or inhibit (antagonize) activity (e.g., induction of Smad 2/3 and/or Smad 1/5/8 signaling) of one or more TGF-beta superfamily ligands. In some embodiments, single-arm heteromultimer complexes of the disclosure comprise at least one BMPRII polypeptide that is at least 70%, 75%, 80%, 85%, 90%, 95%, 97%, 98%, or 99% identical to the amino acid sequence of SEQ ID NO: 46, 47, 71, 72, 107, 109, 405, or 406. In some embodiments, single-arm heteromultimer complexes of the disclosure consist or consist essentially of at least one BMPRII polypeptide that is at least 70%, 75%, 80%, 85%, 90%, 95%, 97%, 98%, or 99% identical to the amino acid sequence of SEQ ID NO: 46, 47, 71, 72, 107, 109, 405, or 406.

In certain aspects, the present disclosure relates to protein complexes that comprise an MISRII polypeptide. As used herein, the term "MISRII" refers to a family of Müllerian inhibiting substance receptor type II (MISRII) proteins from any species and variants derived from such MISRII proteins by mutagenesis or other modification. Reference to MISRII herein is understood to be a reference to any one of the currently identified forms. Members of the MISRII family are generally transmembrane proteins, composed of a ligand-binding extracellular domain with a cysteine-rich region, a transmembrane domain, and a cytoplasmic domain with predicted serine/threonine kinase activity.

The term "MISRII polypeptide" includes polypeptides comprising any naturally occurring polypeptide of an MISRII family member as well as any variants thereof (including mutants, fragments, fusions, and peptidomimetic forms) that retain a useful activity. Numbering of amino acids for all MISRII-related polypeptides described herein is based on the numbering of the human MISRII precursor protein sequence below (SEQ ID NO: 50), unless specifically designated otherwise.

The canonical human MISRII precursor protein sequence (NCBI Ref Seq NP_065434.1) is as follows:

(SEQ ID NO: 50)

1 MLGSLGLWAL LPTAVEAPPN RRTCVFFEAP GVRGSTKTLG ELLDTGTELP

51 RAIRCLYSRC CFGIWNLTQD RAQVEMQGCR DSDEPGCESL HCDPSPRAHP

101 SPGSTLFTCS CGTDFCNANY SHLPPPGSPG TPGSQGPQAA PGESIWMALV

151 LLGLFLLLLL LLGSIILALL QRKNYRVRGE PVPEPRPDSG RDWSVELQEL

201 PELCFSQVIR EGGHAVVWAG QLQGKLVAIK AFPPRSVAQF QAERALYELP

251 GLQHDHIVRF ITASRGGPGR LLSGPLLVLE LHPKGSLCHY LTQYTSDWGS

301 SLRMALSLAQ GLAFLHEERW QNGQYKPGIA HRDLSSQNVL IREDGSCAIG

351 DLGLALVLPG LTQPPAWTPT QPQGPAAIME AGTQRYMAPE LLDKTLDLQD

401 WGMALRRADI YSLALLLWEI LSRCPDLRPD SSPPPFQLAY EAELGNTPTS

451 DELWALAVQE RRRPYIPSTW RCFATDPDGL RELLEDCWDA DPEARLTAEC

501 VQQRLAALAH PQESHPFPES CPRGCPPLCP EDCTSIPAPT ILPCRPQRSA

551 CHFSVQQGPC SRNPQPACTL SPV

The signal peptide is indicated by a single underline and the extracellular domain is indicated in bold font.

The processed extracellular MISRII polypeptide sequence is as follows:

(SEQ ID NO: 51)

PPNRRTCVFFEAPGVRGSTKTLGELLDTGTELPRAIRCLYSRCCFGIWNLT

QDRAQVEMQGCRDSDEPGCESLHCDPSPRAHPSPGSTLFTCSCGTDFCNAN

YSHLPPPGSPGTPGSQGPQAAPGESIWMAL

A nucleic acid sequence encoding the MISRII precursor protein is shown below (SEQ ID NO: 52), corresponding to nucleotides 81-1799 of Genbank Reference Sequence NM_020547.2. The signal sequence is underlined.

(SEQ ID NO: 52)

ATGCTAGGGTCTTTGGGGCTTTGGGCATTACTTCCCACAGCTGTGGAAGC

ACCCCCAAACAGGCGAACCTGTGTGTTCTTTGAGGCCCCTGGAGTGCGGG

GAAGCACAAAGACACTGGGAGAGCTGCTAGATACAGGCACAGAGCTCCCC

AGAGCTATCCGCTGCCTCTACAGCCGCTGCTGCTTTGGGATCTGGAACCT

GACCCAAGACCGGGCACAGGTGGAAATGCAAGGATGCCGAGACAGTGATG

AGCCAGGCTGTGAGTCCCTCCACTGTGACCCAAGTCCCCGAGCCCACCCC

AGCCCTGGCTCCACTCTCTTCACCTGCTCCTGTGGCACTGACTTCTGCAA

TGCCAATTACAGCCATCTGCCTCCTCCAGGGAGCCCTGGGACTCCTGGCT

CCCAGGGTCCCCAGGCTGCCCCAGGTGAGTCCATCTGGATGGCACTGGTG

CTGCTGGGGCTGTTCCTCCTCCTCCTGCTGCTGCTGGGCAGCATCATCTT

GGCCCTGCTACAGCGAAAGAACTACAGAGTGCGAGGTGAGCCAGTGCCAG

AGCCAAGGCCAGACTCAGGCAGGGACTGGAGTGTGGAGCTGCAGGAGCTG

CCTGAGCTGTGTTTCTCCCAGGTAATCCGGGAAGGAGGTCATGCAGTGGT

TTGGGCCGGGCAGCTGCAAGGAAAACTGGTTGCCATCAAGGCCTTCCCAC

CGAGGTCTGTGGCTCAGTTCCAAGCTGAGAGAGCATTGTACGAACTTCCA

GGCCTACAGCACGACCACATTGTCCGATTTATCACTGCCAGCCGGGGGGG

-continued

TCCTGGCCGCCTGCTCTCTGGGCCCCTGCTGGTACTGGAACTGCATCCCA

AGGGCTCCCTGTGCCACTACTTGACCCAGTACACCAGTGACTGGGGAAGT

TCCCTGCGGATGGCACTGTCCCTGGCCCAGGGCCTGGCATTTCTCCATGA

GGAGCGCTGGCAGAATGGCCAATATAAACCAGGTATTGCCCACCGAGATC

TGAGCAGCCAGAATGTGCTCATTCGGGAAGATGGATCGTGTGCCATTGGA

GACCTGGGCCTTGCCTTGGTGCTCCCTGGCCTCACTCAGCCCCCTGCCTG

GACCCCTACTCAACCACAAGGCCCAGCTGCCATCATGGAAGCTGGCACCC

-continued

AGAGGTACATGGCACCAGAGCTCTTGGACAAGACTCTGGACCTACAGGAT

TGGGGCATGGCCCTCCGACGAGCTGATATTTACTCTTTGGCTCTGCTCCT

GTGGGAGATACTGAGCCGCTGCCCAGATTTGAGGCCTGACAGCAGTCCAC

CACCCTTCCAACTGGCCTATGAGGCAGAACTGGGCAATACCCCTACCTCT

GATGAGCTATGGGCCTTGGCAGTGCAGGAGAGGAGGCGTCCCTACATCCC

ATCCACCTGGCGCTGCTTTGCCACAGACCCTGATGGGCTGAGGGAGCTCC

TAGAAGACTGTTGGGATGCAGACCCAGAAGCACGGCTGACAGCTGAGTGT

GTACAGCAGCGCCTGGCTGCCTTGGCCCATCCTCAAGAGAGCCACCCCTT

TCCAGAGAGCTGTCCACGTGGCTGCCCACCTCTCTGCCCAGAAGACTGTA

CTTCAATTCCTGCCCCTACCATCCTCCCCTGTAGGCCTCAGCGGAGTGCC

TGCCACTTCAGCGTTCAGCAAGGCCCTTGTTCCAGGAATCCTCAGCCTGC

CTGTACCCTTTCTCCTGTG

A nucleic acid sequence encoding the extracellular human MISRII polypeptide is as follows:

(SEQ ID NO: 53)

CCCCCAAACAGGCGAACCTGTGTGTTCTTTGAGGCCCCTGGAGTGCGGGG

AAGCACAAAGACACTGGGAGAGCTGCTAGATACAGGCACAGAGCTCCCCA

GAGCTATCCGCTGCCTCTACAGCCGCTGCTGCTTTGGGATCTGGAACCTG

ACCCAAGACCGGGCACAGGTGGAAATGCAAGGATGCCGAGACAGTGATGA

GCCAGGCTGTGAGTCCCTCCACTGTGACCCAAGTCCCCGAGCCCACCCCA

GCCCTGGCTCCACTCTCTTCACCTGCTCCTGTGGCACTGACTTCTGCAAT

GCCAATTACAGCCATCTGCCTCCTCCAGGGAGCCCTGGGACTCCTGGCTC

CCAGGGTCCCCAGGCTGCCCCAGGTGAGTCCATCTGGATGGCACTG

An alternative isoform of the human MISRII precursor protein sequence, isoform 2 (NCBI Ref Seq NP_001158162.1), is as follows:

(SEQ ID NO: 75)

1 MLGSLGLWAL LPTAVEAPPN RRTCVFFEAP GVRGSTKTLG ELLDTGTELP

051 RAIRCLYSRC CFGIWNLTQD RAQVEMQGCR DSDEPGCESL HCDPSPRAHP

101 SPGSTLFTCS CGTDFCNANY SHLPPPGSPG TPGSQGPQAA PGESIWMALV

151 LLGLFLLLLL LLGSIILALL QRKNYRVRGE PVPEPRPDSG RDWSVELQEL

201 PELCFSQVIR EGGHAVVWAG QLQGKLVAIK AFPPRSVAQF QAERALYELP

251 GLQHDHIVRF ITASRGGPGR LLSGPLLVLE LHPKGSLCHY LTQYTSDWGS

301 SLRMALSLAQ GLAFLHEERW QNGQYKPGIA HRDLSSQNVL IREDGSCAIG

351 DLGLALVLPG LTQPPAWTPT QPQGPAAIME AGTQRYMAPE LLDKTLDLQD

401 WGMALRRADI YSLALLLWEI LSRCPDLRPA VHHPSNWPMR QNWAIPLPLM

451 SYGPWQCRRG GVPTSHPPGA ALPQTLMG

The signal peptide is indicated by a single underline and the extracellular domain is indicated in bold font.

The processed extracellular MISRII polypeptide sequence (isoform 2) is as follows:

(SEQ ID NO: 76)

PPNRRTCVFFEAPGVRGSTKTLGELLDTGTELPRAIRCLYSRCCFGIWNLT

QDRAQVEMQGCRDSDEPGCESLHCDPSPRAHPSPGSTLFTCSCGTDFCNAN

YSHLPPPGSPGTPGSQGPQAAPGESIWMAL

A nucleic acid sequence encoding the MISRII precursor protein (isoform 2) is shown below (SEQ ID NO: 77), corresponding to nucleotides 81-1514 of Genbank Reference Sequence NM_001164690.1. The signal sequence is underlined.

(SEQ ID NO: 77)

ATGCTAGGGTCTTTGGGGCTTTGGGCATTACTTCCCACAGCTGTGGAAGC

ACCCCCAAACAGGCGAACCTGTGTGTTCTTTGAGGCCCCTGGAGTGCGGG

GAAGCACAAAGACACTGGGAGAGCTGCTAGATACAGGCACAGAGCTCCCC

AGAGCTATCCGCTGCCTCTACAGCCGCTGCTGCTTTGGGATCTGGAACCT

GACCCAAGACCGGGCACAGGTGGAAATGCAAGGATGCCGAGACAGTGATG

AGCCAGGCTGTGAGTCCCTCCACTGTGACCCAAGTCCCCGAGCCCACCCC

AGCCCTGGCTCCACTCTCTTCACCTGCTCCTGTGGCACTGACTTCTGCAA

TGCCAATTACAGCCATCTGCCTCCTCCAGGGAGCCCTGGGACTCCTGGCT

CCCAGGGTCCCCAGGCTGCCCCAGGTGAGTCCATCTGGATGGCACTGGTG

CTGCTGGGGCTGTTCCTCCTCCTCCTGCTGCTGCTGGGCAGCATCATCTT

GGCCCTGCTACAGCGAAAGAACTACAGAGTGCGAGGTGAGCCAGTGCCAG

AGCCAAGGCCAGACTCAGGCAGGGACTGGAGTGTGGAGCTGCAGGAGCTG

CCTGAGCTGTGTTTCTCCCAGGTAATCCGGGAAGGAGGTCATGCAGTGGT

TTGGGCCGGGCAGCTGCAAGGAAAACTGGTTGCCATCAAGGCCTTCCCAC

CGAGGTCTGTGGCTCAGTTCCAAGCTGAGAGAGCATTGTACGAACTTCCA

GGCCTACAGCACGACCACATTGTCCGATTTATCACTGCCAGCCGGGGGGG

-continued

TCCTGGCCGCCTGCTCTCTGGGCCCCTGCTGGTACTGGAACTGCATCCCA

AGGGCTCCCTGTGCCACTACTTGACCCAGTACACCAGTGACTGGGGAAGT

TCCCTGCGGATGGCACTGTCCCTGGCCCAGGGCCTGGCATTTCTCCATGA

-continued

GGAGCGCTGGCAGAATGGCCAATATAAACCAGGTATTGCCCACCGAGATC

TGAGCAGCCAGAATGTGCTCATTCGGGAAGATGGATCGTGTGCCATTGGA

GACCTGGGCCTTGCCTTGGTGCTCCCTGGCCTCACTCAGCCCCCTGCCTG

GACCCCTACTCAACCACAAGGCCCAGCTGCCATCATGGAAGCTGGCACCC

AGAGGTACATGGCACCAGAGCTCTTGGACAAGACTCTGGACCTACAGGAT

TGGGGCATGGCCCTCCGACGAGCTGATATTTACTCTTTGGCTCTGCTCCT

GTGGGAGATACTGAGCCGCTGCCCAGATTTGAGGCCTGCAGTCCACCACC

CTTCCAACTGGCCTATGAGGCAGAACTGGGCAATACCCCTACCTCTGATG

AGCTATGGGCCTTGGCAGTGCAGGAGAGGAGGCGTCCCTACATCCCATCC

ACCTGGCGCTGCTTTGCCACAGACCCTGATGGGC

The nucleic acid sequence encoding processed soluble (extracellular) human MISRII polypeptide (isoform 2) is as follows:

(SEQ ID NO: 78)

CCCCCAAACAGGCGAACCTGTGTGTTCTTTGAGGCCCCTGGAGTGCGGGG

AAGCACAAAGACACTGGGAGAGCTGCTAGATACAGGCACAGAGCTCCCCA

GAGCTATCCGCTGCCTCTACAGCCGCTGCTGCTTTGGGATCTGGAACCTG

ACCCAAGACCGGGCACAGGTGGAAATGCAAGGATGCCGAGACAGTGATGA

GCCAGGCTGTGAGTCCCTCCACTGTGACCCAAGTCCCCGAGCCCACCCCA

GCCCTGGCTCCACTCTCTTCACCTGCTCCTGTGGCACTGACTTCTGCAAT

GCCAATTACAGCCATCTGCCTCCTCCAGGGAGCCCTGGGACTCCTGGCTC

CCAGGGTCCCCAGGCTGCCCCAGGTGAGTCCATCTGGATGGCACTG

An alternative isoform of the human MISRII precursor protein sequence, isoform 3 (NCBI Ref Seq NP_001158163.1), is as follows:

(SEQ ID NO: 79)

1 MLGSLGLWAL LPTAVEAPPN RRTCVFFEAP GVRGSTKTLG ELLDTGTELP

51 RAIRCLYSRC CFGIWNLTQD RAQVEMQGCR DSDEPGCESL HCDPSPRAHP

101 SPGSTLFTCS CGTDFCNANY SHLPPPGSPG TPGSQGPQAA PGESIWMALV

151 LLGLFLLLLL LLGSIILALL QRKNYRVRGE PVPEPRPDSG RDWSVELQEL

201 PELCFSQVIR EGGHAVVWAG QLQGKLVAIK AFPPRSVAQF QAERALYELP

251 GLQHDHIVRF ITASRGGPGR LLSGPLLVLE LHPKGSLCHY LTQYTSDWGS

301 SLRMALSLAQ GLAFLHEERW QNGQYKPGIA HRDLSSQNVL IREDGSCAIG

351 DLGLALVLPG LTQPPAWTPT QPQGPAAIME DPDGLRELLE DCWDADPEAR

401 LTAECVQQRL AALAHPQESH PFPESCPRGC PPLCPEDCTS IPAPTILPCR

451 PQRSACHFSV QQGPCSRNPQ PACTLSPV

The signal peptide is indicated by a single underline and the extracellular domain is indicated in bold font.

The processed extracellular MISRII polypeptide sequence (isoform 3) is as follows:

(SEQ ID NO: 80)

PPNRRTCVFFEAPGVRGSTKTLGELLDTGTELPRAIRCLYSRCCFGIWNLT

-continued

QDRAQVEMQGCRDSDEPGCESLHCDPSPRAHPSPGSTLFTCSCGTDFCNAN

YSHLPPPGSPGTPGSQGPQAAPGESIWMAL

A nucleic acid sequence encoding human MISRII precursor protein (isoform 3) is shown below (SEQ ID NO: 81), corresponding to nucleotides 81-1514 of Genbank Reference Sequence NM_001164691.1. The signal sequence is underlined.

(SEQ ID NO: 81)

ATGCTAGGGTCTTTGGGGCTTTGGGCATTACTTCCCACAGCTGTGGAAGCA

CCCCCAAACAGGCGAACCTGTGTGTTCTTTGAGGCCCCTGGAGTGCGGGGA

AGCACAAAGACACTGGGAGAGCTGCTAGATACAGGCACAGAGCTCCCCAGA

GCTATCCGCTGCCTCTACAGCCGCTGCTGCTTTGGGATCTGGAACCTGACC

CAAGACCGGGCACAGGTGGAAATGCAAGGATGCCGAGACAGTGATGAGCCA

GGCTGTGAGTCCCTCCACTGTGACCCAAGTCCCCGAGCCCACCCCAGCCCT

GGCTCCACTCTCTTCACCTGCTCCTGTGGCACTGACTTCTGCAATGCCAAT

TACAGCCATCTGCCTCCTCCAGGGAGCCCTGGGACTCCTGGCTCCCAGGGT

CCCCAGGCTGCCCCAGGTGAGTCCATCTGGATGGCACTGGTGCTGCTGGGG

CTGTTCCTCCTCCTCCTGCTGCTGCTGGGCAGCATCATCTTGGCCCTGCTA

CAGCGAAAGAACTACAGAGTGCGAGGTGAGCCAGTGCCAGAGCCAAGGCCA

GACTCAGGCAGGGACTGGAGTGTGGAGCTGCAGGAGCTGCCTGAGCTGTGT

TTCTCCCAGGTAATCCGGGAAGGAGGTCATGCAGTGGTTTGGGCCGGGCAG

CTGCAAGGAAAACTGGTTGCCATCAAGGCCTTCCCACCGAGGTCTGTGGCT

CAGTTCCAAGCTGAGAGAGCATTGTACGAACTTCCAGGCCTACAGCACGAC

CACATTGTCCGATTTATCACTGCCAGCCGGGGGGGTCCTGGCCGCCTGCTC

-continued

TCTGGGCCCCTGCTGGTACTGGAACTGCATCCCAAGGGCTCCCTGTGCCAC

TACTTGACCCAGTACACCAGTGACTGGGGAAGTTCCCTGCGGATGGCACTG

TCCCTGGCCCAGGGCCTGGCATTTCTCCATGAGGAGCGCTGGCAGAATGGC

CAATATAAACCAGGTATTGCCCACCGAGATCTGAGCAGCCAGAATGTGCTC

-continued

```
ATTCGGGAAGATGGATCGTGTGCCATTGGAGACCTGGGCCTTGCCTTGGTG
CTCCCTGGCCTCACTCAGCCCCCTGCCTGGACCCCTACTCAACCACAAGGC
CCAGCTGCCATCATGGAAGACCCTGATGGGCTGAGGGAGCTCCTAGAAGAC
TGTTGGGATGCAGACCCAGAAGCACGGCTGACAGCTGAGTGTGTACAGCAG
CGCCTGGCTGCCTTGGCCCATCCTCAAGAGAGCCACCCCTTTCCAGAGAGC
TGTCCACGTGGCTGCCCACCTCTCTGCCCAGAAGACTGTACTTCAATTCCT
GCCCCTACCATCCTCCCCTGTAGGCCTCAGCGGAGTGCCTGCCACTTCAGC
GTTCAGCAAGGCCCTTGTTCCAGGAATCCTCAGCCTGCCTGTACCCTTTCT
CCTGTG
```

A nucleic acid sequence encoding processed soluble (extracellular) human MISRII polypeptide (isoform 3) is as follows:

```
                                          (SEQ ID NO: 82)
CCCCCAAACAGGCGAACCTGTGTGTTCTTTGAGGCCCCTGGAGTGCGGGGA
AGCACAAAGACACTGGGAGAGCTGCTAGATACAGGCACAGAGCTCCCCAGA
GCTATCCGCTGCCTCTACAGCCGCTGCTGCTTTGGGATCTGGAACCTGACC
CAAGACCGGGCACAGGTGGAAATGCAAGGATGCCGAGACAGTGATGAGCCA
GGCTGTGAGTCCCTCCACTGTGACCCAAGTCCCCGAGCCCACCCCAGCCCT
GGCTCCACTCTCTTCACCTGCTCCTGTGGCACTGACTTCTGCAATGCCAAT
TACAGCCATCTGCCTCCTCCAGGGAGCCCTGGGACTCCTGGCTCCCAGGGT
CCCCAGGCTGCCCCAGGTGAGTCCATCTGGATGGCACTG
```

In certain embodiments, the disclosure relates to single-arm heteromultimer complexes that comprise at least one MISRII polypeptide, which includes fragments, functional variants, and modified forms thereof. Preferably, MISRII polypeptides for use in accordance with inventions of the disclosure (e.g., single-arm heteromultimer complexes comprising a MISRII polypeptide and uses thereof) are soluble (e.g., an extracellular domain of MISRII). In other preferred embodiments, MISRII polypeptides for use in accordance with the inventions of the disclosure bind to and/or inhibit (antagonize) activity (e.g., induction of Smad 2/3 and/or Smad 1/5/8 signaling) of one or more TGF-beta superfamily ligands. In some embodiments, single-arm heteromultimer complexes of the disclosure comprise at least one MISRII polypeptide that is at least 70%, 75%, 80%, 85%, 90%, 95%, 97%, 98%, or 99% identical to the amino acid sequence of SEQ ID NOs: 50, 51, 75, 76, 79, 80, 110, 112, 407, or 408. In some embodiments, single-arm heteromultimer complexes of the disclosure consist or consist essentially of at least one MISRII polypeptide that is at least 70%, 75%, 80%, 85%, 90%, 95%, 97%, 98%, or 99% identical to the amino acid sequence of SEQ ID NOs: 50, 51, 75, 76, 79, 80, 110, 112, 407, or 408.

In certain aspects, the present disclosure relates to protein complexes that comprise an ALK1 polypeptide. As used herein, the term "ALK1" refers to a family of activin receptor-like kinase-1 proteins from any species and variants derived from such ALK1 proteins by mutagenesis or other modification. Reference to ALK1 herein is understood to be a reference to any one of the currently identified forms. Members of the ALK1 family are generally transmembrane proteins, composed of a ligand-binding extracellular domain with a cysteine-rich region, a transmembrane domain, and a cytoplasmic domain with predicted serine/threonine kinase activity.

The term "ALK1 polypeptide" includes polypeptides comprising any naturally occurring polypeptide of an ALK1 family member as well as any variants thereof (including mutants, fragments, fusions, and peptidomimetic forms) that retain a useful activity. Numbering of amino acids for all ALK1-related polypeptides described herein is based on the numbering of the human ALK1 precursor protein sequence below (SEQ ID NO: 14), unless specifically designated otherwise.

The human ALK1 precursor protein sequence (NCBI Ref Seq NP_000011.2) is as follows:

(SEQ ID NO: 14)

1 MTLGSPRKGL LMLLMALVTQ GDPVKPSRGP LVTCTCESPH CKGPTCRGAW

51 CTVVLVREEG RHPQEHRGCG NLHRELCRGR PTEFVNHYCC DSHLCNHNVS

101 LVLEATQPPS EQPGTDGQLA LILGPVLALL ALVALGVLGL WHVRRRQEKQ

151 RGLHSELGES SLILKASEQG DSMLGDLLDS DCTTGSGSGL PFLVQRTVAR

201 QVALVECVGK GRYGEVWRGL WHGESVAVKI FSSRDEQSWF RETEIYNTVL

251 LRHDNILGFI ASDMTSRNSS TQLWLITHYH EHGSLYDFLQ RQTLEPHLAL

301 RLAVSAACGL AHLHVEIFGT QGKPAIAHRD FKSRNVLVKS NLQCCIADLG

351 LAVMHSQGSD YLDIGNNPRV GTKRYMAPEV LDEQIRTDCF ESYKWTDIWA

401 FGLVLWEIAR RTIVNGIVED YRPPFYDVVP NDPSFEDMKK VVCVDQQTPT

451 IPNRLAADPV LSGLAQMMRE CWYPNPSARL TALRIKKTLQ KISNSPEKPK

501 VIQ

The signal peptide is indicated by a single underline and the extracellular domain is indicated in bold font.

The processed extracellular ALK1 polypeptide sequence is as follows:

```
                                          (SEQ ID NO: 15)
DPVKPSRGPLVTCTCESPHCKGPTCRGAWCTVVLVREEGRHPQEHRGCGNL
HRELCRGRPTEFVNHYCCDSHLCNHNVSLVLEATQPPSEQPGTDGQ
```

A nucleic acid sequence encoding human ALK1 precursor protein is shown below (SEQ ID NO: 16), corresponding to nucleotides 284-1792 of Genbank Reference Sequence NM_000020.2. The signal sequence is underlined.

(SEQ ID NO: 16)

ATGACCTTGGGCTCCCCCAGGAAAGGCCTTCTGATGCTGCTGATGGCCTTG

GTGACCCAGGGAGACCCTGTGAAGCCGTCTCGGGGCCCGCTGGTGACCTGC

ACGTGTGAGAGCCCACATTGCAAGGGGCCTACCTGCCGGGGGGCCTGGTGC

ACAGTAGTGCTGGTGCGGGAGGAGGGGAGGCACCCCCAGGAACATCGGGGC

TGCGGGAACTTGCACAGGGAGCTCTGCAGGGGGCGCCCCACCGAGTTCGTC

AACCACTACTGCTGCGACAGCCACCTCTGCAACCACAACGTGTCCCTGGTG

CTGGAGGCCACCCAACCTCCTTCGGAGCAGCCGGGAACAGATGGCCAGCTG

GCCCTGATCCTGGGCCCCGTGCTGGCCTTGCTGGCCCTGGTGGCCCTGGGT

GTCCTGGGCCTGTGGCATGTCCGACGGAGGCAGGAGAAGCAGCGTGGCCTG

CACAGCGAGCTGGGAGAGTCCAGTCTCATCCTGAAAGCATCTGAGCAGGGC

GACAGCATGTTGGGGGACCTCCTGGACAGTGACTGCACCACAGGGAGTGGC

TCAGGGCTCCCCTTCCTGGTGCAGAGGACAGTGGCACGGCAGGTTGCCTTG

GTGGAGTGTGTGGGAAAAGGCCGCTATGGCGAAGTGTGGCGGGGCTTGTGG

CACGGTGAGAGTGTGGCCGTCAAGATCTTCTCCTCGAGGGATGAACAGTCC

TGGTTCCGGGAGACTGAGATCTATAACACAGTGTTGCTCAGACACGACAAC

ATCCTAGGCTTCATCGCCTCAGACATGACCTCCCGCAACTCGAGCACGCAG

CTGTGGCTCATCACGCACTACCACGAGCACGGCTCCCTCTACGACTTTCTG

CAGAGACAGACGCTGGAGCCCCATCTGGCTCTGAGGCTAGCTGTGTCCGCG

GCATGCGGCCTGGCGCACCTGCACGTGGAGATCTTCGGTACACAGGGCAAA

CCAGCCATTGCCCACCGCGACTTCAAGAGCCGCAATGTGCTGGTCAAGAGC

AACCTGCAGTGTTGCATCGCCGACCTGGGCCTGGCTGTGATGCACTCACAG

GGCAGCGATTACCTGGACATCGGCAACAACCCGAGAGTGGGCACCAAGCGG

TACATGGCACCCGAGGTGCTGGACGAGCAGATCCGCACGGACTGCTTTGAG

TCCTACAAGTGGACTGACATCTGGGCCTTTGGCCTGGTGCTGTGGGAGATT

GCCCGCCGGACCATCGTGAATGGCATCGTGGAGGACTATAGACCACCCTTC

TATGATGTGGTGCCCAATGACCCCAGCTTTGAGGACATGAAGAAGGTGGTG

TGTGTGGATCAGCAGACCCCCACCATCCCTAACCGGCTGGCTGCAGACCCG

GTCCTCTCAGGCCTAGCTCAGATGATGCGGGAGTGCTGGTACCCAAACCCC

TCTGCCCGACTCACCGCGCTGCGGATCAAGAAGACACTACAAAAAATTAGC

AACAGTCCAGAGAAGCCTAAAGTGATTCAA

A nucleic acid sequence encoding processed extracellular ALK1 polypeptide is as follows:

(SEQ ID NO: 17)

GACCCTGTGAAGCCGTCTCGGGGCCCGCTGGTGACCTGCACGTGTGAGAGC

CCACATTGCAAGGGGCCTACCTGCCGGGGGGCCTGGTGCACAGTAGTGCTG

GTGCGGGAGGAGGGGAGGCACCCCCAGGAACATCGGGGCTGCGGGAACTTG

CACAGGGAGCTCTGCAGGGGGCGCCCCACCGAGTTCGTCAACCACTACTGC

-continued

TGCGACAGCCACCTCTGCAACCACAACGTGTCCCTGGTGCTGGAGGCCACC

CAACCTCCTTCGGAGCAGCCGGGAACAGATGGCCAG

In certain embodiments, the disclosure relates to single-arm heteromultimer complexes that comprise at least one ALK1 polypeptide, which includes fragments, functional variants, and modified forms thereof. Preferably, ALK1 polypeptides for use in accordance with inventions of the disclosure (e.g., single-arm heteromultimer complexes comprising an ALK1 polypeptide and uses thereof) are soluble (e.g., an extracellular domain of ALK1). In other preferred embodiments, ALK1 polypeptides for use in accordance with the inventions of the disclosure bind to and/or inhibit (antagonize) activity (e.g., induction of Smad 2/3 and/or Smad 1/5/8 signaling) of one or more TGF-beta superfamily ligands. In some embodiments, single-arm heteromultimer complexes of the disclosure comprise at least one ALK1 polypeptide that is at least 70%, 75%, 80%, 85%, 90%, 95%, 97%, 98%, or 99% identical to the amino acid sequence of SEQ ID NO: 14, 15, 116, 118, 411, or 412. In some embodiments, single-arm heteromultimer complexes of the disclosure consist or consist essentially of at least one ALK1 polypeptide that is at least 70%, 75%, 80%, 85%, 90%, 95%, 97%, 98%, or 99% identical to the amino acid sequence of SEQ ID NO: 14, 15, 116, 118, 411, or 412.

In certain aspects, the present disclosure relates to protein complexes that comprise an ALK2 polypeptide. As used herein, the term "ALK2" refers to a family of activin receptor-like kinase-2 proteins from any species and variants derived from such ALK2 proteins by mutagenesis or other modification. Reference to ALK2 herein is understood to be a reference to any one of the currently identified forms. Members of the ALK2 family are generally transmembrane proteins, composed of a ligand-binding extracellular domain with a cysteine-rich region, a transmembrane domain, and a cytoplasmic domain with predicted serine/threonine kinase activity.

The term "ALK2 polypeptide" includes polypeptides comprising any naturally occurring polypeptide of an ALK2 family member as well as any variants thereof (including mutants, fragments, fusions, and peptidomimetic forms) that retain a useful activity. Numbering of amino acids for all ALK2-related polypeptides described herein is based on the numbering of the human ALK2 precursor protein sequence below (SEQ ID NO: 18), unless specifically designated otherwise.

The human ALK2 precursor protein sequence (NCBI Ref Seq NP_001096.1) is as follows:

(SEQ ID NO: 18)

1 MVDGVMILPV LIMIALPSPS MEDEKPKVNP KLYMCVCEGL SCGNEDHCEG

51 QQCFSSLSIN DGFHVYQKGC FQVYEQGKMT CKTPPSPGQA VECCQGDWCN

101 RNITAQLPTK GKSFPGTQNF HLEVGLIILS VVFAVCLLAC LLGVALRKFK

151 RRNQERLNPR DVEYGTIEGL ITTNVGDSTL ADLLDHSCTS GSGSGLPFLV

201 QRTVARQITL LECVGKGRYG EVWRGSWQGE NVAVKIFSSR DEKSWFRETE

251 LYNTVMLRHE NILGFIASDM TSRHSSTQLW LITHYHEMGS LYDYLQLTTL

301 DTVSCLRIVL SIASGLAHLH IEIFGTQGKP AIAHRDLKSK NILVKKNGQC

351 CIADLGLAVM HSQSTNQLDV GNNPRVGTKR YMAPEVLDET IQVDCFDSYK

401 RVDIWAFGLV LWEVARRMVS NGIVEDYKPP FYDVVPNDPS FEDMRKVVCV

451 DQQRPNIPNR WFSDPTLTSL AKLMKECWYQ NPSARLTALR IKKTLTKIDN

501 SLDKLKTDC

The signal peptide is indicated by a single underline and the extracellular domain is indicated in bold font.

The processed extracellular ALK2 polypeptide sequence is as follows:

(SEQ ID NO: 19)

MEDEKPKVNPKLYMCVCEGLSCGNEDHCEGQQCFSSLSINDGFHVYQKGCF

QVYEQGKMTCKTPPSPGQAVECCQGDWCNRNITAQLPTKGKSFPGTQNFHL

E

A nucleic acid sequence encoding human ALK2 precursor protein is shown below (SEQ ID NO: 20), corresponding to nucleotides 431-1957 of Genbank Reference Sequence NM_001105.4. The signal sequence is underlined.

(SEQ ID NO: 20)

ATGGTAGATGGAGTGATGATTCTTCCTGTGCTTATCATGATTGCTCTCCCC

TCCCCTAGTATGGAAGATGAGAAGCCCAAGGTCAACCCCAAACTCTACATG

TGTGTGTGTGAAGGTCTCTCCTGCGGTAATGAGGACCACTGTGAAGGCCAG

CAGTGCTTTTCCTCACTGAGCATCAACGATGGCTTCCACGTCTACCAGAAA

GGCTGCTTCCAGGTTTATGAGCAGGGAAAGATGACCTGTAAGACCCCGCCG

TCCCCTGGCCAAGCCGTGGAGTGCTGCCAAGGGGACTGGTGTAACAGGAAC

ATCACGGCCCAGCTGCCCACTAAAGGAAAATCCTTCCCTGGAACACAGAAT

TTCCACTTGGAGGTTGGCCTCATTATTCTCTCTGTAGTGTTCGCAGTATGT

CTTTTAGCCTGCCTGCTGGGAGTTGCTCTCCGAAAATTTAAAAGGCGCAAC

CAAGAACGCCTCAATCCCCGAGACGTGGAGTATGGCACTATCGAAGGGCTC

ATCACCACCAATGTTGGAGACAGCACTTTAGCAGATTTATTGGATCATTCG

TGTACATCAGGAAGTGGCTCTGGTCTTCCTTTTCTGGTACAAAGAACAGTG

GCTCGCCAGATTACACTGTTGGAGTGTGTCGGGAAAGGCAGGTATGGTGAG

GTGTGGAGGGGCAGCTGGCAAGGGGAGAATGTTGCCGTGAAGATCTTCTCC

TCCCGTGATGAGAAGTCATGGTTCAGGGAAACGGAATTGTACAACACTGTG

ATGCTGAGGCATGAAAATATCTTAGGTTTCATTGCTTCAGACATGACATCA

AGACACTCCAGTACCCAGCTGTGGTTAATTACACATTATCATGAAATGGGA

-continued

TCGTTGTACGACTATCTTCAGCTTACTACTCTGGATACAGTTAGCTGCCTT

CGAATAGTGCTGTCCATAGCTAGTGGTCTTGCACATTTGCACATAGAGATA

TTTGGGACCCAAGGGAAACCAGCCATTGCCCATCGAGATTTAAAGAGCAAA

AATATTCTGGTTAAGAAGAATGGACAGTGTTGCATAGCAGATTTGGGCCTG

GCAGTCATGCATTCCCAGAGCACCAATCAGCTTGATGTGGGGAACAATCCC

CGTGTGGGCACCAAGCGCTACATGGCCCCCGAAGTTCTAGATGAAACCATC

CAGGTGGATTGTTTCGATTCTTATAAAAGGGTCGATATTTGGGCCTTTGGA

CTTGTTTTGTGGGAAGTGGCCAGGCGGATGGTGAGCAATGGTATAGTGGAG

GATTACAAGCCACCGTTCTACGATGTGGTTCCCAATGACCCAAGTTTTGAA

GATATGAGGAAGGTAGTCTGTGTGGATCAACAAAGGCCAAACATACCCAAC

AGATGGTTCTCAGACCCGACATTAACCTCTCTGGCCAAGCTAATGAAAGAA

TGCTGGTATCAAAATCCATCCGCAAGACTCACAGCACTGCGTATCAAAAAG

ACTTTGACCAAAATTGATAATTCCCTCGACAAATTGAAAACTGACTGT

A nucleic acid sequence encoding the extracellular ALK2 polypeptide is as follows:

(SEQ ID NO: 21)

ATGGAAGATGAGAAGCCCAAGGTCAACCCCAAACTCTACATGTGTGTGTGT

GAAGGTCTCTCCTGCGGTAATGAGGACCACTGTGAAGGCCAGCAGTGCTTT

TCCTCACTGAGCATCAACGATGGCTTCCACGTCTACCAGAAAGGCTGCTTC

CAGGTTTATGAGCAGGGAAAGATGACCTGTAAGACCCCGCCGTCCCCTGGC

CAAGCCGTGGAGTGCTGCCAAGGGGACTGGTGTAACAGGAACATCACGGCC

CAGCTGCCCACTAAAGGAAAATCCTTCCCTGGAACACAGAATTTCCACTTG

GAG

In certain embodiments, the disclosure relates to single-arm heteromultimer complexes that comprise at least one ALK2 polypeptide, which includes fragments, functional variants, and modified forms thereof. Preferably, ALK2 polypeptides for use in accordance with inventions of the disclosure (e.g., single-arm heteromultimer complexes comprising an ALK2 polypeptide and uses thereof) are soluble (e.g., an extracellular domain of ALK2). In other preferred embodiments, ALK2 polypeptides for use in accordance with the inventions of the disclosure bind to and/or inhibit (antagonize) activity (e.g., induction of Smad 2/3 and/or Smad 1/5/8 signaling) of one or more TGF-beta superfamily ligands. In some embodiments, single-arm heteromultimer complexes of the disclosure comprise at least one ALK2 polypeptide that is at least 70%, 75%, 80%, 85%, 90%, 95%, 97%, 98%, or 99% identical to the amino acid sequence of SEQ ID NO: 18, 19, 119, 121, 413, or 414. In some embodiments, single-arm heteromultimer complexes of the disclosure consist or consist essentially of at least one ALK2 polypeptide that is at least 70%, 75%, 80%, 85%, 90%, 95%, 97%, 98%, or 99% identical to the amino acid sequence of SEQ ID NO: 18, 19, 119, 121, 413, or 414.

In certain aspects, the present disclosure relates to protein complexes that comprise an ALK3 polypeptide. As used herein, the term "ALK3" refers to a family of activin receptor-like kinase-3 proteins from any species and variants derived from such ALK3 proteins by mutagenesis or other modification. Reference to ALK3 herein is understood to be a reference to any one of the currently identified forms. Members of the ALK3 family are generally transmembrane proteins, composed of a ligand-binding extracellular domain with a cysteine-rich region, a transmembrane domain, and a cytoplasmic domain with predicted serine/threonine kinase activity.

The term "ALK3 polypeptide" includes polypeptides comprising any naturally occurring polypeptide of an ALK3 family member as well as any variants thereof (including mutants, fragments, fusions, and peptidomimetic forms) that retain a useful activity. Numbering of amino acids for all ALK3-related polypeptides described herein is based on the numbering of the human ALK3 precursor protein sequence below (SEQ ID NO: 22), unless specifically designated otherwise.

The human ALK3 precursor protein sequence (NCBI Ref Seq NP_004320.2) is as follows:

(SEQ ID NO: 22)

1 MPQLYIYIRL LGAYLFIISR VQGQNLDSML HGTGMKSDSD QKKSENGVTL APEDTLPFLK

61 CYCSGHCPDD AINNTCITNG HCFAIIEEDD QGETTLASGC MKYEGSDFQC KDSPKAQLRR

121 TIECCRTNLC NQYLQPTLPP VVIGPFFDGS IRWLVLLISM AVCIIAMIIF SSCFCYKHYC

181 KSISSRRRYN RDLEQDEAFI PVGESLKDLI DQSQSSGSGS GLPLLVQRTI AKQIQMVRQV

241 GKGRYGEVWM GKWRGEKVAV KVFFTTEEAS WFRETEIYQT VLMRHENILG FIAADIKGTG

301 SWTQLYLITD YHENGSLYDF LKCATLDTRA LLKLAYSAAC GLCHLHTEIY GTQGKPAIAH

361 RDLKSKNILI KKNGSCCIAD LGLAVKFNSD TNEVDVPLNT RVGTKRYMAP EVLDESLNKN

421 HFQPYIMADI YSFGLIIWEM ARRCITGGIV EEYQLPYYNM VPSDPSYEDM REVVCVKRLR

481 PIVSNRWNSD ECLRAVLKLM SECWAHNPAS RLTALRIKKT LAKMVESQDV KI

The signal peptide is indicated by a single underline and the extracellular domain is indicated in bold font.

The processed extracellular ALK3 polypeptide sequence is as follows:

(SEQ ID NO: 23)

1 QNLDSMLHGT GMKSDSDQKK SENGVTLAPE DTLPFLKCYC SGHCPDDAIN NTCITNGHCF

61 AIIEEDDQGE TTLASGCMKY EGSDFQCKDS PKAQLRRTIE CCRTNLCNQY LQPTLPPVVI

121 GPFFDGSIR

A nucleic acid sequence encoding human ALK3 precursor protein is shown below (SEQ ID NO: 24), corresponding to nucleotides 549-2144 of Genbank Reference Sequence NM_004329.2. The signal sequence is underlined and the extracellular domain is indicated in bold font.

(SEQ ID NO: 24)

1 ATGCCTCAGC TATACATTTA CATCAGATTA TTGGGAGCCT ATTTGTTCAT CATTTCTCGT

61 GTTCAAGGAC AGAATCTGGA TAGTATGCTT CATGGCACTG GGATGAAATC AGACTCCGAC

121 CAGAAAAAGT CAGAAAATGG AGTAACCTTA GCACCAGAGG ATACCTTGCC TTTTTTAAAG

181 TGCTATTGCT CAGGGCACTG TCCAGATGAT GCTATTAATA ACACATGCAT AACTAATGGA

241 CATTGCTTTG CCATCATAGA AGAAGATGAC CAGGGAGAAA CCACATTAGC TTCAGGGTGT

301 ATGAAATATG AAGGATCTGA TTTTCAGTGC AAAGATTCTC CAAAAGCCCA GCTACGCCGG

361 ACAATAGAAT GTTGTCGGAC CAATTTATGT AACCAGTATT TGCAACCCAC ACTGCCCCCT

-continued

```
421 GTTGTCATAG GTCCGTTTTT TGATGGCAGC ATTCGATGGC TGGTTTTGCT CATTTCTATG
481 GCTGTCTGCA TAATTGCTAT GATCATCTTC TCCAGCTGCT TTTGTTACAA ACATTATTGC
541 AAGAGCATCT CAAGCAGACG TCGTTACAAT CGTGATTTGG AACAGGATGA AGCATTTATT
601 CCAGTTGGAG AATCACTAAA AGACCTTATT GACCAGTCAC AAAGTTCTGG TAGTGGGTCT
661 GGACTACCTT TATTGGTTCA GCGAACTATT GCCAAACAGA TTCAGATGGT CCGGCAAGTT
721 GGTAAAGGCC GATATGGAGA AGTATGGATG GGCAAATGGC GTGGCGAAAA AGTGGCGGTG
781 AAAGTATTCT TTACCACTGA AGAAGCCAGC TGGTTTCGAG AAACAGAAAT CTACCAAACT
841 GTGCTAATGC GCCATGAAAA CATACTTGGT TTCATAGCGG CAGACATTAA AGGTACAGGT
901 TCCTGGACTC AGCTCTATTT GATTACTGAT TACCATGAAA ATGGATCTCT CTATGACTTC
961 CTGAAATGTG CTACACTGGA CACCAGAGCC CTGCTTAAAT TGGCTTATTC AGCTGCCTGT
1021 GGTCTGTGCC ACCTGCACAC AGAAATTTAT GGCACCCAAG GAAAGCCCGC AATTGCTCAT
1081 CGAGACCTAA AGAGCAAAAA CATCCTCATC AAGAAAAATG GGAGTTGCTG CATTGCTGAC
1141 CTGGGCCTTG CTGTTAAATT CAACAGTGAC ACAAATGAAG TTGATGTGCC CTTGAATACC
1201 AGGGTGGGCA CCAAACGCTA CATGGCTCCC GAAGTGCTGG ACGAAAGCCT GAACAAAAAC
1261 CACTTCCAGC CCTACATCAT GGCTGACATC TACAGCTTCG GCCTAATCAT TTGGGAGATG
1321 GCTCGTCGTT GTATCACAGG AGGGATCGTG GAAGAATACC AATTGCCATA TTACAACATG
1381 GTACCGAGTG ATCCGTCATA CGAAGATATG CGTGAGGTTG TGTGTGTCAA ACGTTTGCGG
1441 CCAATTGTGT CTAATCGGTG GAACAGTGAT GAATGTCTAC GAGCAGTTTT GAAGCTAATG
1501 TCAGAATGCT GGGCCCACAA TCCAGCCTCC AGACTCACAG CATTGAGAAT TAAGAAGACG
1561 CTTGCCAAGA TGGTTGAATC CCAAGATGTA AAAATC
```

A nucleic acid sequence encoding the extracellular human ALK3 polypeptide is as follows:

(SEQ ID NO: 25)

```
1 CAGAATCTGG ATAGTATGCT TCATGGCACT GGGATGAAAT CAGACTCCGA CCAGAAAAAG
61 TCAGAAAATG GAGTAACCTT AGCACCAGAG GATACCTTGC CTTTTTTAAA GTGCTATTGC
121 TCAGGGCACT GTCCAGATGA TGCTATTAAT AACACATGCA TAACTAATGG ACATTGCTTT
181 GCCATCATAG AAGAAGATGA CCAGGGAGAA ACCACATTAG CTTCAGGGTG TATGAAATAT
241 GAAGGATCTG ATTTTCAGTG CAAAGATTCT CCAAAAGCCC AGCTACGCCG GACAATAGAA
301 TGTTGTCGGA CCAATTTATG TAACCAGTAT TTGCAACCCA CACTGCCCCC TGTTGTCATA
361 GGTCCGTTTT TTGATGGCAG CATTCGA
```

A general formula for an active (e.g., ligand binding) ALK3 polypeptide is one that comprises a polypeptide that begins at any amino acid position 25-31 (i.e., position 25, 26, 27, 28, 29, 30, or 31) of SEQ ID NO: 22 and ends at any amino acid position 140-152 of SEQ ID NO: 22 (i.e., 140, 141, 142, 143, 144, 145, 146, 147, 148, 149, 150, 151, or 152). See U.S. Pat. No. 8,338,377, the teachings of which are incorporated herein by reference in their entirety.

In certain embodiments, the disclosure relates to single-arm heteromultimer complexes that comprise at least one ALK3 polypeptide, which includes fragments, functional variants, and modified forms thereof. Preferably, ALK3 polypeptides for use in accordance with inventions of the disclosure (e.g., single-arm heteromultimer complexes comprising an ALK3 polypeptide and uses thereof) are soluble (e.g., an extracellular domain of ALK3). In other preferred embodiments, ALK3 polypeptides for use in accordance with the inventions of the disclosure bind to and/or inhibit (antagonize) activity (e.g., induction of Smad 2/3 and/or Smad 1/5/8 signaling) of one or more TGF-beta superfamily ligands. In some embodiments, single-arm heteromultimer complexes of the disclosure comprise at least one ALK3 polypeptide that comprises, consists, or consists essentially of an amino acid beginning at any amino acid position 25-31 (i.e., position 25, 26, 27, 28, 29, 30, or 31) of SEQ ID NO: 22 and ending at any amino acid position 140-153 of SEQ ID NO: 22 (i.e., 140, 141, 142, 143, 144, 145, 146, 147, 148, 149, 150, 151, or 152) of SEQ ID NO: 22. In some embodiments, single-arm heteromultimer complexes of the disclosure comprise at least one ALK3 polypeptide that is at least 70%, 75%, 80%, 85%, 90%, 95%, 97%, 98%, or 99% identical to the amino acid sequence of SEQ ID NO: 22, 23, 122, 124, 415, or 416. In some embodiments, single-arm heteromultimer complexes of the disclosure consist or consist essentially of at least one ALK3 polypeptide that is at least 70%, 75%, 80%, 85%, 90%, 95%, 97%, 98%, or 99% identical to the amino acid sequence of SEQ ID NO: 22, 23, 122, 124, 415, or 416.

In certain aspects, the present disclosure relates to protein complexes that comprise an ALK4 polypeptide. As used herein, the term "ALK4" refers to a family of activin receptor-like kinase-4 proteins from any species and variants derived from such ALK4 proteins by mutagenesis or other modification. Reference to ALK4 herein is understood to be a reference to any one of the currently identified forms. Members of the ALK4 family are generally transmembrane proteins, composed of a ligand-binding extracellular domain with a cysteine-rich region, a transmembrane domain, and a cytoplasmic domain with predicted serine/threonine kinase activity.

The term "ALK4 polypeptide" includes polypeptides comprising any naturally occurring polypeptide of an ALK4 family member as well as any variants thereof (including mutants, fragments, fusions, and peptidomimetic forms) that retain a useful activity. Numbering of amino acids for all ALK4-related polypeptides described herein is based on the numbering of the human ALK4 precursor protein sequence below (SEQ ID NO: 26), unless specifically designated otherwise.

The protein sequence of canonical human ALK4 precursor (isoform A, NCBI Ref Seq NP_004293) is as follows:

```
                                                        (SEQ ID NO: 26)
  1 MAESAGASSF FPLVVLLLAG SGGSGPRGVQ ALLCACTSCL QANYTCETDG ACMVSIFNLD

 61 GMEHHVRTCI PKVELVPAGK PFYCLSSEDL RNTHCCYTDY CNRIDLRVPS GHLKEPEHPS

121 MWGPVELVGI IAGPVFLLFL IIIIVFLVIN YHQRVYHNRQ RLDMEDPSCE MCLSKDKTLQ

181 DLVYDLSTSG SGSGLPLFVQ RTVARTIVLQ EIIGKGRFGE VWRGRWRGGD VAVKIFSSRE

241 ERSWFREAEI YQTVMLRHEN ILGFIAADNK DNGTWTQLWL VSDYHEHGSL FDYLNRYTVT

301 IEGMIKLALS AASGLAHLHM EIVGTQGKPG IAHRDLKSKN ILVKKNGMCA IADLGLAVRH

361 DAVTDTIDIA PNQRVGTKRY MAPEVLDETI NMKHFDSFKC ADIYALGLVY WEIARRCNSG

421 GVHEEYQLPY YDLVPSDPSI EEMRKVVCDQ KLRPNIPNWW QSYEALRVMG KMMRECWYAN

481 GAARLTALRI KKTLSQLSVQ EDVKI
```

The signal peptide is indicated by a single underline and the extracellular domain is indicated in bold font.

The processed extracellular human ALK4 polypeptide sequence is as follows:

```
                                                        (SEQ ID NO: 27)
SGPRGVQALLCACTSCLQANYTCETDGACMVSIFNLDGMEHHVRTCIPKV

ELVPAGKPFYCLSSEDLRNTHCCYTDYCNRIDLRVPSGHLKEPEHPSMWG

PVE
```

A nucleic acid sequence encoding the ALK4 precursor protein is shown below (SEQ ID NO: 28), corresponding to nucleotides 78-1592 of Genbank Reference Sequence NM_004302.4. The signal sequence is underlined and the extracellular domain is indicated in bold font.

```
                                                        (SEQ ID NO: 28)
ATGGCGGAGTCGGCCGGAGCCTCCTCCTTCTTCCCCCTTGTTGTCCTCCT

GCTCGCCGGCAGCGGCGGGTCCGGGCCCCGGGGGGTCCAGGCTCTGCTGT

GTGCGTGCACCAGCTGCCTCCAGGCCAACTACACGTGTGAGACAGATGGG

GCCTGCATGGTTTCCATTTTCAATCTGGATGGGATGGAGCACCATGTGCG

CACCTGCATCCCCAAAGTGGAGCTGGTCCCTGCCGGGAAGCCCTTCTACT

GCCTGAGCTCGGAGGACCTGCGCAACACCCACTGCTGCTACACTGACTAC

TGCAACAGGATCGACTTGAGGGTGCCCAGTGGTCACCTCAAGGAGCCTGA

GCACCCGTCCATGTGGGGCCCGGTGGAGCTGGTAGGCATCATCGCCGGCC

CGGTGTTCCTCCTGTTCCTCATCATCATCATTGTTTTCCTTGTCATTAAC

TATCATCAGCGTGTCTATCACAACCGCCAGAGACTGGACATGGAAGATCC

CTCATGTGAGATGTGTCTCTCCAAAGACAAGACGCTCCAGGATCTTGTCT

ACGATCTCTCCACCTCAGGGTCTGGCTCAGGGTTACCCCTCTTTGTCCAG

CGCACAGTGGCCCGAACCATCGTTTTACAAGAGATTATTGGCAAGGGTCG

GTTTGGGGAAGTATGGCGGGGCCGCTGGAGGGGTGGTGATGTGGCTGTGA

AAATATTCTCTTCTCGTGAAGAACGGTCTTGGTTCAGGGAAGCAGAGATA

TACCAGACGGTCATGCTGCGCCATGAAAACATCCTTGGATTTATTGCTGC

TGACAATAAAGATAATGGCACCTGGACACAGCTGTGGCTTGTTTCTGACT

ATCATGAGCACGGGTCCCTGTTTGATTATCTGAACCGGTACACAGTGACA

ATTGAGGGGATGATTAAGCTGGCCTTGTCTGCTGCTAGTGGGCTGGCACA

CCTGCACATGGAGATCGTGGGCACCCAAGGGAAGCCTGGAATTGCTCATC

GAGACTTAAAGTCAAAGAACATTCTGGTGAAGAAAAATGGCATGTGTGCC

ATAGCAGACCTGGGCCTGGCTGTCCGTCATGATGCAGTCACTGACACCAT

TGACATTGCCCCGAATCAGAGGGTGGGGACCAAACGATACATGGCCCCTG

AAGTACTTGATGAAACCATTAATATGAAACACTTTGACTCCTTTAAATGT

GCTGATATTTATGCCCTCGGGCTTGTATATTGGGAGATTGCTCGAAGATG

CAATTCTGGAGGAGTCCATGAAGAATATCAGCTGCCATATTACGACTTAG

TGCCCTCTGACCCTTCCATTGAGGAAATGCGAAAGGTTGTATGTGATCAG

AAGCTGCGTCCCAACATCCCCAACTGGTGGCAGAGTTATGAGGCACTGCG

GGTGATGGGGAAGATGATGCGAGAGTGTTGGTATGCCAACGGCGCAGCCC
```

GCCTGACGGCCCTGCGCATCAAGAAGACCCTCTCCCAGCTCAGCGTGCAG

GAAGACGTGAAGATC

A nucleic acid sequence encoding the extracellular ALK4 polypeptide is as follows:

(SEQ ID NO: 29)
TCCGGGCCCCGGGGGGTCCAGGCTCTGCTGTGTGCGTGCACCAGCTGCCT

CCAGGCCAACTACACGTGTGAGACAGATGGGGCCTGCATGGTTTCCATTT

TCAATCTGGATGGGATGGAGCACCATGTGCGCACCTGCATCCCCAAAGTG

GAGCTGGTCCCTGCCGGGAAGCCCTTCTACTGCCTGAGCTCGGAGGACCT

GCGCAACACCCACTGCTGCTACACTGACTACTGCAACAGGATCGACTTGA

GGGTGCCCAGTGGTCACCTCAAGGAGCCTGAGCACCCGTCCATGTGGGGC

CCGGTGGAG

An alternative isoform of human ALK4 precursor, isoform B (NCBI Ref Seq NP_064732.3), is as follows:

(SEQ ID NO: 83)
```
  1 MVSIFNLDGM EHHVRTCIPK VELVPAGKPF YCLSSEDLRN THCCYTDYCN RIDLRVPSGH

 61 LKEPEHPSMW GPVELVGIIA GPVFLLFLII IIVFLVINYH QRVYHNRQRL DMEDPSCEMC

121 LSKDKTLQDL VYDLSTSGSG SGLPLFVQRT VARTIVLQEI IGKGRFGEVW RGRWRGGDVA

181 VKIFSSREER SWFREAEIYQ TVMLRHENIL GFIAADNKDN GTWTQLWLVS DYHEHGSLFD

241 YLNRYTVTIE GMIKLALSAA SGLAHLHMEI VGTQGKPGIA HRDLKSKNIL VKKNGMCAIA

301 DLGLAVRHDA VTDTIDIAPN QRVGTKRYMA PEVLDETINM KHFDSFKCAD IYALGLVYWE

361 IARRCNSGGV HEEYQLPYYD LVPSDPSIEE MRKVVCDQKL RPNIPNWWQS YEALRVMGKM

421 MRECWYANGA ARLTALRIKK TLSQLSVQED VKI
```

The extracellular domain is indicated in bold font.

The extracellular ALK4 polypeptide sequence (isoform B) is as follows:

(SEQ ID NO: 84)
MVSIFNLDGMEHHVRTCIPKVELVPAGKPFYCLSSEDLRNTHCCYTDYCN

RIDLRVPSGHLKEPEHPSMWGPVE

A nucleic acid sequence encoding isoform B of the ALK4 precursor protein is shown below (SEQ ID NO: 85), corresponding to nucleotides 186-1547 of Genbank Reference Sequence NM_020327.3. The extracellular domain is indicated in bold font.

(SEQ ID NO: 85)
ATGGTTTCCATTTTCAATCTGGATGGGATGGAGCACCATGTGCGCACCTG

CATCCCCAAAGTGGAGCTGGTCCCTGCCGGGAAGCCCTTCTACTGCCTGA

GCTCGGAGGACCTGCGCAAGACCCACTGCTGCTAGACTGACTACTGCAAG

AGGATCGACTTGAGGGTGCCCAGTGGTCACCTCAAGGAGCCTGAGCACCC

GTCCATGTGGGGCCCGGTGGAGCTGGTAGGCATCATCGCCGGCCCGGTGT

TCCTCCTGTTCCTCATCATCATCATTGTTTTCCTTGTCATTAACTATCAT

CAGCGTGTCTATCACAACCGCCAGAGACTGGACATGGAAGATCCCTCATG

TGAGATGTGTCTCTCCAAAGACAAGACGCTCCAGGATCTTGTCTACGATC

TCTCCACCTCAGGGTCTGGCTCAGGGTTACCCCTCTTTGTCCAGCGCACA

GTGGCCCGAACCATCGTTTTACAAGAGATTATTGGCAAGGGTCGGTTTGG

GGAAGTATGGCGGGGCCGCTGGAGGGGTGGTGATGTGGCTGTGAAAATAT

TCTCTTCTCGTGAAGAACGGTCTTGGTTCAGGGAAGCAGAGATATACCAG

ACGGTCATGCTGCGCCATGAAAACATCCTTGGATTTATTGCTGCTGACAA

TAAAGATAATGGCACCTGGACACAGCTGTGGCTTGTTTCTGACTATCATG

AGCACGGGTCCCTGTTTGATTATCTGAACCGGTACACAGTGACAATTGAG

GGGATGATTAAGCTGGCCTTGTCTGCTGCTAGTGGGCTGGCACACCTGCA

CATGGAGATCGTGGGCACCCAAGGGAAGCCTGGAATTGCTCATCGAGACT

TAAAGTCAAAGAACATTCTGGTGAAGAAAAATGGCATGTGTGCCATAGCA

GACCTGGGCCTGGCTGTCCGTCATGATGCAGTCACTGACACCATTGACAT

TGCCCCGAATCAGAGGGTGGGGACCAAACGATACATGGCCCCTGAAGTAC

TTGATGAAACCATTAATATGAAACACTTTGACTCCTTTAAATGTGCTGAT

ATTTATGCCCTCGGGCTTGTATATTGGGAGATTGCTCGAAGATGCAATTC

TGGAGGAGTCCATGAAGAATATCAGCTGCCATATTACGACTTAGTGCCCT

CTGACCCTTCCATTGAGGAAATGCGAAAGGTTGTATGTGATCAGAAGCTG

CGTCCCAACATCCCCAACTGGTGGCAGAGTTATGAGGCACTGCGGGTGAT

GGGGAAGATGATGCGAGAGTGTTGGTATGCCAACGGCGCAGCCCGCCTGA

CGGCCCTGCGCATCAAGAAGACCCTCTCCCAGCTCAGCGTGCAGGAAGAC

GTGAAGATC

A nucleic acid sequence encoding the extracellular domain of ALK4 polypeptide (isoform B) is as follows:

(SEQ ID NO: 86)
ATGGTTTCCATTTTCAATCTGGATGGGATGGAGCACCATGTGCGCACCTG

CATCCCCAAAGTGGAGCTGGTCCCTGCCGGGAAGCCCTTCTACTGCCTGA

GCTCGGAGGACCTGCGCAACACCCACTGCTGCTACACTGACTACTGCAAC

AGGATCGACTTGAGGGTGCCCAGTGGTCACCTCAAGGAGCCTGAGCACCC

GTCCATGTGGGGCCCGGTGGAG

In certain embodiments, the disclosure relates to single-arm heteromultimer complexes that comprise at least one ALK4 polypeptide, which includes fragments, functional variants, and modified forms thereof. Preferably, ALK4 polypeptides for use in accordance with inventions of the disclosure (e.g., single-arm heteromultimer complexes comprising an ALK4 polypeptide and uses thereof) are soluble (e.g., an extracellular domain of ALK4). In other preferred embodiments, ALK4 polypeptides for use in accordance with the inventions of the disclosure bind to and/or inhibit (antagonize) activity (e.g., induction of Smad 2/3 and/or Smad 1/5/8 signaling) of one or more TGF-beta superfamily ligands. In some embodiments, single-arm heteromultimer complexes of the disclosure comprise at least one ALK4 polypeptide that is at least 70%, 75%, 80%, 85%, 90%, 95%, 97%, 98%, or 99% identical to the amino acid sequence of SEQ ID NO: 26, 27, 83, 84, 125, 127, 417, or 418. In some embodiments, single-arm heteromultimer complexes of the disclosure consist or consist essentially of at least one ALK4 polypeptide that is at least 70%, 75%, 80%, 85%, 90%, 95%, 97%, 98%, or 99% identical to the amino acid sequence of SEQ ID NO: 26, 27, 83, 84, 125, 127, 417, or 418.

In certain aspects, the present disclosure relates to protein complexes that comprise an ALK5 polypeptide. As used herein, the term "ALK5" refers to a family of activin receptor-like kinase-5 proteins from any species and variants derived from such ALK4 proteins by mutagenesis or other modification. Reference to ALK5 herein is understood to be a reference to any one of the currently identified forms. Members of the ALK5 family are generally transmembrane proteins, composed of a ligand-binding extracellular domain with a cysteine-rich region, a transmembrane domain, and a cytoplasmic domain with predicted serine/threonine kinase activity.

The term "ALK5 polypeptide" includes polypeptides comprising any naturally occurring polypeptide of an ALK5 family member as well as any variants thereof (including mutants, fragments, fusions, and peptidomimetic forms) that retain a useful activity. Numbering of amino acids for all ALK5-related polypeptides described herein is based on the numbering of the human ALK5 precursor protein sequence below (SEQ ID NO: 30), unless specifically designated otherwise.

The canonical human ALK5 precursor protein sequence (NCBI Ref Seq NP_004603.1) is as follows:

The signal peptide is indicated by a single underline and the extracellular domain is indicated in bold font.

The processed extracellular ALK5 polypeptide sequence is as follows:

```
                                          (SEQ ID NO: 31)
AALLPGATALQCFCHLCTKDNFTCVTDGLCFVSVTETTDKVIHNSMCIAE

IDLIPRDRPFVCAPSSKTGSVTTTYCCNQDHCNKIELPTTVKSSPGLGPV

EL
```

A nucleic acid sequence encoding the ALK5 precursor protein is shown below (SEQ ID NO: 32), corresponding to nucleotides 77-1585 of Genbank Reference Sequence NM_004612.2. The signal sequence is underlined and the extracellular domain is indicated in bold font.

```
                                          (SEQ ID NO: 32)
ATGGAGGCGGCGGTCGCTGCTCCGCGTCCCCGGCTGCTCCTCCTCGTGCT

GGCGGCGGCGGCGGCGGCGGCGGCGGCGCTGCTCCCGGGGGCGACGGCGT

TACAGTGTTTCTGCCACCTCTGTACAAAAGACAATTTTACTTGTGTGACA

GATGGGCTCTGCTTTGTCTCTGTCACAGAGACCACAGACAAAGTTATACA

CAACAGCATGTGTATAGCTGAAATTGACTTAATTCCTCGAGATAGGCCGT

TTGTATGTGCACCCTCTTCAAAAACTGGGTCTGTGACTACAACATATTGC

TGCAATCAGGACCATTGCAATAAAATAGAACTTCCAACTACTGTAAAGTC

ATCACCTGGCCTTGGTCCTGTGGAACTGGCAGCTGTCATTGCTGGACCAG

TGTGCTTCGTCTGCATCTCACTCATGTTGATGGTCTATATCTGCCACAAC

CGCACTGTCATTCACCATCGAGTGCCAAATGAAGAGGACCCTTCATTAGA

TCGCCCTTTTATTTCAGAGGGTACTACGTTGAAAGACTTAATTTATGATA

TGACAACGTCAGGTTCTGGCTCAGGTTTACCATTGCTTGTTCAGAGAACA

ATTGCGAGAACTATTGTGTTACAAGAAAGCATTGGCAAAGGTCGATTTGG

AGAAGTTTGGAGAGGAAAGTGGCGGGGAGAAGAAGTTGCTGTTAAGATAT

TCTCCTCTAGAGAAGAACGTTCGTGGTTCCGTGAGGCAGAGATTTATCAA

ACTGTAATGTTACGTCATGAAAACATCCTGGGATTTATAGCAGCAGACAA

TAAAGACAATGGTACTTGGACTCAGCTCTGGTTGGTGTCAGATTATCATG

AGCATGGATCCCTTTTTGATTACTTAAACAGATACACAGTTACTGTGGAA
```

```
                                          (SEQ ID NO: 30)
1    MEAAVAAPRP RLLLLVLAAA AAAAAALLPG ATALQCFCHL CTKDNFTCVT DGLCFVSVTE

61   TTDKVIHNSM CIAEIDLIPR DRPFVCAPSS KTGSVTTTYC CNQDHCNKIE LPTTVKSSPG

121  LGPVELAAVI AGPVCFVCIS LMLMVYICHN RTVIHHRVPN EEDPSLDRPF ISEGTTLKDL

181  IYDMTTSGSG SGLPLLVQRT IARTIVLQES IGKGRFGEVW RGKWRGEEVA VKIFSSREER

241  SWFREAEIYQ TVMLRHENIL GFIAADNKDN GTWTQLWLVS DYHEHGSLFD YLNRYTVIVE

301  GMIKLALSTA SGLAHLHMEI VGTQGKPAIA HRDLKSKNIL VKKNGTCCIA DLGLAVRHDS

361  ATDTIDIAPN HRVGTKRYMA PEVLDDSINM KHFESFKRAD IYAMGLVFWE IARRCSIGGI

421  HEDYQLPYYD LVPSDPSVEE MRKVVCEQKL RPNIPNRWQS CEALRVMAKI MRECWYANGA

481  ARLTALRIKK TLSQLSQQEG IKM
```

-continued

```
GGAATGATAAAACTTGCTCTGTCCACGGCGAGCGGTCTTGCCCATCTTCA
CATGGAGATTGTTGGTACCCAAGGAAAGCCAGCCATTGCTCATAGAGATT
TGAAATCAAAGAATATCTTGGTAAAGAAGAATGGAACTTGCTGTATTGCA
GACTTAGGACTGGCAGTAAGACATGATTCAGCCACAGATACCATTGATAT
TGCTCCAAACCACAGAGTGGGAACAAAAAGGTACATGGCCCCTGAAGTTC
TCGATGATTCCATAAATATGAAACATTTTGAATCCTTCAAACGTGCTGAC
ATCTATGCAATGGGCTTAGTATTCTGGGAAATTGCTCGACGATGTTCCAT
TGGTGGAATTCATGAAGATTACCAACTGCCTTATTATGATCTTGTACCTT
CTGACCCATCAGTTGAAGAAATGAGAAAAGTTGTTTGTGAACAGAAGTTA
AGGCCAAATATCCCAAACAGATGGCAGAGCTGTGAAGCCTTGAGAGTAAT
GGCTAAAATTATGAGAGAATGTTGGTATGCCAATGGAGCAGCTAGGCTTA
CAGCATTGCGGATTAAGAAAACATTATCGCAACTCAGTCAACAGGAAGGC
ATCAAAATG
```

A nucleic acid sequence encoding the extracellular human ALK5 polypeptide is as follows:

```
                                        (SEQ ID NO: 33)
GCGGCGCTGCTCCCGGGGGCGACGGCGTTACAGTGTTTCTGCCACCTCTG
TACAAAAGACAATTTTACTTGTGTGACAGATGGGCTCTGCTTTGTCTCTG
TCACAGAGACCACAGACAAAGTTATACACAACAGCATGTGTATAGCTGAA
ATTGACTTAATTCCTCGAGATAGGCCGTTTGTATGTGCACCCTCTTCAAA
AACTGGGTCTGTGACTACAACATATTGCTGCAATCAGGACCATTGCAATA
AAATAGAACTTCCAACTACTGTAAAGTCATCACCTGGCCTTGGTCCTGTG
GAACTG
```

An alternative isoform of the human ALK5 precursor protein sequence, isoform 2 (NCBI Ref Seq XP_005252207.1), is as follows:

(SEQ ID NO: 87)

1 MEAAVAAPRP RLLLLVLAAA AAAAALLPG ATALQCFCHL CTKDNFTCVT DGLCFVSVTE

61 TTDKVIHNSM CIAEIDLIPR DRPFVCAPSS KTGSVTTTYC CNQDHCNKIE LPTTGPFSVK

121 SSPGLGPVEL AAVIAGPVCF VCISLMLMVY ICHNRTVIHH RVPNEEDPSL DRPFISEGTT

181 LKDLIYDMTT SGSGSGLPLL VQRTIARTIV LQESIGKGRF GEVWRGKWRG EEVAVKIFSS

241 REERSWFREA EIYQTVMLRH ENILGFIAAD NKDNGTWTQL WLVSDYHEHG SLFDYLNRYT

301 VTVEGMIKLA LSTASGLAHL HMEIVGTQGK PAIAHRDLKS KNILVKKNGT CCIADLGLAV

361 RHDSATDTID IAPNHRVGTK RYMAPEVLDD SINMKHFESF KRADIYAMGL VFWEIARRCS

421 IGGIHEDYQL PYYDLVPSDP SVEEMRKVVC EQKLRPNIPN RWQSCEALRV MAKIMRECWY

481 ANGAARLTAL RIKKTLSQLS QQEGIKM

The signal peptide is indicated by a single underline and the extracellular domain is indicated in bold font.

The processed extracellular ALK5 polypeptide sequence (isoform 2) is as follows:

```
                                        (SEQ ID NO: 88)
AALLPGATALQCFCHLCTKDNFTCVTDGLCFVSVTETTDKVIHNSMCIAE
IDLIPRDRPFVCAPSSKTGSVTTTYCCNQDHCNKIELPTTGPFSVKSSPG
LGPVEL
```

A nucleic acid sequence encoding human ALK5 precursor protein (isoform 2) is shown below (SEQ ID NO: 89), corresponding to nucleotides 77-1597 of Genbank Reference Sequence XM_005252150.1. The signal sequence is underlined and the extracellular domain is indicated in bold font.

(SEQ ID NO: 89)

ATGGAGGCGGCGGTCGCTGCTCCGCGTCCCCGGCTGCTCCTCCTCGTGCT

GGCGGCGGCGGCGGCGGCGGCGGCGGCGCTGCTCCCGGGGGCGACGGCGT

TACAGTGTTTCTGCCACCTCTGTACAAAAGACAATTTTACTTGTGTGACA

GATGGGCTCTGCTTTGTCTCTGTCACAGAGACCACAGACAAAGTTATACA

CAACAGCATGTGTATAGCTGAAATTGACTTAATTCCTCGAGATAGGCCGT

TTGTATGTGCACCCTCTTCAAAAACTGGGTCTGTGACTACAACATATTGC

TGCAATCAGGACCATTGCAATAAAATAGAACTTCCAACTACTGGCCCTTT

TTCAGTAAAGTCATCACCTGGCCTTGGTCCTGTGGAACTGGCAGCTGTCA

TTGCTGGACCAGTGTGCTTCGTCTGCATCTCACTCATGTTGATGGTCTAT

ATCTGCCACAACCGCACTGTCATTCACCATCGAGTGCCAAATGAAGAGGA

CCCTTCATTAGATCGCCCTTTTATTTCAGAGGGTACTACGTTGAAAGACT

TAATTTATGATATGACAACGTCAGGTTCTGGCTCAGGTTTACCATTGCTT

GTTCAGAGAACAATTGCGAGAACTATTGTGTTACAAGAAAGCATTGGCAA

AGGTCGATTTGGAGAAGTTTGGAGAGGAAAGTGGCGGGGAGAAGAAGTTG

CTGTTAAGATATTCTCCTCTAGAGAAGAACGTTCGTGGTTCCGTGAGGCA

GAGATTTATCAAACTGTAATGTTACGTCATGAAAACATCCTGGGATTTAT

AGCAGCAGACAATAAAGACAATGGTACTTGGACTCAGCTCTGGTTGGTGT

-continued

```
CAGATTATCATGAGCATGGATCCCTTTTTGATTACTTAAACAGATACACA
GTTACTGTGGAAGGAATGATAAAACTTGCTCTGTCCACGGCGAGCGGTCT
TGCCCATCTTCACATGGAGATTGTTGGTACCCAAGGAAAGCCAGCCATTG
```

-continued

CTCATAGAGATTTGAAATCAAAGAATATCTTGGTAAAGAAGAATGGAACT

TGCTGTATTGCAGACTTAGGACTGGCAGTAAGACATGATTCAGCCACAGA

TACCATTGATATTGCTCCAAACCACAGAGTGGGAACAAAAAGGTACATGG

CCCCTGAAGTTCTCGATGATTCCATAAATATGAAACATTTTGAATCCTTC

AAACGTGCTGACATCTATGCAATGGGCTTAGTATTCTGGGAAATTGCTCG

ACGATGTTCCATTGGTGGAATTCATGAAGATTACCAACTGCCTTATTATG

ATCTTGTACCTTCTGACCCATCAGTTGAAGAAATGAGAAAAGTTGTTTGT

GAACAGAAGTTAAGGCCAAATATCCCAAACAGATGGCAGAGCTGTGAAGC

CTTGAGAGTAATGGCTAAAATTATGAGAGAATGTTGGTATGCCAATGGAG

CAGCTAGGCTTACAGCATTGCGGATTAAGAAAACATTATCGCAACTCAGT

CAACAGGAAGGCATCAAAATG

A nucleic acid sequence encoding the processed extracellular ALK5 polypeptide is as follows:

(SEQ ID NO: 90)

GCGGCGCTGCTCCCGGGGGCGACGGCGTTACAGTGTTTCTGCCACCTCTG

TACAAAAGACAATTTTACTTGTGTGACAGATGGGCTCTGCTTTGTCTCTG

TCACAGAGACCACAGACAAAGTTATACACAACAGCATGTGTATAGCTGAA

ATTGACTTAATTCCTCGAGATAGGCCGTTTGTATGTGCACCCTCTTCAAA

AACTGGGTCTGTGACTACAACATATTGCTGCAATCAGGACCATTGCAATA

AAATAGAACTTCCAACTACTGGCCCTTTTTCAGTAAAGTCATCACCTGGC

CTTGGTCCTGTGGAACTG polypeptide that is at least 70%, 75%, 80%, 85%, 90%, 95%, 97%, 98%, or 99% identical to the amino acid sequence of SEQ ID NO: 30, 31, 87, 88, 128, 130, 419, or 420. In some embodiments, single-arm heteromultimer complexes of the disclosure consist or consist essentially of at least one ALK5 polypeptide that is at least 70%, 75%, 80%, 85%, 90%, 95%, 97%, 98%, or 99% identical to the amino acid sequence of SEQ ID NO: 30, 31, 87, 88, 128, 130, 419, or 420.

In certain aspects, the present disclosure relates to protein complexes that comprise an ALK6 polypeptide. As used herein, the term "ALK6" refers to a family of activin receptor-like kinase-6 proteins from any species and variants derived from such ALK6 proteins by mutagenesis or other modification. Reference to ALK6 herein is understood to be a reference to any one of the currently identified forms. Members of the ALK6 family are generally transmembrane proteins, composed of a ligand-binding extracellular domain with a cysteine-rich region, a transmembrane domain, and a cytoplasmic domain with predicted serine/threonine kinase activity.

The term "ALK6 polypeptide" includes polypeptides comprising any naturally occurring polypeptide of an ALK6 family member as well as any variants thereof (including mutants, fragments, fusions, and peptidomimetic forms) that retain a useful activity. Numbering of amino acids for all ALK6-related polypeptides described herein is based on the numbering of the human ALK6 precursor protein sequence below (SEQ ID NO: 34), unless specifically designated otherwise.

The canonical human ALK6 precursor protein sequence (NCBI Ref Seq NP_001194.1) is as follows:

(SEQ ID NO: 34)

1 MLLRSAGKLN VGTKKEDGES TAPTPRPKVL RCKCHHHCPE DSVNNICSTD GYCFTMIEED

61 DSGLPVVTSG CLGLEGSDFQ CRDTPIPHQR RSIECCTERN ECNKDLHPTL PPLKNRDFVD

121 GPIHHRALLI SVTVCSLLLV LIILFCYFRY KRQETRPRYS IGLEQDETYI PPGESLRDLI

181 EQSQSSGSGS GLPLLVQRTI AKQIQMVKQI GKGRYGEVWM GKWRGEKVAV KVFFTTEEAS

241 WFRETEIYQT VLMRHENILG FIAADIKGTG SWTQLYLITD YHENGSLYDY LKSTTLDAKS

301 MLKLAYSSVS GLCHLHTEIF STQGKPAIAH RDLKSKNILV KKNGTCCIAD LGLAVKFISD

361 TNEVDIPPNT RVGTKRYMPP EVLDESLNRN HFQSYIMADM YSFGLILWEV ARRCVSGGIV

421 EEYQLPYHDL VPSDPSYEDM REIVCIKKLR PSFPNRWSSD ECLRQMGKLM TECWAHNPAS

481 RLTALRVKKT LAKMSESQDI KL

In certain embodiments, the disclosure relates to single-arm heteromultimer complexes that comprise at least one ALK5 polypeptide, which includes fragments, functional variants, and modified forms thereof. Preferably, ALK5 polypeptides for use in accordance with inventions of the disclosure (e.g., single-arm heteromultimer complexes comprising an ALK5 polypeptide and uses thereof) are soluble (e.g., an extracellular domain of ALK5). In other preferred embodiments, ALK5 polypeptides for use in accordance with the inventions of the disclosure bind to and/or inhibit (antagonize) activity (e.g., induction of Smad 2/3 and/or Smad 1/5/8 signaling) of one or more TGF-beta superfamily ligands. In some embodiments, single-arm heteromultimer complexes of the disclosure comprise at least one ALK5

The signal peptide is indicated by a single underline and the extracellular domain is indicated in bold font.

The processed extracellular ALK6 polypeptide sequence is as follows:

(SEQ ID NO: 35)

KKEDGESTAPTPRPKVLRCKCHHHCPEDSVNNICSTDGYCFTMIEEDDSG

LPVVTSGCLGLEGSDFQCRDTPIPHQRRSIECCTERNECNKDLHPTLPPL

KNRDFVDGPIHHR

A nucleic acid sequence encoding the ALK6 precursor protein is shown below (SEQ ID NO: 36), corresponding to nucleotides 275-1780 of Genbank Reference Sequence NM_001203.2. The signal sequence is underlined and the extracellular domain is indicated in bold font.

(SEQ ID NO: 36)

ATGCTTTTGCGAAGTGCAGGAAAATTAAATGTGGGCACCAAGAAAGAGGA

TGGTGAGAGTAGAGCCCCCACCCCCCGTCCAAAGGTCTTGCGTTGTAAAT

GCCACCACCATTGTCCAGAAGACTCAGTCAACAATATTTGCAGCACAGAC

GGATATTGTTTCACGATGATAGAAGAGGATGACTCTGGGTTGCCTGTGGT

CACTTCTGGTTGCCTAGGACTAGAAGGCTCAGATTTTCAGTGTCGGGACA

CTCCCATTCCTCATCAAAGAAGATCAATTGAATGCTGCACAGAAAGGAAC

GAATGTAATAAAGACCTACACCCTACACTGCCTCCATTGAAAAACAGAGA

TTTTGTTGATGGACCTATACACCACAGGGCTTTACTTATATCTGTGACTG

TCTGTAGTTTGCTCTTGGTCCTTATCATATTATTTTGTTACTTCCGGTAT

AAAAGACAAGAAACCAGACCTCGATACAGCATTGGGTTAGAACAGGATGA

AACTTACATTCCTCCTGGAGAATCCCTGAGAGACTTAATTGAGCAGTCTC

AGAGCTCAGGAAGTGGATCAGGCCTCCCTCTGCTGGTCCAAAGGACTATA

GCTAAGCAGATTCAGATGGTGAAACAGATTGGAAAAGGTCGCTATGGGGA

AGTTTGGATGGGAAAGTGGCGTGGCGAAAAGGTAGCTGTGAAAGTGTTCT

TCACCACAGAGGAAGCCAGCTGGTTCAGAGAGACAGAAATATATCAGACA

GTGTTGATGAGGCATGAAAACATTTTGGGTTTCATTGCTGCAGATATCAA

AGGGACAGGGTCCTGGACCCAGTTGTACCTAATCACAGACTATCATGAAA

-continued

ATGGTTCCCTTTATGATTATCTGAAGTCCACCACCCTAGACGCTAAATCA

ATGCTGAAGTTAGCCTACTCTTCTGTCAGTGGCTTATGTCATTTACACAC

AGAAATCTTTAGTACTCAAGGCAAACCAGCAATTGCCCATCGAGATCTGA

AAAGTAAAAACATTCTGGTGAAGAAAAATGGAACTTGCTGTATTGCTGAC

CTGGGCCTGGCTGTTAAATTTATTAGTGATACAAATGAAGTTGACATACC

ACCTAACACTCGAGTTGGCACCAAACGCTATATGCCTCCAGAAGTGTTGG

ACGAGAGCTTGAACAGAAATCACTTCCAGTCTTACATCATGGCTGACATG

TATAGTTTTGGCCTCATCCTTTGGGAGGTTGCTAGGAGATGTGTATCAGG

-continued

AGGTATAGTGGAAGAATACCAGCTTCCTTATCATGACCTAGTGCCCAGTG

ACCCCTCTTATGAGGACATGAGGGAGATTGTGTGCATCAAGAAGTTACGC

CCCTCATTCCCAAACCGGTGGAGCAGTGATGAGTGTCTAAGGCAGATGGG

AAAACTCATGACAGAATGCTGGGCTCACAATCCTGCATCAAGGCTGACAG

CCCTGCGGGTTAAGAAAACACTTGCCAAAATGTCAGAGTCCCAGGACATT

AAACTC

A nucleic acid sequence encoding processed extracellular ALK6 polypeptide is as follows:

(SEQ ID NO: 37)

AAGAAAGAGGATGGTGAGAGTACAGCCCCCACCCCCCGTCCAAAGGTCTT

GCGTTGTAAATGCCACCACCATTGTCCAGAAGACTCAGTCAACAATATTT

GCAGCACAGACGGATATTGTTTCACGATGATAGAAGAGGATGACTCTGGG

TTGCCTGTGGTCACTTCTGGTTGCCTAGGACTAGAAGGCTCAGATTTTCA

GTGTCGGGACACTCCCATTCCTCATCAAAGAAGATCAATTGAATGCTGCA

CAGAAAGGAACGAATGTAATAAAGACCTACACCCTACACTGCCTCCATTG

AAAAACAGAGATTTTGTTGATGGACCTATACACCACAGG

An alternative isoform of human ALK6 precursor protein sequence, isoform 2 (NCBI Ref Seq NP_001243722.1) is as follows:

(SEQ ID NO: 91)

1 MGWLEELNWQ LHIFLLILLS MHTRANFLDN MLLRSAGKLN VGTKKEDGES TAPTPRPKVL

61 RCKCHHHCPE DSVNNICSTD GYCFTMIEED DSGLPVVTSG CLGLEGSDFQ CRDTPIPHQR

121 RSIECCTERN ECNKDLHPTL PPLKNRDFVD GPIHHRALLI SVTVCSLLLV LIILFCYFRY

181 KRQETRPRYS IGLEQDETYI PPGESLRDLI EQSQSSGSGS GLPLLVQRTI AKQIQMVKQI

241 GKGRYGEVWM GKWRGEKVAV KVFFTTEEAS WFRETEIYQT VLMRHENILG FIAADIKGTG

301 SWTQLYLITD YHENGSLYDY LKSTTLDAKS MLKLAYSSVS GLCHLHTEIF STQGKPAIAH

361 RDLKSKNILV KKNGTCCIAD LGLAVKFISD TNEVDIPPNT RVGTKRYMPP EVLDESLNRN

421 HFQSYIMADM YSFGLILWEV ARRCVSGGIV EEYQLPYHDL VPSDPSYEDM REIVCIKKLR

481 PSFPNRWSSD ECLRQMGKLM TECWAHNPAS RLTALRVKKT LAKMSESQDI KL

The signal peptide is indicated by a single underline and the extracellular domain is indicated in bold font.

The processed extracellular ALK6 polypeptide sequence (isoform 2) is as follows:

(SEQ ID NO: 92)

NFLDNMLLRSAGKLNVGTKKEDGESTAPTPRPKVLRCKCHHHCPEDSVNN

ICSTDGYCFTMIEEDDSGLPVVTSGCLGLEGSDFQCRDTPIPHQRRSIEC

CTERNECNKDLHPTLPPLKNRDFVDGPIHHR

A nucleic acid sequence encoding human ALK6 precursor protein (isoform 2) is shown below, corresponding to nucleotides 22-1617 of Genbank Reference Sequence NM_001256793.1. The signal sequence is underlined and the extracellular domain is indicated in bold font.

(SEQ ID NO: 93)
ATGGGTTGGCTGGAAGAACTAAACTGGCAGCTTCACATTTTCTTGCTCAT
TCTTCTCTCTATGCACACAAGGGCAAACTTCCTTGATAACATGCTTTTGC
GAAGTGCAGGAAAATTAAATGTGGGCACCAAGAAAGAGGATGGTGAGAGT
ACAGCCCCCACCCCCCGTCCAAAGGTCTTGCGTTGTAAATGCCACCACCA
TTGTCCAGAAGACTCAGTCAACAATATTTGCAGCACAGACGGATATTGTT
TCACGATGATAGAAGAGGATGACTCTGGGTTGCCTGTGGTCACTTCTGGT
TGCCTAGGACTAGAAGGCTCAGATTTTCAGTGTCGGGACACTCCCATTCC
TCATCAAAGAAGATCAATTGAATGCTGCACAGAAAGGAACGAATGTAATA
AAGACCTACACCCTACACTGCCTCCATTGAAAAACAGAGATTTTGTTGAT
GGACCTATACACCACAGGGCTTTACTTATATCTGTGACTGTCTGTAGTTT
GCTCTTGGTCCTTATCATATTATTTTGTTACTTCCGGTATAAAAGACAAG
AAACCAGACCTCGATACAGCATTGGGTTAGAACAGGATGAAACTTACATT
CCTCCTGGAGAATCCCTGAGAGACTTAATTGAGCAGTCTCAGAGCTCAGG
AAGTGGATCAGGCCTCCCTCTGCTGGTCCAAAGGACTATAGCTAAGCAGA
TTCAGATGGTGAAACAGATTGGAAAAGGTCGCTATGGGGAAGTTTGGATG
GGAAAGTGGCGTGGCGAAAAGGTAGCTGTGAAAGTGTTCTTCACCACAGA
GGAAGCCAGCTGGTTCAGAGAGACAGAAATATATCAGACAGTGTTGATGA
GGCATGAAAACATTTTGGGTTTCATTGCTGCAGATATCAAAGGGACAGGG
TCCTGGACCCAGTTGTACCTAATCACAGACTATCATGAAAATGGTTCCCT
TTATGATTATCTGAAGTCCACCACCCTAGACGCTAAATCAATGCTGAAGT
TAGCCTACTCTTCTGTCAGTGGCTTATGTCATTTACACACAGAAATCTTT
AGTACTCAAGGCAAACCAGCAATTGCCCATCGAGATCTGAAAAGTAAAAA
CATTCTGGTGAAGAAAAATGGAACTTGCTGTATTGCTGACCTGGGCCTGG
CTGTTAAATTTATTAGTGATACAAATGAAGTTGACATACCACCTAACACT
CGAGTTGGCACCAAACGCTATATGCCTCCAGAAGTGTTGGACGAGAGCTT
GAACAGAAATCACTTCCAGTCTTACATCATGGCTGACATGTATAGTTTTG
GCCTCATCCTTTGGGAGGTTGCTAGGAGATGTGTATCAGGAGGTATAGTG
GAAGAATACCAGCTTCCTTATCATGACCTAGTGCCCAGTGACCCCTCTTA
TGAGGACATGAGGGAGATTGTGTGCATCAAGAAGTTACGCCCCTCATTCC
CAAACCGGTGGAGCAGTGATGAGTGTCTAAGGCAGATGGGAAAACTCATG
ACAGAATGCTGGGCTCACAATCCTGCATCAAGGCTGACAGCCCTGCGGGT
TAAGAAAACACTTGCCAAAATGTCAGAGTCCCAGGACATTAAACTC

A nucleic acid sequence encoding the processed extracellular ALK6 polypeptide is as follows:

(SEQ ID NO: 94)
AACTTCCTTGATAACATGCTTTTGCGAAGTGCAGGAAAATTAAATGTGGG
CACCAAGAAAGAGGATGGTGAGAGTACAGCCCCCACCCCCCGTCCAAAGG
TCTTGCGTTGTAAATGCCACCACCATTGTCCAGAAGACTCAGTCAACAAT

-continued
ATTTGCAGCACAGACGGATATTGTTTCACGATGATAGAAGAGGATGACTC
TGGGTTGCCTGTGGTCACTTCTGGTTGCCTAGGACTAGAAGGCTCAGATT
TTCAGTGTCGGGACACTCCCATTCCTCATCAAAGAAGATCAATTGAATGC
TGCACAGAAAGGAACGAATGTAATAAAGACCTACACCCTACACTGCCTCC
ATTGAAAAACAGAGATTTTGTTGATGGACCTATACACCACAGG In certain embodiments, the disclosure relates to single-arm heteromultimer complexes that comprise at least one ALK6 polypeptide, which includes fragments, functional variants, and modified forms thereof. Preferably, ALK6 polypeptides for use in accordance with inventions of the disclosure (e.g., single-arm heteromultimer complexes comprising an ALK6 polypeptide and uses thereof) are soluble (e.g., an extracellular domain of ALK6). In other preferred embodiments, ALK6 polypeptides for use in accordance with the inventions of the disclosure bind to and/or inhibit (antagonize) activity (e.g., induction of Smad 2/3 and/or Smad 1/5/8 signaling) of one or more TGF-beta superfamily ligands. In some embodiments, single-arm heteromultimer complexes of the disclosure comprise at least one ALK6 polypeptide that is at least 70%, 75%, 80%, 85%, 90%, 95%, 97%, 98%, or 99% identical to the amino acid sequence of SEQ ID NO: 34, 35, 91, 92, 131, 133, 421, or 422. In some embodiments, single-arm heteromultimer complexes of the disclosure consist or consist essentially of at least one ALK6 polypeptide that is at least 70%, 75%, 80%, 85%, 90%, 95%, 97%, 98%, or 99% identical to the amino acid sequence of SEQ ID NO: 34, 35, 91, 92, 131, 133, 421, or 422.

In certain aspects, the present disclosure relates to protein complexes that comprise an ALK7 polypeptide. As used herein, the term "ALK7" refers to a family of activin receptor-like kinase-7 proteins from any species and variants derived from such ALK7 proteins by mutagenesis or other modification. Reference to ALK7 herein is understood to be a reference to any one of the currently identified forms. Members of the ALK7 family are generally transmembrane proteins, composed of a ligand-binding extracellular domain with a cysteine-rich region, a transmembrane domain, and a cytoplasmic domain with predicted serine/threonine kinase activity.

The term "ALK7 polypeptide" includes polypeptides comprising any naturally occurring polypeptide of an ALK7 family member as well as any variants thereof (including mutants, fragments, fusions, and peptidomimetic forms) that retain a useful activity. Numbering of amino acids for all ALK7-related polypeptides described herein is based on the numbering of the human ALK7 precursor protein sequence below (SEQ ID NO: 38), unless specifically designated otherwise.

Several naturally occurring isoforms of human ALK7 have been described. The sequence of canonical human ALK7 isoform 1 precursor protein (NCBI Ref Seq NP_660302.2) is as follows:

(SEQ ID NO: 38)

```
  1 MTRALCSALR QALLLLAAAA ELSPGLKCVC LLCDSSNFTC QTEGACWASV MLTNGKEQVI
 61 KSCVSLPELN AQVFCHSSNN VTKTECCFTD FCNNITLHLP TASPNAPKLG PMELAIIITV
121 PVCLLSIAAM LTVWACQGRQ CSYRKKKRPN VEEPLSECNL VNAGKTLKDL IYDVTASGSG
181 SGLPLLVQRT IARTIVLQEI VGKGRFGEVW HGRWCGEDVA VKIFSSRDER SWFREAEIYQ
241 TVMLRHENIL GFIAADNKDN GTWTQLWLVS EYHEQGSLYD YLNRNIVTVA GMIKLALSIA
301 SGLAHLHMEI VGTQGKPAIA HRDIKSKNIL VKKCETCAIA DLGLAVKHDS ILNTIDIPQN
361 PKVGTKRYMA PEMLDDTMNV NIFESFKRAD IYSVGLVYWE IARRCSVGGI VEEYQLPYYD
421 MVPSDPSIEE MRKVVCDQKF RPSIPNQWQS CEALRVMGRI MRECWYANGA ARLTALRIKK
481 TISQLCVKED CKA
```

The signal peptide is indicated by a single underline and the extracellular domain is indicated in bold font.

The processed extracellular ALK7 isoform 1 polypeptide sequence is as follows:

(SEQ ID NO: 39)

```
ELSPGLKCVCLLCDSSNFTCQTEGACWASVMLTNGKEQVIKSCVSLPELN
AQVFCHSSNNVTKTECCFTDFCNNITLHLPTASPNAPKLGPME
```

A nucleic acid sequence encoding human ALK7 isoform 1 precursor protein is shown below (SEQ ID NO: 40), corresponding to nucleotides 244-1722 of Genbank Reference Sequence NM_145259.2. The signal sequence is underlined and the extracellular domain is indicated in bold font.

(SEQ ID NO: 40)

```
ATGACCCGGGCGCTCTGCTCAGCGCTCCGCCAGGCTCTCCTGCTGCTCGC
AGCGGCCGCCGAGCTCTCGCCAGGACTGAAGTGTGTATGTCTTTTGTGTG
ATTCTTCAAACTTTACCTGCCAAACAGAAGGAGCATGTTGGGCATCAGTC
ATGCTAACCAATGGAAAAGAGCAGGTGATCAAATCCTGTGTCTCCCTTCC
AGAACTGAATGCTCAAGTCTTCTGTCATAGTTCCAACAATGTTACCAAAA
CCGAATGCTGCTTCACAGATTTTTGCAACAACATAACACTGCACCTTCCA
ACAGCATCACCAAATGCCCCAAAACTTGGACCCATGGAGCTGGCCATCAT
TATTACTGTGCCTGTTTGCCTCCTGTCCATAGCTGCGATGCTGACAGTAT
GGGCATGCCAGGGTCGACAGTGCTCCTACAGGAAGAAAAAGAGACCAAAT
GTGGAGGAACCACTCTCTGAGTGCAATCTGGTAAATGCTGGAAAAACTCT
GAAAGATCTGATTTATGATGTGACCGCCTCTGGATCTGGCTCTGGTCTAC
CTCTGTTGGTTCAAAGGACAATTGCAAGGACGATTGTGCTTCAGGAAATA
GTAGGAAAAGGTAGATTTGGTGAGGTGTGGCATGGAAGATGGTGTGGGGA
AGATGTGGCTGTGAAAATATTCTCCTCCAGAGATGAAAGATCTTGGTTTC
GTGAGGCAGAAATTTACCAGACGGTCATGCTGCGACATGAAAACATCCTT
GGTTTCATTGCTGCTGACAACAAAGATAATGGAACTTGGACTCAACTTTG
GCTGGTATCTGAATATCATGAACAGGGCTCCTTATATGACTATTTGAATA
GAAATATAGTGACCGTGGCTGGAATGATCAAGCTGGCGCTCTCAATTGCT
AGTGGTCTGGCACACCTTCATATGGAGATTGTTGGTACACAAGGTAAACC
```

-continued

```
TGCTATTGCTCATCGAGACATAAAATCAAAGAATATCTTAGTGAAAAAGT
GTGAAACTTGTGCCATAGCGGACTTAGGGTTGGCTGTGAAGCATGATTCA
ATACTGAACACTATCGACATACCTCAGAATCCTAAAGTGGGAACCAAGAG
GTATATGGCTCCTGAAATGCTTGATGATACAATGAATGTGAATATCTTTG
AGTCCTTCAAACGAGCTGACATCTATTCTGTTGGTCTGGTTTACTGGGAA
ATAGCCCGGAGGTGTTCAGTCGGAGGAATTGTTGAGGAGTACCAATTGCC
TTATTATGACATGGTGCCTTCAGATCCCTCGATAGAGGAAATGAGAAAGG
TTGTTTGTGACCAGAAGTTTCGACCAAGTATCCCAAACCAGTGGCAAAGT
TGTGAAGCACTCCGAGTCATGGGGAGAATAATGCGTGAGTGTTGGTATGC
CAACGGAGCGGCCCGCCTAACTGCTCTTCGTATTAAGAAGACTATATCTC
AACTTTGTGTCAAAGAAGACTGCAAAGCC
```

A nucleic acid sequence encoding the processed extracellular ALK7 polypeptide (isoform 1) is as follows:

(SEQ ID NO: 41)

```
GAGCTCTCGCCAGGACTGAAGTGTGTATGTCTTTTGTGTGATTCTTCAAA
CTTTACCTGCCAAACAGAAGGAGCATGTTGGGCATCAGTCATGCTAACCA
ATGGAAAAGAGCAGGTGATCAAATCCTGTGTCTCCCTTCCAGAACTGAAT
GCTCAAGTCTTCTGTCATAGTTCCAACAATGTTACCAAAACCGAATGCTG
CTTCACAGATTTTTGCAACAACATAACACTGCACCTTCCAACAGCATCAC
CAAATGCCCCAAAACTTGGACCCATGGAG
```

The amino acid sequence of an alternative isoform of human ALK7, isoform 2 (NCBI Ref Seq NP_001104501.1), is shown in its processed form as follows (SEQ ID NO: 301), where the extracellular domain is indicated in bold font.

(SEQ ID NO: 301)

1 MLTNGKEQVI KSCVSLPELN AQVFCHSSNN VTKTECCFTD FCNNITLHLP TASPNAPKLG

61 PMELAIIITV PVCLLSIAAM LTVWACQGRQ CSYRKKKRPN VEEPLSECNL VNAGKTLKDL

121 IYDVTASGSG SGLPLLVQRT IARTIVLQEI VGKGRFGEVW HGRWCGEDVA VKIFSSRDER

181 SWFREAEIYQ TVMLRHENIL GFIAADNKDN GTWTQLWLVS EYHEQGSLYD YLNRNIVTVA

241 GMIKLALSIA SGLAHLHMEI VGTQGKPAIA HRDIKSKNIL VKKCETCAIA DLGLAVKHDS

301 ILNTIDIPQN PKVGTKRYMA PEMLDDTMNV NIFESFKRAD IYSVGLVYWE IARRCSVGGI

361 VEEYQLPYYD MVPSDPSIEE MRKVVCDQKF RPSIPNQWQS CEALRVMGRI MRECWYANGA

421 ARLTALRIKK TISQLCVKED CKA

The amino acid sequence of the extracellular ALK7 polypeptide (isoform 2) is as follows:

(SEQ ID NO: 302)

MLTNGKEQVIKSCVSLPELNAQVFCHSSNNVTKTECCFTDFCNNITLHL

PTASPNAPKLGPME.

A nucleic acid sequence encoding the processed ALK7 polypeptide (isoform 2) is shown below (SEQ ID NO: 303), corresponding to nucleotides 279-1607 of NCBI Reference Sequence NM_001111031.1. The extracellular domain is indicated in bold font.

(SEQ ID NO: 303)

ATGCTAACCAATGGAAAAGAGCAGGTGATCAAATCCTGTGTCTCCCTTCC

AGAACTGAATGCTCAAGTCTTCTGTCATAGTTCCAACAATGTTACCAAAA

CCGAATGCTGCTTCACAGATTTTTGCAACAACATAACACTGCACCTTCCA

ACAGCATCACCAAATGCCCCAAAACTTGGACCCATGGAGCTGGCCATCAT

TATTACTGTGCCTGTTTGCCTCCTGTCCATAGCTGCGATGCTGACAGTAT

GGGCATGCCAGGGTCGACAGTGCTCCTACAGGAAGAAAAAGAGACCAAAT

GTGGAGGAACCACTCTCTGAGTGCAATCTGGTAAATGCTGGAAAAACTCT

GAAAGATCTGATTTATGATGTGACCGCCTCTGGATCTGGCTCTGGTCTAC

CTCTGTTGGTTCAAAGGACAATTGCAAGGACGATTGTGCTTCAGGAAATA

GTAGGAAAAGGTAGATTTGGTGAGGTGTGGCATGGAAGATGGTGTGGGGA

AGATGTGGCTGTGAAAATATTCTCCTCCAGAGATGAAAGATCTTGGTTTC

GTGAGGCAGAAATTTACCAGACGGTCATGCTGCGACATGAAAACATCCTT

GGTTTCATTGCTGCTGACAACAAAGATAATGGAACTTGGACTCAACTTTG

GCTGGTATCTGAATATCATGAACAGGGCTCCTTATATGACTATTTGAATA

GAAATATAGTGACCGTGGCTGGAATGATCAAGCTGGCGCTCTCAATTGCT

AGTGGTCTGGCACACCTTCATATGGAGATTGTTGGTACACAAGGTAAACC

-continued

TGCTATTGCTCATCGAGACATAAAATCAAAGAATATCTTAGTGAAAAAGT

GTGAAACTTGTGCCATAGCGGACTTAGGGTTGGCTGTGAAGCATGATTCA

ATACTGAACACTATCGACATACCTCAGAATCCTAAAGTGGGAACCAAGAG

GTATATGGCTCCTGAAATGCTTGATGATACAATGAATGTGAATATCTTTG

AGTCCTTCAAACGAGCTGACATCTATTCTGTTGGTCTGGTTTACTGGGAA

ATAGCCCGGAGGTGTTCAGTCGGAGGAATTGTTGAGGAGTACCAATTGCC

TTATTATGACATGGTGCCTTCAGATCCCTCGATAGAGGAAATGAGAAAGG

TTGTTTGTGACCAGAAGTTTCGACCAAGTATCCCAAACCAGTGGCAAAGT

TGTGAAGCACTCCGAGTCATGGGGAGAATAATGCGTGAGTGTTGGTATGC

CAACGGAGCGGCCCGCCTAACTGCTCTTCGTATTAAGAAGACTATATCTC

AACTTTGTGTCAAAGAAGACTGCAAAGCC

A nucleic acid sequence encoding the extracellular ALK7 polypeptide (isoform 2) is as follows (SEQ ID NO: 304):

(SEQ ID NO: 304)

ATGCTAACCAATGGAAAAGAGCAGGTGATCAAATCCTGTGTCTCCCTTC

CAGAACTGAATGCTCAAGTCTTCTGTCATAGTTCCAACAATGTTACCAA

AACCGAATGCTGCTTCACAGATTTTTGCAACAACATAACACTGCACCTT

CCAACAGCATCACCAAATGCCCCAAAACTTGGACCCATGGAG

The amino acid sequence of an alternative human ALK7 precursor protein, isoform 3 (NCBI Ref Seq NP_001104502.1), is shown as follows (SEQ ID NO: 305), where the signal peptide is indicated by a single underline.

(SEQ ID NO: 305)

1 MTRALCSALR QALLLLAAAA ELSPGLKCVC LLCDSSNFTC QTEGACWASV MLTNGKEQVI

61 KSCVSLPELN AQVFCHSSNN VTKTECCFTD FCNNITLHLP TGLPLLVQRT IARTIVLQEI

121 VGKGRFGEVW HGRWCGEDVA VKIFSSRDER SWFREAEIYQ TVMLRHENIL GFIAADNKDN

181 GTWTQLWLVS EYHEQGSLYD YLNRNIVTVA GMIKLALSIA SGLAHLHMEI VGTQGKPAIA

```
241 HRDIKSKNIL VKKCETCAIA DLGLAVKHDS ILNTIDIPQN PKVGTKRYMA PEMLDDTMNV

301 NIFESFKRAD IYSVGLVYWE IARRCSVGGI VEEYQLPYYD MVPSDPSIEE MRKVVCDQKF

361 RPSIPNQWQS CEALRVMGRI MRECWYANGA ARLTALRIKK TISQLCVKED CKA
```

The amino acid sequence of the processed ALK7 polypeptide (isoform 3) is as follows (SEQ ID NO: 306). This isoform lacks a transmembrane domain and is therefore proposed to be soluble in its entirety (Roberts et al., 2003, Biol Reprod 68:1719-1726). N-terminal variants of SEQ ID NO: 306 are predicted as explained below.

```
                                                      (SEQ ID NO: 306)
  1 ELSPGLKCVC LLCDSSNFTC QTEGACWASV MLTNGKEQVI KSCVSLPELN AQVFCHSSNN

 61 VTKTECCFTD FCNNITLHLP TGLPLLVQRT IARTIVLQEI VGKGRFGEVW HGRWCGEDVA

121 VKIFSSRDER SWFREAEIYQ TVMLRHENIL GFIAADNKDN GTWTQLWLVS EYHEQGSLYD

181 YLNRNIVTVA GMIKLALSIA SGLAHLHMEI VGTQGKPAIA HRDIKSKNIL VKKCETCAIA

241 DLGLAVKHDS ILNTIDIPQN PKVGTKRYMA PEMLDDTMNV NIFESFKRAD IYSVGLVYWE

301 IARRCSVGGI VEEYQLPYYD MVPSDPSIEE MRKVVCDQKF RPSIPNQWQS CEALRVMGRI

361 MRECWYANGA ARLTALRIKK TISQLCVKED CKA
```

A nucleic acid sequence encoding the unprocessed ALK7 polypeptide precursor protein (isoform 3) is shown below (SEQ ID NO: 307), corresponding to nucleotides 244-1482 of NCBI Reference Sequence NM_001111032.1. The signal sequence is indicated by solid underline.

```
(SEQ ID NO: 307)
ATGACCCGGGCGCTCTGCTCAGCGCTCCGCCAGGCTCTCCTGCTGCTCGC

AGCGGCCGCCGAGCTCTCGCCAGGACTGAAGTGTGTATGTCTTTTGTGTG

ATTCTTCAAACTTTACCTGCCAAACAGAAGGAGCATGTTGGGCATCAGTC

ATGCTAACCAATGGAAAAGAGCAGGTGATCAAATCCTGTGTCTCCCTTCC

AGAACTGAATGCTCAAGTCTTCTGTCATAGTTCCAACAATGTTACCAAAA

CCGAATGCTGCTTCACAGATTTTTGCAACAACATAACACTGCACCTTCCA

ACAGGTCTACCTCTGTTGGTTCAAAGGACAATTGCAAGGACGATTGTGCT

TCAGGAAATAGTAGGAAAAGGTAGATTTGGTGAGGTGTGGCATGGAAGAT

GGTGTGGGGAAGATGTGGCTGTGAAAATATTCTCCTCCAGAGATGAAAGA

TCTTGGTTTCGTGAGGCAGAAATTTACCAGACGGTCATGCTGCGACATGA

AAACATCCTTGGTTTCATTGCTGCTGACAACAAAGATAATGGAACTTGGA

CTCAACTTTGGCTGGTATCTGAATATCATGAACAGGGCTCCTTATATGAC

TATTTGAATAGAAATATAGTGACCGTGGCTGGAATGATCAAGCTGGCGCT

CTCAATTGCTAGTGGTCTGGCACACCTTCATATGGAGATTGTTGGTACAC

AAGGTAAACCTGCTATTGCTCATCGAGACATAAAATCAAAGAATATCTTA

GTGAAAAAGTGTGAAACTTGTGCCATAGCGGACTTAGGGTTGGCTGTGAA

GCATGATTCAATACTGAACACTATCGACATACCTCAGAATCCTAAAGTGG

GAACCAAGAGGTATATGGCTCCTGAAATGCTTGATGATACAATGAATGTG

AATATCTTTGAGTCCTTCAAACGAGCTGACATCTATTCTGTTGGTCTGGT

TTACTGGGAAATAGCCCGGAGGTGTTCAGTCGGAGGAATTGTTGAGGAGT

ACCAATTGCCTTATTATGACATGGTGCCTTCAGATCCCTCGATAGAGGAA

ATGAGAAAGGTTGTTTGTGACCAGAAGTTTCGACCAAGTATCCCAAACCA

GTGGCAAAGTTGTGAAGCACTCCGAGTCATGGGGAGAATAATGCGTGAGT

GTTGGTATGCCAACGGAGCGGCCCGCCTAACTGCTCTTCGTATTAAGAAG

ACTATATCTCAACTTTGTGTCAAAGAAGACTGCAAAGCC
```

A nucleic acid sequence encoding the processed ALK7 polypeptide (isoform 3) is as follows (SEQ ID NO: 308):

```
(SEQ ID NO: 308)
GAGCTCTCGCCAGGACTGAAGTGTGTATGTCTTTTGTGTGATTCTTCAAA

CTTTACCTGCCAAACAGAAGGAGCATGTTGGGCATCAGTCATGCTAACCA

ATGGAAAAGAGCAGGTGATCAAATCCTGTGTCTCCCTTCCAGAACTGAAT

GCTCAAGTCTTCTGTCATAGTTCCAACAATGTTACCAAAACCGAATGCTG

CTTCACAGATTTTTGCAACAACATAACACTGCACCTTCCAACAGGTCTAC

CTCTGTTGGTTCAAAGGACAATTGCAAGGACGATTGTGCTTCAGGAAATA

GTAGGAAAAGGTAGATTTGGTGAGGTGTGGCATGGAAGATGGTGTGGGGA

AGATGTGGCTGTGAAAATATTCTCCTCCAGAGATGAAAGATCTTGGTTTC

GTGAGGCAGAAATTTACCAGACGGTCATGCTGCGACATGAAAACATCCTT

GGTTTCATTGCTGCTGACAACAAAGATAATGGAACTTGGACTCAACTTTG

GCTGGTATCTGAATATCATGAACAGGGCTCCTTATATGACTATTTGAATA

GAAATATAGTGACCGTGGCTGGAATGATCAAGCTGGCGCTCTCAATTGCT

AGTGGTCTGGCACACCTTCATATGGAGATTGTTGGTACACAAGGTAAACC

TGCTATTGCTCATCGAGACATAAAATCAAAGAATATCTTAGTGAAAAAGT

GTGAAACTTGTGCCATAGCGGACTTAGGGTTGGCTGTGAAGCATGATTCA

ATACTGAACACTATCGACATACCTCAGAATCCTAAAGTGGGAACCAAGAG
```

-continued

GTATATGGCTCCTGAAATGCTTGATGATACAATGAATGTGAATATCTTTG

AGTCCTTCAAACGAGCTGACATCTATTCTGTTGGTCTGGTTTACTGGGAA

ATAGCCCGGAGGTGTTCAGTCGGAGGAATTGTTGAGGAGTACCAATTGCC

TTATTATGACATGGTGCCTTCAGATCCCTCGATAGAGGAAATGAGAAAGG

TTGTTTGTGACCAGAAGTTTCGACCAAGTATCCCAAACCAGTGGCAAAGT

TGTGAAGCACTCCGAGTCATGGGGAGAATAATGCGTGAGTGTTGGTATGC

CAACGGAGCGGCCCGCCTAACTGCTCTTCGTATTAAGAAGACTATATCTC

AACTTTGTGTCAAAGAAGACTGCAAAGCC

The amino acid sequence of an alternative human ALK7 precursor protein, isoform 4 (NCBI Ref Seq NP_001104503.1), is shown as follows (SEQ ID NO: 309), where the signal peptide is indicated by a single underline.

(SEQ ID NO: 309)

1 MTRALCSALR QALLLLAAAA ELSPGLKCVC LLCDSSNFTC QTEGACWASV MLTNGKEQVI

61 KSCVSLPELN AQVFCHSSNN VTKTECCFTD FCNNITLHLP TDNGTWTQLW LVSEYHEQGS

121 LYDYLNRNIV TVAGMIKLAL SIASGLAHLH MEIVGTQGKP AIAHRDIKSK NILVKKCETC

181 AIADLGLAVK HDSILNTIDI PQNPKVGTKR YMAPEMLDDT MNVNIFESFK RADIYSVGLV

241 YWEIARRCSV GGIVEEYQLP YYDMVPSDPS IEEMRKVVCD QKFRPSIPNQ WQSCEALRVM

301 GRIMRECWYA NGAARLTALR IKKTISQLCV KEDCKA

The amino acid sequence of the processed ALK7 polypeptide (isoform 4) is as follows (SEQ ID NO: 310). Like ALK7 isoform 3, isoform 4 lacks a transmembrane domain and is therefore proposed to be soluble in its entirety (Roberts et al., 2003, Biol Reprod 68:1719-1726). N-terminal variants of SEQ ID NO: 310 are predicted as explained below.

(SEQ ID NO: 310)

1 ELSPGLKCVC LLCDSSNFTC QTEGACWASV MLTNGKEQVI KSCVSLPELN AQVFCHSSNN

61 VTKTECCFTD FCNNITLHLP TDNGTWTQLW LVSEYHEQGS LYDYLNRNIV TVAGMIKLAL

121 SIASGLAHLH MEIVGTQGKP AIAHRDIKSK NILVKKCETC AIADLGLAVK HDSILNTIDI

181 PQNPKVGTKR YMAPEMLDDT MNVNIFESFK RADIYSVGLV YWEIARRCSV GGIVEEYQLP

240 YYDMVPSDPS IEEMRKVVCD QKFRPSIPNQ WQSCEALRVM GRIMRECWYA NGAARLTALR

301 IKKTISQLCV KEDCKA

A nucleic acid sequence encoding the unprocessed ALK7 polypeptide precursor protein (isoform 4) is shown below (SEQ ID NO: 311), corresponding to nucleotides 244-1244 of NCBI Reference Sequence NM_001111033.1. The signal sequence is indicated by solid underline.

(SEQ ID NO: 311)

ATGACCCGGGCGCTCTGCTCAGCGCTCCGCCAGGCTCTCCTGCTGCTCGC

AGCGGCCGCCGAGCTCTCGCCAGGACTGAAGTGTGTATGTCTTTTGTGTG

ATTCTTCAAACTTTACCTGCCAAACAGAAGGAGCATGTTGGGCATCAGTC

ATGCTAACCAATGGAAAAGAGCAGGTGATCAAATCCTGTGTCTCCCTTCC

AGAACTGAATGCTCAAGTCTTCTGTCATAGTTCCAACAATGTTACCAAAA

-continued

CCGAATGCTGCTTCACAGATTTTTGCAACAACATAACACTGCACCTTCCA

ACAGATAATGGAACTTGGACTCAACTTTGGCTGGTATCTGAATATCATGA

ACAGGGCTCCTTATATGACTATTTGAATAGAAATATAGTGACCGTGGCTG

GAATGATCAAGCTGGCGCTCTCAATTGCTAGTGGTCTGGCACACCTTCAT

ATGGAGATTGTTGGTACACAAGGTAAACCTGCTATTGCTCATCGAGACAT

AAAATCAAAGAATATCTTAGTGAAAAAGTGTGAAACTTGTGCCATAGCGG

ACTTAGGGTTGGCTGTGAAGCATGATTCAATACTGAACACTATCGACATA

CCTCAGAATCCTAAAGTGGGAACCAAGAGGTATATGGCTCCTGAAATGCT

TGATGATACAATGAATGTGAATATCTTTGAGTCCTTCAAACGAGCTGACA

TCTATTCTGTTGGTCTGGTTTACTGGGAAATAGCCCGGAGGTGTTCAGTC

-continued

GGAGGAATTGTTGAGGAGTACCAATTGCCTTATTATGACATGGTGCCTTC

AGATCCCTCGATAGAGGAAATGAGAAAGGTTGTTTGTGACCAGAAGTTTC

GACCAAGTATCCCAAACCAGTGGCAAAGTTGTGAAGCACTCCGAGTCATG

-continued

GGGAGAATAATGCGTGAGTGTTGGTATGCCAACGGAGCGGCCCGCCTAAC

TGCTCTTCGTATTAAGAAGACTATATCTCAACTTTGTGTCAAAGAAGACT

GCAAAGCCTAA

A nucleic acid sequence encoding the processed ALK7 polypeptide (isoform 4) is as follows (SEQ ID NO: 312):

(SEQ ID NO: 312)

GAGCTCTCGCCAGGACTGAAGTGTGTATGTCTTTTGTGTGATTCTTCAAA

CTTTACCTGCCAAACAGAAGGAGCATGTTGGGCATCAGTCATGCTAACCA

ATGGAAAAGAGCAGGTGATCAAATCCTGTGTCTCCCTTCCAGAACTGAAT

-continued

```
GCTCAAGTCTTCTGTCATAGTTCCAACAATGTTACCAAAACCGAATGCTG

CTTCACAGATTTTTGCAACAACATAACACTGCACCTTCCAACAGATAATG

GAACTTGGACTCAACTTTGGCTGGTATCTGAATATCATGAACAGGGCTCC

TTATATGACTATTTGAATAGAAATATAGTGACCGTGGCTGGAATGATCAA

GCTGGCGCTCTCAATTGCTAGTGGTCTGGCACACCTTCATATGGAGATTG

TTGGTACACAAGGTAAACCTGCTATTGCTCATCGAGACATAAAATCAAAG

AATATCTTAGTGAAAAAGTGTGAAACTTGTGCCATAGCGGACTTAGGGTT

GGCTGTGAAGCATGATTCAATACTGAACACTATCGACATACCTCAGAATC

CTAAAGTGGGAACCAAGAGGTATATGGCTCCTGAAATGCTTGATGATACA

ATGAATGTGAATATCTTTGAGTCCTTCAAACGAGCTGACATCTATTCTGT

TGGTCTGGTTTACTGGGAAATAGCCCGGAGGTGTTCAGTCGGAGGAATTG

TTGAGGAGTACCAATTGCCTTATTATGACATGGTGCCTTCAGATCCCTCG

ATAGAGGAAATGAGAAAGGTTGTTTGTGACCAGAAGTTTCGACCAAGTAT

CCCAAACCAGTGGCAAAGTTGTGAAGCACTCCGAGTCATGGGGAGAATAA

TGCGTGAGTGTTGGTATGCCAACGGAGCGGCCCGCCTAACTGCTCTTCGT

ATTAAGAAGACTATATCTCAACTTTGTGTCAAAGAAGACTGCAAAGCCTA

A
```

Based on the signal sequence of full-length ALK7 (isoform 1) in the rat (see NCBI Reference Sequence NP_620790.1) and on the high degree of sequence identity between human and rat ALK7, it is predicted that a processed form of human ALK7 isoform 1 is as follows (SEQ ID NO: 313).

```
                                                            (SEQ ID NO: 313)
 1 LKCVCLLCDS SNFTCQTEGA CWASVMLTNG KEQVIKSCVS LPELNAQVFC HSSNNVTKTE

61 CCFTDFCNNI TLHLPTASPN APKLGPME
```

Active variants of processed ALK7 isoform 1 are predicted in which SEQ ID NO: 39 is truncated by 1, 2, 3, 4, 5, 6, or 7 amino acids at the N-terminus and SEQ ID NO: 313 is truncated by 1 or 2 amino acids at the N-terminus. Consistent with SEQ ID NO: 313, it is further expected that leucine is the N-terminal amino acid in the processed forms of human ALK7 isoform 3 (SEQ ID NO: 306) and human ALK7 isoform 4 (SEQ ID NO: 310).

In certain embodiments, the disclosure relates to single-arm heteromultimer complexes that comprise at least one ALK7 polypeptide, which includes fragments, functional variants, and modified forms thereof. Preferably, ALK7 polypeptides for use in accordance with inventions of the disclosure (e.g., single-arm heteromultimer complexes comprising an ALK7 polypeptide and uses thereof) are soluble (e.g., an extracellular domain of ALK7). In other preferred embodiments, ALK7 polypeptides for use in accordance with the inventions of the disclosure bind to and/or inhibit (antagonize) activity (e.g., induction of Smad 2/3 and/or Smad 1/5/8 signaling) of one or more TGF-beta superfamily ligands. In some embodiments, single-arm heteromultimer complexes of the disclosure comprise at least one ALK7 polypeptide that is at least 70%, 75%, 80%, 85%, 90%, 95%, 97%, 98%, or 99% identical to the amino acid sequence of SEQ ID NO: 38, 39, 134, 136, 301, 302, 305, 306, 309, 310, 313, 423, or 424. In some embodiments, single-arm heteromultimer complexes of the disclosure consist or consist essentially of at least one ALK7 polypeptide that is at least 70%, 75%, 80%, 85%, 90%, 95%, 97%, 98%, or 99% identical to the amino acid sequence of SEQ ID NO: 38, 39, 134, 136, 301, 302, 305, 306, 309, 310, 313, 423, or 424.

In some embodiments, the present disclosure contemplates making functional variants by modifying the structure of a TGF-beta superfamily type I receptor polypeptide (e.g., ALK1, ALK2, ALK3, ALK4, ALK5, ALK6, and ALK7) or a TGF-beta superfamily type II receptor polypeptide (e.g., ActRIIA, ActRIIB, TGFBRII, BMPRII, and MISRII) for such purposes as enhancing therapeutic efficacy or stability (e.g., shelf-life and resistance to proteolytic degradation in vivo). Variants can be produced by amino acid substitution, deletion, addition, or combinations thereof. For instance, it is reasonable to expect that an isolated replacement of a leucine with an isoleucine or valine, an aspartate with a glutamate, a threonine with a serine, or a similar replacement of an amino acid with a structurally related amino acid (e.g., conservative mutations) will not have a major effect on the biological activity of the resulting molecule. Conservative replacements are those that take place within a family of amino acids that are related in their side chains. Whether a change in the amino acid sequence of a polypeptide of the disclosure results in a functional homolog can be readily determined by assessing the ability of the variant polypeptide to produce a response in cells in a fashion similar to the wild-type polypeptide, or to bind to one or more TGF-beta ligands including, for example, BMP2, BMP2/7, BMP3, BMP4, BMP4/7, BMP5, BMP6, BMP7, BMP8a, BMP8b, BMP9, BMP10, GDF3, GDF5, GDF6/BMP13, GDF7, GDF8, GDF9b/BMP15, GDF11/BMP11, GDF15/MIC1, TGF-β1, TGF-β2, TGF-β3, activin A, activin B, activin C, activin E, activin AB, activin AC, nodal, GDNF, neurturin, artemin, persephin, MIS, and Lefty.

In certain embodiments, the present disclosure contemplates specific mutations of a TGF-beta superfamily type I receptor polypeptide (e.g., ALK1, ALK2, ALK3, ALK4, ALK5, ALK6, and ALK7) or a TGF-beta superfamily type II receptor polypeptide (e.g., ActRIIA, ActRIIB, TGFBRII, BMPRII, and MISRII) of the disclosure so as to alter the glycosylation of the polypeptide. Such mutations may be selected so as to introduce or eliminate one or more glycosylation sites, such as O-linked or N-linked glycosylation sites. Asparagine-linked glycosylation recognition sites generally comprise a tripeptide sequence, asparagine-X-threonine or asparagine-X-serine (where "X" is any amino acid) which is specifically recognized by appropriate cellular glycosylation enzymes. The alteration may also be made by the addition of, or substitution by, one or more serine or threonine residues to the sequence of the polypeptide (for O-linked glycosylation sites). A variety of amino acid substitutions or deletions at one or both of the first or third amino acid positions of a glycosylation recognition site (and/or amino acid deletion at the second position) results in non-glycosylation at the modified tripeptide sequence. Another means of increasing the number of carbohydrate moieties on a polypeptide is by chemical or enzymatic coupling of glycosides to the polypeptide. Depending on the coupling mode used, the sugar(s) may be attached to (a) arginine and histidine; (b) free carboxyl groups; (c) free sulfhydryl groups such as those of cysteine; (d) free hydroxyl groups such as those of serine, threonine, or hydroxyproline; (e) aromatic residues such as those of phenylalanine, tyrosine, or tryptophan; or (f) the amide group of glutamine. Removal of one or more carbohydrate moieties present on a polypeptide may be accomplished chemically and/or enzymatically. Chemical deglycosylation may involve, for example, exposure of a polypeptide to the compound trifluoromethanesulfonic acid, or an equivalent compound. This treatment results in the cleavage of most or all sugars except the linking sugar (N-acetylglucosamine or N-acetylgalactosamine), while leaving the amino acid sequence intact. Enzymatic cleavage of carbohydrate moieties on polypeptides can be achieved by the use of a variety of endo- and exo-glycosidases as described by Thotakura et al. [Meth. Enzymol. (1987) 138:350]. The sequence of a polypeptide may be adjusted, as appropriate, depending on the type of expression system used, as mammalian, yeast, insect, and plant cells may all introduce differing glycosylation patterns that can be affected by the amino acid sequence of the peptide. In general, TGF-beta superfamily type I and II receptor single-arm complexes of the present disclosure for use in humans may be expressed in a mammalian cell line that provides proper glycosylation, such as HEK293 or CHO cell lines, although other mammalian expression cell lines are expected to be useful as well.

The present disclosure further contemplates a method of generating mutants, particularly sets of combinatorial mutants of a TGF-beta superfamily type I receptor polypeptide (e.g., ALK1, ALK2, ALK3, ALK4, ALK5, ALK6, and ALK7) or a TGF-beta superfamily type II receptor polypeptide (e.g., ActRIIA, ActRIIB, TGFBRII, BMPRII, and MISRII) of the present disclosure, as well as truncation mutants. Pools of combinatorial mutants are especially useful for identifying TGF-beta superfamily type I or TGF-beta superfamily type II receptor sequences. The purpose of screening such combinatorial libraries may be to generate, for example, polypeptides variants which have altered properties, such as altered pharmacokinetic or altered ligand binding. A variety of screening assays are provided below, and such assays may be used to evaluate variants. For example, TGF-beta superfamily type I or type II receptor polypeptide variants may be screened for ability to bind to a TGF-beta superfamily ligand (e.g., BMP2, BMP2/7, BMP3, BMP4, BMP4/7, BMP5, BMP6, BMP7, BMP8a, BMP8b, BMP9, BMP10, GDF3, GDF5, GDF6/BMP13, GDF7, GDF8, GDF9b/BMP15, GDF11/BMP11, GDF15/MIC1, TGF-β1, TGF-β2, TGF-β3, activin A, activin B, activin C, activin E, activin AB, activin AC, activin AE, activin BC, activin BE, nodal, GDNF, neurturin, artemin, persephin, MIS, and Lefty), to prevent binding of a TGF-beta superfamily ligand to a TGF-beta superfamily receptor, and/or to interfere with signaling caused by an TGF-beta superfamily ligand.

The activity of a TGF-beta superfamily receptor single-arm heteromultimer complex of the disclosure also may be tested in a cell-based or in vivo assay. For example, the effect of a single-arm heteromultimer complex on the expression of genes involved in muscle production in a muscle cell may be assessed. This may, as needed, be performed in the presence of one or more recombinant TGF-beta superfamily ligand proteins (e.g., BMP2, BMP2/7, BMP3, BMP4, BMP4/7, BMP5, BMP6, BMP7, BMP8a, BMP8b, BMP9, BMP10, GDF3, GDF5, GDF6/BMP13, GDF7, GDF8, GDF9b/BMP15, GDF11/BMP11, GDF15/MIC1, TGF-β1, TGF-β2, TGF-β3, activin A, activin B, activin C, activin E, activin AB, activin AC, activin AE, activin BC, activin BE, nodal, GDNF, neurturin, artemin, persephin, MIS, and Lefty), and cells may be transfected so as to produce a TGF-beta superfamily type I or type II receptor single-arm complex, and optionally, a TGF-beta superfamily ligand. Likewise, a single-arm heteromultimer complex of the disclosure may be administered to a mouse or other animal, and one or more measurements, such as muscle formation and strength may be assessed using art-recognized methods. Similarly, the activity of a TGF-beta superfamily receptor polypeptide or its variants may be tested in osteoblasts, adipocytes, and/or neuronal cells for any effect on growth of these cells, for example, by the assays as described herein and those of common knowledge in the art. A SMAD-responsive reporter gene may be used in such cell lines to monitor effects on downstream signaling.

Combinatorial-derived variants can be generated which have increased selectivity or generally increased potency relative to a reference TGF-beta superfamily receptor single-arm heteromultimer complex. Such variants, when expressed from recombinant DNA constructs, can be used in gene therapy protocols. Likewise, mutagenesis can give rise to variants which have extracellular half-lives dramatically different than the corresponding unmodified TGF-beta superfamily receptor single-arm heteromultimer complex. For example, the altered protein can be rendered either more stable or less stable to proteolytic degradation or other cellular processes which result in destruction, or otherwise inactivation, of an unmodified polypeptide. Such variants, and the genes which encode them, can be utilized to alter polypeptide complex levels by modulating the half-life of the polypeptide. For instance, a short half-life can give rise to more transient biological effects and, when part of an inducible expression system, can allow tighter control of recombinant polypeptide complex levels outside the cell. In an Fc fusion protein, mutations may be made in the linker (if any) and/or the Fc portion to alter the half-life of the TGF-beta superfamily receptor single-arm heteromultimer complex.

A combinatorial library may be produced by way of a degenerate library of genes encoding a library of polypeptides which each include at least a portion of potential TGF-beta superfamily type I or type II receptor sequences. For instance, a mixture of synthetic oligonucleotides can be enzymatically ligated into gene sequences such that the degenerate set of potential TGF-beta superfamily type I or type II receptor encoding nucleotide sequences are expressible as individual polypeptides, or alternatively, as a set of larger fusion proteins (e.g., for phage display).

There are many ways by which the library of potential homologs can be generated from a degenerate oligonucleotide sequence. Chemical synthesis of a degenerate gene sequence can be carried out in an automatic DNA synthesizer, and the synthetic genes can then be ligated into an appropriate vector for expression. The synthesis of degenerate oligonucleotides is well known in the art. See, e.g., Narang, S A (1983) Tetrahedron 39:3; Itakura et al. (1981) Recombinant DNA, Proc. 3rd Cleveland Sympos. Macromolecules, ed. AG Walton, Amsterdam: Elsevier pp 273-289; Itakura et al. (1984) Annu. Rev. Biochem. 53:323; Itakura et al. (1984) Science 198:1056; Ike et al. (1983) Nucleic Acid Res. 11:477. Such techniques have been employed in the directed evolution of other proteins. See, e.g., Scott et al., (1990) Science 249:386-390; Roberts et al. (1992) PNAS USA 89:2429-2433; Devlin et al. (1990)

Science 249: 404-406; Cwirla et al., (1990) PNAS USA 87: 6378-6382; as well as U.S. Pat. Nos. 5,223,409, 5,198,346, and 5,096,815.

Alternatively, other forms of mutagenesis can be utilized to generate a combinatorial library. For example, TGF-beta superfamily receptor single-arm heteromultimer complexes of the disclosure can be generated and isolated from a library by screening using, for example, alanine scanning mutagenesis [see, e.g., Ruf et al. (1994) Biochemistry 33:1565-1572; Wang et al. (1994) J. Biol. Chem. 269:3095-3099; Balint et al. (1993) Gene 137:109-118; Grodberg et al. (1993) Eur. J. Biochem. 218:597-601; Nagashima et al. (1993) J. Biol. Chem. 268:2888-2892; Lowman et al. (1991) Biochemistry 30:10832-10838; and Cunningham et al. (1989) Science 244:1081-1085], by linker scanning mutagenesis [see, e.g., Gustin et al. (1993) Virology 193:653-660; and Brown et al. (1992) Mol. Cell Biol. 12:2644-2652; McKnight et al. (1982) Science 232:316], by saturation mutagenesis [see, e.g., Meyers et al., (1986) Science 232:613]; by PCR mutagenesis [see, e.g., Leung et al. (1989) Method Cell Mol Biol 1:11-19]; or by random mutagenesis, including chemical mutagenesis [see, e.g., Miller et al. (1992) A Short Course in Bacterial Genetics, CSHL Press, Cold Spring Harbor, NY; and Greener et al. (1994) Strategies in Mol Biol 7:32-34]. Linker scanning mutagenesis, particularly in a combinatorial setting, is an attractive method for identifying truncated (bioactive) forms of TGF-beta superfamily type I or type II receptor polypeptides.

A wide range of techniques are known in the art for screening gene products of combinatorial libraries made by point mutations and truncations, and, for that matter, for screening cDNA libraries for gene products having a certain property. Such techniques will be generally adaptable for rapid screening of the gene libraries generated by the combinatorial mutagenesis of TGF-beta superfamily receptor single-arm heteromultimer complexes of the disclosure. The most widely used techniques for screening large gene libraries typically comprise cloning the gene library into replicable expression vectors, transforming appropriate cells with the resulting library of vectors, and expressing the combinatorial genes under conditions in which detection of a desired activity facilitates relatively easy isolation of the vector encoding the gene whose product was detected. Preferred assays include binding assays and/or cell-signaling assays for TGF-beta superfamily ligands (e.g., BMP2, BMP2/7, BMP3, BMP4, BMP4/7, BMP5, BMP6, BMP7, BMP8a, BMP8b, BMP9, BMP10, GDF3, GDF5, GDF6/BMP13, GDF7, GDF8, GDF9b/BMP15, GDF11/BMP11, GDF15/MIC1, TGF-β1, TGF-β2, TGF-β3, activin A, activin B, activin C, activin E, activin AB, activin AC, activin AE, activin BC, activin BE, nodal, GDNF, neurturin, artemin, persephin, MIS, and Lefty).

In certain embodiments, TGF-beta superfamily type I and type II receptor single-arm heteromultimer complexes of the disclosure may further comprise post-translational modifications in addition to any that are naturally present in the TGF-beta superfamily type I or type II receptor polypeptide. Such modifications include, but are not limited to, acetylation, carboxylation, glycosylation, phosphorylation, lipidation, and acylation. As a result, the TGF-beta superfamily type I or type II receptor single-arm heteromultimer complex may comprise non-amino acid elements, such as polyethylene glycols, lipids, polysaccharide or monosaccharide, and phosphates. Effects of such non-amino acid elements on the functionality of a single-arm heteromultimer complex may be tested as described herein for other single-arm heteromultimer complex variants. When a polypeptide of the disclosure is produced in cells by cleaving a nascent form of the polypeptide, post-translational processing may also be important for correct folding and/or function of the protein. Different cells (e.g., CHO, HeLa, MDCK, 293, WI38, NIH-3T3 or HEK293) have specific cellular machinery and characteristic mechanisms for such post-translational activities and may be chosen to ensure the correct modification and processing of the TGF-beta superfamily type I or type II receptor polypeptide.

Figure 2:
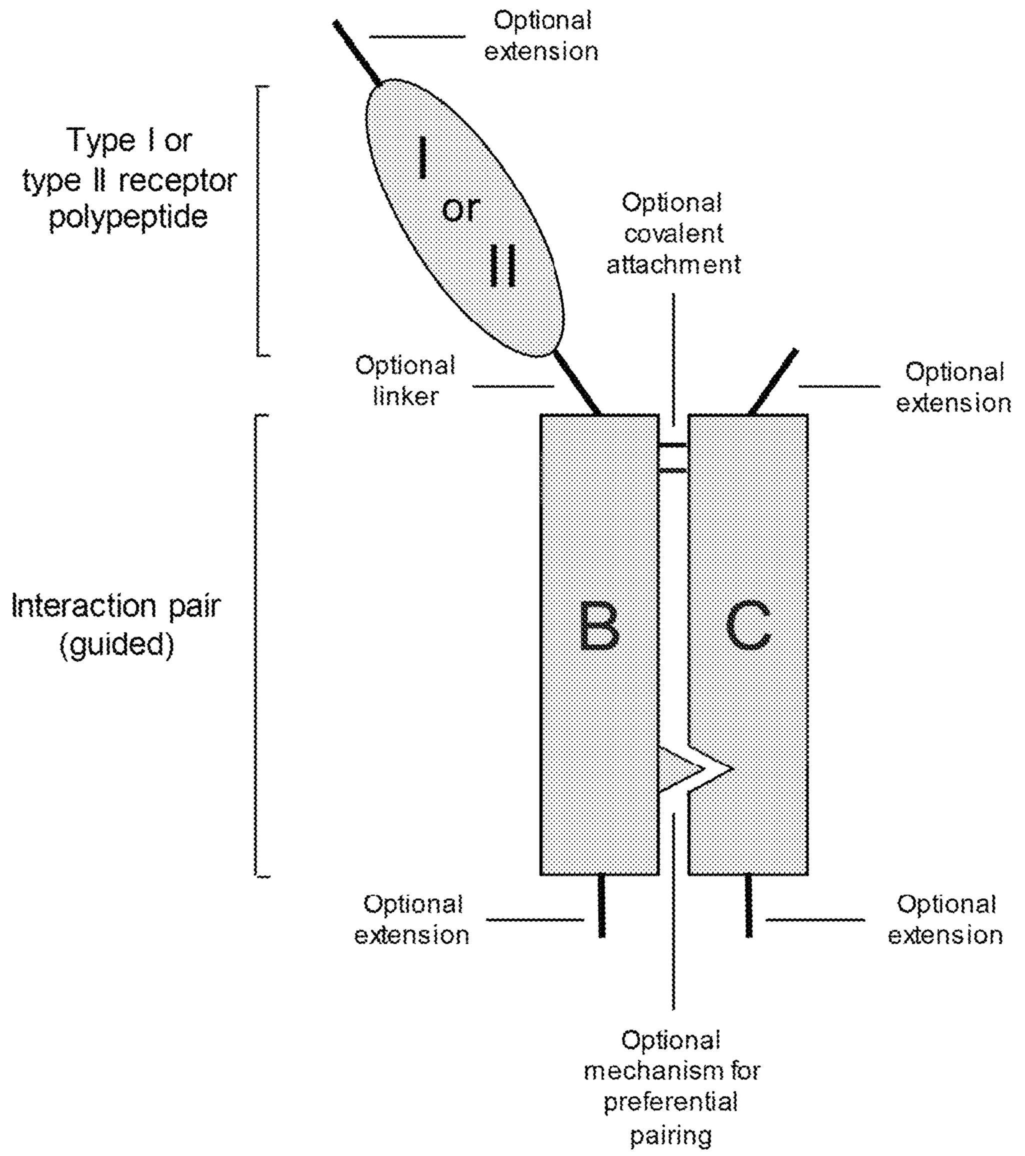
FIG. 2 shows a schematic example of a single-arm heteromeric protein complex comprising a type I receptor polypeptide (indicated as "I") (e.g. a polypeptide that is at least 80%, 85%, 90%, 95%, 97%, 98%, 99% or 100% identical to an extracellular domain of an ALK1, ALK2, ALK3, ALK4, ALK5, ALK6 or ALK7 protein from humans or other species) or a type II receptor polypeptide (indicated as "II") (e.g. a polypeptide that is at least 80%, 85%, 90%, 95%, 97%, 98%, 99% or 100% identical to an extracellular domain of an ActRIIA, ActRIIB, MISRII, BMPRII, or TGFBRII protein from humans or other species). In the illustrated embodiment, the type I or type II receptor polypeptide is part of a fusion polypeptide that comprises a first member of an interaction pair ("B"), which associates with a second member of an interaction pair ("C"). In the fusion polypeptide, a linker may be positioned between the type I or type II receptor polypeptide and the corresponding member of the interaction pair. The first and second members of the interaction pair (B, C) may be a guided (asymmetric) pair, meaning that the members of the pair associate preferentially with each other rather than self-associate, or the interaction pair may be unguided, meaning that the members of the pair may associate with each other or self-associate without substantial preference and may have the same or different amino acid sequences. Traditional Fc fusion proteins and antibodies are examples of unguided interaction pairs, whereas a variety of engineered Fc domains have been designed as guided (asymmetric) interaction pairs.

In certain aspects, the polypeptides disclosed herein may form protein complexes comprising at least one TGF-beta superfamily type I or type II receptor polypeptide associated, covalently or non-covalently, with at least one polypeptide comprising a complementary member of an interaction pair. Preferably, polypeptides disclosed herein form single-arm heterodimeric complexes, although higher order heteromultimeric complexes (heteromultimers) are also included such as, but not limited to, heterotrimers, heterotetramers, and further oligomeric structures (see, e.g., FIG. 1). In some embodiments, TGF-beta superfamily type I or type II receptor polypeptides of the present disclosure comprise at least one multimerization domain. As disclosed herein, the term “multimerization domain” refers to an amino acid or sequence of amino acids that promote covalent or non-covalent interaction between at least a first polypeptide and at least a second polypeptide. Polypeptides disclosed herein may be joined covalently or non-covalently to a multimerization domain. Preferably, a multimerization domain promotes interaction between a single-arm polypeptide (e.g., a fusion polypeptide comprising a TGF-beta superfamily type I receptor polypeptide or TGF-beta superfamily type II receptor polypeptide) and a complementary member of an interaction pair to promote heteromultimer formation (e.g., heterodimer formation), and optionally hinders or otherwise disfavors homomultimer formation (e.g., homodimer formation), thereby increasing the yield of desired heteromultimer (see, e.g., FIG. 2).

Many methods known in the art can be used to generate TGF-beta superfamily receptor single-arm complexes of the disclosure. For example, non-naturally occurring disulfide bonds may be constructed by replacing on a first polypeptide (e.g., a fusion polypeptide comprising a TGF-beta superfamily type I or type II receptor polypeptide) a naturally occurring amino acid with a free thiol-containing residue, such as cysteine, such that the free thiol interacts with another free thiol-containing residue on a second polypeptide (e.g., a complementary member of an interaction pair) such that a disulfide bond is formed between the first and second polypeptides. Additional examples of interactions to promote heteromultimer formation include, but are not limited to, ionic interactions such as described in Kjaergaard et al., WO2007147901; electrostatic steering effects such as described in Kannan et al., U.S. Pat. No. 8,592,562; coiled-coil interactions such as described in Christensen et al., U.S.20120302737; leucine zippers such as described in Pack & Plueckthun, (1992) Biochemistry 31: 1579-1584; and helix-turn-helix motifs such as described in Pack et al., (1993) Bio/Technology 11: 1271-1277. Linkage of the various segments may be obtained via, e.g., covalent binding such as by chemical cross-linking, peptide linkers, disulfide bridges, etc., or affinity interactions such as by avidin-biotin or leucine zipper technology.

In certain aspects, a multimerization domain may comprise one component of an interaction pair. In some embodiments, the polypeptides disclosed herein may form protein complexes comprising a first polypeptide covalently or non-covalently associated with a second polypeptide, wherein the first polypeptide comprises the amino acid sequence of a TGF-beta superfamily type I or type II receptor polypeptide and the amino acid sequence of a first member of an interaction pair; and the second polypeptide comprises the amino acid sequence of a second member of an interaction pair. The interaction pair may be any two polypeptide sequences that interact to form a complex, particularly a heterodimeric complex although operative embodiments may also employ an interaction pair that can form a homodimeric complex. One member of the interaction pair may be fused to a TGF-beta superfamily type I or type II receptor polypeptide as described herein, including for example, a polypeptide sequence comprising, consisting essentially of, or consisting of an amino acid sequence that is at least 80%, 85%, 90%, 95%, 96%, 97%, 98%, 99%, or 100% identical to the sequence of any one of SEQ ID NOs: 2, 3, 5, 6, 10, 11, 15, 19, 23, 27, 31, 35, 39, 43, 47, 51, 68, 72, 76, 80, 84, 88, 92, 302, 306, 310, and 313. An interaction pair may be selected to confer an improved property/activity such as increased serum half-life, or to act as an adaptor on to which another moiety is attached to provide an improved property/activity. For example, a polyethylene glycol moiety may be attached to one or both components of an interaction pair to provide an improved property/activity such as improved serum half-life.

The first and second members of the interaction pair may be an asymmetric pair, meaning that the members of the pair preferentially associate with each other rather than self-associate. Accordingly, first and second members of an asymmetric interaction pair may associate to form a heterodimeric interaction-pair complex (see, e.g., FIG. 2). Alternatively, the interaction pair may be unguided, meaning that the members of the pair may associate with each other or self-associate without substantial preference and thus may have the same or different amino acid sequences. Accordingly, first and second members of an unguided interaction pair may associate to form a homodimer interaction-pair complex or a heterodimeric action-pair complex. Optionally, the first member of the interaction pair (e.g., an asymmetric pair or an unguided interaction pair) associates covalently with the second member of the interaction pair. Optionally, the first member of the interaction pair (e.g., an asymmetric pair or an unguided interaction pair) associates non-covalently with the second member of the interaction pair.

As specific examples, the present disclosure provides fusion protein complexes comprising at least one TGF-beta superfamily type I or type II receptor polypeptide fused to a polypeptide comprising a constant domain of an immunoglobulin, such as a CH1, CH2, or CH3 domain of an immunoglobulin or an Fc domain. Fc domains derived from human IgG1, IgG2, IgG3, and IgG4 are provided herein. Other mutations are known that decrease either CDC or ADCC activity, and collectively, any of these variants are included in the disclosure and may be used as advantageous components of a single-arm heteromultimeric complex of the disclosure. Optionally, the IgG1 Fc domain of SEQ ID NO: 208 has one or more mutations at residues such as Asp-265, Lys-322, and Asn-434 (numbered in accordance with the corresponding full-length IgG1). In certain cases, the mutant Fc domain having one or more of these mutations (e.g., Asp-265 mutation) has reduced ability of binding to the Fcγ receptor relative to a wildtype Fc domain. In other cases, the mutant Fc domain having one or more of these mutations (e.g., Asn-434 mutation) has increased ability of binding to the MHC class I-related Fc-receptor (FcRN) relative to a wildtype Fc domain.

An example of a native amino acid sequence that may be used for the Fc portion of human IgG1 (G1Fc) is shown below (SEQ ID NO: 208). Dotted underline indicates the hinge region, and solid underline indicates positions with naturally occurring variants. In part, the disclosure provides polypeptides comprising amino acid sequences with 80%, 85%, 90%, 95%, 96%, 97%, 98%, or 99% identity to SEQ ID NO: 208. Naturally occurring variants in G1Fc would include E134D and M136L according to the numbering system used in SEQ ID NO: 208 (see Uniprot P01857).

```
                                                  (SEQ ID NO: 208)
  1 THTCPPCPAPELLGGPSVFL FPPKPKDTLM ISRTPEVTCV VVDVSHEDPE

 51 VKFNWYVDGV EVHNAKTKPR EEQYNSTYRV VSVLTVLHQD WLNGKEYKCK

101 VSNKALPAPI EKTISKAKGQ PREPQVYTLP PSREEMTKNQ VSLTCLVKGF

151 YPSDIAVEWE SNGQPENNYK TTPPVLDSDG SFFLYSKLTV DKSRWQQGNV

201 FSCSVMHEAL HNHYTQKSLS LSPGK
```

An example of a native amino acid sequence that may be used for the Fc portion of human IgG2 (G2Fc) is shown below (SEQ ID NO: 209). Dotted underline indicates the hinge region and double underline indicates positions where there are database conflicts in the sequence (according to UniProt P01859). In part, the disclosure provides polypeptides comprising amino acid sequences with 80%, 85%, 90%, 95%, 96%, 97%, 98%, or 99% identity to SEQ ID NO: 209.

```
                                                  (SEQ ID NO: 209)
  1 VECPPCPAPP VAGPSVFLFP PKPKDTLMIS RTPEVTCVVV DVSHEDPEVQ

 51 FNWYVDGVEV HNAKTKPREE QFNSTFRVVS VLTVVHQDWL NGKEYKCKVS

101 NKGLPAPIEK TISKTKGQPR EPQVYTLPPS REEMTKNQVS LTCLVKGFYP

151 SDIAVEWESN GQPENNYKTT PPMLDSDGSF FLYSKLTVDK SRWQQGNVFS

201 CSVMHEALHN HYTQKSLSLS PGK
```

Two examples of amino acid sequences that may be used for the Fc portion of human IgG3 (G3Fc) are shown below.

The hinge region in G3Fc can be up to four times as long as in other Fc chains and contains three identical 15-residue segments preceded by a similar 17-residue segment. The first G3Fc sequence shown below (SEQ ID NO: 210) contains a short hinge region consisting of a single 15-residue segment, whereas the second G3Fc sequence (SEQ ID NO: 211) contains a full-length hinge region. In each case, dotted underline indicates the hinge region, and solid underline indicates positions with naturally occurring variants according to UniProt P01859. In part, the disclosure provides polypeptides comprising amino acid sequences with 80%, 85%, 90%, 95%, 96%, 97%, 98%, or 99% identity to SEQ ID NOs: 210 and 211.

```
                                                     (SEQ ID NO: 210)
  1 EPKSCDTPPP CPRCPAPELL GGPSVFLFPP KPKDTLMISR TPEVTCVVVD

 51 VSHEDPEVQF KWYVDGVEVH NAKTKPREEQ YNSTFRVVSV LTVLHQDWLN

101 GKEYKCKVSN KALPAPIEKT ISKTKGQPRE PQVYTLPPSR EEMTKNQVSL

151 TCLVKGFYPS DIAVEWESSG QPENNYNTTP PMLDSDGSFF LYSKLTVDKS

201 RWQQGNIFSC SVMHEALHNR FTQKSLSLSP GK

                                                     (SEQ ID NO: 211)
  1 ELKTPLGDTT HTCPRCPEPK SCDTPPPCPRCPEPKSCDTPPPCPRCPEPK

 51 SCDTPPPCPRAPELLGGP SVFLFPPKPK DTLMISRTPE VTCVVVDVSH

101 EDPEVQFKWY VDGVEVHNAK TKPREEQYNS TFRVVSVLTV LHQDWLNGKE

151 YKCKVSNKAL PAPIEKTISK TKGQPREPQV YTLPPSREEM TKNQVSLTCL

201 VKGFYPSDIA VEWESSGQPE NNYNTTPPML DSDGSFFLYS KLTVDKSRWQ

251 QGNIFSCSVM HEALHNRFTQ KSLSLSPGK
```

Naturally occurring variants in G3Fc (for example, see Uniprot P01860) include E68Q, P76L, E79Q, Y81F, D97N, N100D, T124A, S169N, S169del, F221Y when converted to the numbering system used in SEQ ID NO: 210, and the present disclosure provides fusion proteins comprising G3Fc domains containing one or more of these variations. In addition, the human immunoglobulin IgG3 gene (IGHG3) shows a structural polymorphism characterized by different hinge lengths [see Uniprot P01859]. Specifically, variant WIS is lacking most of the V region and all of the CH1 region. It has an extra interchain disulfide bond at position 7 in addition to the 11 normally present in the hinge region. Variant ZUC lacks most of the V region, all of the CH1 region, and part of the hinge. Variant OMM may represent an allelic form or another gamma chain subclass. The present disclosure provides additional fusion proteins comprising G3Fc domains containing one or more of these variants.

An example of a native amino acid sequence that may be used for the Fc portion of human IgG4 (G4Fc) is shown below (SEQ ID NO: 212). Dotted underline indicates the hinge region. In part, the disclosure provides polypeptides comprising amino acid sequences with 80%, 85%, 90%, 95%, 96%, 97%, 98%, or 99% identity to SEQ ID NO: 212.

```
                                                     (SEQ ID NO: 212)
  1 ESKYGPPCPS CPAPEFLGGP SVFLFPPKPK DTLMISRTPE VTCVVVDVSQ

 51 EDPEVQFNWY VDGVEVHNAK TKPREEQFNS TYRVVSVLTV LHQDWLNGKE

101 YKCKVSNKGL PSSIEKTISK AKGQPREPQV YTLPPSQEEM TKNQVSLTCL

151 VKGFYPSDIA VEWESNGQPE NNYKTTPPVL DSDGSFFLYS RLTVDKSRWQ

201 EGNVFSCSVM HEALHNHYTQ KSLSLSLGK
```

A variety of engineered mutations in the Fc domain are presented herein with respect to the G1Fc sequence (SEQ ID NO: 208), and analogous mutations in G2Fc, G3Fc, and G4Fc can be derived from their alignment with G1Fc in FIG. 5. Due to unequal hinge lengths, analogous Fc positions based on isotype alignment (FIG. 5) possess different amino acid numbers in SEQ ID NOs: 208, 209, 210, and 212. It can also be appreciated that a given amino acid position in an immunoglobulin sequence consisting of hinge, CH2, and CH3 regions (e.g., SEQ ID NOs: 208, 209, 210, 211, or 212) will be identified by a different number than the same position when numbering encompasses the entire IgG1 heavy-chain constant domain (consisting of the CH1, hinge, CH2, and CH3 regions) as in the Uniprot database. For example, correspondence between selected CH3 positions in a human G1Fc sequence (SEQ ID NO: 208), the human IgG1 heavy chain constant domain (Uniprot P01857), and the human IgG1 heavy chain is as follows.

For example, one means by which interaction between specific polypeptides may be promoted is by engineering protuberance-into-cavity (knob-into-holes) complementary regions such as described in Arathoon et al., U.S. Pat. No. 7,183,076 and Carter et al., U.S. Pat. No. 5,731,168. "Protuberances" are constructed by replacing small amino acid side chains from the interface of the first polypeptide (e.g., a first interaction pair) with larger side chains (e.g., tyrosine or tryptophan). Complementary "cavities" of identical or similar size to the protuberances are optionally created on the interface of the second polypeptide (e.g., a second interaction pair) by replacing large amino acid side chains with smaller ones (e.g., alanine or threonine). Where a suitably positioned and dimensioned protuberance or cavity exists at the interface of either the first or second polypeptide, it is only necessary to engineer a corresponding cavity or protuberance, respectively, at the adjacent interface.

Correspondence of $C_H3$ Positions in Different Numbering Systems

| G1Fc (Numbering begins at first threonine in hinge region) | IgG1 heavy chain constant domain (Numbering begins at $C_H1$) | IgG1 heavy chain (EU numbering scheme of Kabat et al., 1991*) |
|---|---|---|
| Y127 | Y232 | Y349 |
| S132 | S237 | S354 |
| E134 | E239 | E356 |
| T144 | T249 | T366 |
| L146 | L251 | L368 |
| K170 | K275 | K392 |
| D177 | D282 | D399 |
| Y185 | Y290 | Y407 |
| K187 | K292 | K409 |

*Kabat et al. (eds) 1991; pp. 688-696 in *Sequences of Proteins of Immunological Interest*, 5th ed., Vol. 1, NIH, Bethesda, MD.

A problem that arises in large-scale production of asymmetric immunoglobulin-based proteins from a single cell line is known as the "chain association issue". As confronted prominently in the production of bispecific antibodies, the chain association issue concerns the challenge of efficiently producing a desired multichain protein from among the multiple combinations that inherently result when different heavy chains and/or light chains are produced in a single cell line [see, for example, Klein et al (2012) mAbs 4:653-663]. This problem is most acute when two different heavy chains and two different light chains are produced in the same cell, in which case there are a total of 16 possible chain combinations (although some of these are identical) when only one is typically desired. Nevertheless, the same principle accounts for diminished yield of a desired multichain fusion protein that incorporates only two different (asymmetric) heavy chains.

Various methods are known in the art that increase desired pairing of Fc-containing fusion polypeptide chains in a single cell line to produce a preferred asymmetric fusion protein at acceptable yields [see, for example, Klein et al (2012) mAbs 4:653-663]. Methods to obtain desired pairing of Fc-containing chains include, but are not limited to, charge-based pairing (electrostatic steering), "knobs-into-holes" steric pairing, SEEDbody pairing, and leucine zipper-based pairing. See, for example, Ridgway et al (1996) Protein Eng 9:617-621; Merchant et al (1998) Nat Biotech 16:677-681; Davis et al (2010) Protein Eng Des Sel 23:195-202; Gunasekaran et al (2010); 285:19637-19646; Wranik et al (2012) J Biol Chem 287:43331-43339; U.S. Pat. No. 5,932,448; WO 1993/011162; WO 2009/089004, and WO 2011/034605.

At neutral pH (7.0), aspartic acid and glutamic acid are negatively charged and lysine, arginine, and histidine are positively charged. These charged residues can be used to promote heterodimer formation and at the same time hinder homodimer formation. Attractive interactions take place between opposite charges and repulsive interactions occur between like charges. In part, protein complexes disclosed herein make use of the attractive interactions for promoting heteromultimer formation (e.g., heterodimer formation), and optionally repulsive interactions for hindering homodimer formation (e.g., homodimer formation) by carrying out site directed mutagenesis of charged interface residues.

For example, the IgG1 CH3 domain interface comprises four unique charge residue pairs involved in domain-domain interactions: Asp356-Lys439', Glu357-Lys370', Lys392-Asp399', and Asp399-Lys409' [residue numbering in the second chain is indicated by (')]. It should be noted that the numbering scheme used here to designate residues in the IgG1 CH3 domain conforms to the EU numbering scheme of Kabat. Due to the 2-fold symmetry present in the CH3-CH3 domain interactions, each unique interaction will represented twice in the structure (e.g., Asp-399-Lys409' and Lys409-Asp399'). In the wild-type sequence, K409-D399' favors both heterodimer and homodimer formation. A single mutation switching the charge polarity (e.g., K409E; positive to negative charge) in the first chain leads to unfavorable interactions for the formation of the first chain homodimer. The unfavorable interactions arise due to the repulsive interactions occurring between the same charges (negative-negative; K409E-D399' and D399-K409E'). A similar mutation switching the charge polarity (D399K'; negative to positive) in the second chain leads to unfavorable interactions (K409'-D399K' and D399K-K409') for the second chain homodimer formation. But, at the same time, these two mutations (K409E and D399K') lead to favorable interactions (K409E-D399K' and D399-K409') for the heterodimer formation.

The electrostatic steering effect on heterodimer formation and homodimer discouragement can be further enhanced by mutation of additional charge residues which may or may not be paired with an oppositely charged residue in the second chain including, for example, Arg355 and Lys360. The table below lists possible charge change mutations that can be used, alone or in combination, to enhance heteromultimer formation of the polypeptide complexes disclosed herein.

subclasses, electrostatic steering effects disclosed herein can be applied to human and mouse IgG1, IgG2, IgG3, and IgG4. This strategy can also be extended to modifying uncharged residues to charged residues at the CH3 domain interface.

In part, the disclosure provides desired pairing of asymmetric Fc-containing polypeptide chains using Fc sequences engineered to be complementary on the basis of charge pairing (electrostatic steering). One of a pair of Fc sequences with electrostatic complementarity can be arbitrarily fused to the TGF-beta superfamily type I or type II receptor polypeptide of the construct, with or without an optional linker, to generate a TGF-beta superfamily type I or type II receptor fusion polypeptide This single chain can be coexpressed in a cell of choice along with the Fc sequence Examples of Pair-Wise Charged Residue Mutations to Enhance Heterodimer Formation

| Position in first chain | Mutation in first chain | Interacting position in second chain | Corresponding mutation in second chain |
|---|---|---|---|
| Lys409 | Asp or Glu | Asp399' | Lys, Arg, or His |
| Lys392 | Asp or Glu | Asp399' | Lys, Arg, or His |
| Lys439 | Asp or Glu | Asp356' | Lys, Arg, or His |
| Lys370 | Asp or Glu | Glu357' | Lys, Arg, or His |
| Asp399 | Lys, Arg, or His | Lys409' | Asp or Glu |
| Asp399 | Lys, Arg, or His | Lys392' | Asp or Glu |
| Asp356 | Lys, Arg, or His | Lys439' | Asp or Glu |
| Glu357 | Lys, Arg, or His | Lys370' | Asp or Glu |

In some embodiments, one or more residues that make up the CH3-CH3 interface in a fusion protein of the instant application are replaced with a charged amino acid such that the interaction becomes electrostatically unfavorable. For example, a positive-charged amino acid in the interface (e.g., a lysine, arginine, or histidine) is replaced with a negatively charged amino acid (e.g., aspartic acid or glutamic acid). Alternatively, or in combination with the forgoing substitution, a negative-charged amino acid in the interface is replaced with a positive-charged amino acid. In certain embodiments, the amino acid is replaced with a non-naturally occurring amino acid having the desired charge characteristic. It should be noted that mutating negatively charged residues (Asp or Glu) to His will lead to increase in side chain volume, which may cause steric issues. Furthermore, His proton donor- and acceptor-form depends on the localized environment. These issues should be taken into consideration with the design strategy. Because the interface residues are highly conserved in human and mouse IgG complementary to the first Fc to favor generation of the desired multichain construct (e.g., a TGF-beta superfamily receptor single-arm heteromeric complex). In this example based on electrostatic steering, SEQ ID NO: 200 [human G1Fc(E134K/D177K)] and SEQ ID NO: 201 [human G1Fc (K170D/K187D)] are examples of complementary Fc sequences in which the engineered amino acid substitutions are double underlined, and the TGF-beta superfamily type I or type II receptor polypeptide of the construct can be fused to either SEQ ID NO: 200 or SEQ ID NO: 201, but not both. Given the high degree of amino acid sequence identity between native hG1Fc, native hG2Fc, native hG3Fc, and native hG4Fc, it can be appreciated that amino acid substitutions at corresponding positions in hG2Fc, hG3Fc, or hG4Fc (see FIG. 5) will generate complementary Fc pairs which may be used instead of the complementary hG1Fc pair below (SEQ ID NOs: 200 and 201).

```
                                                    (SEQ ID NO: 200)
  1  THTCPPCPAP ELLGGPSVFL FPPKPKDTLM ISRTPEVTCV VVDVSHEDPE

 51  VKFNWYVDGV EVHNAKTKPR EEQYNSTYRV VSVLTVLHQD WLNGKEYKCK

101  VSNKALPAPI EKTISKAKGQ PREPQVYTLP PSRKEMTKNQ VSLTCLVKGF

151  YPSDIAVEWE SNGQPENNYK TTPPVLKSDG SFFLYSKLTV DKSRWQQGNV

201  FSCSVMHEAL HNHYTQKSLS LSPGK
                                                    (SEQ ID NO: 201)
  1  THTCPPCPAP ELLGGPSVFL FPPKPKDTLM ISRTPEVTCV VVDVSHEDPE

 51  VKFNWYVDGV EVHNAKTKPR EEQYNSTYRV VSVLTVLHQD WLNGKEYKCK

101  VSNKALPAPI EKTISKAKGQ PREPQVYTLP PSREEMTKNQ VSLTCLVKGF

151  YPSDIAVEWE SNGQPENNYD TTPPVLDSDG SFFLYSDLTV DKSRWQQGNV

201  FSCSVMHEAL HNHYTQKSLS LSPGK
```

In part, the disclosure provides desired pairing of asymmetric Fc-containing polypeptide chains using Fc sequences engineered for steric complementarity. In part, the disclosure provides knobs-into-holes pairing as an example of steric complementarity. One of a pair of Fc sequences with steric complementarity can be arbitrarily fused to the TGF-beta superfamily type I or type II receptor polypeptide of the construct, with or without an optional linker, to generate a TGF-beta superfamily type I or type II receptor fusion polypeptide. This single chain can be coexpressed in a cell of choice along with the Fc sequence complementary to the first Fc to favor generation of the desired multichain construct (e.g., a TGF-beta superfamily receptor single-arm heteromeric complex). In this example based on knobs-into-holes pairing, SEQ ID NO: 202 [human G1Fc(T144Y)] and SEQ ID NO: 203 [human G1Fc(Y185T)] are examples of complementary Fc sequences in which the engineered amino acid substitutions are double underlined, and the TGF-beta superfamily type I or type II polypeptide of the construct can be fused to either SEQ ID NO: 202 or SEQ ID NO: 203, but not both. Given the high degree of amino acid sequence identity between native hG1Fc, native hG2Fc, native hG3Fc, and native hG4Fc, it can be appreciated that amino acid substitutions at corresponding positions in hG2Fc, hG3Fc, or hG4Fc (see FIG. 5) will generate complementary Fc pairs which may be used instead of the complementary hG1Fc pair below (SEQ ID NOs: 202 and 203).

(SEQ ID NO: 202)

1 THTCPPCPAP ELLGGPSVFL FPPKPKDTLM ISRTPEVTCV VVDVSHEDPE

51 VKFNWYVDGV EVHNAKTKPR EEQYNSTYRV VSVLTVLHQD WLNGKEYKCK

101 VSNKALPAPI EKTISKAKGQ PREPQVYTLP PSREEMTKNQ VSLYCLVKGF

151 YPSDIAVEWE SNGQPENNYK TTPPVLDSDG SFFLYSKLTV DKSRWQQGNV

201 FSCSVMHEAL HNHYTQKSLS LSPGK (SEQ ID NO: 203)

1 THTCPPCPAP ELLGGPSVFL FPPKPKDTLM ISRTPEVTCV VVDVSHEDPE

51 VKFNWYVDGV EVHNAKTKPR EEQYNSTYRV VSVLTVLHQD WLNGKEYKCK

101 VSNKALPAPI EKTISKAKGQ PREPQVYTLP PSREEMTKNQ VSLTCLVKGF

151 YPSDIAVEWE SNGQPENNYK TTPPVLDSDG SFFLTSKLTV DKSRWQQGNV

201 FSCSVMHEAL HNHYTQKSLS LSPGK

An example of Fc complementarity based on knobs-into-holes pairing combined with an engineered disulfide bond is disclosed in SEQ ID NO: 204 [hG1Fc(S132C/T144W)] and SEQ ID NO: 205 [hG1Fc(Y127C/T144S/L146A/Y185V)]. The engineered amino acid substitutions in these sequences are double underlined, and the TGF-beta superfamily type I or type II polypeptide of the construct can be fused to either SEQ ID NO: 204 or SEQ ID NO: 205, but not both. Given the high degree of amino acid sequence identity between native hG1Fc, native hG2Fc, native hG3Fc, and native hG4Fc, it can be appreciated that amino acid substitutions at corresponding positions in hG2Fc, hG3Fc, or hG4Fc (see FIG. 5) will generate complementary Fc pairs which may be used instead of the complementary hG1Fc pair below (SEQ ID NOs: 204 and 205).

(SEQ ID NO: 204)

1 THTCPPCPAP ELLGGPSVFL FPPKPKDTLM ISRTPEVTCV VVDVSHEDPE

51 VKFNWYVDGV EVHNAKTKPR EEQYNSTYRV VSVLTVLHQD WLNGKEYKCK

101 VSNKALPAPI EKTISKAKGQ PREPQVYTLP PCREEMTKNQ VSLWCLVKGF

151 YPSDIAVEWE SNGQPENNYK TTPPVLDSDG SFFLYSKLTV DKSRWQQGNV

201 FSCSVMHEAL HNHYTQKSLS LSPGK (SEQ ID NO: 205)

1 THTCPPCPAP ELLGGPSVFL FPPKPKDTLM ISRTPEVTCV VVDVSHEDPE

51 VKFNWYVDGV EVHNAKTKPR EEQYNSTYRV VSVLTVLHQD WLNGKEYKCK

101 VSNKALPAPI EKTISKAKGQ PREPQVCTLP PSREEMTKNQ VSLSCAVKGF

-continued

```
151      YPSDIAVEWE SNGQPENNYK TTPPVLDSDG SFFLVSKLTV DKSRWQQGNV

201      FSCSVMHEAL HNHYTQKSLS LSPGK
```

In part, the disclosure provides desired pairing of asymmetric Fc-containing polypeptide chains using Fc sequences engineered to generate interdigitating β-strand segments of human IgG and IgA CH3 domains. Such methods include the use of strand-exchange engineered domain (SEED) CH3 heterodimers allowing the formation of SEEDbody fusion proteins [see, for example, Davis et al (2010) Protein Eng Design Sel 23:195-202]. One of a pair of Fc sequences with SEEDbody complementarity can be arbitrarily fused to the TGF-beta superfamily type I or type II receptor polypeptide of the construct, with or without an optional linker, to generate a TGF-beta superfamily type I or type II receptor fusion polypeptide. This single chain can be coexpressed in a cell of choice along with the Fc sequence complementary to the first Fc to favor generation of the desired multichain construct. In this example based on SEEDbody (Sb) pairing, SEQ ID NO: 206 [hG1Fc($Sb_{AG}$)] and SEQ ID NO: 207 [hG1Fc($Sb_{GA}$)] are examples of complementary IgG Fc sequences in which the engineered amino acid substitutions from IgA Fc are double underlined, and the TGF-beta superfamily type I or type II receptor polypeptide of the construct can be fused to either SEQ ID NO: 206 or SEQ ID NO: 207, but not both. Given the high degree of amino acid sequence identity between native hG1Fc, native hG2Fc, native hG3Fc, and native hG4Fc, it can be appreciated that amino acid substitutions at corresponding positions in hG1Fc, hG2Fc, hG3Fc, or hG4Fc (see FIG. 5) will generate an Fc monomer which may be used in the complementary IgG-IgA pair below (SEQ ID NOs: 206 and 207).

```
                                           (SEQ ID NO: 206)
  1      THTCPPCPAP ELLGGPSVFL FPPKPKDTLM ISRTPEVTCV VVDVSHEDPE

 51      VKFNWYVDGV EVHNAKTKPR EEQYNSTYRV VSVLTVLHQD WLNGKEYKCK

101      VSNKALPAPI EKTISKAKGQ PFRPEVHLLP PSREEMTKNQ VSLTCLARGF

151      YPKDIAVEWE SNGQPENNYK TIPSRQEPSQ GTTTFAVTSK LTVDKSRWQQ

201      GNVFSCSVMH EALHNHYTQK TISLSPGK

                                           (SEQ ID NO: 207)
  1      THTCPPCPAP ELLGGPSVFL FPPKPKDTLM ISRTPEVTCV VVDVSHEDPE

 51      VKFNWYVDGV EVHNAKTKPR EEQYNSTYRV VSVLTVLHQD WLNGKEYKCK

101      VSNKALPAPI EKTISKAKGQ PREPQVYTLP PPSEELALNE LVTLTCLVKG

151      FYPSDIAVEW ESNGQELPRE KYLTWAPVLD SDGSFFLYSI LRVAAEDWKK

201      GDTFSCSVMH EALHNHYTQK SLDRSPGK
```

In part, the disclosure provides desired pairing of asymmetric Fc-containing polypeptide chains with a cleavable leucine zipper domain attached at the C-terminus of the Fc $C_H3$ domains. Attachment of a leucine zipper is sufficient to cause preferential assembly of heterodimeric antibody heavy chains. See, e.g., Wranik et al (2012) J Biol Chem 287:43331-43339. As disclosed herein, one of a pair of Fc sequences attached to a leucine zipper-forming strand can be arbitrarily fused to the TGF-beta superfamily type I or type II receptor polypeptide of the construct, with or without an optional linker, to generate a TGF-beta superfamily type I or type II receptor fusion polypeptide. This single chain can be coexpressed in a cell of choice along with the Fc sequence attached to a complementary leucine zipper-forming strand to favor generation of the desired multichain construct. Proteolytic digestion of the construct with the bacterial endoproteinase Lys-C post purification can release the leucine zipper domain, resulting in an Fc construct whose structure is identical to that of native Fc. In this example based on leucine zipper pairing, SEQ ID NO: 213 [hG1Fc-Ap1 (acidic)] and SEQ ID NO: 214 [hG1Fc-Bp1 (basic)] are examples of complementary IgG Fc sequences in which the engineered complimentary leucine zipper sequences are underlined, and the TGF-beta superfamily type I or type II receptor polypeptide of the construct can be fused to either SEQ ID NO: 213 or SEQ ID NO: 214, but not both. Given the high degree of amino acid sequence identity between native hG1Fc, native hG2Fc, native hG3Fc, and native hG4Fc, it can be appreciated that leucine zipper-forming sequences attached, with or without an optional linker, to hG1Fc, hG2Fc, hG3Fc, or hG4Fc (see FIG. 5) will generate an Fc monomer which may be used in the complementary leucine zipper-forming pair below (SEQ ID NOs: 213 and 214).

```
                                           (SEQ ID NO: 213)
  1      THTCPPCPAP ELLGGPSVFL FPPKPKDTLM ISRTPEVTCV VVDVSHEDPE

 51      VKFNWYVDGV EVHNAKTKPR EEQYNSTYRV VSVLTVLHQD WLNGKEYKCK

101      VSNKALPAPI EKTISKAKGQ PREPQVYTLP PSREEMTKNQ VSLTCLVKGF

151      YPSDIAVEWE SNGQPENNYK TTPPVLDSDG SFFLYSKLTV DKSRWQQGNV
```

-continued

```
201      FSCSVMHEAL HNHYTQKSLS LSPGKGGSAQ LEKELQALEK ENAQLEWELQ

251      ALEKELAQGA T

                                          (SEQ ID NO: 214)
  1      THTCPPCPAP ELLGGPSVFL FPPKPKDTLM ISRTPEVTCV VVDVSHEDPE

 51      VKFNWYVDGV EVHNAKTKPR EEQYNSTYRV VSVLTVLHQD WLNGKEYKCK

101      VSNKALPAPI EKTISKAKGQ PREPQVYTLP PSREEMTKNQ VSLTCLVKGF

151      YPSDIAVEWE SNGQPENNYK TTPPVLDSDG SFFLYSKLTV DKSRWQQGNV

201      FSCSVMHEAL HNHYTQKSLS LSPGKGGSAQ LKKKLQALKK KNAQLKWKLQ

251      ALKKKLAQGA T
```

It is understood that different elements of the fusion proteins (e.g., immunoglobulin Fc fusion proteins) may be arranged in any manner that is consistent with desired functionality. For example, a TGF-beta superfamily type I or type II receptor polypeptide domain may be placed C-terminal to a heterologous domain, or alternatively, a heterologous domain may be placed C-terminal to a TGF-beta superfamily type I or type II receptor polypeptide domain. The TGF-beta superfamily type I or type II receptor polypeptide domain and the heterologous domain need not be adjacent in a fusion protein, and additional domains or amino acid sequences may be included C- or N-terminal to either domain or between the domains.

For example, a TGF-beta superfamily type I or type II receptor fusion polypeptide may comprise an amino acid sequence as set forth in the formula A-B-C. The B portion corresponds to a TGF-beta superfamily type I or type II receptor polypeptide domain. The A and C portions may be independently zero, one, or more than one amino acid, and both the A and C portions when present are heterologous to B. The A and/or C portions may be attached to the B portion via a linker sequence. A linker may be rich in glycine (e.g., 2-10, 2-5, 2-4, 2-3 glycine residues) or glycine and proline residues and may, for example, contain a single sequence of threonine/serine and glycines or repeating sequences of threonine/serine and/or glycines, e.g., GGG (SEQ ID NO: 58), GGGG (SEQ ID NO: 59), $TG_4$ (SEQ ID NO: 60), $SG_4$ (SEQ ID NO: 61), $TG_3$ (SEQ ID NO: 62), or $SG_3$ (SEQ ID NO: 63) singlets, or repeats. In certain embodiments, a TGF-beta superfamily type I or type II receptor fusion polypeptide comprises an amino acid sequence as set forth in the formula A-B-C, wherein A is a leader (signal) sequence, B consists of a TGF-beta superfamily type I or type II receptor polypeptide domain, and C is a polypeptide portion that enhances one or more of in vivo stability, in vivo half-life, uptake/administration, tissue localization or distribution, formation of protein complexes, and/or purification. In certain embodiments, a TGF-beta superfamily type I or type II receptor fusion polypeptide comprises an amino acid sequence as set forth in the formula A-B-C, wherein A is a TPA leader sequence, B consists of a TGF-beta superfamily type I or type II receptor polypeptide domain, and C is an immunoglobulin Fc domain. Preferred fusion polypeptides comprise the amino acid sequence set forth in any one of SEQ ID NOs: 101, 103, 104, 106, 107, 109, 110, 112, 113, 115, 116, 118, 119, 121, 122, 124, 125, 127, 128, 130, 131, 133, 134, 136, and 401-424.

In some embodiments, TGF-beta superfamily receptor single-arm heteromultimer complexes of the present disclosure further comprise one or more heterologous portions (domains) so as to confer a desired property. For example, some fusion domains are particularly useful for isolation of the fusion proteins by affinity chromatography. Well-known examples of such fusion domains include, but are not limited to, polyhistidine, Glu-Glu, glutathione S-transferase (GST), thioredoxin, protein A, protein G, an immunoglobulin heavy-chain constant region (Fc), maltose binding protein (MBP), or human serum albumin. For the purpose of affinity purification, relevant matrices for affinity chromatography, such as glutathione-, amylase-, and nickel- or cobalt-conjugated resins are used. Many of such matrices are available in "kit" form, such as the Pharmacia GST purification system and the QIAexpress™ system (Qiagen) useful with ($HIS_6$) (SEQ ID NO: 509) fusion partners. As another example, a fusion domain may be selected so as to facilitate detection of the ligand trap polypeptides. Examples of such detection domains include the various fluorescent proteins (e.g., GFP) as well as "epitope tags," which are usually short peptide sequences for which a specific antibody is available. Well-known epitope tags for which specific monoclonal antibodies are readily available include FLAG, influenza virus haemagglutinin (HA), and c-myc tags. In some cases, the fusion domains have a protease cleavage site, such as for factor Xa or thrombin, which allows the relevant protease to partially digest the fusion proteins and thereby liberate the recombinant proteins therefrom. The liberated proteins can then be isolated from the fusion domain by subsequent chromatographic separation.

In certain embodiments, TGF-beta superfamily type I and/or type II receptor polypeptides of the present disclosure contain one or more modifications that are capable of stabilizing the polypeptides. For example, such modifications enhance the in vitro half-life of the polypeptides, enhance circulatory half-life of the polypeptides, and/or reduce proteolytic degradation of the polypeptides. Such stabilizing modifications include, but are not limited to, fusion polypeptides (including, for example, fusion polypeptides comprising a TGF-beta superfamily type I or type II receptor polypeptide domain and a stabilizer domain), modifications of a glycosylation site (including, for example, addition of a glycosylation site to a polypeptide of the disclosure), and modifications of carbohydrate moiety (including, for example, removal of carbohydrate moieties from a polypeptide of the disclosure). As used herein, the term "stabilizer domain" not only refers to a fusion domain (e.g., an immunoglobulin Fc domain) as in the case of fusion polypeptides, but also includes nonproteinaceous modifications such as a carbohydrate moiety, or nonproteinaceous moiety, such as polyethylene glycol.

In preferred embodiments, TGF-beta superfamily receptor single-arm heteromultimer complexes to be used in accordance with the methods described herein are isolated polypeptide complexes. As used herein, an isolated protein (or protein complex) or polypeptide (or polypeptide complex) is one which has been separated from a component of its natural environment. In some embodiments, a single-arm heteromultimer complex of the disclosure is purified to greater than 95%, 96%, 97%, 98%, or 99% purity as determined by, for example, electrophoretic (e.g., SDS-PAGE, isoelectric focusing (IEF), capillary electrophoresis) or chromatographic (e.g., ion exchange or reverse phase HPLC). Methods for assessment of antibody purity are well known in the art [See, e.g., Flatman et al., (2007) J. Chromatogr. B 848:79-87].

In certain embodiments, TGF-beta superfamily type I or type II receptor polypeptides, as well as single-arm heteromultimer complexes thereof, of the disclosure can be produced by a variety of art-known techniques. For example, polypeptides of the disclosure can be synthesized using standard protein chemistry techniques such as those described in Bodansky, M. Principles of Peptide Synthesis, Springer Verlag, Berlin (1993) and Grant G. A. (ed.), Synthetic Peptides: A User's Guide, W. H. Freeman and Company, New York (1992). In addition, automated peptide synthesizers are commercially available (see, e.g., Advanced ChemTech Model 396; Milligen/Biosearch 9600). Alternatively, the polypeptides and complexes of the disclosure, including fragments or variants thereof, may be recombinantly produced using various expression systems [e.g., *E. coli*, Chinese Hamster Ovary (CHO) cells, COS cells, baculovirus] as is well known in the art. In a further embodiment, the modified or unmodified polypeptides of the disclosure may be produced by digestion of recombinantly produced full-length TGFβ superfamily type I or type II receptor polypeptides by using, for example, a protease, e.g., trypsin, thermolysin, chymotrypsin, pepsin, or paired basic amino acid converting enzyme (PACE). Computer analysis (using a commercially available software, e.g., MacVector, Omega, PCGene, Molecular Simulation, Inc.) can be used to identify proteolytic cleavage sites.

3. Nucleic Acids Encoding TGFβ Superfamily Receptor Polypeptides

In certain embodiments, the present disclosure provides isolated and/or recombinant nucleic acids encoding TGFβ superfamily type I or type II receptors (including fragments, functional variants, and fusion proteins thereof) disclosed herein. For example, SEQ ID NO: 12 encodes the naturally occurring human ActRIIA precursor polypeptide, while SEQ ID NO: 13 encodes the processed extracellular domain of ActRIIA. The subject nucleic acids may be single-stranded or double stranded. Such nucleic acids may be DNA or RNA molecules. These nucleic acids may be used, for example, in methods for making TGF-beta superfamily single-arm heteromultimer complexes of the present disclosure.

As used herein, isolated nucleic acid(s) refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

In certain embodiments, nucleic acids encoding TGFβ superfamily type I or type II receptor polypeptides of the present disclosure are understood to include nucleic acids that are variants of any one of SEQ ID NOs: 7, 8, 12, 13, 16, 17, 20, 21, 24, 25, 28, 29, 32, 33, 36, 37, 40, 41, 44, 45, 48, 49, 52, 53, 69, 70, 73, 74, 77, 78, 81, 82, 85, 86, 89, 90, 93, 94, 102, 105, 108, 114, 117, 120, 123, 126, 129, 132, 135, 303, 304, 307, 308, 311, and 312. Variant nucleotide sequences include sequences that differ by one or more nucleotide substitutions, additions, or deletions including allelic variants, and therefore, will include coding sequences that differ from the nucleotide sequence designated in any one of SEQ ID NOs: 7, 8, 12, 13, 16, 17, 20, 21, 24, 25, 28, 29, 32, 33, 36, 37, 40, 41, 44, 45, 48, 49, 52, 53, 69, 70, 73, 74, 77, 78, 81, 82, 85, 86, 89, 90, 93, 94, 102, 105, 108, 114, 117, 120, 123, 126, 129, 132, 135, 303, 304, 307, 308, 311, and 312.

In certain embodiments, TGFβ superfamily type I or type II receptor polypeptides of the present disclosure are encoded by isolated or recombinant nucleic acid sequences that are at least 80%, 85%, 90%, 95%, 97%, 98%, or 99% identical to SEQ ID NOs: 7, 8, 12, 13, 16, 17, 20, 21, 24, 25, 28, 29, 32, 33, 36, 37, 40, 41, 44, 45, 48, 49, 52, 53, 69, 70, 73, 74, 77, 78, 81, 82, 85, 86, 89, 90, 93, 94, 102, 105, 108, 114, 117, 120, 123, 126, 129, 132, 135, 303, 304, 307, 308, 311, and 312. One of ordinary skill in the art will appreciate that nucleic acid sequences that are at least 80%, 85%, 90%, 95%, 97%, 98%, or 99% identical to the sequences complementary to SEQ ID NOs: 7, 8, 12, 13, 16, 17, 20, 21, 24, 25, 28, 29, 32, 33, 36, 37, 40, 41, 44, 45, 48, 49, 52, 53, 69, 70, 73, 74, 77, 78, 81, 82, 85, 86, 89, 90, 93, 94, 102, 105, 108, 114, 117, 120, 123, 126, 129, 132, 135, 303, 304, 307, 308, 311, and 312 are also within the scope of the present disclosure. In further embodiments, the nucleic acid sequences of the disclosure can be isolated, recombinant, and/or fused with a heterologous nucleotide sequence or in a DNA library.

In other embodiments, nucleic acids of the present disclosure also include nucleotide sequences that hybridize under highly stringent conditions to the nucleotide sequence designated in SEQ ID NOs: 7, 8, 12, 13, 16, 17, 20, 21, 24, 25, 28, 29, 32, 33, 36, 37, 40, 41, 44, 45, 48, 49, 52, 53, 69, 70, 73, 74, 77, 78, 81, 82, 85, 86, 89, 90, 93, 94, 102, 105, 108, 114, 117, 120, 123, 126, 129, 132, 135, 303, 304, 307, 308, 311, and 312, the complement sequence of SEQ ID NOs: 7, 8, 12, 13, 16, 17, 20, 21, 24, 25, 28, 29, 32, 33, 36, 37, 40, 41, 44, 45, 48, 49, 52, 53, 69, 70, 73, 74, 77, 78, 81, 82, 85, 86, 89, 90, 93, 94, 102, 105, 108, 114, 117, 120, 123, 126, 129, 132, 135, 303, 304, 307, 308, 311, and 312, or fragments thereof. One of ordinary skill in the art will understand readily that appropriate stringency conditions which promote DNA hybridization can be varied. For example, one could perform the hybridization at 6.0× sodium chloride/sodium citrate (SSC) at about 45° C., followed by a wash of 2.0×SSC at 50° C. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C. Both temperature and salt may be varied, or temperature or salt concentration may be held constant while the other variable is changed. In one embodiment, the disclosure provides nucleic acids which hybridize under low stringency conditions of 6×SSC at room temperature followed by a wash at 2×SSC at room temperature.

Isolated nucleic acids which differ from the nucleic acids as set forth in SEQ ID NOs: 7, 8, 12, 13, 16, 17, 20, 21, 24, 25, 28, 29, 32, 33, 36, 37, 40, 41, 44, 45, 48, 49, 52, 53, 69, 70, 73, 74, 77, 78, 81, 82, 85, 86, 89, 90, 93, 94, 102, 105, 108, 114, 117, 120, 123, 126, 129, 132, 135, 303, 304, 307, 308, 311, and 312 due to degeneracy in the genetic code are also within the scope of the disclosure. For example, a number of amino acids are designated by more than one triplet. Codons that specify the same amino acid, or synonyms (for example, CAU and CAC are synonyms for histidine) may result in “silent” mutations which do not affect the amino acid sequence of the protein. However, it is expected that DNA sequence polymorphisms that do lead to changes in the amino acid sequences of the subject proteins will exist among mammalian cells. One skilled in the art will appreciate that these variations in one or more nucleotides (up to about 3-5% of the nucleotides) of the nucleic acids encoding a particular protein may exist among individuals of a given species due to natural allelic variation. Any and all such nucleotide variations and resulting amino acid polymorphisms are within the scope of this disclosure.

In certain embodiments, the recombinant nucleic acids of the present disclosure may be operably linked to one or more regulatory nucleotide sequences in an expression construct. Regulatory nucleotide sequences will generally be appropriate to the host cell used for expression. Numerous types of appropriate expression vectors and suitable regulatory sequences are known in the art for a variety of host cells. Typically, said one or more regulatory nucleotide sequences may include, but are not limited to, promoter sequences, leader or signal sequences, ribosomal binding sites, transcriptional start and termination sequences, translational start and termination sequences, and enhancer or activator sequences. Constitutive or inducible promoters as known in the art are contemplated by the disclosure. The promoters may be either naturally occurring promoters, or hybrid promoters that combine elements of more than one promoter. An expression construct may be present in a cell on an episome, such as a plasmid, or the expression construct may be inserted in a chromosome. In some embodiments, the expression vector contains a selectable marker gene to allow the selection of transformed host cells. Selectable marker genes are well known in the art and will vary with the host cell used.

In certain aspects of the present disclosure, the subject nucleic acid is provided in an expression vector comprising a nucleotide sequence encoding a TGFβ superfamily type I or type II receptor polypeptide and operably linked to at least one regulatory sequence. Regulatory sequences are art-recognized and are selected to direct expression of the TGFβ superfamily type I or type II receptor polypeptide. Accordingly, the term regulatory sequence includes promoters, enhancers, and other expression control elements. Exemplary regulatory sequences are described in Goeddel; Gene Expression Technology: Methods in Enzymology, Academic Press, San Diego, CA (1990). For instance, any of a wide variety of expression control sequences that control the expression of a DNA sequence when operatively linked to it may be used in these vectors to express DNA sequences encoding a TGFβ superfamily type I or type II receptor polypeptide. Such useful expression control sequences, include, for example, the early and late promoters of SV40, tet promoter, adenovirus or cytomegalovirus immediate early promoter, RSV promoters, the lac system, the trp system, the TAC or TRC system, T7 promoter whose expression is directed by T7 RNA polymerase, the major operator and promoter regions of phage lambda, the control regions for fd coat protein, the promoter for 3-phosphoglycerate kinase or other glycolytic enzymes, the promoters of acid phosphatase, e.g., Pho5, the promoters of the yeast α-mating factors, the polyhedron promoter of the baculovirus system and other sequences known to control the expression of genes of prokaryotic or eukaryotic cells or their viruses, and various combinations thereof. It should be understood that the design of the expression vector may depend on such factors as the choice of the host cell to be transformed and/or the type of protein desired to be expressed. Moreover, the vector's copy number, the ability to control that copy number and the expression of any other protein encoded by the vector, such as antibiotic markers, should also be considered.

A recombinant nucleic acid of the present disclosure can be produced by ligating the cloned gene, or a portion thereof, into a vector suitable for expression in either prokaryotic cells, eukaryotic cells (yeast, avian, insect or mammalian), or both. Expression vehicles for production of a recombinant TGFβ superfamily type I or type II receptor polypeptide include plasmids and other vectors. For instance, suitable vectors include plasmids of the following types: pBR322-derived plasmids, pEMBL-derived plasmids, pEX-derived plasmids, pBTac-derived plasmids and pUC-derived plasmids for expression in prokaryotic cells, such as *E. coli.*

Some mammalian expression vectors contain both prokaryotic sequences to facilitate the propagation of the vector in bacteria, and one or more eukaryotic transcription units that are expressed in eukaryotic cells. The pcDNAI/amp, pcDNAI/neo, pRc/CMV, pSV2gpt, pSV2neo, pSV2-dhfr, pTk2, pRSVneo, pMSG, pSVT7, pko-neo and pHyg derived vectors are examples of mammalian expression vectors suitable for transfection of eukaryotic cells. Some of these vectors are modified with sequences from bacterial plasmids, such as pBR322, to facilitate replication and drug resistance selection in both prokaryotic and eukaryotic cells. Alternatively, derivatives of viruses such as the bovine papilloma virus (BPV-1), or Epstein-Barr virus (pHEBo, pREP-derived and p205) can be used for transient expression of proteins in eukaryotic cells. Examples of other viral (including retroviral) expression systems can be found below in the description of gene therapy delivery systems. The various methods employed in the preparation of the plasmids and in transformation of host organisms are well known in the art. For other suitable expression systems for both prokaryotic and eukaryotic cells, as well as general recombinant procedures, see, e.g., Molecular Cloning A Laboratory Manual, 3rd Ed., ed. by Sambrook, Fritsch and Maniatis (Cold Spring Harbor Laboratory Press, 2001). In some instances, it may be desirable to express the recombinant polypeptides by the use of a baculovirus expression system. Examples of such baculovirus expression systems include pVL-derived vectors (such as pVL1392, pVL1393 and pVL941), pAcUW-derived vectors (such as pAcUW1), and pBlueBac-derived vectors (such as the β-gal containing pBlueBac III).

In a preferred embodiment, a vector will be designed for production of the subject TGFβ superfamily type I or type II receptor polypeptide in CHO cells, such as a Pcmv-Script vector (Stratagene, La Jolla, Calif), pcDNA4 vectors (Invitrogen, Carlsbad, Calif.) and pCI-neo vectors (Promega, Madison, Wisc.). As will be apparent, the subject gene constructs can be used to cause expression of the subject TGFβ superfamily type I or type II receptor polypeptide in cells propagated in culture, e.g., to produce proteins, including fusion proteins or variant proteins, for purification.

This disclosure also pertains to a host cell transfected with a recombinant gene including a coding sequence for one or more of the subject TGFβ superfamily type I or type II receptor polypeptides. The host cell may be any prokaryotic or eukaryotic cell. For example, a TGFβ superfamily type I or type II receptor polypeptide of the disclosure may be expressed in bacterial cells such as *E. coli*, insect cells (e.g., using a baculovirus expression system), yeast, or mammalian cells [e.g. a Chinese hamster ovary (CHO) cell line]. Other suitable host cells are known to those skilled in the art.

Accordingly, the present disclosure further pertains to methods of producing the subject TGFβ superfamily type I or type II receptor polypeptides. For example, a host cell transfected with an expression vector encoding a TGFβ superfamily type I or type II receptor polypeptide can be cultured under appropriate conditions to allow expression of the TGFβ superfamily type I or type II receptor polypeptide to occur. The polypeptide may be secreted and isolated from a mixture of cells and medium containing the polypeptide. Alternatively, the TGFβ superfamily type I or type II receptor polypeptide may be isolated from a cytoplasmic or membrane fraction obtained from harvested and lysed cells. A cell culture includes host cells, media and other byproducts. Suitable media for cell culture are well known in the art. The subject polypeptides can be isolated from cell culture medium, host cells, or both, using techniques known in the art for purifying proteins, including ion-exchange chromatography, gel filtration chromatography, ultrafiltration, electrophoresis, immunoaffinity purification with antibodies specific for particular epitopes of the TGFβ superfamily type I or type II receptor polypeptides and affinity purification with an agent that binds to a domain fused to TGFβ superfamily type I or type II receptor polypeptide (e.g., a protein A column may be used to purify a TGFβ superfamily type I receptor-Fc or type II receptor-Fc fusion polypeptide or protein complex). In some embodiments, the TGFβ superfamily type I or type II receptor polypeptide is a fusion polypeptide or protein complex containing a domain which facilitates its purification.

In some embodiments, purification is achieved by a series of column chromatography steps, including, for example, three or more of the following, in any order: protein A chromatography, Q sepharose chromatography, phenylsepharose chromatography, size exclusion chromatography, and cation exchange chromatography. The purification could be completed with viral filtration and buffer exchange. A TGFβ superfamily type I receptor-Fc or type II receptor-Fc fusion polypeptide or protein complex may be purified to a purity of >90%, >95%, >96%, >98%, or >99% as determined by size exclusion chromatography and >90%, >95%, >96%, >98%, or >99% as determined by SDS PAGE. The target level of purity should be one that is sufficient to achieve desirable results in mammalian systems, particularly non-human primates, rodents (mice), and humans.

In another embodiment, a fusion gene coding for a purification leader sequence, such as a poly-(His)/enterokinase cleavage site sequence at the N-terminus of the desired portion of the recombinant TGFβ superfamily type I or type II receptor polypeptide, can allow purification of the expressed fusion protein by affinity chromatography using a Ni' metal resin. The purification leader sequence can then be subsequently removed by treatment with enterokinase to provide the purified TGFβ superfamily type I or type II receptor polypeptide or protein complex. See, e.g., Hochuli et al. (1987) *J. Chromatography* 411:177; and Janknecht et al. (1991) *PNAS USA* 88:8972.

Techniques for making fusion genes are well known. Essentially, the joining of various DNA fragments coding for different polypeptide sequences is performed in accordance with conventional techniques, employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed to generate a chimeric gene sequence. See, e.g., Current Protocols in Molecular Biology, eds. Ausubel et al., John Wiley & Sons: 1992.

4. Screening Assays

In certain aspects, the present disclosure relates to the use of TGFβ superfamily type I and type II receptor single-arm heteromultimer complexes to identify compounds (agents) which are agonists or antagonists of TGFβ superfamily receptors. Compounds identified through this screening can be tested to assess their ability to modulate tissues such as bone, cartilage, muscle, fat, and/or neurons, to assess their ability to modulate tissue growth in vivo or in vitro. These compounds can be tested, for example, in animal models.

There are numerous approaches to screening for therapeutic agents for modulating tissue growth by targeting TGFβ superfamily ligand signaling (e.g., SMAD 2/3 and/or SMAD 1/5/8 signaling). In certain embodiments, high-throughput screening of compounds can be carried out to identify agents that perturb TGFβ superfamily receptor-mediated effects on a selected cell line. In certain embodiments, the assay is carried out to screen and identify compounds that specifically inhibit or reduce binding of a TGF-beta superfamily receptor single-arm heteromultimer complex to its binding partner, such as a TGFβ superfamily ligand (e.g., BMP2, BMP2/7, BMP3, BMP4, BMP4/7, BMP5, BMP6, BMP7, BMP8a, BMP8b, BMP9, BMP10, GDF3, GDF5, GDF6/BMP13, GDF7, GDF8, GDF9b/BMP15, GDF11/BMP11, GDF15/MIC1, TGF-β1, TGF-β2, TGF-β3, activin A, activin B, activin C, activin E, activin AB, activin AC, activin AE, activin BC, activin BE, nodal, GDNF, neurturin, artemin, persephin, MIS, and Lefty). Alternatively, the assay can be used to identify compounds that enhance binding of a TGF-beta superfamily receptor single-arm heteromultimer complex to its binding partner such as an TGFβ superfamily ligand. In a further embodiment, the compounds can be identified by their ability to interact with a TGF-beta superfamily receptor single-arm heteromultimer complex of the disclosure.

A variety of assay formats will suffice and, in light of the present disclosure, those not expressly described herein will nevertheless be comprehended by one of ordinary skill in the art. As described herein, the test compounds (agents) of the invention may be created by any combinatorial chemical method. Alternatively, the subject compounds may be naturally occurring biomolecules synthesized in vivo or in vitro. Compounds (agents) to be tested for their ability to act as modulators of tissue growth can be produced, for example, by bacteria, yeast, plants or other organisms (e.g., natural products), produced chemically (e.g., small molecules, including peptidomimetics), or produced recombinantly. Test compounds contemplated by the present invention include non-peptidyl organic molecules, peptides, polypeptides, peptidomimetics, sugars, hormones, and nucleic acid molecules. In certain embodiments, the test agent is a small organic molecule having a molecular weight of less than about 2,000 Daltons.

The test compounds of the disclosure can be provided as single, discrete entities, or provided in libraries of greater complexity, such as made by combinatorial chemistry. These libraries can comprise, for example, alcohols, alkyl halides, amines, amides, esters, aldehydes, ethers and other classes of organic compounds. Presentation of test compounds to the test system can be in either an isolated form or as mixtures of compounds, especially in initial screening steps. Optionally, the compounds may be optionally derivatized with other compounds and have derivatizing groups that facilitate isolation of the compounds. Non-limiting examples of derivatizing groups include biotin, fluorescein, digoxygenin, green fluorescent protein, isotopes, polyhistidine, magnetic beads, glutathione S-transferase (GST), photoactivatible crosslinkers or any combinations thereof.

In many drug-screening programs which test libraries of compounds and natural extracts, high-throughput assays are desirable in order to maximize the number of compounds surveyed in a given period of time. Assays which are performed in cell-free systems, such as may be derived with purified or semi-purified proteins, are often preferred as "primary" screens in that they can be generated to permit rapid development and relatively easy detection of an alteration in a molecular target which is mediated by a test compound. Moreover, the effects of cellular toxicity or bioavailability of the test compound can be generally ignored in the in vitro system, the assay instead being focused primarily on the effect of the drug on the molecular target as may be manifest in an alteration of binding affinity between a TGF-beta superfamily receptor single-arm heteromultimer complex and its binding partner (e.g., BMP2, BMP2/7, BMP3, BMP4, BMP4/7, BMP5, BMP6, BMP7, BMP8a, BMP8b, BMP9, BMP10, GDF3, GDF5, GDF6/BMP13, GDF7, GDF8, GDF9b/BMP15, GDF11/BMP11, GDF15/MIC1, TGF-β1, TGF-β2, TGF-β3, activin A, activin B, activin C, activin E, activin AB, activin AC, activin AE, activin BC, activin BE, nodal, GDNF, neurturin, artemin, persephin, MIS, and Lefty).

Merely to illustrate, in an exemplary screening assay of the present disclosure, the compound of interest is contacted with an isolated and purified TGF-beta superfamily receptor single-arm heteromultimer complex which is ordinarily capable of binding to a TGF-beta superfamily ligand, as appropriate for the intention of the assay. To the mixture of the compound and TGF-beta superfamily receptor single-arm heteromultimer complex is then added the appropriate TGF-beta superfamily ligand (e.g., BMP2, BMP2/7, BMP3, BMP4, BMP4/7, BMP5, BMP6, BMP7, BMP8a, BMP8b, BMP9, BMP10, GDF3, GDF5, GDF6/BMP13, GDF7, GDF8, GDF9b/BMP15, GDF11/BMP11, GDF15/MIC1, TGF-β1, TGF-β2, TGF-β3, activin A, activin B, activin C, activin E, activin AB, activin AC, activin AE, activin BC, activin BE, nodal, GDNF, neurturin, artemin, persephin, MIS, and Lefty). Detection and quantification of complexes between single-arm heteromultimers and superfamily ligands provides a means for determining the compound's efficacy at inhibiting (or potentiating) complex formation between the TGF-beta superfamily receptor single-arm heteromultimer complex and its binding protein. The efficacy of the compound can be assessed by generating dose-response curves from data obtained using various concentrations of the test compound. Moreover, a control assay can also be performed to provide a baseline for comparison. For example, in a control assay, isolated and purified TGF-beta superfamily ligand is added to a composition containing the TGF-beta superfamily receptor single-arm heteromultimer complex, and the formation of heteromultimer-ligand complex is quantitated in the absence of the test compound. It will be understood that, in general, the order in which the reactants may be admixed can be varied, and can be admixed simultaneously. Moreover, in place of purified proteins, cellular extracts and lysates may be used to render a suitable cell-free assay system.

Binding of a TGF-beta superfamily receptor single-arm heteromultimer complex to another protein may be detected by a variety of techniques. For instance, modulation of the formation of complexes can be quantitated using, for example, detectably labeled proteins such as radiolabeled (e.g., $^{32}P$, $^{35}S$, $^{14}C$ or $^{3}H$), fluorescently labeled (e.g., FITC), or enzymatically labeled TGF-beta superfamily receptor single-arm heteromultimer complex and its binding protein by immunoassay or by chromatographic detection.

In certain embodiments, the present disclosure contemplates the use of fluorescence polarization assays and fluorescence resonance energy transfer (FRET) assays in measuring, either directly or indirectly, the degree of interaction between a TGF-beta superfamily receptor single-arm heteromultimer complex and its binding protein. Further, other modes of detection, such as those based on optical waveguides (see, e.g., PCT Publication WO 96/26432 and U.S. Pat. No. 5,677,196), surface plasmon resonance (SPR), surface charge sensors, and surface force sensors, are compatible with many embodiments of the disclosure.

Moreover, the present disclosure contemplates the use of an interaction trap assay, also known as the "two-hybrid assay," for identifying agents that disrupt or potentiate interaction between a TGF-beta superfamily receptor single-arm heteromultimer complex and its binding partner. See, e.g., U.S. Pat. No. 5,283,317; Zervos et al. (1993) Cell 72:223-232; Madura et al. (1993) J Biol Chem 268:12046-12054; Bartel et al. (1993) Biotechniques 14:920-924; and Iwabuchi et al. (1993) Oncogene 8:1693-1696). In a specific embodiment, the present disclosure contemplates the use of reverse two-hybrid systems to identify compounds (e.g., small molecules or peptides) that dissociate interactions between a TGF-beta superfamily receptor single-arm heteromultimer complex and its binding protein [see, e.g., Vidal and Legrain, (1999) Nucleic Acids Res 27:919-29; Vidal and Legrain, (1999) Trends Biotechnol 17:374-81; and U.S. Pat. Nos. 5,525,490; 5,955,280; and 5,965,368].

In certain embodiments, the subject compounds are identified by their ability to interact with a TGF-beta superfamily receptor single-arm heteromultimer complex of the disclosure. The interaction between the compound and the TGF-beta superfamily receptor single-arm heteromultimer complex may be covalent or non-covalent. For example, such interaction can be identified at the protein level using in vitro biochemical methods, including photo-crosslinking, radiolabeled ligand binding, and affinity chromatography. See, e.g., Jakoby W B et al. (1974) Methods in Enzymology 46:1. In certain cases, the compounds may be screened in a mechanism-based assay, such as an assay to detect compounds which bind to a TGF-beta superfamily receptor single-arm heteromultimer complex. This may include a solid-phase or fluid-phase binding event. Alternatively, the gene encoding a TGF-beta superfamily receptor single-arm heteromultimer complex can be transfected with a reporter system (e.g., β-galactosidase, luciferase, or green fluorescent protein) into a cell and screened against the library preferably by high-throughput screening or with individual members of the library. Other mechanism-based binding assays may be used; for example, binding assays which detect changes in free energy. Binding assays can be performed with the target fixed to a well, bead or chip or captured by an immobilized antibody or resolved by capillary electrophoresis. The bound compounds may be detected usually using colorimetric endpoints or fluorescence or surface plasmon resonance.

5. Exemplary Therapeutic Uses

In certain embodiments, a TGF-beta superfamily receptor single-arm heteromultimer complex, or combinations of TGF-beta superfamily receptor single-arm heteromultimer complexes, of the present disclosure can be used to treat or prevent a disease or condition that is associated with abnormal activity of a TGFβ superfamily receptor (e.g., ALK1, ALK2, ALK3, ALK4, ALK5, ALK6, ALK7, ActRIIA, ActRIIB, BMPRII, TGFBRII, and MISRII) and/or a TGFβ superfamily ligand (e.g., BMP2, BMP2/7, BMP3, BMP4, BMP4/7, BMP5, BMP6, BMP7, BMP8a, BMP8b, BMP9, BMP10, GDF3, GDF5, GDF6/BMP13, GDF7, GDF8, GDF9b/BMP15, GDF11/BMP11, GDF15/MIC1, TGF-β1, TGF-β2, TGF-β3, activin A, activin B, activin C, activin E, activin AB, activin AC, activin AE, activin BC, activin BE, nodal, GDNF, neurturin, artemin, persephin, MIS, and Lefty). These diseases, disorders or conditions are generally referred to herein as "TGFβ superfamily-associated conditions." In certain embodiments, the present invention provides methods of treating or preventing an individual in need thereof through administering to the individual a therapeutically effective amount of a TGF-beta superfamily receptor single-arm heteromultimer complex, or combinations of TGF-beta superfamily receptor single-arm heteromultimer complexes, as described herein. The terms "subject," an "individual," or a "patient" are interchangeable throughout the specification. Any of the TGF-beta superfamily receptor single-arm heteromultimer complexes of the present disclosure can potentially be employed individually or in combination for therapeutic uses disclosed herein. These methods are particularly aimed at therapeutic and prophylactic treatments of mammals including, for example, rodents, primates, and humans.

As used herein, a therapeutic that "prevents" a disorder or condition refers to a compound that, in a statistical sample, reduces the occurrence of the disorder or condition in the treated sample relative to an untreated control sample, or delays the onset or reduces the severity of one or more symptoms of the disorder or condition relative to the untreated control sample. The term "treating" as used herein includes amelioration or elimination of the condition once it has been established. In either case, prevention or treatment may be discerned in the diagnosis provided by a physician or other health care provider and the intended result of administration of the therapeutic agent.

Native TGFβ superfamily receptor-ligand complexes play essential roles in tissue growth as well as early developmental processes such as the correct formation of various structures or in one or more post-developmental capacities including sexual development, pituitary hormone production, and creation of bone and cartilage. Thus, TGFβ superfamily-associated conditions/disorders include abnormal tissue growth and developmental defects. In addition, TGFβ superfamily-associated conditions include, but are not limited to, disorders of cell growth and differentiation such as inflammation, allergy, autoimmune diseases, infectious diseases, and tumors.

Exemplary TGFβ superfamily-associated conditions include neuromuscular disorders (e.g., muscular dystrophy and muscle atrophy), congestive obstructive pulmonary disease (and muscle wasting associated with COPD), muscle wasting syndrome, sarcopenia, cachexia, adipose tissue disorders (e.g., obesity), type 2 diabetes (NIDDM, adult-onset diabetes), and bone degenerative disease (e.g., osteoporosis). Other exemplary TGFβ superfamily-associated conditions include musculodegenerative and neuromuscular disorders, tissue repair (e.g., wound healing), neurodegenerative diseases (e.g., amyotrophic lateral sclerosis), and immunologic disorders (e.g., disorders related to abnormal proliferation or function of lymphocytes).

In certain embodiments, a TGF-beta superfamily receptor single-arm heteromultimer complex, or combinations of TGF-beta superfamily receptor single-arm heteromultimer complexes, of the disclosure are used as part of a treatment for a muscular dystrophy. The term "muscular dystrophy" refers to a group of degenerative muscle diseases characterized by gradual weakening and deterioration of skeletal muscles and sometimes the heart and respiratory muscles. Muscular dystrophies are genetic disorders characterized by progressive muscle wasting and weakness that begin with microscopic changes in the muscle. As muscles degenerate over time, the person's muscle strength declines. Exemplary muscular dystrophies that can be treated with a regimen including the subject TGF-beta superfamily receptor single-arm heteromultimer complexes include: Duchenne muscular dystrophy (DMD), Becker muscular dystrophy (BMD), Emery-Dreifuss muscular dystrophy (EDMD), limb-girdle muscular dystrophy (LGMD), facioscapulohumeral muscular dystrophy (FSH or FSHD) (also known as Landouzy-Dejerine), myotonic dystrophy (MMD; also known as Steinert's Disease), oculopharyngeal muscular dystrophy (OPMD), distal muscular dystrophy (DD), congenital muscular dystrophy (CMD).

Duchenne muscular dystrophy (DMD) was first described by the French neurologist Guillaume Benjamin Amand Duchenne in the 1860s. Becker muscular dystrophy (BMD) is named after the German doctor Peter Emil Becker, who first described this variant of DMD in the 1950s. DMD is one of the most frequent inherited diseases in males, affecting one in 3,500 boys. DMD occurs when the dystrophin gene, located on the short arm of the X chromosome, is defective. Since males only carry one copy of the X chromosome, they only have one copy of the dystrophin gene. Without the dystrophin protein, muscle is easily damaged during cycles of contraction and relaxation. While early in the disease muscle compensates by regeneration, later on muscle progenitor cells cannot keep up with the ongoing damage and healthy muscle is replaced by non-functional fibro-fatty tissue.

BMD results from different mutations in the dystrophin gene. BMD patients have some dystrophin, but it is either of insufficient quantity or poor quality. The presence of some dystrophin protects the muscles of patients with BMD from degenerating as severely or as quickly as those of patients with DMD.

Studies in animals indicate that inhibition of the GDF8 signaling pathway may effectively treat various aspects of disease in DMD and BMD patients (Bogdanovich et al., 2002, Nature 420:418-421; Pistilli et al., 2011, Am J Pathol 178:1287-1297). Thus, TGF-beta superfamily receptor single-arm heteromultimer complexes of the disclosure may act as GDF8 inhibitors (antagonists), and constitute an alternative means of blocking signaling by GDF8 and/or related TGFβ superfamily ligands in vivo in DMD and BMD patients.

Similarly, TGF-beta superfamily receptor single-arm heteromultimer complexes of the disclosure may provide an effective means to increase muscle mass in other disease conditions that are in need of muscle growth. For example, amyotrophic lateral sclerosis (ALS), also called Lou Gehrig's disease or motor neuron disease, is a chronic, progressive, and incurable CNS disorder that attacks motor neurons, which are components of the central nervous system required for initiation of skeletal muscle contraction. In ALS, motor neurons deteriorate and eventually die, and though a person's brain normally remains fully functioning and alert, initiation of muscle contraction is blocked at the spinal level. Individuals who develop ALS are typically between 40 and 70 years old, and the first motor neurons to degenerate are those innervating the arms or legs. Patients with ALS may have trouble walking, may drop things, fall, slur their speech, and laugh or cry uncontrollably. As the disease progresses, muscles in the limbs begin to atrophy from disuse. Muscle weakness becomes debilitating, and patients eventually require a wheel chair or become confined to bed. Most ALS patients die from respiratory failure or from complications of ventilator assistance like pneumonia 3-5 years from disease onset.

Promotion of increased muscle mass by TGF-beta superfamily receptor single-arm heteromultimer complexes might also benefit those suffering from muscle wasting diseases. Gonzalez-Cadavid et al. (supra) reported that GDF8 expression correlates inversely with fat-free mass in humans and that increased expression of the GDF8 gene is associated with weight loss in men with AIDS wasting syndrome. By inhibiting the function of GDF8 in AIDS patients, at least certain symptoms of AIDS may be alleviated, if not completely eliminated, thus significantly improving quality of life in AIDS patients.

Since loss of GDF8 function is also associated with fat loss without diminution of nutrient intake (Zimmers et al., supra; McPherron and Lee, supra), the subject TGF-beta superfamily receptor single-arm heteromultimer complexes may further be used as a therapeutic agent for slowing or preventing the development of obesity and type 2 diabetes.

Cancer anorexia-cachexia syndrome is among the most debilitating and life-threatening aspects of cancer. This syndrome is a common feature of many types of cancer—present in approximately 80% of cancer patients at death—and is responsible not only for a poor quality of life and poor response to chemotherapy but also a shorter survival time than is found in patients with comparable tumors but without weight loss. Cachexia is typically suspected in patients with cancer if an involuntary weight loss of greater than five percent of premorbid weight occurs within a six-month period. Associated with anorexia, wasting of fat and muscle tissue, and psychological distress, cachexia arises from a complex interaction between the cancer and the host. Cancer cachexia affects cytokine production, release of lipid-mobilizing and proteolysis-inducing factors, and alterations in intermediary metabolism. Although anorexia is common, a decreased food intake alone is unable to account for the changes in body composition seen in cancer patients, and increasing nutrient intake is unable to reverse the wasting syndrome. Currently, there is no treatment to control or reverse the cachexic process. Since systemic overexpression of GDF8 in adult mice was found to induce profound muscle and fat loss analogous to that seen in human cachexia syndromes (Zimmers et al., supra), the subject TGF-beta superfamily receptor single-arm heteromultimer complex pharmaceutical compositions may be beneficially used to prevent, treat, or alleviate the symptoms of the cachexia syndrome, where muscle growth is desired.

In certain embodiments, a TGF-beta superfamily receptor single-arm heteromultimer complex, or combinations of TGF-beta superfamily receptor single-arm heteromultimer complexes, of the present disclosure may be used in methods of inducing bone and/or cartilage formation, preventing bone loss, increasing bone mineralization, preventing the demineralization of bone, and/or increasing bone density. TGF-beta superfamily receptor single-arm heteromultimer complexes may be useful in patients who are diagnosed with subclinical low bone density, as a protective measure against the development of osteoporosis.

In some embodiments, a TGF-beta superfamily receptor single-arm heteromultimer complex, or combinations of TGF-beta superfamily receptor single-arm heteromultimer complexes, of the present disclosure may find medical utility in the healing of bone fractures and cartilage defects in humans and other animals. The subject methods and compositions may also have prophylactic use in closed as well as open fracture reduction and also in the improved fixation of artificial joints. De novo bone formation induced by an osteogenic agent is useful for repair of craniofacial defects that are congenital, trauma-induced, or caused by oncologic resection, and is also useful in cosmetic plastic surgery. Further, methods and compositions of the invention may be used in the treatment of periodontal disease and in other tooth repair processes. In certain cases, a TGF-beta superfamily receptor single-arm heteromultimer complex, or combinations of TGF-beta superfamily receptor single-arm heteromultimer complexes, may provide an environment to attract bone-forming cells, stimulate growth of bone-forming cells, or induce differentiation of progenitors of bone-forming cells. TGF-beta superfamily receptor single-arm heteromultimer complexes of the disclosure may also be useful in the treatment of osteoporosis. Further, TGF-beta superfamily receptor single-arm heteromultimer complexes may be used in repair of cartilage defects and prevention/reversal of osteoarthritis.

Rosen et al. (ed) Primer on the Metabolic Bone Diseases and Disorders of Mineral Metabolism, 7th ed. American Society for Bone and Mineral Research, Washington D.C. (incorporated herein by reference) provides an extensive discussion of bone disorders that may be subject to treatment with a TGF-beta superfamily receptor single-arm heteromultimer complex or with combinations of TGF-beta superfamily receptor single-arm heteromultimer complexes. A partial listing is provided herein. Methods and compositions of the invention can be applied to conditions characterized by or causing bone loss, such as osteoporosis (including secondary osteoporosis), hyperparathyroidism, chronic kidney disease mineral bone disorder, sex hormone deprivation or ablation (e.g. androgen and/or estrogen), glucocorticoid treatment, rheumatoid arthritis, severe burns, hyperparathyroidism, hypercalcemia, hypocalcemia, hypophosphatemia, osteomalacia (including tumor-induced osteomalacia), hyperphosphatemia, vitamin D deficiency, hyperparathyroidism (including familial hyperparathyroidism) and pseudohypoparathyroidism, tumor metastases to bone, bone loss as a consequence of a tumor or chemotherapy, tumors of the bone and bone marrow (e.g., multiple myeloma), ischemic bone disorders, periodontal disease and oral bone loss, Cushing's disease, Paget's disease, thyrotoxicosis, chronic diarrheal state or malabsorption, renal tubular acidosis, or anorexia nervosa. Methods and compositions of the invention may also be applied to conditions characterized by a failure of bone formation or healing, including non-union fractures, fractures that are otherwise slow to heal, fetal and neonatal bone dysplasias (e.g., hypocalcemia, hypercalcemia, calcium receptor defects and vitamin D deficiency), osteonecrosis (including osteonecrosis of the jaw) and osteogenesis imperfecta. Additionally, the anabolic effects will cause such antagonists to diminish bone pain associated with bone damage or erosion. As a consequence of the antiresorptive effects, such antagonists may be useful to treat disorders of abnormal bone formation, such as osteoblastic tumor metastases (e.g., associated with primary prostate or breast cancer), osteogenic osteosarcoma, osteopetrosis, progressive diaphyseal dysplasia, endosteal hyperostosis, osteopoikilosis, and melorheostosis. Other disorders that may be treated include fibrous dysplasia and chondrodysplasias.

In another specific embodiment, the disclosure provides a therapeutic method and composition for repairing fractures and other conditions related to cartilage and/or bone defects or periodontal diseases. The invention further provides therapeutic methods and compositions for wound healing and tissue repair. The types of wounds include, but are not limited to, burns, incisions and ulcers. See, e.g., PCT Publication No. WO 84/01106. Such compositions comprise a therapeutically effective amount of at least one of the TGF-beta superfamily receptor single-arm heteromultimer complexes of the disclosure in admixture with a pharmaceutically acceptable vehicle, carrier, or matrix.

In some embodiments, a TGF-beta superfamily receptor single-arm heteromultimer complex, or combinations of TGF-beta superfamily receptor single-arm heteromultimer complexes, of the disclosure can be applied to conditions causing bone loss such as osteoporosis, hyperparathyroidism, Cushing's disease, thyrotoxicosis, chronic diarrheal state or malabsorption, renal tubular acidosis, or anorexia nervosa. It is commonly appreciated that being female, having a low body weight, and leading a sedentary lifestyle are risk factors for osteoporosis (loss of bone mineral density, leading to fracture risk). However, osteoporosis can also result from the long-term use of certain medications. Osteoporosis resulting from drugs or another medical condition is known as secondary osteoporosis. In Cushing's disease, the excess amount of cortisol produced by the body results in osteoporosis and fractures. The most common medications associated with secondary osteoporosis are the corticosteroids, a class of drugs that act like cortisol, a hormone produced naturally by the adrenal glands. Although adequate levels of thyroid hormones are needed for the development of the skeleton, excess thyroid hormone can decrease bone mass over time. Antacids that contain aluminum can lead to bone loss when taken in high doses by people with kidney problems, particularly those undergoing dialysis. Other medications that can cause secondary osteoporosis include phenytoin (Dilantin) and barbiturates that are used to prevent seizures; methotrexate (Rheumatrex, Immunex, Folex PFS), a drug for some forms of arthritis, cancer, and immune disorders; cyclosporine (Sandimmune, Neoral), a drug used to treat some autoimmune diseases and to suppress the immune system in organ transplant patients; luteinizing hormone-releasing hormone agonists (Lupron, Zoladex), used to treat prostate cancer and endometriosis; heparin (Calciparine, Liquaemin), an anticlotting medication; and cholestyramine (Questran) and colestipol (Colestid), used to treat high cholesterol. Bone loss resulting from cancer therapy is widely recognized and termed cancer therapy-induced bone loss (CTIBL). Bone metastases can create cavities in the bone that may be corrected by treatment with a TGF-beta superfamily heteromultimer complex. Bone loss can also be caused by gum disease, a chronic infection in which bacteria located in gum recesses produce toxins and harmful enzymes.

In a further embodiment, the present disclosure provides methods and therapeutic agents for treating diseases or disorders associated with abnormal or unwanted bone growth. For example, patients with the congenital disorder fibrodysplasia ossificans progressiva (FOP) are afflicted by progressive ectopic bone growth in soft tissues spontaneously or in response to tissue trauma, with a major impact on quality of life. Additionally, abnormal bone growth can occur after hip replacement surgery and thus ruin the surgical outcome. This is a more common example of pathological bone growth and a situation in which the subject methods and compositions may be therapeutically useful. The same methods and compositions may also be useful for treating other forms of abnormal bone growth (e.g., pathological growth of bone following trauma, burns or spinal cord injury), and for treating or preventing the undesirable conditions associated with the abnormal bone growth seen in connection with metastatic prostate cancer or osteosarcoma.

In certain embodiments, a TGF-beta superfamily receptor single-arm heteromultimer complex, or combinations of TGF-beta superfamily receptor single-arm heteromultimer complexes, of the disclosure may be used to promote bone formation in patients with cancer. Patients having certain tumors (e.g. prostate, breast, multiple myeloma or any tumor causing hyperparathyroidism) are at high risk for bone loss due to tumor-induced bone loss, bone metastases, and therapeutic agents. Such patients may be treated with a TGF-beta superfamily receptor single-arm heteromultimer complex, or a combination of complexes, even in the absence of evidence of bone loss or bone metastases. Patients may also be monitored for evidence of bone loss or bone metastases, and may be treated with a TGF-beta superfamily receptor single-arm heteromultimer complex in the event that indicators suggest an increased risk. Generally, DEXA scans are employed to assess changes in bone density, while indicators of bone remodeling may be used to assess the likelihood of bone metastases. Serum markers may be monitored. Bone specific alkaline phosphatase (BSAP) is an enzyme that is present in osteoblasts. Blood levels of BSAP are increased in patients with bone metastasis and other conditions that result in increased bone remodeling. Osteocalcin and procollagen peptides are also associated with bone formation and bone metastases. Increases in BSAP have been detected in patients with bone metastasis caused by prostate cancer, and to a lesser degree, in bone metastases from breast cancer. BMP7 levels are high in prostate cancer that has metastasized to bone, but not in bone metastases due to bladder, skin, liver, or lung cancer. Type I carboxy-terminal telopeptide (ICTP) is a crosslink found in collagen that is formed during to the resorption of bone. Since bone is constantly being broken down and reformed, ICTP will be found throughout the body. However, at the site of bone metastasis, the level will be significantly higher than in an area of normal bone. ICTP has been found in high levels in bone metastasis due to prostate, lung, and breast cancer. Another collagen crosslink, Type I N-terminal telopeptide (NTx), is produced along with ICTP during bone turnover. The amount of NTx is increased in bone metastasis caused by many different types of cancer including lung, prostate, and breast cancer. Also, the levels of NTx increase with the progression of the bone metastasis. Therefore, this marker can be used to both detect metastasis as well as measure the extent of the disease. Other markers of resorption include pyridinoline and deoxypyridinoline. Any increase in resorption markers or markers of bone metastases indicate the need for therapy with a TGF-beta superfamily receptor single-arm heteromultimer complex, or combinations of TGF-beta superfamily receptor single-arm heteromultimer complexes, in a patient.

In another embodiment, a TGF-beta superfamily receptor single-arm heteromultimer complex, or combinations of TGF-beta superfamily receptor single-arm heteromultimer complexes, may be used in patients with chronic kidney disease mineral bone disorder (CKD-MBD), a broad syndrome of interrelated skeletal, cardiovascular, and mineral-metabolic disorders arising from kidney disease. CKD-MBD encompasses various skeletal pathologies often referred to as renal osteodystrophy (ROD), which is a preferred embodiment for treatment with a TGF-beta superfamily receptor single-arm heteromultimer complex, or combinations of TGF-beta superfamily receptor single-arm heteromultimer complexes. Depending on the relative contribution of different pathogenic factors, ROD is manifested as diverse pathologic patterns of bone remodeling (Hruska et al., 2008, Chronic kidney disease mineral bone disorder (CKD-MBD); in Rosen et al. (ed) Primer on the Metabolic Bone Diseases and Disorders of Mineral Metabolism, 7th ed. American Society for Bone and Mineral Research, Washington D.C., pp 343-349). At one end of the spectrum is ROD with uremic osteodystrophy and low bone turnover, characterized by a low number of active remodeling sites, profoundly suppressed bone formation, and low bone resorption. At the other extreme is ROD with hyperparathyroidism, high bone turnover, and osteitis fibrosa. Given that a TGF-beta superfamily receptor single-arm heteromultimer complex, or combinations of TGF-beta superfamily receptor single-arm heteromultimer complexes, may exert both anabolic and antiresorptive effects, these agents may be useful in patients across the ROD pathology spectrum.

A TGF-beta superfamily receptor single-arm heteromultimer complex, or combinations of TGF-beta superfamily receptor single-arm heteromultimer complexes, of the disclosure may be conjointly administered with other bone-active pharmaceutical agents. Conjoint administration may be accomplished by administration of a single co-formulation, by simultaneous administration, or by administration at separate times. TGF-beta superfamily receptor single-arm heteromultimer complexes may be particularly advantageous if administered with other bone-active agents. A patient may benefit from conjointly receiving a TGF-beta superfamily receptor single-arm heteromultimer complex and taking calcium supplements, vitamin D, appropriate exercise and/or, in some cases, other medication. Examples of other medications include, bisphosphonates (alendronate, ibandronate and risedronate), calcitonin, estrogens, parathyroid hormone and raloxifene. The bisphosphonates (alendronate, ibandronate and risedronate), calcitonin, estrogens and raloxifene affect the bone remodeling cycle and are classified as anti-resorptive medications. Bone remodeling consists of two distinct stages: bone resorption and bone formation. Anti-resorptive medications slow or stop the bone-resorbing portion of the bone-remodeling cycle but do not slow the bone-forming portion of the cycle. As a result, new formation continues at a greater rate than bone resorption, and bone density may increase over time. Teriparatide, a form of parathyroid hormone, increases the rate of bone formation in the bone remodeling cycle. Alendronate is approved for both the prevention (5 mg per day or 35 mg once a week) and treatment (10 mg per day or 70 mg once a week) of postmenopausal osteoporosis. Alendronate reduces bone loss, increases bone density and reduces the risk of spine, wrist and hip fractures. Alendronate also is approved for treatment of glucocorticoid-induced osteoporosis in men and women as a result of long-term use of these medications (i.e., prednisone and cortisone) and for the treatment of osteoporosis in men. Alendronate plus vitamin D is approved for the treatment of osteoporosis in postmenopausal women (70 mg once a week plus vitamin D), and for treatment to improve bone mass in men with osteoporosis. Ibandronate is approved for the prevention and treatment of postmenopausal osteoporosis. Taken as a once-a-month pill (150 mg), ibandronate should be taken on the same day each month. Ibandronate reduces bone loss, increases bone density and reduces the risk of spine fractures. Risedronate is approved for the prevention and treatment of postmenopausal osteoporosis. Taken daily (5 mg dose) or weekly (35 mg dose or 35 mg dose with calcium), risedronate slows bone loss, increases bone density and reduces the risk of spine and non-spine fractures. Risedronate also is approved for use by men and women to prevent and/or treat glucocorticoid-induced osteoporosis that results from long-term use of these medications (i.e., prednisone or cortisone). Calcitonin is a naturally occurring hormone involved in calcium regulation and bone metabolism. In women who are more than 5 years beyond menopause, calcitonin slows bone loss, increases spinal bone density, and may relieve the pain associated with bone fractures. Calcitonin reduces the risk of spinal fractures. Calcitonin is available as an injection (50-100 IU daily) or nasal spray (200 IU daily).

A patient may also benefit from conjointly receiving a TGF-beta superfamily receptor single-arm heteromultimer complex, or combinations of TGF-beta superfamily receptor single-arm heteromultimer complexes, and additional bone-active medications. Estrogen therapy (ET)/hormone therapy (HT) is approved for the prevention of osteoporosis. ET has been shown to reduce bone loss, increase bone density in both the spine and hip, and reduce the risk of hip and spinal fractures in postmenopausal women. ET is administered most commonly in the form of a pill or skin patch that delivers a low dose of approximately 0.3 mg daily or a standard dose of approximately 0.625 mg daily and is effective even when started after age 70. When estrogen is taken alone, it can increase a woman's risk of developing cancer of the uterine lining (endometrial cancer). To eliminate this risk, healthcare providers prescribe the hormone progestin in combination with estrogen (hormone replacement therapy or HT) for those women who have an intact uterus. ET/HT relieves menopause symptoms and has been shown to have a beneficial effect on bone health. Side effects may include vaginal bleeding, breast tenderness, mood disturbances and gallbladder disease. Raloxifene, 60 mg a day, is approved for the prevention and treatment of postmenopausal osteoporosis. It is from a class of drugs called selective estrogen receptor modulators (SERMs) that have been developed to provide the beneficial effects of estrogens without their potential disadvantages. Raloxifene increases bone mass and reduces the risk of spine fractures. Data are not yet available to demonstrate that raloxifene can reduce the risk of hip and other non-spine fractures. Teriparatide, a form of parathyroid hormone, is approved for the treatment of osteoporosis in postmenopausal women and men who are at high risk for a fracture. This medication stimulates new bone formation and significantly increases bone mineral density. In postmenopausal women, fracture reduction was noted in the spine, hip, foot, ribs and wrist. In men, fracture reduction was noted in the spine, but there were insufficient data to evaluate fracture reduction at other sites. Teriparatide is self-administered as a daily injection for up to 24 months.

In other embodiments, a TGF-beta superfamily receptor single-arm heteromultimer complex, or combinations of TGF-beta superfamily receptor single-arm heteromultimer complexes can be used for regulating body fat content in an animal and for treating or preventing conditions related thereto, and particularly, health-compromising conditions related thereto. According to the present invention, to regulate (control) body weight can refer to reducing or increasing body weight, reducing or increasing the rate of weight gain, or increasing or reducing the rate of weight loss, and also includes actively maintaining, or not significantly changing body weight (e.g., against external or internal influences which may otherwise increase or decrease body weight). One embodiment of the present disclosure relates to regulating body weight by administering to an animal (e.g., a human) in need thereof a TGF-beta superfamily receptor single-arm heteromultimer complex, or combinations of TGF-beta superfamily receptor single-arm heteromultimer complexes, of the disclosure.

In some embodiments, a TGF-beta superfamily receptor single-arm heteromultimer complex, or combinations of TGF-beta superfamily receptor single-arm heteromultimer complexes, of the present disclosure can be used for reducing body weight and/or reducing weight gain in an animal, and more particularly, for treating or ameliorating obesity in patients at risk for or suffering from obesity. In another specific embodiment, the present invention is directed to methods and compounds for treating an animal that is unable to gain or retain weight (e.g., an animal with a wasting syndrome). Such methods are effective to increase body weight and/or mass, or to reduce weight and/or mass loss, or to improve conditions associated with or caused by undesirably low (e.g., unhealthy) body weight and/or mass. In addition, disorders of high cholesterol (e.g., hypercholesterolemia or dislipidemia) may be treated with a TGF-beta superfamily receptor single-arm heteromultimer complex, or combinations of TGF-beta superfamily receptor single-arm heteromultimer complexes, of the disclosure.

In certain aspects, a TGF-beta superfamily receptor single-arm heteromultimer complex, or a combination of TGF-beta superfamily receptor single-arm heteromultimer complexes, of the present disclosure can be used to increase red blood cell levels, treat or prevent an anemia, and/or treat or prevent ineffective erythropoiesis in a subject in need thereof. In certain aspects, a TGF-beta superfamily receptor single-arm heteromultimer complex, or a combination of TGF-beta superfamily receptor single-arm heteromultimer complexes, of the present disclosure may be used in combination with conventional therapeutic approaches for increasing red blood cell levels, particularly those used to treat anemias of multifactorial origin. Conventional therapeutic approaches for increasing red blood cell levels include, for example, red blood cell transfusion, administration of one or more EPO receptor activators, hematopoietic stem cell transplantation, immunosuppressive biologics and drugs (e.g., corticosteroids). In certain embodiments, a TGF-beta superfamily receptor single-arm heteromultimer complex, or a combination of TGF-beta superfamily receptor single-arm heteromultimer complexes, of the present disclosure can be used to treat or prevent ineffective erythropoiesis and/or the disorders associated with ineffective erythropoiesis in a subject in need thereof. In certain aspects, a TGF-beta superfamily receptor single-arm heteromultimer complex, or a combination of TGF-beta superfamily receptor single-arm heteromultimer complexes, of the present disclosure can be used in combination with conventional therapeutic approaches for treating or preventing an anemia or ineffective erythropoiesis disorder, particularly those used to treat anemias of multifactorial origin.

In general, treatment or prevention of a disease or condition as described in the present disclosure is achieved by administering a TGF-beta superfamily receptor single-arm heteromultimer complex, or a combination of TGF-beta superfamily receptor single-arm heteromultimer complexes, of the present disclosure in an "effective amount". An effective amount of an agent refers to an amount effective, at dosages and for periods of time necessary, to achieve the desired therapeutic or prophylactic result. A "therapeutically effective amount" of an agent of the present disclosure may vary according to factors such as the disease state, age, sex, and weight of the individual, and the ability of the agent to elicit a desired response in the individual. A "prophylactically effective amount" refers to an amount effective, at dosages and for periods of time necessary, to achieve the desired prophylactic result.

In certain embodiments, a TGF-beta superfamily receptor single-arm heteromultimer complex, or a combination of TGF-beta superfamily receptor single-arm heteromultimer complexes, optionally combined with an EPO receptor activator, may be used to increase red blood cell, hemoglobin, or reticulocyte levels in healthy individuals and selected patient populations. Examples of appropriate patient populations include those with undesirably low red blood cell or hemoglobin levels, such as patients having an anemia, and those that are at risk for developing undesirably low red blood cell or hemoglobin levels, such as those patients who are about to undergo major surgery or other procedures that may result in substantial blood loss. In one embodiment, a patient with adequate red blood cell levels is treated with a TGF-beta superfamily receptor single-arm heteromultimer complex, or a combination of TGF-beta superfamily receptor single-arm heteromultimer complexes, to increase red blood cell levels, and then blood is drawn and stored for later use in transfusions.

One or more TGF-beta superfamily receptor single-arm heteromultimer complexes of the disclosure, optionally combined with an EPO receptor activator, may be used to increase red blood cell levels, hemoglobin levels, and/or hematocrit levels in a patient having an anemia. When observing hemoglobin and/or hematocrit levels in humans, a level of less than normal for the appropriate age and gender category may be indicative of anemia, although individual variations are taken into account. For example, a hemoglobin level from 10-12.5 g/dl, and typically about 11.0 g/dl is considered to be within the normal range in health adults, although, in terms of therapy, a lower target level may cause fewer cardiovascular side effects [see, e.g., Jacobs et al. (2000) Nephrol Dial Transplant 15, 15-19]. Alternatively, hematocrit levels (percentage of the volume of a blood sample occupied by the cells) can be used as a measure for anemia. Hematocrit levels for healthy individuals range from about 41-51% for adult males and from 35-45% for adult females. In certain embodiments, a patient may be treated with a dosing regimen intended to restore the patient to a target level of red blood cells, hemoglobin, and/or hematocrit. As hemoglobin and hematocrit levels vary from person to person, optimally, the target hemoglobin and/or hematocrit level can be individualized for each patient.

Anemia is frequently observed in patients having a tissue injury, an infection, and/or a chronic disease, particularly cancer. In some subjects, anemia is distinguished by low erythropoietin levels and/or an inadequate response to erythropoietin in the bone marrow [see, e.g., Adamson (2008) Harrison's Principles of Internal Medicine, 17th ed.; McGraw Hill, New York, pp 628-634]. Potential causes of anemia include, for example, blood loss, nutritional deficits (e.g. reduced dietary intake of protein), medication reaction, various problems associated with the bone marrow, and many diseases. More particularly, anemia has been associated with a variety of disorders and conditions that include, for example, bone marrow transplantation; solid tumors (e.g., breast cancer, lung cancer, and colon cancer); tumors of the lymphatic system (e.g., chronic lymphocyte leukemia, non-Hodgkins lymphoma, and Hodgkins lymphoma); tumors of the hematopoietic system (e.g., leukemia, a myelodysplastic syndrome and multiple myeloma); radiation therapy; chemotherapy (e.g., platinum containing regimens); inflammatory and autoimmune diseases, including, but not limited to, rheumatoid arthritis, other inflammatory arthritides, systemic lupus erythematosis (SLE), acute or chronic skin diseases (e.g., psoriasis), inflammatory bowel disease (e.g., Crohn's disease and ulcerative colitis); acute or chronic renal disease or failure, including idiopathic or congenital conditions; acute or chronic liver disease; acute or chronic bleeding; situations where transfusion of red blood cells is not possible due to patient allo- or auto-antibodies and/or for religious reasons (e.g., some Jehovah's Witnesses); infections (e.g., malaria and osteomyelitis); hemoglobinopathies including, for example, sickle cell disease (anemia), thalassemias; drug use or abuse (e.g., alcohol misuse); pediatric patients with anemia from any cause to avoid transfusion; and elderly patients or patients with underlying cardiopulmonary disease with anemia who cannot receive transfusions due to concerns about circulatory overload [see, e.g., Adamson (2008) Harrison's Principles of Internal Medicine, 17th ed.; McGraw Hill, New York, pp 628-634].

Many factors can contribute to cancer-related anemia. Some are associated with the disease process itself and the generation of inflammatory cytokines such as interleukin-1, interferon-gamma, and tumor necrosis factor [Bron et al. (2001) Semin Oncol 28(Suppl 8):1-6]. Among its effects, inflammation induces the key iron-regulatory peptide hepcidin, thereby inhibiting iron export from macrophages and generally limiting iron availability for erythropoiesis [see, e.g., Ganz (2007) J Am Soc Nephrol 18:394-400]. Blood loss through various routes can also contribute to cancer-related anemia. The prevalence of anemia due to cancer progression varies with cancer type, ranging from 5% in prostate cancer up to 90% in multiple myeloma. Cancer-related anemia has profound consequences for patients, including fatigue and reduced quality of life, reduced treatment efficacy, and increased mortality. In some embodiments, one or more TGF-beta superfamily receptor single-arm heteromultimer complexes of the disclosure, optionally combined with an EPO receptor activator, could be used to treat a cancer-related anemia.

A hypoproliferative anemia can result from primary dysfunction or failure of the bone marrow. Hypoproliferative anemias include: anemia of chronic disease, anemia of kidney disease, anemia associated with hypometabolic states, and anemia associated with cancer. In each of these types, endogenous erythropoietin levels are inappropriately low for the degree of anemia observed. Other hypoproliferative anemias include: early-stage iron-deficient anemia, and anemia caused by damage to the bone marrow. In these types, endogenous erythropoietin levels are appropriately elevated for the degree of anemia observed. Prominent examples would be myelosuppression caused by cancer and/or chemotherapeutic drugs or cancer radiation therapy. A broad review of clinical trials found that mild anemia can occur in 100% of patients after chemotherapy, while more severe anemia can occur in up to 80% of such patients [see, e.g., Groopman et al. (1999) J Natl Cancer Inst 91:1616-1634]. Myelosuppressive drugs include, for example: 1) alkylating agents such as nitrogen mustards (e.g., melphalan) and nitrosoureas (e.g., streptozocin); 2) antimetabolites such as folic acid antagonists (e.g., methotrexate), purine analogs (e.g., thioguanine), and pyrimidine analogs (e.g., gemcitabine); 3) cytotoxic antibiotics such as anthracyclines (e.g., doxorubicin); 4) kinase inhibitors (e.g., gefitinib); 5) mitotic inhibitors such as taxanes (e.g., paclitaxel) and *vinca* alkaloids (e.g., vinorelbine); 6) monoclonal antibodies (e.g., rituximab); and 7) topoisomerase inhibitors (e.g., topotecan and etoposide). In addition, conditions resulting in a hypometabolic rate can produce a mild-to-moderate hypoproliferative anemia. Among such conditions are endocrine deficiency states. For example, anemia can occur in Addison's disease, hypothyroidism, hyperparathyroidism, or males who are castrated or treated with estrogen. In some embodiments, one or more TGF-beta superfamily receptor single-arm heteromultimer complexes of the disclosure, optionally combined with an EPO receptor activator, could be used to treat a hyperproliferative anemia.

Chronic kidney disease is sometimes associated with hypoproliferative anemia, and the degree of the anemia varies in severity with the level of renal impairment. Such anemia is primarily due to inadequate production of erythropoietin and reduced survival of red blood cells. Chronic kidney disease usually proceeds gradually over a period of years or decades to end-stage (Stage 5) disease, at which point dialysis or kidney transplantation is required for patient survival. Anemia often develops early in this process and worsens as disease progresses. The clinical consequences of anemia of kidney disease are well-documented and include development of left ventricular hypertrophy, impaired cognitive function, reduced quality of life, and altered immune function [see, e.g., Levin et al. (1999) Am J Kidney Dis 27:347-354; Nissenson (1992) Am J Kidney Dis 20(Suppl 1):21-24; Revicki et al. (1995) Am J Kidney Dis 25:548-554; Gafter et al., (1994) Kidney Int 45:224-231]. In some embodiments, one or more TGF-beta superfamily receptor single-arm heteromultimer complexes of the disclosure, optionally combined with an EPO receptor activator, could be used to treat anemia associated with acute or chronic renal disease or failure.

Anemia resulting from acute blood loss of sufficient volume, such as from trauma or postpartum hemorrhage, is known as acute post-hemorrhagic anemia. Acute blood loss initially causes hypovolemia without anemia since there is proportional depletion of RBCs along with other blood constituents. However, hypovolemia will rapidly trigger physiologic mechanisms that shift fluid from the extravascular to the vascular compartment, which results in hemodilution and anemia. If chronic, blood loss gradually depletes body iron stores and eventually leads to iron deficiency. In some embodiments, one or more TGF-beta superfamily receptor single-arm heteromultimer complexes of the disclosure, optionally combined with an EPO receptor activator, could be used to treat anemia resulting from acute blood loss.

Iron-deficiency anemia is the final stage in a graded progression of increasing iron deficiency which includes negative iron balance and iron-deficient erythropoiesis as intermediate stages. Iron deficiency can result from increased iron demand, decreased iron intake, or increased iron loss, as exemplified in conditions such as pregnancy, inadequate diet, intestinal malabsorption, acute or chronic inflammation, and acute or chronic blood loss. With mild-to-moderate anemia of this type, the bone marrow remains hypoproliferative, and RBC morphology is largely normal; however, even mild anemia can result in some microcytic hypochromic RBCs, and the transition to severe iron-deficient anemia is accompanied by hyperproliferation of the bone marrow and increasingly prevalent microcytic and hypochromic RBCs [see, e.g., Adamson (2008) Harrison's Principles of Internal Medicine, 17th ed.; McGraw Hill, New York, pp 628-634]. Appropriate therapy for iron-deficiency anemia depends on its cause and severity, with oral iron preparations, parenteral iron formulations, and RBC transfusion as major conventional options. In some embodiments, one or more TGF-beta superfamily receptor single-arm heteromultimer complexes of the disclosure, optionally combined with an EPO receptor activator, could be used to treat a chronic iron-deficiency.

Myelodysplastic syndrome (MDS) is a diverse collection of hematological conditions characterized by ineffective production of myeloid blood cells and risk of transformation to acute myelogenous leukemia. In MDS patients, blood stem cells do not mature into healthy red blood cells, white blood cells, or platelets. MDS disorders include, for example, refractory anemia, refractory anemia with ringed sideroblasts, refractory anemia with excess blasts, refractory anemia with excess blasts in transformation, refractory cytopenia with multilineage dysplasia, and myelodysplastic syndrome associated with an isolated 5q chromosome abnormality. As these disorders manifest as irreversible defects in both quantity and quality of hematopoietic cells, most MDS patients are afflicted with chronic anemia. Therefore, MDS patients eventually require blood transfusions and/or treatment with growth factors (e.g., erythropoietin or G-CSF) to increase red blood cell levels. However, many MDS patients develop side-effects due to frequency of such therapies. For example, patients who receive frequent red blood cell transfusion can exhibit tissue and organ damage from the buildup of extra iron. Accordingly, one or more TGF-beta superfamily receptor single-arm heteromultimer complexes of the disclosure, may be used to treat patients having MDS. In certain embodiments, patients suffering from MDS may be treated using one or more TGF-beta superfamily receptor single-arm heteromultimer complexes of the disclosure, optionally in combination with an EPO receptor activator. In other embodiments, patients suffering from MDS may be treated using a combination of one or more TGF-beta superfamily receptor single-arm heteromultimer complexes of the disclosure and one or more additional therapeutic agents for treating MDS including, for example, thalidomide, lenalidomide, azacitadine, decitabine, erythropoietins, deferoxamine, antithymocyte globulin, and filgrastrim (G-CSF).

Originally distinguished from aplastic anemia, hemorrhage, or peripheral hemolysis on the basis of ferrokinetic studies [see, e.g., Ricketts et al. (1978) Clin Nucl Med 3:159-164], ineffective erythropoiesis describes a diverse group of anemias in which production of mature RBCs is less than would be expected given the number of erythroid precursors (erythroblasts) present in the bone marrow [Tanno et al. (2010) Adv Hematol 2010:358283]. In such anemias, tissue hypoxia persists despite elevated erythropoietin levels due to ineffective production of mature RBCs. A vicious cycle eventually develops in which elevated erythropoietin levels drive massive expansion of erythroblasts, potentially leading to splenomegaly (spleen enlargement) due to extramedullary erythropoiesis [see, e.g., Aizawa et al. (2003) Am J Hematol 74:68-72], erythroblast-induced bone pathology [see, e.g., Di Matteo et al. (2008) J Biol Regul Homeost Agents 22:211-216], and tissue iron overload, even in the absence of therapeutic RBC transfusions [see, e.g., Pippard et al. (1979) Lancet 2:819-821]. Thus, by boosting erythropoietic effectiveness, one or more TGF-beta superfamily receptor single-arm heteromultimer complexes of the present disclosure may break the aforementioned cycle and thus alleviate not only the underlying anemia but also the associated complications of elevated erythropoietin levels, splenomegaly, bone pathology, and tissue iron overload. In some embodiments, one or more TGF-beta superfamily receptor single-arm heteromultimer complexes of the present disclosure can be used to treat or prevent ineffective erythropoiesis, including anemia and elevated EPO levels as well as complications such as splenomegaly, erythroblast-induced bone pathology, iron overload, and their attendant pathologies. With splenomegaly, such pathologies include thoracic or abdominal pain and reticuloendothelial hyperplasia. Extramedullary hematopoiesis can occur not only in the spleen but potentially in other tissues in the form of extramedullary hematopoietic pseudotumors [see, e.g., Musallam et al. (2012) Cold Spring Harb Perspect Med 2:a013482]. With erythroblast-induced bone pathology, attendant pathologies include low bone mineral density, osteoporosis, and bone pain [see, e.g., Haidar et al. (2011) Bone 48:425-432]. With iron overload, attendant pathologies include hepcidin suppression and hyperabsorption of dietary iron [see, e.g., Musallam et al. (2012) Blood Rev 26(Suppl 1):516-519], multiple endocrinopathies and liver fibrosis/cirrhosis [see, e.g., Galanello et al. (2010) Orphanet J Rare Dis 5:11], and iron-overload cardiomyopathy [Lekawanvijit et al., 2009, Can J Cardiol 25:213-218].

The most common causes of ineffective erythropoiesis are the thalassemia syndromes, hereditary hemoglobinopathies in which imbalances in the production of intact alpha- and beta-hemoglobin chains lead to increased apoptosis during erythroblast maturation [see, e.g., Schrier (2002) Curr Opin Hematol 9:123-126]. Thalassemias are collectively among the most frequent genetic disorders worldwide, with changing epidemiologic patterns predicted to contribute to a growing public health problem in both the U.S. and globally [Vichinsky (2005) Ann NY Acad Sci 1054:18-24]. Thalassemia syndromes are named according to their severity. Thus, α-thalassemias include α-thalassemia minor (also known as α-thalassemia trait; two affected α-globin genes), hemoglobin H disease (three affected α-globin genes), and α-thalassemia major (also known as hydrops fetalis; four affected α-globin genes). β-Thalassemias include β-thalassemia minor (also known as β-thalassemia trait; one affected β-globin gene), β-thalassemia intermedia (two affected β-globin genes), hemoglobin E thalassemia (two affected β-globin genes), and β-thalassemia major (also known as Cooley's anemia; two affected β-globin genes resulting in a complete absence of β-globin protein). β-Thalassemia impacts multiple organs, is associated with considerable morbidity and mortality, and currently requires life-long care. Although life expectancy in patients with β-thalassemia has increased in recent years due to use of regular blood transfusions in combination with iron chelation, iron overload resulting both from transfusions and from excessive gastrointestinal absorption of iron can cause serious complications such as heart disease, thrombosis, hypogonadism, hypothyroidism, diabetes, osteoporosis, and osteopenia [see, e.g., Rund et al. (2005) N Engl J Med 353:1135-1146]. In certain embodiments, one or more TGF-beta superfamily receptor single-arm heteromultimer complexes of the disclosure, optionally combined with an EPO receptor activator, can be used to treat or prevent a thalassemia syndrome.

In some embodiments, one or more TGF-beta superfamily receptor single-arm heteromultimer complexes of the disclosure, optionally combined with an EPO receptor activator, can be used for treating disorders of ineffective erythropoiesis besides thalassemia syndromes. Such disorders include siderblastic anemia (inherited or acquired); dyserythropoietic anemia (types I and II); sickle cell anemia; hereditary spherocytosis; pyruvate kinase deficiency; megaloblastic anemias, potentially caused by conditions such as folate deficiency (due to congenital diseases, decreased intake, or increased requirements), cobalamin deficiency (due to congenital diseases, pernicious anemia, impaired absorption, pancreatic insufficiency, or decreased intake), certain drugs, or unexplained causes (congenital dyserythropoietic anemia, refractory megaloblastic anemia, or erythroleukemia); myelophthisic anemias including, for example, myelofibrosis (myeloid metaplasia) and myelophthisis; congenital erythropoietic porphyria; and lead poisoning.

In certain embodiments, one or more TGF-beta superfamily receptor single-arm heteromultimer complexes of the disclosure may be used in combination with supportive therapies for ineffective erythropoiesis. Such therapies include transfusion with either red blood cells or whole blood to treat anemia. In chronic or hereditary anemias, normal mechanisms for iron homeostasis are overwhelmed by repeated transfusions, eventually leading to toxic and potentially fatal accumulation of iron in vital tissues such as heart, liver, and endocrine glands. Thus, supportive therapies for patients chronically afflicted with ineffective erythropoiesis also include treatment with one or more iron-chelating molecules to promote iron excretion in the urine and/or stool and thereby prevent, or reverse, tissue iron overload [see, e.g., Hershko (2006) Haematologica 91:1307-1312; Cao et al. (2011), Pediatr Rep 3(2):e17]. Effective iron-chelating agents should be able to selectively bind and neutralize ferric iron, the oxidized form of non-transferrin bound iron which likely accounts for most iron toxicity through catalytic production of hydroxyl radicals and oxidation products [see, e.g., Esposito et al. (2003) Blood 102:2670-2677]. These agents are structurally diverse, but all possess oxygen or nitrogen donor atoms able to form neutralizing octahedral coordination complexes with individual iron atoms in stoichiometries of 1:1 (hexadentate agents), 2:1 (tridentate), or 3:1 (bidentate) [Kalinowski et al. (2005) Pharmacol Rev 57:547-583]. In general, effective iron-chelating agents also are relatively low molecular weight (e.g., less than 700 daltons), with solubility in both water and lipids to enable access to affected tissues. Specific examples of iron-chelating molecules include deferoxamine, a hexadentate agent of bacterial origin requiring daily parenteral administration, and the orally active synthetic agents deferiprone (bidentate) and deferasirox (tridentate). Combination therapy consisting of same-day administration of two iron-chelating agents shows promise in patients unresponsive to chelation monotherapy and also in overcoming issues of poor patient compliance with dereroxamine alone [Cao et al. (2011) Pediatr Rep 3(2):e17; Galanello et al. (2010) Ann NY Acad Sci 1202:79-86].

As used herein, "in combination with" or "conjoint administration" refers to any form of administration such that the second therapy is still effective in the body (e.g., the two compounds are simultaneously effective in the patient, which may include synergistic effects of the two compounds). Effectiveness may not correlate to measurable concentration of the agent in blood, serum, or plasma. For example, the different therapeutic compounds can be administered either in the same formulation or in separate formulations, either concomitantly or sequentially, and on different schedules. Thus, an individual who receives such treatment can benefit from a combined effect of different therapies. One or more TGF-beta superfamily receptor single-arm heteromultimer complexes of the disclosure can be administered concurrently with, prior to, or subsequent to, one or more other additional agents or supportive therapies. In general, each therapeutic agent will be administered at a dose and/or on a time schedule determined for that particular agent. The particular combination to employ in a regimen will take into account compatibility of the antagonist of the present disclosure with the therapy and/or the desired therapeutic effect to be achieved.

In certain embodiments, one or more TGF-beta superfamily receptor single-arm heteromultimer complexes of the disclosure may be used in combination with hepcidin or a hepcidin agonist for ineffective erythropoiesis. A circulating polypeptide produced mainly in the liver, hepcidin is considered a master regulator of iron metabolism by virtue of its ability to induce the degradation of ferroportin, an iron-export protein localized on absorptive enterocytes, hepatocytes, and macrophages. Broadly speaking, hepcidin reduces availability of extracellular iron, so hepcidin agonists may be beneficial in the treatment of ineffective erythropoiesis [see, e.g., Nemeth (2010) Adv Hematol 2010:750643]. This view is supported by beneficial effects of increased hepcidin expression in a mouse model of β-thalassemia [Gardenghi et al. (2010) J Clin Invest 120:4466-4477].

One or more TGF-beta superfamily receptor single-arm heteromultimer complexes of the disclosure, optionally combined with an EPO receptor activator, would also be appropriate for treating anemias of disordered RBC maturation, which are characterized in part by undersized (microcytic), oversized (macrocytic), misshapen, or abnormally colored (hypochromic) RBCs.

In certain embodiments, the present disclosure provides methods of treating or preventing anemia in an individual in need thereof by administering to the individual a therapeutically effective amount of one or more TGF-beta superfamily receptor single-arm heteromultimer complexes of the disclosure and a EPO receptor activator. In certain embodiments, one or more TGF-beta superfamily receptor single-arm heteromultimer complexes of the disclosure may be used in combination with EPO receptor activators to reduce the required dose of these activators in patients that are susceptible to adverse effects of EPO. These methods may be used for therapeutic and prophylactic treatments of a patient.

One or more TGF-beta superfamily receptor single-arm heteromultimer complexes of the disclosure may be used in combination with EPO receptor activators to achieve an increase in red blood cells, particularly at lower dose ranges of EPO receptor activators. This may be beneficial in reducing the known off-target effects and risks associated with high doses of EPO receptor activators. The primary adverse effects of EPO include, for example, an excessive increase in the hematocrit or hemoglobin levels and polycythemia. Elevated hematocrit levels can lead to hypertension (more particularly aggravation of hypertension) and vascular thrombosis. Other adverse effects of EPO which have been reported, some of which relate to hypertension, are headaches, influenza-like syndrome, obstruction of shunts, myocardial infarctions and cerebral convulsions due to thrombosis, hypertensive encephalopathy, and red cell blood cell aplasia. See, e.g., Singibarti (1994) J. Clin Investig 72(suppl 6), S36-S43; Horl et al. (2000) Nephrol Dial Transplant 15(suppl 4), 51-56; Delanty et al. (1997) Neurology 49, 686-689; and Bunn (2002) N Engl J Med 346(7), 522-523).

Provided that TGF-beta superfamily receptor single-arm heteromultimer complexes of the present disclosure act by a different mechanism than EPO, these antagonists may be useful for increasing red blood cell and hemoglobin levels in patients that do not respond well to EPO. For example, a TGF-beta superfamily receptor single-arm heteromultimer complex of the present disclosure may be beneficial for a patient in which administration of a normal-to-increased dose of EPO (>300 IU/kg/week) does not result in the increase of hemoglobin level up to the target level. Patients with an inadequate EPO response are found in all types of anemia, but higher numbers of non-responders have been observed particularly frequently in patients with cancers and patients with end-stage renal disease. An inadequate response to EPO can be either constitutive (observed upon the first treatment with EPO) or acquired (observed upon repeated treatment with EPO).

In certain embodiments, the present disclosure provides methods for managing a patient that has been treated with, or is a candidate to be treated with, one or more TGF-beta superfamily receptor single-arm heteromultimer complexes of the disclosure by measuring one or more hematologic parameters in the patient. The hematologic parameters may be used to evaluate appropriate dosing for a patient who is a candidate to be treated with the antagonist of the present disclosure, to monitor the hematologic parameters during treatment, to evaluate whether to adjust the dosage during treatment with one or more antagonist of the disclosure, and/or to evaluate an appropriate maintenance dose of one or more antagonists of the disclosure. If one or more of the hematologic parameters are outside the normal level, dosing with one or more TGF-beta superfamily receptor single-arm heteromultimer complexes of the disclosure may be reduced, delayed or terminated.

Hematologic parameters that may be measured in accordance with the methods provided herein include, for example, red blood cell levels, blood pressure, iron stores, and other agents found in bodily fluids that correlate with increased red blood cell levels, using art-recognized methods. Such parameters may be determined using a blood sample from a patient. Increases in red blood cell levels, hemoglobin levels, and/or hematocrit levels may cause increases in blood pressure.

In one embodiment, if one or more hematologic parameters are outside the normal range or on the high side of normal in a patient who is a candidate to be treated with one or more TGF-beta superfamily receptor single-arm heteromultimer complexes of the disclosure, then onset of administration of the one or more TGF-beta superfamily receptor single-arm heteromultimer complexes of the disclosure may be delayed until the hematologic parameters have returned to a normal or acceptable level either naturally or via therapeutic intervention. For example, if a candidate patient is hypertensive or pre-hypertensive, then the patient may be treated with a blood pressure lowering agent in order to reduce the patient's blood pressure. Any blood pressure lowering agent appropriate for the individual patient's condition may be used including, for example, diuretics, adrenergic inhibitors (including alpha blockers and beta blockers), vasodilators, calcium channel blockers, angiotensin-converting enzyme (ACE) inhibitors, or angiotensin II receptor blockers. Blood pressure may alternatively be treated using a diet and exercise regimen. Similarly, if a candidate patient has iron stores that are lower than normal, or on the low side of normal, then the patient may be treated with an appropriate regimen of diet and/or iron supplements until the patient's iron stores have returned to a normal or acceptable level. For patients having higher than normal red blood cell levels and/or hemoglobin levels, then administration of the one or more TGF-beta superfamily receptor single-arm heteromultimer complexes of the disclosure may be delayed until the levels have returned to a normal or acceptable level.

In certain embodiments, if one or more hematologic parameters are outside the normal range or on the high side of normal in a patient who is a candidate to be treated with one or more TGF-beta superfamily receptor single-arm heteromultimer complexes of the disclosure, then the onset of administration may not be delayed. However, the dosage amount or frequency of dosing of the one or more TGF-beta superfamily receptor single-arm heteromultimer complexes of the disclosure may be set at an amount that would reduce the risk of an unacceptable increase in the hematologic parameters arising upon administration of the one or more TGF-beta superfamily receptor single-arm heteromultimer complexes of the disclosure. Alternatively, a therapeutic regimen may be developed for the patient that combines one or more TGF-beta superfamily receptor single-arm heteromultimer complexes of the disclosure with a therapeutic agent that addresses the undesirable level of the hematologic parameter. For example, if the patient has elevated blood pressure, then a therapeutic regimen involving administration of one or more TGF-beta superfamily receptor single-arm heteromultimer complexes of the disclosure and a blood pressure-lowering agent may be designed. For a patient having lower than desired iron stores, a therapeutic regimen of one or more TGF-beta superfamily receptor single-arm heteromultimer complexes of the disclosure and iron supplementation may be developed.

In one embodiment, baseline parameter(s) for one or more hematologic parameters may be established for a patient who is a candidate to be treated with one or more TGF-beta superfamily receptor single-arm heteromultimer complexes of the disclosure and an appropriate dosing regimen established for that patient based on the baseline value(s). Alternatively, established baseline parameters based on a patient's medical history could be used to inform an appropriate dosing regimen for a patient. For example, if a healthy patient has an established baseline blood pressure reading that is above the defined normal range it may not be necessary to bring the patient's blood pressure into the range that is considered normal for the general population prior to treatment with the one or more TGF-beta superfamily heteromultimer complexes of the disclosure. A patient's baseline values for one or more hematologic parameters prior to treatment with one or more TGF-beta superfamily receptor single-arm heteromultimer complexes of the disclosure may also be used as the relevant comparative values for monitoring any changes to the hematologic parameters during treatment with the one or more TGF-beta superfamily receptor single-arm heteromultimer complexes of the disclosure.

In certain embodiments, one or more hematologic parameters are measured in patients who are being treated with a one or more TGF-beta superfamily receptor single-arm heteromultimer complexes of the disclosure. The hematologic parameters may be used to monitor the patient during treatment and permit adjustment or termination of the dosing with the one or more TGF-beta superfamily receptor single-arm heteromultimer complexes of the disclosure or additional dosing with another therapeutic agent. For example, if administration of one or more TGF-beta superfamily receptor single-arm heteromultimer complexes of the disclosure of the disclosure results in an increase in blood pressure, red blood cell level, or hemoglobin level, or a reduction in iron stores, then the dose of the one or more TGF-beta superfamily receptor single-arm heteromultimer complexes of the disclosure may be reduced in amount or frequency in order to decrease the effects of the one or more TGF-beta superfamily receptor single-arm heteromultimer complexes of the disclosure on the one or more hematologic parameters. If administration of one or more TGF-beta superfamily receptor single-arm heteromultimer complexes of the disclosure results in a change in one or more hematologic parameters that is adverse to the patient, then the dosing of the one or more TGF-beta superfamily receptor single-arm heteromultimer complexes of the disclosure may be terminated either temporarily, until the hematologic parameter(s) return to an acceptable level, or permanently. Similarly, if one or more hematologic parameters are not brought within an acceptable range after reducing the dose or frequency of administration of the one or more TGF-beta superfamily receptor single-arm heteromultimer complexes of the disclosure, then the dosing may be terminated. As an alternative, or in addition to, reducing or terminating the dosing with the one or more TGF-beta superfamily receptor single-arm heteromultimer complexes of the disclosure, the patient may be dosed with an additional therapeutic agent that addresses the undesirable level in the hematologic parameter(s), such as, for example, a blood pressure-lowering agent or an iron supplement. For example, if a patient being treated with one or more TGF-beta superfamily receptor single-arm heteromultimer complexes of the disclosure has elevated blood pressure, then dosing with the one or more TGF-beta superfamily receptor single-arm heteromultimer complexes of the disclosure may continue at the same level and a blood pressure-lowering agent is added to the treatment regimen, dosing with the one or more TGF-beta superfamily receptor single-arm heteromultimer complexes of the disclosure may be reduced (e.g., in amount and/or frequency) and a blood pressure-lowering agent is added to the treatment regimen, or dosing with the one or more TGF-beta superfamily receptor single-arm heteromultimer complexes of the disclosure may be terminated and the patient may be treated with a blood pressure-lowering agent.

6. Pharmaceutical Compositions

In certain aspects, TGF-beta superfamily receptor single-arm heteromultimer complexes of the present disclosure can be administered alone or as a component of a pharmaceutical formulation (also referred to as a therapeutic composition or pharmaceutical composition). A pharmaceutical formation refers to a preparation which is in such form as to permit the biological activity of an active ingredient (e.g., an agent of the present disclosure) contained therein to be effective and which contains no additional components which are unacceptably toxic to a subject to which the formulation would be administered. The subject compounds may be formulated for administration in any convenient way for use in human or veterinary medicine. For example, one or more agents of the present disclosure may be formulated with a pharmaceutically acceptable carrier. A pharmaceutically acceptable carrier refers to an ingredient in a pharmaceutical formulation, other than an active ingredient, which is generally nontoxic to a subject. A pharmaceutically acceptable carrier includes, but is not limited to, a buffer, excipient, stabilizer, and/or preservative. In general, pharmaceutical formulations for use in the present disclosure are in a pyrogen-free, physiologically-acceptable form when administered to a subject. Therapeutically useful agents other than those described herein, which may optionally be included in the formulation as described above, may be administered in combination with the subject agents in the methods of the present disclosure.

In certain embodiments, compositions will be administered parenterally [e.g., by intravenous (I. V.) injection, intraarterial injection, intraosseous injection, intramuscular injection, intrathecal injection, subcutaneous injection, or intradermal injection]. Pharmaceutical compositions suitable for parenteral administration may comprise one or more agents of the disclosure in combination with one or more pharmaceutically acceptable sterile isotonic aqueous or nonaqueous solutions, dispersions, suspensions or emulsions, or sterile powders which may be reconstituted into sterile injectable solutions or dispersions just prior to use. Injectable solutions or dispersions may contain antioxidants, buffers, bacteriostats, suspending agents, thickening agents, or solutes which render the formulation isotonic with the blood of the intended recipient. Examples of suitable aqueous and nonaqueous carriers which may be employed in the pharmaceutical formulations of the present disclosure include water, ethanol, polyols (e.g., glycerol, propylene glycol, polyethylene glycol, etc.), vegetable oils (e.g., olive oil), injectable organic esters (e.g., ethyl oleate), and suitable mixtures thereof. Proper fluidity can be maintained, for example, by the use of coating materials (e.g., lecithin), by the maintenance of the required particle size in the case of dispersions, and by the use of surfactants.

In some embodiments, a therapeutic method of the present disclosure includes administering the pharmaceutical composition systemically, or locally, from an implant or device. Further, the pharmaceutical composition may be encapsulated or injected in a form for delivery to a target tissue site (e.g., bone marrow or muscle). In certain embodiments, compositions of the present disclosure may include a matrix capable of delivering one or more of the agents of the present disclosure to a target tissue site (e.g., bone marrow or muscle), providing a structure for the developing tissue and optimally capable of being resorbed into the body. For example, the matrix may provide slow release of one or more agents of the present disclosure. Such matrices may be formed of materials presently in use for other implanted medical applications.

The choice of matrix material may be based on one or more of: biocompatibility, biodegradability, mechanical properties, cosmetic appearance, and interface properties. The particular application of the subject compositions will define the appropriate formulation. Potential matrices for the compositions may be biodegradable and chemically defined calcium sulfate, tricalciumphosphate, hydroxyapatite, polylactic acid, and polyanhydrides. Other potential materials are biodegradable and biologically well-defined including, for example, bone or dermal collagen. Further matrices are comprised of pure proteins or extracellular matrix components. Other potential matrices are non-biodegradable and chemically defined including, for example, sintered hydroxyapatite, bioglass, aluminates, or other ceramics. Matrices may be comprised of combinations of any of the above mentioned types of material including, for example, polylactic acid and hydroxyapatite or collagen and tricalciumphosphate. The bioceramics may be altered in composition (e.g., calcium-aluminate-phosphate) and processing to alter one or more of pore size, particle size, particle shape, and biodegradability.

In certain embodiments, pharmaceutical compositions of the present disclosure can be administered topically. "Topical application" or "topically" means contact of the pharmaceutical composition with body surfaces including, for example, the skin, wound sites, and mucous membranes. The topical pharmaceutical compositions can have various application forms and typically comprises a drug-containing layer, which is adapted to be placed near to or in direct contact with the tissue upon topically administering the composition. Pharmaceutical compositions suitable for topical administration may comprise one or more TGFβ superfamily receptor single-arm heteromultimer complexes of the disclosure in combination formulated as a liquid, a gel, a cream, a lotion, an ointment, a foam, a paste, a putty, a semi-solid, or a solid. Compositions in the liquid, gel, cream, lotion, ointment, foam, paste, or putty form can be applied by spreading, spraying, smearing, dabbing or rolling the composition on the target tissue. The compositions also may be impregnated into sterile dressings, transdermal patches, plasters, and bandages. Compositions of the putty, semi-solid or solid forms may be deformable. They may be elastic or non-elastic (e.g., flexible or rigid). In certain aspects, the composition forms part of a composite and can include fibers, particulates, or multiple layers with the same or different compositions.

Topical compositions in the liquid form may include pharmaceutically acceptable solutions, emulsions, microemulsions, and suspensions. In addition to the active ingredient(s), the liquid dosage form may contain an inert diluent commonly used in the art including, for example, water or other solvent, a solubilizing agent and/or emulsifier [e.g., ethyl alcohol, isopropyl alcohol, ethyl carbonate, ethyl acetate, benzyl alcohol, benzyl benzoate, propylene glycol, or 1,3-butylene glycol, an oil (e.g., cottonseed, groundnut, corn, germ, olive, castor, and sesame oil), glycerol, tetrahydrofuryl alcohol, a polyethylene glycol, a fatty acid ester of sorbitan, and mixtures thereof].

Topical gel, cream, lotion, ointment, semi-solid or solid compositions may include one or more thickening agents, such as a polysaccharide, synthetic polymer or protein-based polymer. In one embodiment of the invention, the gelling agent herein is one that is suitably nontoxic and gives the desired viscosity. The thickening agents may include polymers, copolymers, and monomers of: vinylpyrrolidones, methacrylamides, acrylamides N-vinylimidazoles, carboxy vinyls, vinyl esters, vinyl ethers, silicones, polyethyleneoxides, polyethyleneglycols, vinylalcohols, sodium acrylates, acrylates, maleic acids, NN-dimethylacrylamides, diacetone acrylamides, acrylamides, acryloyl morpholine, pluronic, collagens, polyacrylamides, polyacrylates, polyvinyl alcohols, polyvinylenes, polyvinyl silicates, polyacrylates substituted with a sugar (e.g., sucrose, glucose, glucosamines, galactose, trehalose, mannose, or lactose), acylamidopropane sulfonic acids, tetramethoxyorthosilicates, methyltrimethoxyorthosilicates, tetraalkoxyorthosilicates, trialkoxyorthosilicates, glycols, propylene glycol, glycerine, polysaccharides, alginates, dextrans, cyclodextrin, celluloses, modified celluloses, oxidized celluloses, chitosans, chitins, guars, carrageenans, hyaluronic acids, inulin, starches, modified starches, agarose, methylcelluloses, plant gums, hylaronans, hydrogels, gelatins, glycosaminoglycans, carboxymethyl celluloses, hydroxyethyl celluloses, hydroxy propyl methyl celluloses, pectins, low-methoxy pectins, cross-linked dextrans, starch-acrylonitrile graft copolymers, starch sodium polyacrylate, hydroxyethyl methacrylates, hydroxyl ethyl acrylates, polyvinylene, polyethylvinylethers, polymethyl methacrylates, polystyrenes, polyurethanes, polyalkanoates, polylactic acids, polylactates, poly (3-hydroxybutyrate), sulfonated hydrogels, AMPS (2-acrylamido-2-methyl-1-propanesulfonic acid), SEM (sulfoethylmethacrylate), SPM (sulfopropyl methacrylate), SPA (sulfopropyl acrylate), N,N-dimethyl-N-methacryloxyethyl-N-(3-sulfopropyl)ammonium betaine, methacryllic acid amidopropyl-dimethyl ammonium sulfobetaine, SPI (itaconic acid-bis(1-propyl sulfonizacid-3) ester di-potassium salt), itaconic acids, AMBC (3-acrylamido-3-methylbutanoic acid), beta-carboxyethyl acrylate (acrylic acid dimers), and maleic anhydride-methylvinyl ether polymers, derivatives thereof, salts thereof, acids thereof, and combinations thereof. In certain embodiments, pharmaceutical compositions of present disclosure can be administered orally, for example, in the form of capsules, cachets, pills, tablets, lozenges (using a flavored basis such as sucrose and acacia or tragacanth), powders, granules, a solution or a suspension in an aqueous or non-aqueous liquid, an oil-in-water or water-in-oil liquid emulsion, or an elixir or syrup, or pastille (using an inert base, such as gelatin and glycerin, or sucrose and acacia), and/or a mouth wash, each containing a predetermined amount of a compound of the present disclosure and optionally one or more other active ingredients. A compound of the present disclosure and optionally one or more other active ingredients may also be administered as a bolus, electuary, or paste.

In solid dosage forms for oral administration (e.g., capsules, tablets, pills, dragees, powders, and granules), one or more compounds of the present disclosure may be mixed with one or more pharmaceutically acceptable carriers including, for example, sodium citrate, dicalcium phosphate, a filler or extender (e.g., a starch, lactose, sucrose, glucose, mannitol, and silicic acid), a binder (e.g. carboxymethylcellulose, an alginate, gelatin, polyvinyl pyrrolidone, sucrose, and acacia), a humectant (e.g., glycerol), a disintegrating agent (e.g., agar-agar, calcium carbonate, potato or tapioca starch, alginic acid, a silicate, and sodium carbonate), a solution retarding agent (e.g. paraffin), an absorption accelerator (e.g. a quaternary ammonium compound), a wetting agent (e.g., cetyl alcohol and glycerol monostearate), an absorbent (e.g., kaolin and bentonite clay), a lubricant (e.g., a talc, calcium stearate, magnesium stearate, solid polyethylene glycols, sodium lauryl sulfate), a coloring agent, and mixtures thereof. In the case of capsules, tablets, and pills, the pharmaceutical formulation (composition) may also comprise a buffering agent. Solid compositions of a similar type may also be employed as fillers in soft and hard-filled gelatin capsules using one or more excipients including, e.g., lactose or a milk sugar as well as a high molecular-weight polyethylene glycol.

Liquid dosage forms for oral administration of the pharmaceutical composition may include pharmaceutically acceptable emulsions, microemulsions, solutions, suspensions, syrups, and elixirs. In addition to the active ingredient (s), the liquid dosage form may contain an inert diluent commonly used in the art including, for example, water or other solvent, a solubilizing agent and/or emulsifier [e.g., ethyl alcohol, isopropyl alcohol, ethyl carbonate, ethyl acetate, benzyl alcohol, benzyl benzoate, propylene glycol, or 1,3-butylene glycol, an oil (e.g., cottonseed, groundnut, corn, germ, olive, castor, and sesame oil), glycerol, tetrahydrofuryl alcohol, a polyethylene glycol, a fatty acid ester of sorbitan, and mixtures thereof]. Besides inert diluents, the oral formulation can also include an adjuvant including, for example, a wetting agent, an emulsifying and suspending agent, a sweetening agent, a flavoring agent, a coloring agent, a perfuming agent, a preservative agent, and combinations thereof.

Suspensions, in addition to the active compounds, may contain suspending agents including, for example, an ethoxylated isostearyl alcohol, polyoxyethylene sorbitol, a sorbitan ester, microcrystalline cellulose, aluminum metahydroxide, bentonite, agar-agar, tragacanth, and combinations thereof.

Prevention of the action and/or growth of microorganisms may be ensured by the inclusion of various antibacterial and antifungal agents including, for example, paraben, chlorobutanol, and phenol sorbic acid.

In certain embodiments, it may be desirable to include an isotonic agent including, for example, a sugar or sodium chloride into the compositions. In addition, prolonged absorption of an injectable pharmaceutical form may be brought about by the inclusion of an agent that delay absorption including, for example, aluminum monostearate and gelatin.

It is understood that the dosage regimen will be determined by the attending physician considering various factors which modify the action of the one or more of the agents of the present disclosure. In the case of a TGF-beta superfamily receptor single-arm heteromultimer complex that promotes red blood cell formation, various factors may include, but are not limited to, the patient's red blood cell count, hemoglobin level, the desired target red blood cell count, the patient's age, the patient's sex, the patient's diet, the severity of any disease that may be contributing to a depressed red blood cell level, the time of administration, and other clinical factors. The addition of other known active agents to the final composition may also affect the dosage. Progress can be monitored by periodic assessment of one or more of red blood cell levels, hemoglobin levels, reticulocyte levels, and other indicators of the hematopoietic process.

In certain embodiments, the present disclosure also provides gene therapy for the in vivo production of one or more of the agents of the present disclosure. Such therapy would achieve its therapeutic effect by introduction of the agent sequences into cells or tissues having one or more of the disorders as listed above. Delivery of the agent sequences can be achieved, for example, by using a recombinant expression vector such as a chimeric virus or a colloidal dispersion system. Preferred therapeutic delivery of one or more of agent sequences of the disclosure is the use of targeted liposomes.

Various viral vectors which can be utilized for gene therapy as taught herein include adenovirus, herpes virus, vaccinia, or an RNA virus (e.g., a retrovirus). The retroviral vector may be a derivative of a murine or avian retrovirus. Examples of retroviral vectors in which a single foreign gene can be inserted include, but are not limited to: Moloney murine leukemia virus (MoMuLV), Harvey murine sarcoma virus (HaMuSV), murine mammary tumor virus (MuMTV), and Rous Sarcoma Virus (RSV). A number of additional retroviral vectors can incorporate multiple genes. All of these vectors can transfer or incorporate a gene for a selectable marker so that transduced cells can be identified and generated. Retroviral vectors can be made target-specific by attaching, for example, a sugar, a glycolipid, or a protein. Preferred targeting is accomplished by using an antibody. Those of skill in the art will recognize that specific polynucleotide sequences can be inserted into the retroviral genome or attached to a viral envelope to allow target specific delivery of the retroviral vector containing one or more of the agents of the present disclosure.

Alternatively, tissue culture cells can be directly transfected with plasmids encoding the retroviral structural genes (gag, pol, and env), by conventional calcium phosphate transfection. These cells are then transfected with the vector plasmid containing the genes of interest. The resulting cells release the retroviral vector into the culture medium.

Another targeted delivery system for one or more of the agents of the present disclosure is a colloidal dispersion system. Colloidal dispersion systems include, for example, macromolecule complexes, nanocapsules, microspheres, beads, and lipid-based systems including oil-in-water emulsions, micelles, mixed micelles, and liposomes. In certain embodiments, the preferred colloidal system of this disclosure is a liposome. Liposomes are artificial membrane vesicles which are useful as delivery vehicles in vitro and in vivo. RNA, DNA, and intact virions can be encapsulated within the aqueous interior and be delivered to cells in a biologically active form. See, e.g., Fraley, et al. (1981) Trends Biochem. Sci., 6:77. Methods for efficient gene transfer using a liposome vehicle are known in the art. See, e.g., Mannino, et al. (1988) Biotechniques, 6:682, 1988.

The composition of the liposome is usually a combination of phospholipids, which may include a steroid (e.g. cholesterol). The physical characteristics of liposomes depend on pH, ionic strength, and the presence of divalent cations. Other phospholipids or other lipids may also be used including, for example a phosphatidyl compound (e.g., phosphatidylglycerol, phosphatidylcholine, phosphatidylserine, phosphatidylethanolamine, a sphingolipid, a cerebroside, and a ganglioside), egg phosphatidylcholine, dipalmitoylphosphatidylcholine, and distearoylphosphatidylcholine. The targeting of liposomes is also possible based on, for example, organ-specificity, cell-specificity, and organelle-specificity and is known in the art.

EXEMPLIFICATION

The invention now being generally described, it will be more readily understood by reference to the following examples, which are included merely for purposes of illustration of certain embodiments of the present invention, and are not intended to limit the invention.

Example 1. Generation and Characterization of a Single-Arm ActRIIB-Fc Heterodimer Applicants constructed a soluble single-arm ActRIIB-Fc heterodimeric complex comprising a monomeric Fc polypeptide with a short N-terminal extension and a second polypeptide in which the extracellular domain of human ActRIIB was fused to a separate Fc domain with a linker positioned between the extracellular domain and this second Fc domain. The individual constructs are referred to as monomeric Fc polypeptide and ActRIIB-Fc fusion polypeptide, respectively, and the sequences for each are provided below.

A methodology for promoting formation of ActRIIB-Fc:Fc heteromeric complexes rather than ActRIIB-Fc:ActRIIB-Fc or Fc:Fc homodimeric complexes is to introduce alterations in the amino acid sequence of the Fc domains to guide the formation of asymmetric heteromeric complexes. Many different approaches to making asymmetric interaction pairs using Fc domains are described in this disclosure.

In one approach, illustrated in the ActRIIB-Fc and monomeric Fc polypeptide sequences of SEQ ID NOs: 104-106 and 137-139, respectively, one Fc domain is altered to introduce cationic amino acids at the interaction face, while the other Fc domain is altered to introduce anionic amino acids at the interaction face. The ActRIIB-Fc fusion polypeptide and monomeric Fc polypeptide each employ the tissue plasminogen activator (TPA) leader:

```
                                    (SEQ ID NO: 100)
          MDAMKRGLCCVLLLCGAVFVSP.
```

The ActRIIB-Fc polypeptide sequence (SEQ ID NO: 104) is shown below:

(SEQ ID NO: 104)

```
1    MDAMKRGLCC VLLLCGAVFV SPGASGRGEA ETRECIYYNA NWELERTNQS
51   GLERCEGEQD KRLHCYASWR NSSGTIELVK KGCWLDDFNC YDRQECVATE
101  ENPQVYFCCC EGNFCNERFT HLPEAGGPEV TYEPPPTAPT GGGTHTCPPC
151  PAPELLGGPS VFLFPPKPKD TLMISRTPEV TCVVVDVSHE DPEVKFNWYV
201  DGVEVHNAKT KPREEQYNST YRVVSVLTVL HQDWLNGKEY KCKVSNKALP
251  APIEKTISKA KGQPREPQVY TLPPSRKEMT KNQVSLTCLV KGFYPSDIAV
301  EWESNGQPEN NYKTTPPVLK SDGSFFLYSK LTVDKSRWQQ GNVFSCSVMH
351  EALHNHYTQK SLSLSPGK
```

The leader (signal) sequence and linker are underlined. To promote formation of the ActRIIB-Fc:Fc heterodimer rather than either of the possible homodimeric complexes (ActRIIB-Fc:ActRIIB-Fc or Fc:Fc), two amino acid substitutions (replacing acidic amino acids with lysine) can be introduced into the Fc domain of the ActRIIB fusion protein as indicated by double underline above. The amino acid sequence of SEQ ID NO: 104 may optionally be provided with the C-terminal lysine (K) removed.

This ActRIIB-Fc fusion polypeptide is encoded by the following nucleic acid sequence (SEQ ID NO: 105):

(SEQ ID NO: 105)

```
1     ATGGATGCAA TGAAGAGAGG GCTCTGCTGT GTGCTGCTGC TGTGTGGAGC
51    AGTCTTCGTT TCGCCCGGCG CCTCTGGGCG TGGGGAGGCT GAGACACGGG
101   AGTGCATCTA CTACAACGCC AACTGGGAGC TGGAGCGCAC CAACCAGAGC
151   GGCCTGGAGC GCTGCGAAGG CGAGCAGGAC AAGCGGCTGC ACTGCTACGC
201   CTCCTGGCGC AACAGCTCTG GCACCATCGA GCTCGTGAAG AAGGGCTGCT
251   GGCTAGATGA CTTCAACTGC TACGATAGGC AGGAGTGTGT GGCCACTGAG
301   GAGAACCCCC AGGTGTACTT CTGCTGCTGT GAAGGCAACT TCTGCAACGA
351   GCGCTTCACT CATTTGCCAG AGGCTGGGGG CCCGGAAGTC ACGTACGAGC
401   CACCCCCGAC AGCCCCCACC GGTGGTGGAA CTCACACATG CCCACCGTGC
451   CCAGCACCTG AACTCCTGGG GGGACCGTCA GTCTTCCTCT TCCCCCCAAA
501   ACCCAAGGAC ACCCTCATGA TCTCCCGGAC CCCTGAGGTC ACATGCGTGG
551   TGGTGGACGT GAGCCACGAA GACCCTGAGG TCAAGTTCAA CTGGTACGTG
601   GACGGCGTGG AGGTGCATAA TGCCAAGACA AAGCCGCGGG AGGAGCAGTA
651   CAACAGCACG TACCGTGTGG TCAGCGTCCT CACCGTCCTG CACCAGGACT
701   GGCTGAATGG CAAGGAGTAC AAGTGCAAGG TCTCCAACAA AGCCCTCCCA
751   GCCCCCATCG AGAAAACCAT CTCCAAAGCC AAAGGGCAGC CCCGAGAACC
801   ACAGGTGTAC ACCCTGCCCC CATCCCGGAA GGAGATGACC AAGAACCAGG
851   TCAGCCTGAC CTGCCTGGTC AAAGGCTTCT ATCCCAGCGA CATCGCCGTG
901   GAGTGGGAGA GCAATGGGCA GCCGGAGAAC AACTACAAGA CCACGCCTCC
951   CGTGCTGAAG TCCGACGGCT CCTTCTTCCT CTATAGCAAG CTCACCGTGG
1001  ACAAGAGCAG GTGGCAGCAG GGGAACGTCT TCTCATGCTC CGTGATGCAT
1051  GAGGCTCTGC ACAACCACTA CACGCAGAAG AGCCTCTCCC TGTCTCCGGG
1101  TAA
```

The mature ActRIIB-Fc fusion polypeptide (SEQ ID NO: 106) is as follows and may optionally be provided with the C-terminal lysine removed.

```
                                          (SEQ ID NO: 106)
  1    GRGEAETREC IYYNANWELE RTNQSGLERC EGEQDKRLHC YASWRNSSGT

 51    IELVKKGCWL DDFNCYDRQE CVATEENPQV YFCCCEGNFC NERFTHLPEA

101    GGPEVTYEPP PTAPTGGGTH TCPPCPAPEL LGGPSVFLFP PKPKDTLMIS

151    RTPEVTCVVV DVSHEDPEVK FNWYVDGVEV HNAKTKPREE QYNSTYRVVS

201    VLTVLHQDWL NGKEYKCKVS NKALPAPIEK TISKAKGQPR EPQVYTLPPS

251    RKEMTKNQVS LTCLVKGFYP SDIAVEWESN GQPENNYKTT PPVLKSDGSF

301    FLYSKLTVDK SRWQQGNVFS CSVMHEALHN HYTQKSLSLS PGK
```

The complementary human G1Fc polypeptide (SEQ ID NO: 137) employs the TPA leader and is as follows:

```
                                          (SEQ ID NO: 137)
  1    MDAMKRGLCC VLLLCGAVFV SPGASNTKVD KRVTGGGTHT CPPCPAPELL

 51    GGPSVFLFPP KPKDTLMISR TPEVTCVVVD VSHEDPEVKF NWYVDGVEVH

101    NAKTKPREEQ YNSTYRVVSV LTVLHQDWLN GKEYKCKVSN KALPAPIEKT

151    ISKAKGQPRE PQVYTLPPSR EEMTKNQVSL TCLVKGFYPS DIAVEWESNG

201    QPENNYDTTP PVLDSDGSFF LYSDLTVDKS RWQQGNVFSC SVMHEALHNH

251    YTQKSLSLSP GK
```

The leader sequence is underlined, and an optional N-terminal extension of the Fc polypeptide is indicated by double underline. To promote formation of the ActRIIB-Fc:Fc heterodimer rather than either of the possible homodimeric complexes, two amino acid substitutions (replacing lysines with anionic residues) can be introduced into the monomeric Fc polypeptide as indicated by double underline above. The amino acid sequence of SEQ ID NO: 137 may optionally be provided with the C-terminal lysine removed.

This complementary Fc polypeptide is encoded by the following nucleic acid (SEQ ID NO: 138).

```
                                          (SEQ ID NO: 138)
  1    ATGGATGCAA TGAAGAGAGG GCTCTGCTGT GTGCTGCTGC TGTGTGGAGC

 51    AGTCTTCGTT TCGCCCGGCG CCAGCAACAC CAAGGTGGAC AAGAGAGTTA

101    CCGGTGGTGG AACTCACACA TGCCCACCGT GCCCAGCACC TGAACTCCTG

151    GGGGGACCGT CAGTCTTCCT CTTCCCCCCA AAACCCAAGG ACACCCTCAT

201    GATCTCCCGG ACCCCTGAGG TCACATGCGT GGTGGTGGAC GTGAGCCACG

251    AAGACCCTGA GGTCAAGTTC AACTGGTACG TGGACGGCGT GGAGGTGCAT

301    AATGCCAAGA CAAAGCCGCG GGAGGAGCAG TACAACAGCA CGTACCGTGT

351    GGTCAGCGTC CTCACCGTCC TGCACCAGGA CTGGCTGAAT GGCAAGGAGT

401    ACAAGTGCAA GGTCTCCAAC AAAGCCCTCC CAGCCCCCAT CGAGAAAACC

451    ATCTCCAAAG CCAAAGGGCA GCCCCGAGAA CCACAGGTGT ACACCCTGCC

501    CCCATCCCGG GAGGAGATGA CCAAGAACCA GGTCAGCCTG ACCTGCCTGG

551    TCAAAGGCTT CTATCCCAGC GACATCGCCG TGGAGTGGGA GAGCAATGGG

601    CAGCCGGAGA ACAACTACGA CACCACGCCT CCCGTGCTGG ACTCCGACGG

651    CTCCTTCTTC CTCTATAGCG ACCTCACCGT GGACAAGAGC AGGTGGCAGC

701    AGGGGAACGT CTTCTCATGC TCCGTGATGC ATGAGGCTCT GCACAACCAC

751    TACACGCAGA AGAGCCTCTC CCTGTCTCCG GGTAAA
```

The sequence of the mature monomeric Fc polypeptide is as follows (SEQ ID NO: 139) and may optionally be provided with the C-terminal lysine removed.

```
                                     (SEQ ID NO: 139)
1    SNTKVDKRVT GGGTHTCPPC PAPELLGGPS VFLFPPKPKD TLMISRTPEV

51   TCVVVDVSHE DPEVKFNWYV DGVEVHNAKT KPREEQYNST YRVVSVLTVL

101  HQDWLNGKEY KCKVSNKALP APIEKTISKA KGQPREPQVY TLPPSREEMT

151  KNQVSLTCLV KGFYPSDIAV EWESNGQPEN NYDTTPPVLD SDGSFFLYSD

201  LTVDKSRWQQ GNVFSCSVMH EALHNHYTQK SLSLSPGK
```

The ActRIIB-Fc fusion polypeptide and monomeric Fc polypeptide of SEQ ID NO: 106 and SEQ ID NO: 139, respectively, may be co-expressed and purified from a CHO cell line to give rise to a single-arm heteromeric protein complex comprising ActRIIB-Fc:Fc.

In another approach to promote the formation of heteromultimer complexes using asymmetric Fc fusion polypeptides, the Fc domains are altered to introduce complementary hydrophobic interactions and an additional intermolecular disulfide bond, as illustrated in the ActRIIB-Fc and monomeric Fc polypeptide sequences of SEQ ID NOs: 403-404 and 425-426, respectively.

The ActRIIB-Fc polypeptide sequence (SEQ ID NO: 403) employs the TPA leader and is shown below:

```
                                     (SEQ ID NO: 403)
1    MDAMKRGLCC VLLLCGAVFV SPGASGRGEA ETRECIYYNA NWELERTNQS

51   GLERCEGEQD KRLHCYASWR NSSGTIELVK KGCWLDDFNC YDRQECVATE

101  ENPQVYFCCC EGNFCNERFT HLPEAGGPEV TYEPPPTAPT GGGTHTCPPC

151  PAPELLGGPS VFLFPPKPKD TLMISRTPEV TCVVVDVSHE DPEVKFNWYV

201  DGVEVHNAKT KPREEQYNST YRVVSVLTVL HQDWLNGKEY KCKVSNKALP

251  APIEKTISKA KGQPREPQVY TLPPCREEMT KNQVSLWCLV KGFYPSDIAV

301  EWESNGQPEN NYKTTPPVLD SDGSFFLYSK LTVDKSRWQQ GNVFSCSVMH

351  EALHNHYTQK SLSLSPGK
```

-

The leader sequence and linker are underlined. To promote formation of the ActRIIB-Fc:Fc heterodimer rather than either of the possible homodimeric complexes, two amino acid substitutions (replacing a serine with a cysteine and a threonine with a tryptophan) can be introduced into the Fc domain of the fusion protein as indicated by double underline above. The amino acid sequence of SEQ ID NO: 403 may optionally be provided with the C-terminal lysine removed.

The mature ActRIIB-Fc fusion polypeptide is as follows:

```
                                     (SEQ ID NO: 404)
1    GRGEAETREC IYYNANWELE RTNQSGLERC EGEQDKRLHC YASWRNSSGT

51   IELVKKGCWL DDFNCYDRQE CVATEENPQV YFCCCEGNFC NERFTHLPEA

101  GGPEVTYEPP PTAPTGGGTH TCPPCPAPEL LGGPSVFLFP PKPKDTLMIS

151  RTPEVTCVVV DVSHEDPEVK FNWYVDGVEV HNAKTKPREE QYNSTYRVVS

201  VLTVLHQDWL NGKEYKCKVS NKALPAPIEK TISKAKGQPR EPQVYTLPPC

251  REEMTKNQVS LWCLVKGFYP SDIAVEWESN GQPENNYKTT PPVLDSDGSF

301  FLYSKLTVDK SRWQQGNVFS CSVMHEALHN HYTQKSLSLS PGK
```

The complementary form of monomeric Fc polypeptide (SEQ ID NO: 425) uses the TPA leader and is as follows.

```
                                        (SEQ ID NO: 425)
1     MDAMKRGLCC VLLLCGAVFV SPGASNTKVD KRVTGGGTHT CPPCPAPELL

51    GGPSVFLFPP KPKDTLMISR TPEVTCVVVD VSHEDPEVKF NWYVDGVEVH

101   NAKTKPREEQ YNSTYRVVSV LTVLHQDWLN GKEYKCKVSN KALPAPIEKT

151   ISKAKGQPRE PQVCTLPPSR EEMTKNQVSL SCAVKGFYPS DIAVEWESNG

201   QPENNYKTTP PVLDSDGSFF LVSKLTVDKS RWQQGNVFSC SVMHEALHNH

251   YTQKSLSLSP GK
```

The leader sequence is underlined, and an optional N-terminal extension of the Fc polypeptide is indicated by double underline. To promote formation of the ActRIIB-Fc:Fc heterodimer rather than either of the possible homodimeric complexes, four amino acid substitutions can be introduced into the monomeric Fc polypeptide as indicated by double underline above. The amino acid sequence of SEQ ID NO: 425 may optionally be provided with the C-terminal lysine removed.

The mature monomeric Fc polypeptide sequence (SEQ ID NO: 426) is as follows and may optionally be provided with the C-terminal lysine removed.

```
                                        (SEQ ID NO: 426)
1     SNTKVDKRVT GGGTHTCPPC PAPELLGGPS VFLFPPKPKD TLMISRTPEV

51    TCVVVDVSHE DPEVKFNWYV DGVEVHNAKT KPREEQYNST YRVVSVLTVL

101   HQDWLNGKEY KCKVSNKALP APIEKTISKA KGQPREPQVC TLPPSREEMT

151   KNQVSLSCAV KGFYPSDIAV EWESNGQPEN NYKTTPPVLD SDGSFFLVSK

201   LTVDKSRWQQ GNVFSCSVMH EALHNHYTQK SLSLSPGK
```

The ActRIIB-Fc fusion polypeptide and monomeric Fc polypeptide of SEQ ID NO: 404 and SEQ ID NO: 426, respectively, may be co-expressed and purified from a CHO cell line to give rise to a single-arm heteromeric protein complex comprising ActRIIB-Fc:Fc.

Purification of various ActRIIB-Fc:Fc complexes could be achieved by a series of column chromatography steps, including, for example, three or more of the following, in any order: protein A chromatography, Q sepharose chromatography, phenylsepharose chromatography, size exclusion chromatography, and cation exchange chromatography. The purification could be completed with viral filtration and buffer exchange.

A Biacore™-based binding assay was used to compare ligand binding selectivity of the single-arm ActRIIB-Fc heterodimeric complex described above with that of ActRIIB-Fc homodimeric complex. Single-arm ActRIIB-Fc and homodimeric ActRIIB-Fc were independently captured onto the system using an anti-Fc antibody. Ligands were injected and allowed to flow over the captured receptor protein. Results are summarized in the table below, in which ligand off-rates ($k_d$) typically associated with the most effective ligand traps are denoted by bold text.

Ligand binding by single-arm ActRIIB-Fc compared to ActRIIB-Fc homodimer

| | ActRIIB-Fc homodimer | | | Single-arm ActRIIB-Fc | | |
|---|---|---|---|---|---|---|
| Ligand | $k_a$ (1/Ms) | $k_d$ (1/s) | $K_D$ (pM) | $k_a$ (1/Ms) | $k_d$ (1/s) | $K_D$ (pM) |
| Activin A | $1.2 \times 10^7$ | $2.3 \times 10^{-4}$ | 19 | $3.0 \times 10^7$ | $3.0 \times 10^{-3}$ | 99 |
| Activin B | $5.1 \times 10^6$ | $1.0 \times 10^{-4}$ | 20 | $3.5 \times 10^6$ | $4.2 \times 10^{-4}$ | 120 |
| BMP6 | $3.2 \times 10^7$ | $6.8 \times 10^{-3}$ | 210 | $4.2 \times 10^7$ | $2.9 \times 10^{-2}$ | 690 |
| BMP9 | $1.4 \times 10^7$ | $1.1 \times 10^{-3}$ | 78 | No binding | | |
| BMP10 | $2.3 \times 10^7$ | $2.6 \times 10^{-4}$ | 11 | $8.0 \times 10^7$ | $9.7 \times 10^{-3}$ | 120 |
| GDF3 | $1.4 \times 10^6$ | $2.2 \times 10^{-3}$ | 1500 | $1.1 \times 10^6$ | $1.3 \times 10^{-2}$ | 12000 |
| GDF8 | $8.3 \times 10^5$ | $2.3 \times 10^{-4}$ | 280 | $3.5 \times 10^6$ | $1.0 \times 10^{-3}$ | 290 |
| GDF11 | $5.0 \times 10^7$ | $1.1 \times 10^{-4}$ | 2 | $3.6 \times 10^7$ | $7.2 \times 10^{-4}$ | 20 |

Figure 6:
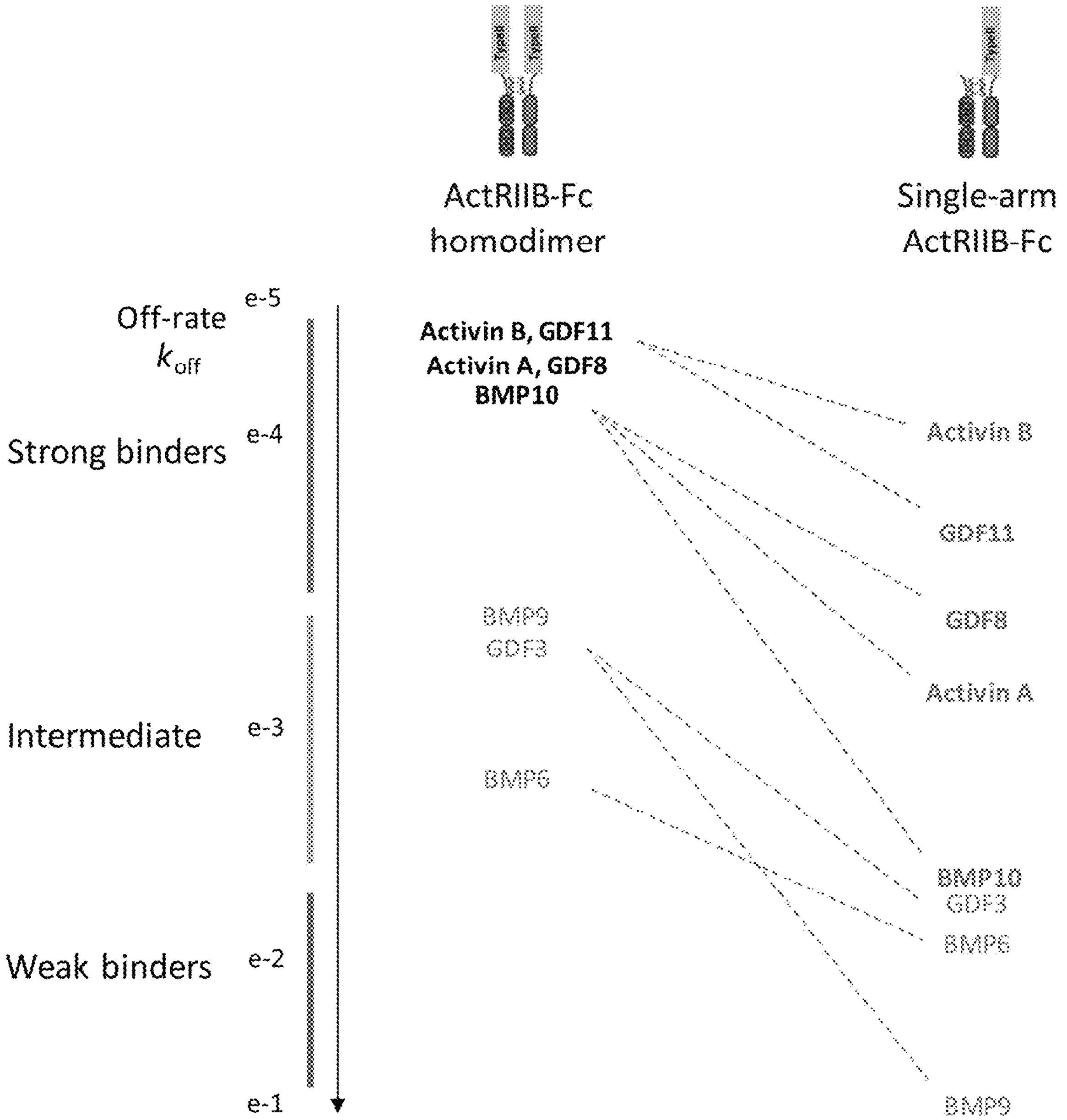
FIG. 6 shows ligand binding data for a single-arm ActRIIB-Fc:Fc heterodimeric protein complex compared to ActRIIB-Fc homodimer. For each protein complex, ligands are ranked by off-rate ($k_{off}$ or $k_d$), a kinetic constant that correlates well with ligand signaling inhibition, and listed in descending order of binding affinity (ligands bound most tightly are listed at the top). At left, yellow, red, green, and blue lines indicate magnitude of the off-rate constant. Ligands of particular interest are highlighted in bold while others are represented in gray, and solid black lines indicate ligands whose binding to heterodimer is enhanced or unchanged compared with homodimer, whereas dashed lines indicate substantially reduced binding compared with homodimer. As shown, ActRIIB-Fc homodimer binds to each of five high affinity ligands with similarly high affinity, whereas single-arm ActRIIB-Fc discriminates more readily among these ligands. Thus, single-arm ActRIIB-Fc binds strongly to activin B and GDF11 and with intermediate strength to GDF8 and activin A. In further contrast to ActRIIB-Fc homodimer, single-arm ActRIIB-Fc displays only weak binding to BMP10 and no binding to BMP9. These data indicate that single-arm ActRIIB-Fc has greater ligand selectivity than homodimeric ActRIIB-Fc.

These comparative binding data demonstrate that single-arm ActRIIB-Fc has greater ligand selectivity than homodimeric ActRIIB-Fc. Whereas ActRIIB-Fc homodimer binds strongly to five important ligands (see cluster of activin A, activin B, BMP10, GDF8, and GDF11 in FIG. 6), single-arm ActRIIB-Fc discriminates more readily among these ligands. Thus, single-arm ActRIIB-Fc binds strongly to activin B and GDF11 and with intermediate strength to GDF8 and activin A. In further contrast to ActRIIB-Fc homodimer, single-arm ActRIIB-Fc displays only weak binding to BMP10 and no binding to BMP9. See FIG. 6.

These results indicate that single-arm ActRIIB-Fc is a more selective antagonist than ActRIIB-Fc homodimer. Accordingly, single-arm ActRIIB-Fc will be more useful than ActRIIB-Fc homodimer in certain applications where such selective antagonism is advantageous. Examples include therapeutic applications where it is desirable to retain antagonism of one or more of activin A, activin B, GDF8, and GDF11 but minimize antagonism of one or more of BMP9, BMP10, BMP6, and GDF3. Selective inhibition of ligands in the former group would be particularly advantageous therapeutically because they constitute a subfamily which tends to differ functionally from the latter group and its associated set of clinical conditions.

Example 2. Generation and Characterization of a Single-Arm ALK3-Fc Heterodimer Applicants constructed a soluble single-arm ALK3-Fc heterodimeric complex comprising a monomeric Fc polypeptide with a short N-terminal extension and a second polypeptide in which the extracellular domain of human ALK3 was fused to a separate Fc domain with a linker positioned between the extracellular domain and this second Fc domain. The individual constructs are referred to as monomeric Fc polypeptide and ALK3-Fc fusion polypeptide, respectively, and the sequences for each are provided below.

Formation of a single-arm ALK3-Fc heterodimer may be guided by approaches similar to those described for single-arm ActRIIB-Fc heterodimer in Example 1. In a first approach, illustrated in the ALK3-Fc and monomeric Fc polypeptide sequences of SEQ ID NOs: 122-124 and 140-142, respectively, one Fc domain is altered to introduce cationic amino acids at the interaction face, while the other Fc domain is altered to introduce anionic amino acids at the interaction face.

The ALK3-Fc fusion polypeptide employs the TPA leader and is as follows:

```
                                                       (SEQ ID NO: 122)
  1  MDAMKRGLCC VLLLCGAVFV SPGAQNLDSM LHGTGMKSDS DQKKSENGVT

 51  LAPEDTLPFL KCYCSGHCPD DAINNTCITN GHCFAIIEED DQGETTLASG

101  CMKYEGSDFQ CKDSPKAQLR RTIECCRTNL CNQYLQPTLP PVVIGPFFDG

151  SIRTGGGTHT CPPCPAPELL GGPSVFLFPP KPKDTLMISR TPEVTCVVVD

201  VSHEDPEVKF NWYVDGVEVH NAKTKPREEQ YNSTYRVVSV LTVLHQDWLN

251  GKEYKCKVSN KALPAPIEKT ISKAKGQPRE PQVYTLPPSR EEMTKNQVSL

301  TCLVKGFYPS DIAVEWESNG QPENNYDTTP PVLDSDGSFF LYSDLTVDKS

351  RWQQGNVFSC SVMHEALHNH YTQKSLSLSP G
```

-

The leader and linker sequences are underlined. To promote formation of the ALK3-Fc:Fc heterodimer rather than either of the possible homodimeric complexes (ALK3-Fc: ALK3-Fc or Fc:Fc, two amino acid substitutions (replacing lysines with anionic amino acids) can be introduced into the Fc domain of the fusion protein as indicated by double underline above. The amino acid sequence of SEQ ID NO: 122 may optionally be provided with a lysine added at the C-terminus.

This ALK3-Fc fusion polypeptide is encoded by the following nucleic acid (SEQ ID NO: 123).

```
                                                       (SEQ ID NO: 123)
  1  ATGGATGCAA TGAAGAGAGG GCTCTGCTGT GTGCTGCTGC TGTGTGGAGC

 51  AGTCTTCGTT TCGCCCGGCG CCCAGAATCT GGATAGTATG CTTCATGGCA

101  CTGGGATGAA ATCAGACTCC GACCAGAAAA AGTCAGAAAA TGGAGTAACC

151  TTAGCACCAG AGGATACCTT GCCTTTTTTA AAGTGCTATT GCTCAGGGCA

201  CTGTCCAGAT GATGCTATTA ATAACACATG CATAACTAAT GGACATTGCT

251  TTGCCATCAT AGAAGAAGAT GACCAGGGAG AAACCACATT AGCTTCAGGG

301  TGTATGAAAT ATGAAGGATC TGATTTTCAG TGCAAAGATT CTCCAAAAGC

351  CCAGCTACGC CGGACAATAG AATGTTGTCG GACCAATTTA TGTAACCAGT

401  ATTTGCAACC CACACTGCCC CCTGTTGTCA TAGGTCCGTT TTTTGATGGC

451  AGCATTCGAA CCGGTGGTGG AACTCACACA TGCCCACCGT GCCCAGCACC

501  TGAACTCCTG GGGGGACCGT CAGTCTTCCT CTTCCCCCCA AAACCCAAGG

551  ACACCCTCAT GATCTCCCGG ACCCCTGAGG TCACATGCGT GGTGGTGGAC

601  GTGAGCCACG AAGACCCTGA GGTCAAGTTC AACTGGTACG TGGACGGCGT
```

-continued

```
651   GGAGGTGCAT AATGCCAAGA CAAAGCCGCG GGAGGAGCAG TACAACAGCA

701   CGTACCGTGT GGTCAGCGTC CTCACCGTCC TGCACCAGGA CTGGCTGAAT

751   GGCAAGGAGT ACAAGTGCAA GGTCTCCAAC AAAGCCCTCC CAGCCCCCAT

801   CGAGAAAACC ATCTCCAAAG CCAAAGGGCA GCCCCGAGAA CCACAGGTGT

851   ACACCCTGCC CCCATCCCGG GAGGAGATGA CCAAGAACCA GGTCAGCCTG

901   ACCTGCCTGG TCAAAGGCTT CTATCCCAGC GACATCGCCG TGGAGTGGGA

951   GAGCAATGGG CAGCCGGAGA ACAACTACGA CACCACGCCT CCCGTGCTGG

1001  ACTCCGACGG CTCCTTCTTC CTCTATAGCG ACCTCACCGT GGACAAGAGC

1051  AGGTGGCAGC AGGGGAACGT CTTCTCATGC TCCGTGATGC ATGAGGCTCT

1101  GCACAACCAC TACACGCAGA AGAGCCTCTC CCTGTCTCCG GGT
```

The mature ALK3-Fc fusion polypeptide sequence is as follows (SEQ ID NO: 124) and may optionally be provided with a lysine added at the C-terminus.

```
                                              (SEQ ID NO: 124)
1     GAQNLDSMLH GTGMKSDSDQ KKSENGVTLA PEDTLPFLKC YCSGHCPDDA

51    INNTCITNGH CFAIIEEDDQ GETTLASGCM KYEGSDFQCK DSPKAQLRRT

101   IECCRTNLCN QYLQPTLPPV VIGPFFDGSI RTGGGTHTCP PCPAPELLGG

151   PSVFLFPPKP KDTLMISRTP EVTCVVVDVS HEDPEVKFNW YVDGVEVHNA

201   KTKPREEQYN STYRVVSVLT VLHQDWLNGK EYKCKVSNKA LPAPIEKTIS

251   KAKGQPREPQ VYTLPPSREE MTKNQVSLTC LVKGFYPSDI AVEWESNGQP

301   ENNYDTTPPV LDSDGSFFLY SDLTVDKSRW QQGNVFSCSV MHEALHNHYT

351   QKSLSLSPG
```

The complementary human G1Fc polypeptide (SEQ ID NO: 140) employs the TPA leader and is as follows:

```
                                              (SEQ ID NO: 140)
1     MDAMKRGLCC VLLLCGAVFV SPGASNTKVD KRVTGGGTHT CPPCPAPELL

51    GGPSVFLFPP KPKDTLMISR TPEVTCVVVD VSHEDPEVKF NWYVDGVEVH

101   NAKTKPREEQ YNSTYRVVSV LTVLHQDWLN GKEYKCKVSN KALPAPIEKT

151   ISKAKGQPRE PQVYTLPPSR KEMTKNQVSL TCLVKGFYPS DIAVEWESNG

201   QPENNYKTTP PVLKSDGSFF LYSKLTVDKS RWQQGNVFSC SVMHEALHNH

251   YTQKSLSLSP GK
```

The leader sequence is underlined, and an optional N-terminal extension of the Fc polypeptide is indicated by double underline. To promote formation of the ALK3-Fc:Fc heterodimer rather than either of the possible homodimeric complexes, two amino acid substitutions (replacing anionic residues with lysines) can be introduced into the monomeric Fc polypeptide as indicated by double underline above. The amino acid sequence of SEQ ID NO: 140 may optionally be provided with the C-terminal lysine removed.

This complementary Fc polypeptide is encoded by the following nucleic acid (SEQ ID NO: 141).

```
                                              (SEQ ID NO: 141)
1     ATGGATGCAA TGAAGAGAGG GCTCTGCTGT GTGCTGCTGC TGTGTGGAGC

51    AGTCTTCGTT TCGCCCGGCG CCAGCAACAC CAAGGTGGAC AAGAGAGTTA

101   CCGGTGGTGG AACTCACACA TGCCCACCGT GCCCAGCACC TGAACTCCTG

151   GGGGGACCGT CAGTCTTCCT CTTCCCCCCA AAACCCAAGG ACACCCTCAT

201   GATCTCCCGG ACCCCTGAGG TCACATGCGT GGTGGTGGAC GTGAGCCACG
```

-continued

```
251    AAGACCCTGA GGTCAAGTTC AACTGGTACG TGGACGGCGT GGAGGTGCAT
301    AATGCCAAGA CAAAGCCGCG GGAGGAGCAG TACAACAGCA CGTACCGTGT
351    GGTCAGCGTC CTCACCGTCC TGCACCAGGA CTGGCTGAAT GGCAAGGAGT
401    ACAAGTGCAA GGTCTCCAAC AAAGCCCTCC CAGCCCCCAT CGAGAAAACC
451    ATCTCCAAAG CCAAAGGGCA GCCCCGAGAA CCACAGGTGT ACACCCTGCC
501    CCCATCCCGG AAGGAGATGA CCAAGAACCA GGTCAGCCTG ACCTGCCTGG
551    TCAAAGGCTT CTATCCCAGC GACATCGCCG TGGAGTGGGA GAGCAATGGG
601    CAGCCGGAGA ACAACTACAA GACCACGCCT CCCGTGCTGA AGTCCGACGG
651    CTCCTTCTTC CTCTATAGCA AGCTCACCGT GGACAAGAGC AGGTGGCAGC
701    AGGGGAACGT CTTCTCATGC TCCGTGATGC ATGAGGCTCT GCACAACCAC
751    TACACGCAGA AGAGCCTCTC CCTGTCTCCG GGTAAA
```

The sequence of the mature monomeric Fc polypeptide is as follows (SEQ ID NO: 142) and may optionally be provided with the C-terminal lysine removed.

```
                                       (SEQ ID NO: 142)
  1    SNTKVDKRVT GGGTHTCPPC PAPELLGGPS VFLFPPKPKD TLMISRTPEV
 51    TCVVVDVSHE DPEVKFNWYV DGVEVHNAKT KPREEQYNST YRVVSVLTVL
101    HQDWLNGKEY KCKVSNKALP APIEKTISKA KGQPREPQVY TLPPSRKEMT
151    KNQVSLTCLV KGFYPSDIAV EWESNGQPEN NYKTTPPVLK SDGSFFLYSK
201    LTVDKSRWQQ GNVFSCSVMH EALHNHYTQK SLSLSPGK
```

The ALK3-Fc fusion polypeptide and monomeric Fc polypeptide of SEQ ID NO: 124 and SEQ ID NO: 142, respectively, may be co-expressed and purified from a CHO cell line to give rise to a single-arm heteromeric protein complex comprising ALK3-Fc:Fc.

In another approach to promoting the formation of heteromultimer complexes using asymmetric Fc fusion polypeptides, the Fc domains are altered to introduce complementary hydrophobic interactions and an additional intermolecular disulfide bond as illustrated in the ALK3-Fc and Fc polypeptide sequences of SEQ ID NOs: 415-416 and 427-428, respectively.

The ALK3-Fc fusion polypeptide (SEQ ID NO: 415) uses the TPA leader and is as follows:

The leader sequence and linker are underlined. To promote formation of the ALK3-Fc:Fc heterodimer rather than either of the possible homodimeric complexes, four amino acid substitutions can be introduced into the Fc domain of the ALK3 fusion polypeptide as indicated by double underline above. The amino acid sequence of SEQ ID NO: 415 may optionally be provided with the C-terminal lysine removed.

The mature ALK3-Fc fusion polypeptide (SEQ ID NO: 416) is as follows and may optionally be provided with the C-terminal lysine removed.

```
                                          (SEQ ID NO: 415)
  1    MDAMKRGLCC VLLLCGAVFV SPGAQNLDSM LHGTGMKSDS DQKKSENGVT
 51    LAPEDTLPFL KCYCSGHCPD DAINNTCITN GHCFAIIEED DQGETTLASG
101    CMKYEGSDFQ CKDSPKAQLR RTIECCRTNL CNQYLQPTLP PVVIGPFFDG
151    SIRTGGGTHT CPPCPAPELL GGPSVFLFPP KPKDTLMISR TPEVTCVVVD
201    VSHEDPEVKF NWYVDGVEVH NAKTKPREEQ YNSTYRVVSV LTVLHQDWLN
251    GKEYKCKVSN KALPAPIEKT ISKAKGQPRE PQVCTLPPSR EEMTKNQVSL
301    SCAVKGFYPS DIAVEWESNG QPENNYKTTP PVLDSDGSFF LVSKLTVDKS
351    RWQQGNVFSC SVMHEALHNH YTQKSLSLSP GK
```

(SEQ ID NO: 416)

```
1    GAQNLDSMLH GTGMKSDSDQ KKSENGVTLA PEDTLPFLKC YCSGHCPDDA
51   INNTCITNGH CFAIIEEDDQ GETTLASGCM KYEGSDFQCK DSPKAQLRRT
101  IECCRTNLCN QYLQPTLPPV VIGPFFDGSI RTGGGTHTCP PCPAPELLGG
151  PSVFLFPPKP KDTLMISRTP EVTCVVVDVS HEDPEVKFNW YVDGVEVHNA
201  KTKPREEQYN STYRVVSVLT VLHQDWLNGK EYKCKVSNKA LPAPIEKTIS
251  KAKGQPREPQ VCTLPPSREE MTKNQVSLSC AVKGFYPSDI AVEWESNGQP
301  ENNYKTTPPV LDSDGSFFLV SKLTVDKSRW QQGNVFSCSV MHEALHNHYT
351  QKSLSLSPGK
```

The complementary form of monomeric G1Fc polypeptide (SEQ ID NO: 427) employs the TPA leader and is as follows:

(SEQ ID NO: 427)

```
1    MDAMKRGLCC VLLLCGAVFV SPGASNTKVD KRVTGGGTHT CPPCPAPELL
51   GGPSVFLFPP KPKDTLMISR TPEVTCVVVD VSHEDPEVKF NWYVDGVEVH
101  NAKTKPREEQ YNSTYRVVSV LTVLHQDWLN GKEYKCKVSN KALPAPIEKT
151  ISKAKGQPRE PQVYTLPPCR EEMTKNQVSL WCLVKGFYPS DIAVEWESNG
201  QPENNYKTTP PVLDSDGSFF LYSKLTVDKS RWQQGNVFSC SVMHEALHNH
251  YTQKSLSLSP GK
```

The leader sequence is underlined, and an optional N-terminal extension of the Fc polypeptide is indicated by double underline. To promote formation of the ALK3-Fc:Fc heterodimer rather than either of the possible homodimeric complexes, two amino acid substitutions (replacing a serine with a cysteine and a threonine with a tryptophan) can be introduced into the monomeric Fc polypeptide as indicated by double underline above. The amino acid sequence of SEQ ID NO: 427 may optionally be provided with the C-terminal lysine removed.

The sequence of the mature monomeric Fc polypeptide is as follows (SEQ ID NO: 428) and may optionally be provided with the C-terminal lysine removed.

(SEQ ID NO: 428)

```
1    SNTKVDKRVT GGGTHTCPPC PAPELLGGPS VFLFPPKPKD TLMISRTPEV
51   TCVVVDVSHE DPEVKFNWYV DGVEVHNAKT KPREEQYNST YRVVSVLTVL
101  HQDWLNGKEY KCKVSNKALP APIEKTISKA KGQPREPQVY TLPPCREEMT
151  KNQVSLWCLV KGFYPSDIAV EWESNGQPEN NYKTTPPVLD SDGSFFLYSK
201  LTVDKSRWQQ GNVFSCSVMH EALHNHYTQK SLSLSPGK
```

The ALK3-Fc fusion polypeptide and monomeric Fc polypeptide of SEQ ID NO: 416 and SEQ ID NO: 428, respectively, may be co-expressed and purified from a CHO cell line to give rise to a single-arm heteromeric complex comprising ALK3-Fc:Fc.

Purification of various ALK3-Fc:Fc complexes could be achieved by a series of column chromatography steps, including, for example, three or more of the following, in any order: protein A chromatography, Q sepharose chromatography, phenylsepharose chromatography, size exclusion chromatography, and cation exchange chromatography. The purification could be completed with viral filtration and buffer exchange.

A Biacore™-based binding assay was used to compare ligand binding selectivity of the single-arm ALK3-Fc heterodimeric complex described above with that of an ALK3-Fc homodimeric complex. The single-arm ALK3-Fc and homodimeric ALK3-Fc were independently captured onto the system using an anti-Fc antibody. Ligands were injected and allowed to flow over the captured receptor protein. Results are summarized in the table below, in which ligand off-rates ($k_d$) typically associated with the most effective ligand traps are denoted by bold text.

| Ligand binding of single-arm ALK3-Fc compared to ALK3-Fc homodimer | | | | | | |
|---|---|---|---|---|---|---|
| | ALK3-Fc homodimer | | | Single-arm ALK3-Fc | | |
| Ligand | $k_a$ (1/Ms) | $k_d$ (1/s) | $K_D$ (pM) | $k_a$ (1/Ms) | $k_d$ (1/s) | $K_D$ (pM) |
| Activin A | | No binding | | | No binding | |
| Activin B | | No binding | | | No binding | |
| Activin AB | | No binding | | | No binding | |
| Activin AC | | No binding | | | No binding | |
| BMP2 | $6.8 \times 10^5$ | $8.9 \times 10^{-5}$ | 130 | $7.9 \times 10^5$ | $2.5 \times 10^{-4}$ | 310 |
| BMP4 | $3.0 \times 10^5$ | $5.3 \times 10^{-5}$ | 178 | $4.9 \times 10^5$ | $4.6 \times 10^{-5}$ | 93 |
| BMP5 | $2.9 \times 10^4$ | $2.0 \times 10^{-3}$ | 70000 | $1.2 \times 10^5$ | $5.3 \times 10^{-3}$ | 45000 |
| BMP6 | $1.4 \times 10^5$ | $4.9 \times 10^{-3}$ | 35000 | | No binding | |
| BMP7 | $1.2 \times 10^6$ | $1.8 \times 10^{-2}$ | 15000 | | No binding | |
| BMP10 | | No binding | | | No binding | |
| GDF5 | $4.8 \times 10^5$ | $1.1 \times 10^{-2}$ | 22000 | | No binding | |
| GDF6 | $3.4 \times 10^4$ | $1.3 \times 10^{-3}$ | 40000 | | No binding | |
| GDF7 | $2.2 \times 10^5$ | $2.7 \times 10^{-3}$ | 12000 | $4.6 \times 10^5$ | $1.0 \times 10^{-2}$ | 22000 |
| GDF8 | | No binding | | | No binding | |
| GDF11 | | No binding | | | No binding | |

Figure 7:
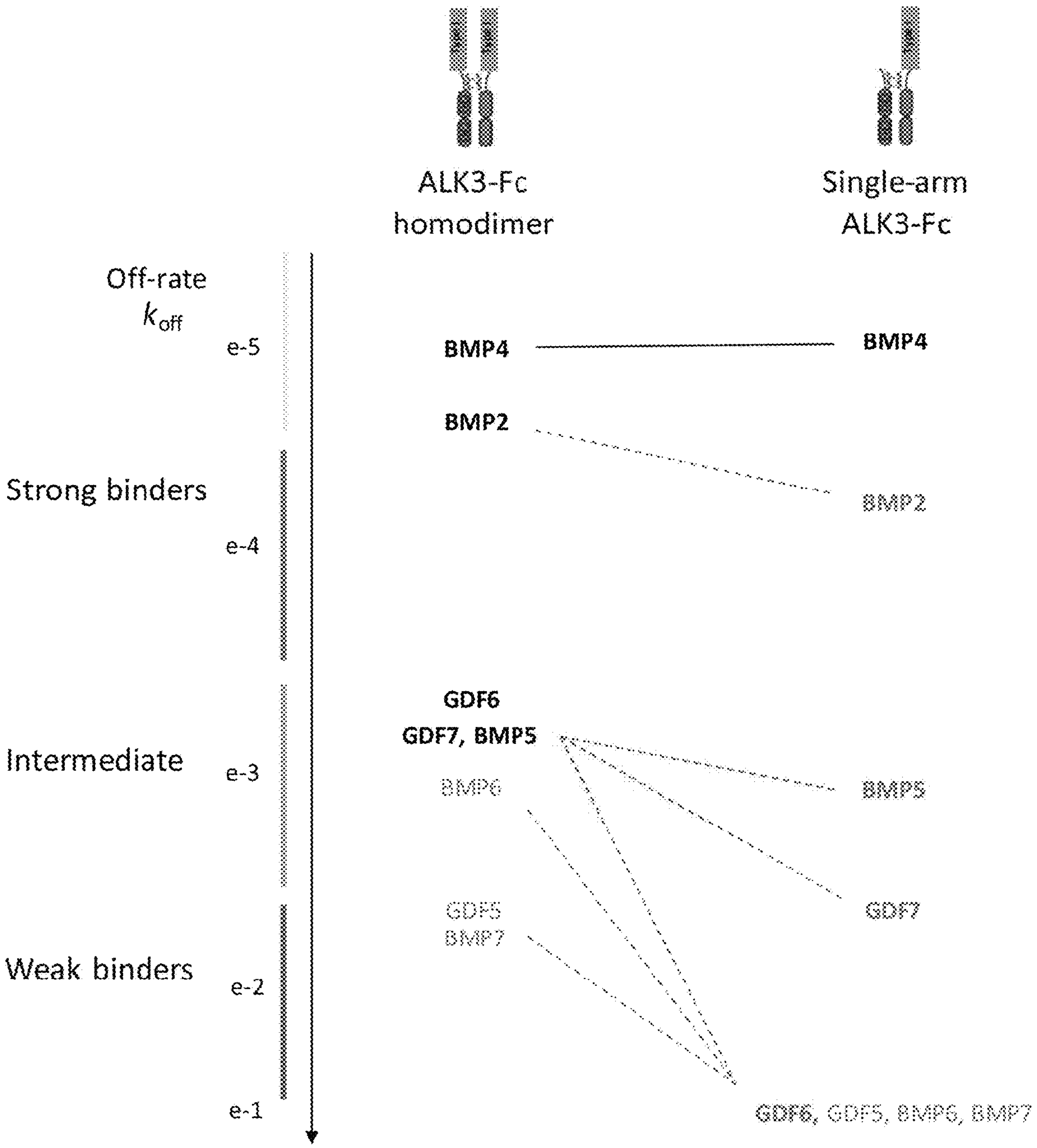
FIG. 7 shows ligand binding data for a single-arm ALK3-Fc:Fc heterodimeric protein complex compared to ALK3-Fc homodimer. Format is the same as for FIG. 6. As shown, single-arm ALK3-Fc heterodimer retains the exceptionally tight binding to BMP4 observed with ALK3-Fc homodimer, whereas it exhibits reduced strength of binding to BMP2 and therefore discriminates better between BMP4 and BMP2 than does ALK3-Fc homodimer. Single-arm ALK3-Fc also discriminates better among BMP5 (intermediate binding), GDF7 (weak binding), and GDF6 (no binding) compared to ALK3-Fc homodimer, which binds these three ligands with very similar strength (all intermediate). These data indicate that single-arm ALK3-Fc has greater ligand selectivity than homodimeric ALK3-Fc.

These comparative data indicate that single-arm ALK3-Fc has greater ligand selectivity than homodimeric ALK3-Fc. Whereas single-arm ALK3-Fc heterodimer retains the exceptionally tight binding to BMP4 observed with ALK3-Fc homodimer, it exhibits reduced strength of binding to BMP2 and therefore discriminates better between BMP4 and BMP2 (still a strong binder) than does ALK3-Fc homodimer. Single-arm ALK3-Fc also discriminates better among BMP5 (intermediate binding), GDF7 (weak binding), and GDF6 (no binding) compared to ALK3-Fc homodimer, which binds these three ligands with very similar strength (all intermediate). See FIG. 7. Unlike constructs disclosed in Example 1, neither single-arm ALK3-Fc nor homodimeric ALK3-Fc binds activins, GDF8, GDF11, or BMP10.

These results therefore indicate that single-arm ALK3-Fc is a more selective antagonist of BMP4 than is ALK3-Fc homodimer. Single-arm ALK3-Fc can be expected to antagonize BMP4 in a more targeted manner—with reduced effects from concurrent antagonism of BMP2 or BMP5 and especially GDF6 or GDF7—compared to ALK3-Fc homodimer. Accordingly, single-arm ALK3-Fc will be more useful than ALK3-Fc homodimer in certain applications where such selective antagonism is advantageous. Examples include therapeutic applications where it is desirable to retain antagonism of one or more of BMP4, BMP2, and potentially BMP5 but minimize antagonism of one or more of BMP6, GDF6, and GDF7.

Example 3. Generation and Characterization of a Single-Arm ActRIIA-Fc Heterodimer Applicants constructed a soluble single-arm ActRIIA-Fc heterodimeric complex comprising a monomeric Fc polypeptide with a short N-terminal extension and a second polypeptide in which the extracellular domain of human ActRIIA was fused to a separate Fc domain with a linker positioned between the extracellular domain and this second Fc domain. The individual constructs are referred to as monomeric Fc polypeptide and ActRIIA-Fc fusion polypeptide, respectively, and the sequences for each are provided below.

Formation of a single-arm ActRIIA-Fc heterodimer may be guided by approaches similar to those described for single-arm ActRIIB-Fc heterodimer in Example 1. In a first approach, illustrated in the ActRIIA-Fc and monomeric Fc polypeptide sequences of SEQ ID NOs: 101-103 and 137-139, respectively, one Fc domain is altered to introduce cationic amino acids at the interaction face, while the other Fc domain is altered to introduce anionic amino acids at the interaction face.

The ActRIIA-Fc fusion polypeptide employs the TPA leader and is as follows:

```
                                                     (SEQ ID NO: 101)
  1   MDAMKRGLCC VLLLCGAVFV SPGAAILGRS ETQECLFFNA NWEKDRTNQT

 51   GVEPCYGDKD KRRHCFATWK NISGSIEIVK QGCWLDDINC YDRTDCVEKK

101   DSPEVYFCCC EGNMCNEKFS YFPEMEVTQP TSNPVTPKPP TGGGTHTCPP

151   CPAPELLGGP SVFLFPPKPK DTLMISRTPE VTCVVVDVSH EDPEVKFNWY

201   VDGVEVHNAK TKPREEQYNS TYRVVSVLTV LHQDWLNGKE YKCKVSNKAL

251   PAPIEKTISK AKGQPREPQV YTLPPSRKEM TKNQVSLTCL VKGFYPSDIA

301   VEWESNGQPE NNYKTTPPVL KSDGSFFLYS KLTVDKSRWQ QGNVFSCSVM

351   HEALHNHYTQ KSLSLSPGK
```

The leader and linker sequences are underlined. To promote formation of the ActRIIA-Fc:Fc heterodimer rather than either of the possible homodimeric complexes (ActRIIA-Fc:ActRIIA-Fc or Fc-Fc), two amino acid substitutions (replacing anionic residues with lysines) can be introduced into the Fc domain of the fusion polypeptide as indicated by double underline above. The amino acid sequence of SEQ ID NO: 101 may optionally be provided with the C-terminal lysine removed.

This ActRIIA-Fc fusion polypeptide is encoded by the following nucleic acid (SEQ ID NO: 102).

```
                                                     (SEQ ID NO: 102)
   1  ATGGATGCAA TGAAGAGAGG GCTCTGCTGT GTGCTGCTGC TGTGTGGAGC
  51  AGTCTTCGTT TCGCCCGGCG CCGCTATACT TGGTAGATCA GAAACTCAGG
 101  AGTGTCTTTT CTTTAATGCT AATTGGGAAA AAGACAGAAC CAATCAAACT
 151  GGTGTTGAAC CGTGTTATGG TGACAAAGAT AAACGGCGGC ATTGTTTTGC
 201  TACCTGGAAG AATATTTCTG GTTCCATTGA AATAGTGAAA CAAGGTTGTT
 251  GGCTGGATGA TATCAACTGC TATGACAGGA CTGATTGTGT AGAAAAAAAA
 301  GACAGCCCTG AAGTATATTT CTGTTGCTGT GAGGGCAATA TGTGTAATGA
 351  AAAGTTTTCT TATTTTCCGG AGATGGAAGT CACACAGCCC ACTTCAAATC
 401  CAGTTACACC TAAGCCACCC ACCGGTGGTG GAACTCACAC ATGCCCACCG
 451  TGCCCAGCAC CTGAACTCCT GGGGGGACCG TCAGTCTTCC TCTTCCCCCC
 501  AAAACCCAAG GACACCCTCA TGATCTCCCG GACCCCTGAG GTCACATGCG
 551  TGGTGGTGGA CGTGAGCCAC GAAGACCCTG AGGTCAAGTT CAACTGGTAC
 601  GTGGACGGCG TGGAGGTGCA TAATGCCAAG ACAAAGCCGC GGGAGGAGCA
 651  GTACAACAGC ACGTACCGTG TGGTCAGCGT CCTCACCGTC CTGCACCAGG
 701  ACTGGCTGAA TGGCAAGGAG TACAAGTGCA AGGTCTCCAA CAAAGCCCTC
 751  CCAGCCCCCA TCGAGAAAAC CATCTCCAAA GCCAAAGGGC AGCCCCGAGA
 801  ACCACAGGTG TACACCCTGC CCCCATCCCG GAAGGAGATG ACCAAGAACC
 851  AGGTCAGCCT GACCTGCCTG GTCAAAGGCT TCTATCCCAG CGACATCGCC
 901  GTGGAGTGGG AGAGCAATGG GCAGCCGGAG AACAACTACA AGACCACGCC
 951  TCCCGTGCTG AAGTCCGACG GCTCCTTCTT CCTCTATAGC AAGCTCACCG
1001  TGGACAAGAG CAGGTGGCAG CAGGGGAACG TCTTCTCATG CTCCGTGATG
1051  CATGAGGCTC TGCACAACCA CTACACGCAG AAGAGCCTCT CCCTGTCTCC
1101  GGGTAAA
```

The mature ActRIIA-Fc fusion polypeptide sequence is as follows (SEQ ID NO: 103) and may optionally be provided with the C-terminal lysine removed.

```
                                                     (SEQ ID NO: 103)
  1   ILGRSETQEC LFFNANWEKD RTNQTGVEPC YGDKDKRRHC FATWKNISGS
 51   IEIVKQGCWL DDINCYDRTD CVEKKDSPEV YFCCCEGNMC NEKFSYFPEM
101   EVTQPTSNPV TPKPPTGGGT HTCPPCPAPE LLGGPSVFLF PPKPKDTLMI
151   SRTPEVTCVV VDVSHEDPEV KFNWYVDGVE VHNAKTKPRE EQYNSTYRVV
201   SVLTVLHQDW LNGKEYKCKV SNKALPAPIE KTISKAKGQP REPQVYTLPP
251   SRKEMTKNQV SLTCLVKGFY PSDIAVEWES NGQPENNYKT TPPVLKSDGS
301   FFLYSKLTVD KSRWQQGNVF SCSVMHEALH NHYTQKSLSL SPGK
```

As described in Example 1, the complementary form of monomeric human G1Fc polypeptide (SEQ ID NO: 137) employs the TPA leader and incorporates an optional N-terminal extension. To promote formation of the ActRIIA-Fc:Fc heterodimer rather than either of the possible homodimeric complexes, two amino acid substitutions (replacing lysines with anionic residues) can be introduced into the monomeric Fc polypeptide. The amino acid sequence of SEQ ID NO: 137 may optionally be provided without the C-terminal lysine. This complementary Fc polypeptide is encoded by the nucleic acid of SEQ ID NO: 138, and the mature monomeric Fc polypeptide (SEQ ID NO: 139) may optionally be provided with the C-terminal lysine removed.

The ActRIIA-Fc fusion polypeptide and monomeric Fc polypeptide of SEQ ID NO: 103 and SEQ ID NO: 139, respectively, may be co-expressed and purified from a CHO cell line to give rise to a single-arm heteromeric protein complex comprising ActRIIA-Fc:Fc.

In another approach to promoting the formation of heteromultimer complexes using asymmetric Fc fusion polypeptides, the Fc domains are altered to introduce complementary hydrophobic interactions and an additional intermolecular disulfide bond as illustrated in the ActRIIA-Fc and Fc polypeptide sequences of SEQ ID NOs: 401-402 and 425-426, respectively.

The ActRIIA-Fc fusion polypeptide (SEQ ID NO: 401) uses the TPA leader and is as follows:

```
                                      (SEQ ID NO: 401)
  1  MDAMKRGLCC VLLLCGAVFV SPGAAILGRS ETQECLFFNA NWEKDRTNQT

 51  GVEPCYGDKD KRRHCFATWK NISGSIEIVK QGCWLDDINC YDRTDCVEKK

101  DSPEVYFCCC EGNMCNEKFS YFPEMEVTQP TSNPVTPKPP TGGGTHTCPP

151  CPAPELLGGP SVFLFPPKPK DTLMISRTPE VTCVVVDVSH EDPEVKFNWY

201  VDGVEVHNAK TKPREEQYNS TYRVVSVLTV LHQDWLNGKE YKCKVSNKAL

251  PAPIEKTISK AKGQPREPQV YTLPPCREEM TKNQVSLWCL VKGFYPSDIA

301  VEWESNGQPE NNYKTTPPVL DSDGSFFLYS KLTVDKSRWQ QGNVFSCSVM

351  HEALHNHYTQ KSLSLSPGK
```

The leader sequence and linker are underlined. To promote formation of the ActRIIA-Fc:Fc heterodimer rather than either of the possible homodimeric complexes, two amino acid substitutions (replacing a serine with a cysteine and a threonine with a tryptophan) can be introduced into the Fc domain of the ActRIIA fusion polypeptide as indicated by double underline above. The amino acid sequence of SEQ ID NO: 401 may optionally be provided with the C-terminal lysine removed.

The mature ActRIIA-Fc fusion polypeptide (SEQ ID NO: 402) is as follows and may optionally be provided with the C-terminal lysine removed.

```
                                      (SEQ ID NO: 402)
  1  ILGRSETQEC LFFNANWEKD RTNQTGVEPC YGDKDKRRHC FATWKNISGS

 51  IEIVKQGCWL DDINCYDRTD CVEKKDSPEV YFCCCEGNMC NEKFSYFPEM

101  EVTQPTSNPV TPKPPTGGGT HTCPPCPAPE LLGGPSVFLF PPKPKDTLMI

151  SRTPEVTCVV VDVSHEDPEV KFNWYVDGVE VHNAKTKPRE EQYNSTYRVV

201  SVLTVLHQDW LNGKEYKCKV SNKALPAPIE KTISKAKGQP REPQVYTLPP

251  CREEMTKNQV SLWCLVKGFY PSDIAVEWES NGQPENNYKT TPPVLDSDGS

301  FFLYSKLTVD KSRWQQGNVF SCSVMHEALH NHYTQKSLSL SPGK
```

As described in Example 1, the complementary form of monomeric human G1Fc polypeptide (SEQ ID NO: 425) employs the TPA leader and incorporates an optional N-terminal extension. To promote formation of the ActRIIA-Fc:Fc heterodimer rather than either of the possible homodimeric complexes, four amino acid substitutions can be introduced into the monomeric Fc polypeptide as indicated. The amino acid sequence of SEQ ID NO: 425 and the mature G1Fc polypeptide (SEQ ID NO: 426) may optionally be provided with the C-terminal lysine removed.

The ActRIIA-Fc fusion polypeptide and monomeric Fc polypeptide of SEQ ID NO: 402 and SEQ ID NO: 426, respectively, may be co-expressed and purified from a CHO cell line to give rise to a single-arm heteromeric protein complex comprising ActRIIA-Fc:Fc.

Purification of various ActRIIA-Fc:Fc complexes could be achieved by a series of column chromatography steps, including, for example, three or more of the following, in any order: protein A chromatography, Q sepharose chromatography, phenylsepharose chromatography, size exclusion chromatography, and cation exchange chromatography. The purification could be completed with viral filtration and buffer exchange.

A Biacore™-based binding assay was used to compare ligand binding selectivity of the single-arm ActRIIA-Fc heterodimeric complex described above with that of an ActRIIA-Fc homodimeric complex. The single-arm ActRIIA-Fc and homodimeric ActRIIA-Fc were independently captured onto the system using an anti-Fc antibody. Ligands were injected and allowed to flow over the captured receptor protein. Results are summarized in the table below, in which ligand off-rates ($k_d$) typically associated with the most effective ligand traps are denoted by bold text.

Ligand binding of single-arm ActRIIA-Fc compared to ActRIIA-Fc homodimer

| | ActRIIA-Fc homodimer | | | Single-arm ActRIIA-Fc | | |
|---|---|---|---|---|---|---|
| Ligand | $k_a$ (1/Ms) | $k_d$ (1/s) | $K_D$ (pM) | $k_a$ (1/Ms) | $k_d$ (1/s) | $K_D$ (pM) |
| Activin A | $1.4 \times 10^7$ | $6.2 \times 10^{-4}$ | 45 | $3.0 \times 10^7$ | $9.0 \times 10^{-4}$ | 30 |
| Activin B | $7.9 \times 10^6$ | $2.0 \times 10^{-4}$ | 25 | $2.9 \times 10^7$ | $1.4 \times 10^{-3}$ | 46 |
| BMP5 | $4.0 \times 10^6$ | $4.5 \times 10^{-3}$ | 1100 | $4.8 \times 10^7$ | $5.8 \times 10^{-2}$ | 1200 |
| BMP10 | $2.9 \times 10^7$ | $2.5 \times 10^{-3}$ | 86 | $2.3 \times 10^7$ | $5.9 \times 10^{-3}$ | 250 |
| GDF8 | $1.4 \times 10^7$ | $1.4 \times 10^{-3}$ | 99 | $4.7 \times 10^6$ | $5.0 \times 10^{-3}$ | 1100 |
| GDF11 | $2.6 \times 10^7$ | $7.2 \times 10^{-4}$ | 28 | $4.9 \times 10^7$ | $1.1 \times 10^{-2}$ | 220 |

Figure 8:
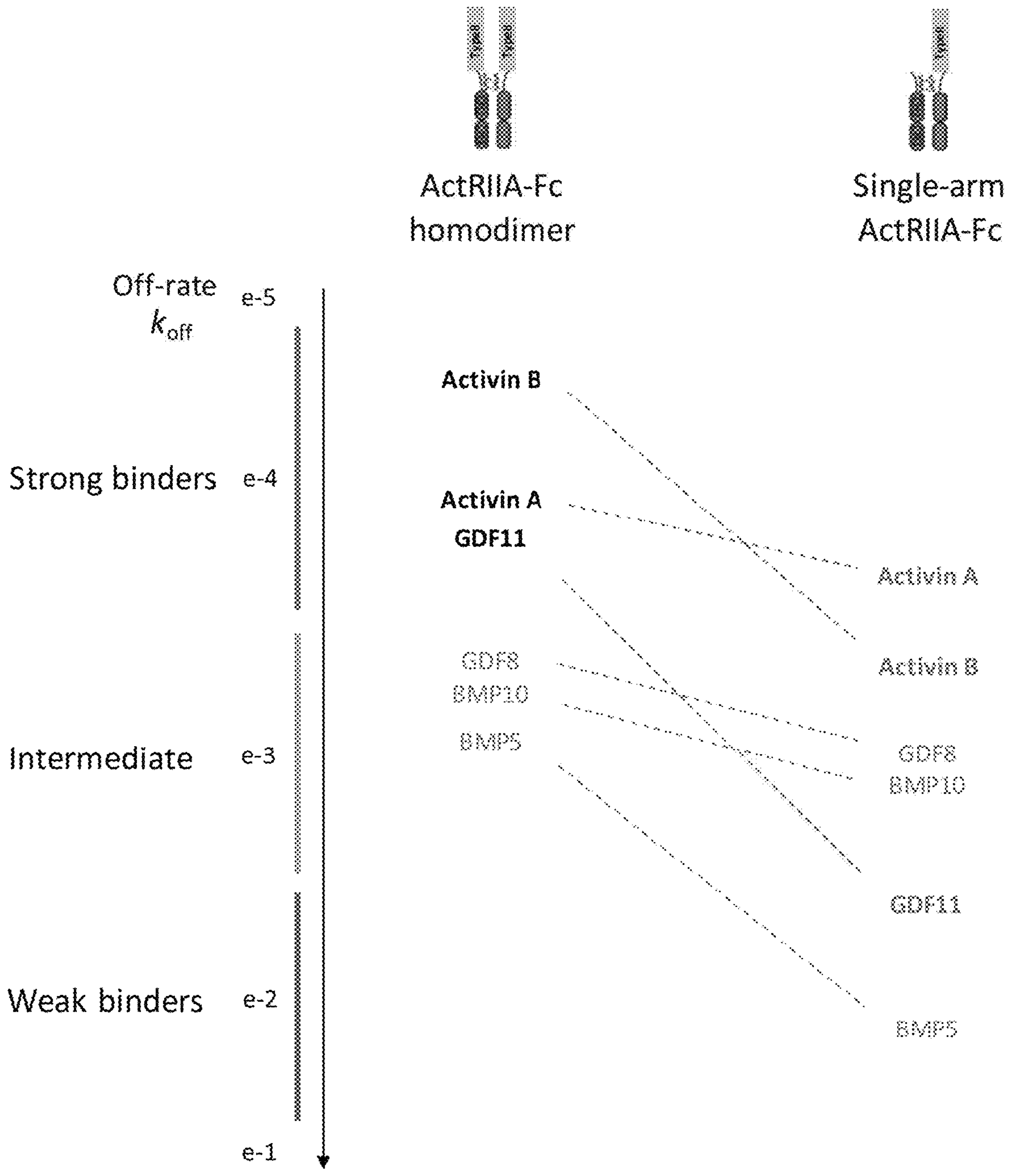
FIG. 8 shows ligand binding data for a single-arm ActRIIA-Fc:Fc heterodimeric protein complex compared to ActRIIA-Fc homodimer. Format is the same as for FIG. 6. As shown, ActRIIA-Fc homodimer exhibits preferential binding to activin B combined with strong binding to activin A and GDF11, whereas single-arm ActRIIA-Fc has a reversed preference for activin A over activin B combined with greatly enhanced selectivity for activin A over GDF11 (weak binder). These data indicate that single-arm ActRIIA-Fc has substantially different ligand selectivity than homodimeric ActRIIA-Fc.

These comparative binding data indicate that single-arm ActRIIA-Fc has different ligand selectivity than homodimeric ActRIIA-Fc (and also different than single-arm ActRIIB-Fc or homomeric ActRIIB-Fc—see Example 1). Whereas ActRIIA-Fc homodimer exhibits preferential binding to activin B combined with strong binding to activin A and GDF11, single-arm ActRIIA-Fc has a reversed preference for activin A over activin B combined with greatly enhanced selectivity for activin A over GDF11 (weak binder). See FIG. 8. In addition, single-arm ActRIIA-Fc largely retains the intermediate binding to GDF8 and BMP10 observed with ActRIIA-Fc homodimer.

These results indicate that single-arm ActRIIA-Fc heterodimer is an antagonist with substantially altered ligand selectivity compared to ActRIIA-Fc homodimer. Accordingly, single-arm ActRIIA-Fc will be more useful than ActRIIA-Fc homodimer in certain applications where such antagonism is advantageous. Examples include therapeutic applications where it is desirable to antagonize activin A preferentially over activin B while minimizing antagonism of GDF11.

Together the foregoing examples demonstrate that type I or type II receptor polypeptides, when placed in the context of a single-arm heteromeric protein complex, form novel binding pockets that exhibit altered selectivity relative to either type of homomeric protein complex, allowing the formation of novel protein agents for possible use as therapeutic agents.

Example 4. Generation and Characterization of a Single-Arm BMPRII-Fc Heterodimer Applicants constructed a soluble single-arm BMPRII-Fc heterodimeric complex comprising a monomeric Fc polypeptide with a short N-terminal extension and a second polypeptide in which the extracellular domain of human BMPRII was fused to a separate Fc domain with a linker positioned between the extracellular domain and this second Fc domain. The individual constructs are referred to as monomeric Fc polypeptide and BMPRII-Fc fusion polypeptide, respectively, and the sequences for each are provided below. Applicants also envision additional single-arm BMPRII-Fc heterodimeric complexes comprising the extracellular domain of BMPRII isoform A (SEQ ID NO: 72).

Formation of a single-arm BMPRII-Fc heterodimer may be guided by approaches similar to those described for single-arm ActRIIB-Fc heterodimer in Example 1. In a first approach, illustrated in the BMPRII-Fc and monomeric Fc polypeptide sequences of SEQ ID NOs: 107-109 and 137-139, respectively, one Fc domain is altered to introduce cationic amino acids at the interaction face, while the other Fc domain is altered to introduce anionic amino acids at the interaction face.

The BMPRII-Fc fusion polypeptide employs the TPA leader and is as follows:

```
                                                       (SEQ ID NO: 107)
  1  MDAMKRGLCC VLLLCGAVFV SPGASQNQER LCAFKDPYQQ DLGIGESRIS

 51  HENGTILCSK GSTCYGLWEK SKGDINLVKQ GCWSHIGDPQ ECHYEECVVT

101  TTPPSIQNGT YRFCCCSTDL CNVNFTENFP PPDTTPLSPP HSFNRDETGG

151  GTHTCPPCPA PELLGGPSVF LFPPKPKDTL MISRTPEVTC VVVDVSHEDP

201  EVKFNWYVDG VEVHNAKTKP REEQYNSTYR VVSVLTVLHQ DWLNGKEYKC

251  KVSNKALPAP IEKTISKAKG QPREPQVYTL PPSRKEMTKN QVSLTCLVKG

301  FYPSDIAVEW ESNGQPENNY KTTPPVLKSD GSFFLYSKLT VDKSRWQQGN

351  VFSCSVMHEA LHNHYTQKSL SLSPGK
```

The leader and linker sequences are underlined. To promote formation of the BMPRII-Fc:Fc heterodimer rather than either of the possible homodimeric complexes (BMPRII-Fc:BMPRII-Fc or Fc:Fc), two amino acid substitutions (replacing anionic residues with lysines) can be introduced into the Fc domain of the fusion polypeptide as indicated by double underline above. The amino acid sequence of SEQ ID NO: 107 may optionally be provided with the C-terminal lysine removed.

This BMPRII-Fc fusion polypeptide is encoded by the following nucleic acid (SEQ ID NO: 108).

```
                                                       (SEQ ID NO: 108)
  1  ATGGATGCAA TGAAGAGAGG GCTCTGCTGT GTGCTGCTGC TGTGTGGAGC

 51  AGTCTTCGTT TCGCCCGGCG CCTCGCAGAA TCAAGAACGC CTATGTGCGT

101  TTAAAGATCC GTATCAGCAA GACCTTGGGA TAGGTGAGAG TAGAATCTCT

151  CATGAAAATG GGACAATATT ATGCTCGAAA GGTAGCACCT GCTATGGCCT

201  TTGGGAGAAA TCAAAAGGGG ACATAAATCT TGTAAAACAA GGATGTTGGT

251  CTCACATTGG AGATCCCCAA GAGTGTCACT ATGAAGAATG TGTAGTAACT

301  ACCACTCCTC CCTCAATTCA GAATGGAACA TACCGTTTCT GCTGTTGTAG

351  CACAGATTTA TGTAATGTCA ACTTTACTGA GAATTTTCCA CCTCCTGACA

401  CAACACCACT CAGTCCACCT CATTCATTTA ACCGAGATGA GACCGGTGGT
```

-continued

```
451  GGAACTCACA CATGCCCACC GTGCCCAGCA CCTGAACTCC TGGGGGGACC

501  GTCAGTCTTC CTCTTCCCCC CAAAACCCAA GGACACCCTC ATGATCTCCC

551  GGACCCCTGA GGTCACATGC GTGGTGGTGG ACGTGAGCCA CGAAGACCCT

601  GAGGTCAAGT TCAACTGGTA CGTGGACGGC GTGGAGGTGC ATAATGCCAA

651  GACAAAGCCG CGGGAGGAGC AGTACAACAG CACGTACCGT GTGGTCAGCG

701  TCCTCACCGT CCTGCACCAG GACTGGCTGA ATGGCAAGGA GTACAAGTGC

751  AAGGTCTCCA ACAAAGCCCT CCCAGCCCCC ATCGAGAAAA CCATCTCCAA

801  AGCCAAAGGG CAGCCCCGAG AACCACAGGT GTACACCCTG CCCCCATCCC

851  GGAAGGAGAT GACCAAGAAC CAGGTCAGCC TGACCTGCCT GGTCAAAGGC

901  TTCTATCCCA GCGACATCGC CGTGGAGTGG GAGAGCAATG GGCAGCCGGA

951  GAACAACTAC AAGACCACGC CTCCCGTGCT GAAGTCCGAC GGCTCCTTCT

1001 TCCTCTATAG CAAGCTCACC GTGGACAAGA GCAGGTGGCA GCAGGGGAAC

1051 GTCTTCTCAT GCTCCGTGAT GCATGAGGCT CTGCACAACC ACTACACGCA

1101 GAAGAGCCTC TCCCTGTCTC CGGGTAAA
```

The mature BMPRII-Fc fusion polypeptide sequence is as follows (SEQ ID NO: 109) and may optionally be provided with the C-terminal lysine removed.

```
                                           (SEQ ID NO: 109)
  1  SQNQERLCAF KDPYQQDLGI GESRISHENG TILCSKGSTC YGLWEKSKGD

 51  INLVKQGCWS HIGDPQECHY EECVVTTTPP SIQNGTYRFC CCSTDLCNVN

101  FTENFPPPDT TPLSPPHSFN RDETGGGTHT CPPCPAPELL GGPSVFLFPP

151  KPKDTLMISR TPEVTCVVVD VSHEDPEVKF NWYVDGVEVH NAKTKPREEQ

201  YNSTYRVVSV LTVLHQDWLN GKEYKCKVSN KALPAPIEKT ISKAKGQPRE

251  PQVYTLPPSR KEMTKNQVSL TCLVKGFYPS DIAVEWESNG QPENNYKTTP

301  PVLKSDGSFF LYSKLTVDKS RWQQGNVFSC SVMHEALHNH YTQKSLSLSP

351  GK
```

As described in Example 1, the complementary form of monomeric human G1Fc polypeptide (SEQ ID NO: 137) uses the TPA leader and incorporates an optional N-terminal extension. To promote formation of the BMPRII-Fc:Fc heterodimer rather than either of the possible homodimeric complexes, two amino acid substitutions (replacing lysines with anionic residues) can be introduced into the monomeric Fc polypeptide. The amino acid sequence of SEQ ID NO: 137 may optionally be provided with the C-terminal lysine removed. This complementary Fc polypeptide is encoded by the nucleic acid of SEQ ID NO: 138), and the mature monomeric Fc polypeptide (SEQ ID NO: 139) may optionally be provided with the C-terminal lysine removed.

The BMPRII-Fc fusion polypeptide and monomeric Fc polypeptide of SEQ ID NO: 103 and SEQ ID NO: 139, respectively, may be co-expressed and purified from a CHO cell line to give rise to a single-arm heteromeric protein complex comprising BMPRII-Fc:Fc.

In another approach to promoting the formation of heteromultimer complexes using asymmetric Fc fusion polypeptides, the Fc domains are altered to introduce complementary hydrophobic interactions and an additional intermolecular disulfide bond as illustrated in the BMPRII-Fc and Fc polypeptide sequences of SEQ ID NOs: 405-406 and 425-426, respectively.

The BMPRII-Fc fusion polypeptide (SEQ ID NO: 405) uses the TPA leader and is as follows:

```
                                           (SEQ ID NO: 405)
  1  MDAMKRGLCC VLLLCGAVFV SPGASQNQER LCAFKDPYQQ DLGIGESRIS

 51  HENGTILCSK GSTCYGLWEK SKGDINLVKQ GCWSHIGDPQ ECHYEECVVT

101  TTPPSIQNGT YRFCCCSTDL CNVNFTENFP PPDTTPLSPP HSFNRDETGG

151  GTHTCPPCPA PELLGGPSVF LFPPKPKDTL MISRTPEVTC VVVDVSHEDP

201  EVKFNWYVDG VEVHNAKTKP REEQYNSTYR VVSVLTVLHQ DWLNGKEYKC
```

-continued

```
251  KVSNKALPAP IEKTISKAKG QPREPQVYTL PPCREEMTKN QVSLWCLVKG

301  FYPSDIAVEW ESNGQPENNY KTTPPVLDSD GSFFLYSKLT VDKSRWQQGN

351  VFSCSVMHEA LHNHYTQKSL SLSPGK
```

The leader sequence and linker are underlined. To promote formation of the BMPRII-Fc:Fc heterodimer rather than either of the possible homodimeric complexes, two amino acid substitutions (replacing a serine with a cysteine and a threonine with a tryptophan) can be introduced into the Fc domain of the BMPRII fusion polypeptide as indicated by double underline above. The amino acid sequence of SEQ ID NO: 405 may optionally be provided with the C-terminal lysine removed.

The mature BMPRII-Fc fusion polypeptide (SEQ ID NO: 406) is as follows and may optionally be provided with the C-terminal lysine removed.

```
                                                    (SEQ ID NO: 406)
  1  SQNQERLCAF KDPYQQDLGI GESRISHENG TILCSKGSTC YGLWEKSKGD

 51  INLVKQGCWS HIGDPQECHY EECVVTTTPP SIQNGTYRFC CCSTDLCNVN

101  FTENFPPPDT TPLSPPHSFN RDETGGGTHT CPPCPAPELL GGPSVFLFPP

151  KPKDTLMISR TPEVTCVVVD VSHEDPEVKF NWYVDGVEVH NAKTKPREEQ

201  YNSTYRVVSV LTVLHQDWLN GKEYKCKVSN KALPAPIEKT ISKAKGQPRE

251  PQVYTLPPCR EEMTKNQVSL WCLVKGFYPS DIAVEWESNG QPENNYKTTP

301  PVLDSDGSFF LYSKLTVDKS RWQQGNVFSC SVMHEALHNH YTQKSLSLSP

351  GK
```

As described in Example 1, the complementary form of monomeric G1Fc polypeptide (SEQ ID NO: 425) employs the TPA leader and incorporates an optional N-terminal extension. To promote formation of the BMPRII-Fc:Fc heterodimer rather than either of the possible homodimeric complexes, four amino acid substitutions can be introduced into the monomeric Fc polypeptide as indicated. The amino acid sequence of SEQ ID NO: 425 and the mature Fc polypeptide (SEQ ID NO: 426) may optionally be provided with the C-terminal lysine removed.

The BMPRII-Fc fusion polypeptide and monomeric Fc polypeptide of SEQ ID NO: 406 and SEQ ID NO: 426, respectively, may be co-expressed and purified from a CHO cell line to give rise to a single-arm heteromeric protein complex comprising BMPRII-Fc:Fc.

Purification of various BMPRII-Fc:Fc complexes could be achieved by a series of column chromatography steps, including, for example, three or more of the following, in any order: protein A chromatography, Q sepharose chromatography, phenylsepharose chromatography, size exclusion chromatography, and cation exchange chromatography. The purification could be completed with viral filtration and buffer exchange.

A Biacore™-based binding assay was used to compare ligand binding selectivity of the single-arm BMPRII-Fc heterodimeric complex described above with that of an BMPRII-Fc homodimeric complex. The single-arm BMPRII-Fc and homodimeric BMPRII-Fc were independently captured onto the system using an anti-Fc antibody. Ligands were injected and allowed to flow over the captured receptor protein. Results are summarized in the table below.

Ligand binding by single-arm BMPRII-Fc compared to BMPRII-Fc homodimer

| | BMPRII-Fc homodimer | | | Single-arm BMPRII-Fc | | |
|---|---|---|---|---|---|---|
| Ligand | $k_a$ (1/Ms) | $k_d$ (1/s) | $K_D$ (pM) | $k_a$ (1/Ms) | $k_d$ (1/s) | $K_D$ (pM) |
| Activin B | $2.0 \times 10^{-7}$ | $7.5 \times 10^{-2}$ | 3800 | Minimal binding | | |
| BMP2 | Transient * | | $>2 \times 10^6$ | No binding | | |
| BMP4 | — | | | No binding | | |

-continued

Ligand binding by single-arm BMPRII-Fc compared to BMPRII-Fc homodimer

| | BMPRII-Fc homodimer | | | Single-arm BMPRII-Fc | | |
|---|---|---|---|---|---|---|
| Ligand | $k_a$ (1/Ms) | $k_d$ (1/s) | $K_D$ (pM) | $k_a$ (1/Ms) | $k_d$ (1/s) | $K_D$ (pM) |
| BMP5 | — | | | $4.1 \times 10^5$ | $1.5 \times 10^{-2}$ | 36000 |
| BMP6 | Transient * | | >8900 | No binding | | |
| BMP7 | Transient * | | >38000 | No binding | | |
| BMP9 | $1.2 \times 10^7$ | $2.6 \times 10^{-2}$ | 2100 | Minimal binding | | |
| BMP10 | $2.6 \times 10^7$ | $2.5 \times 10^{-3}$ | 98 | $2.1 \times 10^7$ | $9.1 \times 10^{-3}$ | 430 |
| BMP15 | $9.9 \times 10^6$ | $2.8 \times 10^{-3}$ | 280 | $7.1 \times 10^7$ | $6.7 \times 10^{-2}$ | 940 |
| GDF6 | Transient * | | >88000 | Minimal binding | | |
| GDF7 | — | | | Transient * | | >190000 |

*Indeterminate due to transient nature of interaction
—Not tested

These comparative binding data indicate that single-arm BMPRII-Fc heterodimer retains binding to only a subset of ligands bound by BMPRII-Fc homodimer. In particular, while the single-arm BMPRII-Fc heterodimer retains binding to BMP10 and BMP15, binding to BMP9 is essentially eliminated.

Example 5. Generation of a Single-Arm MISRII-Fc Heterodimer

Applicants envision construction of a soluble single-arm MISRII-Fc heterodimeric complex comprising a monomeric Fc polypeptide with a short N-terminal extension and a second polypeptide in which the extracellular domain of human MISRII is fused to a separate Fc domain with a linker positioned between the extracellular domain and this second Fc domain. The individual constructs are referred to as monomeric Fc polypeptide and MISRII-Fc fusion polypeptide, respectively, and the sequences for each are provided below. Applicants also envision additional single-arm MISRII-Fc heterodimeric complexes comprising the extracellular domain of MISRII isoform 2 or 3 (SEQ ID NOs: 76, 80).

Formation of a single-arm MISRII-Fc heterodimer may be guided by approaches similar to those described for single-arm ActRIIB-Fc heterodimer in Example 1. In a first approach, illustrated in the MISRII-Fc and monomeric Fc polypeptide sequences of SEQ ID NOs: 110-112 and 137-139, respectively, one Fc domain is altered to introduce cationic amino acids at the interaction face, while the other Fc domain is altered to introduce anionic amino acids at the interaction face.

The MISRII-Fc fusion polypeptide employs the TPA leader and is as follows:

As described in Example 1, the complementary form of monomeric human G1Fc polypeptide (SEQ ID NO: 137) employs the TPA leader and incorporates an optional N-terminal extension. To promote formation of the MISRII-Fc:Fc heterodimer rather than either of the possible homodimeric complexes, two amino acid substitutions (replacing lysines with anionic residues) can be introduced into the monomeric Fc polypeptide as indicated. The amino acid sequence of SEQ ID NO: 137 may optionally be provided with the C-terminal lysine removed. This complementary Fc polypeptide is encoded by the nucleic acid of SEQ ID NO: 138, and the mature monomeric Fc polypeptide (SEQ ID NO: 139) may optionally be provided with the C-terminal lysine removed.

The MISRII-Fc fusion polypeptide and monomeric Fc polypeptide of SEQ ID NO: 112 and SEQ ID NO: 139, respectively, may be co-expressed and purified from a CHO cell line to give rise to a single-arm heteromeric protein complex comprising MISRII-Fc:Fc.

```
                                            (SEQ ID NO: 110)
  1  MDAMKRGLCC VLLLCGAVFV SPGAPPNRRT CVFFEAPGVR GSTKTLGELL

 51  DTGTELPRAI RCLYSRCCFG IWNLTQDRAQ VEMQGCRDSD EPGCESLHCD

101  PSPRAHPSPG STLFTCSCGT DFCNANYSHL PPPGSPGTPG SQGPQAAPGE

151  SIWMALTGGG THTCPPCPAP ELLGGPSVFL FPPKPKDTLM ISRTPEVTCV

201  VVDVSHEDPE VKFNWYVDGV EVHNAKTKPR EEQYNSTYRV VSVLTVLHQD

251  WLNGKEYKCK VSNKALPAPI EKTISKAKGQ PREPQVYTLP PSRKEMTKNQ

301  VSLTCLVKGF YPSDIAVEWE SNGQPENNYK TTPPVLKSDG SFFLYSKLTV

351  DKSRWQQGNV FSCSVMHEAL HNHYTQKSLS LSPGK
```

The leader and linker sequences are underlined. To promote formation of the MISRII-Fc:Fc heterodimer rather than either of the possible homodimeric complexes (MISRII-Fc: MISRII-Fc or Fc:Fc), two amino acid substitutions (replacing anionic residues with lysines) can be introduced into the Fc domain of the fusion polypeptide as indicated by double underline above. The amino acid sequence of SEQ ID NO: 110 may optionally be provided with the C-terminal lysine removed.

The mature MISRII-Fc fusion polypeptide sequence is as follows (SEQ ID NO: 112) and may optionally be provided with the C-terminal lysine removed.

In another approach to promoting the formation of heteromultimer complexes using asymmetric Fc fusion polypeptides, the Fc domains are altered to introduce complementary hydrophobic interactions and an additional intermolecular disulfide bond as illustrated in the MISRII-Fc and Fc polypeptide sequences of SEQ ID NOs: 407-408 and 425-426, respectively.

The MISRII-Fc fusion polypeptide (SEQ ID NO: 407) uses the TPA leader and is as follows:

```
                                            (SEQ ID NO: 112)
  1  PPNRRTCVFF EAPGVRGSTK TLGELLDTGT ELPRAIRCLY SRCCFGIWNL

 51  TQDRAQVEMQ GCRDSDEPGC ESLHCDPSPR AHPSPGSTLF TCSCGTDFCN

101  ANYSHLPPPG SPGTPGSQGP QAAPGESIWM ALTGGGTHTC PPCPAPELLG

151  GPSVFLFPPK PKDTLMISRT PEVTCVVVDV SHEDPEVKFN WYVDGVEVHN

201  AKTKPREEQY NSTYRVVSVL TVLHQDWLNG KEYKCKVSNK ALPAPIEKTI

251  SKAKGQPREP QVYTLPPSRK EMTKNQVSLT CLVKGFYPSD IAVEWESNGQ

301  PENNYKTTPP VLKSDGSFFL YSKLTVDKSR WQQGNVFSCS VMHEALHNHY

351  TQKSLSLSPG K
```

(SEQ ID NO: 407)
```
1   MDAMKRGLCC VLLLCGAVFV SPGAPPNRRT CVFFEAPGVR GSTKTLGELL
51  DTGTELPRAI RCLYSRCCFG IWNLTQDRAQ VEMQGCRDSD EPGCESLHCD
101 PSPRAHPSPG STLFTCSCGT DFCNANYSHL PPPGSPGTPG SQGPQAAPGE
151 SIWMALTGGG THTCPPCPAP ELLGGPSVFL FPPKPKDTLM ISRTPEVTCV
201 VVDVSHEDPE VKFNWYVDGV EVHNAKTKPR EEQYNSTYRV VSVLTVLHQD
251 WLNGKEYKCK VSNKALPAPI EKTISKAKGQ PREPQVYTLP PCREEMTKNQ
301 VSLWCLVKGF YPSDIAVEWE SNGQPENNYK TTPPVLDSDG SFFLYSKLTV
351 DKSRWQQGNV FSCSVMHEAL HNHYTQKSLS LSPGK
```

The leader sequence and linker are underlined. To promote formation of the MISRII-Fc:Fc heterodimer rather than either of the possible homodimeric complexes, two amino acid substitutions (replacing a serine with a cysteine and a threonine with a tryptophan) can be introduced into the Fc domain of the MISRII fusion polypeptide as indicated by double underline above. The amino acid sequence of SEQ ID NO: 407 may optionally be provided with the C-terminal lysine removed.

The mature MISRII-Fc fusion polypeptide (SEQ ID NO: 408) is as follows and may optionally be provided with the C-terminal lysine removed.

(SEQ ID NO: 408)
```
1   PPNRRTCVFF EAPGVRGSTK TLGELLDTGT ELPRAIRCLY SRCCFGIWNL
51  TQDRAQVEMQ GCRDSDEPGC ESLHCDPSPR AHPSPGSTLF TCSCGTDFCN
101 ANYSHLPPPG SPGTPGSQGP QAAPGESIWM ALTGGGTHTC PPCPAPELLG
151 GPSVFLFPPK PKDTLMISRT PEVTCVVVDV SHEDPEVKFN WYVDGVEVHN
201 AKTKPREEQY NSTYRVVSVL TVLHQDWLNG KEYKCKVSNK ALPAPIEKTI
251 SKAKGQPREP QVYTLPPCRE EMTKNQVSLW CLVKGFYPSD IAVEWESNGQ
301 PENNYKTTPP VLDSDGSFFL YSKLTVDKSR WQQGNVFSCS VMHEALHNHY
351 TQKSLSLSPG K
```

As described in Example 1, the complementary form of monomeric G1Fc polypeptide (SEQ ID NO: 425) employs the TPA leader and incorporates an optional N-terminal extension. To promote formation of the MISRII-Fc:Fc heterodimer rather than either of the possible homodimeric complexes, four amino acid substitutions can be introduced into the monomeric Fc polypeptide as indicated. The amino acid sequence of SEQ ID NO: 425 and the mature Fc polypeptide (SEQ ID NO: 426) may optionally be provided with the C-terminal lysine removed.

The MISRII-Fc fusion polypeptide and monomeric Fc polypeptide of SEQ ID NO: 408 and SEQ ID NO: 426, respectively, may be co-expressed and purified from a CHO cell line to give rise to a single-arm heteromeric protein complex comprising MISRII-Fc:Fc.

Purification of various MISRII-Fc:Fc complexes could be achieved by a series of column chromatography steps, including, for example, three or more of the following, in any order: protein A chromatography, Q sepharose chromatography, phenylsepharose chromatography, size exclusion chromatography, and cation exchange chromatography. The purification could be completed with viral filtration and buffer exchange.

Example 6. Generation and Characterization of a Single-Arm TGFβRII-Fc Heterodimer Applicants constructed a soluble single-arm TGFβRII-Fc heterodimeric complex comprising a monomeric Fc polypeptide with a short N-terminal extension and a second polypeptide in which the extracellular domain of human TGFβRII (short isoform, SEQ ID NO: 43) was fused to a separate Fc domain with a linker positioned between the extracellular domain and this second Fc domain. The individual constructs are referred to as monomeric Fc polypeptide and TGFβRII-Fc fusion polypeptide, respectively, and the sequences for each are provided below. Applicants also envision additional single-arm TGFβRII-Fc complexes comprising the extracellular domain of TGFβRII isoform A (SEQ ID NO: 68) as well as single-arm TGFβRII-Fc complexes in which the extracellular domain of canonical TGFβRII (short isoform, SEQ ID NO: 43) or that of TGFβRII isoform A (SEQ ID NO: 68) contain a 36-amino-acid insert (SEQ ID NO: 95) derived from TGFβRII isoform C as described herein.

Formation of a single-arm TGFβRII-Fc heterodimer may be guided by approaches similar to those described for single-arm ActRIIB-Fc heterodimer in Example 1. In a first approach, illustrated in the TGFβRII-Fc and monomeric Fc polypeptide sequences of SEQ ID NOs: 113-115 and 137-139, respectively, one Fc domain is altered to introduce cationic amino acids at the interaction face, while the other Fc domain is altered to introduce anionic amino acids at the interaction face.

The TGFβRII-Fc fusion polypeptide employs the TPA leader and is as follows:

(SEQ ID NO: 113)

```
  1 MDAMKRGLCC VLLLCGAVFV SPGATIPPHV QKSVNNDMIV TDNNGAVKFP
 51 QLCKFCDVRF STCDNQKSCM SNCSITSICE KPQEVCVAVW RKNDENITLE
101 TVCHDPKLPY HDFILEDAAS PKCIMKEKKK PGETFFMCSC SSDECNDNII
151 FSEEYNTSNP DTGGGTHTCP PCPAPELLGG PSVFLFPPKP KDTLMISRTP
201 EVTCVVVDVS HEDPEVKFNW YVDGVEVHNA KTKPREEQYN STYRVVSVLT
251 VLHQDWLNGK EYKCKVSNKA LPAPIEKTIS KAKGQPREPQ VYTLPPSRKE
301 MTKNQVSLTC LVKGFYPSDI AVEWESNGQP ENNYKTTPPV LKSDGSFFLY
351 SKLTVDKSRW QQGNVFSCSV MHEALHNHYT QKSLSLSPGK
```

The leader and linker sequences are underlined. To promote formation of the TGFβRII-Fc:Fc heterodimer rather than either of the possible homodimeric complexes (TGFβRII-Fc: TGFβRII-Fc or Fc:Fc), two amino acid substitutions (replacing anionic residues with lysines) can be introduced into the Fc domain of the fusion polypeptide as indicated by double underline above. The amino acid sequence of SEQ ID NO: 113 may optionally be provided with the C-terminal lysine removed.

This TGFβRII-Fc fusion polypeptide is encoded by the following nucleic acid (SEQ ID NO: 114).

(SEQ ID NO: 114)

```
   1 ATGGATGCAA TGAAGAGAGG GCTCTGCTGT GTGCTGCTGC TGTGTGGAGC
  51 AGTCTTCGTT TCGCCCGGCG CCACGATCCC ACCGCACGTT CAGAAGTCGG
 101 TTAATAACGA CATGATAGTC ACTGACAACA ACGGTGCAGT CAAGTTTCCA
 151 CAACTGTGTA AATTTTGTGA TGTGAGATTT TCCACCTGTG ACAACCAGAA
 201 ATCCTGCATG AGCAACTGCA GCATCACCTC CATCTGTGAG AAGCCACAGG
 251 AAGTCTGTGT GGCTGTATGG AGAAAGAATG ACGAGAACAT AACACTAGAG
 301 ACAGTTTGCC ATGACCCCAA GCTCCCCTAC CATGACTTTA TTCTGGAAGA
 351 TGCTGCTTCT CCAAAGTGCA TTATGAAGGA AAAAAAAAAG CCTGGTGAGA
 401 CTTTCTTCAT GTGTTCCTGT AGCTCTGATG AGTGCAATGA CAACATCATC
 451 TTCTCAGAAG AATATAACAC CAGCAATCCT GACACCGGTG GTGGAACTCA
 501 CACATGCCCA CCGTGCCCAG CACCTGAACT CCTGGGGGGA CCGTCAGTCT
 551 TCCTCTTCCC CCCAAAACCC AAGGACACCC TCATGATCTC CCGGACCCCT
 601 GAGGTCACAT GCGTGGTGGT GGACGTGAGC CACGAAGACC CTGAGGTCAA
 651 GTTCAACTGG TACGTGGACG GCGTGGAGGT GCATAATGCC AAGACAAAGC
 701 CGCGGGAGGA GCAGTACAAC AGCACGTACC GTGTGGTCAG CGTCCTCACC
 751 GTCCTGCACC AGGACTGGCT GAATGGCAAG GAGTACAAGT GCAAGGTCTC
 801 CAACAAAGCC CTCCCAGCCC CCATCGAGAA AACCATCTCC AAAGCCAAAG
 851 GGCAGCCCCG AGAACCACAG GTGTACACCC TGCCCCCATC CCGGAAGGAG
 901 ATGACCAAGA ACCAGGTCAG CCTGACCTGC CTGGTCAAAG GCTTCTATCC
 951 CAGCGACATC GCCGTGGAGT GGGAGAGCAA TGGGCAGCCG GAGAACAACT
1001 ACAAGACCAC GCCTCCCGTG CTGAAGTCCG ACGGCTCCTT CTTCCTCTAT
1051 AGCAAGCTCA CCGTGGACAA GAGCAGGTGG CAGCAGGGGA ACGTCTTCTC
1101 ATGCTCCGTG ATGCATGAGG CTCTGCACAA CCACTACACG CAGAAGAGCC
1151 TCTCCCTGTC TCCGGGTAAA
```

The mature TGFβRII-Fc fusion polypeptide sequence is as follows (SEQ ID NO: 115) and may optionally be provided with the C-terminal lysine removed.

```
                                          (SEQ ID NO: 115)
  1  TIPPHVQKSV NNDMIVTDNN GAVKFPQLCK FCDVRFSTCD NQKSCMSNCS

 51  ITSICEKPQE VCVAVWRKND ENITLETVCH DPKLPYHDFI LEDAASPKCI

101  MKEKKKPGET FFMCSCSSDE CNDNIIFSEE YNTSNPDTGG GTHTCPPCPA

151  PELLGGPSVF LFPPKPKDTL MISRTPEVTC VVVDVSHEDP EVKFNWYVDG

201  VEVHNAKTKP REEQYNSTYR VVSVLTVLHQ DWLNGKEYKC KVSNKALPAP

251  IEKTISKAKG QPREPQVYTL PPSRKEMTKN QVSLTCLVKG FYPSDIAVEW

301  ESNGQPENNY KTTPPVLKSD GSFFLYSKLT VDKSRWQQGN VFSCSVMHEA

351  LHNHYTQKSL SLSPGK
```

As described in Example 1, the complementary form of monomeric human G1Fc polypeptide (SEQ ID NO: 137) employs the TPA leader and incorporates an optional N-terminal extension. To promote formation of the TGFβRII-Fc:Fc heterodimer rather than either of the possible homodimeric complexes, two amino acid substitutions (replacing lysines with anionic residues) can be introduced into the monomeric Fc polypeptide as indicated. The amino acid sequence of SEQ ID NO: 137 may optionally be provided with the C-terminal lysine removed. This complementary Fc polypeptide is encoded by the nucleic acid of SEQ ID NO: 138, and the mature monomeric Fc polypeptide (SEQ ID NO: 139) may optionally be provided with the C-terminal lysine removed.

-

The TGFβRII-Fc fusion polypeptide and monomeric Fc polypeptide of SEQ ID NO: 115 and SEQ ID NO: 139, respectively, may be co-expressed and purified from a CHO cell line to give rise to a single-arm heteromeric protein complex comprising TGFβRII-Fc:Fc.

In another approach to promoting the formation of heteromultimer complexes using asymmetric Fc fusion polypeptides, the Fc domains are altered to introduce complementary hydrophobic interactions and an additional intermolecular disulfide bond as illustrated in the TGFβRII-Fc and Fc polypeptide sequences of SEQ ID NOs: 409-410 and 425-426, respectively.

The TGFβRII-Fc fusion polypeptide (SEQ ID NO: 409) uses the TPA leader and is as follows:

```
                                          (SEQ ID NO: 409)
  1  MDAMKRGLCC VLLLCGAVFV SPGATIPPHV QKSVNNDMIV TDNNGAVKFP

 51  QLCKFCDVRF STCDNQKSCM SNCSITSICE KPQEVCVAVW RKNDENITLE

101  TVCHDPKLPY HDFILEDAAS PKCIMKEKKK PGETFFMCSC SSDECNDNII

151  FSEEYNTSNP DTGGGTHTCP PCPAPELLGG PSVFLFPPKP KDTLMISRTP

201  EVTCVVVDVS HEDPEVKFNW YVDGVEVHNA KTKPREEQYN STYRVVSVLT

251  VLHQDWLNGK EYKCKVSNKA LPAPIEKTIS KAKGQPREPQ VYTLPPCREE

301  MTKNQVSLWC LVKGFYPSDI AVEWESNGQP ENNYKTTPPV LDSDGSFFLY

351  SKLTVDKSRW QQGNVFSCSV MHEALHNHYT QKSLSLSPGK
```

The leader sequence and linker are underlined. To promote formation of the TGFβRII-Fc:Fc heterodimer rather than either of the possible homodimeric complexes, two amino acid substitutions (replacing a serine with a cysteine and a threonine with a tryptophan) can be introduced into the Fc domain of the TGFβRII fusion polypeptide as indicated by double underline above. The amino acid sequence of SEQ ID NO: 409 may optionally be provided with the C-terminal lysine removed.

The mature TGFβRII-Fc fusion polypeptide (SEQ ID NO: 410) is as follows and may optionally be provided with the C-terminal lysine removed.

```
                                          (SEQ ID NO: 410)
  1  TIPPHVQKSV NNDMIVTDNN GAVKFPQLCK FCDVRFSTCD NQKSCMSNCS

 51  ITSICEKPQE VCVAVWRKND ENITLETVCH DPKLPYHDFI LEDAASPKCI
```

-continued

```
101 MKEKKKPGET FFMCSCSSDE CNDNIIFSEE YNTSNPDTGG GTHTCPPCPA

151 PELLGGPSVF LFPPKPKDTL MISRTPEVTC VVVDVSHEDP EVKFNWYVDG

201 VEVHNAKTKP REEQYNSTYR VVSVLIVLHQ DWLNGKEYKC KVSNKALPAP

251 IEKTISKAKG QPREPQVYTL PPCREEMTKN QVSLWCLVKG FYPSDIAVEW

301 ESNGQPENNY KTTPPVLDSD GSFFLYSKLT VDKSRWQQGN VFSCSVMHEA

351 LHNHYTQKSL SLSPGK
```

As described in Example 1, the complementary form of monomeric G1Fc polypeptide (SEQ ID NO: 425) employs the TPA leader and incorporates an optional N-terminal extension. To promote formation of the TGFβRII-Fc:Fc heterodimer rather than either of the possible homodimeric complexes, four amino acid substitutions can be introduced into the monomeric Fc polypeptide as indicated. The amino acid sequence of SEQ ID NO: 425 and the mature monomeric Fc polypeptide (SEQ ID NO: 426) may optionally be provided with the C-terminal lysine removed.

The TGFβRII-Fc fusion polypeptide and monomeric Fc polypeptide of SEQ ID NO: 410 and SEQ ID NO: 426, respectively, may be co-expressed and purified from a CHO cell line to give rise to a single-arm heteromeric protein complex comprising TGFβRII-Fc:Fc.

Purification of various TGFβRII-Fc:Fc complexes could be achieved by a series of column chromatography steps, including, for example, three or more of the following, in any order: protein A chromatography, Q sepharose chromatography, phenylsepharose chromatography, size exclusion chromatography, and cation exchange chromatography. The purification could be completed with viral filtration and buffer exchange.

A Biacore™-based binding assay was used to compare ligand binding selectivity of the single-arm TGFβRII-Fc heterodimeric complex described above with that of an TGFβRII-Fc homodimeric complex. The single-arm TGFβRII-Fc and homodimeric TGFβRII-Fc were independently captured onto the system using an anti-Fc antibody. Ligands were injected and allowed to flow over the captured receptor protein. Results are summarized in the table below.

Ligand binding by single-arm TGFβRII-Fc compared to TGFβRII-Fc homodimer

| | TGFβRII-Fc homodimer | | | Single-arm TGFβRII-Fc | | |
|---|---|---|---|---|---|---|
| Ligand | $k_a$ (1/Ms) | $k_d$ (1/s) | $K_D$ (pM) | $k_a$ (1/Ms) | $k_d$ (1/s) | $K_D$ (pM) |
| TGFβ1 | $4.2 \times 10^7$ | $1.1 \times 10^{-3}$ | 25 | $1.5 \times 10^8$ | $4.7 \times 10^{-3}$ | 31 |
| TGFβ2 | Transient* | | >44000 | Transient* | | >61000 |
| TGFβ3 | $5.9 \times 10^7$ | $5.9 \times 10^{-3}$ | 99 | $1.4 \times 10^8$ | $9.9 \times 10^{-3}$ | 73 |

*Indeterminate due to transient nature of interaction

Example 7. Generation and Characterization of a Single-Arm ALK1-Fc Heterodimer Applicants constructed a soluble single-arm ALK1-Fc heterodimeric complex comprising a monomeric Fc polypeptide with a short N-terminal extension and a second polypeptide in which the extracellular domain of human ALK1 was fused to a separate Fc domain with a linker positioned between the extracellular domain and this second Fc domain. The individual constructs are referred to as monomeric Fc polypeptide and ALK1-Fc fusion polypeptide, respectively, and the sequences for each are provided below.

Formation of a single-arm ALK1-Fc heterodimer may be guided by approaches similar to those described for single-arm ActRIIB-Fc heterodimer in Example 1. In a first approach, illustrated in the ALK1-Fc and monomeric Fc polypeptide sequences of SEQ ID NOs: 116-118 and 140-142, respectively, one Fc domain is altered to introduce cationic amino acids at the interaction face, while the other Fc domain is altered to introduce anionic amino acids at the interaction face.

The ALK1-Fc fusion polypeptide employs the TPA leader and is as follows:

```
                                                   (SEQ ID NO: 116)
  1 MDAMKRGLCC VLLLCGAVFV SPGADPVKPS RGPLVTCTCE SPHCKGPTCR

 51 GAWCTVVLVR EEGRHPQEHR GCGNLHRELC RGRPTEFVNH YCCDSHLCNH

101 NVSLVLEATQ PPSEQPGTDG QLATGGGTHT CPPCPAPELL GGPSVFLFPP

151 KPKDTLMISR TPEVTCVVVD VSHEDPEVKF NWYVDGVEVH NAKTKPREEQ

201 YNSTYRVVSV LTVLHQDWLN GKEYKCKVSN KALPAPIEKT ISKAKGQPRE

251 PQVYTLPPSR EEMTKNQVSL TCLVKGFYPS DIAVEWESNG QPENNYDTTP

301 PVLDSDGSFF LYSDLTVDKS RWQQGNVFSC SVMHEALHNH YTQKSLSLSP

351 G
```

The leader and linker sequences are underlined. To promote formation of the ALK1-Fc:Fc heterodimer rather than either of the possible homodimeric complexes (ALK1-Fc: ALK1-Fc or Fc:Fc), two amino acid substitutions (replacing lysines with anionic amino acids) can be introduced into the Fc domain of the fusion polypeptide as indicated by double underline above. The amino acid sequence of SEQ ID NO: 116 may optionally be provided with a lysine added at the C-terminus.

This ALK1-Fc fusion polypeptide is encoded by the following nucleic acid (SEQ ID NO: 117).

As described in Example 2, the complementary form of monomeric human G1Fc polypeptide (SEQ ID NO: 140) employs the TPA leader and incorporates an optional N-terminal extension. To promote formation of the ALK1-Fc:Fc heterodimer rather than either of the possible homodimeric complexes, two amino acid substitutions (replacing anionic residues with lysines) can be introduced into the monomeric Fc polypeptide as indicated. The amino acid sequence of SEQ ID NO: 140 may optionally be provided with the C-terminal lysine removed. This complementary Fc polypeptide is encoded by the nucleic acid of SEQ ID NO: 141,

```
                                        (SEQ ID NO: 117)
   1 ATGGATGCAA TGAAGAGAGG GCTCTGCTGT GTGCTGCTGC TGTGTGGAGC

  51 AGTCTTCGTT TCGCCCGGCG CCGACCCTGT GAAGCCGTCT CGGGGCCCGC

 101 TGGTGACCTG CACGTGTGAG AGCCCACATT GCAAGGGGCC TACCTGCCGG

 151 GGGGCCTGGT GCACAGTAGT GCTGGTGCGG GAGGAGGGGA GGCACCCCCA

 201 GGAACATCGG GGCTGCGGGA ACTTGCACAG GGAGCTCTGC AGGGGCCGCC

 251 CCACCGAGTT CGTCAACCAC TACTGCTGCG ACAGCCACCT CTGCAACCAC

 301 AACGTGTCCC TGGTGCTGGA GGCCACCCAA CCTCCTTCGG AGCAGCCGGG

 351 AACAGATGGC CAGCTGGCCA CCGGTGGTGG AACTCACACA TGCCCACCGT

 401 GCCCAGCACC TGAACTCCTG GGGGGACCGT CAGTCTTCCT CTTCCCCCCA

 451 AAACCCAAGG ACACCCTCAT GATCTCCCGG ACCCCTGAGG TCACATGCGT

 501 GGTGGTGGAC GTGAGCCACG AAGACCCTGA GGTCAAGTTC AACTGGTACG

 551 TGGACGGCGT GGAGGTGCAT AATGCCAAGA CAAAGCCGCG GGAGGAGCAG

 601 TACAACAGCA CGTACCGTGT GGTCAGCGTC CTCACCGTCC TGCACCAGGA

 651 CTGGCTGAAT GGCAAGGAGT ACAAGTGCAA GGTCTCCAAC AAAGCCCTCC

 701 CAGCCCCCAT CGAGAAAACC ATCTCCAAAG CCAAAGGGCA GCCCCGAGAA

 751 CCACAGGTGT ACACCCTGCC CCCATCCCGG GAGGAGATGA CCAAGAACCA

 801 GGTCAGCCTG ACCTGCCTGG TCAAAGGCTT CTATCCCAGC GACATCGCCG

 851 TGGAGTGGGA GAGCAATGGG CAGCCGGAGA ACAACTACGA CACCACGCCT

 901 CCCGTGCTGG ACTCCGACGG CTCCTTCTTC CTCTATAGCG ACCTCACCGT

 951 GGACAAGAGC AGGTGGCAGC AGGGGAACGT CTTCTCATGC TCCGTGATGC

1001 ATGAGGCTCT GCACAACCAC TACACGCAGA AGAGCCTCTC CCTGTCTCCG

1051 GGT
```

The mature ALK1-Fc fusion polypeptide sequence is as follows (SEQ ID NO: 118) and may optionally be provided with a lysine added at the C-terminus.

and the mature monomeric Fc polypeptide (SEQ ID NO: 142) may optionally be provided with the C-terminal lysine removed.

```
                                        (SEQ ID NO: 118)
  1 DPVKPSRGPL VTCTCESPHC KGPTCRGAWC TVVLVREEGR HPQEHRGCGN

 51 LHRELCRGRP TEFVNHYCCD SHLCNHNVSL VLEATQPPSE QPGTDGQLAT

101 GGGTHTCPPC PAPELLGGPS VFLFPPKPKD TLMISRTPEV TCVVVDVSHE

151 DPEVKFNWYV DGVEVHNAKT KPREEQYNST YRVVSVLTVL HQDWLNGKEY

201 KCKVSNKALP APIEKTISKA KGQPREPQVY TLPPSREEMT KNQVSLTCLV

251 KGFYPSDIAV EWESNGQPEN NYDTTPPVLD SDGSFFLYSD LTVDKSRWQQ

301 GNVFSCSVMH EALHNHYTQK SLSLSPG
```

The ALK1-Fc fusion polypeptide and monomeric Fc polypeptide of SEQ ID NO: 118 and SEQ ID NO: 142, respectively, may be co-expressed and purified from a CHO cell line to give rise to a single-arm heteromeric protein complex comprising ALK1-Fc:Fc.

In another approach to promoting the formation of heteromultimer complexes using asymmetric Fc fusion proteins, the Fc domains are altered to introduce complementary hydrophobic interactions and an additional intermolecular disulfide bond as illustrated in the ALK1-Fc and Fc polypeptide sequences of SEQ ID NOs: 411-412 and 427-428, respectively.

The ALK1-Fc fusion polypeptide (SEQ ID NO: 411) uses the TPA leader and is as follows:

```
                                            (SEQ ID NO: 411)
  1 MDAMKRGLCC VLLLCGAVFV SPGADPVKPS RGPLVTCTCE SPHCKGPTCR

 51 GAWCTVVLVR EEGRHPQEHR GCGNLHRELC RGRPTEFVNH YCCDSHLCNH

101 NVSLVLEATQ PPSEQPGTDG QLATGGGTHT CPPCPAPELL GGPSVFLFPP

151 KPKDTLMISR TPEVTCVVVD VSHEDPEVKF NWYVDGVEVH NAKTKPREEQ

201 YNSTYRVVSV LTVLHQDWLN GKEYKCKVSN KALPAPIEKT ISKAKGQPRE

251 PQVCTLPPSR EEMTKNQVSL SCAVKGFYPS DIAVEWESNG QPENNYKTTP

301 PVLDSDGSFF LVSKLTVDKS RWQQGNVFSC SVMHEALHNH YTQKSLSLSP

351 GK
```

The leader sequence and linker are underlined. To promote formation of the ALK1-Fc:Fc heterodimer rather than either of the possible homodimeric complexes, four amino acid substitutions can be introduced into the Fc domain of the ALK1 fusion polypeptide as indicated by double underline above. The amino acid sequence of SEQ ID NO: 411 may optionally be provided with the C-terminal lysine removed.

The mature ALK1-Fc fusion polypeptide (SEQ ID NO: 412) is as follows and may optionally be provided with the C-terminal lysine removed.

```
                                            (SEQ ID NO: 412)
  1 DPVKPSRGPL VTCTCESPHC KGPTCRGAWC TVVLVREEGR HPQEHRGCGN

 51 LHRELCRGRP TEFVNHYCCD SHLCNHNVSL VLEATQPPSE QPGTDGQLAT

101 GGGTHTCPPC PAPELLGGPS VFLFPPKPKD TLMISRTPEV TCVVVDVSHE

151 DPEVKFNWYV DGVEVHNAKT KPREEQYNST YRVVSVLTVL HQDWLNGKEY

201 KCKVSNKALP APIEKTISKA KGQPREPQVC TLPPSREEMT KNQVSLSCAV

251 KGFYPSDIAV EWESNGQPEN NYKTTPPVLD SDGSFFLVSK LTVDKSRWQQ

301 GNVFSCSVMH EALHNHYTQK SLSLSPGK
```

As described in Example 2, the complementary form of monomeric G1Fc polypeptide (SEQ ID NO: 427) employs the TPA leader and incorporates an optional N-terminal extension. To promote formation of the ALK1-Fc:Fc heterodimer rather than either of the possible homodimeric complexes, two amino acid substitutions (replacing a serine with a cysteine and a threonine with a tryptophan) can be introduced into the monomeric Fc polypeptide as indicated. The amino acid sequence of SEQ ID NO: 427 and the mature Fc polypeptide (SEQ ID NO: 428) may optionally be provided with the C-terminal lysine removed.

The ALK1-Fc fusion polypeptide and monomeric Fc polypeptide of SEQ ID NO: 412 and SEQ ID NO: 428, respectively, may be co-expressed and purified from a CHO cell line to give rise to a single-arm heteromeric protein complex comprising ALK1-Fc:Fc.

Purification of various ALK1-Fc:Fc complexes could be achieved by a series of column chromatography steps, including, for example, three or more of the following, in any order: protein A chromatography, Q sepharose chromatography, phenylsepharose chromatography, size exclusion chromatography, and cation exchange chromatography. The purification could be completed with viral filtration and buffer exchange.

A Biacore™-based binding assay was used to compare ligand binding selectivity of the single-arm ALK1-Fc heterodimeric complex described above with that of an ALK1-Fc homodimeric complex. The single-arm ALK1-Fc and homodimeric ALK1-Fc were independently captured onto the system using an anti-Fc antibody. Ligands were injected and allowed to flow over the captured receptor protein. Results are summarized in the table below, in which ligand off-rates ($k_d$) typically associated with the most effective ligand traps are denoted by bold text.

| Ligand binding by single-arm ALK1-Fc compared to ALK1-Fc homodimer | | | | | | |
|---|---|---|---|---|---|---|
| | ALK1-Fc homodimer | | | Single-arm ALK1-Fc | | |
| Ligand | $k_a$ (1/Ms) | $k_d$ (1/s) | $K_D$ (pM) | $k_a$ (1/Ms) | $k_d$ (1/s) | $K_D$ (pM) |
| BMP9 | $7.9 \times 10^6$ | $1.3 \times 10^{-4}$ | 16 | $1.2 \times 10^7$ | $1.7 \times 10^{-3}$ | 140 |
| BMP10 | $1.7 \times 10^7$ | $1.1 \times 10^{-4}$ | 6 | $2.8 \times 10^6$ | $3.0 \times 10^{-4}$ | 100 |

These comparative binding data indicate that single-arm ALK1-Fc has altered ligand selectivity compared to homodimeric ALK1-Fc. Single-arm ALK1-FRc retains the strong binding to BMP10 observed with homodimeric ALK1-Fc while binding BMP9 less tightly than does ALK1-Fc homodimer, as the off-rate of BMP9 binding to single-arm ALK1-Fc is approximately 10-fold faster than it is for binding to homodimeric AK1-Fc. These results indicate that single-arm ALK1-Fc is a more selective antagonist than ActRIIB-Fc homodimer. Accordingly, single-arm ALK1-Fc will be more useful than homodimeric ALK1-Fc in certain applications where such selective antagonism is advantageous. Examples include therapeutic applications where it is desirable to retain antagonism of BMP10 but reduce antagonism of BMP9.

Example 8. Generation of a Single-Arm ALK2-Fc Heterodimer

Applicants envision construction of a soluble single-arm ALK2-Fc heterodimeric complex comprising a monomeric Fc polypeptide with a short N-terminal extension and a second polypeptide in which the extracellular domain of human ALK2 is fused to a separate Fc domain with a linker positioned between the extracellular domain and this second Fc domain. The individual constructs are referred to as monomeric Fc polypeptide and ALK2-Fc fusion polypeptide, respectively, and the sequences for each are provided below.

Formation of a single-arm ALK2-Fc heterodimer may be guided by approaches similar to those described for single-arm ActRIIB-Fc heterodimer in Example 1. In a first approach, illustrated in the ALK2-Fc and monomeric Fc polypeptide sequences of SEQ ID NOs: 119-121 and 140-142, respectively, one Fc domain is altered to introduce cationic amino acids at the interaction face, while the other Fc domain is altered to introduce anionic amino acids at the interaction face.

The ALK2-Fc fusion polypeptide employs the TPA leader and is as follows:

```
                                                (SEQ ID NO: 119)
  1 MDAMKRGLCC VLLLCGAVFV SPGAMEDEKP KVNPKLYMCV CEGLSCGNED

 51 HCEGQQCFSS LSINDGFHVY QKGCFQVYEQ GKMTCKTPPS PGQAVECCQG

101 DWCNRNITAQ LPTKGKSFPG TQNFHLETGG GTHTCPPCPA PELLGGPSVF

151 LFPPKPKDTL MISRTPEVTC VVVDVSHEDP EVKFNWYVDG VEVHNAKTKP

201 REEQYNSTYR VVSVLTVLHQ DWLNGKEYKC KVSNKALPAP IEKTISKAKG

251 QPREPQVYTL PPSREEMTKN QVSLTCLVKG FYPSDIAVEW ESNGQPENNY

301 DTTPPVLDSD GSFFLYSDLT VDKSRWQQGN VFSCSVMHEA LHNHYTQKSL

351 SLSPG
```

The leader and linker sequences are underlined. To promote formation of the ALK2-Fc:Fc heterodimer rather than either of the possible homodimeric complexes (ALK2-Fc: ALK2-Fc or Fc:Fc), two amino acid substitutions (replacing lysines with anionic amino acids) can be introduced into the Fc domain of the fusion polypeptide as indicated by double underline above. The amino acid sequence of SEQ ID NO: 119 may optionally be provided with a lysine added at the C-terminus.

This ALK2-Fc fusion polypeptide is encoded by the following nucleic acid (SEQ ID NO: 120).

```
                                                (SEQ ID NO: 120)
  1 ATGGATGCAA TGAAGAGAGG GCTCTGCTGT GTGCTGCTGC TGTGTGGAGC

 51 AGTCTTCGTT TCGCCCGGCG CCATGGAAGA TGAGAAGCCC AAGGTCAACC

101 CCAAACTCTA CATGTGTGTG TGTGAAGGTC TCTCCTGCGG TAATGAGGAC

151 CACTGTGAAG GCCAGCAGTG CTTTTCCTCA CTGAGCATCA ACGATGGCTT
```

-continued

```
 201 CCACGTCTAC CAGAAAGGCT GCTTCCAGGT TTATGAGCAG GGAAAGATGA
 251 CCTGTAAGAC CCCGCCGTCC CCTGGCCAAG CTGTGGAGTG CTGCCAAGGG
 301 GACTGGTGTA ACAGGAACAT CACGGCCCAG CTGCCCACTA AAGGAAAATC
 351 CTTCCCTGGA ACACAGAATT TCCACTTGGA GACCGGTGGT GGAACTCACA
 401 CATGCCCACC GTGCCCAGCA CCTGAACTCC TGGGGGGACC GTCAGTCTTC
 451 CTCTTCCCCC CAAAACCCAA GGACACCCTC ATGATCTCCC GGACCCCTGA
 501 GGTCACATGC GTGGTGGTGG ACGTGAGCCA CGAAGACCCT GAGGTCAAGT
 551 TCAACTGGTA CGTGGACGGC GTGGAGGTGC ATAATGCCAA GACAAAGCCG
 601 CGGGAGGAGC AGTACAACAG CACGTACCGT GTGGTCAGCG TCCTCACCGT
 651 CCTGCACCAG GACTGGCTGA ATGGCAAGGA GTACAAGTGC AAGGTCTCCA
 701 ACAAAGCCCT CCCAGCCCCC ATCGAGAAAA CCATCTCCAA AGCCAAAGGG
 751 CAGCCCCGAG AACCACAGGT GTACACCCTG CCCCCATCCC GGGAGGAGAT
 801 GACCAAGAAC CAGGTCAGCC TGACCTGCCT GGTCAAAGGC TTCTATCCCA
 851 GCGACATCGC CGTGGAGTGG GAGAGCAATG GGCAGCCGGA GAACAACTAC
 901 GACACCACGC CTCCCGTGCT GGACTCCGAC GGCTCCTTCT TCCTCTATAG
 951 CGACCTCACC GTGGACAAGA GCAGGTGGCA GCAGGGGAAC GTCTTCTCAT
1001 GCTCCGTGAT GCATGAGGCT CTGCACAACC ACTACACGCA GAAGAGCCTC
1051 TCCCTGTCTC CGGGT
```

The mature ALK2-Fc fusion polypeptide sequence is as follows (SEQ ID NO: 121) and may optionally be provided with a lysine added at the C-terminus.

```
                                          (SEQ ID NO: 121)
  1 MEDEKPKVNP KLYMCVCEGL SCGNEDHCEG QQCFSSLSIN DGFHVYQKGC
 51 FQVYEQGKMT CKTPPSPGQA VECCQGDWCN RNITAQLPTK GKSFPGTQNF
101 HLETGGGTHT CPPCPAPELL GGPSVFLFPP KPKDTLMISR TPEVTCVVVD
151 VSHEDPEVKF NWYVDGVEVH NAKTKPREEQ YNSTYRVVSV LTVLHQDWLN
201 GKEYKCKVSN KALPAPIEKT ISKAKGQPRE PQVYTLPPSR EEMTKNQVSL
251 TCLVKGFYPS DIAVEWESNG QPENNYDTTP PVLDSDGSFF LYSDLTVDKS
301 RWQQGNVFSC SVMHEALHNH YTQKSLSLSP G
```

As described in Example 2, the complementary form of monomeric human G1Fc polypeptide (SEQ ID NO: 140) employs the TPA leader and incorporates an optional N-terminal extension. To promote formation of the ALK2-Fc:Fc heterodimer rather than either of the possible homodimeric complexes, two amino acid substitutions (replacing anionic residues with lysines) can be introduced into the monomeric Fc polypeptide as indicated. The amino acid sequence of SEQ ID NO: 140 may optionally be provided with the C-terminal lysine removed. This complementary Fc polypeptide is encoded by the nucleic acid of SEQ ID NO: 141, and the mature monomeric Fc polypeptide (SEQ ID NO: 142) may optionally be provided with the C-terminal lysine removed.

The ALK2-Fc fusion polypeptide and monomeric Fc polypeptide of SEQ ID NO: 121 and SEQ ID NO: 142, respectively, may be co-expressed and purified from a CHO cell line to give rise to a single-arm heteromeric protein complex comprising ALK2-Fc:Fc.

In another approach to promoting the formation of heteromultimer complexes using asymmetric Fc fusion polypeptides, the Fc domains are altered to introduce complementary hydrophobic interactions and an additional intermolecular disulfide bond as illustrated in the ALK2-Fc and Fc polypeptide sequences of SEQ ID NOs: 413-414 and 427-428, respectively.

The ALK2-Fc fusion polypeptide (SEQ ID NO: 413) uses the TPA leader and is as follows:

```
                                          (SEQ ID NO: 413)
  1 MDAMKRGLCC VLLLCGAVFV SPGAMEDEKP KVNPKLYMCV CEGLSCGNED
```

-continued

```
51 HCEGQQCFSS LSINDGFHVY QKGCFQVYEQ GKMTCKTPPS PGQAVECCQG

101 DWCNRNITAQ LPTKGKSFPG TQNFHLETGG GTHTCPPCPA PELLGGPSVF

151 LFPPKPKDTL MISRTPEVTC VVVDVSHEDP EVKFNWYVDG VEVHNAKTKP

201 REEQYNSTYR VVSVLTVLHQ DWLNGKEYKC KVSNKALPAP IEKTISKAKG

251 QPREPQVCTL PPSREEMTKN QVSLSCAVKG FYPSDIAVEW ESNGQPENNY

301 KTTPPVLDSD GSFFLVSKLT VDKSRWQQGN VFSCSVMHEA LHNHYTQKSL

351 SLSPGK
```

The leader sequence and linker are underlined. To promote formation of the ALK2-Fc:Fc heterodimer rather than either of the possible homodimeric complexes, four amino acid substitutions can be introduced into the Fc domain of the ALK2 fusion polypeptide as indicated by double underline above. The amino acid sequence of SEQ ID NO: 413 may optionally be provided with the C-terminal lysine removed.

The mature ALK2-Fc fusion polypeptide (SEQ ID NO: 414) is as follows and may optionally be provided with the C-terminal lysine removed.

```
(SEQ ID NO: 414)
1 MEDEKPKVNP KLYMCVCEGL SCGNEDHCEG QQCFSSLSIN DGFHVYQKGC

51 FQVYEQGKMT CKTPPSPGQA VECCQGDWCN RNITAQLPTK GKSFPGTQNF

101 HLETGGGTHT CPPCPAPELL GGPSVFLFPP KPKDTLMISR TPEVTCVVVD

151 VSHEDPEVKF NWYVDGVEVH NAKTKPREEQ YNSTYRVVSV LTVLHQDWLN

201 GKEYKCKVSN KALPAPIEKT ISKAKGQPRE PQVCTLPPSR EEMTKNQVSL

251 SCAVKGFYPS DIAVEWESNG QPENNYKTTP PVLDSDGSFF LVSKLTVDKS

301 RWQQGNVFSC SVMHEALHNH YTQKSLSLSP GK
```

As described in Example 2, the complementary form of monomeric G1Fc polypeptide (SEQ ID NO: 427) employs the TPA leader and incorporates an optional N-terminal extension. To promote formation of the ALK2-Fc:Fc heterodimer rather than either of the possible homodimeric complexes, two amino acid substitutions (replacing a serine with a cysteine and a threonine with a tryptophan) can be introduced into the monomeric Fc polypeptide as indicated. The amino acid sequence of SEQ ID NO: 427 and the mature Fc polypeptide (SEQ ID NO: 428) may optionally be provided with the C-terminal lysine removed.

The ALK2-Fc fusion polypeptide and monomeric Fc polypeptide of SEQ ID NO: 414 and SEQ ID NO: 428, respectively, may be co-expressed and purified from a CHO cell line to give rise to a single-arm heteromeric protein complex comprising ALK2-Fc:Fc.

Purification of various ALK2-Fc:Fc complexes could be achieved by a series of column chromatography steps, including, for example, three or more of the following, in any order: protein A chromatography, Q sepharose chromatography, phenylsepharose chromatography, size exclusion chromatography, and cation exchange chromatography. The purification could be completed with viral filtration and buffer exchange.

Example 9. Generation of a Single-Arm ALK4-Fc Heterodimer

Applicants envision construction of a soluble single-arm ALK4-Fc heterodimeric complex comprising a monomeric Fc polypeptide with a short N-terminal extension and a second polypeptide in which the extracellular domain of human ALK4 is fused to a separate Fc domain with a linker positioned between the extracellular domain and this second Fc domain. The individual constructs are referred to as monomeric Fc polypeptide and ALK4-Fc fusion polypeptide, respectively, and the sequences for each are provided below. Applicants also envision additional single-arm ALK4-Fc heterodimeric complexes comprising the extracellular domain of ALK4 isoform B (SEQ ID NO: 84).

Formation of a single-arm ALK4-Fc heterodimer may be guided by approaches similar to those described for single-arm ActRIIB-Fc heterodimer in Example 1. In a first approach, illustrated in the ALK4-Fc and monomeric Fc polypeptide sequences of SEQ ID NOs: 125-127 and 140-142, respectively, one Fc domain is altered to introduce cationic amino acids at the interaction face, while the other Fc domain is altered to introduce anionic amino acids at the interaction face.

The ALK4-Fc fusion polypeptide employs the TPA leader and is as follows:

(SEQ ID NO: 125)

```
1 MDAMKRGLCC VLLLCGAVFV SPGASGPRGV QALLCACTSC LQANYTCETD
51 GACMVSIFNL DGMEHHVRTC IPKVELVPAG KPFYCLSSED LRNTHCCYTD
101 YCNRIDLRVP SGHLKEPEHP SMWGPVETGG GTHTCPPCPA PELLGGPSVF
151 LFPPKPKDTL MISRTPEVTC VVVDVSHEDP EVKFNWYVDG VEVHNAKTKP
201 REEQYNSTYR VVSVLTVLHQ DWLNGKEYKC KVSNKALPAP IEKTISKAKG
251 QPREPQVYTL PPSREEMTKN QVSLTCLVKG FYPSDIAVEW ESNGQPENNY
301 DTTPPVLDSD GSFFLYSDLT VDKSRWQQGN VFSCSVMHEA LHNHYTQKSL
351 SLSPG
```

The leader and linker sequences are underlined. To promote formation of the ALK4-Fc:Fc heterodimer rather than either of the possible homodimeric complexes (ALK4-Fc: ALK4-Fc or Fc:Fc), two amino acid substitutions (replacing lysines with anionic amino acids) can be introduced into the Fc domain of the fusion polypeptide as indicated by double underline above. The amino acid sequence of SEQ ID NO: 125 may optionally be provided with a lysine added at the C-terminus.

This ALK4-Fc fusion polypeptide is encoded by the following nucleic acid (SEQ ID NO: 126).

(SEQ ID NO: 126)

```
1 ATGGATGCAA TGAAGAGAGG GCTCTGCTGT GTGCTGCTGC TGTGTGGAGC
51 AGTCTTCGTT TCGCCCGGCG CCTCCGGGCC CCGGGGGGTC CAGGCTCTGC
101 TGTGTGCGTG CACCAGCTGC CTCCAGGCCA ACTACACGTG TGAGACAGAT
151 GGGGCCTGCA TGGTTTCCAT TTTCAATCTG GATGGGATGG AGCACCATGT
201 GCGCACCTGC ATCCCCAAAG TGGAGCTGGT CCCTGCCGGG AAGCCCTTCT
251 ACTGCCTGAG CTCGGAGGAC CTGCGCAACA CCCACTGCTG CTACACTGAC
301 TACTGCAACA GGATCGACTT GAGGGTGCCC AGTGGTCACC TCAAGGAGCC
351 TGAGCACCCG TCCATGTGGG GCCCGGTGGA GACCGGTGGT GGAACTCACA
401 CATGCCCACC GTGCCCAGCA CCTGAACTCC TGGGGGGACC GTCAGTCTTC
451 CTCTTCCCCC CAAAACCCAA GGACACCCTC ATGATCTCCC GGACCCCTGA
501 GGTCACATGC GTGGTGGTGG ACGTGAGCCA CGAAGACCCT GAGGTCAAGT
551 TCAACTGGTA CGTGGACGGC GTGGAGGTGC ATAATGCCAA GACAAAGCCG
601 CGGGAGGAGC AGTACAACAG CACGTACCGT GTGGTCAGCG TCCTCACCGT
651 CCTGCACCAG GACTGGCTGA ATGGCAAGGA GTACAAGTGC AAGGTCTCCA
701 ACAAAGCCCT CCCAGCCCCC ATCGAGAAAA CCATCTCCAA AGCCAAAGGG
751 CAGCCCCGAG AACCACAGGT GTACACCCTG CCCCCATCCC GGGAGGAGAT
801 GACCAAGAAC CAGGTCAGCC TGACCTGCCT GGTCAAAGGC TTCTATCCCA
851 GCGACATCGC CGTGGAGTGG GAGAGCAATG GGCAGCCGGA GAACAACTAC
901 GACACCACGC CTCCCGTGCT GGACTCCGAC GGCTCCTTCT TCCTCTATAG
951 CGACCTCACC GTGGACAAGA GCAGGTGGCA GCAGGGGAAC GTCTTCTCAT
1001 GCTCCGTGAT GCATGAGGCT CTGCACAACC ACTACACGCA GAAGAGCCTC
1051 TCCCTGTCTC CGGGT
```

The mature ALK4-Fc fusion polypeptide sequence is as follows (SEQ ID NO: 127) and may optionally be provided with a lysine added at the C-terminus.

```
                                              (SEQ ID NO: 127)
  1  SGPRGVQALL CACTSCLQAN YTCETDGACM VSIFNLDGME HHVRTCIPKV

 51  ELVPAGKPFY CLSSEDLRNT HCCYTDYCNR IDLRVPSGHL KEPEHPSMWG

101  PVETGGGTHT CPPCPAPELL GGPSVFLFPP KPKDTLMISR TPEVTCVVVD

151  VSHEDPEVKF NWYVDGVEVH NAKTKPREEQ YNSTYRVVSV LTVLHQDWLN

201  GKEYKCKVSN KALPAPIEKT ISKAKGQPRE PQVYTLPPSR EEMTKNQVSL

251  TCLVKGFYPS DIAVEWESNG QPENNYDTTP PVLDSDGSFF LYSDLTVDKS

301  RWQQGNVFSC SVMHEALHNH YTQKSLSLSP G
```

As described in Example 2, the complementary form of monomeric human G1Fc polypeptide (SEQ ID NO: 140) employs the TPA leader and incorporates an optional N-terminal extension. To promote formation of the ALK4-Fc:Fc heterodimer rather than either of the possible homodimeric complexes, two amino acid substitutions (replacing anionic residues with lysines) can be introduced into the monomeric Fc polypeptide as indicated. The amino acid sequence of SEQ ID NO: 140 may optionally be provided with the C-terminal lysine removed. This complementary Fc polypeptide is encoded by the nucleic acid of SEQ ID NO: 141, and the mature monomeric Fc polypeptide (SEQ ID NO: 142) may optionally be provided with the C-terminal lysine removed.

The ALK4-Fc fusion polypeptide and monomeric Fc polypeptide of SEQ ID NO: 127 and SEQ ID NO: 142, respectively, may be co-expressed and purified from a CHO cell line to give rise to a single-arm heteromeric protein complex comprising ALK4-Fc:Fc.

In another approach to promoting the formation of heteromultimer complexes using asymmetric Fc fusion polypeptides, the Fc domains are altered to introduce complementary hydrophobic interactions and an additional intermolecular disulfide bond as illustrated in the ALK4-Fc and Fc polypeptide sequences of SEQ ID NOs: 417-418 and 427-428, respectively.

The ALK4-Fc fusion polypeptide (SEQ ID NO: 417) uses the TPA leader and is as follows:

```
                                              (SEQ ID NO: 417)
  1  MDAMKRGLCC VLLLCGAVFV SPGASGPRGV QALLCACTSC LQANYTCETD

 51  GACMVSIFNL DGMEHHVRTC IPKVELVPAG KPFYCLSSED LRNTHCCYTD

101  YCNRIDLRVP SGHLKEPEHP SMWGPVETGG GTHTCPPCPA PELLGGPSVF

151  LFPPKPKDTL MISRTPEVTC VVVDVSHEDP EVKFNWYVDG VEVHNAKTKP

201  REEQYNSTYR VVSVLTVLHQ DWLNGKEYKC KVSNKALPAP IEKTISKAKG

251  QPREPQVCTL PPSREEMTKN QVSLSCAVKG FYPSDIAVEW ESNGQPENNY

301  KTTPPVLDSD GSFFLVSKLT VDKSRWQQGN VFSCSVMHEA LHNHYTQKSL

351  SLSPGK
```

-

The leader sequence and linker are underlined. To promote formation of the ALK4-Fc:Fc heterodimer rather than either of the possible homodimeric complexes, four amino acid substitutions can be introduced into the Fc domain of the ALK4 fusion polypeptide as indicated by double underline above. The amino acid sequence of SEQ ID NO: 417 may optionally be provided with the C-terminal lysine removed.

The mature ALK4-Fc fusion polypeptide (SEQ ID NO: 418) is as follows and may optionally be provided with the C-terminal lysine removed.

```
                                              (SEQ ID NO: 418)
  1  SGPRGVQALL CACTSCLQAN YTCETDGACM VSIFNLDGME HHVRTCIPKV

 51  ELVPAGKPFY CLSSEDLRNT HCCYTDYCNR IDLRVPSGHL KEPEHPSMWG

101  PVETGGGTHT CPPCPAPELL GGPSVFLFPP KPKDTLMISR TPEVTCVVVD

151  VSHEDPEVKF NWYVDGVEVH NAKTKPREEQ YNSTYRVVSV LTVLHQDWLN
```

-continued

```
201  GKEYKCKVSN KALPAPIEKT ISKAKGQPRE PQVCTLPPSR EEMTKNQVSL

251  SCAVKGFYPS DIAVEWESNG QPENNYKTTP PVLDSDGSFF LVSKLTVDKS

301  RWQQGNVFSC SVMHEALHNH YTQKSLSLSP GK
```

As described in Example 2, the complementary form of monomeric G1Fc polypeptide (SEQ ID NO: 427) employs the TPA leader and incorporates an optional N-terminal extension. To promote formation of the ALK4-Fc:Fc heterodimer rather than either of the possible homodimeric complexes, two amino acid substitutions (replacing a serine with a cysteine and a threonine with a tryptophan) can be introduced into the monomeric Fc polypeptide as indicated. The amino acid sequence of SEQ ID NO: 427 and the mature Fc polypeptide (SEQ ID NO: 428) may optionally be provided with the C-terminal lysine removed.

The ALK4-Fc fusion polypeptide and monomeric Fc polypeptide of SEQ ID NO: 418 and SEQ ID NO: 428, respectively, may be co-expressed and purified from a CHO cell line to give rise to a single-arm heteromeric protein complex comprising ALK4-Fc:Fc.

Purification of various ALK4-Fc:Fc complexes could be achieved by a series of column chromatography steps, including, for example, three or more of the following, in any order: protein A chromatography, Q sepharose chromatography, phenylsepharose chromatography, size exclusion chromatography, and cation exchange chromatography. The purification could be completed with viral filtration and buffer exchange.

Example 10. Generation of a Single-Arm ALK5-Fc Heterodimer

Applicants envision construction of a soluble single-arm ALK5-Fc heterodimeric complex comprising a monomeric Fc polypeptide with a short N-terminal extension and a second polypeptide in which the extracellular domain of human ALK5 is fused to a separate Fc domain with a linker positioned between the extracellular domain and this second Fc domain. The individual constructs are referred to as monomeric Fc polypeptide and ALK5-Fc fusion polypeptide, respectively, and the sequences for each are provided below. Applicants also envision additional single-arm ALK5-Fc heterodimeric complexes comprising the extracellular domain of ALK5 isoform 2 (SEQ ID NO: 88).

Formation of a single-arm ALK5-Fc heterodimer may be guided by approaches similar to those described for single-arm ActRIIB-Fc heterodimer in Example 1. In a first approach, illustrated in the ALK5-Fc and monomeric Fc polypeptide sequences of SEQ ID NOs: 128-130 and 140-142, respectively, one Fc domain is altered to introduce cationic amino acids at the interaction face, while the other Fc domain is altered to introduce anionic amino acids at the interaction face.

The ALK5-Fc fusion polypeptide employs the TPA leader and is as follows:

```
                                                          (SEQ ID NO: 128)
  1  MDAMKRGLCC VLLLCGAVFV SPGAALLPGA TALQCFCHLC TKDNFTCVTD

 51  GLCFVSVTET TDKVIHNSMC IAEIDLIPRD RPFVCAPSSK TGSVTTTYCC

101  NQDHCNKIEL PTTVKSSPGL GPVETGGGTH TCPPCPAPEL LGGPSVFLFP

151  PKPKDTLMIS RTPEVTCVVV DVSHEDPEVK FNWYVDGVEV HNAKTKPREE

201  QYNSTYRVVS VLTVLHQDWL NGKEYKCKVS NKALPAPIEK TISKAKGQPR

251  EPQVYTLPPS REEMTKNQVS LTCLVKGFYP SDIAVEWESN GQPENNYDTT

301  PPVLDSDGSF FLYSDLTVDK SRWQQGNVFS CSVMHEALHN HYTQKSLSLS

351  PG
```

The leader and linker sequences are underlined. To promote formation of the ALK5-Fc:Fc heterodimer rather than either of the possible homodimeric complexes (ALK5-Fc:ALK5-Fc or Fc:Fc), two amino acid substitutions (replacing lysines with anionic amino acids) can be introduced into the Fc domain of the fusion polypeptide as indicated. The amino acid sequence of SEQ ID NO: 128 may optionally be provided with a lysine added at the C-terminus.

This ALK5-Fc fusion polypeptide is encoded by the following nucleic acid (SEQ ID NO: 129).

```
                                                          (SEQ ID NO: 129)
  1  ATGGATGCAA TGAAGAGAGG GCTCTGCTGT GTGCTGCTGC TGTGTGGAGC

 51  AGTCTTCGTT TCGCCCGGCG CCGCGCTGCT CCCGGGGGCG ACGGCGTTAC

101  AGTGTTTCTG CCACCTCTGT ACAAAAGACA ATTTTACTTG TGTGACAGAT

151  GGGCTCTGCT TTGTCTCTGT CACAGAGACC ACAGACAAAG TTATACACAA

201  CAGCATGTGT ATAGCTGAAA TTGACTTAAT TCCTCGAGAT AGGCCGTTTG
```

-continued

```
251 TATGTGCACC CTCTTCAAAA ACTGGGTCTG TGACTACAAC ATATTGCTGC

301 AATCAGGACC ATTGCAATAA AATAGAACTT CCAACTACTG TAAAGTCATC

351 ACCTGGCCTT GGTCCTGTGG AAACCGGTGG TGGAACTCAC ACATGCCCAC

401 CGTGCCCAGC ACCTGAACTC CTGGGGGGAC CGTCAGTCTT CCTCTTCCCC

451 CCAAAACCCA AGGACACCCT CATGATCTCC CGGACCCCTG AGGTCACATG

501 CGTGGTGGTG GACGTGAGCC ACGAAGACCC TGAGGTCAAG TTCAACTGGT

551 ACGTGGACGG CGTGGAGGTG CATAATGCCA AGACAAAGCC GCGGGAGGAG

601 CAGTACAACA GCACGTACCG TGTGGTCAGC GTCCTCACCG TCCTGCACCA

651 GGACTGGCTG AATGGCAAGG AGTACAAGTG CAAGGTCTCC AACAAAGCCC

701 TCCCAGCCCC CATCGAGAAA ACCATCTCCA AAGCCAAAGG GCAGCCCCGA

751 GAACCACAGG TGTACACCCT GCCCCCATCC CGGGAGGAGA TGACCAAGAA

801 CCAGGTCAGC CTGACCTGCC TGGTCAAAGG CTTCTATCCC AGCGACATCG

851 CCGTGGAGTG GGAGAGCAAT GGGCAGCCGG AGAACAACTA CGACACCACG

901 CCTCCCGTGC TGGACTCCGA CGGCTCCTTC TTCCTCTATA GCGACCTCAC

951 CGTGGACAAG AGCAGGTGGC AGCAGGGGAA CGTCTTCTCA TGCTCCGTGA

1001 TGCATGAGGC TCTGCACAAC CACTACACGC AGAAGAGCCT CTCCCTGTCT

1051 CCGGGT
```

The mature ALK5-Fc fusion polypeptide sequence is as follows (SEQ ID NO: 130) and may optionally be provided with a lysine added at the C-terminus.

```
                                              (SEQ ID NO: 130)
  1 ALLPGATALQ CFCHLCTKDN FTCVTDGLCF VSVTETTDKV IHNSMCIAEI

 51 DLIPRDRPFV CAPSSKTGSV TTTYCCNQDH CNKIELPTTV KSSPGLGPVE

101 TGGGTHTCPP CPAPELLGGP SVFLFPPKPK DTLMISRTPE VTCVVVDVSH

151 EDPEVKFNWY VDGVEVHNAK TKPREEQYNS TYRVVSVLTV LHQDWLNGKE

201 YKCKVSNKAL PAPIEKTISK AKGQPREPQV YTLPPSREEM TKNQVSLTCL

251 VKGFYPSDIA VEWESNGQPE NNYDTTPPVL DSDGSFFLYS DLTVDKSRWQ

301 QGNVFSCSVM HEALHNHYTQ KSLSLSPG
```

As described in Example 2, the complementary form of monomeric human G1Fc polypeptide (SEQ ID NO: 140) employs the TPA leader and incorporates an optional N-terminal extension. To promote formation of the ALK5-Fc:Fc heterodimer rather than either of the possible homodimeric complexes, two amino acid substitutions (replacing anionic residues with lysines) can be introduced into the monomeric Fc polypeptide as indicated. The amino acid sequence of SEQ ID NO: 140 may optionally be provided with the C-terminal lysine removed. This complementary Fc polypeptide is encoded by the nucleic acid of SEQ ID NO: 141, and the mature monomeric Fc polypeptide (SEQ ID NO: 142) may optionally be provided with the C-terminal lysine removed.

The ALK5-Fc fusion polypeptide and monomeric Fc polypeptide of SEQ ID NO: 130 and SEQ ID NO: 142, respectively, may be co-expressed and purified from a CHO cell line to give rise to a single-arm heteromeric protein complex comprising ALK5-Fc:Fc.

In another approach to promoting the formation of heteromultimer complexes using asymmetric Fc fusion polypeptides, the Fc domains are altered to introduce complementary hydrophobic interactions and an additional intermolecular disulfide bond as illustrated in the ALK5-Fc and Fc polypeptide sequences of SEQ ID NOs: 419-420 and 427-428, respectively.

The ALK5-Fc fusion polypeptide (SEQ ID NO: 419) uses the TPA leader and is as follows:

```
                                              (SEQ ID NO: 419)
 1 MDAMKRGLCC VLLLCGAVFV SPGAALLPGA TALQCFCHLC TKDNFTCVTD

51 GLCFVSVTET TDKVIHNSMC IAEIDLIPRD RPFVCAPSSK TGSVTTTYCC
```

-continued

```
101 NQDHCNKIEL PTTVKSSPGL GPVETGGGTH TCPPCPAPEL LGGPSVFLFP

151 PKPKDTLMIS RTPEVTCVVV DVSHEDPEVK FNWYVDGVEV HNAKTKPREE

201 QYNSTYRVVS VLTVLHQDWL NGKEYKCKVS NKALPAPIEK TISKAKGQPR

251 EPQVCTLPPS REEMTKNQVS LSCAVKGFYP SDIAVEWESN GQPENNYKTT

301 PPVLDSDGSF FLVSKLTVDK SRWQQGNVFS CSVMHEALHN HYTQKSLSLS

351 PGK
```

The leader sequence and linker are underlined. To promote formation of the ALK5-Fc:Fc heterodimer rather than either of the possible homodimeric complexes, four amino acid substitutions can be introduced into the Fc domain of the ALK5 fusion polypeptide as indicated by double underline above. The amino acid sequence of SEQ ID NO: 419 may optionally be provided with the C-terminal lysine removed.

The mature ALK5-Fc fusion polypeptide (SEQ ID NO: 420) is as follows and may optionally be provided with the C-terminal lysine removed.

```
                                            (SEQ ID NO: 420)
  1 ALLPGATALQ CFCHLCTKDN FTCVTDGLCF VSVTETTDKV IHNSMCIAEI

 51 DLIPRDRPFV CAPSSKTGSV TTTYCCNQDH CNKIELPTTV KSSPGLGPVE

101 TGGGTHTCPP CPAPELLGGP SVFLFPPKPK DTLMISRTPE VTCVVVDVSH

151 EDPEVKFNWY VDGVEVHNAK TKPREEQYNS TYRVVSVLTV LHQDWLNGKE

201 YKCKVSNKAL PAPIEKTISK AKGQPREPQV CTLPPSREEM TKNQVSLSCA

251 VKGFYPSDIA VEWESNGQPE NNYKTTPPVL DSDGSFFLVS KLTVDKSRWQ

301 QGNVFSCSVM HEALHNHYTQ KSLSLSPGK
```

As described in Example 2, the complementary form of monomeric G1Fc polypeptide (SEQ ID NO: 427) employs the TPA leader and incorporates an optional N-terminal extension. To promote formation of the ALK5-Fc:Fc heterodimer rather than either of the possible homodimeric complexes, two amino acid substitutions (replacing a serine with a cysteine and a threonine with a tryptophan) can be introduced into the monomeric Fc polypeptide as indicated. The amino acid sequence of SEQ ID NO: 427 and the mature monomeric G1Fc polypeptide (SEQ ID NO: 428) may optionally be provided with the C-terminal lysine removed.

The ALK5-Fc fusion polypeptide and monomeric Fc polypeptide of SEQ ID NO: 420 and SEQ ID NO: 428, respectively, may be co-expressed and purified from a CHO cell line to give rise to a single-arm heteromeric protein complex comprising ALK5-Fc:Fc.

Purification of various ALK5-Fc:Fc complexes could be achieved by a series of column chromatography steps, including, for example, three or more of the following, in any order: protein A chromatography, Q sepharose chromatography, phenylsepharose chromatography, size exclusion chromatography, and cation exchange chromatography. The purification could be completed with viral filtration and buffer exchange.

Example 11. Generation of a Single-Arm ALK6-Fc Heterodimer

Applicants envision construction of a soluble single-arm ALK6-Fc heterodimeric complex comprising a monomeric Fc polypeptide with a short N-terminal extension and a second polypeptide in which the extracellular domain of human ALK6 is fused to a separate Fc domain with a linker positioned between the extracellular domain and this second Fc domain. The individual constructs are referred to as monomeric Fc polypeptide and ALK6-Fc fusion polypeptide, respectively, and the sequences for each are provided below. Applicants also envision additional single-arm ALK6-Fc heterodimeric complexes comprising the extracellular domain of ALK6 isoform 2 (SEQ ID NO: 92).

Formation of a single-arm ALK6-Fc heterodimer may be guided by approaches similar to those described for single-arm ActRIIB-Fc heterodimer in Example 1. In a first approach, illustrated in the ALK6-Fc and monomeric Fc polypeptide sequences of SEQ ID NOs: 131-133 and 140-142, respectively, one Fc domain is altered to introduce cationic amino acids at the interaction face, while the other Fc domain is altered to introduce anionic amino acids at the interaction face.

The ALK6-Fc fusion polypeptide employs the TPA leader and is as follows:

```
                                            (SEQ ID NO: 131)
  1 MDAMKRGLCC VLLLCGAVFV SPGAKKEDGE STAPTPRPKV LRCKCHHHCP

 51 EDSVNNICST DGYCFTMIEE DDSGLPVVTS GCLGLEGSDF QCRDTPIPHQ

101 RRSIECCTER NECNKDLHPT LPPLKNRDFV DGPIHHRTGG GTHTCPPCPA

151 PELLGGPSVF LFPPKPKDTL MISRTPEVTC VVVDVSHEDP EVKFNWYVDG
```

-continued

```
201 VEVHNAKTKP REEQYNSTYR VVSVLTVLHQ DWLNGKEYKC KVSNKALPAP

251 IEKTISKAKG QPREPQVYTL PPSREEMTKN QVSLTCLVKG FYPSDIAVEW

301 ESNGQPENNY DTTPPVLDSD GSFFLYSDLT VDKSRWQQGN VFSCSVMHEA

351 LHNHYTQKSL SLSPG
```

The leader and linker sequences are underlined. To promote formation of the ALK6-Fc:Fc heterodimer rather than either of the possible homodimeric complexes (ALK6-Fc:ALK6-Fc or Fc:Fc), two amino acid substitutions (replacing lysines with anionic amino acids) can be introduced into the Fc domain of the fusion polypeptide as indicated by double underline above. The amino acid sequence of SEQ ID NO: 131 may optionally be provided with a lysine added at the C-terminus.

This ALK6-Fc fusion polypeptide is encoded by the following nucleic acid (SEQ ID NO: 132).

```
                                                    (SEQ ID NO: 132)
   1 ATGGATGCAA TGAAGAGAGG GCTCTGCTGT GTGCTGCTGC TGTGTGGAGC

  51 AGTCTTCGTT TCGCCCGGCG CCAAGAAAGA GGATGGTGAG AGTACAGCCC

 101 CCACCCCCCG TCCAAAGGTC TTGCGTTGTA AATGCCACCA CCATTGTCCA

 151 GAAGACTCAG TCAACAATAT TTGCAGCACA GACGGATATT GTTTCACGAT

 201 GATAGAAGAG GATGACTCTG GGTTGCCTGT GGTCACTTCT GGTTGCCTAG

 251 GACTAGAAGG CTCAGATTTT CAGTGTCGGG ACACTCCCAT TCCTCATCAA

 301 AGAAGATCAA TTGAATGCTG CACAGAAAGG AACGAATGTA ATAAAGACCT

 351 ACACCCTACA CTGCCTCCAT TGAAAAACAG AGATTTTGTT GATGGACCTA

 401 TACACCACAG GACCGGTGGT GGAACTCACA CATGCCCACC GTGCCCAGCA

 451 CCTGAACTCC TGGGGGGACC GTCAGTCTTC CTCTTCCCCC CAAAACCCAA

 501 GGACACCCTC ATGATCTCCC GGACCCCTGA GGTCACATGC GTGGTGGTGG

 551 ACGTGAGCCA CGAAGACCCT GAGGTCAAGT TCAACTGGTA CGTGGACGGC

 601 GTGGAGGTGC ATAATGCCAA GACAAAGCCG CGGGAGGAGC AGTACAACAG

 651 CACGTACCGT GTGGTCAGCG TCCTCACCGT CCTGCACCAG GACTGGCTGA

 701 ATGGCAAGGA GTACAAGTGC AAGGTCTCCA ACAAAGCCCT CCCAGCCCCC

 751 ATCGAGAAAA CCATCTCCAA AGCCAAAGGG CAGCCCCGAG AACCACAGGT

 801 GTACACCCTG CCCCCATCCC GGGAGGAGAT GACCAAGAAC CAGGTCAGCC

 851 TGACCTGCCT GGTCAAAGGC TTCTATCCCA GCGACATCGC CGTGGAGTGG

 901 GAGAGCAATG GGCAGCCGGA GAACAACTAC GACACCACGC CTCCCGTGCT

 951 GGACTCCGAC GGCTCCTTCT TCCTCTATAG CGACCTCACC GTGGACAAGA

1001 GCAGGTGGCA GCAGGGGAAC GTCTTCTCAT GCTCCGTGAT GCATGAGGCT

1051 CTGCACAACC ACTACACGCA GAAGAGCCTC TCCCTGTCTC CGGGT
```

The mature ALK6-Fc fusion polypeptide sequence is as follows (SEQ ID NO: 133) and may optionally be provided with a lysine added at the C-terminus.

(SEQ ID NO: 133)
```
  1 KKEDGESTAP TPRPKVLRCK CHHHCPEDSV NNICSTDGYC FTMIEEDDSG
 51 LPVVTSGCLG LEGSDFQCRD TPIPHQRRSI ECCTERNECN KDLHPTLPPL
101 KNRDFVDGPI HHRTGGGTHT CPPCPAPELL GGPSVFLFPP KPKDTLMISR
151 TPEVTCVVVD VSHEDPEVKF NWYVDGVEVH NAKTKPREEQ YNSTYRVVSV
201 LTVLHQDWLN GKEYKCKVSN KALPAPIEKT ISKAKGQPRE PQVYTLPPSR
251 EEMTKNQVSL TCLVKGFYPS DIAVEWESNG QPENNYDTTP PVLDSDGSFF
301 LYSDLTVDKS RWQQGNVFSC SVMHEALHNH YTQKSLSLSP G
```

As described in Example 2, the complementary form of monomeric human G1Fc polypeptide (SEQ ID NO: 140) employs the TPA leader and incorporates an optional N-terminal extension. To promote formation of the ALK6-Fc:Fc heterodimer rather than either of the possible homodimeric complexes, two amino acid substitutions (replacing anionic residues with lysines) can be introduced into the monomeric Fc polypeptide as indicated. The amino acid sequence of SEQ ID NO: 140 may optionally be provided with the C-terminal lysine removed. This complementary Fc polypeptide is encoded by the nucleic acid of SEQ ID NO: 141, and the mature monomeric Fc protein (SEQ ID NO: 142) may optionally be provided with the C-terminal lysine removed.

The ALK6-Fc fusion polypeptide and monomeric Fc polypeptide of SEQ ID NO: 133 and SEQ ID NO: 142, respectively, may be co-expressed and purified from a CHO cell line to give rise to a single-arm heteromeric protein complex comprising ALK6-Fc:Fc.

In another approach to promoting the formation of heteromultimer complexes using asymmetric Fc fusion polypeptides, the Fc domains are altered to introduce complementary hydrophobic interactions and an additional intermolecular disulfide bond as illustrated in the ALK6-Fc and Fc polypeptide sequences of SEQ ID NOs: 421-422 and 427-428, respectively.

The ALK6-Fc fusion polypeptide (SEQ ID NO: 421) uses the TPA leader and is as follows:

(SEQ ID NO: 421)
```
  1 MDAMKRGLCC VLLLCGAVFV SPGAKKEDGE STAPTPRPKV LRCKCHHHCP
 51 EDSVNNICST DGYCFTMIEE DDSGLPVVTS GCLGLEGSDF QCRDTPIPHQ
101 RRSIECCTER NECNKDLHPT LPPLKNRDFV DGPIHHRTGG GTHTCPPCPA
151 PELLGGPSVF LFPPKPKDTL MISRTPEVTC VVVDVSHEDP EVKFNWYVDG
201 VEVHNAKTKP REEQYNSTYR VVSVLTVLHQ DWLNGKEYKC KVSNKALPAP
251 IEKTISKAKG QPREPQVCTL PPSREEMTKN QVSLSCAVKG FYPSDIAVEW
301 ESNGQPENNY KTTPPVLDSD GSFFLVSKLT VDKSRWQQGN VFSCSVMHEA
351 LHNHYTQKSL SLSPGK
```

-

The leader sequence and linker are underlined. To promote formation of the ALK6-Fc:Fc heterodimer rather than either of the possible homodimeric complexes, four amino acid substitutions can be introduced into the Fc domain of the ALK6 fusion polypeptide as indicated by double underline above. The amino acid sequence of SEQ ID NO: 421 may optionally be provided with the C-terminal lysine removed.

The mature ALK6-Fc fusion polypeptide (SEQ ID NO: 422) is as follows and may optionally be provided with the C-terminal lysine removed.

(SEQ ID NO: 422)
```
  1 KKEDGESTAP TPRPKVLRCK CHHHCPEDSV NNICSTDGYC FTMIEEDDSG
 51 LPVVTSGCLG LEGSDFQCRD TPIPHQRRSI ECCTERNECN KDLHPTLPPL
101 KNRDFVDGPI HHRTGGGTHT CPPCPAPELL GGPSVFLFPP KPKDTLMISR
151 TPEVTCVVVD VSHEDPEVKF NWYVDGVEVH NAKTKPREEQ YNSTYRVVSV
201 LTVLHQDWLN GKEYKCKVSN KALPAPIEKT ISKAKGQPRE PQVCTLPPSR
```

-continued

```
251 EEMTKNQVSL SCAVKGFYPS DIAVEWESNG QPENNYKTTP PVLDSDGSFF

301 LVSKLTVDKS RWQQGNVFSC SVMHEALHNH YTQKSLSLSP GK
```

As described in Example 2, the complementary form of monomeric G1Fc polypeptide (SEQ ID NO: 427) employs the TPA leader and incorporates an optional N-terminal extension. To promote formation of the ALK6-Fc:Fc heterodimer rather than either of the possible homodimeric complexes, two amino acid substitutions (replacing a serine with a cysteine and a threonine with a tryptophan) can be introduced into the monomeric Fc polypeptide as indicated. The amino acid sequence of SEQ ID NO: 427 and the mature monomeric G1Fc polypeptide (SEQ ID NO: 428) may optionally be provided with the C-terminal lysine removed.

The ALK6-Fc fusion polypeptide and monomeric Fc polypeptide of SEQ ID NO: 422 and SEQ ID NO: 428, respectively, may be co-expressed and purified from a CHO cell line to give rise to a single-arm heteromeric protein complex comprising ALK6-Fc:Fc.

Purification of various ALK6-Fc:Fc complexes could be achieved by a series of column chromatography steps, including, for example, three or more of the following, in any order: protein A chromatography, Q sepharose chromatography, phenylsepharose chromatography, size exclusion chromatography, and cation exchange chromatography. The purification could be completed with viral filtration and buffer exchange.

Example 12. Generation of a Single-Arm ALK7-Fc Heterodimer

Applicants envision construction of a soluble single-arm ALK7-Fc heterodimeric complex comprising a monomeric Fc polypeptide with a short N-terminal extension and a second polypeptide in which the N-terminally truncated (NM) extracellular domain of human ALK7 is fused to a separate Fc domain with a linker positioned between the extracellular domain and this second Fc domain. The individual constructs are referred to as monomeric Fc polypeptide and ALK7-Fc fusion polypeptide, respectively, and the sequences for each are provided below. Applicants also envision additional single-arm ALK7-Fc heterodimeric complexes comprising other N-terminally truncated variants (e.g., NΔ5 variant) of ALK7 isoform 1 (SEQ ID NO: 313), the extracellular domain of ALK7 isoform 2 (SEQ ID NO: 302), or native processed sequences of ALK7 isoforms 3 and 4 (SEQ ID NOs: 306, 310).

Formation of a single-arm ALK7-Fc heterodimer may be guided by approaches similar to those described for single-arm ActRIIB-Fc heterodimer in Example 1. In a first approach, illustrated in the ALK7-Fc and monomeric Fc polypeptide sequences of SEQ ID NOs: 134-136 and 140-142, respectively, one Fc domain is altered to introduce cationic amino acids at the interaction face, while the other Fc domain is altered to introduce anionic amino acids at the interaction face.

The ALK7-Fc fusion polypeptide employs the TPA leader and is as follows:

```
                                                  (SEQ ID NO: 134)
  1 MDAMKRGLCC VLLLCGAVFV SPGAGLKCVC LLCDSSNFTC QTEGACWASV

 51 MLTNGKEQVI KSCVSLPELN AQVFCHSSNN VTKTECCFTD FCNNITLHLP

101 TASPNAPKLG PMETGGGTHT CPPCPAPELL GGPSVFLFPP KPKDTLMISR

151 TPEVTCVVVD VSHEDPEVKF NWYVDGVEVH NAKTKPREEQ YNSTYRVVSV

201 LTVLHQDWLN GKEYKCKVSN KALPAPIEKT ISKAKGQPRE PQVYTLPPSR

251 EEMTKNQVSL TCLVKGFYPS DIAVEWESNG QPENNYDTTP PVLDSDGSFF

301 LYSDLTVDKS RWQQGNVFSC SVMHEALHNH YTQKSLSLSP G
```

The leader and linker sequences are underlined. To promote formation of the ALK7-Fc:Fc heterodimer rather than either of the possible homodimeric complexes (ALK7-Fc: ALK7-Fc or Fc:Fc), two amino acid substitutions (replacing lysines with anionic amino acids) can be introduced into the Fc domain of the fusion polypeptide as indicated by double underline above. The amino acid sequence of SEQ ID NO: 134 may optionally be provided with a lysine added at the C-terminus.

This ALK7-Fc fusion polypeptide is encoded by the following nucleic acid (SEQ ID NO: 135).

```
                                                  (SEQ ID NO: 135)
  1 ATGGATGCAA TGAAGAGAGG GCTCTGCTGT GTGCTGCTGC TGTGTGGAGC

 51 AGTCTTCGTT TCGCCCGGCG CCGGACTGAA GTGTGTATGT CTTTTGTGTG

101 ATTCTTCAAA CTTTACCTGC CAAACAGAAG GAGCATGTTG GGCATCAGTC

151 ATGCTAACCA ATGGAAAAGA GCAGGTGATC AAATCCTGTG TCTCCCTTCC

201 AGAACTGAAT GCTCAAGTCT TCTGTCATAG TTCCAACAAT GTTACCAAAA

251 CCGAATGCTG CTTCACAGAT TTTTGCAACA ACATAACACT GCACCTTCCA
```

-continued

```
301 ACAGCATCAC CAAATGCCCC AAAACTTGGA CCCATGGAGA CCGGTGGTGG
351 AACTCACACA TGCCCACCGT GCCCAGCACC TGAACTCCTG GGGGGACCGT
401 CAGTCTTCCT CTTCCCCCCA AAACCCAAGG ACACCCTCAT GATCTCCCGG
451 ACCCCTGAGG TCACATGCGT GGTGGTGGAC GTGAGCCACG AAGACCCTGA
501 GGTCAAGTTC AACTGGTACG TGGACGGCGT GGAGGTGCAT AATGCCAAGA
551 CAAAGCCGCG GGAGGAGCAG TACAACAGCA CGTACCGTGT GGTCAGCGTC
601 CTCACCGTCC TGCACCAGGA CTGGCTGAAT GGCAAGGAGT ACAAGTGCAA
651 GGTCTCCAAC AAAGCCCTCC CAGCCCCCAT CGAGAAAACC ATCTCCAAAG
701 CCAAAGGGCA GCCCCGAGAA CCACAGGTGT ACACCCTGCC CCCATCCCGG
751 GAGGAGATGA CCAAGAACCA GGTCAGCCTG ACCTGCCTGG TCAAAGGCTT
801 CTATCCCAGC GACATCGCCG TGGAGTGGGA GAGCAATGGG CAGCCGGAGA
851 ACAACTACGA CACCACGCCT CCCGTGCTGG ACTCCGACGG CTCCTTCTTC
901 CTCTATAGCG ACCTCACCGT GGACAAGAGC AGGTGGCAGC AGGGGAACGT
951 CTTCTCATGC TCCGTGATGC ATGAGGCTCT GCACAACCAC TACACGCAGA
1001 AGAGCCTCTC CCTGTCTCCG GGT
```

The mature ALK7-Fc fusion polypeptide sequence is expected to be as follows (SEQ ID NO: 136) and may optionally be provided with a lysine added at the C-terminus.

```
                                                   (SEQ ID NO: 136)
  1 GLKCVCLLCD SSNFTCQTEG ACWASVMLTN GKEQVIKSCV SLPELNAQVF
 51 CHSSNNVTKT ECCFTDFCNN ITLHLPTASP NAPKLGPMET GGGTHTCPPC
101 PAPELLGGPS VFLFPPKPKD TLMISRTPEV TCVVVDVSHE DPEVKFNWYV
151 DGVEVHNAKT KPREEQYNST YRVVSVLTVL HQDWLNGKEY KCKVSNKALP
201 APIEKTISKA KGQPREPQVY TLPPSREEMT KNQVSLTCLV KGFYPSDIAV
251 EWESNGQPEN NYDTTPPVLD SDGSFFLYSD LTVDKSRWQQ GNVFSCSVMH
301 EALHNHYTQK SLSLSPG
```

As described in Example 2, the complementary form of monomeric human G1Fc polypeptide (SEQ ID NO: 140) employs the TPA leader and incorporates an optional N-terminal extension. To promote formation of the ALK7-Fc:Fc heterodimer rather than either of the possible homodimeric complexes, two amino acid substitutions (replacing anionic residues with lysines) can be introduced into the monomeric Fc polypeptide as indicated. The amino acid sequence of SEQ ID NO: 140 may optionally be provided with the C-terminal lysine removed. This complementary Fc polypeptide is encoded by the nucleic acid of SEQ ID NO: 141, and the mature monomeric Fc polypeptide (SEQ ID NO: 142) may optionally be provided with the C-terminal lysine removed.

The ALK7-Fc fusion polypeptide and monomeric Fc polypeptide of SEQ ID NO: 136 and SEQ ID NO: 142, respectively, may be co-expressed and purified from a CHO cell line to give rise to a single-arm heteromeric protein complex comprising ALK7-Fc:Fc.

In another approach to promoting the formation of heteromultimer complexes using asymmetric Fc fusion polypeptides, the Fc domains are altered to introduce complementary hydrophobic interactions and an additional intermolecular disulfide bond as illustrated in the ALK7-Fc and Fc polypeptide sequences of SEQ ID NOs: 423-424 and 427-428, respectively.

The ALK7-Fc fusion polypeptide (SEQ ID NO: 423) uses the TPA leader and is as follows:

(SEQ ID NO: 423)

```
  1 MDAMKRGLCC VLLLCGAVFV SPGAGLKCVC LLCDSSNFTC QTEGACWASV
 51 MLTNGKEQVI KSCVSLPELN AQVFCHSSNN VTKTECCFTD FCNNITLHLP
101 TASPNAPKLG PMETGGGTHT CPPCPAPELL GGPSVFLFPP KPKDTLMISR
151 TPEVTCVVVD VSHEDPEVKF NWYVDGVEVH NAKTKPREEQ YNSTYRVVSV
201 LTVLHQDWLN GKEYKCKVSN KALPAPIEKT ISKAKGQPRE PQVCTLPPSR
251 EEMTKNQVSL SCAVKGFYPS DIAVEWESNG QPENNYKTTP PVLDSDGSFF
301 LVSKLTVDKS RWQQGNVFSC SVMHEALHNH YTQKSLSLSP GK
```

The leader sequence and linker are underlined. To promote formation of the ALK7-Fc:Fc heterodimer rather than either of the possible homodimeric complexes, four amino acid substitutions can be introduced into the Fc domain of the ALK7 fusion polypeptide as indicated by double underline above. The amino acid sequence of SEQ ID NO: 423 may optionally be provided with the C-terminal lysine removed.

The mature ALK7-Fc fusion polypeptide (SEQ ID NO: 424) is expected to be as follows and may optionally be provided with the C-terminal lysine removed.

(SEQ ID NO: 424)

```
  1 GLKCVCLLCD SSNFTCQTEG ACWASVMLTN GKEQVIKSCV SLPELNAQVF
 51 CHSSNNVTKT ECCFTDFCNN ITLHLPTASP NAPKLGPMET GGGTHTCPPC
101 PAPELLGGPS VFLFPPKPKD TLMISRTPEV TCVVVDVSHE DPEVKFNWYV
151 DGVEVHNAKT KPREEQYNST YRVVSVLTVL HQDWLNGKEY KCKVSNKALP
201 APIEKTISKA KGQPREPQVC TLPPSREEMT KNQVSLSCAV KGFYPSDIAV
251 EWESNGQPEN NYKTTPPVLD SDGSFFLVSK LTVDKSRWQQ GNVFSCSVMH
301 EALHNHYTQK SLSLSPGK
```

As described in Example 2, the complementary form of monomeric G1Fc polypeptide (SEQ ID NO: 427) employs the TPA leader and incorporates an optional N-terminal extension. To promote formation of the ALK7-Fc:Fc heterodimer rather than either of the possible homodimeric complexes, two amino acid substitutions (replacing a serine with a cysteine and a threonine with a tryptophan) can be introduced into the monomeric Fc polypeptide as indicated. The amino acid sequence of SEQ ID NO: 427 and the mature monomeric G1Fc polypeptide (SEQ ID NO: 428) may optionally be provided with the C-terminal lysine removed.

The ALK7-Fc fusion polypeptide and monomeric Fc polypeptide of SEQ ID NO: 424 and SEQ ID NO: 428, respectively, may be co-expressed and purified from a CHO cell line to give rise to a single-arm heteromeric protein complex comprising ALK7-Fc:Fc.

Purification of various ALK7-Fc:Fc complexes could be achieved by a series of column chromatography steps, including, for example, three or more of the following, in any order: protein A chromatography, Q sepharose chromatography, phenylsepharose chromatography, size exclusion chromatography, and cation exchange chromatography. The purification could be completed with viral filtration and buffer exchange.

Together these examples demonstrate that type I or type II receptor polypeptides, when placed in the context of a single-arm heteromeric protein complex, form novel binding pockets that exhibit altered selectivity relative to a homodimeric complex of the same receptor polypeptide, allowing the formation of novel protein agents for possible use as therapeutic agents.

We claim:

1. A protein complex comprising a first polypeptide covalently or non-covalently associated with a second polypeptide, wherein:

a. the first polypeptide comprises a TGFβ superfamily type I or type II receptor polypeptide, wherein the TGFβ superfamily type I or type II receptor polypeptide is TGFBRII, and a first constant region from an IgG heavy chain, and wherein the first polypeptide comprises an amino acid sequence that is at least 90% identical to the sequence of any of SEQ ID NOS: 113, 115, 409 and 410; and b. the second polypeptide comprises a second constant region from an IgG heavy chain, and wherein the second polypeptide does not comprise a TGFβ superfamily type I or type II receptor polypeptide, and wherein the protein complex exhibits binding to one or more TGF-beta superfamily ligands selected from TGF-β1, TGF-β2, and TGF-β3.

2. The protein complex of claim 1, wherein the protein complex is a recombinant heterodimer.

3. The protein complex of claim 1, wherein the second constant region from an IgG heavy chain is an immunoglobulin Fc domain.

4. The protein complex of claim 1, wherein the first constant region from an IgG heavy chain comprises an amino acid sequence that is at least 90% identical to a sequence selected from any one of SEQ ID NOs: 200-214.

5. The protein complex of claim 1, wherein the second constant region from an IgG heavy chain comprises an amino acid sequence that is at least 90% identical to a sequence selected from any one of SEQ ID NOs: 200-214.

6. The protein complex of claim 1, wherein the first polypeptide comprises an amino acid sequence that is at least 95% identical to a sequence selected from any one of SEQ ID NOs: 113, 115, 409, and 410.

7. The protein complex of claim 1, wherein the second constant region from an IgG heavy chain comprises an amino acid sequence comprises an amino acid sequence that is at least 95% identical to a sequence selected from any one of SEQ ID NOs: 139 and 426.

8. The protein complex of claim 1, wherein the first polypeptide and/or second polypeptide comprises one or more modified amino acid residues selected from: a glycosylated amino acid, a PEGylated amino acid, a farnesylated amino acid, an acetylated amino acid, a biotinylated amino acid, and an amino acid conjugated to a lipid moiety.

9. The protein complex of claim 1, wherein the first polypeptide and/or second polypeptide is glycosylated and has a glycosylation pattern obtainable from expression of the type I receptor polypeptide in a CHO cell.

10. The protein complex of claim 1, wherein the protein complex has one or more of the following characteristics: i) binds to the TGF-beta superfamily ligand with a $K_D$ of less than or equal to 10-7; and ii) inhibits TGF-beta superfamily type I and/or type II receptor-mediated signaling transduction in a cell.

11. A pharmaceutical preparation comprising the protein complex of claim 1 and a pharmaceutically acceptable carrier.

12. The pharmaceutical preparation of claim 11, wherein the preparation is adapted for parenteral administration.

13. The protein complex of claim 1, wherein the first polypeptide comprises the amino acid sequence of any one of SEQ ID NOs: 113, 115, 409, and 410.

14. The protein complex of claim 1, wherein the second constant region from an IgG heavy chain comprises the amino acid sequence of SEQ ID NO: 139 or 426.

15. The recombinant protein complex of claim 1, wherein the protein complex exhibits weak or substantially no binding to BMP9 and/or BMP10.

* * * * *

SEQUENCE LISTING

<160> NUMBER OF SEQ ID NOS: 510

<210> SEQ ID NO 1
<211> LENGTH: 512
<212> TYPE: PRT
<213> ORGANISM: Homo sapiens

<400> SEQUENCE: 1

Met Thr Ala Pro Trp Val Ala Leu Ala Leu Leu Trp Gly Ser Leu Cys
1 5 10 15

Ala Gly Ser Gly Arg Gly Glu Ala Glu Thr Arg Glu Cys Ile Tyr Tyr
20 25 30

Asn Ala Asn Trp Glu Leu Glu Arg Thr Asn Gln Ser Gly Leu Glu Arg
35 40 45

Cys Glu Gly Glu Gln Asp Lys Arg Leu His Cys Tyr Ala Ser Trp Arg
50 55 60

Asn Ser Ser Gly Thr Ile Glu Leu Val Lys Lys Gly Cys Trp Leu Asp
65 70 75 80

Asp Phe Asn Cys Tyr Asp Arg Gln Glu Cys Val Ala Thr Glu Glu Asn
85 90 95

Pro Gln Val Tyr Phe Cys Cys Cys Glu Gly Asn Phe Cys Asn Glu Arg
100 105 110

Phe Thr His Leu Pro Glu Ala Gly Gly Pro Glu Val Thr Tyr Glu Pro
115 120 125

Pro Pro Thr Ala Pro Thr Leu Leu Thr Val Leu Ala Tyr Ser Leu Leu
130 135 140

Pro Ile Gly Gly Leu Ser Leu Ile Val Leu Leu Ala Phe Trp Met Tyr
145 150 155 160

Arg His Arg Lys Pro Pro Tyr Gly His Val Asp Ile His Glu Asp Pro
165 170 175

Gly Pro Pro Pro Pro Ser Pro Leu Val Gly Leu Lys Pro Leu Gln Leu
180 185 190

Leu Glu Ile Lys Ala Arg Gly Arg Phe Gly Cys Val Trp Lys Ala Gln
195 200 205

Leu Met Asn Asp Phe Val Ala Val Lys Ile Phe Pro Leu Gln Asp Lys
210 215 220

Gln Ser Trp Gln Ser Glu Arg Glu Ile Phe Ser Thr Pro Gly Met Lys
225 230 235 240

His Glu Asn Leu Leu Gln Phe Ile Ala Ala Glu Lys Arg Gly Ser Asn
245 250 255

Leu Glu Val Glu Leu Trp Leu Ile Thr Ala Phe His Asp Lys Gly Ser
260 265 270

Leu Thr Asp Tyr Leu Lys Gly Asn Ile Ile Thr Trp Asn Glu Leu Cys
275 280 285

His Val Ala Glu Thr Met Ser Arg Gly Leu Ser Tyr Leu His Glu Asp
290 295 300

Val Pro Trp Cys Arg Gly Glu Gly His Lys Pro Ser Ile Ala His Arg
305 310 315 320

Asp Phe Lys Ser Lys Asn Val Leu Leu Lys Ser Asp Leu Thr Ala Val
325 330 335

Leu Ala Asp Phe Gly Leu Ala Val Arg Phe Glu Pro Gly Lys Pro Pro
340 345 350

Gly Asp Thr His Gly Gln Val Gly Thr Arg Arg Tyr Met Ala Pro Glu
355 360 365

Val Leu Glu Gly Ala Ile Asn Phe Gln Arg Asp Ala Phe Leu Arg Ile
370 375 380

Asp Met Tyr Ala Met Gly Leu Val Leu Trp Glu Leu Val Ser Arg Cys
385 390 395 400

Lys Ala Ala Asp Gly Pro Val Asp Glu Tyr Met Leu Pro Phe Glu Glu
405 410 415

Glu Ile Gly Gln His Pro Ser Leu Glu Glu Leu Gln Glu Val Val Val
420 425 430

His Lys Lys Met Arg Pro Thr Ile Lys Asp His Trp Leu Lys His Pro
435 440 445

Gly Leu Ala Gln Leu Cys Val Thr Ile Glu Glu Cys Trp Asp His Asp
450 455 460

Ala Glu Ala Arg Leu Ser Ala Gly Cys Val Glu Glu Arg Val Ser Leu
465 470 475 480

Ile Arg Arg Ser Val Asn Gly Thr Thr Ser Asp Cys Leu Val Ser Leu
485 490 495

Val Thr Ser Val Thr Asn Val Asp Leu Pro Pro Lys Glu Ser Ser Ile
500 505 510

<210> SEQ ID NO 2
<211> LENGTH: 115
<212> TYPE: PRT
<213> ORGANISM: Homo sapiens

<400> SEQUENCE: 2

Gly Arg Gly Glu Ala Glu Thr Arg Glu Cys Ile Tyr Tyr Asn Ala Asn
1 5 10 15

Trp Glu Leu Glu Arg Thr Asn Gln Ser Gly Leu Glu Arg Cys Glu Gly
20 25 30

Glu Gln Asp Lys Arg Leu His Cys Tyr Ala Ser Trp Arg Asn Ser Ser
35 40 45

Gly Thr Ile Glu Leu Val Lys Lys Gly Cys Trp Leu Asp Asp Phe Asn
50 55 60

Cys Tyr Asp Arg Gln Glu Cys Val Ala Thr Glu Glu Asn Pro Gln Val
65 70 75 80

Tyr Phe Cys Cys Cys Glu Gly Asn Phe Cys Asn Glu Arg Phe Thr His
85 90 95

Leu Pro Glu Ala Gly Gly Pro Glu Val Thr Tyr Glu Pro Pro Pro Thr
100 105 110

Ala Pro Thr
115

<210> SEQ ID NO 3
<211> LENGTH: 100
<212> TYPE: PRT
<213> ORGANISM: Homo sapiens

<400> SEQUENCE: 3

Gly Arg Gly Glu Ala Glu Thr Arg Glu Cys Ile Tyr Tyr Asn Ala Asn
1 5 10 15

Trp Glu Leu Glu Arg Thr Asn Gln Ser Gly Leu Glu Arg Cys Glu Gly
20 25 30

Glu Gln Asp Lys Arg Leu His Cys Tyr Ala Ser Trp Arg Asn Ser Ser
35 40 45

Gly Thr Ile Glu Leu Val Lys Lys Gly Cys Trp Leu Asp Asp Phe Asn
50 55 60

Cys Tyr Asp Arg Gln Glu Cys Val Ala Thr Glu Glu Asn Pro Gln Val
65 70 75 80

Tyr Phe Cys Cys Cys Glu Gly Asn Phe Cys Asn Glu Arg Phe Thr His
85 90 95

Leu Pro Glu Ala
100

<210> SEQ ID NO 4
<211> LENGTH: 512
<212> TYPE: PRT
<213> ORGANISM: Homo sapiens

<400> SEQUENCE: 4

Met Thr Ala Pro Trp Val Ala Leu Ala Leu Leu Trp Gly Ser Leu Cys
1 5 10 15

Ala Gly Ser Gly Arg Gly Glu Ala Glu Thr Arg Glu Cys Ile Tyr Tyr
20 25 30

Asn Ala Asn Trp Glu Leu Glu Arg Thr Asn Gln Ser Gly Leu Glu Arg
35 40 45

Cys Glu Gly Glu Gln Asp Lys Arg Leu His Cys Tyr Ala Ser Trp Ala
50 55 60

Asn Ser Ser Gly Thr Ile Glu Leu Val Lys Lys Gly Cys Trp Leu Asp
65 70 75 80

Asp Phe Asn Cys Tyr Asp Arg Gln Glu Cys Val Ala Thr Glu Glu Asn
85 90 95

Pro Gln Val Tyr Phe Cys Cys Cys Glu Gly Asn Phe Cys Asn Glu Arg
100 105 110

Phe Thr His Leu Pro Glu Ala Gly Gly Pro Glu Val Thr Tyr Glu Pro
115 120 125

Pro Pro Thr Ala Pro Thr Leu Leu Thr Val Leu Ala Tyr Ser Leu Leu
130 135 140

Pro Ile Gly Gly Leu Ser Leu Ile Val Leu Leu Ala Phe Trp Met Tyr
145 150 155 160

Arg His Arg Lys Pro Pro Tyr Gly His Val Asp Ile His Glu Asp Pro
165 170 175

Gly Pro Pro Pro Pro Ser Pro Leu Val Gly Leu Lys Pro Leu Gln Leu
180 185 190

Leu Glu Ile Lys Ala Arg Gly Arg Phe Gly Cys Val Trp Lys Ala Gln
195 200 205

Leu Met Asn Asp Phe Val Ala Val Lys Ile Phe Pro Leu Gln Asp Lys
210 215 220

Gln Ser Trp Gln Ser Glu Arg Glu Ile Phe Ser Thr Pro Gly Met Lys
225 230 235 240

His Glu Asn Leu Leu Gln Phe Ile Ala Ala Glu Lys Arg Gly Ser Asn
245 250 255

Leu Glu Val Glu Leu Trp Leu Ile Thr Ala Phe His Asp Lys Gly Ser
260 265 270

Leu Thr Asp Tyr Leu Lys Gly Asn Ile Ile Thr Trp Asn Glu Leu Cys
275 280 285

His Val Ala Glu Thr Met Ser Arg Gly Leu Ser Tyr Leu His Glu Asp
290 295 300

Val Pro Trp Cys Arg Gly Glu Gly His Lys Pro Ser Ile Ala His Arg
305 310 315 320

Asp Phe Lys Ser Lys Asn Val Leu Leu Lys Ser Asp Leu Thr Ala Val
325 330 335

-continued

Leu Ala Asp Phe Gly Leu Ala Val Arg Phe Glu Pro Gly Lys Pro Pro
340 345 350

Gly Asp Thr His Gly Gln Val Gly Thr Arg Arg Tyr Met Ala Pro Glu
355 360 365

Val Leu Glu Gly Ala Ile Asn Phe Gln Arg Asp Ala Phe Leu Arg Ile
370 375 380

Asp Met Tyr Ala Met Gly Leu Val Leu Trp Glu Leu Val Ser Arg Cys
385 390 395 400

Lys Ala Ala Asp Gly Pro Val Asp Glu Tyr Met Leu Pro Phe Glu Glu
405 410 415

Glu Ile Gly Gln His Pro Ser Leu Glu Glu Leu Gln Glu Val Val Val
420 425 430

His Lys Lys Met Arg Pro Thr Ile Lys Asp His Trp Leu Lys His Pro
435 440 445

Gly Leu Ala Gln Leu Cys Val Thr Ile Glu Glu Cys Trp Asp His Asp
450 455 460

Ala Glu Ala Arg Leu Ser Ala Gly Cys Val Glu Glu Arg Val Ser Leu
465 470 475 480

Ile Arg Arg Ser Val Asn Gly Thr Thr Ser Asp Cys Leu Val Ser Leu
485 490 495

Val Thr Ser Val Thr Asn Val Asp Leu Pro Pro Lys Glu Ser Ser Ile
500 505 510

<210> SEQ ID NO 5
<211> LENGTH: 115
<212> TYPE: PRT
<213> ORGANISM: Homo sapiens

<400> SEQUENCE: 5

Gly Arg Gly Glu Ala Glu Thr Arg Glu Cys Ile Tyr Tyr Asn Ala Asn
1 5 10 15

Trp Glu Leu Glu Arg Thr Asn Gln Ser Gly Leu Glu Arg Cys Glu Gly
20 25 30

Glu Gln Asp Lys Arg Leu His Cys Tyr Ala Ser Trp Ala Asn Ser Ser
35 40 45

Gly Thr Ile Glu Leu Val Lys Lys Gly Cys Trp Leu Asp Asp Phe Asn
50 55 60

Cys Tyr Asp Arg Gln Glu Cys Val Ala Thr Glu Glu Asn Pro Gln Val
65 70 75 80

Tyr Phe Cys Cys Cys Glu Gly Asn Phe Cys Asn Glu Arg Phe Thr His
85 90 95

Leu Pro Glu Ala Gly Gly Pro Glu Val Thr Tyr Glu Pro Pro Pro Thr
100 105 110

Ala Pro Thr
115

<210> SEQ ID NO 6
<211> LENGTH: 100
<212> TYPE: PRT
<213> ORGANISM: Homo sapiens

<400> SEQUENCE: 6

Gly Arg Gly Glu Ala Glu Thr Arg Glu Cys Ile Tyr Tyr Asn Ala Asn
1 5 10 15

Trp Glu Leu Glu Arg Thr Asn Gln Ser Gly Leu Glu Arg Cys Glu Gly
20 25 30

```
Glu Gln Asp Lys Arg Leu His Cys Tyr Ala Ser Trp Ala Asn Ser Ser
        35                  40                  45

Gly Thr Ile Glu Leu Val Lys Lys Gly Cys Trp Leu Asp Asp Phe Asn
    50                  55                  60

Cys Tyr Asp Arg Gln Glu Cys Val Ala Thr Glu Glu Asn Pro Gln Val
65                  70                  75                  80

Tyr Phe Cys Cys Cys Glu Gly Asn Phe Cys Asn Glu Arg Phe Thr His
                85                  90                  95

Leu Pro Glu Ala
            100


<210> SEQ ID NO 7
<211> LENGTH: 1536
<212> TYPE: DNA
<213> ORGANISM: Homo sapiens

<400> SEQUENCE: 7

atgacggcgc cctgggtggc cctcgccctc ctctggggat cgctgtgcgc cggctctggg     60

cgtggggagg ctgagacacg ggagtgcatc tactacaacg ccaactggga gctggagcgc    120

accaaccaga gcggcctgga gcgctgcgaa ggcgagcagg acaagcggct gcactgctac    180

gcctcctggc gcaacagctc tggcaccatc gagctcgtga agaagggctg ctggctagat    240

gacttcaact gctacgatag gcaggagtgt gtggccactg aggagaaccc ccaggtgtac    300

ttctgctgct gtgaaggcaa cttctgcaac gaacgcttca ctcatttgcc agaggctggg    360

ggcccggaag tcacgtacga gccacccccg acagccccca ccctgctcac ggtgctggcc    420

tactcactgc tgcccatcgg gggcctttcc ctcatcgtcc tgctggcctt ttggatgtac    480

cggcatcgca agccccccta cggtcatgtg gacatccatg aggaccctgg gcctccacca    540

ccatcccctc tggtgggcct gaagccactg cagctgctgg agatcaaggc tcgggggcgc    600

tttggctgtg tctggaaggc ccagctcatg aatgactttg tagctgtcaa gatcttccca    660

ctccaggaca agcagtcgtg gcagagtgaa cgggagatct tcagcacacc tggcatgaag    720

cacgagaacc tgctacagtt cattgctgcc gagaagcgag gctccaacct cgaagtagag    780

ctgtggctca tcacggcctt ccatgacaag ggctccctca cggattacct caaggggaac    840

atcatcacat ggaacgaact gtgtcatgta gcagagacga tgtcacgagg cctctcatac    900

ctgcatgagg atgtgccctg gtgccgtggc gagggccaca agccgtctat tgcccacagg    960

gactttaaaa gtaagaatgt attgctgaag agcgacctca cagccgtgct ggctgacttt   1020

ggcttggctg ttcgatttga gccagggaaa cctccagggg acacccacgg acaggtaggc   1080

acgagacggt acatggctcc tgaggtgctc gagggagcca tcaacttcca gagagatgcc   1140

ttcctgcgca ttgacatgta tgccatgggg ttggtgctgt gggagcttgt gtctcgctgc   1200

aaggctgcag acggacccgt ggatgagtac atgctgccct ttgaggaaga gattggccag   1260

cacccttcgt tggaggagct gcaggaggtg gtggtgcaca agaagatgag gcccaccatt   1320

aaagatcact ggttgaaaca cccgggcctg gcccagcttt gtgtgaccat cgaggagtgc   1380

tgggaccatg atgcagaggc tcgcttgtcc gcgggctgtg tggaggagcg ggtgtccctg   1440

attcggaggt cggtcaacgg cactacctcg gactgtctcg tttccctggt gacctctgtc   1500

accaatgtgg acctgccccc taaagagtca agcatc                              1536


<210> SEQ ID NO 8
<211> LENGTH: 345
```

<212> TYPE: DNA
<213> ORGANISM: Homo sapiens

<400> SEQUENCE: 8
gggcgtgggg aggctgagac acgggagtgc atctactaca acgccaactg ggagctggag 60
cgcaccaacc agagcggcct ggagcgctgc gaaggcgagc aggacaagcg gctgcactgc 120
tacgcctcct ggcgcaacag ctctggcacc atcgagctcg tgaagaaggg ctgctggcta 180
gatgacttca actgctacga taggcaggag tgtgtggcca ctgaggagaa cccccaggtg 240
tacttctgct gctgtgaagg caacttctgc aacgaacgct tcactcattt gccagaggct 300
gggggcccgg aagtcacgta cgagccaccc ccgacagccc ccacc 345

<210> SEQ ID NO 9
<211> LENGTH: 513
<212> TYPE: PRT
<213> ORGANISM: Homo sapiens

<400> SEQUENCE: 9

Met Gly Ala Ala Ala Lys Leu Ala Phe Ala Val Phe Leu Ile Ser Cys
1 5 10 15

Ser Ser Gly Ala Ile Leu Gly Arg Ser Glu Thr Gln Glu Cys Leu Phe
20 25 30

Phe Asn Ala Asn Trp Glu Lys Asp Arg Thr Asn Gln Thr Gly Val Glu
35 40 45

Pro Cys Tyr Gly Asp Lys Asp Lys Arg Arg His Cys Phe Ala Thr Trp
50 55 60

Lys Asn Ile Ser Gly Ser Ile Glu Ile Val Lys Gln Gly Cys Trp Leu
65 70 75 80

Asp Asp Ile Asn Cys Tyr Asp Arg Thr Asp Cys Val Glu Lys Lys Asp
85 90 95

Ser Pro Glu Val Tyr Phe Cys Cys Cys Glu Gly Asn Met Cys Asn Glu
100 105 110

Lys Phe Ser Tyr Phe Pro Glu Met Glu Val Thr Gln Pro Thr Ser Asn
115 120 125

Pro Val Thr Pro Lys Pro Pro Tyr Tyr Asn Ile Leu Leu Tyr Ser Leu
130 135 140

Val Pro Leu Met Leu Ile Ala Gly Ile Val Ile Cys Ala Phe Trp Val
145 150 155 160

Tyr Arg His His Lys Met Ala Tyr Pro Pro Val Leu Val Pro Thr Gln
165 170 175

Asp Pro Gly Pro Pro Pro Pro Ser Pro Leu Leu Gly Leu Lys Pro Leu
180 185 190

Gln Leu Leu Glu Val Lys Ala Arg Gly Arg Phe Gly Cys Val Trp Lys
195 200 205

Ala Gln Leu Leu Asn Glu Tyr Val Ala Val Lys Ile Phe Pro Ile Gln
210 215 220

Asp Lys Gln Ser Trp Gln Asn Glu Tyr Glu Val Tyr Ser Leu Pro Gly
225 230 235 240

Met Lys His Glu Asn Ile Leu Gln Phe Ile Gly Ala Glu Lys Arg Gly
245 250 255

Thr Ser Val Asp Val Asp Leu Trp Leu Ile Thr Ala Phe His Glu Lys
260 265 270

Gly Ser Leu Ser Asp Phe Leu Lys Ala Asn Val Val Ser Trp Asn Glu
275 280 285

```
Leu Cys His Ile Ala Glu Thr Met Ala Arg Gly Leu Ala Tyr Leu His
    290                 295                 300

Glu Asp Ile Pro Gly Leu Lys Asp Gly His Lys Pro Ala Ile Ser His
305                 310                 315                 320

Arg Asp Ile Lys Ser Lys Asn Val Leu Leu Lys Asn Asn Leu Thr Ala
                325                 330                 335

Cys Ile Ala Asp Phe Gly Leu Ala Leu Lys Phe Glu Ala Gly Lys Ser
            340                 345                 350

Ala Gly Asp Thr His Gly Gln Val Gly Thr Arg Arg Tyr Met Ala Pro
        355                 360                 365

Glu Val Leu Glu Gly Ala Ile Asn Phe Gln Arg Asp Ala Phe Leu Arg
    370                 375                 380

Ile Asp Met Tyr Ala Met Gly Leu Val Leu Trp Glu Leu Ala Ser Arg
385                 390                 395                 400

Cys Thr Ala Ala Asp Gly Pro Val Asp Glu Tyr Met Leu Pro Phe Glu
                405                 410                 415

Glu Glu Ile Gly Gln His Pro Ser Leu Glu Asp Met Gln Glu Val Val
            420                 425                 430

Val His Lys Lys Lys Arg Pro Val Leu Arg Asp Tyr Trp Gln Lys His
        435                 440                 445

Ala Gly Met Ala Met Leu Cys Glu Thr Ile Glu Glu Cys Trp Asp His
    450                 455                 460

Asp Ala Glu Ala Arg Leu Ser Ala Gly Cys Val Gly Glu Arg Ile Thr
465                 470                 475                 480

Gln Met Gln Arg Leu Thr Asn Ile Ile Thr Thr Glu Asp Ile Val Thr
                485                 490                 495

Val Val Thr Met Val Thr Asn Val Asp Phe Pro Pro Lys Glu Ser Ser
            500                 505                 510

Leu


<210> SEQ ID NO 10
<211> LENGTH: 115
<212> TYPE: PRT
<213> ORGANISM: Homo sapiens

<400> SEQUENCE: 10

Ile Leu Gly Arg Ser Glu Thr Gln Glu Cys Leu Phe Phe Asn Ala Asn
1               5                   10                  15

Trp Glu Lys Asp Arg Thr Asn Gln Thr Gly Val Glu Pro Cys Tyr Gly
            20                  25                  30

Asp Lys Asp Lys Arg Arg His Cys Phe Ala Thr Trp Lys Asn Ile Ser
        35                  40                  45

Gly Ser Ile Glu Ile Val Lys Gln Gly Cys Trp Leu Asp Asp Ile Asn
    50                  55                  60

Cys Tyr Asp Arg Thr Asp Cys Val Glu Lys Lys Asp Ser Pro Glu Val
65                  70                  75                  80

Tyr Phe Cys Cys Cys Glu Gly Asn Met Cys Asn Glu Lys Phe Ser Tyr
                85                  90                  95

Phe Pro Glu Met Glu Val Thr Gln Pro Thr Ser Asn Pro Val Thr Pro
            100                 105                 110

Lys Pro Pro
        115


<210> SEQ ID NO 11
<211> LENGTH: 100
```

<212> TYPE: PRT
<213> ORGANISM: Homo sapiens

<400> SEQUENCE: 11

Ile Leu Gly Arg Ser Glu Thr Gln Glu Cys Leu Phe Phe Asn Ala Asn
1               5                   10                  15

Trp Glu Lys Asp Arg Thr Asn Gln Thr Gly Val Glu Pro Cys Tyr Gly
            20                  25                  30

Asp Lys Asp Lys Arg Arg His Cys Phe Ala Thr Trp Lys Asn Ile Ser
        35                  40                  45

Gly Ser Ile Glu Ile Val Lys Gln Gly Cys Trp Leu Asp Asp Ile Asn
    50                  55                  60

Cys Tyr Asp Arg Thr Asp Cys Val Glu Lys Lys Asp Ser Pro Glu Val
65                  70                  75                  80

Tyr Phe Cys Cys Cys Glu Gly Asn Met Cys Asn Glu Lys Phe Ser Tyr
                85                  90                  95

Phe Pro Glu Met
            100

<210> SEQ ID NO 12
<211> LENGTH: 1539
<212> TYPE: DNA
<213> ORGANISM: Homo sapiens

<400> SEQUENCE: 12
atgggagctg ctgcaaagtt ggcgtttgcc gtctttctta tctcctgttc ttcaggtgct 60
atacttggta gatcagaaac tcaggagtgt cttttcttta atgctaattg ggaaaaagac 120
agaaccaatc aaactggtgt tgaaccgtgt tatggtgaca aagataaacg gcggcattgt 180
tttgctacct ggaagaatat ttctggttcc attgaaatag tgaaacaagg ttgttggctg 240
gatgatatca actgctatga caggactgat tgtgtagaaa aaaaagacag ccctgaagta 300
tatttttgtt gctgtgaggg caatatgtgt aatgaaaagt ttcttattt tccggagatg 360 gaagtcacac agcccacttc aaatccagtt acacctaagc caccctatta caacatcctg 420
ctctattcct tggtgccact tatgttaatt gcggggattg tcatttgtgc attttgggtg 480
tacaggcatc acaagatggc ctaccctcct gtacttgttc caactcaaga cccaggacca 540
cccccacctt ctccattact aggtttgaaa ccactgcagt tattagaagt gaaagcaagg 600
ggaagatttg gttgtgtctg gaaagcccag ttgcttaacg aatatgtggc tgtcaaaata 660
tttccaatac aggacaaaca gtcatggcaa aatgaatacg aagtctacag tttgcctgga 720
atgaagcatg agaacatatt acagttcatt ggtgcagaaa aacgaggcac cagtgttgat 780
gtggatcttt ggctgatcac agcatttcat gaaaagggtt cactatcaga ctttcttaag 840
gctaatgtgg tctcttggaa tgaactgtgt catattgcag aaaccatggc tagaggattg 900
gcatatttac atgaggatat acctggccta aaagatggcc acaaacctgc catatctcac 960
agggacatca aaagtaaaaa tgtgctgttg aaaaacaacc tgacagcttg cattgctgac 1020
tttgggttgg ccttaaaatt tgaggctggc aagtctgcag gcgataccca tggacaggtt 1080
ggtacccgga ggtacatggc tccagaggta ttagagggtg ctataaactt ccaaagggat 1140
gcatttttga ggatagatat gtatgccatg ggattagtcc tatgggaact ggcttctcgc 1200
tgtactgctg cagatggacc tgtagatgaa tacatgttgc catttgagga ggaaattggc 1260
cagcatccat ctcttgaaga catgcaggaa gttgttgtgc ataaaaaaaa gaggcctgtt 1320
ttaagagatt attggcagaa acatgctgga atggcaatgc tctgtgaaac cattgaagaa 1380
tgttgggatc acgacgcaga agccaggtta tcagctggat gtgtaggtga aagaattacc 1440
cagatgcaga gactaacaaa tattattacc acagaggaca ttgtaacagt ggtcacaatg 1500
gtgacaaatg ttgactttcc tcccaaagaa tctagtcta 1539

<210> SEQ ID NO 13
<211> LENGTH: 345
<212> TYPE: DNA
<213> ORGANISM: Homo sapiens

<400> SEQUENCE: 13
atacttggta gatcagaaac tcaggagtgt cttttcttta atgctaattg ggaaaaagac 60
agaaccaatc aaactggtgt tgaaccgtgt tatggtgaca aagataaacg gcggcattgt 120
tttgctacct ggaagaatat ttctggttcc attgaaatag tgaaacaagg ttgttggctg 180
gatgatatca actgctatga caggactgat tgtgtagaaa aaaaagacag ccctgaagta 240
tatttttgtt gctgtgaggg caatatgtgt aatgaaaagt tttcttattt tccggagatg 300
gaagtcacac agcccacttc aaatccagtt acacctaagc caccc 345

<210> SEQ ID NO 14
<211> LENGTH: 503
<212> TYPE: PRT
<213> ORGANISM: Homo sapiens

<400> SEQUENCE: 14

Met Thr Leu Gly Ser Pro Arg Lys Gly Leu Leu Met Leu Leu Met Ala
1 5 10 15

Leu Val Thr Gln Gly Asp Pro Val Lys Pro Ser Arg Gly Pro Leu Val
20 25 30

Thr Cys Thr Cys Glu Ser Pro His Cys Lys Gly Pro Thr Cys Arg Gly
35 40 45

Ala Trp Cys Thr Val Val Leu Val Arg Glu Glu Gly Arg His Pro Gln
50 55 60

Glu His Arg Gly Cys Gly Asn Leu His Arg Glu Leu Cys Arg Gly Arg
65 70 75 80

Pro Thr Glu Phe Val Asn His Tyr Cys Cys Asp Ser His Leu Cys Asn
85 90 95

His Asn Val Ser Leu Val Leu Glu Ala Thr Gln Pro Pro Ser Glu Gln
100 105 110

Pro Gly Thr Asp Gly Gln Leu Ala Leu Ile Leu Gly Pro Val Leu Ala
115 120 125

Leu Leu Ala Leu Val Ala Leu Gly Val Leu Gly Leu Trp His Val Arg
130 135 140

Arg Arg Gln Glu Lys Gln Arg Gly Leu His Ser Glu Leu Gly Glu Ser
145 150 155 160

Ser Leu Ile Leu Lys Ala Ser Glu Gln Gly Asp Ser Met Leu Gly Asp
165 170 175

Leu Leu Asp Ser Asp Cys Thr Thr Gly Ser Gly Ser Gly Leu Pro Phe
180 185 190

Leu Val Gln Arg Thr Val Ala Arg Gln Val Ala Leu Val Glu Cys Val
195 200 205

Gly Lys Gly Arg Tyr Gly Glu Val Trp Arg Gly Leu Trp His Gly Glu
210 215 220

Ser Val Ala Val Lys Ile Phe Ser Ser Arg Asp Glu Gln Ser Trp Phe
225 230 235 240

```
Arg Glu Thr Glu Ile Tyr Asn Thr Val Leu Leu Arg His Asp Asn Ile
                245                 250                 255

Leu Gly Phe Ile Ala Ser Asp Met Thr Ser Arg Asn Ser Ser Thr Gln
            260                 265                 270

Leu Trp Leu Ile Thr His Tyr His Glu His Gly Ser Leu Tyr Asp Phe
        275                 280                 285

Leu Gln Arg Gln Thr Leu Glu Pro His Leu Ala Leu Arg Leu Ala Val
    290                 295                 300

Ser Ala Ala Cys Gly Leu Ala His Leu His Val Glu Ile Phe Gly Thr
305                 310                 315                 320

Gln Gly Lys Pro Ala Ile Ala His Arg Asp Phe Lys Ser Arg Asn Val
                325                 330                 335

Leu Val Lys Ser Asn Leu Gln Cys Cys Ile Ala Asp Leu Gly Leu Ala
            340                 345                 350

Val Met His Ser Gln Gly Ser Asp Tyr Leu Asp Ile Gly Asn Asn Pro
        355                 360                 365

Arg Val Gly Thr Lys Arg Tyr Met Ala Pro Glu Val Leu Asp Glu Gln
    370                 375                 380

Ile Arg Thr Asp Cys Phe Glu Ser Tyr Lys Trp Thr Asp Ile Trp Ala
385                 390                 395                 400

Phe Gly Leu Val Leu Trp Glu Ile Ala Arg Arg Thr Ile Val Asn Gly
                405                 410                 415

Ile Val Glu Asp Tyr Arg Pro Pro Phe Tyr Asp Val Val Pro Asn Asp
            420                 425                 430

Pro Ser Phe Glu Asp Met Lys Lys Val Val Cys Val Asp Gln Gln Thr
        435                 440                 445

Pro Thr Ile Pro Asn Arg Leu Ala Ala Asp Pro Val Leu Ser Gly Leu
    450                 455                 460

Ala Gln Met Met Arg Glu Cys Trp Tyr Pro Asn Pro Ser Ala Arg Leu
465                 470                 475                 480

Thr Ala Leu Arg Ile Lys Lys Thr Leu Gln Lys Ile Ser Asn Ser Pro
                485                 490                 495

Glu Lys Pro Lys Val Ile Gln
            500


<210> SEQ ID NO 15
<211> LENGTH: 97
<212> TYPE: PRT
<213> ORGANISM: Homo sapiens

<400> SEQUENCE: 15

Asp Pro Val Lys Pro Ser Arg Gly Pro Leu Val Thr Cys Thr Cys Glu
1               5                   10                  15

Ser Pro His Cys Lys Gly Pro Thr Cys Arg Gly Ala Trp Cys Thr Val
            20                  25                  30

Val Leu Val Arg Glu Glu Gly Arg His Pro Gln Glu His Arg Gly Cys
        35                  40                  45

Gly Asn Leu His Arg Glu Leu Cys Arg Gly Arg Pro Thr Glu Phe Val
    50                  55                  60

Asn His Tyr Cys Cys Asp Ser His Leu Cys Asn His Asn Val Ser Leu
65                  70                  75                  80

Val Leu Glu Ala Thr Gln Pro Pro Ser Glu Gln Pro Gly Thr Asp Gly
                85                  90                  95

Gln
```

<210> SEQ ID NO 16
<211> LENGTH: 1509
<212> TYPE: DNA
<213> ORGANISM: Homo sapiens

<400> SEQUENCE: 16

```
atgaccttgg gctcccccag gaaaggcctt ctgatgctgc tgatggcctt ggtgacccag      60
ggagaccctg tgaagccgtc tcggggcccg ctggtgacct gcacgtgtga gagcccacat     120
tgcaaggggc ctacctgccg gggggcctgg tgcacagtag tgctggtgcg ggaggagggg     180
aggcaccccc aggaacatcg ggctgcggg aacttgcaca gggagctctg caggggggcgc     240
cccaccgagt tcgtcaacca ctactgctgc gacagccacc tctgcaacca caacgtgtcc     300
ctggtgctgg aggccaccca acctccttcg gagcagccgg gaacagatgg ccagctggcc     360
ctgatcctgg gccccgtgct ggccttgctg gccctggtgg ccctgggtgt cctgggcctg     420
tggcatgtcc gacggaggca ggagaagcag cgtggcctgc acagcgagct gggagagtcc     480
agtctcatcc tgaaagcatc tgagcagggc gacagcatgt tgggggacct cctggacagt     540
gactgcacca cagggagtgg ctcagggctc cccttcctgg tgcagaggac agtggcacgg     600
caggttgcct tggtggagtg tgtgggaaaa ggccgctatg gcgaagtgtg gcggggcttg     660
tggcacggtg agagtgtggc cgtcaagatc ttctcctcga gggatgaaca gtcctggttc     720
cgggagactg agatctataa cacagtgttg ctcagacacg acaacatcct aggcttcatc     780
gcctcagaca tgacctcccg caactcgagc acgcagctgt ggctcatcac gcactaccac     840
gagcacggct ccctctacga ctttctgcag agacagacgc tggagcccca tctggctctg     900
aggctagctg tgtccgcggc atgcggcctg gcgcacctgc acgtggagat cttcggtaca     960
cagggcaaac cagccattgc ccaccgcgac ttcaagagcc gcaatgtgct ggtcaagagc    1020
aacctgcagt gttgcatcgc cgacctgggc ctggctgtga tgcactcaca gggcagcgat    1080
tacctggaca tcggcaacaa cccgagagtg ggcaccaagc ggtacatggc acccgaggtg    1140
ctggacgagc agatccgcac ggactgcttt gagtcctaca agtggactga catctgggcc    1200
tttggcctgg tgctgtggga gattgcccgc cggaccatcg tgaatggcat cgtggaggac    1260
tatagaccac ccttctatga tgtggtgccc aatgacccca gctttgagga catgaagaag    1320
gtggtgtgtg tggatcagca gacccccacc atccctaacc ggctggctgc agacccggtc    1380
ctctcaggcc tagctcagat gatgcgggag tgctggtacc caaacccctc tgcccgactc    1440
accgcgctgc ggatcaagaa gacactacaa aaaattagca acagtccaga gaagcctaaa    1500
gtgattcaa                                                            1509
```

<210> SEQ ID NO 17
<211> LENGTH: 291
<212> TYPE: DNA
<213> ORGANISM: Homo sapiens

<400> SEQUENCE: 17

```
gaccctgtga agccgtctcg ggcccgctg gtgacctgca cgtgtgagag cccacattgc      60
aaggggccta cctgccgggg ggcctggtgc acagtagtgc tggtgcggga ggaggggagg     120
cacccccagg aacatcgggg ctgcgggaac ttgcacaggg agctctgcag gggggcgcccc     180
accgagttcg tcaaccacta ctgctgcgac agccacctct gcaaccacaa cgtgtccctg     240
gtgctggagg ccacccaacc tccttcggag cagccgggaa cagatggcca g              291
```

<210> SEQ ID NO 18
<211> LENGTH: 509
<212> TYPE: PRT
<213> ORGANISM: Homo sapiens

<400> SEQUENCE: 18

```
Met Val Asp Gly Val Met Ile Leu Pro Val Leu Ile Met Ile Ala Leu
1               5                   10                  15

Pro Ser Pro Ser Met Glu Asp Glu Lys Pro Lys Val Asn Pro Lys Leu
            20                  25                  30

Tyr Met Cys Val Cys Glu Gly Leu Ser Cys Gly Asn Glu Asp His Cys
        35                  40                  45

Glu Gly Gln Gln Cys Phe Ser Ser Leu Ser Ile Asn Asp Gly Phe His
    50                  55                  60

Val Tyr Gln Lys Gly Cys Phe Gln Val Tyr Glu Gln Gly Lys Met Thr
65                  70                  75                  80

Cys Lys Thr Pro Pro Ser Pro Gly Gln Ala Val Glu Cys Cys Gln Gly
                85                  90                  95

Asp Trp Cys Asn Arg Asn Ile Thr Ala Gln Leu Pro Thr Lys Gly Lys
            100                 105                 110

Ser Phe Pro Gly Thr Gln Asn Phe His Leu Glu Val Gly Leu Ile Ile
        115                 120                 125

Leu Ser Val Val Phe Ala Val Cys Leu Leu Ala Cys Leu Leu Gly Val
    130                 135                 140

Ala Leu Arg Lys Phe Lys Arg Arg Asn Gln Glu Arg Leu Asn Pro Arg
145                 150                 155                 160

Asp Val Glu Tyr Gly Thr Ile Glu Gly Leu Ile Thr Thr Asn Val Gly
                165                 170                 175

Asp Ser Thr Leu Ala Asp Leu Leu Asp His Ser Cys Thr Ser Gly Ser
            180                 185                 190

Gly Ser Gly Leu Pro Phe Leu Val Gln Arg Thr Val Ala Arg Gln Ile
        195                 200                 205

Thr Leu Leu Glu Cys Val Gly Lys Gly Arg Tyr Gly Glu Val Trp Arg
    210                 215                 220

Gly Ser Trp Gln Gly Glu Asn Val Ala Val Lys Ile Phe Ser Ser Arg
225                 230                 235                 240

Asp Glu Lys Ser Trp Phe Arg Glu Thr Glu Leu Tyr Asn Thr Val Met
                245                 250                 255

Leu Arg His Glu Asn Ile Leu Gly Phe Ile Ala Ser Asp Met Thr Ser
            260                 265                 270

Arg His Ser Ser Thr Gln Leu Trp Leu Ile Thr His Tyr His Glu Met
        275                 280                 285

Gly Ser Leu Tyr Asp Tyr Leu Gln Leu Thr Thr Leu Asp Thr Val Ser
    290                 295                 300

Cys Leu Arg Ile Val Leu Ser Ile Ala Ser Gly Leu Ala His Leu His
305                 310                 315                 320

Ile Glu Ile Phe Gly Thr Gln Gly Lys Pro Ala Ile Ala His Arg Asp
                325                 330                 335

Leu Lys Ser Lys Asn Ile Leu Val Lys Lys Asn Gly Gln Cys Cys Ile
            340                 345                 350

Ala Asp Leu Gly Leu Ala Val Met His Ser Gln Ser Thr Asn Gln Leu
        355                 360                 365

Asp Val Gly Asn Asn Pro Arg Val Gly Thr Lys Arg Tyr Met Ala Pro
    370                 375                 380
```

-continued

```
Glu Val Leu Asp Glu Thr Ile Gln Val Asp Cys Phe Asp Ser Tyr Lys
385                 390                 395                 400

Arg Val Asp Ile Trp Ala Phe Gly Leu Val Leu Trp Glu Val Ala Arg
                405                 410                 415

Arg Met Val Ser Asn Gly Ile Val Glu Asp Tyr Lys Pro Pro Phe Tyr
            420                 425                 430

Asp Val Val Pro Asn Asp Pro Ser Phe Glu Asp Met Arg Lys Val Val
        435                 440                 445

Cys Val Asp Gln Gln Arg Pro Asn Ile Pro Asn Arg Trp Phe Ser Asp
    450                 455                 460

Pro Thr Leu Thr Ser Leu Ala Lys Leu Met Lys Glu Cys Trp Tyr Gln
465                 470                 475                 480

Asn Pro Ser Ala Arg Leu Thr Ala Leu Arg Ile Lys Lys Thr Leu Thr
                485                 490                 495

Lys Ile Asp Asn Ser Leu Asp Lys Leu Lys Thr Asp Cys
            500                 505
```

<210> SEQ ID NO 19
<211> LENGTH: 103
<212> TYPE: PRT
<213> ORGANISM: Homo sapiens

<400> SEQUENCE: 19

```
Met Glu Asp Glu Lys Pro Lys Val Asn Pro Lys Leu Tyr Met Cys Val
1               5                   10                  15

Cys Glu Gly Leu Ser Cys Gly Asn Glu Asp His Cys Glu Gly Gln Gln
            20                  25                  30

Cys Phe Ser Ser Leu Ser Ile Asn Asp Gly Phe His Val Tyr Gln Lys
        35                  40                  45

Gly Cys Phe Gln Val Tyr Glu Gln Gly Lys Met Thr Cys Lys Thr Pro
    50                  55                  60

Pro Ser Pro Gly Gln Ala Val Glu Cys Cys Gln Gly Asp Trp Cys Asn
65                  70                  75                  80

Arg Asn Ile Thr Ala Gln Leu Pro Thr Lys Gly Lys Ser Phe Pro Gly
                85                  90                  95

Thr Gln Asn Phe His Leu Glu
            100
```

<210> SEQ ID NO 20
<211> LENGTH: 1527
<212> TYPE: DNA
<213> ORGANISM: Homo sapiens

<400> SEQUENCE: 20

```
atggtagatg gagtgatgat tcttcctgtg cttatcatga ttgctctccc ctcccctagt      60

atggaagatg agaagcccaa ggtcaacccc aaactctaca tgtgtgtgtg tgaaggtctc     120

tcctgcggta atgaggacca ctgtgaaggc cagcagtgct tttcctcact gagcatcaac     180

gatggcttcc acgtctacca gaaaggctgc ttccaggttt atgagcaggg aaagatgacc     240

tgtaagaccc cgccgtcccc tggccaagcc gtggagtgct gccaaggggga ctggtgtaac     300

aggaacatca cggcccagct gcccactaaa ggaaaatcct tccctggaac acagaatttc     360

cacttggagg ttggcctcat tattctctct gtagtgttcg cagtatgtct tttagcctgc     420

ctgctgggag ttgctctccg aaaatttaaa aggcgcaacc aagaacgcct caatccccga     480

gacgtggagt atggcactat cgaagggctc atcaccacca atgttggaga cagcacttta     540
```

-continued

```
gcagatttat tggatcattc gtgtacatca ggaagtggct ctggtcttcc ttttctggta    600

caaagaacag tggctcgcca gattacactg ttggagtgtg tcgggaaagg caggtatggt    660

gaggtgtgga ggggcagctg gcaaggggag aatgttgccg tgaagatctt ctcctcccgt    720

gatgagaagt catggttcag ggaaacggaa ttgtacaaca ctgtgatgct gaggcatgaa    780

aatatcttag gtttcattgc ttcagacatg acatcaagac actccagtac ccagctgtgg    840

ttaattacac attatcatga aatgggatcg ttgtacgact atcttcagct tactactctg    900

gatacagtta gctgccttcg aatagtgctg tccatagcta gtggtcttgc acatttgcac    960

atagagatat ttgggaccca agggaaacca gccattgccc atcgagattt aaagagcaaa   1020

aatattctgg ttaagaagaa tggacagtgt tgcatagcag atttgggcct ggcagtcatg   1080

cattcccaga gcaccaatca gcttgatgtg gggaacaatc cccgtgtggg caccaagcgc   1140

tacatggccc ccgaagttct agatgaaacc atccaggtgg attgtttcga ttcttataaa   1200

agggtcgata tttgggcctt tggacttgtt ttgtgggaag tggccaggcg gatggtgagc   1260

aatggtatag tggaggatta caagccaccg ttctacgatg tggttcccaa tgacccaagt   1320

tttgaagata tgaggaaggt agtctgtgtg gatcaacaaa ggccaaacat acccaacaga   1380

tggttctcag acccgacatt aacctctctg gccaagctaa tgaaagaatg ctggtatcaa   1440

aatccatccg caagactcac agcactgcgt atcaaaaaga ctttgaccaa aattgataat   1500

tccctcgaca aattgaaaac tgactgt                                       1527
```

<210> SEQ ID NO 21
<211> LENGTH: 309
<212> TYPE: DNA
<213> ORGANISM: Homo sapiens

<400> SEQUENCE: 21

```
atggaagatg agaagcccaa ggtcaacccc aaactctaca tgtgtgtgtg tgaaggtctc     60

tcctgcggta atgaggacca ctgtgaaggc cagcagtgct tttcctcact gagcatcaac    120

gatggcttcc acgtctacca gaaaggctgc ttccaggttt atgagcaggg aaagatgacc    180

tgtaagaccc cgccgtcccc tggccaagcc gtggagtgct gccaaggggga ctggtgtaac    240

aggaacatca cggcccagct gcccactaaa ggaaaatcct tccctggaac acagaatttc    300

cacttggag                                                            309
```

<210> SEQ ID NO 22
<211> LENGTH: 532
<212> TYPE: PRT
<213> ORGANISM: Homo sapiens

<400> SEQUENCE: 22

```
Met Pro Gln Leu Tyr Ile Tyr Ile Arg Leu Leu Gly Ala Tyr Leu Phe
1               5                   10                  15

Ile Ile Ser Arg Val Gln Gly Gln Asn Leu Asp Ser Met Leu His Gly
            20                  25                  30

Thr Gly Met Lys Ser Asp Ser Asp Gln Lys Lys Ser Glu Asn Gly Val
        35                  40                  45

Thr Leu Ala Pro Glu Asp Thr Leu Pro Phe Leu Lys Cys Tyr Cys Ser
    50                  55                  60

Gly His Cys Pro Asp Asp Ala Ile Asn Asn Thr Cys Ile Thr Asn Gly
65                  70                  75                  80

His Cys Phe Ala Ile Ile Glu Glu Asp Asp Gln Gly Glu Thr Thr Leu
```

-continued

```
                85                  90                  95

Ala Ser Gly Cys Met Lys Tyr Glu Gly Ser Asp Phe Gln Cys Lys Asp
            100                 105                 110

Ser Pro Lys Ala Gln Leu Arg Arg Thr Ile Glu Cys Cys Arg Thr Asn
        115                 120                 125

Leu Cys Asn Gln Tyr Leu Gln Pro Thr Leu Pro Pro Val Val Ile Gly
    130                 135                 140

Pro Phe Phe Asp Gly Ser Ile Arg Trp Leu Val Leu Leu Ile Ser Met
145                 150                 155                 160

Ala Val Cys Ile Ile Ala Met Ile Ile Phe Ser Ser Cys Phe Cys Tyr
                165                 170                 175

Lys His Tyr Cys Lys Ser Ile Ser Ser Arg Arg Arg Tyr Asn Arg Asp
            180                 185                 190

Leu Glu Gln Asp Glu Ala Phe Ile Pro Val Gly Glu Ser Leu Lys Asp
        195                 200                 205

Leu Ile Asp Gln Ser Gln Ser Ser Gly Ser Gly Ser Gly Leu Pro Leu
    210                 215                 220

Leu Val Gln Arg Thr Ile Ala Lys Gln Ile Gln Met Val Arg Gln Val
225                 230                 235                 240

Gly Lys Gly Arg Tyr Gly Glu Val Trp Met Gly Lys Trp Arg Gly Glu
                245                 250                 255

Lys Val Ala Val Lys Val Phe Phe Thr Thr Glu Glu Ala Ser Trp Phe
            260                 265                 270

Arg Glu Thr Glu Ile Tyr Gln Thr Val Leu Met Arg His Glu Asn Ile
        275                 280                 285

Leu Gly Phe Ile Ala Ala Asp Ile Lys Gly Thr Gly Ser Trp Thr Gln
    290                 295                 300

Leu Tyr Leu Ile Thr Asp Tyr His Glu Asn Gly Ser Leu Tyr Asp Phe
305                 310                 315                 320

Leu Lys Cys Ala Thr Leu Asp Thr Arg Ala Leu Leu Lys Leu Ala Tyr
                325                 330                 335

Ser Ala Ala Cys Gly Leu Cys His Leu His Thr Glu Ile Tyr Gly Thr
            340                 345                 350

Gln Gly Lys Pro Ala Ile Ala His Arg Asp Leu Lys Ser Lys Asn Ile
        355                 360                 365

Leu Ile Lys Lys Asn Gly Ser Cys Cys Ile Ala Asp Leu Gly Leu Ala
    370                 375                 380

Val Lys Phe Asn Ser Asp Thr Asn Glu Val Asp Val Pro Leu Asn Thr
385                 390                 395                 400

Arg Val Gly Thr Lys Arg Tyr Met Ala Pro Glu Val Leu Asp Glu Ser
                405                 410                 415

Leu Asn Lys Asn His Phe Gln Pro Tyr Ile Met Ala Asp Ile Tyr Ser
            420                 425                 430

Phe Gly Leu Ile Ile Trp Glu Met Ala Arg Arg Cys Ile Thr Gly Gly
        435                 440                 445

Ile Val Glu Glu Tyr Gln Leu Pro Tyr Tyr Asn Met Val Pro Ser Asp
    450                 455                 460

Pro Ser Tyr Glu Asp Met Arg Glu Val Val Cys Val Lys Arg Leu Arg
465                 470                 475                 480

Pro Ile Val Ser Asn Arg Trp Asn Ser Asp Glu Cys Leu Arg Ala Val
                485                 490                 495

Leu Lys Leu Met Ser Glu Cys Trp Ala His Asn Pro Ala Ser Arg Leu
            500                 505                 510
```

Thr Ala Leu Arg Ile Lys Lys Thr Leu Ala Lys Met Val Glu Ser Gln
        515                 520                 525

Asp Val Lys Ile
    530

<210> SEQ ID NO 23
<211> LENGTH: 129
<212> TYPE: PRT
<213> ORGANISM: Homo sapiens

<400> SEQUENCE: 23

Gln Asn Leu Asp Ser Met Leu His Gly Thr Gly Met Lys Ser Asp Ser
1               5                   10                  15

Asp Gln Lys Lys Ser Glu Asn Gly Val Thr Leu Ala Pro Glu Asp Thr
            20                  25                  30

Leu Pro Phe Leu Lys Cys Tyr Cys Ser Gly His Cys Pro Asp Asp Ala
        35                  40                  45

Ile Asn Asn Thr Cys Ile Thr Asn Gly His Cys Phe Ala Ile Ile Glu
    50                  55                  60

Glu Asp Asp Gln Gly Glu Thr Thr Leu Ala Ser Gly Cys Met Lys Tyr
65                  70                  75                  80

Glu Gly Ser Asp Phe Gln Cys Lys Asp Ser Pro Lys Ala Gln Leu Arg
                85                  90                  95

Arg Thr Ile Glu Cys Cys Arg Thr Asn Leu Cys Asn Gln Tyr Leu Gln
            100                 105                 110

Pro Thr Leu Pro Pro Val Val Ile Gly Pro Phe Phe Asp Gly Ser Ile
        115                 120                 125

Arg

<210> SEQ ID NO 24
<211> LENGTH: 1596
<212> TYPE: DNA
<213> ORGANISM: Homo sapiens

<400> SEQUENCE: 24
atgcctcagc tatacattta catcagatta ttgggagcct atttgttcat catttctcgt 60
gttcaaggac agaatctgga tagtatgctt catggcactg ggatgaaatc agactccgac 120
cagaaaaagt cagaaaatgg agtaacctta gcaccagagg ataccttgcc ttttttaaag 180
tgctattgct cagggcactg tccagatgat gctattaata acacatgcat aactaatgga 240
cattgctttg ccatcataga agaagatgac cagggagaaa ccacattagc ttcagggtgt 300
atgaaatatg aaggatctga ttttcagtgc aaagattctc caaaagccca gctacgccgg 360
acaatagaat gttgtcggac caatttatgt aaccagtatt tgcaacccac actgccccct 420
gttgtcatag gtccgttttt tgatggcagc attcgatggc tggttttgct catttctatg 480
gctgtctgca taattgctat gatcatcttc tccagctgct tttgttacaa acattattgc 540
aagagcatct caagcagacg tcgttacaat cgtgatttgg aacaggatga agcatttatt 600
ccagttggag aatcactaaa agaccttatt gaccagtcac aaagttctgg tagtgggtct 660
ggactacctt tattggttca gcgaactatt gccaaacaga ttcagatggt ccggcaagtt 720
ggtaaaggcc gatatggaga agtatggatg ggcaaatggc gtggcgaaaa agtggcggtg 780
aaagtattct ttaccactga agaagccagc tggtttcgag aaacagaaat ctaccaaact 840
gtgctaatgc gccatgaaaa catacttggt ttcatagcgg cagacattaa aggtacaggt 900

```
tcctggactc agctctattt gattactgat taccatgaaa atggatctct ctatgacttc    960

ctgaaatgtg ctacactgga caccagagcc ctgcttaaat tggcttattc agctgcctgt   1020

ggtctgtgcc acctgcacac agaaatttat ggcacccaag gaaagcccgc aattgctcat   1080

cgagacctaa agagcaaaaa catcctcatc aagaaaaatg ggagttgctg cattgctgac   1140

ctgggccttg ctgttaaatt caacagtgac acaaatgaag ttgatgtgcc cttgaatacc   1200

agggtgggca ccaaacgcta catggctccc gaagtgctgg acgaaagcct gaacaaaaac   1260

cacttccagc cctacatcat ggctgacatc tacagcttcg gcctaatcat ttgggagatg   1320

gctcgtcgtt gtatcacagg agggatcgtg gaagaatacc aattgccata ttacaacatg   1380

gtaccgagtg atccgtcata cgaagatatg cgtgaggttg tgtgtgtcaa acgtttgcgg   1440

ccaattgtgt ctaatcggtg gaacagtgat gaatgtctac gagcagtttt gaagctaatg   1500

tcagaatgct gggcccacaa tccagcctcc agactcacag cattgagaat taagaagacg   1560

cttgccaaga tggttgaatc ccaagatgta aaaatc                             1596
```

<210> SEQ ID NO 25
<211> LENGTH: 387
<212> TYPE: DNA
<213> ORGANISM: Homo sapiens

<400> SEQUENCE: 25

```
cagaatctgg atagtatgct tcatggcact gggatgaaat cagactccga ccagaaaaag     60

tcagaaaatg gagtaacctt agcaccagag gataccttgc cttttttaaa gtgctattgc    120

tcagggcact gtccagatga tgctattaat aacacatgca taactaatgg acattgcttt    180

gccatcatag aagaagatga ccagggagaa accacattag cttcagggtg tatgaaatat    240

gaaggatctg attttcagtg caaagattct ccaaaagccc agctacgccg gacaatagaa    300

tgttgtcgga ccaatttatg taaccagtat ttgcaaccca cactgccccc tgttgtcata    360

ggtccgtttt ttgatggcag cattcga                                        387
```

<210> SEQ ID NO 26
<211> LENGTH: 505
<212> TYPE: PRT
<213> ORGANISM: Homo sapiens

<400> SEQUENCE: 26

```
Met Ala Glu Ser Ala Gly Ala Ser Ser Phe Phe Pro Leu Val Val Leu
1               5                   10                  15

Leu Leu Ala Gly Ser Gly Gly Ser Gly Pro Arg Gly Val Gln Ala Leu
            20                  25                  30

Leu Cys Ala Cys Thr Ser Cys Leu Gln Ala Asn Tyr Thr Cys Glu Thr
        35                  40                  45

Asp Gly Ala Cys Met Val Ser Ile Phe Asn Leu Asp Gly Met Glu His
    50                  55                  60

His Val Arg Thr Cys Ile Pro Lys Val Glu Leu Val Pro Ala Gly Lys
65                  70                  75                  80

Pro Phe Tyr Cys Leu Ser Ser Glu Asp Leu Arg Asn Thr His Cys Cys
                85                  90                  95

Tyr Thr Asp Tyr Cys Asn Arg Ile Asp Leu Arg Val Pro Ser Gly His
            100                 105                 110

Leu Lys Glu Pro Glu His Pro Ser Met Trp Gly Pro Val Glu Leu Val
        115                 120                 125

Gly Ile Ile Ala Gly Pro Val Phe Leu Leu Phe Leu Ile Ile Ile Ile
```

-continued

```
    130                 135                 140

Val Phe Leu Val Ile Asn Tyr His Gln Arg Val Tyr His Asn Arg Gln
145                 150                 155                 160

Arg Leu Asp Met Glu Asp Pro Ser Cys Glu Met Cys Leu Ser Lys Asp
                165                 170                 175

Lys Thr Leu Gln Asp Leu Val Tyr Asp Leu Ser Thr Ser Gly Ser Gly
            180                 185                 190

Ser Gly Leu Pro Leu Phe Val Gln Arg Thr Val Ala Arg Thr Ile Val
        195                 200                 205

Leu Gln Glu Ile Ile Gly Lys Gly Arg Phe Gly Glu Val Trp Arg Gly
    210                 215                 220

Arg Trp Arg Gly Gly Asp Val Ala Val Lys Ile Phe Ser Ser Arg Glu
225                 230                 235                 240

Glu Arg Ser Trp Phe Arg Glu Ala Glu Ile Tyr Gln Thr Val Met Leu
                245                 250                 255

Arg His Glu Asn Ile Leu Gly Phe Ile Ala Ala Asp Asn Lys Asp Asn
            260                 265                 270

Gly Thr Trp Thr Gln Leu Trp Leu Val Ser Asp Tyr His Glu His Gly
        275                 280                 285

Ser Leu Phe Asp Tyr Leu Asn Arg Tyr Thr Val Thr Ile Glu Gly Met
    290                 295                 300

Ile Lys Leu Ala Leu Ser Ala Ala Ser Gly Leu Ala His Leu His Met
305                 310                 315                 320

Glu Ile Val Gly Thr Gln Gly Lys Pro Gly Ile Ala His Arg Asp Leu
                325                 330                 335

Lys Ser Lys Asn Ile Leu Val Lys Lys Asn Gly Met Cys Ala Ile Ala
            340                 345                 350

Asp Leu Gly Leu Ala Val Arg His Asp Ala Val Thr Asp Thr Ile Asp
        355                 360                 365

Ile Ala Pro Asn Gln Arg Val Gly Thr Lys Arg Tyr Met Ala Pro Glu
    370                 375                 380

Val Leu Asp Glu Thr Ile Asn Met Lys His Phe Asp Ser Phe Lys Cys
385                 390                 395                 400

Ala Asp Ile Tyr Ala Leu Gly Leu Val Tyr Trp Glu Ile Ala Arg Arg
                405                 410                 415

Cys Asn Ser Gly Gly Val His Glu Glu Tyr Gln Leu Pro Tyr Tyr Asp
            420                 425                 430

Leu Val Pro Ser Asp Pro Ser Ile Glu Glu Met Arg Lys Val Val Cys
        435                 440                 445

Asp Gln Lys Leu Arg Pro Asn Ile Pro Asn Trp Trp Gln Ser Tyr Glu
    450                 455                 460

Ala Leu Arg Val Met Gly Lys Met Met Arg Glu Cys Trp Tyr Ala Asn
465                 470                 475                 480

Gly Ala Ala Arg Leu Thr Ala Leu Arg Ile Lys Lys Thr Leu Ser Gln
                485                 490                 495

Leu Ser Val Gln Glu Asp Val Lys Ile
            500                 505


<210> SEQ ID NO 27
<211> LENGTH: 103
<212> TYPE: PRT
<213> ORGANISM: Homo sapiens

<400> SEQUENCE: 27
```

-continued

```
Ser Gly Pro Arg Gly Val Gln Ala Leu Leu Cys Ala Cys Thr Ser Cys
1               5                   10                  15

Leu Gln Ala Asn Tyr Thr Cys Glu Thr Asp Gly Ala Cys Met Val Ser
            20                  25                  30

Ile Phe Asn Leu Asp Gly Met Glu His His Val Arg Thr Cys Ile Pro
        35                  40                  45

Lys Val Glu Leu Val Pro Ala Gly Lys Pro Phe Tyr Cys Leu Ser Ser
    50                  55                  60

Glu Asp Leu Arg Asn Thr His Cys Cys Tyr Thr Asp Tyr Cys Asn Arg
65                  70                  75                  80

Ile Asp Leu Arg Val Pro Ser Gly His Leu Lys Glu Pro Glu His Pro
                85                  90                  95

Ser Met Trp Gly Pro Val Glu
            100


<210> SEQ ID NO 28
<211> LENGTH: 1515
<212> TYPE: DNA
<213> ORGANISM: Homo sapiens

<400> SEQUENCE: 28

atggcggagt cggccggagc ctcctccttc ttccccccttg ttgtcctcct gctcgccggc      60

agcggcgggt ccgggccccg gggggtccag gctctgctgt gtgcgtgcac cagctgcctc     120

caggccaact acacgtgtga gacagatggg gcctgcatgg tttccatttt caatctggat     180

gggatggagc accatgtgcg cacctgcatc cccaaagtgg agctggtccc tgccgggaag     240

cccttctact gcctgagctc ggaggacctg cgcaacaccc actgctgcta cactgactac     300

tgcaacagga tcgacttgag ggtgcccagt ggtcacctca aggagcctga gcacccgtcc     360

atgtggggcc cggtggagct ggtaggcatc atcgccggcc cggtgttcct cctgttcctc     420

atcatcatca ttgttttcct tgtcattaac tatcatcagc gtgtctatca caaccgccag     480

agactggaca tggaagatcc ctcatgtgag atgtgtctct ccaaagacaa gacgctccag     540

gatcttgtct acgatctctc cacctcaggg tctggctcag ggttacccct ctttgtccag     600

cgcacagtgg cccgaaccat cgttttacaa gagattattg gcaagggtcg gtttggggaa     660

gtatggcggg gccgctggag gggtggtgat gtggctgtga aaatattctc ttctcgtgaa     720

gaacggtctt ggttcaggga agcagagata taccagacgg tcatgctgcg ccatgaaaac     780

atccttggat ttattgctgc tgacaataaa gataatggca cctggacaca gctgtggctt     840

gtttctgact atcatgagca cgggtccctg tttgattatc tgaaccggta cacagtgaca     900

attgagggga tgattaagct ggccttgtct gctgctagtg ggctggcaca cctgcacatg     960

gagatcgtgg gcacccaagg gaagcctgga attgctcatc gagacttaaa gtcaaagaac    1020

attctggtga agaaaaatgg catgtgtgcc atagcagacc tgggcctggc tgtccgtcat    1080

gatgcagtca ctgacaccat tgacattgcc ccgaatcaga gggtggggac caaacgatac    1140

atggcccctg aagtacttga tgaaaccatt aatatgaaac actttgactc ctttaaatgt    1200

gctgatattt atgccctcgg gcttgtatat tgggagattg ctcgaagatg caattctgga    1260

ggagtccatg aagaatatca gctgccatat tacgacttag tgccctctga cccttccatt    1320

gaggaaatgc gaaaggttgt atgtgatcag aagctgcgtc ccaacatccc caactggtgg    1380

cagagttatg aggcactgcg ggtgatgggg aagatgatgc gagagtgttg gtatgccaac    1440

ggcgcagccc gcctgacggc cctgcgcatc aagaagaccc tctcccagct cagcgtgcag    1500
```

gaagacgtga agatc 1515

<210> SEQ ID NO 29
<211> LENGTH: 309
<212> TYPE: DNA
<213> ORGANISM: Homo sapiens

<400> SEQUENCE: 29
tccgggcccc ggggggtcca ggctctgctg tgtgcgtgca ccagctgcct ccaggccaac 60
tacacgtgtg agacagatgg ggcctgcatg gtttccattt tcaatctgga tgggatggag 120
caccatgtgc gcacctgcat ccccaaagtg gagctggtcc ctgccgggaa gcccttctac 180
tgcctgagct cggaggacct gcgcaacacc cactgctgct acactgacta ctgcaacagg 240
atcgacttga gggtgcccag tggtcacctc aaggagcctg agcacccgtc catgtggggc 300
ccggtggag 309

<210> SEQ ID NO 30
<211> LENGTH: 503
<212> TYPE: PRT
<213> ORGANISM: Homo sapiens

<400> SEQUENCE: 30

Met Glu Ala Ala Val Ala Ala Pro Arg Pro Arg Leu Leu Leu Leu Val
1 5 10 15

Leu Ala Ala Ala Ala Ala Ala Ala Ala Ala Leu Leu Pro Gly Ala Thr
20 25 30

Ala Leu Gln Cys Phe Cys His Leu Cys Thr Lys Asp Asn Phe Thr Cys
35 40 45

Val Thr Asp Gly Leu Cys Phe Val Ser Val Thr Glu Thr Thr Asp Lys
50 55 60

Val Ile His Asn Ser Met Cys Ile Ala Glu Ile Asp Leu Ile Pro Arg
65 70 75 80

Asp Arg Pro Phe Val Cys Ala Pro Ser Ser Lys Thr Gly Ser Val Thr
85 90 95

Thr Thr Tyr Cys Cys Asn Gln Asp His Cys Asn Lys Ile Glu Leu Pro
100 105 110

Thr Thr Val Lys Ser Ser Pro Gly Leu Gly Pro Val Glu Leu Ala Ala
115 120 125

Val Ile Ala Gly Pro Val Cys Phe Val Cys Ile Ser Leu Met Leu Met
130 135 140

Val Tyr Ile Cys His Asn Arg Thr Val Ile His His Arg Val Pro Asn
145 150 155 160

Glu Glu Asp Pro Ser Leu Asp Arg Pro Phe Ile Ser Glu Gly Thr Thr
165 170 175

Leu Lys Asp Leu Ile Tyr Asp Met Thr Thr Ser Gly Ser Gly Ser Gly
180 185 190

Leu Pro Leu Leu Val Gln Arg Thr Ile Ala Arg Thr Ile Val Leu Gln
195 200 205

Glu Ser Ile Gly Lys Gly Arg Phe Gly Glu Val Trp Arg Gly Lys Trp
210 215 220

Arg Gly Glu Glu Val Ala Val Lys Ile Phe Ser Ser Arg Glu Glu Arg
225 230 235 240

Ser Trp Phe Arg Glu Ala Glu Ile Tyr Gln Thr Val Met Leu Arg His
245 250 255

Glu Asn Ile Leu Gly Phe Ile Ala Ala Asp Asn Lys Asp Asn Gly Thr

```
            260                 265                 270

Trp Thr Gln Leu Trp Leu Val Ser Asp Tyr His Glu His Gly Ser Leu
        275                 280                 285

Phe Asp Tyr Leu Asn Arg Tyr Thr Val Thr Val Glu Gly Met Ile Lys
    290                 295                 300

Leu Ala Leu Ser Thr Ala Ser Gly Leu Ala His Leu His Met Glu Ile
305                 310                 315                 320

Val Gly Thr Gln Gly Lys Pro Ala Ile Ala His Arg Asp Leu Lys Ser
                325                 330                 335

Lys Asn Ile Leu Val Lys Lys Asn Gly Thr Cys Cys Ile Ala Asp Leu
            340                 345                 350

Gly Leu Ala Val Arg His Asp Ser Ala Thr Asp Thr Ile Asp Ile Ala
        355                 360                 365

Pro Asn His Arg Val Gly Thr Lys Arg Tyr Met Ala Pro Glu Val Leu
    370                 375                 380

Asp Asp Ser Ile Asn Met Lys His Phe Glu Ser Phe Lys Arg Ala Asp
385                 390                 395                 400

Ile Tyr Ala Met Gly Leu Val Phe Trp Glu Ile Ala Arg Arg Cys Ser
                405                 410                 415

Ile Gly Gly Ile His Glu Asp Tyr Gln Leu Pro Tyr Tyr Asp Leu Val
            420                 425                 430

Pro Ser Asp Pro Ser Val Glu Glu Met Arg Lys Val Val Cys Glu Gln
        435                 440                 445

Lys Leu Arg Pro Asn Ile Pro Asn Arg Trp Gln Ser Cys Glu Ala Leu
    450                 455                 460

Arg Val Met Ala Lys Ile Met Arg Glu Cys Trp Tyr Ala Asn Gly Ala
465                 470                 475                 480

Ala Arg Leu Thr Ala Leu Arg Ile Lys Lys Thr Leu Ser Gln Leu Ser
                485                 490                 495

Gln Gln Glu Gly Ile Lys Met
            500


<210> SEQ ID NO 31
<211> LENGTH: 102
<212> TYPE: PRT
<213> ORGANISM: Homo sapiens

<400> SEQUENCE: 31

Ala Ala Leu Leu Pro Gly Ala Thr Ala Leu Gln Cys Phe Cys His Leu
1               5                   10                  15

Cys Thr Lys Asp Asn Phe Thr Cys Val Thr Asp Gly Leu Cys Phe Val
            20                  25                  30

Ser Val Thr Glu Thr Thr Asp Lys Val Ile His Asn Ser Met Cys Ile
        35                  40                  45

Ala Glu Ile Asp Leu Ile Pro Arg Asp Arg Pro Phe Val Cys Ala Pro
    50                  55                  60

Ser Ser Lys Thr Gly Ser Val Thr Thr Thr Tyr Cys Cys Asn Gln Asp
65                  70                  75                  80

His Cys Asn Lys Ile Glu Leu Pro Thr Thr Val Lys Ser Ser Pro Gly
                85                  90                  95

Leu Gly Pro Val Glu Leu
            100


<210> SEQ ID NO 32
<211> LENGTH: 1509
```

<212> TYPE: DNA
<213> ORGANISM: Homo sapiens

<400> SEQUENCE: 32
atggaggcgg cggtcgctgc tccgcgtccc cggctgctcc tcctcgtgct ggcggcggcg 60
gcggcggcgg cggcggcgct gctcccgggg gcgacggcgt tacagtgttt ctgccacctc 120
tgtacaaaag acaattttac ttgtgtgaca gatgggctct gctttgtctc tgtcacagag 180
accacagaca aagttataca caacagcatg tgtatagctg aaattgactt aattcctcga 240
gataggccgt ttgtatgtgc accctcttca aaaactgggt ctgtgactac aacatattgc 300
tgcaatcagg accattgcaa taaaatagaa cttccaacta ctgtaaagtc atcacctggc 360
cttggtcctg tggaactggc agctgtcatt gctggaccag tgtgcttcgt ctgcatctca 420
ctcatgttga tggtctatat ctgccacaac cgcactgtca ttcaccatcg agtgccaaat 480
gaagaggacc cttcattaga tcgccctttt atttcagagg gtactacgtt gaaagactta 540
atttatgata tgacaacgtc aggttctggc tcaggtttac cattgcttgt tcagagaaca 600
attgcgagaa ctattgtgtt acaagaaagc attggcaaag gtcgatttgg agaagtttgg 660
agaggaaagt ggcggggaga agaagttgct gttaagatat tctcctctag agaagaacgt 720
tcgtggttcc gtgaggcaga gatttatcaa actgtaatgt tacgtcatga aaacatcctg 780
ggatttatag cagcagacaa taaagacaat ggtacttgga ctcagctctg gttggtgtca 840
gattatcatg agcatggatc cctttttgat tacttaaaca gatacacagt tactgtggaa 900
ggaatgataa aacttgctct gtccacggcg agcggtcttg cccatcttca catggagatt 960
gttggtaccc aaggaaagcc agccattgct catagagatt tgaaatcaaa gaatatcttg 1020
gtaaagaaga atggaacttg ctgtattgca gacttaggac tggcagtaag acatgattca 1080
gccacagata ccattgatat tgctccaaac cacagagtgg gaacaaaaag gtacatggcc 1140
cctgaagttc tcgatgattc cataaatatg aaacattttg aatccttcaa acgtgctgac 1200
atctatgcaa tgggcttagt attctgggaa attgctcgac gatgttccat tggtggaatt 1260
catgaagatt accaactgcc ttattatgat cttgtacctt ctgacccatc agttgaagaa 1320
atgagaaaag ttgtttgtga acagaagtta aggccaaata tcccaaacag atggcagagc 1380
tgtgaagcct tgagagtaat ggctaaaatt atgagagaat gttggtatgc caatggagca 1440
gctaggctta cagcattgcg gattaagaaa acattatcgc aactcagtca acaggaaggc 1500
atcaaaatg 1509

<210> SEQ ID NO 33
<211> LENGTH: 306
<212> TYPE: DNA
<213> ORGANISM: Homo sapiens

<400> SEQUENCE: 33
gcggcgctgc tcccgggggc gacggcgtta cagtgtttct gccacctctg tacaaaagac 60
aattttactt gtgtgacaga tgggctctgc tttgtctctg tcacagagac cacagacaaa 120
gttatacaca acagcatgtg tatagctgaa attgacttaa ttcctcgaga taggccgttt 180
gtatgtgcac cctcttcaaa aactgggtct gtgactacaa catattgctg caatcaggac 240
cattgcaata aaatagaact tccaactact gtaaagtcat cacctggcct tggtcctgtg 300
gaactg 306

<210> SEQ ID NO 34

<211> LENGTH: 502
<212> TYPE: PRT
<213> ORGANISM: Homo sapiens

<400> SEQUENCE: 34

Met Leu Leu Arg Ser Ala Gly Lys Leu Asn Val Gly Thr Lys Lys Glu
1 5 10 15

Asp Gly Glu Ser Thr Ala Pro Thr Pro Arg Pro Lys Val Leu Arg Cys
20 25 30

Lys Cys His His His Cys Pro Glu Asp Ser Val Asn Asn Ile Cys Ser
35 40 45

Thr Asp Gly Tyr Cys Phe Thr Met Ile Glu Glu Asp Asp Ser Gly Leu
50 55 60

Pro Val Val Thr Ser Gly Cys Leu Gly Leu Glu Gly Ser Asp Phe Gln
65 70 75 80

Cys Arg Asp Thr Pro Ile Pro His Gln Arg Arg Ser Ile Glu Cys Cys
85 90 95

Thr Glu Arg Asn Glu Cys Asn Lys Asp Leu His Pro Thr Leu Pro Pro
100 105 110

Leu Lys Asn Arg Asp Phe Val Asp Gly Pro Ile His His Arg Ala Leu
115 120 125

Leu Ile Ser Val Thr Val Cys Ser Leu Leu Leu Val Leu Ile Ile Leu
130 135 140

Phe Cys Tyr Phe Arg Tyr Lys Arg Gln Glu Thr Arg Pro Arg Tyr Ser
145 150 155 160

Ile Gly Leu Glu Gln Asp Glu Thr Tyr Ile Pro Pro Gly Glu Ser Leu
165 170 175

Arg Asp Leu Ile Glu Gln Ser Gln Ser Ser Gly Ser Gly Ser Gly Leu
180 185 190

Pro Leu Leu Val Gln Arg Thr Ile Ala Lys Gln Ile Gln Met Val Lys
195 200 205

Gln Ile Gly Lys Gly Arg Tyr Gly Glu Val Trp Met Gly Lys Trp Arg
210 215 220

Gly Glu Lys Val Ala Val Lys Val Phe Phe Thr Thr Glu Glu Ala Ser
225 230 235 240

Trp Phe Arg Glu Thr Glu Ile Tyr Gln Thr Val Leu Met Arg His Glu
245 250 255

Asn Ile Leu Gly Phe Ile Ala Ala Asp Ile Lys Gly Thr Gly Ser Trp
260 265 270

Thr Gln Leu Tyr Leu Ile Thr Asp Tyr His Glu Asn Gly Ser Leu Tyr
275 280 285

Asp Tyr Leu Lys Ser Thr Thr Leu Asp Ala Lys Ser Met Leu Lys Leu
290 295 300

Ala Tyr Ser Ser Val Ser Gly Leu Cys His Leu His Thr Glu Ile Phe
305 310 315 320

Ser Thr Gln Gly Lys Pro Ala Ile Ala His Arg Asp Leu Lys Ser Lys
325 330 335

Asn Ile Leu Val Lys Lys Asn Gly Thr Cys Cys Ile Ala Asp Leu Gly
340 345 350

Leu Ala Val Lys Phe Ile Ser Asp Thr Asn Glu Val Asp Ile Pro Pro
355 360 365

Asn Thr Arg Val Gly Thr Lys Arg Tyr Met Pro Pro Glu Val Leu Asp
370 375 380

Glu Ser Leu Asn Arg Asn His Phe Gln Ser Tyr Ile Met Ala Asp Met 385 390 395 400

Tyr Ser Phe Gly Leu Ile Leu Trp Glu Val Ala Arg Arg Cys Val Ser
405 410 415

Gly Gly Ile Val Glu Glu Tyr Gln Leu Pro Tyr His Asp Leu Val Pro
420 425 430

Ser Asp Pro Ser Tyr Glu Asp Met Arg Glu Ile Val Cys Ile Lys Lys
435 440 445

Leu Arg Pro Ser Phe Pro Asn Arg Trp Ser Ser Asp Glu Cys Leu Arg
450 455 460

Gln Met Gly Lys Leu Met Thr Glu Cys Trp Ala His Asn Pro Ala Ser
465 470 475 480

Arg Leu Thr Ala Leu Arg Val Lys Lys Thr Leu Ala Lys Met Ser Glu
485 490 495

Ser Gln Asp Ile Lys Leu
500

<210> SEQ ID NO 35
<211> LENGTH: 113
<212> TYPE: PRT
<213> ORGANISM: Homo sapiens

<400> SEQUENCE: 35

Lys Lys Glu Asp Gly Glu Ser Thr Ala Pro Thr Pro Arg Pro Lys Val
1 5 10 15

Leu Arg Cys Lys Cys His His His Cys Pro Glu Asp Ser Val Asn Asn
20 25 30

Ile Cys Ser Thr Asp Gly Tyr Cys Phe Thr Met Ile Glu Glu Asp Asp
35 40 45

Ser Gly Leu Pro Val Val Thr Ser Gly Cys Leu Gly Leu Glu Gly Ser
50 55 60

Asp Phe Gln Cys Arg Asp Thr Pro Ile Pro His Gln Arg Arg Ser Ile
65 70 75 80

Glu Cys Cys Thr Glu Arg Asn Glu Cys Asn Lys Asp Leu His Pro Thr
85 90 95

Leu Pro Pro Leu Lys Asn Arg Asp Phe Val Asp Gly Pro Ile His His
100 105 110

Arg

<210> SEQ ID NO 36
<211> LENGTH: 1506
<212> TYPE: DNA
<213> ORGANISM: Homo sapiens

<400> SEQUENCE: 36
atgcttttgc gaagtgcagg aaaattaaat gtgggcacca agaaagagga tggtgagagt 60
acagccccca ccccccgtcc aaaggtcttg cgttgtaaat gccaccacca ttgtccagaa 120
gactcagtca acaatatttg cagcacagac ggatattgtt tcacgatgat agaagaggat 180
gactctgggt tgcctgtggt cacttctggt tgcctaggac tagaaggctc agattttcag 240
tgtcgggaca ctcccattcc tcatcaaaga agatcaattg aatgctgcac agaaaggaac 300
gaatgtaata aagacctaca ccctacactg cctccattga aaaacagaga ttttgttgat 360
ggacctatac accacagggc tttacttata tctgtgactg tctgtagttt gctcttggtc 420
cttatcatat tattttgtta cttccggtat aaaagacaag aaaccagacc tcgatacagc 480
attgggttag aacaggatga aacttacatt cctcctggag aatccctgag agacttaatt 540

```
gagcagtctc agagctcagg aagtggatca ggcctccctc tgctggtcca aaggactata    600

gctaagcaga ttcagatggt gaaacagatt ggaaaaggtc gctatgggga agtttggatg    660

ggaaagtggc gtggcgaaaa ggtagctgtg aaagtgttct tcaccacaga ggaagccagc    720

tggttcagag agacagaaat atatcagaca gtgttgatga ggcatgaaaa cattttgggt    780

ttcattgctg cagatatcaa agggacaggg tcctggaccc agttgtacct aatcacagac    840

tatcatgaaa atggttccct ttatgattat ctgaagtcca ccaccctaga cgctaaatca    900

atgctgaagt tagcctactc ttctgtcagt ggcttatgtc atttacacac agaaatcttt    960

agtactcaag gcaaaccagc aattgcccat cgagatctga aaagtaaaaa cattctggtg   1020

aagaaaaatg gaacttgctg tattgctgac ctgggcctgg ctgttaaatt tattagtgat   1080

acaaatgaag ttgacatacc acctaacact cgagttggca ccaaacgcta tatgcctcca   1140

gaagtgttgg acgagagctt gaacagaaat cacttccagt cttacatcat ggctgacatg   1200

tatagttttg gcctcatcct ttgggaggtt gctaggagat gtgtatcagg aggtatagtg   1260

gaagaatacc agcttcctta tcatgaccta gtgcccagtg acccctctta tgaggacatg   1320

agggagattg tgtgcatcaa gaagttacgc ccctcattcc caaaccggtg gagcagtgat   1380

gagtgtctaa ggcagatggg aaaactcatg acagaatgct gggctcacaa tcctgcatca   1440

aggctgacag ccctgcgggt taagaaaaca cttgccaaaa tgtcagagtc ccaggacatt   1500

aaactc                                                              1506
```

<210> SEQ ID NO 37
<211> LENGTH: 339
<212> TYPE: DNA
<213> ORGANISM: Homo sapiens

<400> SEQUENCE: 37

```
aagaaagagg atggtgagag tacagccccc acccccc gtc caaaggtctt gcgttgtaaa     60

tgccaccacc attgtccaga agactcagtc aacaatattt gcagcacaga cggatattgt    120

ttcacgatga tagaagagga tgactctggg ttgcctgtgg tcacttctgg ttgcctagga    180

ctagaaggct cagattttca gtgtcgggac actcccattc ctcatcaaag aagatcaatt    240

gaatgctgca cagaaaggaa cgaatgtaat aaagacctac accctacact gcctccattg    300

aaaaacagag attttgttga tggacctata caccacagg                           339
```

<210> SEQ ID NO 38
<211> LENGTH: 493
<212> TYPE: PRT
<213> ORGANISM: Homo sapiens

<400> SEQUENCE: 38

```
Met Thr Arg Ala Leu Cys Ser Ala Leu Arg Gln Ala Leu Leu Leu Leu
1               5                   10                  15

Ala Ala Ala Ala Glu Leu Ser Pro Gly Leu Lys Cys Val Cys Leu Leu
            20                  25                  30

Cys Asp Ser Ser Asn Phe Thr Cys Gln Thr Glu Gly Ala Cys Trp Ala
        35                  40                  45

Ser Val Met Leu Thr Asn Gly Lys Glu Gln Val Ile Lys Ser Cys Val
    50                  55                  60

Ser Leu Pro Glu Leu Asn Ala Gln Val Phe Cys His Ser Ser Asn Asn
65                  70                  75                  80

Val Thr Lys Thr Glu Cys Cys Phe Thr Asp Phe Cys Asn Asn Ile Thr
```

```
                85                  90                  95

Leu His Leu Pro Thr Ala Ser Pro Asn Ala Pro Lys Leu Gly Pro Met
            100                 105                 110

Glu Leu Ala Ile Ile Ile Thr Val Pro Val Cys Leu Leu Ser Ile Ala
        115                 120                 125

Ala Met Leu Thr Val Trp Ala Cys Gln Gly Arg Gln Cys Ser Tyr Arg
    130                 135                 140

Lys Lys Lys Arg Pro Asn Val Glu Glu Pro Leu Ser Glu Cys Asn Leu
145                 150                 155                 160

Val Asn Ala Gly Lys Thr Leu Lys Asp Leu Ile Tyr Asp Val Thr Ala
                165                 170                 175

Ser Gly Ser Gly Ser Gly Leu Pro Leu Leu Val Gln Arg Thr Ile Ala
            180                 185                 190

Arg Thr Ile Val Leu Gln Glu Ile Val Gly Lys Gly Arg Phe Gly Glu
        195                 200                 205

Val Trp His Gly Arg Trp Cys Gly Glu Asp Val Ala Val Lys Ile Phe
    210                 215                 220

Ser Ser Arg Asp Glu Arg Ser Trp Phe Arg Glu Ala Glu Ile Tyr Gln
225                 230                 235                 240

Thr Val Met Leu Arg His Glu Asn Ile Leu Gly Phe Ile Ala Ala Asp
                245                 250                 255

Asn Lys Asp Asn Gly Thr Trp Thr Gln Leu Trp Leu Val Ser Glu Tyr
            260                 265                 270

His Glu Gln Gly Ser Leu Tyr Asp Tyr Leu Asn Arg Asn Ile Val Thr
        275                 280                 285

Val Ala Gly Met Ile Lys Leu Ala Leu Ser Ile Ala Ser Gly Leu Ala
    290                 295                 300

His Leu His Met Glu Ile Val Gly Thr Gln Gly Lys Pro Ala Ile Ala
305                 310                 315                 320

His Arg Asp Ile Lys Ser Lys Asn Ile Leu Val Lys Lys Cys Glu Thr
                325                 330                 335

Cys Ala Ile Ala Asp Leu Gly Leu Ala Val Lys His Asp Ser Ile Leu
            340                 345                 350

Asn Thr Ile Asp Ile Pro Gln Asn Pro Lys Val Gly Thr Lys Arg Tyr
        355                 360                 365

Met Ala Pro Glu Met Leu Asp Asp Thr Met Asn Val Asn Ile Phe Glu
    370                 375                 380

Ser Phe Lys Arg Ala Asp Ile Tyr Ser Val Gly Leu Val Tyr Trp Glu
385                 390                 395                 400

Ile Ala Arg Arg Cys Ser Val Gly Gly Ile Val Glu Glu Tyr Gln Leu
                405                 410                 415

Pro Tyr Tyr Asp Met Val Pro Ser Asp Pro Ser Ile Glu Glu Met Arg
            420                 425                 430

Lys Val Val Cys Asp Gln Lys Phe Arg Pro Ser Ile Pro Asn Gln Trp
        435                 440                 445

Gln Ser Cys Glu Ala Leu Arg Val Met Gly Arg Ile Met Arg Glu Cys
    450                 455                 460

Trp Tyr Ala Asn Gly Ala Ala Arg Leu Thr Ala Leu Arg Ile Lys Lys
465                 470                 475                 480

Thr Ile Ser Gln Leu Cys Val Lys Glu Asp Cys Lys Ala
                485                 490
```

<210> SEQ ID NO 39

<211> LENGTH: 93
<212> TYPE: PRT
<213> ORGANISM: Homo sapiens

<400> SEQUENCE: 39

Glu Leu Ser Pro Gly Leu Lys Cys Val Cys Leu Leu Cys Asp Ser Ser
1               5                   10                  15

Asn Phe Thr Cys Gln Thr Glu Gly Ala Cys Trp Ala Ser Val Met Leu
            20                  25                  30

Thr Asn Gly Lys Glu Gln Val Ile Lys Ser Cys Val Ser Leu Pro Glu
        35                  40                  45

Leu Asn Ala Gln Val Phe Cys His Ser Ser Asn Asn Val Thr Lys Thr
    50                  55                  60

Glu Cys Cys Phe Thr Asp Phe Cys Asn Asn Ile Thr Leu His Leu Pro
65                  70                  75                  80

Thr Ala Ser Pro Asn Ala Pro Lys Leu Gly Pro Met Glu
                85                  90

<210> SEQ ID NO 40
<211> LENGTH: 1479
<212> TYPE: DNA
<213> ORGANISM: Homo sapiens

<400> SEQUENCE: 40
atgacccggg cgctctgctc agcgctccgc caggctctcc tgctgctcgc agcggccgcc 60
gagctctcgc caggactgaa gtgtgtatgt cttttgtgtg attcttcaaa ctttacctgc 120
caaacagaag gagcatgttg ggcatcagtc atgctaacca atggaaaaga gcaggtgatc 180
aaatcctgtg tctcccttcc agaactgaat gctcaagtct tctgtcatag ttccaacaat 240
gttaccaaaa ccgaatgctg cttcacagat tttgcaaca acataacact gcaccttcca 300
acagcatcac caaatgcccc aaaacttgga cccatggagc tggccatcat tattactgtg 360
cctgtttgcc tcctgtccat agctgcgatg ctgacagtat gggcatgcca gggtcgacag 420
tgctcctaca ggaagaaaaa gagaccaaat gtggaggaac cactctctga gtgcaatctg 480
gtaaatgctg gaaaaactct gaaagatctg atttatgatg tgaccgcctc tggatctggc 540
tctggtctac ctctgttggt tcaaaggaca attgcaagga cgattgtgct tcaggaaata 600
gtaggaaaag gtagatttgg tgaggtgtgg catggaagat ggtgtgggga agatgtggct 660
gtgaaaatat tctcctccag agatgaaaga tcttggtttc gtgaggcaga aatttaccag 720
acggtcatgc tgcgacatga aaacatcctt ggtttcattg ctgctgacaa caaagataat 780
ggaacttgga ctcaactttg gctggtatct gaatatcatg aacagggctc cttatatgac 840
tatttgaata gaaatatagt gaccgtggct ggaatgatca agctggcgct ctcaattgct 900
agtggtctgg cacaccttca tatggagatt gttggtacac aaggtaaacc tgctattgct 960
catcgagaca taaaatcaaa gaatatctta gtgaaaaagt gtgaaacttg tgccatagcg 1020
gacttagggt tggctgtgaa gcatgattca atactgaaca ctatcgacat acctcagaat 1080
cctaaagtgg gaaccaagag gtatatggct cctgaaatgc ttgatgatac aatgaatgtg 1140
aatatctttg agtccttcaa acgagctgac atctattctg ttggtctggt ttactgggaa 1200
atagcccgga ggtgttcagt cggaggaatt gttgaggagt accaattgcc ttattatgac 1260
atggtgcctt cagatccctc gatagaggaa atgagaaagg ttgtttgtga ccagaagttt 1320
cgaccaagta tcccaaacca gtggcaaagt tgtgaagcac tccgagtcat ggggagaata 1380
atgcgtgagt gttggtatgc caacggagcg gcccgcctaa ctgctcttcg tattaagaag 1440
actatatctc aactttgtgt caaagaagac tgcaaagcc 1479

<210> SEQ ID NO 41
<211> LENGTH: 279
<212> TYPE: DNA
<213> ORGANISM: Homo sapiens

<400> SEQUENCE: 41
gagctctcgc caggactgaa gtgtgtatgt cttttgtgtg attcttcaaa ctttacctgc 60
caaacagaag gagcatgttg ggcatcagtc atgctaacca atggaaaaga gcaggtgatc 120
aaatcctgtg tctcccttcc agaactgaat gctcaagtct tctgtcatag ttccaacaat 180
gttaccaaaa ccgaatgctg cttcacagat tttgcaaca acataacact gcaccttcca 240
acagcatcac caaatgcccc aaaacttgga cccatggag 279

<210> SEQ ID NO 42
<211> LENGTH: 567
<212> TYPE: PRT
<213> ORGANISM: Homo sapiens

<400> SEQUENCE: 42

Met Gly Arg Gly Leu Leu Arg Gly Leu Trp Pro Leu His Ile Val Leu
1 5 10 15

Trp Thr Arg Ile Ala Ser Thr Ile Pro Pro His Val Gln Lys Ser Val
20 25 30

Asn Asn Asp Met Ile Val Thr Asp Asn Asn Gly Ala Val Lys Phe Pro
35 40 45

Gln Leu Cys Lys Phe Cys Asp Val Arg Phe Ser Thr Cys Asp Asn Gln
50 55 60

Lys Ser Cys Met Ser Asn Cys Ser Ile Thr Ser Ile Cys Glu Lys Pro
65 70 75 80

Gln Glu Val Cys Val Ala Val Trp Arg Lys Asn Asp Glu Asn Ile Thr
85 90 95

Leu Glu Thr Val Cys His Asp Pro Lys Leu Pro Tyr His Asp Phe Ile
100 105 110

Leu Glu Asp Ala Ala Ser Pro Lys Cys Ile Met Lys Glu Lys Lys Lys
115 120 125

Pro Gly Glu Thr Phe Phe Met Cys Ser Cys Ser Ser Asp Glu Cys Asn
130 135 140

Asp Asn Ile Ile Phe Ser Glu Glu Tyr Asn Thr Ser Asn Pro Asp Leu
145 150 155 160

Leu Leu Val Ile Phe Gln Val Thr Gly Ile Ser Leu Leu Pro Pro Leu
165 170 175

Gly Val Ala Ile Ser Val Ile Ile Ile Phe Tyr Cys Tyr Arg Val Asn
180 185 190

Arg Gln Gln Lys Leu Ser Ser Thr Trp Glu Thr Gly Lys Thr Arg Lys
195 200 205

Leu Met Glu Phe Ser Glu His Cys Ala Ile Ile Leu Glu Asp Asp Arg
210 215 220

Ser Asp Ile Ser Ser Thr Cys Ala Asn Asn Ile Asn His Asn Thr Glu
225 230 235 240

Leu Leu Pro Ile Glu Leu Asp Thr Leu Val Gly Lys Gly Arg Phe Ala
245 250 255

Glu Val Tyr Lys Ala Lys Leu Lys Gln Asn Thr Ser Glu Gln Phe Glu
260 265 270

```
Thr Val Ala Val Lys Ile Phe Pro Tyr Glu Glu Tyr Ala Ser Trp Lys
        275                 280                 285

Thr Glu Lys Asp Ile Phe Ser Asp Ile Asn Leu Lys His Glu Asn Ile
    290                 295                 300

Leu Gln Phe Leu Thr Ala Glu Glu Arg Lys Thr Glu Leu Gly Lys Gln
305                 310                 315                 320

Tyr Trp Leu Ile Thr Ala Phe His Ala Lys Gly Asn Leu Gln Glu Tyr
                325                 330                 335

Leu Thr Arg His Val Ile Ser Trp Glu Asp Leu Arg Lys Leu Gly Ser
            340                 345                 350

Ser Leu Ala Arg Gly Ile Ala His Leu His Ser Asp His Thr Pro Cys
        355                 360                 365

Gly Arg Pro Lys Met Pro Ile Val His Arg Asp Leu Lys Ser Ser Asn
    370                 375                 380

Ile Leu Val Lys Asn Asp Leu Thr Cys Cys Leu Cys Asp Phe Gly Leu
385                 390                 395                 400

Ser Leu Arg Leu Asp Pro Thr Leu Ser Val Asp Asp Leu Ala Asn Ser
                405                 410                 415

Gly Gln Val Gly Thr Ala Arg Tyr Met Ala Pro Glu Val Leu Glu Ser
            420                 425                 430

Arg Met Asn Leu Glu Asn Val Glu Ser Phe Lys Gln Thr Asp Val Tyr
        435                 440                 445

Ser Met Ala Leu Val Leu Trp Glu Met Thr Ser Arg Cys Asn Ala Val
    450                 455                 460

Gly Glu Val Lys Asp Tyr Glu Pro Pro Phe Gly Ser Lys Val Arg Glu
465                 470                 475                 480

His Pro Cys Val Glu Ser Met Lys Asp Asn Val Leu Arg Asp Arg Gly
                485                 490                 495

Arg Pro Glu Ile Pro Ser Phe Trp Leu Asn His Gln Gly Ile Gln Met
            500                 505                 510

Val Cys Glu Thr Leu Thr Glu Cys Trp Asp His Asp Pro Glu Ala Arg
        515                 520                 525

Leu Thr Ala Gln Cys Val Ala Glu Arg Phe Ser Glu Leu Glu His Leu
    530                 535                 540

Asp Arg Leu Ser Gly Arg Ser Cys Ser Glu Glu Lys Ile Pro Glu Asp
545                 550                 555                 560

Gly Ser Leu Asn Thr Thr Lys
                565


<210> SEQ ID NO 43
<211> LENGTH: 144
<212> TYPE: PRT
<213> ORGANISM: Homo sapiens

<400> SEQUENCE: 43

Thr Ile Pro Pro His Val Gln Lys Ser Val Asn Asn Asp Met Ile Val
1               5                   10                  15

Thr Asp Asn Asn Gly Ala Val Lys Phe Pro Gln Leu Cys Lys Phe Cys
            20                  25                  30

Asp Val Arg Phe Ser Thr Cys Asp Asn Gln Lys Ser Cys Met Ser Asn
        35                  40                  45

Cys Ser Ile Thr Ser Ile Cys Glu Lys Pro Gln Glu Val Cys Val Ala
    50                  55                  60

Val Trp Arg Lys Asn Asp Glu Asn Ile Thr Leu Glu Thr Val Cys His
```

```
65                  70                  75                  80

Asp Pro Lys Leu Pro Tyr His Asp Phe Ile Leu Glu Asp Ala Ala Ser
                85                  90                  95

Pro Lys Cys Ile Met Lys Glu Lys Lys Lys Pro Gly Glu Thr Phe Phe
            100                 105                 110

Met Cys Ser Cys Ser Ser Asp Glu Cys Asn Asp Asn Ile Ile Phe Ser
        115                 120                 125

Glu Glu Tyr Asn Thr Ser Asn Pro Asp Leu Leu Leu Val Ile Phe Gln
    130                 135                 140


<210> SEQ ID NO 44
<211> LENGTH: 1701
<212> TYPE: DNA
<213> ORGANISM: Homo sapiens

<400> SEQUENCE: 44

atgggtcggg ggctgctcag gggcctgtgg ccgctgcaca tcgtcctgtg gacgcgtatc      60

gccagcacga tcccaccgca cgttcagaag tcggttaata acgacatgat agtcactgac     120

aacaacggtg cagtcaagtt tccacaactg tgtaaatttt gtgatgtgag attttccacc     180

tgtgacaacc agaaatcctg catgagcaac tgcagcatca cctccatctg tgagaagcca     240

caggaagtct gtgtggctgt atggagaaag aatgacgaga acataacact agagacagtt     300

tgccatgacc ccaagctccc ctaccatgac tttattctgg aagatgctgc ttctccaaag     360

tgcattatga aggaaaaaaa aaagcctggt gagactttct tcatgtgttc ctgtagctct     420

gatgagtgca atgacaacat catcttctca gaagaatata acaccagcaa tcctgacttg     480

ttgctagtca tatttcaagt gacaggcatc agcctcctgc caccactggg agttgccata     540

tctgtcatca tcatcttcta ctgctaccgc gttaaccggc agcagaagct gagttcaacc     600

tgggaaaccg gcaagacgcg gaagctcatg gagttcagcg agcactgtgc catcatcctg     660

gaagatgacc gctctgacat cagctccacg tgtgccaaca acatcaacca caacacagag     720

ctgctgccca ttgagctgga caccctggtg gggaaaggtc gctttgctga ggtctataag     780

gccaagctga agcagaacac ttcagagcag tttgagacag tggcagtcaa gatctttccc     840

tatgaggagt atgcctcttg gaagacagag aaggacatct tctcagacat caatctgaag     900

catgagaaca tactccagtt cctgacggct gaggagcgga agacggagtt ggggaaacaa     960

tactggctga tcaccgcctt ccacgccaag ggcaacctac aggagtacct gacgcggcat    1020

gtcatcagct gggaggacct gcgcaagctg ggcagctccc tcgcccgggg gattgctcac    1080

ctccacagtg atcacactcc atgtgggagg cccaagatgc ccatcgtgca cagggacctc    1140

aagagctcca atatcctcgt gaagaacgac ctaacctgct gcctgtgtga ctttgggctt    1200

tccctgcgtc tggaccctac tctgtctgtg gatgacctgg ctaacagtgg gcaggtggga    1260

actgcaagat acatggctcc agaagtccta gaatccagga tgaatttgga gaatgttgag    1320

tccttcaagc agaccgatgt ctactccatg gctctggtgc tctgggaaat gacatctcgc    1380

tgtaatgcag tgggagaagt aaaagattat gagcctccat ttggttccaa ggtgcgggag    1440

cacccctgtg tcgaaagcat gaaggacaac gtgttgagag atcgagggcg accagaaatt    1500

cccagcttct ggctcaacca ccagggcatc cagatggtgt gtgagacgtt gactgagtgc    1560

tgggaccacg acccagaggc ccgtctcaca gcccagtgtg tggcagaacg cttcagtgag    1620

ctggagcatc tggacaggct ctcggggagg agctgctcgg aggagaagat tcctgaagac    1680

ggctccctaa acactaccaa a                                              1701
```

<210> SEQ ID NO 45
<211> LENGTH: 432
<212> TYPE: DNA
<213> ORGANISM: Homo sapiens

<400> SEQUENCE: 45
acgatcccac cgcacgttca gaagtcggtt aataacgaca tgatagtcac tgacaacaac 60
ggtgcagtca agtttccaca actgtgtaaa ttttgtgatg tgagattttc cacctgtgac 120
aaccagaaat cctgcatgag caactgcagc atcacctcca tctgtgagaa gccacaggaa 180
gtctgtgtgg ctgtatggag aaagaatgac gagaacataa cactagagac agtttgccat 240
gaccccaagc tcccctacca tgactttatt ctggaagatg ctgcttctcc aaagtgcatt 300
atgaaggaaa aaaaaaagcc tggtgagact ttcttcatgt gttcctgtag ctctgatgag 360
tgcaatgaca acatcatctt ctcagaagaa tataacacca gcaatcctga cttgttgcta 420
gtcatatttc aa 432

<210> SEQ ID NO 46
<211> LENGTH: 1038
<212> TYPE: PRT
<213> ORGANISM: Homo sapiens

<400> SEQUENCE: 46

Met Thr Ser Ser Leu Gln Arg Pro Trp Arg Val Pro Trp Leu Pro Trp
1 5 10 15

Thr Ile Leu Leu Val Ser Thr Ala Ala Ala Ser Gln Asn Gln Glu Arg
20 25 30

Leu Cys Ala Phe Lys Asp Pro Tyr Gln Gln Asp Leu Gly Ile Gly Glu
35 40 45

Ser Arg Ile Ser His Glu Asn Gly Thr Ile Leu Cys Ser Lys Gly Ser
50 55 60

Thr Cys Tyr Gly Leu Trp Glu Lys Ser Lys Gly Asp Ile Asn Leu Val
65 70 75 80

Lys Gln Gly Cys Trp Ser His Ile Gly Asp Pro Gln Glu Cys His Tyr
85 90 95

Glu Glu Cys Val Val Thr Thr Thr Pro Pro Ser Ile Gln Asn Gly Thr
100 105 110

Tyr Arg Phe Cys Cys Cys Ser Thr Asp Leu Cys Asn Val Asn Phe Thr
115 120 125

Glu Asn Phe Pro Pro Pro Asp Thr Thr Pro Leu Ser Pro Pro His Ser
130 135 140

Phe Asn Arg Asp Glu Thr Ile Ile Ile Ala Leu Ala Ser Val Ser Val
145 150 155 160

Leu Ala Val Leu Ile Val Ala Leu Cys Phe Gly Tyr Arg Met Leu Thr
165 170 175

Gly Asp Arg Lys Gln Gly Leu His Ser Met Asn Met Met Glu Ala Ala
180 185 190

Ala Ser Glu Pro Ser Leu Asp Leu Asp Asn Leu Lys Leu Leu Glu Leu
195 200 205

Ile Gly Arg Gly Arg Tyr Gly Ala Val Tyr Lys Gly Ser Leu Asp Glu
210 215 220

Arg Pro Val Ala Val Lys Val Phe Ser Phe Ala Asn Arg Gln Asn Phe
225 230 235 240

Ile Asn Glu Lys Asn Ile Tyr Arg Val Pro Leu Met Glu His Asp Asn

-continued

```
                245                 250                 255

Ile Ala Arg Phe Ile Val Gly Asp Glu Arg Val Thr Ala Asp Gly Arg
            260                 265                 270

Met Glu Tyr Leu Leu Val Met Glu Tyr Tyr Pro Asn Gly Ser Leu Cys
        275                 280                 285

Lys Tyr Leu Ser Leu His Thr Ser Asp Trp Val Ser Ser Cys Arg Leu
    290                 295                 300

Ala His Ser Val Thr Arg Gly Leu Ala Tyr Leu His Thr Glu Leu Pro
305                 310                 315                 320

Arg Gly Asp His Tyr Lys Pro Ala Ile Ser His Arg Asp Leu Asn Ser
                325                 330                 335

Arg Asn Val Leu Val Lys Asn Asp Gly Thr Cys Val Ile Ser Asp Phe
            340                 345                 350

Gly Leu Ser Met Arg Leu Thr Gly Asn Arg Leu Val Arg Pro Gly Glu
        355                 360                 365

Glu Asp Asn Ala Ala Ile Ser Glu Val Gly Thr Ile Arg Tyr Met Ala
    370                 375                 380

Pro Glu Val Leu Glu Gly Ala Val Asn Leu Arg Asp Cys Glu Ser Ala
385                 390                 395                 400

Leu Lys Gln Val Asp Met Tyr Ala Leu Gly Leu Ile Tyr Trp Glu Ile
                405                 410                 415

Phe Met Arg Cys Thr Asp Leu Phe Pro Gly Glu Ser Val Pro Glu Tyr
            420                 425                 430

Gln Met Ala Phe Gln Thr Glu Val Gly Asn His Pro Thr Phe Glu Asp
        435                 440                 445

Met Gln Val Leu Val Ser Arg Glu Lys Gln Arg Pro Lys Phe Pro Glu
    450                 455                 460

Ala Trp Lys Glu Asn Ser Leu Ala Val Arg Ser Leu Lys Glu Thr Ile
465                 470                 475                 480

Glu Asp Cys Trp Asp Gln Asp Ala Glu Ala Arg Leu Thr Ala Gln Cys
                485                 490                 495

Ala Glu Glu Arg Met Ala Glu Leu Met Met Ile Trp Glu Arg Asn Lys
            500                 505                 510

Ser Val Ser Pro Thr Val Asn Pro Met Ser Thr Ala Met Gln Asn Glu
        515                 520                 525

Arg Asn Leu Ser His Asn Arg Arg Val Pro Lys Ile Gly Pro Tyr Pro
    530                 535                 540

Asp Tyr Ser Ser Ser Ser Tyr Ile Glu Asp Ser Ile His His Thr Asp
545                 550                 555                 560

Ser Ile Val Lys Asn Ile Ser Ser Glu His Ser Met Ser Ser Thr Pro
                565                 570                 575

Leu Thr Ile Gly Glu Lys Asn Arg Asn Ser Ile Asn Tyr Glu Arg Gln
            580                 585                 590

Gln Ala Gln Ala Arg Ile Pro Ser Pro Glu Thr Ser Val Thr Ser Leu
        595                 600                 605

Ser Thr Asn Thr Thr Thr Thr Asn Thr Thr Gly Leu Thr Pro Ser Thr
    610                 615                 620

Gly Met Thr Thr Ile Ser Glu Met Pro Tyr Pro Asp Glu Thr Asn Leu
625                 630                 635                 640

His Thr Thr Asn Val Ala Gln Ser Ile Gly Pro Thr Pro Val Cys Leu
                645                 650                 655

Gln Leu Thr Glu Glu Asp Leu Glu Thr Asn Lys Leu Asp Pro Lys Glu
            660                 665                 670
```

Val Asp Lys Asn Leu Lys Glu Ser Ser Asp Glu Asn Leu Met Glu His
675 680 685

Ser Leu Lys Gln Phe Ser Gly Pro Asp Pro Leu Ser Ser Thr Ser Ser
690 695 700

Ser Leu Leu Tyr Pro Leu Ile Lys Leu Ala Val Glu Ala Thr Gly Gln
705 710 715 720

Gln Asp Phe Thr Gln Thr Ala Asn Gly Gln Ala Cys Leu Ile Pro Asp
725 730 735

Val Leu Pro Thr Gln Ile Tyr Pro Leu Pro Lys Gln Gln Asn Leu Pro
740 745 750

Lys Arg Pro Thr Ser Leu Pro Leu Asn Thr Lys Asn Ser Thr Lys Glu
755 760 765

Pro Arg Leu Lys Phe Gly Ser Lys His Lys Ser Asn Leu Lys Gln Val
770 775 780

Glu Thr Gly Val Ala Lys Met Asn Thr Ile Asn Ala Ala Glu Pro His
785 790 795 800

Val Val Thr Val Thr Met Asn Gly Val Ala Gly Arg Asn His Ser Val
805 810 815

Asn Ser His Ala Ala Thr Thr Gln Tyr Ala Asn Gly Thr Val Leu Ser
820 825 830

Gly Gln Thr Thr Asn Ile Val Thr His Arg Ala Gln Glu Met Leu Gln
835 840 845

Asn Gln Phe Ile Gly Glu Asp Thr Arg Leu Asn Ile Asn Ser Ser Pro
850 855 860

Asp Glu His Glu Pro Leu Leu Arg Arg Glu Gln Gln Ala Gly His Asp
865 870 875 880

Glu Gly Val Leu Asp Arg Leu Val Asp Arg Arg Glu Arg Pro Leu Glu
885 890 895

Gly Gly Arg Thr Asn Ser Asn Asn Asn Asn Ser Asn Pro Cys Ser Glu
900 905 910

Gln Asp Val Leu Ala Gln Gly Val Pro Ser Thr Ala Ala Asp Pro Gly
915 920 925

Pro Ser Lys Pro Arg Arg Ala Gln Arg Pro Asn Ser Leu Asp Leu Ser
930 935 940

Ala Thr Asn Val Leu Asp Gly Ser Ser Ile Gln Ile Gly Glu Ser Thr
945 950 955 960

Gln Asp Gly Lys Ser Gly Ser Gly Glu Lys Ile Lys Lys Arg Val Lys
965 970 975

Thr Pro Tyr Ser Leu Lys Arg Trp Arg Pro Ser Thr Trp Val Ile Ser
980 985 990

Thr Glu Ser Leu Asp Cys Glu Val Asn Asn Asn Gly Ser Asn Arg Ala
995 1000 1005

Val His Ser Lys Ser Ser Thr Ala Val Tyr Leu Ala Glu Gly Gly
1010 1015 1020

Thr Ala Thr Thr Met Val Ser Lys Asp Ile Gly Met Asn Cys Leu
1025 1030 1035

<210> SEQ ID NO 47
<211> LENGTH: 124
<212> TYPE: PRT
<213> ORGANISM: Homo sapiens

<400> SEQUENCE: 47

Ser Gln Asn Gln Glu Arg Leu Cys Ala Phe Lys Asp Pro Tyr Gln Gln

-continued

```
1               5                   10                  15

Asp Leu Gly Ile Gly Glu Ser Arg Ile Ser His Glu Asn Gly Thr Ile
            20                  25                  30

Leu Cys Ser Lys Gly Ser Thr Cys Tyr Gly Leu Trp Glu Lys Ser Lys
        35                  40                  45

Gly Asp Ile Asn Leu Val Lys Gln Gly Cys Trp Ser His Ile Gly Asp
    50                  55                  60

Pro Gln Glu Cys His Tyr Glu Glu Cys Val Val Thr Thr Thr Pro Pro
65                  70                  75                  80

Ser Ile Gln Asn Gly Thr Tyr Arg Phe Cys Cys Cys Ser Thr Asp Leu
                85                  90                  95

Cys Asn Val Asn Phe Thr Glu Asn Phe Pro Pro Pro Asp Thr Thr Pro
            100                 105                 110

Leu Ser Pro Pro His Ser Phe Asn Arg Asp Glu Thr
        115                 120


<210> SEQ ID NO 48
<211> LENGTH: 3114
<212> TYPE: DNA
<213> ORGANISM: Homo sapiens

<400> SEQUENCE: 48

atgacttcct cgctgcagcg gccctggcgg gtgccctggc taccatggac catcctgctg     60

gtcagcactg cggctgcttc gcagaatcaa gaacggctat gtgcgtttaa agatccgtat    120

cagcaagacc ttgggatagg tgagagtaga atctctcatg aaaatgggac aatattatgc    180

tcgaaaggta gcacctgcta tggcctttgg gagaaatcaa aaggggacat aaatcttgta    240

aaacaaggat gttggtctca cattggagat ccccaagagt gtcactatga agaatgtgta    300

gtaactacca ctcctccctc aattcagaat ggaacatacc gtttctgctg ttgtagcaca    360

gatttatgta atgtcaactt tactgagaat tttccacctc ctgacacaac accactcagt    420

ccacctcatt catttaaccg agatgagaca ataatcattg ctttggcatc agtctctgta    480

ttagctgttt tgatagttgc cttatgcttt ggatacagaa tgttgacagg agaccgtaaa    540

caaggtcttc acagtatgaa catgatggag gcagcagcat ccgaaccctc tcttgatcta    600

gataatctga aactgttgga gctgattggc cgaggtcgat atggagcagt atataaaggc    660

tccttggatg agcgtccagt tgctgtaaaa gtgttttcct ttgcaaaccg tcagaatttt    720

atcaacgaaa agaacattta cagagtgcct ttgatggaac atgacaacat tgcccgcttt    780

atagttggag atgagagagt cactgcagat ggacgcatgg aatatttgct tgtgatggag    840

tactatccca atggatcttt atgcaagtat ttaagtctcc acacaagtga ctgggtaagc    900

tcttgccgtc ttgctcattc tgttactaga ggactggctt atcttcacac agaattacca    960

cgaggagatc attataaacc tgcaatttcc catcgagatt taaacagcag aaatgtccta   1020

gtgaaaaatg atggaacctg tgttattagt gactttggac tgtccatgag gctgactgga   1080

aatagactgg tgcgcccagg ggaggaagat aatgcagcca taagcgaggt tggcactatc   1140

agatatatgg caccagaagt gctagaagga gctgtgaact tgagggactg tgaatcagct   1200

ttgaaacaag tagacatgta tgctcttgga ctaatctatt gggagatatt tatgagatgt   1260

acagacctct tcccagggga atccgtacca gagtaccaga tggcttttca gacagaggtt   1320

ggaaaccatc ccacttttga ggatatgcag gttctcgtgt ctagggaaaa acagagaccc   1380

aagttcccag aagcctggaa agaaaatagc ctggcagtga ggtcactcaa ggagacaatc   1440
```

-continued gaagactgtt gggaccagga tgcagaggct cggcttactg cacagtgtgc tgaggaaagg 1500
atggctgaac ttatgatgat ttgggaaaga aacaaatctg tgagcccaac agtcaatcca 1560
atgtctactg ctatgcagaa tgaacgcaac ctgtcacata ataggcgtgt gccaaaaatt 1620
ggtccttatc cagattattc ttcctcctca tacattgaag actctatcca tcatactgac 1680
agcatcgtga agaatatttc ctctgagcat tctatgtcca gcacaccttt gactataggg 1740
gaaaaaaacc gaaattcaat taactatgaa cgacagcaag cacaagctcg aatccccagc 1800
cctgaaacaa gtgtcaccag cctctccacc aacacaacaa ccacaaacac cacaggactc 1860
acgccaagta ctggcatgac tactatatct gagatgccat acccagatga aacaaatctg 1920
cataccacaa atgttgcaca gtcaattggg ccaacccctg tctgcttaca gctgacagaa 1980
gaagacttgg aaaccaacaa gctagaccca aaagaagttg ataagaacct caaggaaagc 2040
tctgatgaga atctcatgga gcactctctt aaacagttca gtggcccaga cccactgagc 2100
agtactagtt ctagcttgct ttacccactc ataaaacttg cagtagaagc aactggacag 2160
caggacttca cacagactgc aaatggccaa gcatgtttga ttcctgatgt tctgcctact 2220
cagatctatc ctctccccaa gcagcagaac cttcccaaga gacctactag tttgcctttg 2280
aacaccaaaa attcaacaaa agagccccgg ctaaaatttg gcagcaagca caaatcaaac 2340
ttgaaacaag tcgaaactgg agttgccaag atgaatacaa tcaatgcagc agaacctcat 2400
gtggtgacag tcaccatgaa tggtgtggca ggtagaaacc acagtgttaa ctcccatgct 2460
gccacaaccc aatatgccaa tgggacagta ctatctggcc aaacaaccaa catagtgaca 2520
catagggccc aagaaatgtt gcagaatcag tttattggtg aggacacccg gctgaatatt 2580
aattccagtc ctgatgagca tgagccttta ctgagacgag agcaacaagc tggccatgat 2640
gaaggtgttc tggatcgtct tgtggacagg agggaacggc cactagaagg tggccgaact 2700
aattccaata acaacaacag caatccatgt tcagaacaag atgttcttgc acagggtgtt 2760
ccaagcacag cagcagatcc tgggccatca aagcccagaa gagcacagag gcctaattct 2820
ctggatcttt cagccacaaa tgtcctggat ggcagcagta tacagatagg tgagtcaaca 2880
caagatggca aatcaggatc aggtgaaaag atcaagaaac gtgtgaaaac tccctattct 2940
cttaagcggt ggcgcccctc cacctgggtc atctccactg aatcgctgga ctgtgaagtc 3000
aacaataatg gcagtaacag ggcagttcat tccaaatcca gcactgctgt ttaccttgca 3060
gaaggaggca ctgctacaac catggtgtct aaagatatag gaatgaactg tctg 3114

<210> SEQ ID NO 49
<211> LENGTH: 372
<212> TYPE: DNA
<213> ORGANISM: Homo sapiens

<400> SEQUENCE: 49
tcgcagaatc aagaacggct atgtgcgttt aaagatccgt atcagcaaga ccttgggata 60
ggtgagagta gaatctctca tgaaaatggg acaatattat gctcgaaagg tagcacctgc 120
tatggccttt gggagaaatc aaaaggggac ataaatcttg taaaacaagg atgttggtct 180
cacattggag atccccaaga gtgtcactat gaagaatgtg tagtaactac cactcctccc 240
tcaattcaga atggaacata ccgtttctgc tgttgtagca cagatttatg taatgtcaac 300
tttactgaga attttccacc tcctgacaca acaccactca gtccacctca ttcatttaac 360
cgagatgaga ca 372

<210> SEQ ID NO 50
<211> LENGTH: 573
<212> TYPE: PRT
<213> ORGANISM: Homo sapiens

<400> SEQUENCE: 50

```
Met Leu Gly Ser Leu Gly Leu Trp Ala Leu Leu Pro Thr Ala Val Glu
1               5                   10                  15

Ala Pro Pro Asn Arg Arg Thr Cys Val Phe Phe Glu Ala Pro Gly Val
            20                  25                  30

Arg Gly Ser Thr Lys Thr Leu Gly Glu Leu Leu Asp Thr Gly Thr Glu
        35                  40                  45

Leu Pro Arg Ala Ile Arg Cys Leu Tyr Ser Arg Cys Cys Phe Gly Ile
    50                  55                  60

Trp Asn Leu Thr Gln Asp Arg Ala Gln Val Glu Met Gln Gly Cys Arg
65                  70                  75                  80

Asp Ser Asp Glu Pro Gly Cys Glu Ser Leu His Cys Asp Pro Ser Pro
                85                  90                  95

Arg Ala His Pro Ser Pro Gly Ser Thr Leu Phe Thr Cys Ser Cys Gly
            100                 105                 110

Thr Asp Phe Cys Asn Ala Asn Tyr Ser His Leu Pro Pro Pro Gly Ser
        115                 120                 125

Pro Gly Thr Pro Gly Ser Gln Gly Pro Gln Ala Ala Pro Gly Glu Ser
    130                 135                 140

Ile Trp Met Ala Leu Val Leu Leu Gly Leu Phe Leu Leu Leu Leu Leu
145                 150                 155                 160

Leu Leu Gly Ser Ile Ile Leu Ala Leu Leu Gln Arg Lys Asn Tyr Arg
                165                 170                 175

Val Arg Gly Glu Pro Val Pro Glu Pro Arg Pro Asp Ser Gly Arg Asp
            180                 185                 190

Trp Ser Val Glu Leu Gln Glu Leu Pro Glu Leu Cys Phe Ser Gln Val
        195                 200                 205

Ile Arg Glu Gly Gly His Ala Val Val Trp Ala Gly Gln Leu Gln Gly
    210                 215                 220

Lys Leu Val Ala Ile Lys Ala Phe Pro Pro Arg Ser Val Ala Gln Phe
225                 230                 235                 240

Gln Ala Glu Arg Ala Leu Tyr Glu Leu Pro Gly Leu Gln His Asp His
                245                 250                 255

Ile Val Arg Phe Ile Thr Ala Ser Arg Gly Gly Pro Gly Arg Leu Leu
            260                 265                 270

Ser Gly Pro Leu Leu Val Leu Glu Leu His Pro Lys Gly Ser Leu Cys
        275                 280                 285

His Tyr Leu Thr Gln Tyr Thr Ser Asp Trp Gly Ser Ser Leu Arg Met
    290                 295                 300

Ala Leu Ser Leu Ala Gln Gly Leu Ala Phe Leu His Glu Glu Arg Trp
305                 310                 315                 320

Gln Asn Gly Gln Tyr Lys Pro Gly Ile Ala His Arg Asp Leu Ser Ser
                325                 330                 335

Gln Asn Val Leu Ile Arg Glu Asp Gly Ser Cys Ala Ile Gly Asp Leu
            340                 345                 350

Gly Leu Ala Leu Val Leu Pro Gly Leu Thr Gln Pro Pro Ala Trp Thr
        355                 360                 365

Pro Thr Gln Pro Gln Gly Pro Ala Ala Ile Met Glu Ala Gly Thr Gln
    370                 375                 380
```

```
Arg Tyr Met Ala Pro Glu Leu Leu Asp Lys Thr Leu Asp Leu Gln Asp
385                 390                 395                 400

Trp Gly Met Ala Leu Arg Arg Ala Asp Ile Tyr Ser Leu Ala Leu Leu
                405                 410                 415

Leu Trp Glu Ile Leu Ser Arg Cys Pro Asp Leu Arg Pro Asp Ser Ser
            420                 425                 430

Pro Pro Pro Phe Gln Leu Ala Tyr Glu Ala Glu Leu Gly Asn Thr Pro
        435                 440                 445

Thr Ser Asp Glu Leu Trp Ala Leu Ala Val Gln Glu Arg Arg Arg Pro
    450                 455                 460

Tyr Ile Pro Ser Thr Trp Arg Cys Phe Ala Thr Asp Pro Asp Gly Leu
465                 470                 475                 480

Arg Glu Leu Leu Glu Asp Cys Trp Asp Ala Asp Pro Glu Ala Arg Leu
                485                 490                 495

Thr Ala Glu Cys Val Gln Gln Arg Leu Ala Ala Leu Ala His Pro Gln
            500                 505                 510

Glu Ser His Pro Phe Pro Glu Ser Cys Pro Arg Gly Cys Pro Pro Leu
        515                 520                 525

Cys Pro Glu Asp Cys Thr Ser Ile Pro Ala Pro Thr Ile Leu Pro Cys
    530                 535                 540

Arg Pro Gln Arg Ser Ala Cys His Phe Ser Val Gln Gln Gly Pro Cys
545                 550                 555                 560

Ser Arg Asn Pro Gln Pro Ala Cys Thr Leu Ser Pro Val
                565                 570
```

<210> SEQ ID NO 51
<211> LENGTH: 132
<212> TYPE: PRT
<213> ORGANISM: Homo sapiens

<400> SEQUENCE: 51

```
Pro Pro Asn Arg Arg Thr Cys Val Phe Phe Glu Ala Pro Gly Val Arg
1               5                   10                  15

Gly Ser Thr Lys Thr Leu Gly Glu Leu Leu Asp Thr Gly Thr Glu Leu
            20                  25                  30

Pro Arg Ala Ile Arg Cys Leu Tyr Ser Arg Cys Cys Phe Gly Ile Trp
        35                  40                  45

Asn Leu Thr Gln Asp Arg Ala Gln Val Glu Met Gln Gly Cys Arg Asp
    50                  55                  60

Ser Asp Glu Pro Gly Cys Glu Ser Leu His Cys Asp Pro Ser Pro Arg
65                  70                  75                  80

Ala His Pro Ser Pro Gly Ser Thr Leu Phe Thr Cys Ser Cys Gly Thr
                85                  90                  95

Asp Phe Cys Asn Ala Asn Tyr Ser His Leu Pro Pro Pro Gly Ser Pro
            100                 105                 110

Gly Thr Pro Gly Ser Gln Gly Pro Gln Ala Ala Pro Gly Glu Ser Ile
        115                 120                 125

Trp Met Ala Leu
    130
```

<210> SEQ ID NO 52
<211> LENGTH: 1719
<212> TYPE: DNA
<213> ORGANISM: Homo sapiens

<400> SEQUENCE: 52

-continued

```
atgctagggt ctttggggct ttgggcatta cttcccacag ctgtggaagc acccccaaac     60

aggcgaacct gtgtgttctt tgaggcccct ggagtgcggg gaagcacaaa gacactggga    120

gagctgctag atacaggcac agagctcccc agagctatcc gctgcctcta cagccgctgc    180

tgctttggga tctggaacct gacccaagac cgggcacagg tggaaatgca aggatgccga    240

gacagtgatg agccaggctg tgagtccctc cactgtgacc caagtccccg agcccacccc    300

agccctggct ccactctctt cacctgctcc tgtggcactg acttctgcaa tgccaattac    360

agccatctgc ctcctccagg gagccctggg actcctggct cccagggtcc ccaggctgcc    420

ccaggtgagt ccatctggat ggcactggtg ctgctggggc tgttcctcct cctcctgctg    480

ctgctgggca gcatcatctt ggccctgcta cagcgaaaga actacagagt gcgaggtgag    540

ccagtgccag agccaaggcc agactcaggc agggactgga gtgtggagct gcaggagctg    600

cctgagctgt gtttctccca ggtaatccgg gaaggaggtc atgcagtggt ttgggccggg    660

cagctgcaag gaaaactggt tgccatcaag gccttcccac cgaggtctgt ggctcagttc    720

caagctgaga gagcattgta cgaacttcca ggcctacagc acgaccacat tgtccgattt    780

atcactgcca gccggggggg tcctggccgc ctgctctctg ggcccctgct ggtactggaa    840

ctgcatccca agggctccct gtgccactac ttgacccagt acaccagtga ctggggaagt    900

tccctgcgga tggcactgtc cctggcccag ggcctggcat ttctccatga ggagcgctgg    960

cagaatggcc aatataaacc aggtattgcc caccgagatc tgagcagcca gaatgtgctc   1020

attcgggaag atggatcgtg tgccattgga gacctgggcc ttgccttggt gctccctggc   1080

ctcactcagc cccctgcctg gacccctact caaccacaag gcccagctgc catcatggaa   1140

gctggcaccc agaggtacat ggcaccagag ctcttggaca agactctgga cctacaggat   1200

tggggcatgg ccctccgacg agctgatatt tactctttgg ctctgctcct gtgggagata   1260

ctgagccgct gcccagattt gaggcctgac agcagtccac caccccttcca actggcctat   1320

gaggcagaac tgggcaatac ccctacctct gatgagctat gggccttggc agtgcaggag   1380

aggaggcgtc cctacatccc atccacctgg cgctgctttg ccacagaccc tgatgggctg   1440

agggagctcc tagaagactg ttgggatgca gacccagaag cacggctgac agctgagtgt   1500

gtacagcagc gcctggctgc cttggcccat cctcaagaga gccacccctt tccagagagc   1560

tgtccacgtg gctgcccacc tctctgccca gaagactgta cttcaattcc tgcccctacc   1620

atcctcccct gtaggcctca gcggagtgcc tgccacttca gcgttcagca aggcccttgt   1680

tccaggaatc ctcagcctgc ctgtaccctt tctcctgtg                          1719
```

<210> SEQ ID NO 53
<211> LENGTH: 396
<212> TYPE: DNA
<213> ORGANISM: Homo sapiens

<400> SEQUENCE: 53

```
cccccaaaca ggcgaacctg tgtgttcttt gaggcccctg gagtgcgggg aagcacaaag     60

acactgggag agctgctaga tacaggcaca gagctcccca gagctatccg ctgcctctac    120

agccgctgct gctttgggat ctggaacctg acccaagacc gggcacaggt ggaaatgcaa    180

ggatgccgag acagtgatga gccaggctgt gagtccctcc actgtgaccc aagtccccga    240

gcccacccca gccctggctc cactctcttc acctgctcct gtggcactga cttctgcaat    300

gccaattaca gccatctgcc tcctccaggg agccctggga ctcctggctc ccagggtccc    360

caggctgccc caggtgagtc catctggatg gcactg                              396
```

<210> SEQ ID NO 54

<400> SEQUENCE: 54

000

<210> SEQ ID NO 55

<400> SEQUENCE: 55

000

<210> SEQ ID NO 56

<400> SEQUENCE: 56

000

<210> SEQ ID NO 57

<400> SEQUENCE: 57

000

<210> SEQ ID NO 58
<211> LENGTH: 3
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 58

Gly Gly Gly
1

<210> SEQ ID NO 59
<211> LENGTH: 4
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 59

Gly Gly Gly Gly
1

<210> SEQ ID NO 60
<211> LENGTH: 5
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 60

Thr Gly Gly Gly Gly
1               5

<210> SEQ ID NO 61
<211> LENGTH: 5
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 61

Ser Gly Gly Gly Gly
1 5

<210> SEQ ID NO 62
<211> LENGTH: 4
<212> TYPE: PRT
<213> ORGANISM: Artificial Sequence
<220> FEATURE:
<223> OTHER INFORMATION: Description of Artificial Sequence: Synthetic peptide

<400> SEQUENCE: 62

Thr Gly Gly Gly
1

<210> SEQ ID NO 63
<211> LENGTH: 4
<212> TYPE: PRT
<213> ORGANISM: Artificial Sequence
<220> FEATURE:
<223> OTHER INFORMATION: Description of Artificial Sequence: Synthetic peptide

<400> SEQUENCE: 63

Ser Gly Gly Gly
1

<210> SEQ ID NO 64

<400> SEQUENCE: 64

000

<210> SEQ ID NO 65

<400> SEQUENCE: 65

000

<210> SEQ ID NO 66

<400> SEQUENCE: 66

000

<210> SEQ ID NO 67
<211> LENGTH: 592
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 67

Met Gly Arg Gly Leu Leu Arg Gly Leu Trp Pro Leu His Ile Val Leu
1 5 10 15

Trp Thr Arg Ile Ala Ser Thr Ile Pro Pro His Val Gln Lys Ser Asp
20 25 30

Val Glu Met Glu Ala Gln Lys Asp Glu Ile Ile Cys Pro Ser Cys Asn
35 40 45

Arg Thr Ala His Pro Leu Arg His Ile Asn Asn Asp Met Ile Val Thr
50 55 60

Asp Asn Asn Gly Ala Val Lys Phe Pro Gln Leu Cys Lys Phe Cys Asp

-continued

```
65                  70                  75                  80

Val Arg Phe Ser Thr Cys Asp Asn Gln Lys Ser Cys Met Ser Asn Cys
                85                  90                  95

Ser Ile Thr Ser Ile Cys Glu Lys Pro Gln Glu Val Cys Val Ala Val
            100                 105                 110

Trp Arg Lys Asn Asp Glu Asn Ile Thr Leu Glu Thr Val Cys His Asp
        115                 120                 125

Pro Lys Leu Pro Tyr His Asp Phe Ile Leu Glu Asp Ala Ala Ser Pro
    130                 135                 140

Lys Cys Ile Met Lys Glu Lys Lys Lys Pro Gly Glu Thr Phe Phe Met
145                 150                 155                 160

Cys Ser Cys Ser Ser Asp Glu Cys Asn Asp Asn Ile Ile Phe Ser Glu
                165                 170                 175

Glu Tyr Asn Thr Ser Asn Pro Asp Leu Leu Leu Val Ile Phe Gln Val
            180                 185                 190

Thr Gly Ile Ser Leu Leu Pro Pro Leu Gly Val Ala Ile Ser Val Ile
        195                 200                 205

Ile Ile Phe Tyr Cys Tyr Arg Val Asn Arg Gln Gln Lys Leu Ser Ser
    210                 215                 220

Thr Trp Glu Thr Gly Lys Thr Arg Lys Leu Met Glu Phe Ser Glu His
225                 230                 235                 240

Cys Ala Ile Ile Leu Glu Asp Asp Arg Ser Asp Ile Ser Ser Thr Cys
                245                 250                 255

Ala Asn Asn Ile Asn His Asn Thr Glu Leu Leu Pro Ile Glu Leu Asp
            260                 265                 270

Thr Leu Val Gly Lys Gly Arg Phe Ala Glu Val Tyr Lys Ala Lys Leu
        275                 280                 285

Lys Gln Asn Thr Ser Glu Gln Phe Glu Thr Val Ala Val Lys Ile Phe
    290                 295                 300

Pro Tyr Glu Glu Tyr Ala Ser Trp Lys Thr Glu Lys Asp Ile Phe Ser
305                 310                 315                 320

Asp Ile Asn Leu Lys His Glu Asn Ile Leu Gln Phe Leu Thr Ala Glu
                325                 330                 335

Glu Arg Lys Thr Glu Leu Gly Lys Gln Tyr Trp Leu Ile Thr Ala Phe
            340                 345                 350

His Ala Lys Gly Asn Leu Gln Glu Tyr Leu Thr Arg His Val Ile Ser
        355                 360                 365

Trp Glu Asp Leu Arg Lys Leu Gly Ser Ser Leu Ala Arg Gly Ile Ala
    370                 375                 380

His Leu His Ser Asp His Thr Pro Cys Gly Arg Pro Lys Met Pro Ile
385                 390                 395                 400

Val His Arg Asp Leu Lys Ser Ser Asn Ile Leu Val Lys Asn Asp Leu
                405                 410                 415

Thr Cys Cys Leu Cys Asp Phe Gly Leu Ser Leu Arg Leu Asp Pro Thr
            420                 425                 430

Leu Ser Val Asp Asp Leu Ala Asn Ser Gly Gln Val Gly Thr Ala Arg
        435                 440                 445

Tyr Met Ala Pro Glu Val Leu Glu Ser Arg Met Asn Leu Glu Asn Val
    450                 455                 460

Glu Ser Phe Lys Gln Thr Asp Val Tyr Ser Met Ala Leu Val Leu Trp
465                 470                 475                 480

Glu Met Thr Ser Arg Cys Asn Ala Val Gly Glu Val Lys Asp Tyr Glu
                485                 490                 495
```

```
Pro Pro Phe Gly Ser Lys Val Arg Glu His Pro Cys Val Glu Ser Met
            500                 505                 510

Lys Asp Asn Val Leu Arg Asp Arg Gly Arg Pro Glu Ile Pro Ser Phe
        515                 520                 525

Trp Leu Asn His Gln Gly Ile Gln Met Val Cys Glu Thr Leu Thr Glu
    530                 535                 540

Cys Trp Asp His Asp Pro Glu Ala Arg Leu Thr Ala Gln Cys Val Ala
545                 550                 555                 560

Glu Arg Phe Ser Glu Leu Glu His Leu Asp Arg Leu Ser Gly Arg Ser
                565                 570                 575

Cys Ser Glu Glu Lys Ile Pro Glu Asp Gly Ser Leu Asn Thr Thr Lys
            580                 585                 590


<210> SEQ ID NO 68
<211> LENGTH: 169
<212> TYPE: PRT
<213> ORGANISM: Homo sapiens

<400> SEQUENCE: 68

Thr Ile Pro Pro His Val Gln Lys Ser Asp Val Glu Met Glu Ala Gln
1               5                   10                  15

Lys Asp Glu Ile Ile Cys Pro Ser Cys Asn Arg Thr Ala His Pro Leu
            20                  25                  30

Arg His Ile Asn Asn Asp Met Ile Val Thr Asp Asn Asn Gly Ala Val
        35                  40                  45

Lys Phe Pro Gln Leu Cys Lys Phe Cys Asp Val Arg Phe Ser Thr Cys
    50                  55                  60

Asp Asn Gln Lys Ser Cys Met Ser Asn Cys Ser Ile Thr Ser Ile Cys
65                  70                  75                  80

Glu Lys Pro Gln Glu Val Cys Val Ala Val Trp Arg Lys Asn Asp Glu
                85                  90                  95

Asn Ile Thr Leu Glu Thr Val Cys His Asp Pro Lys Leu Pro Tyr His
            100                 105                 110

Asp Phe Ile Leu Glu Asp Ala Ala Ser Pro Lys Cys Ile Met Lys Glu
        115                 120                 125

Lys Lys Lys Pro Gly Glu Thr Phe Phe Met Cys Ser Cys Ser Ser Asp
    130                 135                 140

Glu Cys Asn Asp Asn Ile Ile Phe Ser Glu Glu Tyr Asn Thr Ser Asn
145                 150                 155                 160

Pro Asp Leu Leu Leu Val Ile Phe Gln
                165


<210> SEQ ID NO 69
<211> LENGTH: 1776
<212> TYPE: DNA
<213> ORGANISM: Homo sapiens

<400> SEQUENCE: 69

atgggtcggg ggctgctcag gggcctgtgg ccgctgcaca tcgtcctgtg gacgcgtatc      60

gccagcacga tcccaccgca cgttcagaag tcggatgtgg aaatggaggc ccagaaagat     120

gaaatcatct gccccagctg taataggact gcccatccac tgagacatat taataacgac     180

atgatagtca ctgacaacaa cggtgcagtc aagtttccac aactgtgtaa attttgtgat     240

gtgagatttt ccacctgtga caaccagaaa tcctgcatga gcaactgcag catcacctcc     300

atctgtgaga agccacagga agtctgtgtg gctgtatgga gaaagaatga cgagaacata     360
```

acactagaga cagtttgcca tgaccccaag ctcccctacc atgactttat tctggaagat 420
gctgcttctc caaagtgcat tatgaaggaa aaaaaaaagc ctggtgagac tttcttcatg 480
tgttcctgta gctctgatga gtgcaatgac aacatcatct tctcagaaga atataacacc 540
agcaatcctg acttgttgct agtcatattt caagtgacag gcatcagcct cctgccacca 600
ctgggagttg ccatatctgt catcatcatc ttctactgct accgcgttaa ccggcagcag 660
aagctgagtt caacctggga aaccggcaag acgcggaagc tcatggagtt cagcgagcac 720
tgtgccatca tcctggaaga tgaccgctct gacatcagct ccacgtgtgc caacaacatc 780
aaccacaaca cagagctgct gcccattgag ctggacaccc tggtggggaa aggtcgcttt 840
gctgaggtct ataaggccaa gctgaagcag aacacttcag agcagtttga gacagtggca 900
gtcaagatct ttccctatga ggagtatgcc tcttggaaga cagagaagga catcttctca 960
gacatcaatc tgaagcatga gaacatactc cagttcctga cggctgagga gcggaagacg 1020
gagttgggga aacaatactg gctgatcacc gccttccacg ccaagggcaa cctacaggag 1080
tacctgacgc ggcatgtcat cagctgggag gacctgcgca agctgggcag ctccctcgcc 1140
cgggggattg ctcacctcca cagtgatcac actccatgtg ggaggcccaa gatgcccatc 1200
gtgcacaggg acctcaagag ctccaatatc ctcgtgaaga acgacctaac ctgctgcctg 1260
tgtgactttg ggctttccct gcgtctggac cctactctgt ctgtggatga cctggctaac 1320
agtgggcagg tgggaactgc aagatacatg gctccagaag tcctagaatc caggatgaat 1380
ttggagaatg ttgagtcctt caagcagacc gatgtctact ccatggctct ggtgctctgg 1440
gaaatgacat ctcgctgtaa tgcagtggga gaagtaaaag attatgagcc tccatttggt 1500
tccaaggtgc gggagcaccc ctgtgtcgaa agcatgaagg acaacgtgtt gagagatcga 1560
gggcgaccag aaattcccag cttctggctc aaccaccagg gcatccagat ggtgtgtgag 1620
acgttgactg agtgctggga ccacgaccca gaggcccgtc tcacagccca gtgtgtggca 1680
gaacgcttca gtgagctgga gcatctggac aggctctcgg ggaggagctg ctcggaggag 1740
aagattcctg aagacggctc cctaaacact accaaa 1776

<210> SEQ ID NO 70
<211> LENGTH: 507
<212> TYPE: DNA
<213> ORGANISM: Homo sapiens

<400> SEQUENCE: 70
acgatcccac cgcacgttca gaagtcggat gtggaaatgg aggcccagaa agatgaaatc 60
atctgcccca gctgtaatag gactgcccat ccactgagac atattaataa cgacatgata 120
gtcactgaca acaacggtgc agtcaagttt ccacaactgt gtaaattttg tgatgtgaga 180
ttttccacct gtgacaacca gaaatcctgc atgagcaact gcagcatcac ctccatctgt 240
gagaagccac aggaagtctg tgtggctgta tggagaaaga atgacgagaa cataacacta 300
gagacagttt gccatgaccc caagctcccc taccatgact ttattctgga agatgctgct 360
tctccaaagt gcattatgaa ggaaaaaaaa aagcctggtg agactttctt catgtgttcc 420
tgtagctctg atgagtgcaa tgacaacatc atcttctcag aagaatataa caccagcaat 480
cctgacttgt tgctagtcat atttcaa 507

<210> SEQ ID NO 71
<211> LENGTH: 530
<212> TYPE: PRT

<213> ORGANISM: Homo sapiens

<400> SEQUENCE: 71

Met Thr Ser Ser Leu Gln Arg Pro Trp Arg Val Pro Trp Leu Pro Trp
1               5                   10                  15

Thr Ile Leu Leu Val Ser Thr Ala Ala Ala Ser Gln Asn Gln Glu Arg
            20                  25                  30

Leu Cys Ala Phe Lys Asp Pro Tyr Gln Gln Asp Leu Gly Ile Gly Glu
        35                  40                  45

Ser Arg Ile Ser His Glu Asn Gly Thr Ile Leu Cys Ser Lys Gly Ser
    50                  55                  60

Thr Cys Tyr Gly Leu Trp Glu Lys Ser Lys Gly Asp Ile Asn Leu Val
65                  70                  75                  80

Lys Gln Gly Cys Trp Ser His Ile Gly Asp Pro Gln Glu Cys His Tyr
                85                  90                  95

Glu Glu Cys Val Val Thr Thr Thr Pro Pro Ser Ile Gln Asn Gly Thr
            100                 105                 110

Tyr Arg Phe Cys Cys Cys Ser Thr Asp Leu Cys Asn Val Asn Phe Thr
        115                 120                 125

Glu Asn Phe Pro Pro Pro Asp Thr Thr Pro Leu Ser Pro Pro His Ser
    130                 135                 140

Phe Asn Arg Asp Glu Thr Ile Ile Ile Ala Leu Ala Ser Val Ser Val
145                 150                 155                 160

Leu Ala Val Leu Ile Val Ala Leu Cys Phe Gly Tyr Arg Met Leu Thr
                165                 170                 175

Gly Asp Arg Lys Gln Gly Leu His Ser Met Asn Met Met Glu Ala Ala
            180                 185                 190

Ala Ser Glu Pro Ser Leu Asp Leu Asp Asn Leu Lys Leu Leu Glu Leu
        195                 200                 205

Ile Gly Arg Gly Arg Tyr Gly Ala Val Tyr Lys Gly Ser Leu Asp Glu
    210                 215                 220

Arg Pro Val Ala Val Lys Val Phe Ser Phe Ala Asn Arg Gln Asn Phe
225                 230                 235                 240

Ile Asn Glu Lys Asn Ile Tyr Arg Val Pro Leu Met Glu His Asp Asn
                245                 250                 255

Ile Ala Arg Phe Ile Val Gly Asp Glu Arg Val Thr Ala Asp Gly Arg
            260                 265                 270

Met Glu Tyr Leu Leu Val Met Glu Tyr Tyr Pro Asn Gly Ser Leu Cys
        275                 280                 285

Lys Tyr Leu Ser Leu His Thr Ser Asp Trp Val Ser Ser Cys Arg Leu
    290                 295                 300

Ala His Ser Val Thr Arg Gly Leu Ala Tyr Leu His Thr Glu Leu Pro
305                 310                 315                 320

Arg Gly Asp His Tyr Lys Pro Ala Ile Ser His Arg Asp Leu Asn Ser
                325                 330                 335

Arg Asn Val Leu Val Lys Asn Asp Gly Thr Cys Val Ile Ser Asp Phe
            340                 345                 350

Gly Leu Ser Met Arg Leu Thr Gly Asn Arg Leu Val Arg Pro Gly Glu
        355                 360                 365

Glu Asp Asn Ala Ala Ile Ser Glu Val Gly Thr Ile Arg Tyr Met Ala
    370                 375                 380

Pro Glu Val Leu Glu Gly Ala Val Asn Leu Arg Asp Cys Glu Ser Ala
385                 390                 395                 400

-continued

```
Leu Lys Gln Val Asp Met Tyr Ala Leu Gly Leu Ile Tyr Trp Glu Ile
                405                 410                 415

Phe Met Arg Cys Thr Asp Leu Phe Pro Gly Glu Ser Val Pro Glu Tyr
            420                 425                 430

Gln Met Ala Phe Gln Thr Glu Val Gly Asn His Pro Thr Phe Glu Asp
        435                 440                 445

Met Gln Val Leu Val Ser Arg Glu Lys Gln Arg Pro Lys Phe Pro Glu
    450                 455                 460

Ala Trp Lys Glu Asn Ser Leu Ala Val Arg Ser Leu Lys Glu Thr Ile
465                 470                 475                 480

Glu Asp Cys Trp Asp Gln Asp Ala Glu Ala Arg Leu Thr Ala Gln Cys
                485                 490                 495

Ala Glu Glu Arg Met Ala Glu Leu Met Met Ile Trp Glu Arg Asn Lys
            500                 505                 510

Ser Val Ser Pro Thr Val Asn Pro Met Ser Thr Ala Met Gln Asn Glu
        515                 520                 525

Arg Arg
    530


<210> SEQ ID NO 72
<211> LENGTH: 124
<212> TYPE: PRT
<213> ORGANISM: Homo sapiens

<400> SEQUENCE: 72

Ser Gln Asn Gln Glu Arg Leu Cys Ala Phe Lys Asp Pro Tyr Gln Gln
1               5                   10                  15

Asp Leu Gly Ile Gly Glu Ser Arg Ile Ser His Glu Asn Gly Thr Ile
            20                  25                  30

Leu Cys Ser Lys Gly Ser Thr Cys Tyr Gly Leu Trp Glu Lys Ser Lys
        35                  40                  45

Gly Asp Ile Asn Leu Val Lys Gln Gly Cys Trp Ser His Ile Gly Asp
    50                  55                  60

Pro Gln Glu Cys His Tyr Glu Glu Cys Val Val Thr Thr Thr Pro Pro
65                  70                  75                  80

Ser Ile Gln Asn Gly Thr Tyr Arg Phe Cys Cys Cys Ser Thr Asp Leu
                85                  90                  95

Cys Asn Val Asn Phe Thr Glu Asn Phe Pro Pro Pro Asp Thr Thr Pro
            100                 105                 110

Leu Ser Pro Pro His Ser Phe Asn Arg Asp Glu Thr
        115                 120


<210> SEQ ID NO 73
<211> LENGTH: 1590
<212> TYPE: DNA
<213> ORGANISM: Homo sapiens

<400> SEQUENCE: 73

atgacttcct cgctgcagcg gccctggcgg gtgccctggc taccatggac catcctgctg      60

gtcagcactg cggctgcttc gcagaatcaa gaacggctat gtgcgtttaa agatccgtat     120

cagcaagacc ttgggatagg tgagagtaga atctctcatg aaaatgggac aatattatgc     180

tcgaaaggta gcacctgcta tggcctttgg gagaaatcaa aaggggacat aaatcttgta     240

aaacaaggat gttggtctca cattggagat ccccaagagt gtcactatga agaatgtgta     300

gtaactacca ctcctccctc aattcagaat ggaacatacc gtttctgctg ttgtagcaca     360
```

gatttatgta atgtcaactt tactgagaat tttccacctc ctgacacaac accactcagt 420
ccacctcatt catttaaccg agatgagaca ataatcattg ctttggcatc agtctctgta 480
ttagctgttt tgatagttgc cttatgcttt ggatacagaa tgttgacagg agaccgtaaa 540
caaggtcttc acagtatgaa catgatggag gcagcagcat ccgaaccctc tcttgatcta 600
gataatctga aactgttgga gctgattggc cgaggtcgat atggagcagt atataaaggc 660
tccttggatg agcgtccagt tgctgtaaaa gtgttttcct ttgcaaaccg tcagaatttt 720
atcaacgaaa agaacattta cagagtgcct ttgatggaac atgacaacat tgcccgcttt 780
atagttggag atgagagagt cactgcagat ggacgcatgg aatatttgct tgtgatggag 840
tactatccca atggatcttt atgcaagtat ttaagtctcc acacaagtga ctgggtaagc 900
tcttgccgtc ttgctcattc tgttactaga ggactggctt atcttcacac agaattacca 960
cgaggagatc attataaacc tgcaatttcc catcgagatt taaacagcag aaatgtccta 1020
gtgaaaaatg atggaacctg tgttattagt gactttggac tgtccatgag gctgactgga 1080
aatagactgg tgcgcccagg ggaggaagat aatgcagcca taagcgaggt tggcactatc 1140
agatatatgg caccagaagt gctagaagga gctgtgaact tgagggactg tgaatcagct 1200
ttgaaacaag tagacatgta tgctcttgga ctaatctatt gggagatatt tatgagatgt 1260
acagacctct tcccagggga atccgtacca gagtaccaga tggcttttca gacagaggtt 1320
ggaaaccatc ccacttttga ggatatgcag gttctcgtgt ctagggaaaa acagagaccc 1380
aagttcccag aagcctggaa agaaaatagc ctggcagtga ggtcactcaa ggagacaatc 1440
gaagactgtt gggaccagga tgcagaggct cggcttactg cacagtgtgc tgaggaaagg 1500
atggctgaac ttatgatgat ttgggaaaga aacaaatctg tgagcccaac agtcaatcca 1560
atgtctactg ctatgcagaa tgaacgtagg 1590

<210> SEQ ID NO 74
<211> LENGTH: 372
<212> TYPE: DNA
<213> ORGANISM: Homo sapiens

<400> SEQUENCE: 74
tcgcagaatc aagaacggct atgtgcgttt aaagatccgt atcagcaaga ccttgggata 60
ggtgagagta gaatctctca tgaaaatggg acaatattat gctcgaaagg tagcacctgc 120
tatggccttt gggagaaatc aaaaggggac ataaatcttg taaaacaagg atgttggtct 180
cacattggag atccccaaga gtgtcactat gaagaatgtg tagtaactac cactcctccc 240
tcaattcaga atggaacata ccgtttctgc tgttgtagca cagatttatg taatgtcaac 300
tttactgaga attttccacc tcctgacaca acaccactca gtccacctca ttcatttaac 360
cgagatgaga ca 372

<210> SEQ ID NO 75
<211> LENGTH: 478
<212> TYPE: PRT
<213> ORGANISM: Homo sapiens

<400> SEQUENCE: 75

Met Leu Gly Ser Leu Gly Leu Trp Ala Leu Leu Pro Thr Ala Val Glu
1 5 10 15

Ala Pro Pro Asn Arg Arg Thr Cys Val Phe Phe Glu Ala Pro Gly Val
20 25 30

Arg Gly Ser Thr Lys Thr Leu Gly Glu Leu Leu Asp Thr Gly Thr Glu

```
        35                  40                  45

Leu Pro Arg Ala Ile Arg Cys Leu Tyr Ser Arg Cys Cys Phe Gly Ile
    50                  55                  60

Trp Asn Leu Thr Gln Asp Arg Ala Gln Val Glu Met Gln Gly Cys Arg
65                  70                  75                  80

Asp Ser Asp Glu Pro Gly Cys Glu Ser Leu His Cys Asp Pro Ser Pro
                85                  90                  95

Arg Ala His Pro Ser Pro Gly Ser Thr Leu Phe Thr Cys Ser Cys Gly
            100                 105                 110

Thr Asp Phe Cys Asn Ala Asn Tyr Ser His Leu Pro Pro Pro Gly Ser
        115                 120                 125

Pro Gly Thr Pro Gly Ser Gln Gly Pro Gln Ala Ala Pro Gly Glu Ser
    130                 135                 140

Ile Trp Met Ala Leu Val Leu Leu Gly Leu Phe Leu Leu Leu Leu Leu
145                 150                 155                 160

Leu Leu Gly Ser Ile Ile Leu Ala Leu Leu Gln Arg Lys Asn Tyr Arg
                165                 170                 175

Val Arg Gly Glu Pro Val Pro Glu Pro Arg Pro Asp Ser Gly Arg Asp
            180                 185                 190

Trp Ser Val Glu Leu Gln Glu Leu Pro Glu Leu Cys Phe Ser Gln Val
        195                 200                 205

Ile Arg Glu Gly Gly His Ala Val Val Trp Ala Gly Gln Leu Gln Gly
    210                 215                 220

Lys Leu Val Ala Ile Lys Ala Phe Pro Pro Arg Ser Val Ala Gln Phe
225                 230                 235                 240

Gln Ala Glu Arg Ala Leu Tyr Glu Leu Pro Gly Leu Gln His Asp His
                245                 250                 255

Ile Val Arg Phe Ile Thr Ala Ser Arg Gly Gly Pro Gly Arg Leu Leu
            260                 265                 270

Ser Gly Pro Leu Leu Val Leu Glu Leu His Pro Lys Gly Ser Leu Cys
        275                 280                 285

His Tyr Leu Thr Gln Tyr Thr Ser Asp Trp Gly Ser Ser Leu Arg Met
    290                 295                 300

Ala Leu Ser Leu Ala Gln Gly Leu Ala Phe Leu His Glu Glu Arg Trp
305                 310                 315                 320

Gln Asn Gly Gln Tyr Lys Pro Gly Ile Ala His Arg Asp Leu Ser Ser
                325                 330                 335

Gln Asn Val Leu Ile Arg Glu Asp Gly Ser Cys Ala Ile Gly Asp Leu
            340                 345                 350

Gly Leu Ala Leu Val Leu Pro Gly Leu Thr Gln Pro Pro Ala Trp Thr
        355                 360                 365

Pro Thr Gln Pro Gln Gly Pro Ala Ala Ile Met Glu Ala Gly Thr Gln
    370                 375                 380

Arg Tyr Met Ala Pro Glu Leu Leu Asp Lys Thr Leu Asp Leu Gln Asp
385                 390                 395                 400

Trp Gly Met Ala Leu Arg Arg Ala Asp Ile Tyr Ser Leu Ala Leu Leu
                405                 410                 415

Leu Trp Glu Ile Leu Ser Arg Cys Pro Asp Leu Arg Pro Ala Val His
            420                 425                 430

His Pro Ser Asn Trp Pro Met Arg Gln Asn Trp Ala Ile Pro Leu Pro
        435                 440                 445

Leu Met Ser Tyr Gly Pro Trp Gln Cys Arg Arg Gly Gly Val Pro Thr
    450                 455                 460
```

Ser His Pro Pro Gly Ala Ala Leu Pro Gln Thr Leu Met Gly
465 470 475

<210> SEQ ID NO 76
<211> LENGTH: 132
<212> TYPE: PRT
<213> ORGANISM: Homo sapiens

<400> SEQUENCE: 76

Pro Pro Asn Arg Arg Thr Cys Val Phe Phe Glu Ala Pro Gly Val Arg
1 5 10 15

Gly Ser Thr Lys Thr Leu Gly Glu Leu Leu Asp Thr Gly Thr Glu Leu
20 25 30

Pro Arg Ala Ile Arg Cys Leu Tyr Ser Arg Cys Cys Phe Gly Ile Trp
35 40 45

Asn Leu Thr Gln Asp Arg Ala Gln Val Glu Met Gln Gly Cys Arg Asp
50 55 60

Ser Asp Glu Pro Gly Cys Glu Ser Leu His Cys Asp Pro Ser Pro Arg
65 70 75 80

Ala His Pro Ser Pro Gly Ser Thr Leu Phe Thr Cys Ser Cys Gly Thr
85 90 95

Asp Phe Cys Asn Ala Asn Tyr Ser His Leu Pro Pro Pro Gly Ser Pro
100 105 110

Gly Thr Pro Gly Ser Gln Gly Pro Gln Ala Ala Pro Gly Glu Ser Ile
115 120 125

Trp Met Ala Leu
130

<210> SEQ ID NO 77
<211> LENGTH: 1434
<212> TYPE: DNA
<213> ORGANISM: Homo sapiens

<400> SEQUENCE: 77
atgctagggt ctttggggct ttgggcatta cttcccacag ctgtggaagc acccccaaac 60
aggcgaacct gtgtgttctt tgaggcccct ggagtgcggg gaagcacaaa gacactggga 120
gagctgctag atacaggcac agagctcccc agagctatcc gctgcctcta cagccgctgc 180
tgctttggga tctggaacct gacccaagac cgggcacagg tggaaatgca aggatgccga 240
gacagtgatg agccaggctg tgagtccctc cactgtgacc caagtccccg agcccacccc 300
agccctggct ccactctctt cacctgctcc tgtggcactg acttctgcaa tgccaattac 360
agccatctgc ctcctccagg gagccctggg actcctggct cccagggtcc ccaggctgcc 420
ccaggtgagt ccatctggat ggcactggtg ctgctggggc tgttcctcct cctcctgctg 480
ctgctgggca gcatcatctt ggccctgcta cagcgaaaga actacagagt gcgaggtgag 540
ccagtgccag agccaaggcc agactcaggc agggactgga gtgtggagct gcaggagctg 600
cctgagctgt gtttctccca ggtaatccgg gaaggaggtc atgcagtggt ttgggccggg 660
cagctgcaag gaaaactggt tgccatcaag gccttcccac cgaggtctgt ggctcagttc 720
caagctgaga gagcattgta cgaacttcca ggcctacagc acgaccacat tgtccgattt 780
atcactgcca gccggggggg tcctggccgc ctgctctctg ggcccctgct ggtactggaa 840
ctgcatccca agggctccct gtgccactac ttgacccagt acaccagtga ctggggaagt 900
tccctgcgga tggcactgtc cctggcccag ggcctggcat ttctccatga ggagcgctgg 960

-continued

```
cagaatggcc aatataaacc aggtattgcc caccgagatc tgagcagcca gaatgtgctc   1020

attcgggaag atggatcgtg tgccattgga gacctgggcc ttgccttggt gctccctggc   1080

ctcactcagc cccctgcctg gacccctact caaccacaag gcccagctgc catcatggaa   1140

gctggcaccc agaggtacat ggcaccagag ctcttggaca agactctgga cctacaggat   1200

tggggcatgg ccctccgacg agctgatatt tactctttgg ctctgctcct gtgggagata   1260

ctgagccgct gcccagattt gaggcctgca gtccaccacc cttccaactg gcctatgagg   1320

cagaactggg caataccccct acctctgatg agctatgggc cttggcagtg caggagagga   1380

ggcgtcccta catcccatcc acctggcgct gctttgccac agaccctgat gggc         1434
```

<210> SEQ ID NO 78
<211> LENGTH: 396
<212> TYPE: DNA
<213> ORGANISM: Homo sapiens

<400> SEQUENCE: 78

```
cccccaaaca ggcgaacctg tgtgttcttt gaggcccctg gagtgcgggg aagcacaaag     60

acactgggag agctgctaga tacaggcaca gagctcccca gagctatccg ctgcctctac    120

agccgctgct gctttgggat ctggaacctg acccaagacc gggcacaggt ggaaatgcaa    180

ggatgccgag acagtgatga gccaggctgt gagtccctcc actgtgaccc aagtccccga    240

gcccacccca gccctggctc cactctcttc acctgctcct gtggcactga cttctgcaat    300

gccaattaca gccatctgcc tcctccaggg agccctggga ctcctggctc ccagggtccc    360

caggctgccc caggtgagtc catctggatg gcactg                              396
```

<210> SEQ ID NO 79
<211> LENGTH: 478
<212> TYPE: PRT
<213> ORGANISM: Homo sapiens

<400> SEQUENCE: 79

```
Met Leu Gly Ser Leu Gly Leu Trp Ala Leu Leu Pro Thr Ala Val Glu
1               5                   10                  15

Ala Pro Pro Asn Arg Arg Thr Cys Val Phe Phe Glu Ala Pro Gly Val
            20                  25                  30

Arg Gly Ser Thr Lys Thr Leu Gly Glu Leu Leu Asp Thr Gly Thr Glu
        35                  40                  45

Leu Pro Arg Ala Ile Arg Cys Leu Tyr Ser Arg Cys Cys Phe Gly Ile
    50                  55                  60

Trp Asn Leu Thr Gln Asp Arg Ala Gln Val Glu Met Gln Gly Cys Arg
65                  70                  75                  80

Asp Ser Asp Glu Pro Gly Cys Glu Ser Leu His Cys Asp Pro Ser Pro
                85                  90                  95

Arg Ala His Pro Ser Pro Gly Ser Thr Leu Phe Thr Cys Ser Cys Gly
            100                 105                 110

Thr Asp Phe Cys Asn Ala Asn Tyr Ser His Leu Pro Pro Pro Gly Ser
        115                 120                 125

Pro Gly Thr Pro Gly Ser Gln Gly Pro Gln Ala Ala Pro Gly Glu Ser
    130                 135                 140

Ile Trp Met Ala Leu Val Leu Leu Gly Leu Phe Leu Leu Leu Leu Leu
145                 150                 155                 160

Leu Leu Gly Ser Ile Ile Leu Ala Leu Leu Gln Arg Lys Asn Tyr Arg
                165                 170                 175
```

-continued

```
Val Arg Gly Glu Pro Val Pro Glu Pro Arg Pro Asp Ser Gly Arg Asp
            180                 185                 190

Trp Ser Val Glu Leu Gln Glu Leu Pro Glu Leu Cys Phe Ser Gln Val
        195                 200                 205

Ile Arg Glu Gly Gly His Ala Val Val Trp Ala Gly Gln Leu Gln Gly
    210                 215                 220

Lys Leu Val Ala Ile Lys Ala Phe Pro Pro Arg Ser Val Ala Gln Phe
225                 230                 235                 240

Gln Ala Glu Arg Ala Leu Tyr Glu Leu Pro Gly Leu Gln His Asp His
                245                 250                 255

Ile Val Arg Phe Ile Thr Ala Ser Arg Gly Gly Pro Gly Arg Leu Leu
            260                 265                 270

Ser Gly Pro Leu Leu Val Leu Glu Leu His Pro Lys Gly Ser Leu Cys
        275                 280                 285

His Tyr Leu Thr Gln Tyr Thr Ser Asp Trp Gly Ser Ser Leu Arg Met
    290                 295                 300

Ala Leu Ser Leu Ala Gln Gly Leu Ala Phe Leu His Glu Glu Arg Trp
305                 310                 315                 320

Gln Asn Gly Gln Tyr Lys Pro Gly Ile Ala His Arg Asp Leu Ser Ser
                325                 330                 335

Gln Asn Val Leu Ile Arg Glu Asp Gly Ser Cys Ala Ile Gly Asp Leu
            340                 345                 350

Gly Leu Ala Leu Val Leu Pro Gly Leu Thr Gln Pro Pro Ala Trp Thr
        355                 360                 365

Pro Thr Gln Pro Gln Gly Pro Ala Ala Ile Met Glu Asp Pro Asp Gly
    370                 375                 380

Leu Arg Glu Leu Leu Glu Asp Cys Trp Asp Ala Asp Pro Glu Ala Arg
385                 390                 395                 400

Leu Thr Ala Glu Cys Val Gln Gln Arg Leu Ala Ala Leu Ala His Pro
                405                 410                 415

Gln Glu Ser His Pro Phe Pro Glu Ser Cys Pro Arg Gly Cys Pro Pro
            420                 425                 430

Leu Cys Pro Glu Asp Cys Thr Ser Ile Pro Ala Pro Thr Ile Leu Pro
        435                 440                 445

Cys Arg Pro Gln Arg Ser Ala Cys His Phe Ser Val Gln Gln Gly Pro
    450                 455                 460

Cys Ser Arg Asn Pro Gln Pro Ala Cys Thr Leu Ser Pro Val
465                 470                 475
```

<210> SEQ ID NO 80
<211> LENGTH: 132
<212> TYPE: PRT
<213> ORGANISM: Homo sapiens

<400> SEQUENCE: 80

```
Pro Pro Asn Arg Arg Thr Cys Val Phe Phe Glu Ala Pro Gly Val Arg
1               5                   10                  15

Gly Ser Thr Lys Thr Leu Gly Glu Leu Leu Asp Thr Gly Thr Glu Leu
            20                  25                  30

Pro Arg Ala Ile Arg Cys Leu Tyr Ser Arg Cys Cys Phe Gly Ile Trp
        35                  40                  45

Asn Leu Thr Gln Asp Arg Ala Gln Val Glu Met Gln Gly Cys Arg Asp
    50                  55                  60

Ser Asp Glu Pro Gly Cys Glu Ser Leu His Cys Asp Pro Ser Pro Arg
65                  70                  75                  80
```

```
Ala His Pro Ser Pro Gly Ser Thr Leu Phe Thr Cys Ser Cys Gly Thr
                85                  90                  95

Asp Phe Cys Asn Ala Asn Tyr Ser His Leu Pro Pro Pro Gly Ser Pro
            100                 105                 110

Gly Thr Pro Gly Ser Gln Gly Pro Gln Ala Ala Pro Gly Glu Ser Ile
        115                 120                 125

Trp Met Ala Leu
    130


<210> SEQ ID NO 81
<211> LENGTH: 1434
<212> TYPE: DNA
<213> ORGANISM: Homo sapiens

<400> SEQUENCE: 81

atgctagggt ctttggggct ttgggcatta cttcccacag ctgtggaagc acccccaaac     60

aggcgaacct gtgtgttctt tgaggcccct ggagtgcggg gaagcacaaa gacactggga    120

gagctgctag atacaggcac agagctcccc agagctatcc gctgcctcta cagccgctgc    180

tgctttggga tctggaacct gacccaagac cgggcacagg tggaaatgca aggatgccga    240

gacagtgatg agccaggctg tgagtccctc cactgtgacc caagtccccg agcccacccc    300

agccctggct ccactctctt cacctgctcc tgtggcactg acttctgcaa tgccaattac    360

agccatctgc ctcctccagg gagccctggg actcctggct cccagggtcc ccaggctgcc    420

ccaggtgagt ccatctggat ggcactggtg ctgctggggc tgttcctcct cctcctgctg    480

ctgctgggca gcatcatctt ggccctgcta cagcgaaaga actacagagt gcgaggtgag    540

ccagtgccag agccaaggcc agactcaggc agggactgga gtgtggagct gcaggagctg    600

cctgagctgt gtttctccca ggtaatccgg gaaggaggtc atgcagtggt ttgggccggg    660

cagctgcaag gaaaactggt tgccatcaag gccttcccac cgaggtctgt ggctcagttc    720

caagctgaga gagcattgta cgaacttcca ggcctacagc acgaccacat tgtccgattt    780

atcactgcca gccggggggg tcctggccgc ctgctctctg ggcccctgct ggtactggaa    840

ctgcatccca agggctccct gtgccactac ttgacccagt acaccagtga ctggggaagt    900

tccctgcgga tggcactgtc cctggcccag ggcctggcat ttctccatga ggagcgctgg    960

cagaatggcc aatataaacc aggtattgcc caccgagatc tgagcagcca gaatgtgctc   1020

attcgggaag atggatcgtg tgccattgga gacctgggcc ttgccttggt gctccctggc   1080

ctcactcagc cccctgcctg gacccctact caaccacaag gcccagctgc catcatggaa   1140

gaccctgatg ggctgaggga gctcctagaa gactgttggg atgcagaccc agaagcacgg   1200

ctgacagctg agtgtgtaca gcagcgcctg gctgccttgg cccatcctca agagagccac   1260

ccctttccag agagctgtcc acgtggctgc ccacctctct gcccagaaga ctgtacttca   1320

attcctgccc ctaccatcct cccctgtagg cctcagcgga gtgcctgcca cttcagcgtt   1380

cagcaaggcc cttgttccag gaatcctcag cctgcctgta ccctttctcc tgtg          1434


<210> SEQ ID NO 82
<211> LENGTH: 396
<212> TYPE: DNA
<213> ORGANISM: Homo sapiens

<400> SEQUENCE: 82

cccccaaaca ggcgaacctg tgtgttcttt gaggcccctg gagtgcgggg aagcacaaag     60
```

-continued acactgggag agctgctaga tacaggcaca gagctcccca gagctatccg ctgcctctac 120
agccgctgct gctttgggat ctggaacctg acccaagacc gggcacaggt ggaaatgcaa 180
ggatgccgag acagtgatga gccaggctgt gagtccctcc actgtgaccc aagtccccga 240
gcccacccca gccctggctc cactctcttc acctgctcct gtggcactga cttctgcaat 300
gccaattaca gccatctgcc tcctccaggg agccctggga ctcctggctc ccagggtccc 360
caggctgccc caggtgagtc catctggatg gcactg 396

<210> SEQ ID NO 83
<211> LENGTH: 453
<212> TYPE: PRT
<213> ORGANISM: Homo sapiens

<400> SEQUENCE: 83

Met Val Ser Ile Phe Asn Leu Asp Gly Met Glu His His Val Arg Thr
1 5 10 15

Cys Ile Pro Lys Val Glu Leu Val Pro Ala Gly Lys Pro Phe Tyr Cys
20 25 30

Leu Ser Ser Glu Asp Leu Arg Asn Thr His Cys Cys Tyr Thr Asp Tyr
35 40 45

Cys Asn Arg Ile Asp Leu Arg Val Pro Ser Gly His Leu Lys Glu Pro
50 55 60

Glu His Pro Ser Met Trp Gly Pro Val Glu Leu Val Gly Ile Ile Ala
65 70 75 80

Gly Pro Val Phe Leu Leu Phe Leu Ile Ile Ile Ile Val Phe Leu Val
85 90 95

Ile Asn Tyr His Gln Arg Val Tyr His Asn Arg Gln Arg Leu Asp Met
100 105 110

Glu Asp Pro Ser Cys Glu Met Cys Leu Ser Lys Asp Lys Thr Leu Gln
115 120 125

Asp Leu Val Tyr Asp Leu Ser Thr Ser Gly Ser Gly Ser Gly Leu Pro
130 135 140

Leu Phe Val Gln Arg Thr Val Ala Arg Thr Ile Val Leu Gln Glu Ile
145 150 155 160

Ile Gly Lys Gly Arg Phe Gly Glu Val Trp Arg Gly Arg Trp Arg Gly
165 170 175

Gly Asp Val Ala Val Lys Ile Phe Ser Ser Arg Glu Glu Arg Ser Trp
180 185 190

Phe Arg Glu Ala Glu Ile Tyr Gln Thr Val Met Leu Arg His Glu Asn
195 200 205

Ile Leu Gly Phe Ile Ala Ala Asp Asn Lys Asp Asn Gly Thr Trp Thr
210 215 220

Gln Leu Trp Leu Val Ser Asp Tyr His Glu His Gly Ser Leu Phe Asp
225 230 235 240

Tyr Leu Asn Arg Tyr Thr Val Thr Ile Glu Gly Met Ile Lys Leu Ala
245 250 255

Leu Ser Ala Ala Ser Gly Leu Ala His Leu His Met Glu Ile Val Gly
260 265 270

Thr Gln Gly Lys Pro Gly Ile Ala His Arg Asp Leu Lys Ser Lys Asn
275 280 285

Ile Leu Val Lys Lys Asn Gly Met Cys Ala Ile Ala Asp Leu Gly Leu
290 295 300

Ala Val Arg His Asp Ala Val Thr Asp Thr Ile Asp Ile Ala Pro Asn
305 310 315 320

```
Gln Arg Val Gly Thr Lys Arg Tyr Met Ala Pro Glu Val Leu Asp Glu
                325                 330                 335

Thr Ile Asn Met Lys His Phe Asp Ser Phe Lys Cys Ala Asp Ile Tyr
            340                 345                 350

Ala Leu Gly Leu Val Tyr Trp Glu Ile Ala Arg Arg Cys Asn Ser Gly
        355                 360                 365

Gly Val His Glu Glu Tyr Gln Leu Pro Tyr Tyr Asp Leu Val Pro Ser
    370                 375                 380

Asp Pro Ser Ile Glu Glu Met Arg Lys Val Val Cys Asp Gln Lys Leu
385                 390                 395                 400

Arg Pro Asn Ile Pro Asn Trp Trp Gln Ser Tyr Glu Ala Leu Arg Val
                405                 410                 415

Met Gly Lys Met Met Arg Glu Cys Trp Tyr Ala Asn Gly Ala Ala Arg
            420                 425                 430

Leu Thr Ala Leu Arg Ile Lys Lys Thr Leu Ser Gln Leu Ser Val Gln
        435                 440                 445

Glu Asp Val Lys Ile
    450
```

<210> SEQ ID NO 84
<211> LENGTH: 74
<212> TYPE: PRT
<213> ORGANISM: Homo sapiens

<400> SEQUENCE: 84

```
Met Val Ser Ile Phe Asn Leu Asp Gly Met Glu His His Val Arg Thr
1               5                   10                  15

Cys Ile Pro Lys Val Glu Leu Val Pro Ala Gly Lys Pro Phe Tyr Cys
            20                  25                  30

Leu Ser Ser Glu Asp Leu Arg Asn Thr His Cys Cys Tyr Thr Asp Tyr
        35                  40                  45

Cys Asn Arg Ile Asp Leu Arg Val Pro Ser Gly His Leu Lys Glu Pro
    50                  55                  60

Glu His Pro Ser Met Trp Gly Pro Val Glu
65                  70
```

<210> SEQ ID NO 85
<211> LENGTH: 1359
<212> TYPE: DNA
<213> ORGANISM: Homo sapiens

<400> SEQUENCE: 85

```
atggtttcca ttttcaatct ggatgggatg gagcaccatg tgcgcacctg catccccaaa      60

gtggagctgg tccctgccgg gaagcccttc tactgcctga gctcggagga cctgcgcaac     120

acccactgct gctacactga ctactgcaac aggatcgact tgagggtgcc cagtggtcac     180

ctcaaggagc ctgagcaccc gtccatgtgg ggcccggtgg agctggtagg catcatcgcc     240

ggcccggtgt tcctcctgtt cctcatcatc atcattgttt tccttgtcat taactatcat     300

cagcgtgtct atcacaaccg ccagagactg gacatggaag atccctcatg tgagatgtgt     360

ctctccaaag acaagacgct ccaggatctt gtctacgatc tctccacctc agggtctggc     420

tcagggttac ccctctttgt ccagcgcaca gtggcccgaa ccatcgtttt acaagagatt     480

attggcaagg gtcggtttgg ggaagtatgg cggggccgct ggaggggtgg tgatgtggct     540

gtgaaaatat tctcttctcg tgaagaacgg tcttggttca gggaagcaga gatataccag     600
```

acggtcatgc tgcgccatga aaacatcctt ggatttattg ctgctgacaa taaagataat 660
ggcacctgga cacagctgtg gcttgtttct gactatcatg agcacgggtc cctgtttgat 720
tatctgaacc ggtacacagt gacaattgag ggcatgatta agctggcctt gtctgctgct 780
agtgggctgg cacacctgca catggagatc gtgggcaccc aagggaagcc tggaattgct 840
catcgagact taaagtcaaa gaacattctg gtgaagaaaa atggcatgtg tgccatagca 900
gacctgggcc tggctgtccg tcatgatgca gtcactgaca ccattgacat tgccccgaat 960
cagagggtgg ggaccaaacg atacatggcc cctgaagtac ttgatgaaac cattaatatg 1020
aaacactttg actcctttaa atgtgctgat atttatgccc tcgggcttgt atattgggag 1080
attgctcgaa gatgcaattc tggaggagtc catgaagaat atcagctgcc atattacgac 1140
ttagtgccct ctgacccttc cattgaggaa atgcgaaagg ttgtatgtga tcagaagctg 1200
cgtcccaaca tccccaactg gtggcagagt tatgaggcac tgcgggtgat ggggaagatg 1260
atgcgagagt gttggtatgc caacggcgca gcccgcctga cggccctgcg catcaagaag 1320
accctctccc agctcagcgt gcaggaagac gtgaagatc 1359

<210> SEQ ID NO 86
<211> LENGTH: 222
<212> TYPE: DNA
<213> ORGANISM: Homo sapiens

<400> SEQUENCE: 86
atggtttcca ttttcaatct ggatgggatg gagcaccatg tgcgcacctg catccccaaa 60
gtggagctgg tccctgccgg gaagcccttc tactgcctga gctcggagga cctgcgcaac 120
acccactgct gctacactga ctactgcaac aggatcgact tgagggtgcc cagtggtcac 180
ctcaaggagc ctgagcaccc gtccatgtgg ggcccggtgg ag 222

<210> SEQ ID NO 87
<211> LENGTH: 507
<212> TYPE: PRT
<213> ORGANISM: Homo sapiens

<400> SEQUENCE: 87

Met Glu Ala Ala Val Ala Ala Pro Arg Pro Arg Leu Leu Leu Leu Val
1 5 10 15

Leu Ala Ala Ala Ala Ala Ala Ala Ala Ala Leu Leu Pro Gly Ala Thr
20 25 30

Ala Leu Gln Cys Phe Cys His Leu Cys Thr Lys Asp Asn Phe Thr Cys
35 40 45

Val Thr Asp Gly Leu Cys Phe Val Ser Val Thr Glu Thr Thr Asp Lys
50 55 60

Val Ile His Asn Ser Met Cys Ile Ala Glu Ile Asp Leu Ile Pro Arg
65 70 75 80

Asp Arg Pro Phe Val Cys Ala Pro Ser Ser Lys Thr Gly Ser Val Thr
85 90 95

Thr Thr Tyr Cys Cys Asn Gln Asp His Cys Asn Lys Ile Glu Leu Pro
100 105 110

Thr Thr Gly Pro Phe Ser Val Lys Ser Ser Pro Gly Leu Gly Pro Val
115 120 125

Glu Leu Ala Ala Val Ile Ala Gly Pro Val Cys Phe Val Cys Ile Ser
130 135 140

Leu Met Leu Met Val Tyr Ile Cys His Asn Arg Thr Val Ile His His
145 150 155 160

Arg Val Pro Asn Glu Glu Asp Pro Ser Leu Asp Arg Pro Phe Ile Ser
165 170 175

Glu Gly Thr Thr Leu Lys Asp Leu Ile Tyr Asp Met Thr Thr Ser Gly
180 185 190

Ser Gly Ser Gly Leu Pro Leu Leu Val Gln Arg Thr Ile Ala Arg Thr
195 200 205

Ile Val Leu Gln Glu Ser Ile Gly Lys Gly Arg Phe Gly Glu Val Trp
210 215 220

Arg Gly Lys Trp Arg Gly Glu Glu Val Ala Val Lys Ile Phe Ser Ser
225 230 235 240

Arg Glu Glu Arg Ser Trp Phe Arg Glu Ala Glu Ile Tyr Gln Thr Val
245 250 255

Met Leu Arg His Glu Asn Ile Leu Gly Phe Ile Ala Ala Asp Asn Lys
260 265 270

Asp Asn Gly Thr Trp Thr Gln Leu Trp Leu Val Ser Asp Tyr His Glu
275 280 285

His Gly Ser Leu Phe Asp Tyr Leu Asn Arg Tyr Thr Val Thr Val Glu
290 295 300

Gly Met Ile Lys Leu Ala Leu Ser Thr Ala Ser Gly Leu Ala His Leu
305 310 315 320

His Met Glu Ile Val Gly Thr Gln Gly Lys Pro Ala Ile Ala His Arg
325 330 335

Asp Leu Lys Ser Lys Asn Ile Leu Val Lys Lys Asn Gly Thr Cys Cys
340 345 350

Ile Ala Asp Leu Gly Leu Ala Val Arg His Asp Ser Ala Thr Asp Thr
355 360 365

Ile Asp Ile Ala Pro Asn His Arg Val Gly Thr Lys Arg Tyr Met Ala
370 375 380

Pro Glu Val Leu Asp Asp Ser Ile Asn Met Lys His Phe Glu Ser Phe
385 390 395 400

Lys Arg Ala Asp Ile Tyr Ala Met Gly Leu Val Phe Trp Glu Ile Ala
405 410 415

Arg Arg Cys Ser Ile Gly Gly Ile His Glu Asp Tyr Gln Leu Pro Tyr
420 425 430

Tyr Asp Leu Val Pro Ser Asp Pro Ser Val Glu Glu Met Arg Lys Val
435 440 445

Val Cys Glu Gln Lys Leu Arg Pro Asn Ile Pro Asn Arg Trp Gln Ser
450 455 460

Cys Glu Ala Leu Arg Val Met Ala Lys Ile Met Arg Glu Cys Trp Tyr
465 470 475 480

Ala Asn Gly Ala Ala Arg Leu Thr Ala Leu Arg Ile Lys Lys Thr Leu
485 490 495

Ser Gln Leu Ser Gln Gln Glu Gly Ile Lys Met
500 505

<210> SEQ ID NO 88
<211> LENGTH: 106
<212> TYPE: PRT
<213> ORGANISM: Homo sapiens

<400> SEQUENCE: 88

Ala Ala Leu Leu Pro Gly Ala Thr Ala Leu Gln Cys Phe Cys His Leu
1 5 10 15

Cys Thr Lys Asp Asn Phe Thr Cys Val Thr Asp Gly Leu Cys Phe Val

```
            20                  25                  30

Ser Val Thr Glu Thr Thr Asp Lys Val Ile His Asn Ser Met Cys Ile
        35                  40                  45

Ala Glu Ile Asp Leu Ile Pro Arg Asp Arg Pro Phe Val Cys Ala Pro
    50                  55                  60

Ser Ser Lys Thr Gly Ser Val Thr Thr Thr Tyr Cys Cys Asn Gln Asp
65                  70                  75                  80

His Cys Asn Lys Ile Glu Leu Pro Thr Thr Gly Pro Phe Ser Val Lys
                85                  90                  95

Ser Ser Pro Gly Leu Gly Pro Val Glu Leu
            100                 105


<210> SEQ ID NO 89
<211> LENGTH: 1521
<212> TYPE: DNA
<213> ORGANISM: Homo sapiens

<400> SEQUENCE: 89

atggaggcgg cggtcgctgc tccgcgtccc cggctgctcc tcctcgtgct ggcggcggcg      60

gcggcggcgg cggcggcgct gctcccgggg gcgacggcgt tacagtgttt ctgccacctc     120

tgtacaaaag acaattttac ttgtgtgaca gatgggctct gctttgtctc tgtcacagag     180

accacagaca aagttataca caacagcatg tgtatagctg aaattgactt aattcctcga     240

gataggccgt ttgtatgtgc accctcttca aaaactgggt ctgtgactac aacatattgc     300

tgcaatcagg accattgcaa taaaatagaa cttccaacta ctggcccttt ttcagtaaag     360

tcatcacctg gccttggtcc tgtggaactg gcagctgtca ttgctggacc agtgtgcttc     420

gtctgcatct cactcatgtt gatggtctat atctgccaca accgcactgt cattcaccat     480

cgagtgccaa atgaagagga cccttcatta gatcgccctt ttatttcaga gggtactacg     540

ttgaaagact taatttatga tatgacaacg tcaggttctg gctcaggttt accattgctt     600

gttcagagaa caattgcgag aactattgtg ttacaagaaa gcattggcaa aggtcgattt     660

ggagaagttt ggagaggaaa gtggcgggga gaagaagttg ctgttaagat attctcctct     720

agagaagaac gttcgtggtt ccgtgaggca gagatttatc aaactgtaat gttacgtcat     780

gaaaacatcc tgggatttat agcagcagac aataaagaca atggtacttg gactcagctc     840

tggttggtgt cagattatca tgagcatgga tccctttttg attacttaaa cagatacaca     900

gttactgtgg aaggaatgat aaaacttgct ctgtccacgg cgagcggtct tgcccatctt     960

cacatggaga ttgttggtac ccaaggaaag ccagccattg ctcatagaga tttgaaatca    1020

aagaatatct tggtaaagaa gaatggaact tgctgtattg cagacttagg actggcagta    1080

agacatgatt cagccacaga taccattgat attgctccaa accacagagt gggaacaaaa    1140

aggtacatgg cccctgaagt tctcgatgat tccataaata tgaaacattt tgaatccttc    1200

aaacgtgctg acatctatgc aatgggctta gtattctggg aaattgctcg acgatgttcc    1260

attggtggaa ttcatgaaga ttaccaactg ccttattatg atcttgtacc ttctgaccca    1320

tcagttgaag aaatgagaaa agttgtttgt gaacagaagt taaggccaaa tatcccaaac    1380

agatggcaga gctgtgaagc cttgagagta atggctaaaa ttatgagaga atgttggtat    1440

gccaatggag cagctaggct tacagcattg cggattaaga aaacattatc gcaactcagt    1500

caacaggaag gcatcaaaat g                                               1521


<210> SEQ ID NO 90
```

<211> LENGTH: 318
<212> TYPE: DNA
<213> ORGANISM: Homo sapiens

<400> SEQUENCE: 90
gcggcgctgc tcccgggggc gacggcgtta cagtgtttct gccacctctg tacaaaagac 60
aattttactt gtgtgacaga tgggctctgc tttgtctctg tcacagagac cacagacaaa 120
gttatacaca acagcatgtg tatagctgaa attgacttaa ttcctcgaga taggccgttt 180
gtatgtgcac cctcttcaaa aactgggtct gtgactacaa catattgctg caatcaggac 240
cattgcaata aaatagaact tccaactact ggcccttttt cagtaaagtc atcacctggc 300
cttggtcctg tggaactg 318

<210> SEQ ID NO 91
<211> LENGTH: 532
<212> TYPE: PRT
<213> ORGANISM: Homo sapiens

<400> SEQUENCE: 91

Met Gly Trp Leu Glu Glu Leu Asn Trp Gln Leu His Ile Phe Leu Leu
1 5 10 15

Ile Leu Leu Ser Met His Thr Arg Ala Asn Phe Leu Asp Asn Met Leu
20 25 30

Leu Arg Ser Ala Gly Lys Leu Asn Val Gly Thr Lys Lys Glu Asp Gly
35 40 45

Glu Ser Thr Ala Pro Thr Pro Arg Pro Lys Val Leu Arg Cys Lys Cys
50 55 60

His His His Cys Pro Glu Asp Ser Val Asn Asn Ile Cys Ser Thr Asp
65 70 75 80

Gly Tyr Cys Phe Thr Met Ile Glu Glu Asp Asp Ser Gly Leu Pro Val
85 90 95

Val Thr Ser Gly Cys Leu Gly Leu Glu Gly Ser Asp Phe Gln Cys Arg
100 105 110

Asp Thr Pro Ile Pro His Gln Arg Arg Ser Ile Glu Cys Cys Thr Glu
115 120 125

Arg Asn Glu Cys Asn Lys Asp Leu His Pro Thr Leu Pro Pro Leu Lys
130 135 140

Asn Arg Asp Phe Val Asp Gly Pro Ile His His Arg Ala Leu Leu Ile
145 150 155 160

Ser Val Thr Val Cys Ser Leu Leu Leu Val Leu Ile Ile Leu Phe Cys
165 170 175

Tyr Phe Arg Tyr Lys Arg Gln Glu Thr Arg Pro Arg Tyr Ser Ile Gly
180 185 190

Leu Glu Gln Asp Glu Thr Tyr Ile Pro Pro Gly Glu Ser Leu Arg Asp
195 200 205

Leu Ile Glu Gln Ser Gln Ser Ser Gly Ser Gly Ser Gly Leu Pro Leu
210 215 220

Leu Val Gln Arg Thr Ile Ala Lys Gln Ile Gln Met Val Lys Gln Ile
225 230 235 240

Gly Lys Gly Arg Tyr Gly Glu Val Trp Met Gly Lys Trp Arg Gly Glu
245 250 255

Lys Val Ala Val Lys Val Phe Phe Thr Thr Glu Glu Ala Ser Trp Phe
260 265 270

Arg Glu Thr Glu Ile Tyr Gln Thr Val Leu Met Arg His Glu Asn Ile
275 280 285

Leu Gly Phe Ile Ala Ala Asp Ile Lys Gly Thr Gly Ser Trp Thr Gln
    290                 295                 300

Leu Tyr Leu Ile Thr Asp Tyr His Glu Asn Gly Ser Leu Tyr Asp Tyr
305                 310                 315                 320

Leu Lys Ser Thr Thr Leu Asp Ala Lys Ser Met Leu Lys Leu Ala Tyr
                325                 330                 335

Ser Ser Val Ser Gly Leu Cys His Leu His Thr Glu Ile Phe Ser Thr
            340                 345                 350

Gln Gly Lys Pro Ala Ile Ala His Arg Asp Leu Lys Ser Lys Asn Ile
        355                 360                 365

Leu Val Lys Lys Asn Gly Thr Cys Cys Ile Ala Asp Leu Gly Leu Ala
    370                 375                 380

Val Lys Phe Ile Ser Asp Thr Asn Glu Val Asp Ile Pro Pro Asn Thr
385                 390                 395                 400

Arg Val Gly Thr Lys Arg Tyr Met Pro Pro Glu Val Leu Asp Glu Ser
                405                 410                 415

Leu Asn Arg Asn His Phe Gln Ser Tyr Ile Met Ala Asp Met Tyr Ser
            420                 425                 430

Phe Gly Leu Ile Leu Trp Glu Val Ala Arg Arg Cys Val Ser Gly Gly
        435                 440                 445

Ile Val Glu Glu Tyr Gln Leu Pro Tyr His Asp Leu Val Pro Ser Asp
    450                 455                 460

Pro Ser Tyr Glu Asp Met Arg Glu Ile Val Cys Ile Lys Lys Leu Arg
465                 470                 475                 480

Pro Ser Phe Pro Asn Arg Trp Ser Ser Asp Glu Cys Leu Arg Gln Met
                485                 490                 495

Gly Lys Leu Met Thr Glu Cys Trp Ala His Asn Pro Ala Ser Arg Leu
            500                 505                 510

Thr Ala Leu Arg Val Lys Lys Thr Leu Ala Lys Met Ser Glu Ser Gln
        515                 520                 525

Asp Ile Lys Leu
    530

<210> SEQ ID NO 92
<211> LENGTH: 131
<212> TYPE: PRT
<213> ORGANISM: Homo sapiens

<400> SEQUENCE: 92

Asn Phe Leu Asp Asn Met Leu Leu Arg Ser Ala Gly Lys Leu Asn Val
1               5                   10                  15

Gly Thr Lys Lys Glu Asp Gly Glu Ser Thr Ala Pro Thr Pro Arg Pro
            20                  25                  30

Lys Val Leu Arg Cys Lys Cys His His His Cys Pro Glu Asp Ser Val
        35                  40                  45

Asn Asn Ile Cys Ser Thr Asp Gly Tyr Cys Phe Thr Met Ile Glu Glu
    50                  55                  60

Asp Asp Ser Gly Leu Pro Val Val Thr Ser Gly Cys Leu Gly Leu Glu
65                  70                  75                  80

Gly Ser Asp Phe Gln Cys Arg Asp Thr Pro Ile Pro His Gln Arg Arg
                85                  90                  95

Ser Ile Glu Cys Cys Thr Glu Arg Asn Glu Cys Asn Lys Asp Leu His
            100                 105                 110

Pro Thr Leu Pro Pro Leu Lys Asn Arg Asp Phe Val Asp Gly Pro Ile

```
        115                 120                 125

His His Arg
    130


<210> SEQ ID NO 93
<211> LENGTH: 1596
<212> TYPE: DNA
<213> ORGANISM: Homo sapiens

<400> SEQUENCE: 93

atgggttggc tggaagaact aaactggcag cttcacattt tcttgctcat tcttctctct      60

atgcacacaa gggcaaactt ccttgataac atgcttttgc gaagtgcagg aaaattaaat     120

gtgggcacca agaaagagga tggtgagagt acagccccca ccccccgtcc aaaggtcttg     180

cgttgtaaat gccaccacca ttgtccagaa gactcagtca acaatatttg cagcacagac     240

ggatattgtt tcacgatgat agaagaggat gactctgggt tgcctgtggt cacttctggt     300

tgcctaggac tagaaggctc agattttcag tgtcgggaca ctcccattcc tcatcaaaga     360

agatcaattg aatgctgcac agaaaggaac gaatgtaata aagacctaca ccctacactg     420

cctccattga aaaacagaga ttttgttgat ggacctatac accacagggc tttacttata     480

tctgtgactg tctgtagttt gctcttggtc cttatcatat tattttgtta cttccggtat     540

aaaagacaag aaaccagacc tcgatacagc attgggttag aacaggatga aacttacatt     600

cctcctggag aatccctgag agacttaatt gagcagtctc agagctcagg aagtggatca     660

ggcctccctc tgctggtcca aaggactata gctaagcaga ttcagatggt gaaacagatt     720

ggaaaaggtc gctatgggga agtttggatg ggaaagtggc gtggcgaaaa ggtagctgtg     780

aaagtgttct tcaccacaga ggaagccagc tggttcagag agacagaaat atatcagaca     840

gtgttgatga ggcatgaaaa cattttgggt ttcattgctg cagatatcaa agggacaggg     900

tcctggaccc agttgtacct aatcacagac tatcatgaaa atggttccct ttatgattat     960

ctgaagtcca ccaccctaga cgctaaatca atgctgaagt tagcctactc ttctgtcagt    1020

ggcttatgtc atttacacac agaaatcttt agtactcaag gcaaaccagc aattgcccat    1080

cgagatctga aaagtaaaaa cattctggtg aagaaaaatg gaacttgctg tattgctgac    1140

ctgggcctgg ctgttaaatt tattagtgat acaaatgaag ttgacatacc acctaacact    1200

cgagttggca ccaaacgcta tatgcctcca gaagtgttgg acgagagctt gaacagaaat    1260

cacttccagt cttacatcat ggctgacatg tatagttttg gcctcatcct ttgggaggtt    1320

gctaggagat gtgtatcagg aggtatagtg gaagaatacc agcttcctta tcatgaccta    1380

gtgcccagtg acccctctta tgaggacatg agggagattg tgtgcatcaa gaagttacgc    1440

ccctcattcc caaaccggtg gagcagtgat gagtgtctaa ggcagatggg aaaactcatg    1500

acagaatgct gggctcacaa tcctgcatca aggctgacag ccctgcgggt taagaaaaca    1560

cttgccaaaa tgtcagagtc ccaggacatt aaactc                              1596


<210> SEQ ID NO 94
<211> LENGTH: 393
<212> TYPE: DNA
<213> ORGANISM: Homo sapiens

<400> SEQUENCE: 94

aacttccttg ataacatgct tttgcgaagt gcaggaaaat taaatgtggg caccaagaaa      60

gaggatggtg agagtacagc ccccaccccc cgtccaaagg tcttgcgttg taaatgccac     120
```

caccattgtc cagaagactc agtcaacaat atttgcagca cagacggata ttgtttcacg 180
atgatagaag aggatgactc tgggttgcct gtggtcactt ctggttgcct aggactagaa 240
ggctcagatt ttcagtgtcg ggacactccc attcctcatc aaagaagatc aattgaatgc 300
tgcacagaaa ggaacgaatg taataaagac ctacacccta cactgcctcc attgaaaaac 360
agagattttg ttgatggacc tatacaccac agg 393

<210> SEQ ID NO 95
<211> LENGTH: 36
<212> TYPE: PRT
<213> ORGANISM: Homo sapiens

<400> SEQUENCE: 95

Gly Arg Cys Lys Ile Arg His Ile Gly Ser Asn Asn Arg Leu Gln Arg
1 5 10 15

Ser Thr Cys Gln Asn Thr Gly Trp Glu Ser Ala His Val Met Lys Thr
20 25 30

Pro Gly Phe Arg
35

<210> SEQ ID NO 96

<400> SEQUENCE: 96

000

<210> SEQ ID NO 97

<400> SEQUENCE: 97

000

<210> SEQ ID NO 98

<400> SEQUENCE: 98

000

<210> SEQ ID NO 99

<400> SEQUENCE: 99

000

<210> SEQ ID NO 100
<211> LENGTH: 22
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 100

Met Asp Ala Met Lys Arg Gly Leu Cys Cys Val Leu Leu Leu Cys Gly
1 5 10 15

Ala Val Phe Val Ser Pro
20

<210> SEQ ID NO 101
<211> LENGTH: 369
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 101

Met Asp Ala Met Lys Arg Gly Leu Cys Cys Val Leu Leu Leu Cys Gly
1 5 10 15

Ala Val Phe Val Ser Pro Gly Ala Ala Ile Leu Gly Arg Ser Glu Thr
20 25 30

Gln Glu Cys Leu Phe Phe Asn Ala Asn Trp Glu Lys Asp Arg Thr Asn
35 40 45

Gln Thr Gly Val Glu Pro Cys Tyr Gly Asp Lys Asp Lys Arg Arg His
50 55 60

Cys Phe Ala Thr Trp Lys Asn Ile Ser Gly Ser Ile Glu Ile Val Lys
65 70 75 80

Gln Gly Cys Trp Leu Asp Asp Ile Asn Cys Tyr Asp Arg Thr Asp Cys
85 90 95

Val Glu Lys Lys Asp Ser Pro Glu Val Tyr Phe Cys Cys Cys Glu Gly
100 105 110

Asn Met Cys Asn Glu Lys Phe Ser Tyr Phe Pro Glu Met Glu Val Thr
115 120 125

Gln Pro Thr Ser Asn Pro Val Thr Pro Lys Pro Pro Thr Gly Gly Gly
130 135 140

Thr His Thr Cys Pro Pro Cys Pro Ala Pro Glu Leu Leu Gly Gly Pro
145 150 155 160

Ser Val Phe Leu Phe Pro Pro Lys Pro Lys Asp Thr Leu Met Ile Ser
165 170 175

Arg Thr Pro Glu Val Thr Cys Val Val Val Asp Val Ser His Glu Asp
180 185 190

Pro Glu Val Lys Phe Asn Trp Tyr Val Asp Gly Val Glu Val His Asn
195 200 205

Ala Lys Thr Lys Pro Arg Glu Glu Gln Tyr Asn Ser Thr Tyr Arg Val
210 215 220

Val Ser Val Leu Thr Val Leu His Gln Asp Trp Leu Asn Gly Lys Glu
225 230 235 240

Tyr Lys Cys Lys Val Ser Asn Lys Ala Leu Pro Ala Pro Ile Glu Lys
245 250 255

Thr Ile Ser Lys Ala Lys Gly Gln Pro Arg Glu Pro Gln Val Tyr Thr
260 265 270

Leu Pro Pro Ser Arg Lys Glu Met Thr Lys Asn Gln Val Ser Leu Thr
275 280 285

Cys Leu Val Lys Gly Phe Tyr Pro Ser Asp Ile Ala Val Glu Trp Glu
290 295 300

Ser Asn Gly Gln Pro Glu Asn Asn Tyr Lys Thr Thr Pro Pro Val Leu
305 310 315 320

Lys Ser Asp Gly Ser Phe Phe Leu Tyr Ser Lys Leu Thr Val Asp Lys
325 330 335

Ser Arg Trp Gln Gln Gly Asn Val Phe Ser Cys Ser Val Met His Glu
340 345 350

Ala Leu His Asn His Tyr Thr Gln Lys Ser Leu Ser Leu Ser Pro Gly
355 360 365

Lys

<210> SEQ ID NO 102
<211> LENGTH: 1107
<212> TYPE: DNA

<213> ORGANISM: Artificial Sequence
<220> FEATURE:
<223> OTHER INFORMATION: Description of Artificial Sequence: Synthetic
polynucleotide

<400> SEQUENCE: 102

```
atggatgcaa tgaagagagg gctctgctgt gtgctgctgc tgtgtggagc agtcttcgtt     60

tcgcccggcg ccgctatact tggtagatca gaaactcagg agtgtctttt ctttaatgct    120

aattgggaaa aagacagaac caatcaaact ggtgttgaac cgtgttatgg tgacaaagat    180

aaacggcggc attgttttgc tacctggaag aatatttctg gttccattga aatagtgaaa    240

caaggttgtt ggctggatga tatcaactgc tatgacagga ctgattgtgt agaaaaaaaa    300

gacagccctg aagtatattt ctgttgctgt gagggcaata tgtgtaatga aaagttttct    360

tattttccgg agatggaagt cacacagccc acttcaaatc cagttacacc taagccaccc    420

accggtggtg gaactcacac atgcccaccg tgcccagcac ctgaactcct ggggggaccg    480

tcagtcttcc tcttcccccc aaaacccaag gacaccctca tgatctcccg gacccctgag    540

gtcacatgcg tggtggtgga cgtgagccac gaagaccctg aggtcaagtt caactggtac    600

gtggacggcg tggaggtgca taatgccaag acaaagccgc gggaggagca gtacaacagc    660

acgtaccgtg tggtcagcgt cctcaccgtc ctgcaccagg actggctgaa tggcaaggag    720

tacaagtgca aggtctccaa caaagccctc ccagccccca tcgagaaaac catctccaaa    780

gccaaagggc agccccgaga accacaggtg tacaccctgc ccccatcccg gaaggagatg    840

accaagaacc aggtcagcct gacctgcctg gtcaaaggct tctatcccag cgacatcgcc    900

gtggagtggg agagcaatgg gcagccggag aacaactaca agaccacgcc tcccgtgctg    960

aagtccgacg gctccttctt cctctatagc aagctcaccg tggacaagag caggtggcag   1020

caggggaacg tcttctcatg ctccgtgatg catgaggctc tgcacaacca ctacacgcag   1080

aagagcctct ccctgtctcc gggtaaa                                       1107
```

<210> SEQ ID NO 103
<211> LENGTH: 344
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 103

```
Ile Leu Gly Arg Ser Glu Thr Gln Glu Cys Leu Phe Phe Asn Ala Asn
1               5                   10                  15

Trp Glu Lys Asp Arg Thr Asn Gln Thr Gly Val Glu Pro Cys Tyr Gly
            20                  25                  30

Asp Lys Asp Lys Arg Arg His Cys Phe Ala Thr Trp Lys Asn Ile Ser
        35                  40                  45

Gly Ser Ile Glu Ile Val Lys Gln Gly Cys Trp Leu Asp Asp Ile Asn
    50                  55                  60

Cys Tyr Asp Arg Thr Asp Cys Val Glu Lys Lys Asp Ser Pro Glu Val
65                  70                  75                  80

Tyr Phe Cys Cys Cys Glu Gly Asn Met Cys Asn Glu Lys Phe Ser Tyr
                85                  90                  95

Phe Pro Glu Met Glu Val Thr Gln Pro Thr Ser Asn Pro Val Thr Pro
            100                 105                 110

Lys Pro Pro Thr Gly Gly Gly Thr His Thr Cys Pro Pro Cys Pro Ala
        115                 120                 125
```

Pro Glu Leu Leu Gly Gly Pro Ser Val Phe Leu Phe Pro Pro Lys Pro
130 135 140

Lys Asp Thr Leu Met Ile Ser Arg Thr Pro Glu Val Thr Cys Val Val
145 150 155 160

Val Asp Val Ser His Glu Asp Pro Glu Val Lys Phe Asn Trp Tyr Val
165 170 175

Asp Gly Val Glu Val His Asn Ala Lys Thr Lys Pro Arg Glu Glu Gln
180 185 190

Tyr Asn Ser Thr Tyr Arg Val Val Ser Val Leu Thr Val Leu His Gln
195 200 205

Asp Trp Leu Asn Gly Lys Glu Tyr Lys Cys Lys Val Ser Asn Lys Ala
210 215 220

Leu Pro Ala Pro Ile Glu Lys Thr Ile Ser Lys Ala Lys Gly Gln Pro
225 230 235 240

Arg Glu Pro Gln Val Tyr Thr Leu Pro Pro Ser Arg Lys Glu Met Thr
245 250 255

Lys Asn Gln Val Ser Leu Thr Cys Leu Val Lys Gly Phe Tyr Pro Ser
260 265 270

Asp Ile Ala Val Glu Trp Glu Ser Asn Gly Gln Pro Glu Asn Asn Tyr
275 280 285

Lys Thr Thr Pro Pro Val Leu Lys Ser Asp Gly Ser Phe Phe Leu Tyr
290 295 300

Ser Lys Leu Thr Val Asp Lys Ser Arg Trp Gln Gln Gly Asn Val Phe
305 310 315 320

Ser Cys Ser Val Met His Glu Ala Leu His Asn His Tyr Thr Gln Lys
325 330 335

Ser Leu Ser Leu Ser Pro Gly Lys
340

<210> SEQ ID NO 104
<211> LENGTH: 368
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 104

Met Asp Ala Met Lys Arg Gly Leu Cys Cys Val Leu Leu Leu Cys Gly
1 5 10 15

Ala Val Phe Val Ser Pro Gly Ala Ser Gly Arg Gly Glu Ala Glu Thr
20 25 30

Arg Glu Cys Ile Tyr Tyr Asn Ala Asn Trp Glu Leu Glu Arg Thr Asn
35 40 45

Gln Ser Gly Leu Glu Arg Cys Glu Gly Glu Gln Asp Lys Arg Leu His
50 55 60

Cys Tyr Ala Ser Trp Arg Asn Ser Ser Gly Thr Ile Glu Leu Val Lys
65 70 75 80

Lys Gly Cys Trp Leu Asp Asp Phe Asn Cys Tyr Asp Arg Gln Glu Cys
85 90 95

Val Ala Thr Glu Glu Asn Pro Gln Val Tyr Phe Cys Cys Cys Glu Gly
100 105 110

Asn Phe Cys Asn Glu Arg Phe Thr His Leu Pro Glu Ala Gly Gly Pro
115 120 125

Glu Val Thr Tyr Glu Pro Pro Pro Thr Ala Pro Thr Gly Gly Gly Thr

```
    130                 135                 140

His Thr Cys Pro Pro Cys Pro Ala Pro Glu Leu Leu Gly Gly Pro Ser
145                 150                 155                 160

Val Phe Leu Phe Pro Pro Lys Pro Lys Asp Thr Leu Met Ile Ser Arg
                165                 170                 175

Thr Pro Glu Val Thr Cys Val Val Val Asp Val Ser His Glu Asp Pro
            180                 185                 190

Glu Val Lys Phe Asn Trp Tyr Val Asp Gly Val Glu Val His Asn Ala
        195                 200                 205

Lys Thr Lys Pro Arg Glu Glu Gln Tyr Asn Ser Thr Tyr Arg Val Val
    210                 215                 220

Ser Val Leu Thr Val Leu His Gln Asp Trp Leu Asn Gly Lys Glu Tyr
225                 230                 235                 240

Lys Cys Lys Val Ser Asn Lys Ala Leu Pro Ala Pro Ile Glu Lys Thr
                245                 250                 255

Ile Ser Lys Ala Lys Gly Gln Pro Arg Glu Pro Gln Val Tyr Thr Leu
            260                 265                 270

Pro Pro Ser Arg Lys Glu Met Thr Lys Asn Gln Val Ser Leu Thr Cys
        275                 280                 285

Leu Val Lys Gly Phe Tyr Pro Ser Asp Ile Ala Val Glu Trp Glu Ser
    290                 295                 300

Asn Gly Gln Pro Glu Asn Asn Tyr Lys Thr Thr Pro Pro Val Leu Lys
305                 310                 315                 320

Ser Asp Gly Ser Phe Phe Leu Tyr Ser Lys Leu Thr Val Asp Lys Ser
                325                 330                 335

Arg Trp Gln Gln Gly Asn Val Phe Ser Cys Ser Val Met His Glu Ala
            340                 345                 350

Leu His Asn His Tyr Thr Gln Lys Ser Leu Ser Leu Ser Pro Gly Lys
        355                 360                 365
```

<210> SEQ ID NO 105
<211> LENGTH: 1104
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 105

```
atggatgcaa tgaagagagg gctctgctgt gtgctgctgc tgtgtggagc agtcttcgtt     60

tcgcccggcg cctctgggcg tggggaggct gagacacggg agtgcatcta ctacaacgcc    120

aactgggagc tggagcgcac caaccagagc ggcctggagc gctgcgaagg cgagcaggac    180

aagcggctgc actgctacgc ctcctggcgc aacagctctg gcaccatcga gctcgtgaag    240

aagggctgct ggctagatga cttcaactgc tacgataggc aggagtgtgt ggccactgag    300

gagaaccccc aggtgtactt ctgctgctgt gaaggcaact tctgcaacga gcgcttcact    360

catttgccag aggctggggg cccggaagtc acgtacgagc caccccgac agcccccacc     420

ggtggtggaa ctcacacatg cccaccgtgc ccagcacctg aactcctggg gggaccgtca    480

gtcttcctct tccccccaaa acccaaggac accctcatga tctcccggac ccctgaggtc    540

acatgcgtgg tggtggacgt gagccacgaa gaccctgagg tcaagttcaa ctggtacgtg    600

gacggcgtgg aggtgcataa tgccaagaca aagccgcggg aggagcagta caacagcacg    660

taccgtgtgg tcagcgtcct caccgtcctg caccaggact ggctgaatgg caaggagtac    720
```

```
aagtgcaagg tctccaacaa agccctccca gcccccatcg agaaaaccat ctccaaagcc    780

aaagggcagc cccgagaacc acaggtgtac accctgcccc catcccggaa ggagatgacc    840

aagaaccagg tcagcctgac ctgcctggtc aaaggcttct atcccagcga catcgccgtg    900

gagtgggaga gcaatgggca gccggagaac aactacaaga ccacgcctcc cgtgctgaag    960

tccgacggct ccttcttcct ctatagcaag ctcaccgtgg acaagagcag gtggcagcag   1020

gggaacgtct tctcatgctc cgtgatgcat gaggctctgc acaaccacta cacgcagaag   1080

agcctctccc tgtctccggg taaa                                          1104
```

<210> SEQ ID NO 106
<211> LENGTH: 343
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 106

```
Gly Arg Gly Glu Ala Glu Thr Arg Glu Cys Ile Tyr Tyr Asn Ala Asn
1               5                   10                  15

Trp Glu Leu Glu Arg Thr Asn Gln Ser Gly Leu Glu Arg Cys Glu Gly
            20                  25                  30

Glu Gln Asp Lys Arg Leu His Cys Tyr Ala Ser Trp Arg Asn Ser Ser
        35                  40                  45

Gly Thr Ile Glu Leu Val Lys Lys Gly Cys Trp Leu Asp Asp Phe Asn
    50                  55                  60

Cys Tyr Asp Arg Gln Glu Cys Val Ala Thr Glu Glu Asn Pro Gln Val
65                  70                  75                  80

Tyr Phe Cys Cys Cys Glu Gly Asn Phe Cys Asn Glu Arg Phe Thr His
                85                  90                  95

Leu Pro Glu Ala Gly Gly Pro Glu Val Thr Tyr Glu Pro Pro Pro Thr
            100                 105                 110

Ala Pro Thr Gly Gly Gly Thr His Thr Cys Pro Pro Cys Pro Ala Pro
        115                 120                 125

Glu Leu Leu Gly Gly Pro Ser Val Phe Leu Phe Pro Pro Lys Pro Lys
    130                 135                 140

Asp Thr Leu Met Ile Ser Arg Thr Pro Glu Val Thr Cys Val Val Val
145                 150                 155                 160

Asp Val Ser His Glu Asp Pro Glu Val Lys Phe Asn Trp Tyr Val Asp
                165                 170                 175

Gly Val Glu Val His Asn Ala Lys Thr Lys Pro Arg Glu Glu Gln Tyr
            180                 185                 190

Asn Ser Thr Tyr Arg Val Val Ser Val Leu Thr Val Leu His Gln Asp
        195                 200                 205

Trp Leu Asn Gly Lys Glu Tyr Lys Cys Lys Val Ser Asn Lys Ala Leu
    210                 215                 220

Pro Ala Pro Ile Glu Lys Thr Ile Ser Lys Ala Lys Gly Gln Pro Arg
225                 230                 235                 240

Glu Pro Gln Val Tyr Thr Leu Pro Pro Ser Arg Lys Glu Met Thr Lys
                245                 250                 255

Asn Gln Val Ser Leu Thr Cys Leu Val Lys Gly Phe Tyr Pro Ser Asp
            260                 265                 270

Ile Ala Val Glu Trp Glu Ser Asn Gly Gln Pro Glu Asn Asn Tyr Lys
        275                 280                 285
```

Thr Thr Pro Pro Val Leu Lys Ser Asp Gly Ser Phe Phe Leu Tyr Ser
290 295 300

Lys Leu Thr Val Asp Lys Ser Arg Trp Gln Gln Gly Asn Val Phe Ser
305 310 315 320

Cys Ser Val Met His Glu Ala Leu His Asn His Tyr Thr Gln Lys Ser
325 330 335

Leu Ser Leu Ser Pro Gly Lys
340

<210> SEQ ID NO 107
<211> LENGTH: 376
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 107

Met Asp Ala Met Lys Arg Gly Leu Cys Cys Val Leu Leu Leu Cys Gly
1 5 10 15

Ala Val Phe Val Ser Pro Gly Ala Ser Gln Asn Gln Glu Arg Leu Cys
20 25 30

Ala Phe Lys Asp Pro Tyr Gln Gln Asp Leu Gly Ile Gly Glu Ser Arg
35 40 45

Ile Ser His Glu Asn Gly Thr Ile Leu Cys Ser Lys Gly Ser Thr Cys
50 55 60

Tyr Gly Leu Trp Glu Lys Ser Lys Gly Asp Ile Asn Leu Val Lys Gln
65 70 75 80

Gly Cys Trp Ser His Ile Gly Asp Pro Gln Glu Cys His Tyr Glu Glu
85 90 95

Cys Val Val Thr Thr Thr Pro Pro Ser Ile Gln Asn Gly Thr Tyr Arg
100 105 110

Phe Cys Cys Cys Ser Thr Asp Leu Cys Asn Val Asn Phe Thr Glu Asn
115 120 125

Phe Pro Pro Pro Asp Thr Thr Pro Leu Ser Pro Pro His Ser Phe Asn
130 135 140

Arg Asp Glu Thr Gly Gly Gly Thr His Thr Cys Pro Pro Cys Pro Ala
145 150 155 160

Pro Glu Leu Leu Gly Gly Pro Ser Val Phe Leu Phe Pro Pro Lys Pro
165 170 175

Lys Asp Thr Leu Met Ile Ser Arg Thr Pro Glu Val Thr Cys Val Val
180 185 190

Val Asp Val Ser His Glu Asp Pro Glu Val Lys Phe Asn Trp Tyr Val
195 200 205

Asp Gly Val Glu Val His Asn Ala Lys Thr Lys Pro Arg Glu Glu Gln
210 215 220

Tyr Asn Ser Thr Tyr Arg Val Val Ser Val Leu Thr Val Leu His Gln
225 230 235 240

Asp Trp Leu Asn Gly Lys Glu Tyr Lys Cys Lys Val Ser Asn Lys Ala
245 250 255

Leu Pro Ala Pro Ile Glu Lys Thr Ile Ser Lys Ala Lys Gly Gln Pro
260 265 270

Arg Glu Pro Gln Val Tyr Thr Leu Pro Pro Ser Arg Lys Glu Met Thr
275 280 285

Lys Asn Gln Val Ser Leu Thr Cys Leu Val Lys Gly Phe Tyr Pro Ser
290 295 300

```
Asp Ile Ala Val Glu Trp Glu Ser Asn Gly Gln Pro Glu Asn Asn Tyr
305                 310                 315                 320

Lys Thr Thr Pro Pro Val Leu Lys Ser Asp Gly Ser Phe Phe Leu Tyr
                325                 330                 335

Ser Lys Leu Thr Val Asp Lys Ser Arg Trp Gln Gln Gly Asn Val Phe
            340                 345                 350

Ser Cys Ser Val Met His Glu Ala Leu His Asn His Tyr Thr Gln Lys
        355                 360                 365

Ser Leu Ser Leu Ser Pro Gly Lys
    370                 375


<210> SEQ ID NO 108
<211> LENGTH: 1128
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 108

atggatgcaa tgaagagagg gctctgctgt gtgctgctgc tgtgtggagc agtcttcgtt     60

tcgcccggcg cctcgcagaa tcaagaacgc ctatgtgcgt ttaaagatcc gtatcagcaa    120

gaccttggga taggtgagag tagaatctct catgaaaatg ggacaatatt atgctcgaaa    180

ggtagcacct gctatggcct ttgggagaaa tcaaaagggg acataaatct tgtaaaacaa    240

ggatgttggt ctcacattgg agatccccaa gagtgtcact atgaagaatg tgtagtaact    300

accactcctc cctcaattca gaatggaaca taccgtttct gctgttgtag cacagattta    360

tgtaatgtca actttactga gaattttcca cctcctgaca caacaccact cagtccacct    420

cattcattta accgagatga gaccggtggt ggaactcaca catgcccacc gtgcccagca    480

cctgaactcc tggggggacc gtcagtcttc ctcttccccc caaaacccaa ggacaccctc    540

atgatctccc ggacccctga ggtcacatgc gtggtggtgg acgtgagcca cgaagaccct    600

gaggtcaagt tcaactggta cgtggacggc gtggaggtgc ataatgccaa gacaaagccg    660

cgggaggagc agtacaacag cacgtaccgt gtggtcagcg tcctcaccgt cctgcaccag    720

gactggctga atggcaagga gtacaagtgc aaggtctcca acaaagccct cccagccccc    780

atcgagaaaa ccatctccaa agccaaaggg cagccccgag aaccacaggt gtacaccctg    840

cccccatccc ggaaggagat gaccaagaac caggtcagcc tgacctgcct ggtcaaaggc    900

ttctatccca gcgacatcgc cgtggagtgg gagagcaatg ggcagccgga gaacaactac    960

aagaccacgc ctcccgtgct gaagtccgac ggctccttct tcctctatag caagctcacc   1020

gtggacaaga gcaggtggca gcaggggaac gtcttctcat gctccgtgat gcatgaggct   1080

ctgcacaacc actacacgca gaagagcctc tccctgtctc cgggtaaa                1128


<210> SEQ ID NO 109
<211> LENGTH: 352
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 109

Ser Gln Asn Gln Glu Arg Leu Cys Ala Phe Lys Asp Pro Tyr Gln Gln
1               5                   10                  15
```

-continued

```
Asp Leu Gly Ile Gly Glu Ser Arg Ile Ser His Glu Asn Gly Thr Ile
            20                  25                  30

Leu Cys Ser Lys Gly Ser Thr Cys Tyr Gly Leu Trp Glu Lys Ser Lys
        35                  40                  45

Gly Asp Ile Asn Leu Val Lys Gln Gly Cys Trp Ser His Ile Gly Asp
    50                  55                  60

Pro Gln Glu Cys His Tyr Glu Glu Cys Val Val Thr Thr Thr Pro Pro
65                  70                  75                  80

Ser Ile Gln Asn Gly Thr Tyr Arg Phe Cys Cys Cys Ser Thr Asp Leu
                85                  90                  95

Cys Asn Val Asn Phe Thr Glu Asn Phe Pro Pro Pro Asp Thr Thr Pro
            100                 105                 110

Leu Ser Pro Pro His Ser Phe Asn Arg Asp Glu Thr Gly Gly Gly Thr
        115                 120                 125

His Thr Cys Pro Pro Cys Pro Ala Pro Glu Leu Leu Gly Gly Pro Ser
    130                 135                 140

Val Phe Leu Phe Pro Pro Lys Pro Lys Asp Thr Leu Met Ile Ser Arg
145                 150                 155                 160

Thr Pro Glu Val Thr Cys Val Val Val Asp Val Ser His Glu Asp Pro
                165                 170                 175

Glu Val Lys Phe Asn Trp Tyr Val Asp Gly Val Glu Val His Asn Ala
            180                 185                 190

Lys Thr Lys Pro Arg Glu Glu Gln Tyr Asn Ser Thr Tyr Arg Val Val
        195                 200                 205

Ser Val Leu Thr Val Leu His Gln Asp Trp Leu Asn Gly Lys Glu Tyr
    210                 215                 220

Lys Cys Lys Val Ser Asn Lys Ala Leu Pro Ala Pro Ile Glu Lys Thr
225                 230                 235                 240

Ile Ser Lys Ala Lys Gly Gln Pro Arg Glu Pro Gln Val Tyr Thr Leu
                245                 250                 255

Pro Pro Ser Arg Lys Glu Met Thr Lys Asn Gln Val Ser Leu Thr Cys
            260                 265                 270

Leu Val Lys Gly Phe Tyr Pro Ser Asp Ile Ala Val Glu Trp Glu Ser
        275                 280                 285

Asn Gly Gln Pro Glu Asn Asn Tyr Lys Thr Thr Pro Pro Val Leu Lys
    290                 295                 300

Ser Asp Gly Ser Phe Phe Leu Tyr Ser Lys Leu Thr Val Asp Lys Ser
305                 310                 315                 320

Arg Trp Gln Gln Gly Asn Val Phe Ser Cys Ser Val Met His Glu Ala
                325                 330                 335

Leu His Asn His Tyr Thr Gln Lys Ser Leu Ser Leu Ser Pro Gly Lys
            340                 345                 350
```

<210> SEQ ID NO 110
<211> LENGTH: 385
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 110

```
Met Asp Ala Met Lys Arg Gly Leu Cys Cys Val Leu Leu Leu Cys Gly
1               5                   10                  15

Ala Val Phe Val Ser Pro Gly Ala Pro Pro Asn Arg Arg Thr Cys Val
            20                  25                  30
```

Phe Phe Glu Ala Pro Gly Val Arg Gly Ser Thr Lys Thr Leu Gly Glu
35 40 45

Leu Leu Asp Thr Gly Thr Glu Leu Pro Arg Ala Ile Arg Cys Leu Tyr
50 55 60

Ser Arg Cys Cys Phe Gly Ile Trp Asn Leu Thr Gln Asp Arg Ala Gln
65 70 75 80

Val Glu Met Gln Gly Cys Arg Asp Ser Asp Glu Pro Gly Cys Glu Ser
85 90 95

Leu His Cys Asp Pro Ser Pro Arg Ala His Pro Ser Pro Gly Ser Thr
100 105 110

Leu Phe Thr Cys Ser Cys Gly Thr Asp Phe Cys Asn Ala Asn Tyr Ser
115 120 125

His Leu Pro Pro Pro Gly Ser Pro Gly Thr Pro Gly Ser Gln Gly Pro
130 135 140

Gln Ala Ala Pro Gly Glu Ser Ile Trp Met Ala Leu Thr Gly Gly Gly
145 150 155 160

Thr His Thr Cys Pro Pro Cys Pro Ala Pro Glu Leu Leu Gly Gly Pro
165 170 175

Ser Val Phe Leu Phe Pro Pro Lys Pro Lys Asp Thr Leu Met Ile Ser
180 185 190

Arg Thr Pro Glu Val Thr Cys Val Val Val Asp Val Ser His Glu Asp
195 200 205

Pro Glu Val Lys Phe Asn Trp Tyr Val Asp Gly Val Glu Val His Asn
210 215 220

Ala Lys Thr Lys Pro Arg Glu Glu Gln Tyr Asn Ser Thr Tyr Arg Val
225 230 235 240

Val Ser Val Leu Thr Val Leu His Gln Asp Trp Leu Asn Gly Lys Glu
245 250 255

Tyr Lys Cys Lys Val Ser Asn Lys Ala Leu Pro Ala Pro Ile Glu Lys
260 265 270

Thr Ile Ser Lys Ala Lys Gly Gln Pro Arg Glu Pro Gln Val Tyr Thr
275 280 285

Leu Pro Pro Ser Arg Lys Glu Met Thr Lys Asn Gln Val Ser Leu Thr
290 295 300

Cys Leu Val Lys Gly Phe Tyr Pro Ser Asp Ile Ala Val Glu Trp Glu
305 310 315 320

Ser Asn Gly Gln Pro Glu Asn Asn Tyr Lys Thr Thr Pro Pro Val Leu
325 330 335

Lys Ser Asp Gly Ser Phe Phe Leu Tyr Ser Lys Leu Thr Val Asp Lys
340 345 350

Ser Arg Trp Gln Gln Gly Asn Val Phe Ser Cys Ser Val Met His Glu
355 360 365

Ala Leu His Asn His Tyr Thr Gln Lys Ser Leu Ser Leu Ser Pro Gly
370 375 380

Lys
385

<210> SEQ ID NO 111

<400> SEQUENCE: 111

000

<210> SEQ ID NO 112

<211> LENGTH: 361
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 112

Pro Pro Asn Arg Arg Thr Cys Val Phe Phe Glu Ala Pro Gly Val Arg
1               5                   10                  15

Gly Ser Thr Lys Thr Leu Gly Glu Leu Leu Asp Thr Gly Thr Glu Leu
            20                  25                  30

Pro Arg Ala Ile Arg Cys Leu Tyr Ser Arg Cys Cys Phe Gly Ile Trp
        35                  40                  45

Asn Leu Thr Gln Asp Arg Ala Gln Val Glu Met Gln Gly Cys Arg Asp
    50                  55                  60

Ser Asp Glu Pro Gly Cys Glu Ser Leu His Cys Asp Pro Ser Pro Arg
65                  70                  75                  80

Ala His Pro Ser Pro Gly Ser Thr Leu Phe Thr Cys Ser Cys Gly Thr
                85                  90                  95

Asp Phe Cys Asn Ala Asn Tyr Ser His Leu Pro Pro Pro Gly Ser Pro
            100                 105                 110

Gly Thr Pro Gly Ser Gln Gly Pro Gln Ala Ala Pro Gly Glu Ser Ile
        115                 120                 125

Trp Met Ala Leu Thr Gly Gly Gly Thr His Thr Cys Pro Pro Cys Pro
    130                 135                 140

Ala Pro Glu Leu Leu Gly Gly Pro Ser Val Phe Leu Phe Pro Pro Lys
145                 150                 155                 160

Pro Lys Asp Thr Leu Met Ile Ser Arg Thr Pro Glu Val Thr Cys Val
                165                 170                 175

Val Val Asp Val Ser His Glu Asp Pro Glu Val Lys Phe Asn Trp Tyr
            180                 185                 190

Val Asp Gly Val Glu Val His Asn Ala Lys Thr Lys Pro Arg Glu Glu
        195                 200                 205

Gln Tyr Asn Ser Thr Tyr Arg Val Val Ser Val Leu Thr Val Leu His
    210                 215                 220

Gln Asp Trp Leu Asn Gly Lys Glu Tyr Lys Cys Lys Val Ser Asn Lys
225                 230                 235                 240

Ala Leu Pro Ala Pro Ile Glu Lys Thr Ile Ser Lys Ala Lys Gly Gln
                245                 250                 255

Pro Arg Glu Pro Gln Val Tyr Thr Leu Pro Pro Ser Arg Lys Glu Met
            260                 265                 270

Thr Lys Asn Gln Val Ser Leu Thr Cys Leu Val Lys Gly Phe Tyr Pro
        275                 280                 285

Ser Asp Ile Ala Val Glu Trp Glu Ser Asn Gly Gln Pro Glu Asn Asn
    290                 295                 300

Tyr Lys Thr Thr Pro Pro Val Leu Lys Ser Asp Gly Ser Phe Phe Leu
305                 310                 315                 320

Tyr Ser Lys Leu Thr Val Asp Lys Ser Arg Trp Gln Gln Gly Asn Val
                325                 330                 335

Phe Ser Cys Ser Val Met His Glu Ala Leu His Asn His Tyr Thr Gln
            340                 345                 350

Lys Ser Leu Ser Leu Ser Pro Gly Lys
        355                 360

```
<210> SEQ ID NO 113
<211> LENGTH: 390
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 113

Met Asp Ala Met Lys Arg Gly Leu Cys Cys Val Leu Leu Leu Cys Gly
1               5                   10                  15

Ala Val Phe Val Ser Pro Gly Ala Thr Ile Pro Pro His Val Gln Lys
            20                  25                  30

Ser Val Asn Asn Asp Met Ile Val Thr Asp Asn Asn Gly Ala Val Lys
        35                  40                  45

Phe Pro Gln Leu Cys Lys Phe Cys Asp Val Arg Phe Ser Thr Cys Asp
    50                  55                  60

Asn Gln Lys Ser Cys Met Ser Asn Cys Ser Ile Thr Ser Ile Cys Glu
65                  70                  75                  80

Lys Pro Gln Glu Val Cys Val Ala Val Trp Arg Lys Asn Asp Glu Asn
                85                  90                  95

Ile Thr Leu Glu Thr Val Cys His Asp Pro Lys Leu Pro Tyr His Asp
            100                 105                 110

Phe Ile Leu Glu Asp Ala Ala Ser Pro Lys Cys Ile Met Lys Glu Lys
        115                 120                 125

Lys Lys Pro Gly Glu Thr Phe Phe Met Cys Ser Cys Ser Ser Asp Glu
    130                 135                 140

Cys Asn Asp Asn Ile Ile Phe Ser Glu Glu Tyr Asn Thr Ser Asn Pro
145                 150                 155                 160

Asp Thr Gly Gly Gly Thr His Thr Cys Pro Pro Cys Pro Ala Pro Glu
                165                 170                 175

Leu Leu Gly Gly Pro Ser Val Phe Leu Phe Pro Pro Lys Pro Lys Asp
            180                 185                 190

Thr Leu Met Ile Ser Arg Thr Pro Glu Val Thr Cys Val Val Val Asp
        195                 200                 205

Val Ser His Glu Asp Pro Glu Val Lys Phe Asn Trp Tyr Val Asp Gly
    210                 215                 220

Val Glu Val His Asn Ala Lys Thr Lys Pro Arg Glu Glu Gln Tyr Asn
225                 230                 235                 240

Ser Thr Tyr Arg Val Val Ser Val Leu Thr Val Leu His Gln Asp Trp
                245                 250                 255

Leu Asn Gly Lys Glu Tyr Lys Cys Lys Val Ser Asn Lys Ala Leu Pro
            260                 265                 270

Ala Pro Ile Glu Lys Thr Ile Ser Lys Ala Lys Gly Gln Pro Arg Glu
        275                 280                 285

Pro Gln Val Tyr Thr Leu Pro Pro Ser Arg Lys Glu Met Thr Lys Asn
    290                 295                 300

Gln Val Ser Leu Thr Cys Leu Val Lys Gly Phe Tyr Pro Ser Asp Ile
305                 310                 315                 320

Ala Val Glu Trp Glu Ser Asn Gly Gln Pro Glu Asn Asn Tyr Lys Thr
                325                 330                 335

Thr Pro Pro Val Leu Lys Ser Asp Gly Ser Phe Phe Leu Tyr Ser Lys
            340                 345                 350

Leu Thr Val Asp Lys Ser Arg Trp Gln Gln Gly Asn Val Phe Ser Cys
        355                 360                 365
```

Ser Val Met His Glu Ala Leu His Asn His Tyr Thr Gln Lys Ser Leu
    370                 375                 380

Ser Leu Ser Pro Gly Lys
385                 390

<210> SEQ ID NO 114
<211> LENGTH: 1170
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 114
atggatgcaa tgaagagagg gctctgctgt gtgctgctgc tgtgtggagc agtcttcgtt      60
tcgcccggcg ccacgatccc accgcacgtt cagaagtcgg ttaataacga catgatagtc     120
actgacaaca acggtgcagt caagtttcca caactgtgta aattttgtga tgtgagattt     180
tccacctgtg acaaccagaa atcctgcatg agcaactgca gcatcacctc catctgtgag     240
aagccacagg aagtctgtgt ggctgtatgg agaaagaatg acgagaacat aacactagag     300
acagtttgcc atgaccccaa gctcccctac catgacttta ttctggaaga tgctgcttct     360
ccaaagtgca ttatgaagga aaaaaaaaag cctggtgaga ctttcttcat gtgttcctgt     420
agctctgatg agtgcaatga caacatcatc ttctcagaag aatataacac cagcaatcct     480
gacaccggtg gtggaactca cacatgccca ccgtgcccag cacctgaact cctgggggga     540
ccgtcagtct tcctcttccc cccaaaaccc aaggacaccc tcatgatctc ccggacccct     600
gaggtcacat gcgtggtggt ggacgtgagc cacgaagacc ctgaggtcaa gttcaactgg     660
tacgtggacg gcgtggaggt gcataatgcc aagacaaagc cgcgggagga gcagtacaac     720
agcacgtacc gtgtggtcag cgtcctcacc gtcctgcacc aggactggct gaatggcaag     780
gagtacaagt gcaaggtctc caacaaagcc ctcccagccc ccatcgagaa aaccatctcc     840
aaagccaaag ggcagccccg agaaccacag gtgtacaccc tgcccccatc ccggaaggag     900
atgaccaaga accaggtcag cctgacctgc ctggtcaaag gcttctatcc cagcgacatc     960
gccgtggagt gggagagcaa tgggcagccg gagaacaact acaagaccac gcctcccgtg    1020
ctgaagtccg acggctcctt cttcctctat agcaagctca ccgtggacaa gagcaggtgg    1080
cagcagggga acgtcttctc atgctccgtg atgcatgagg ctctgcacaa ccactacacg    1140
cagaagagcc tctccctgtc tccgggtaaa                                     1170

<210> SEQ ID NO 115
<211> LENGTH: 366
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 115

Thr Ile Pro Pro His Val Gln Lys Ser Val Asn Asn Asp Met Ile Val
1               5                   10                  15

Thr Asp Asn Asn Gly Ala Val Lys Phe Pro Gln Leu Cys Lys Phe Cys
            20                  25                  30

Asp Val Arg Phe Ser Thr Cys Asp Asn Gln Lys Ser Cys Met Ser Asn
        35                  40                  45

Cys Ser Ile Thr Ser Ile Cys Glu Lys Pro Gln Glu Val Cys Val Ala
    50                  55                  60

```
Val Trp Arg Lys Asn Asp Glu Asn Ile Thr Leu Glu Thr Val Cys His
65                  70                  75                  80

Asp Pro Lys Leu Pro Tyr His Asp Phe Ile Leu Glu Asp Ala Ala Ser
                85                  90                  95

Pro Lys Cys Ile Met Lys Glu Lys Lys Lys Pro Gly Glu Thr Phe Phe
            100                 105                 110

Met Cys Ser Cys Ser Ser Asp Glu Cys Asn Asp Asn Ile Ile Phe Ser
        115                 120                 125

Glu Glu Tyr Asn Thr Ser Asn Pro Asp Thr Gly Gly Gly Thr His Thr
    130                 135                 140

Cys Pro Pro Cys Pro Ala Pro Glu Leu Leu Gly Gly Pro Ser Val Phe
145                 150                 155                 160

Leu Phe Pro Pro Lys Pro Lys Asp Thr Leu Met Ile Ser Arg Thr Pro
                165                 170                 175

Glu Val Thr Cys Val Val Val Asp Val Ser His Glu Asp Pro Glu Val
            180                 185                 190

Lys Phe Asn Trp Tyr Val Asp Gly Val Glu Val His Asn Ala Lys Thr
        195                 200                 205

Lys Pro Arg Glu Glu Gln Tyr Asn Ser Thr Tyr Arg Val Val Ser Val
    210                 215                 220

Leu Thr Val Leu His Gln Asp Trp Leu Asn Gly Lys Glu Tyr Lys Cys
225                 230                 235                 240

Lys Val Ser Asn Lys Ala Leu Pro Ala Pro Ile Glu Lys Thr Ile Ser
                245                 250                 255

Lys Ala Lys Gly Gln Pro Arg Glu Pro Gln Val Tyr Thr Leu Pro Pro
            260                 265                 270

Ser Arg Lys Glu Met Thr Lys Asn Gln Val Ser Leu Thr Cys Leu Val
        275                 280                 285

Lys Gly Phe Tyr Pro Ser Asp Ile Ala Val Glu Trp Glu Ser Asn Gly
    290                 295                 300

Gln Pro Glu Asn Asn Tyr Lys Thr Thr Pro Pro Val Leu Lys Ser Asp
305                 310                 315                 320

Gly Ser Phe Phe Leu Tyr Ser Lys Leu Thr Val Asp Lys Ser Arg Trp
                325                 330                 335

Gln Gln Gly Asn Val Phe Ser Cys Ser Val Met His Glu Ala Leu His
            340                 345                 350

Asn His Tyr Thr Gln Lys Ser Leu Ser Leu Ser Pro Gly Lys
        355                 360                 365
```

<210> SEQ ID NO 116
<211> LENGTH: 351
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 116

```
Met Asp Ala Met Lys Arg Gly Leu Cys Cys Val Leu Leu Leu Cys Gly
1               5                   10                  15

Ala Val Phe Val Ser Pro Gly Ala Asp Pro Val Lys Pro Ser Arg Gly
            20                  25                  30

Pro Leu Val Thr Cys Thr Cys Glu Ser Pro His Cys Lys Gly Pro Thr
        35                  40                  45

Cys Arg Gly Ala Trp Cys Thr Val Val Leu Val Arg Glu Glu Gly Arg
```

```
    50                  55                  60

His Pro Gln Glu His Arg Gly Cys Gly Asn Leu His Arg Glu Leu Cys
65                  70                  75                  80

Arg Gly Arg Pro Thr Glu Phe Val Asn His Tyr Cys Cys Asp Ser His
                85                  90                  95

Leu Cys Asn His Asn Val Ser Leu Val Leu Glu Ala Thr Gln Pro Pro
            100                 105                 110

Ser Glu Gln Pro Gly Thr Asp Gly Gln Leu Ala Thr Gly Gly Gly Thr
        115                 120                 125

His Thr Cys Pro Pro Cys Pro Ala Pro Glu Leu Leu Gly Gly Pro Ser
    130                 135                 140

Val Phe Leu Phe Pro Pro Lys Pro Lys Asp Thr Leu Met Ile Ser Arg
145                 150                 155                 160

Thr Pro Glu Val Thr Cys Val Val Val Asp Val Ser His Glu Asp Pro
                165                 170                 175

Glu Val Lys Phe Asn Trp Tyr Val Asp Gly Val Glu Val His Asn Ala
            180                 185                 190

Lys Thr Lys Pro Arg Glu Glu Gln Tyr Asn Ser Thr Tyr Arg Val Val
        195                 200                 205

Ser Val Leu Thr Val Leu His Gln Asp Trp Leu Asn Gly Lys Glu Tyr
    210                 215                 220

Lys Cys Lys Val Ser Asn Lys Ala Leu Pro Ala Pro Ile Glu Lys Thr
225                 230                 235                 240

Ile Ser Lys Ala Lys Gly Gln Pro Arg Glu Pro Gln Val Tyr Thr Leu
                245                 250                 255

Pro Pro Ser Arg Glu Glu Met Thr Lys Asn Gln Val Ser Leu Thr Cys
            260                 265                 270

Leu Val Lys Gly Phe Tyr Pro Ser Asp Ile Ala Val Glu Trp Glu Ser
        275                 280                 285

Asn Gly Gln Pro Glu Asn Asn Tyr Asp Thr Thr Pro Pro Val Leu Asp
    290                 295                 300

Ser Asp Gly Ser Phe Phe Leu Tyr Ser Asp Leu Thr Val Asp Lys Ser
305                 310                 315                 320

Arg Trp Gln Gln Gly Asn Val Phe Ser Cys Ser Val Met His Glu Ala
                325                 330                 335

Leu His Asn His Tyr Thr Gln Lys Ser Leu Ser Leu Ser Pro Gly
            340                 345                 350


<210> SEQ ID NO 117
<211> LENGTH: 1053
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 117

atggatgcaa tgaagagagg gctctgctgt gtgctgctgc tgtgtggagc agtcttcgtt      60

tcgcccggcg ccgaccctgt gaagccgtct cggggcccgc tggtgacctg cacgtgtgag     120

agcccacatt gcaaggggcc tacctgccgg ggggcctggt gcacagtagt gctggtgcgg     180

gaggagggga ggcacccccca ggaacatcgg ggctgcggga acttgcacag ggagctctgc    240

aggggccgcc ccaccgagtt cgtcaaccac tactgctgcg acagccacct ctgcaaccac     300

aacgtgtccc tggtgctgga ggccacccaa cctccttcgg agcagccggg aacagatggc     360
```

-continued

```
cagctggcca ccggtggtgg aactcacaca tgcccaccgt gcccagcacc tgaactcctg    420

gggggaccgt cagtcttcct cttcccccca aaacccaagg acaccctcat gatctcccgg    480

acccctgagg tcacatgcgt ggtggtggac gtgagccacg aagaccctga ggtcaagttc    540

aactggtacg tggacggcgt ggaggtgcat aatgccaaga caaagccgcg ggaggagcag    600

tacaacagca cgtaccgtgt ggtcagcgtc ctcaccgtcc tgcaccagga ctggctgaat    660

ggcaaggagt acaagtgcaa ggtctccaac aaagccctcc cagcccccat cgagaaaacc    720

atctccaaag ccaaagggca gccccgagaa ccacaggtgt acaccctgcc cccatcccgg    780

gaggagatga ccaagaacca ggtcagcctg acctgcctgg tcaaaggctt ctatcccagc    840

gacatcgccg tggagtggga gagcaatggg cagccggaga acaactacga caccacgcct    900

cccgtgctgg actccgacgg ctccttcttc ctctatagcg acctcaccgt ggacaagagc    960

aggtggcagc aggggaacgt cttctcatgc tccgtgatgc atgaggctct gcacaaccac   1020

tacacgcaga agagcctctc cctgtctccg ggt                                1053


<210> SEQ ID NO 118
<211> LENGTH: 327
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 118

Asp Pro Val Lys Pro Ser Arg Gly Pro Leu Val Thr Cys Thr Cys Glu
1               5                   10                  15

Ser Pro His Cys Lys Gly Pro Thr Cys Arg Gly Ala Trp Cys Thr Val
            20                  25                  30

Val Leu Val Arg Glu Glu Gly Arg His Pro Gln Glu His Arg Gly Cys
        35                  40                  45

Gly Asn Leu His Arg Glu Leu Cys Arg Gly Arg Pro Thr Glu Phe Val
    50                  55                  60

Asn His Tyr Cys Cys Asp Ser His Leu Cys Asn His Asn Val Ser Leu
65                  70                  75                  80

Val Leu Glu Ala Thr Gln Pro Pro Ser Glu Gln Pro Gly Thr Asp Gly
                85                  90                  95

Gln Leu Ala Thr Gly Gly Gly Thr His Thr Cys Pro Pro Cys Pro Ala
            100                 105                 110

Pro Glu Leu Leu Gly Gly Pro Ser Val Phe Leu Phe Pro Pro Lys Pro
        115                 120                 125

Lys Asp Thr Leu Met Ile Ser Arg Thr Pro Glu Val Thr Cys Val Val
    130                 135                 140

Val Asp Val Ser His Glu Asp Pro Glu Val Lys Phe Asn Trp Tyr Val
145                 150                 155                 160

Asp Gly Val Glu Val His Asn Ala Lys Thr Lys Pro Arg Glu Glu Gln
                165                 170                 175

Tyr Asn Ser Thr Tyr Arg Val Val Ser Val Leu Thr Val Leu His Gln
            180                 185                 190

Asp Trp Leu Asn Gly Lys Glu Tyr Lys Cys Lys Val Ser Asn Lys Ala
        195                 200                 205

Leu Pro Ala Pro Ile Glu Lys Thr Ile Ser Lys Ala Lys Gly Gln Pro
    210                 215                 220

Arg Glu Pro Gln Val Tyr Thr Leu Pro Pro Ser Arg Glu Glu Met Thr
225                 230                 235                 240
```

Lys Asn Gln Val Ser Leu Thr Cys Leu Val Lys Gly Phe Tyr Pro Ser
245 250 255

Asp Ile Ala Val Glu Trp Glu Ser Asn Gly Gln Pro Glu Asn Asn Tyr
260 265 270

Asp Thr Thr Pro Pro Val Leu Asp Ser Asp Gly Ser Phe Phe Leu Tyr
275 280 285

Ser Asp Leu Thr Val Asp Lys Ser Arg Trp Gln Gln Gly Asn Val Phe
290 295 300

Ser Cys Ser Val Met His Glu Ala Leu His Asn His Tyr Thr Gln Lys
305 310 315 320

Ser Leu Ser Leu Ser Pro Gly
325

<210> SEQ ID NO 119
<211> LENGTH: 355
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 119

Met Asp Ala Met Lys Arg Gly Leu Cys Cys Val Leu Leu Leu Cys Gly
1 5 10 15

Ala Val Phe Val Ser Pro Gly Ala Met Glu Asp Glu Lys Pro Lys Val
20 25 30

Asn Pro Lys Leu Tyr Met Cys Val Cys Glu Gly Leu Ser Cys Gly Asn
35 40 45

Glu Asp His Cys Glu Gly Gln Gln Cys Phe Ser Ser Leu Ser Ile Asn
50 55 60

Asp Gly Phe His Val Tyr Gln Lys Gly Cys Phe Gln Val Tyr Glu Gln
65 70 75 80

Gly Lys Met Thr Cys Lys Thr Pro Pro Ser Pro Gly Gln Ala Val Glu
85 90 95

Cys Cys Gln Gly Asp Trp Cys Asn Arg Asn Ile Thr Ala Gln Leu Pro
100 105 110

Thr Lys Gly Lys Ser Phe Pro Gly Thr Gln Asn Phe His Leu Glu Thr
115 120 125

Gly Gly Gly Thr His Thr Cys Pro Pro Cys Pro Ala Pro Glu Leu Leu
130 135 140

Gly Gly Pro Ser Val Phe Leu Phe Pro Pro Lys Pro Lys Asp Thr Leu
145 150 155 160

Met Ile Ser Arg Thr Pro Glu Val Thr Cys Val Val Val Asp Val Ser
165 170 175

His Glu Asp Pro Glu Val Lys Phe Asn Trp Tyr Val Asp Gly Val Glu
180 185 190

Val His Asn Ala Lys Thr Lys Pro Arg Glu Glu Gln Tyr Asn Ser Thr
195 200 205

Tyr Arg Val Val Ser Val Leu Thr Val Leu His Gln Asp Trp Leu Asn
210 215 220

Gly Lys Glu Tyr Lys Cys Lys Val Ser Asn Lys Ala Leu Pro Ala Pro
225 230 235 240

Ile Glu Lys Thr Ile Ser Lys Ala Lys Gly Gln Pro Arg Glu Pro Gln
245 250 255

Val Tyr Thr Leu Pro Pro Ser Arg Glu Glu Met Thr Lys Asn Gln Val

-continued

```
            260                 265                 270

Ser Leu Thr Cys Leu Val Lys Gly Phe Tyr Pro Ser Asp Ile Ala Val
        275                 280                 285

Glu Trp Glu Ser Asn Gly Gln Pro Glu Asn Asn Tyr Asp Thr Thr Pro
    290                 295                 300

Pro Val Leu Asp Ser Asp Gly Ser Phe Phe Leu Tyr Ser Asp Leu Thr
305                 310                 315                 320

Val Asp Lys Ser Arg Trp Gln Gln Gly Asn Val Phe Ser Cys Ser Val
                325                 330                 335

Met His Glu Ala Leu His Asn His Tyr Thr Gln Lys Ser Leu Ser Leu
            340                 345                 350

Ser Pro Gly
        355


<210> SEQ ID NO 120
<211> LENGTH: 1065
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 120

atggatgcaa tgaagagagg gctctgctgt gtgctgctgc tgtgtggagc agtcttcgtt     60

tcgcccggcg ccatggaaga tgagaagccc aaggtcaacc ccaaactcta catgtgtgtg    120

tgtgaaggtc tctcctgcgg taatgaggac cactgtgaag gccagcagtg cttttcctca    180

ctgagcatca acgatggctt ccacgtctac cagaaaggct gcttccaggt ttatgagcag    240

ggaaagatga cctgtaagac cccgccgtcc cctggccaag ctgtggagtg ctgccaaggg    300

gactggtgta acaggaacat cacggcccag ctgcccacta aaggaaaatc cttccctgga    360

acacagaatt tccacttgga gaccggtggt ggaactcaca catgcccacc gtgcccagca    420

cctgaactcc tggggggacc gtcagtcttc ctcttccccc caaaacccaa ggacaccctc    480

atgatctccc ggacccctga ggtcacatgc gtggtggtgg acgtgagcca cgaagaccct    540

gaggtcaagt tcaactggta cgtggacggc gtggaggtgc ataatgccaa gacaaagccg    600

cgggaggagc agtacaacag cacgtaccgt gtggtcagcg tcctcaccgt cctgcaccag    660

gactggctga atggcaagga gtacaagtgc aaggtctcca acaaagccct cccagccccc    720

atcgagaaaa ccatctccaa agccaaaggg cagccccgag aaccacaggt gtacaccctg    780

cccccatccc gggaggagat gaccaagaac caggtcagcc tgacctgcct ggtcaaaggc    840

ttctatccca gcgacatcgc cgtggagtgg gagagcaatg ggcagccgga gaacaactac    900

gacaccacgc ctcccgtgct ggactccgac ggctccttct tcctctatag cgacctcacc    960

gtggacaaga gcaggtggca gcaggggaac gtcttctcat gctccgtgat gcatgaggct   1020

ctgcacaacc actacacgca gaagagcctc tccctgtctc cgggt                   1065


<210> SEQ ID NO 121
<211> LENGTH: 331
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 121

Met Glu Asp Glu Lys Pro Lys Val Asn Pro Lys Leu Tyr Met Cys Val
```

1 5 10 15

Cys Glu Gly Leu Ser Cys Gly Asn Glu Asp His Cys Glu Gly Gln Gln
20 25 30

Cys Phe Ser Ser Leu Ser Ile Asn Asp Gly Phe His Val Tyr Gln Lys
35 40 45

Gly Cys Phe Gln Val Tyr Glu Gln Gly Lys Met Thr Cys Lys Thr Pro
50 55 60

Pro Ser Pro Gly Gln Ala Val Glu Cys Cys Gln Gly Asp Trp Cys Asn
65 70 75 80

Arg Asn Ile Thr Ala Gln Leu Pro Thr Lys Gly Lys Ser Phe Pro Gly
85 90 95

Thr Gln Asn Phe His Leu Glu Thr Gly Gly Gly Thr His Thr Cys Pro
100 105 110

Pro Cys Pro Ala Pro Glu Leu Leu Gly Gly Pro Ser Val Phe Leu Phe
115 120 125

Pro Pro Lys Pro Lys Asp Thr Leu Met Ile Ser Arg Thr Pro Glu Val
130 135 140

Thr Cys Val Val Val Asp Val Ser His Glu Asp Pro Glu Val Lys Phe
145 150 155 160

Asn Trp Tyr Val Asp Gly Val Glu Val His Asn Ala Lys Thr Lys Pro
165 170 175

Arg Glu Glu Gln Tyr Asn Ser Thr Tyr Arg Val Val Ser Val Leu Thr
180 185 190

Val Leu His Gln Asp Trp Leu Asn Gly Lys Glu Tyr Lys Cys Lys Val
195 200 205

Ser Asn Lys Ala Leu Pro Ala Pro Ile Glu Lys Thr Ile Ser Lys Ala
210 215 220

Lys Gly Gln Pro Arg Glu Pro Gln Val Tyr Thr Leu Pro Pro Ser Arg
225 230 235 240

Glu Glu Met Thr Lys Asn Gln Val Ser Leu Thr Cys Leu Val Lys Gly
245 250 255

Phe Tyr Pro Ser Asp Ile Ala Val Glu Trp Glu Ser Asn Gly Gln Pro
260 265 270

Glu Asn Asn Tyr Asp Thr Thr Pro Pro Val Leu Asp Ser Asp Gly Ser
275 280 285

Phe Phe Leu Tyr Ser Asp Leu Thr Val Asp Lys Ser Arg Trp Gln Gln
290 295 300

Gly Asn Val Phe Ser Cys Ser Val Met His Glu Ala Leu His Asn His
305 310 315 320

Tyr Thr Gln Lys Ser Leu Ser Leu Ser Pro Gly
325 330

<210> SEQ ID NO 122
<211> LENGTH: 381
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 122

Met Asp Ala Met Lys Arg Gly Leu Cys Cys Val Leu Leu Leu Cys Gly
1 5 10 15

Ala Val Phe Val Ser Pro Gly Ala Gln Asn Leu Asp Ser Met Leu His
20 25 30

```
Gly Thr Gly Met Lys Ser Asp Ser Asp Gln Lys Lys Ser Glu Asn Gly
        35                  40                  45

Val Thr Leu Ala Pro Glu Asp Thr Leu Pro Phe Leu Lys Cys Tyr Cys
    50                  55                  60

Ser Gly His Cys Pro Asp Asp Ala Ile Asn Asn Thr Cys Ile Thr Asn
65                  70                  75                  80

Gly His Cys Phe Ala Ile Ile Glu Glu Asp Asp Gln Gly Glu Thr Thr
                85                  90                  95

Leu Ala Ser Gly Cys Met Lys Tyr Glu Gly Ser Asp Phe Gln Cys Lys
            100                 105                 110

Asp Ser Pro Lys Ala Gln Leu Arg Arg Thr Ile Glu Cys Cys Arg Thr
        115                 120                 125

Asn Leu Cys Asn Gln Tyr Leu Gln Pro Thr Leu Pro Pro Val Val Ile
    130                 135                 140

Gly Pro Phe Phe Asp Gly Ser Ile Arg Thr Gly Gly Gly Thr His Thr
145                 150                 155                 160

Cys Pro Pro Cys Pro Ala Pro Glu Leu Leu Gly Gly Pro Ser Val Phe
                165                 170                 175

Leu Phe Pro Pro Lys Pro Lys Asp Thr Leu Met Ile Ser Arg Thr Pro
            180                 185                 190

Glu Val Thr Cys Val Val Val Asp Val Ser His Glu Asp Pro Glu Val
        195                 200                 205

Lys Phe Asn Trp Tyr Val Asp Gly Val Glu Val His Asn Ala Lys Thr
    210                 215                 220

Lys Pro Arg Glu Glu Gln Tyr Asn Ser Thr Tyr Arg Val Val Ser Val
225                 230                 235                 240

Leu Thr Val Leu His Gln Asp Trp Leu Asn Gly Lys Glu Tyr Lys Cys
                245                 250                 255

Lys Val Ser Asn Lys Ala Leu Pro Ala Pro Ile Glu Lys Thr Ile Ser
            260                 265                 270

Lys Ala Lys Gly Gln Pro Arg Glu Pro Gln Val Tyr Thr Leu Pro Pro
        275                 280                 285

Ser Arg Glu Glu Met Thr Lys Asn Gln Val Ser Leu Thr Cys Leu Val
    290                 295                 300

Lys Gly Phe Tyr Pro Ser Asp Ile Ala Val Glu Trp Glu Ser Asn Gly
305                 310                 315                 320

Gln Pro Glu Asn Asn Tyr Asp Thr Thr Pro Pro Val Leu Asp Ser Asp
                325                 330                 335

Gly Ser Phe Phe Leu Tyr Ser Asp Leu Thr Val Asp Lys Ser Arg Trp
            340                 345                 350

Gln Gln Gly Asn Val Phe Ser Cys Ser Val Met His Glu Ala Leu His
        355                 360                 365

Asn His Tyr Thr Gln Lys Ser Leu Ser Leu Ser Pro Gly
    370                 375                 380
```

<210> SEQ ID NO 123
<211> LENGTH: 1143
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 123

```
atggatgcaa tgaagagagg gctctgctgt gtgctgctgc tgtgtggagc agtcttcgtt      60
```

-continued

```
tcgcccggcg cccagaatct ggatagtatg cttcatggca ctgggatgaa atcagactcc    120

gaccagaaaa agtcagaaaa tggagtaacc ttagcaccag aggatacctt gccttttta     180

aagtgctatt gctcagggca ctgtccagat gatgctatta ataacacatg cataactaat    240

ggacattgct ttgccatcat agaagaagat gaccagggag aaaccacatt agcttcaggg    300

tgtatgaaat atgaaggatc tgattttcag tgcaaagatt ctccaaaagc ccagctacgc    360

cggacaatag aatgttgtcg gaccaattta tgtaaccagt atttgcaacc cacactgccc    420

cctgttgtca taggtccgtt ttttgatggc agcattcgaa ccggtggtgg aactcacaca    480

tgcccaccgt gcccagcacc tgaactcctg gggggaccgt cagtcttcct cttcccccca    540

aaacccaagg acaccctcat gatctcccgg acccctgagg tcacatgcgt ggtggtggac    600

gtgagccacg aagaccctga ggtcaagttc aactggtacg tggacggcgt ggaggtgcat    660

aatgccaaga caaagccgcg ggaggagcag tacaacagca cgtaccgtgt ggtcagcgtc    720

ctcaccgtcc tgcaccagga ctggctgaat ggcaaggagt acaagtgcaa ggtctccaac    780

aaagccctcc cagcccccat cgagaaaacc atctccaaag ccaaagggca gccccgagaa    840

ccacaggtgt acaccctgcc cccatcccgg gaggagatga ccaagaacca ggtcagcctg    900

acctgcctgg tcaaaggctt ctatcccagc gacatcgccg tggagtggga gagcaatggg    960

cagccggaga acaactacga caccacgcct cccgtgctgg actccgacgg ctccttcttc   1020

ctctatagcg acctcaccgt ggacaagagc aggtggcagc aggggaacgt cttctcatgc   1080

tccgtgatgc atgaggctct gcacaaccac tacacgcaga agagcctctc cctgtctccg   1140

ggt                                                                 1143
```

<210> SEQ ID NO 124
<211> LENGTH: 359
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 124

```
Gly Ala Gln Asn Leu Asp Ser Met Leu His Gly Thr Gly Met Lys Ser
1               5                   10                  15

Asp Ser Asp Gln Lys Lys Ser Glu Asn Gly Val Thr Leu Ala Pro Glu
            20                  25                  30

Asp Thr Leu Pro Phe Leu Lys Cys Tyr Cys Ser Gly His Cys Pro Asp
        35                  40                  45

Asp Ala Ile Asn Asn Thr Cys Ile Thr Asn Gly His Cys Phe Ala Ile
    50                  55                  60

Ile Glu Glu Asp Asp Gln Gly Glu Thr Thr Leu Ala Ser Gly Cys Met
65                  70                  75                  80

Lys Tyr Glu Gly Ser Asp Phe Gln Cys Lys Asp Ser Pro Lys Ala Gln
                85                  90                  95

Leu Arg Arg Thr Ile Glu Cys Cys Arg Thr Asn Leu Cys Asn Gln Tyr
            100                 105                 110

Leu Gln Pro Thr Leu Pro Pro Val Val Ile Gly Pro Phe Phe Asp Gly
        115                 120                 125

Ser Ile Arg Thr Gly Gly Gly Thr His Thr Cys Pro Pro Cys Pro Ala
    130                 135                 140

Pro Glu Leu Leu Gly Gly Pro Ser Val Phe Leu Phe Pro Pro Lys Pro
145                 150                 155                 160
```

-continued

```
Lys Asp Thr Leu Met Ile Ser Arg Thr Pro Glu Val Thr Cys Val Val
                165                 170                 175

Val Asp Val Ser His Glu Asp Pro Glu Val Lys Phe Asn Trp Tyr Val
            180                 185                 190

Asp Gly Val Glu Val His Asn Ala Lys Thr Lys Pro Arg Glu Glu Gln
        195                 200                 205

Tyr Asn Ser Thr Tyr Arg Val Val Ser Val Leu Thr Val Leu His Gln
    210                 215                 220

Asp Trp Leu Asn Gly Lys Glu Tyr Lys Cys Lys Val Ser Asn Lys Ala
225                 230                 235                 240

Leu Pro Ala Pro Ile Glu Lys Thr Ile Ser Lys Ala Lys Gly Gln Pro
                245                 250                 255

Arg Glu Pro Gln Val Tyr Thr Leu Pro Pro Ser Arg Glu Glu Met Thr
            260                 265                 270

Lys Asn Gln Val Ser Leu Thr Cys Leu Val Lys Gly Phe Tyr Pro Ser
        275                 280                 285

Asp Ile Ala Val Glu Trp Glu Ser Asn Gly Gln Pro Glu Asn Asn Tyr
    290                 295                 300

Asp Thr Thr Pro Pro Val Leu Asp Ser Asp Gly Ser Phe Phe Leu Tyr
305                 310                 315                 320

Ser Asp Leu Thr Val Asp Lys Ser Arg Trp Gln Gln Gly Asn Val Phe
                325                 330                 335

Ser Cys Ser Val Met His Glu Ala Leu His Asn His Tyr Thr Gln Lys
            340                 345                 350

Ser Leu Ser Leu Ser Pro Gly
        355


<210> SEQ ID NO 125
<211> LENGTH: 355
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 125

Met Asp Ala Met Lys Arg Gly Leu Cys Cys Val Leu Leu Leu Cys Gly
1               5                   10                  15

Ala Val Phe Val Ser Pro Gly Ala Ser Gly Pro Arg Gly Val Gln Ala
            20                  25                  30

Leu Leu Cys Ala Cys Thr Ser Cys Leu Gln Ala Asn Tyr Thr Cys Glu
        35                  40                  45

Thr Asp Gly Ala Cys Met Val Ser Ile Phe Asn Leu Asp Gly Met Glu
    50                  55                  60

His His Val Arg Thr Cys Ile Pro Lys Val Glu Leu Val Pro Ala Gly
65                  70                  75                  80

Lys Pro Phe Tyr Cys Leu Ser Ser Glu Asp Leu Arg Asn Thr His Cys
                85                  90                  95

Cys Tyr Thr Asp Tyr Cys Asn Arg Ile Asp Leu Arg Val Pro Ser Gly
            100                 105                 110

His Leu Lys Glu Pro Glu His Pro Ser Met Trp Gly Pro Val Glu Thr
        115                 120                 125

Gly Gly Gly Thr His Thr Cys Pro Pro Cys Pro Ala Pro Glu Leu Leu
    130                 135                 140

Gly Gly Pro Ser Val Phe Leu Phe Pro Pro Lys Pro Lys Asp Thr Leu
145                 150                 155                 160
```

Met Ile Ser Arg Thr Pro Glu Val Thr Cys Val Val Val Asp Val Ser
165 170 175

His Glu Asp Pro Glu Val Lys Phe Asn Trp Tyr Val Asp Gly Val Glu
180 185 190

Val His Asn Ala Lys Thr Lys Pro Arg Glu Glu Gln Tyr Asn Ser Thr
195 200 205

Tyr Arg Val Val Ser Val Leu Thr Val Leu His Gln Asp Trp Leu Asn
210 215 220

Gly Lys Glu Tyr Lys Cys Lys Val Ser Asn Lys Ala Leu Pro Ala Pro
225 230 235 240

Ile Glu Lys Thr Ile Ser Lys Ala Lys Gly Gln Pro Arg Glu Pro Gln
245 250 255

Val Tyr Thr Leu Pro Pro Ser Arg Glu Glu Met Thr Lys Asn Gln Val
260 265 270

Ser Leu Thr Cys Leu Val Lys Gly Phe Tyr Pro Ser Asp Ile Ala Val
275 280 285

Glu Trp Glu Ser Asn Gly Gln Pro Glu Asn Asn Tyr Asp Thr Thr Pro
290 295 300

Pro Val Leu Asp Ser Asp Gly Ser Phe Phe Leu Tyr Ser Asp Leu Thr
305 310 315 320

Val Asp Lys Ser Arg Trp Gln Gln Gly Asn Val Phe Ser Cys Ser Val
325 330 335

Met His Glu Ala Leu His Asn His Tyr Thr Gln Lys Ser Leu Ser Leu
340 345 350

Ser Pro Gly
355

<210> SEQ ID NO 126
<211> LENGTH: 1065
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 126
atggatgcaa tgaagagagg gctctgctgt gtgctgctgc tgtgtggagc agtcttcgtt 60
tcgcccggcg cctccgggcc ccgggggtc caggctctgc tgtgtgcgtg caccagctgc 120
ctccaggcca actacacgtg tgagacagat ggggcctgca tggtttccat tttcaatctg 180
gatgggatgg agcaccatgt gcgcacctgc atccccaaag tggagctggt ccctgccggg 240
aagcccttct actgcctgag ctcggaggac ctgcgcaaca cccactgctg ctacactgac 300
tactgcaaca ggatcgactt gagggtgccc agtggtcacc tcaaggagcc tgagcacccg 360
tccatgtggg gcccggtgga gaccggtggt ggaactcaca catgcccacc gtgcccagca 420
cctgaactcc tggggggacc gtcagtcttc ctcttccccc caaaacccaa ggacaccctc 480
atgatctccc ggacccctga ggtcacatgc gtggtggtgg acgtgagcca cgaagaccct 540
gaggtcaagt tcaactggta cgtggacggc gtggaggtgc ataatgccaa gacaaagccg 600
cgggaggagc agtacaacag cacgtaccgt gtggtcagcg tcctcaccgt cctgcaccag 660
gactggctga atggcaagga gtacaagtgc aaggtctcca acaaagccct cccagccccc 720
atcgagaaaa ccatctccaa agccaaaggg cagccccgag aaccacaggt gtacaccctg 780
cccccatccc gggaggagat gaccaagaac caggtcagcc tgacctgcct ggtcaaaggc 840

-continued

```
ttctatccca gcgacatcgc cgtggagtgg gagagcaatg ggcagccgga gaacaactac    900

gacaccacgc ctcccgtgct ggactccgac ggctccttct tcctctatag cgacctcacc    960

gtggacaaga gcaggtggca gcaggggaac gtcttctcat gctccgtgat gcatgaggct   1020

ctgcacaacc actacacgca gaagagcctc tccctgtctc cgggt                   1065


<210> SEQ ID NO 127
<211> LENGTH: 331
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 127

Ser Gly Pro Arg Gly Val Gln Ala Leu Leu Cys Ala Cys Thr Ser Cys
1               5                   10                  15

Leu Gln Ala Asn Tyr Thr Cys Glu Thr Asp Gly Ala Cys Met Val Ser
            20                  25                  30

Ile Phe Asn Leu Asp Gly Met Glu His His Val Arg Thr Cys Ile Pro
        35                  40                  45

Lys Val Glu Leu Val Pro Ala Gly Lys Pro Phe Tyr Cys Leu Ser Ser
    50                  55                  60

Glu Asp Leu Arg Asn Thr His Cys Cys Tyr Thr Asp Tyr Cys Asn Arg
65                  70                  75                  80

Ile Asp Leu Arg Val Pro Ser Gly His Leu Lys Glu Pro Glu His Pro
                85                  90                  95

Ser Met Trp Gly Pro Val Glu Thr Gly Gly Gly Thr His Thr Cys Pro
            100                 105                 110

Pro Cys Pro Ala Pro Glu Leu Leu Gly Gly Pro Ser Val Phe Leu Phe
        115                 120                 125

Pro Pro Lys Pro Lys Asp Thr Leu Met Ile Ser Arg Thr Pro Glu Val
    130                 135                 140

Thr Cys Val Val Val Asp Val Ser His Glu Asp Pro Glu Val Lys Phe
145                 150                 155                 160

Asn Trp Tyr Val Asp Gly Val Glu Val His Asn Ala Lys Thr Lys Pro
                165                 170                 175

Arg Glu Glu Gln Tyr Asn Ser Thr Tyr Arg Val Val Ser Val Leu Thr
            180                 185                 190

Val Leu His Gln Asp Trp Leu Asn Gly Lys Glu Tyr Lys Cys Lys Val
        195                 200                 205

Ser Asn Lys Ala Leu Pro Ala Pro Ile Glu Lys Thr Ile Ser Lys Ala
    210                 215                 220

Lys Gly Gln Pro Arg Glu Pro Gln Val Tyr Thr Leu Pro Pro Ser Arg
225                 230                 235                 240

Glu Glu Met Thr Lys Asn Gln Val Ser Leu Thr Cys Leu Val Lys Gly
                245                 250                 255

Phe Tyr Pro Ser Asp Ile Ala Val Glu Trp Glu Ser Asn Gly Gln Pro
            260                 265                 270

Glu Asn Asn Tyr Asp Thr Thr Pro Pro Val Leu Asp Ser Asp Gly Ser
        275                 280                 285

Phe Phe Leu Tyr Ser Asp Leu Thr Val Asp Lys Ser Arg Trp Gln Gln
    290                 295                 300

Gly Asn Val Phe Ser Cys Ser Val Met His Glu Ala Leu His Asn His
305                 310                 315                 320
```

```
Tyr Thr Gln Lys Ser Leu Ser Leu Ser Pro Gly
                325                 330


<210> SEQ ID NO 128
<211> LENGTH: 352
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 128

Met Asp Ala Met Lys Arg Gly Leu Cys Cys Val Leu Leu Leu Cys Gly
1               5                   10                  15

Ala Val Phe Val Ser Pro Gly Ala Ala Leu Leu Pro Gly Ala Thr Ala
            20                  25                  30

Leu Gln Cys Phe Cys His Leu Cys Thr Lys Asp Asn Phe Thr Cys Val
        35                  40                  45

Thr Asp Gly Leu Cys Phe Val Ser Val Thr Glu Thr Thr Asp Lys Val
    50                  55                  60

Ile His Asn Ser Met Cys Ile Ala Glu Ile Asp Leu Ile Pro Arg Asp
65                  70                  75                  80

Arg Pro Phe Val Cys Ala Pro Ser Ser Lys Thr Gly Ser Val Thr Thr
                85                  90                  95

Thr Tyr Cys Cys Asn Gln Asp His Cys Asn Lys Ile Glu Leu Pro Thr
            100                 105                 110

Thr Val Lys Ser Ser Pro Gly Leu Gly Pro Val Glu Thr Gly Gly Gly
        115                 120                 125

Thr His Thr Cys Pro Pro Cys Pro Ala Pro Glu Leu Leu Gly Gly Pro
    130                 135                 140

Ser Val Phe Leu Phe Pro Pro Lys Pro Lys Asp Thr Leu Met Ile Ser
145                 150                 155                 160

Arg Thr Pro Glu Val Thr Cys Val Val Val Asp Val Ser His Glu Asp
                165                 170                 175

Pro Glu Val Lys Phe Asn Trp Tyr Val Asp Gly Val Glu Val His Asn
            180                 185                 190

Ala Lys Thr Lys Pro Arg Glu Glu Gln Tyr Asn Ser Thr Tyr Arg Val
        195                 200                 205

Val Ser Val Leu Thr Val Leu His Gln Asp Trp Leu Asn Gly Lys Glu
    210                 215                 220

Tyr Lys Cys Lys Val Ser Asn Lys Ala Leu Pro Ala Pro Ile Glu Lys
225                 230                 235                 240

Thr Ile Ser Lys Ala Lys Gly Gln Pro Arg Glu Pro Gln Val Tyr Thr
                245                 250                 255

Leu Pro Pro Ser Arg Glu Glu Met Thr Lys Asn Gln Val Ser Leu Thr
            260                 265                 270

Cys Leu Val Lys Gly Phe Tyr Pro Ser Asp Ile Ala Val Glu Trp Glu
        275                 280                 285

Ser Asn Gly Gln Pro Glu Asn Asn Tyr Asp Thr Thr Pro Pro Val Leu
    290                 295                 300

Asp Ser Asp Gly Ser Phe Phe Leu Tyr Ser Asp Leu Thr Val Asp Lys
305                 310                 315                 320

Ser Arg Trp Gln Gln Gly Asn Val Phe Ser Cys Ser Val Met His Glu
                325                 330                 335

Ala Leu His Asn His Tyr Thr Gln Lys Ser Leu Ser Leu Ser Pro Gly
            340                 345                 350
```

<210> SEQ ID NO 129
<211> LENGTH: 1056
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 129
atggatgcaa tgaagagagg gctctgctgt gtgctgctgc tgtgtggagc agtcttcgtt 60
tcgcccggcg ccgcgctgct cccgggggcg acggcgttac agtgtttctg ccacctctgt 120
acaaaagaca attttacttg tgtgacagat gggctctgct ttgtctctgt cacagagacc 180
acagacaaag ttatacacaa cagcatgtgt atagctgaaa ttgacttaat tcctcgagat 240
aggccgtttg tatgtgcacc ctcttcaaaa actgggtctg tgactacaac atattgctgc 300
aatcaggacc attgcaataa aatagaactt ccaactactg taaagtcatc acctggcctt 360
ggtcctgtgg aaaccggtgg tggaactcac acatgcccac cgtgcccagc acctgaactc 420
ctggggggac cgtcagtctt cctcttcccc ccaaaaccca aggacaccct catgatctcc 480
cggacccctg aggtcacatg cgtggtggtg gacgtgagcc acgaagaccc tgaggtcaag 540
ttcaactggt acgtggacgg cgtggaggtg cataatgcca agacaaagcc gcgggaggag 600
cagtacaaca gcacgtaccg tgtggtcagc gtcctcaccg tcctgcacca ggactggctg 660
aatggcaagg agtacaagtg caaggtctcc aacaaagccc tcccagcccc catcgagaaa 720
accatctcca aagccaaagg gcagccccga gaaccacagg tgtacaccct gcccccatcc 780
cgggaggaga tgaccaagaa ccaggtcagc ctgacctgcc tggtcaaagg cttctatccc 840
agcgacatcg ccgtggagtg ggagagcaat gggcagccgg agaacaacta cgacaccacg 900
cctcccgtgc tggactccga cggctccttc ttcctctata gcgacctcac cgtggacaag 960
agcaggtggc agcaggggaa cgtcttctca tgctccgtga tgcatgaggc tctgcacaac 1020
cactacacgc agaagagcct ctccctgtct ccgggt 1056

<210> SEQ ID NO 130
<211> LENGTH: 328
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 130

Ala Leu Leu Pro Gly Ala Thr Ala Leu Gln Cys Phe Cys His Leu Cys
1 5 10 15

Thr Lys Asp Asn Phe Thr Cys Val Thr Asp Gly Leu Cys Phe Val Ser
20 25 30

Val Thr Glu Thr Thr Asp Lys Val Ile His Asn Ser Met Cys Ile Ala
35 40 45

Glu Ile Asp Leu Ile Pro Arg Asp Arg Pro Phe Val Cys Ala Pro Ser
50 55 60

Ser Lys Thr Gly Ser Val Thr Thr Thr Tyr Cys Cys Asn Gln Asp His
65 70 75 80

Cys Asn Lys Ile Glu Leu Pro Thr Thr Val Lys Ser Ser Pro Gly Leu
85 90 95

Gly Pro Val Glu Thr Gly Gly Gly Thr His Thr Cys Pro Pro Cys Pro
100 105 110

```
Ala Pro Glu Leu Leu Gly Gly Pro Ser Val Phe Leu Phe Pro Pro Lys
        115                 120                 125

Pro Lys Asp Thr Leu Met Ile Ser Arg Thr Pro Glu Val Thr Cys Val
    130                 135                 140

Val Val Asp Val Ser His Glu Asp Pro Glu Val Lys Phe Asn Trp Tyr
145                 150                 155                 160

Val Asp Gly Val Glu Val His Asn Ala Lys Thr Lys Pro Arg Glu Glu
                165                 170                 175

Gln Tyr Asn Ser Thr Tyr Arg Val Val Ser Val Leu Thr Val Leu His
            180                 185                 190

Gln Asp Trp Leu Asn Gly Lys Glu Tyr Lys Cys Lys Val Ser Asn Lys
        195                 200                 205

Ala Leu Pro Ala Pro Ile Glu Lys Thr Ile Ser Lys Ala Lys Gly Gln
    210                 215                 220

Pro Arg Glu Pro Gln Val Tyr Thr Leu Pro Pro Ser Arg Glu Glu Met
225                 230                 235                 240

Thr Lys Asn Gln Val Ser Leu Thr Cys Leu Val Lys Gly Phe Tyr Pro
                245                 250                 255

Ser Asp Ile Ala Val Glu Trp Glu Ser Asn Gly Gln Pro Glu Asn Asn
            260                 265                 270

Tyr Asp Thr Thr Pro Pro Val Leu Asp Ser Asp Gly Ser Phe Phe Leu
        275                 280                 285

Tyr Ser Asp Leu Thr Val Asp Lys Ser Arg Trp Gln Gln Gly Asn Val
    290                 295                 300

Phe Ser Cys Ser Val Met His Glu Ala Leu His Asn His Tyr Thr Gln
305                 310                 315                 320

Lys Ser Leu Ser Leu Ser Pro Gly
                325


<210> SEQ ID NO 131
<211> LENGTH: 365
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 131

Met Asp Ala Met Lys Arg Gly Leu Cys Cys Val Leu Leu Leu Cys Gly
1               5                   10                  15

Ala Val Phe Val Ser Pro Gly Ala Lys Lys Glu Asp Gly Glu Ser Thr
            20                  25                  30

Ala Pro Thr Pro Arg Pro Lys Val Leu Arg Cys Lys Cys His His His
        35                  40                  45

Cys Pro Glu Asp Ser Val Asn Asn Ile Cys Ser Thr Asp Gly Tyr Cys
    50                  55                  60

Phe Thr Met Ile Glu Glu Asp Asp Ser Gly Leu Pro Val Val Thr Ser
65                  70                  75                  80

Gly Cys Leu Gly Leu Glu Gly Ser Asp Phe Gln Cys Arg Asp Thr Pro
                85                  90                  95

Ile Pro His Gln Arg Arg Ser Ile Glu Cys Cys Thr Glu Arg Asn Glu
            100                 105                 110

Cys Asn Lys Asp Leu His Pro Thr Leu Pro Pro Leu Lys Asn Arg Asp
        115                 120                 125

Phe Val Asp Gly Pro Ile His His Arg Thr Gly Gly Gly Thr His Thr
```

-continued 130 135 140

Cys Pro Pro Cys Pro Ala Pro Glu Leu Leu Gly Gly Pro Ser Val Phe
145 150 155 160

Leu Phe Pro Pro Lys Pro Lys Asp Thr Leu Met Ile Ser Arg Thr Pro
165 170 175

Glu Val Thr Cys Val Val Val Asp Val Ser His Glu Asp Pro Glu Val
180 185 190

Lys Phe Asn Trp Tyr Val Asp Gly Val Glu Val His Asn Ala Lys Thr
195 200 205

Lys Pro Arg Glu Glu Gln Tyr Asn Ser Thr Tyr Arg Val Val Ser Val
210 215 220

Leu Thr Val Leu His Gln Asp Trp Leu Asn Gly Lys Glu Tyr Lys Cys
225 230 235 240

Lys Val Ser Asn Lys Ala Leu Pro Ala Pro Ile Glu Lys Thr Ile Ser
245 250 255

Lys Ala Lys Gly Gln Pro Arg Glu Pro Gln Val Tyr Thr Leu Pro Pro
260 265 270

Ser Arg Glu Glu Met Thr Lys Asn Gln Val Ser Leu Thr Cys Leu Val
275 280 285

Lys Gly Phe Tyr Pro Ser Asp Ile Ala Val Glu Trp Glu Ser Asn Gly
290 295 300

Gln Pro Glu Asn Asn Tyr Asp Thr Thr Pro Pro Val Leu Asp Ser Asp
305 310 315 320

Gly Ser Phe Phe Leu Tyr Ser Asp Leu Thr Val Asp Lys Ser Arg Trp
325 330 335

Gln Gln Gly Asn Val Phe Ser Cys Ser Val Met His Glu Ala Leu His
340 345 350

Asn His Tyr Thr Gln Lys Ser Leu Ser Leu Ser Pro Gly
355 360 365

<210> SEQ ID NO 132
<211> LENGTH: 1095
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 132
atggatgcaa tgaagagagg gctctgctgt gtgctgctgc tgtgtggagc agtcttcgtt 60
tcgcccggcg ccaagaaaga ggatggtgag agtacagccc ccaccccccg tccaaaggtc 120
ttgcgttgta aatgccacca ccattgtcca gaagactcag tcaacaatat ttgcagcaca 180
gacggatatt gtttcacgat gatagaagag gatgactctg ggttgcctgt ggtcacttct 240
ggttgcctag gactagaagg ctcagatttt cagtgtcggg acactcccat tcctcatcaa 300
agaagatcaa ttgaatgctg cacagaaagg aacgaatgta ataaagacct acaccctaca 360
ctgcctccat tgaaaaacag agattttgtt gatggaccta tacaccacag gaccggtggt 420
ggaactcaca catgcccacc gtgcccagca cctgaactcc tggggggacc gtcagtcttc 480
ctcttccccc caaaacccaa ggacaccctc atgatctccc ggacccctga ggtcacatgc 540
gtggtggtgg acgtgagcca cgaagaccct gaggtcaagt tcaactggta cgtggacggc 600
gtggaggtgc ataatgccaa gacaaagccg cgggaggagc agtacaacag cacgtaccgt 660
gtggtcagcg tcctcaccgt cctgcaccag gactggctga atggcaagga gtacaagtgc 720

-continued

```
aaggtctcca acaaagccct cccagccccc atcgagaaaa ccatctccaa agccaaaggg    780

cagccccgag aaccacaggt gtacaccctg cccccatccc gggaggagat gaccaagaac    840

caggtcagcc tgacctgcct ggtcaaaggc ttctatccca gcgacatcgc cgtggagtgg    900

gagagcaatg ggcagccgga gaacaactac gacaccacgc ctcccgtgct ggactccgac    960

ggctccttct tcctctatag cgacctcacc gtggacaaga gcaggtggca gcaggggaac   1020

gtcttctcat gctccgtgat gcatgaggct ctgcacaacc actacacgca gaagagcctc   1080

tccctgtctc cgggt                                                    1095
```

<210> SEQ ID NO 133
<211> LENGTH: 341
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 133

```
Lys Lys Glu Asp Gly Glu Ser Thr Ala Pro Thr Pro Arg Pro Lys Val
1               5                   10                  15

Leu Arg Cys Lys Cys His His His Cys Pro Glu Asp Ser Val Asn Asn
            20                  25                  30

Ile Cys Ser Thr Asp Gly Tyr Cys Phe Thr Met Ile Glu Glu Asp Asp
        35                  40                  45

Ser Gly Leu Pro Val Val Thr Ser Gly Cys Leu Gly Leu Glu Gly Ser
    50                  55                  60

Asp Phe Gln Cys Arg Asp Thr Pro Ile Pro His Gln Arg Arg Ser Ile
65                  70                  75                  80

Glu Cys Cys Thr Glu Arg Asn Glu Cys Asn Lys Asp Leu His Pro Thr
                85                  90                  95

Leu Pro Pro Leu Lys Asn Arg Asp Phe Val Asp Gly Pro Ile His His
            100                 105                 110

Arg Thr Gly Gly Gly Thr His Thr Cys Pro Pro Cys Pro Ala Pro Glu
        115                 120                 125

Leu Leu Gly Gly Pro Ser Val Phe Leu Phe Pro Pro Lys Pro Lys Asp
    130                 135                 140

Thr Leu Met Ile Ser Arg Thr Pro Glu Val Thr Cys Val Val Val Asp
145                 150                 155                 160

Val Ser His Glu Asp Pro Glu Val Lys Phe Asn Trp Tyr Val Asp Gly
                165                 170                 175

Val Glu Val His Asn Ala Lys Thr Lys Pro Arg Glu Glu Gln Tyr Asn
            180                 185                 190

Ser Thr Tyr Arg Val Val Ser Val Leu Thr Val Leu His Gln Asp Trp
        195                 200                 205

Leu Asn Gly Lys Glu Tyr Lys Cys Lys Val Ser Asn Lys Ala Leu Pro
    210                 215                 220

Ala Pro Ile Glu Lys Thr Ile Ser Lys Ala Lys Gly Gln Pro Arg Glu
225                 230                 235                 240

Pro Gln Val Tyr Thr Leu Pro Pro Ser Arg Glu Glu Met Thr Lys Asn
                245                 250                 255

Gln Val Ser Leu Thr Cys Leu Val Lys Gly Phe Tyr Pro Ser Asp Ile
            260                 265                 270

Ala Val Glu Trp Glu Ser Asn Gly Gln Pro Glu Asn Asn Tyr Asp Thr
        275                 280                 285
```

```
Thr Pro Pro Val Leu Asp Ser Asp Gly Ser Phe Phe Leu Tyr Ser Asp
    290                 295                 300

Leu Thr Val Asp Lys Ser Arg Trp Gln Gln Gly Asn Val Phe Ser Cys
305                 310                 315                 320

Ser Val Met His Glu Ala Leu His Asn His Tyr Thr Gln Lys Ser Leu
                325                 330                 335

Ser Leu Ser Pro Gly
            340
```

<210> SEQ ID NO 134
<211> LENGTH: 341
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 134

```
Met Asp Ala Met Lys Arg Gly Leu Cys Cys Val Leu Leu Leu Cys Gly
1               5                   10                  15

Ala Val Phe Val Ser Pro Gly Ala Gly Leu Lys Cys Val Cys Leu Leu
            20                  25                  30

Cys Asp Ser Ser Asn Phe Thr Cys Gln Thr Glu Gly Ala Cys Trp Ala
        35                  40                  45

Ser Val Met Leu Thr Asn Gly Lys Glu Gln Val Ile Lys Ser Cys Val
    50                  55                  60

Ser Leu Pro Glu Leu Asn Ala Gln Val Phe Cys His Ser Ser Asn Asn
65                  70                  75                  80

Val Thr Lys Thr Glu Cys Cys Phe Thr Asp Phe Cys Asn Asn Ile Thr
                85                  90                  95

Leu His Leu Pro Thr Ala Ser Pro Asn Ala Pro Lys Leu Gly Pro Met
            100                 105                 110

Glu Thr Gly Gly Gly Thr His Thr Cys Pro Pro Cys Pro Ala Pro Glu
        115                 120                 125

Leu Leu Gly Gly Pro Ser Val Phe Leu Phe Pro Pro Lys Pro Lys Asp
    130                 135                 140

Thr Leu Met Ile Ser Arg Thr Pro Glu Val Thr Cys Val Val Val Asp
145                 150                 155                 160

Val Ser His Glu Asp Pro Glu Val Lys Phe Asn Trp Tyr Val Asp Gly
                165                 170                 175

Val Glu Val His Asn Ala Lys Thr Lys Pro Arg Glu Glu Gln Tyr Asn
            180                 185                 190

Ser Thr Tyr Arg Val Val Ser Val Leu Thr Val Leu His Gln Asp Trp
        195                 200                 205

Leu Asn Gly Lys Glu Tyr Lys Cys Lys Val Ser Asn Lys Ala Leu Pro
    210                 215                 220

Ala Pro Ile Glu Lys Thr Ile Ser Lys Ala Lys Gly Gln Pro Arg Glu
225                 230                 235                 240

Pro Gln Val Tyr Thr Leu Pro Pro Ser Arg Glu Glu Met Thr Lys Asn
                245                 250                 255

Gln Val Ser Leu Thr Cys Leu Val Lys Gly Phe Tyr Pro Ser Asp Ile
            260                 265                 270

Ala Val Glu Trp Glu Ser Asn Gly Gln Pro Glu Asn Asn Tyr Asp Thr
        275                 280                 285

Thr Pro Pro Val Leu Asp Ser Asp Gly Ser Phe Phe Leu Tyr Ser Asp
    290                 295                 300
```

Leu Thr Val Asp Lys Ser Arg Trp Gln Gln Gly Asn Val Phe Ser Cys
305 310 315 320

Ser Val Met His Glu Ala Leu His Asn His Tyr Thr Gln Lys Ser Leu
325 330 335

Ser Leu Ser Pro Gly
340

<210> SEQ ID NO 135
<211> LENGTH: 1023
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 135
atggatgcaa tgaagagagg gctctgctgt gtgctgctgc tgtgtggagc agtcttcgtt 60
tcgcccggcg ccggactgaa gtgtgtatgt cttttgtgtg attcttcaaa ctttacctgc 120
caaacagaag gagcatgttg ggcatcagtc atgctaacca atggaaaaga gcaggtgatc 180
aaatcctgtg tctcccttcc agaactgaat gctcaagtct tctgtcatag ttccaacaat 240
gttaccaaaa ccgaatgctg cttcacagat tttgcaaca acataacact gcaccttcca 300
acagcatcac caaatgcccc aaaacttgga cccatggaga ccggtggtgg aactcacaca 360
tgcccaccgt gcccagcacc tgaactcctg gggggaccgt cagtcttcct cttcccccca 420
aaacccaagg acaccctcat gatctcccgg acccctgagg tcacatgcgt ggtggtggac 480
gtgagccacg aagaccctga ggtcaagttc aactggtacg tggacggcgt ggaggtgcat 540
aatgccaaga caaagccgcg ggaggagcag tacaacagca cgtaccgtgt ggtcagcgtc 600
ctcaccgtcc tgcaccagga ctggctgaat ggcaaggagt acaagtgcaa ggtctccaac 660
aaagccctcc cagcccccat cgagaaaacc atctccaaag ccaaagggca gccccgagaa 720
ccacaggtgt acaccctgcc cccatcccgg gaggagatga ccaagaacca ggtcagcctg 780
acctgcctgg tcaaaggctt ctatcccagc gacatcgccg tggagtggga gagcaatggg 840
cagccggaga acaactacga caccacgcct cccgtgctgg actccgacgg ctccttcttc 900
ctctatagcg acctcaccgt ggacaagagc aggtggcagc aggggaacgt cttctcatgc 960
tccgtgatgc atgaggctct gcacaaccac tacacgcaga agagcctctc cctgtctccg 1020
ggt 1023

<210> SEQ ID NO 136
<211> LENGTH: 317
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 136

Gly Leu Lys Cys Val Cys Leu Leu Cys Asp Ser Ser Asn Phe Thr Cys
1 5 10 15

Gln Thr Glu Gly Ala Cys Trp Ala Ser Val Met Leu Thr Asn Gly Lys
20 25 30

Glu Gln Val Ile Lys Ser Cys Val Ser Leu Pro Glu Leu Asn Ala Gln
35 40 45

Val Phe Cys His Ser Ser Asn Asn Val Thr Lys Thr Glu Cys Cys Phe
50 55 60

```
Thr Asp Phe Cys Asn Asn Ile Thr Leu His Leu Pro Thr Ala Ser Pro
65                  70                  75                  80

Asn Ala Pro Lys Leu Gly Pro Met Glu Thr Gly Gly Gly Thr His Thr
                85                  90                  95

Cys Pro Pro Cys Pro Ala Pro Glu Leu Leu Gly Gly Pro Ser Val Phe
            100                 105                 110

Leu Phe Pro Pro Lys Pro Lys Asp Thr Leu Met Ile Ser Arg Thr Pro
        115                 120                 125

Glu Val Thr Cys Val Val Val Asp Val Ser His Glu Asp Pro Glu Val
    130                 135                 140

Lys Phe Asn Trp Tyr Val Asp Gly Val Glu Val His Asn Ala Lys Thr
145                 150                 155                 160

Lys Pro Arg Glu Glu Gln Tyr Asn Ser Thr Tyr Arg Val Val Ser Val
                165                 170                 175

Leu Thr Val Leu His Gln Asp Trp Leu Asn Gly Lys Glu Tyr Lys Cys
            180                 185                 190

Lys Val Ser Asn Lys Ala Leu Pro Ala Pro Ile Glu Lys Thr Ile Ser
        195                 200                 205

Lys Ala Lys Gly Gln Pro Arg Glu Pro Gln Val Tyr Thr Leu Pro Pro
    210                 215                 220

Ser Arg Glu Glu Met Thr Lys Asn Gln Val Ser Leu Thr Cys Leu Val
225                 230                 235                 240

Lys Gly Phe Tyr Pro Ser Asp Ile Ala Val Glu Trp Glu Ser Asn Gly
                245                 250                 255

Gln Pro Glu Asn Asn Tyr Asp Thr Thr Pro Pro Val Leu Asp Ser Asp
            260                 265                 270

Gly Ser Phe Phe Leu Tyr Ser Asp Leu Thr Val Asp Lys Ser Arg Trp
        275                 280                 285

Gln Gln Gly Asn Val Phe Ser Cys Ser Val Met His Glu Ala Leu His
    290                 295                 300

Asn His Tyr Thr Gln Lys Ser Leu Ser Leu Ser Pro Gly
305                 310                 315


<210> SEQ ID NO 137
<211> LENGTH: 262
<212> TYPE: PRT
<213> ORGANISM: Homo sapiens

<400> SEQUENCE: 137

Met Asp Ala Met Lys Arg Gly Leu Cys Cys Val Leu Leu Leu Cys Gly
1               5                   10                  15

Ala Val Phe Val Ser Pro Gly Ala Ser Asn Thr Lys Val Asp Lys Arg
            20                  25                  30

Val Thr Gly Gly Gly Thr His Thr Cys Pro Pro Cys Pro Ala Pro Glu
        35                  40                  45

Leu Leu Gly Gly Pro Ser Val Phe Leu Phe Pro Pro Lys Pro Lys Asp
    50                  55                  60

Thr Leu Met Ile Ser Arg Thr Pro Glu Val Thr Cys Val Val Val Asp
65                  70                  75                  80

Val Ser His Glu Asp Pro Glu Val Lys Phe Asn Trp Tyr Val Asp Gly
                85                  90                  95

Val Glu Val His Asn Ala Lys Thr Lys Pro Arg Glu Glu Gln Tyr Asn
            100                 105                 110

Ser Thr Tyr Arg Val Val Ser Val Leu Thr Val Leu His Gln Asp Trp
```

```
        115                 120                 125

Leu Asn Gly Lys Glu Tyr Lys Cys Lys Val Ser Asn Lys Ala Leu Pro
    130                 135                 140

Ala Pro Ile Glu Lys Thr Ile Ser Lys Ala Lys Gly Gln Pro Arg Glu
145                 150                 155                 160

Pro Gln Val Tyr Thr Leu Pro Pro Ser Arg Glu Glu Met Thr Lys Asn
                165                 170                 175

Gln Val Ser Leu Thr Cys Leu Val Lys Gly Phe Tyr Pro Ser Asp Ile
            180                 185                 190

Ala Val Glu Trp Glu Ser Asn Gly Gln Pro Glu Asn Asn Tyr Asp Thr
        195                 200                 205

Thr Pro Pro Val Leu Asp Ser Asp Gly Ser Phe Phe Leu Tyr Ser Asp
    210                 215                 220

Leu Thr Val Asp Lys Ser Arg Trp Gln Gln Gly Asn Val Phe Ser Cys
225                 230                 235                 240

Ser Val Met His Glu Ala Leu His Asn His Tyr Thr Gln Lys Ser Leu
                245                 250                 255

Ser Leu Ser Pro Gly Lys
            260


<210> SEQ ID NO 138
<211> LENGTH: 786
<212> TYPE: DNA
<213> ORGANISM: Homo sapiens

<400> SEQUENCE: 138

atggatgcaa tgaagagagg gctctgctgt gtgctgctgc tgtgtggagc agtcttcgtt      60

tcgcccggcg ccagcaacac caaggtggac aagagagtta ccggtggtgg aactcacaca     120

tgcccaccgt gcccagcacc tgaactcctg gggggaccgt cagtcttcct cttcccccca     180

aaacccaagg acaccctcat gatctcccgg acccctgagg tcacatgcgt ggtggtggac     240

gtgagccacg aagaccctga ggtcaagttc aactggtacg tggacggcgt ggaggtgcat     300

aatgccaaga caaagccgcg ggaggagcag tacaacagca cgtaccgtgt ggtcagcgtc     360

ctcaccgtcc tgcaccagga ctggctgaat ggcaaggagt acaagtgcaa ggtctccaac     420

aaagccctcc cagcccccat cgagaaaacc atctccaaag ccaaagggca gccccgagaa     480

ccacaggtgt acaccctgcc cccatcccgg gaggagatga ccaagaacca ggtcagcctg     540

acctgcctgg tcaaaggctt ctatcccagc gacatcgccg tggagtggga gagcaatggg     600

cagccggaga acaactacga caccacgcct cccgtgctgg actccgacgg ctccttcttc     660

ctctatagcg acctcaccgt ggacaagagc aggtggcagc aggggaacgt cttctcatgc     720

tccgtgatgc atgaggctct gcacaaccac tacacgcaga agagcctctc cctgtctccg     780

ggtaaa                                                                786


<210> SEQ ID NO 139
<211> LENGTH: 238
<212> TYPE: PRT
<213> ORGANISM: Homo sapiens

<400> SEQUENCE: 139

Ser Asn Thr Lys Val Asp Lys Arg Val Thr Gly Gly Gly Thr His Thr
1               5                   10                  15

Cys Pro Pro Cys Pro Ala Pro Glu Leu Leu Gly Gly Pro Ser Val Phe
            20                  25                  30
```

Leu Phe Pro Pro Lys Pro Lys Asp Thr Leu Met Ile Ser Arg Thr Pro
35 40 45

Glu Val Thr Cys Val Val Val Asp Val Ser His Glu Asp Pro Glu Val
50 55 60

Lys Phe Asn Trp Tyr Val Asp Gly Val Glu Val His Asn Ala Lys Thr
65 70 75 80

Lys Pro Arg Glu Glu Gln Tyr Asn Ser Thr Tyr Arg Val Val Ser Val
85 90 95

Leu Thr Val Leu His Gln Asp Trp Leu Asn Gly Lys Glu Tyr Lys Cys
100 105 110

Lys Val Ser Asn Lys Ala Leu Pro Ala Pro Ile Glu Lys Thr Ile Ser
115 120 125

Lys Ala Lys Gly Gln Pro Arg Glu Pro Gln Val Tyr Thr Leu Pro Pro
130 135 140

Ser Arg Glu Glu Met Thr Lys Asn Gln Val Ser Leu Thr Cys Leu Val
145 150 155 160

Lys Gly Phe Tyr Pro Ser Asp Ile Ala Val Glu Trp Glu Ser Asn Gly
165 170 175

Gln Pro Glu Asn Asn Tyr Asp Thr Thr Pro Pro Val Leu Asp Ser Asp
180 185 190

Gly Ser Phe Phe Leu Tyr Ser Asp Leu Thr Val Asp Lys Ser Arg Trp
195 200 205

Gln Gln Gly Asn Val Phe Ser Cys Ser Val Met His Glu Ala Leu His
210 215 220

Asn His Tyr Thr Gln Lys Ser Leu Ser Leu Ser Pro Gly Lys
225 230 235

<210> SEQ ID NO 140
<211> LENGTH: 262
<212> TYPE: PRT
<213> ORGANISM: Homo sapiens

<400> SEQUENCE: 140

Met Asp Ala Met Lys Arg Gly Leu Cys Cys Val Leu Leu Leu Cys Gly
1 5 10 15

Ala Val Phe Val Ser Pro Gly Ala Ser Asn Thr Lys Val Asp Lys Arg
20 25 30

Val Thr Gly Gly Gly Thr His Thr Cys Pro Pro Cys Pro Ala Pro Glu
35 40 45

Leu Leu Gly Gly Pro Ser Val Phe Leu Phe Pro Pro Lys Pro Lys Asp
50 55 60

Thr Leu Met Ile Ser Arg Thr Pro Glu Val Thr Cys Val Val Val Asp
65 70 75 80

Val Ser His Glu Asp Pro Glu Val Lys Phe Asn Trp Tyr Val Asp Gly
85 90 95

Val Glu Val His Asn Ala Lys Thr Lys Pro Arg Glu Glu Gln Tyr Asn
100 105 110

Ser Thr Tyr Arg Val Val Ser Val Leu Thr Val Leu His Gln Asp Trp
115 120 125

Leu Asn Gly Lys Glu Tyr Lys Cys Lys Val Ser Asn Lys Ala Leu Pro
130 135 140

Ala Pro Ile Glu Lys Thr Ile Ser Lys Ala Lys Gly Gln Pro Arg Glu
145 150 155 160

Pro Gln Val Tyr Thr Leu Pro Pro Ser Arg Lys Glu Met Thr Lys Asn
165 170 175

```
Gln Val Ser Leu Thr Cys Leu Val Lys Gly Phe Tyr Pro Ser Asp Ile
            180                 185                 190

Ala Val Glu Trp Glu Ser Asn Gly Gln Pro Glu Asn Asn Tyr Lys Thr
        195                 200                 205

Thr Pro Pro Val Leu Lys Ser Asp Gly Ser Phe Phe Leu Tyr Ser Lys
    210                 215                 220

Leu Thr Val Asp Lys Ser Arg Trp Gln Gln Gly Asn Val Phe Ser Cys
225                 230                 235                 240

Ser Val Met His Glu Ala Leu His Asn His Tyr Thr Gln Lys Ser Leu
                245                 250                 255

Ser Leu Ser Pro Gly Lys
            260
```

<210> SEQ ID NO 141
<211> LENGTH: 786
<212> TYPE: DNA
<213> ORGANISM: Homo sapiens

<400> SEQUENCE: 141

```
atggatgcaa tgaagagagg gctctgctgt gtgctgctgc tgtgtggagc agtcttcgtt      60

tcgcccggcg ccagcaacac caaggtggac aagagagtta ccggtggtgg aactcacaca     120

tgcccaccgt gcccagcacc tgaactcctg gggggaccgt cagtcttcct cttcccccca     180

aaacccaagg acaccctcat gatctcccgg acccctgagg tcacatgcgt ggtggtggac     240

gtgagccacg aagaccctga ggtcaagttc aactggtacg tggacggcgt ggaggtgcat     300

aatgccaaga caaagccgcg ggaggagcag tacaacagca cgtaccgtgt ggtcagcgtc     360

ctcaccgtcc tgcaccagga ctggctgaat ggcaaggagt acaagtgcaa ggtctccaac     420

aaagccctcc cagcccccat cgagaaaacc atctccaaag ccaaagggca gccccgagaa     480

ccacaggtgt acaccctgcc cccatcccgg aaggagatga ccaagaacca ggtcagcctg     540

acctgcctgg tcaaaggctt ctatcccagc gacatcgccg tggagtggga gagcaatggg     600

cagccggaga acaactacaa gaccacgcct cccgtgctga agtccgacgg ctccttcttc     660

ctctatagca agctcaccgt ggacaagagc aggtggcagc aggggaacgt cttctcatgc     720

tccgtgatgc atgaggctct gcacaaccac tacacgcaga agagcctctc cctgtctccg     780

ggtaaa                                                                786
```

<210> SEQ ID NO 142
<211> LENGTH: 238
<212> TYPE: PRT
<213> ORGANISM: Homo sapiens

<400> SEQUENCE: 142

```
Ser Asn Thr Lys Val Asp Lys Arg Val Thr Gly Gly Gly Thr His Thr
1               5                   10                  15

Cys Pro Pro Cys Pro Ala Pro Glu Leu Leu Gly Gly Pro Ser Val Phe
            20                  25                  30

Leu Phe Pro Pro Lys Pro Lys Asp Thr Leu Met Ile Ser Arg Thr Pro
        35                  40                  45

Glu Val Thr Cys Val Val Val Asp Val Ser His Glu Asp Pro Glu Val
    50                  55                  60

Lys Phe Asn Trp Tyr Val Asp Gly Val Glu Val His Asn Ala Lys Thr
65                  70                  75                  80

Lys Pro Arg Glu Glu Gln Tyr Asn Ser Thr Tyr Arg Val Val Ser Val
```

-continued

```
                85                  90                  95

Leu Thr Val Leu His Gln Asp Trp Leu Asn Gly Lys Glu Tyr Lys Cys
            100                 105                 110

Lys Val Ser Asn Lys Ala Leu Pro Ala Pro Ile Glu Lys Thr Ile Ser
        115                 120                 125

Lys Ala Lys Gly Gln Pro Arg Glu Pro Gln Val Tyr Thr Leu Pro Pro
    130                 135                 140

Ser Arg Lys Glu Met Thr Lys Asn Gln Val Ser Leu Thr Cys Leu Val
145                 150                 155                 160

Lys Gly Phe Tyr Pro Ser Asp Ile Ala Val Glu Trp Glu Ser Asn Gly
                165                 170                 175

Gln Pro Glu Asn Asn Tyr Lys Thr Thr Pro Pro Val Leu Lys Ser Asp
            180                 185                 190

Gly Ser Phe Phe Leu Tyr Ser Lys Leu Thr Val Asp Lys Ser Arg Trp
        195                 200                 205

Gln Gln Gly Asn Val Phe Ser Cys Ser Val Met His Glu Ala Leu His
    210                 215                 220

Asn His Tyr Thr Gln Lys Ser Leu Ser Leu Ser Pro Gly Lys
225                 230                 235


<210> SEQ ID NO 143

<400> SEQUENCE: 143

000


<210> SEQ ID NO 144

<400> SEQUENCE: 144

000


<210> SEQ ID NO 145

<400> SEQUENCE: 145

000


<210> SEQ ID NO 146

<400> SEQUENCE: 146

000


<210> SEQ ID NO 147

<400> SEQUENCE: 147

000


<210> SEQ ID NO 148

<400> SEQUENCE: 148

000


<210> SEQ ID NO 149

<400> SEQUENCE: 149

000
```

-continued

<210> SEQ ID NO 150

<400> SEQUENCE: 150

000

<210> SEQ ID NO 151

<400> SEQUENCE: 151

000

<210> SEQ ID NO 152

<400> SEQUENCE: 152

000

<210> SEQ ID NO 153

<400> SEQUENCE: 153

000

<210> SEQ ID NO 154

<400> SEQUENCE: 154

000

<210> SEQ ID NO 155

<400> SEQUENCE: 155

000

<210> SEQ ID NO 156

<400> SEQUENCE: 156

000

<210> SEQ ID NO 157

<400> SEQUENCE: 157

000

<210> SEQ ID NO 158

<400> SEQUENCE: 158

000

<210> SEQ ID NO 159

<400> SEQUENCE: 159

000

<210> SEQ ID NO 160

<400> SEQUENCE: 160

000

<210> SEQ ID NO 161

<400> SEQUENCE: 161

000

<210> SEQ ID NO 162

<400> SEQUENCE: 162

000

<210> SEQ ID NO 163

<400> SEQUENCE: 163

000

<210> SEQ ID NO 164

<400> SEQUENCE: 164

000

<210> SEQ ID NO 165

<400> SEQUENCE: 165

000

<210> SEQ ID NO 166

<400> SEQUENCE: 166

000

<210> SEQ ID NO 167

<400> SEQUENCE: 167

000

<210> SEQ ID NO 168

<400> SEQUENCE: 168

000

<210> SEQ ID NO 169

<400> SEQUENCE: 169

000

<210> SEQ ID NO 170

<400> SEQUENCE: 170

000

<210> SEQ ID NO 171

<400> SEQUENCE: 171

000

<210> SEQ ID NO 172

<400> SEQUENCE: 172

-continued

000

<210> SEQ ID NO 173

<400> SEQUENCE: 173

000

<210> SEQ ID NO 174

<400> SEQUENCE: 174

000

<210> SEQ ID NO 175

<400> SEQUENCE: 175

000

<210> SEQ ID NO 176

<400> SEQUENCE: 176

000

<210> SEQ ID NO 177

<400> SEQUENCE: 177

000

<210> SEQ ID NO 178

<400> SEQUENCE: 178

000

<210> SEQ ID NO 179

<400> SEQUENCE: 179

000

<210> SEQ ID NO 180

<400> SEQUENCE: 180

000

<210> SEQ ID NO 181

<400> SEQUENCE: 181

000

<210> SEQ ID NO 182

<400> SEQUENCE: 182

000

<210> SEQ ID NO 183

<400> SEQUENCE: 183

000

<210> SEQ ID NO 184

<400> SEQUENCE: 184

000

<210> SEQ ID NO 185

<400> SEQUENCE: 185

000

<210> SEQ ID NO 186

<400> SEQUENCE: 186

000

<210> SEQ ID NO 187

<400> SEQUENCE: 187

000

<210> SEQ ID NO 188

<400> SEQUENCE: 188

000

<210> SEQ ID NO 189

<400> SEQUENCE: 189

000

<210> SEQ ID NO 190

<400> SEQUENCE: 190

000

<210> SEQ ID NO 191

<400> SEQUENCE: 191

000

<210> SEQ ID NO 192

<400> SEQUENCE: 192

000

<210> SEQ ID NO 193

<400> SEQUENCE: 193

000

<210> SEQ ID NO 194

<400> SEQUENCE: 194

000

<210> SEQ ID NO 195

<400> SEQUENCE: 195

000

<210> SEQ ID NO 196

<400> SEQUENCE: 196

000

<210> SEQ ID NO 197

<400> SEQUENCE: 197

000

<210> SEQ ID NO 198

<400> SEQUENCE: 198

000

<210> SEQ ID NO 199

<400> SEQUENCE: 199

000

<210> SEQ ID NO 200
<211> LENGTH: 225
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 200

```
Thr His Thr Cys Pro Pro Cys Pro Ala Pro Glu Leu Leu Gly Gly Pro
1               5                   10                  15

Ser Val Phe Leu Phe Pro Pro Lys Pro Lys Asp Thr Leu Met Ile Ser
            20                  25                  30

Arg Thr Pro Glu Val Thr Cys Val Val Val Asp Val Ser His Glu Asp
        35                  40                  45

Pro Glu Val Lys Phe Asn Trp Tyr Val Asp Gly Val Glu Val His Asn
    50                  55                  60

Ala Lys Thr Lys Pro Arg Glu Glu Gln Tyr Asn Ser Thr Tyr Arg Val
65                  70                  75                  80

Val Ser Val Leu Thr Val Leu His Gln Asp Trp Leu Asn Gly Lys Glu
                85                  90                  95

Tyr Lys Cys Lys Val Ser Asn Lys Ala Leu Pro Ala Pro Ile Glu Lys
            100                 105                 110

Thr Ile Ser Lys Ala Lys Gly Gln Pro Arg Glu Pro Gln Val Tyr Thr
        115                 120                 125

Leu Pro Pro Ser Arg Lys Glu Met Thr Lys Asn Gln Val Ser Leu Thr
    130                 135                 140

Cys Leu Val Lys Gly Phe Tyr Pro Ser Asp Ile Ala Val Glu Trp Glu
145                 150                 155                 160

Ser Asn Gly Gln Pro Glu Asn Asn Tyr Lys Thr Thr Pro Pro Val Leu
                165                 170                 175

Lys Ser Asp Gly Ser Phe Phe Leu Tyr Ser Lys Leu Thr Val Asp Lys
            180                 185                 190
```

Ser Arg Trp Gln Gln Gly Asn Val Phe Ser Cys Ser Val Met His Glu
195 200 205

Ala Leu His Asn His Tyr Thr Gln Lys Ser Leu Ser Leu Ser Pro Gly
210 215 220

Lys
225

<210> SEQ ID NO 201
<211> LENGTH: 225
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 201

Thr His Thr Cys Pro Pro Cys Pro Ala Pro Glu Leu Leu Gly Gly Pro
1 5 10 15

Ser Val Phe Leu Phe Pro Pro Lys Pro Lys Asp Thr Leu Met Ile Ser
20 25 30

Arg Thr Pro Glu Val Thr Cys Val Val Val Asp Val Ser His Glu Asp
35 40 45

Pro Glu Val Lys Phe Asn Trp Tyr Val Asp Gly Val Glu Val His Asn
50 55 60

Ala Lys Thr Lys Pro Arg Glu Glu Gln Tyr Asn Ser Thr Tyr Arg Val
65 70 75 80

Val Ser Val Leu Thr Val Leu His Gln Asp Trp Leu Asn Gly Lys Glu
85 90 95

Tyr Lys Cys Lys Val Ser Asn Lys Ala Leu Pro Ala Pro Ile Glu Lys
100 105 110

Thr Ile Ser Lys Ala Lys Gly Gln Pro Arg Glu Pro Gln Val Tyr Thr
115 120 125

Leu Pro Pro Ser Arg Glu Glu Met Thr Lys Asn Gln Val Ser Leu Thr
130 135 140

Cys Leu Val Lys Gly Phe Tyr Pro Ser Asp Ile Ala Val Glu Trp Glu
145 150 155 160

Ser Asn Gly Gln Pro Glu Asn Asn Tyr Asp Thr Thr Pro Pro Val Leu
165 170 175

Asp Ser Asp Gly Ser Phe Phe Leu Tyr Ser Asp Leu Thr Val Asp Lys
180 185 190

Ser Arg Trp Gln Gln Gly Asn Val Phe Ser Cys Ser Val Met His Glu
195 200 205

Ala Leu His Asn His Tyr Thr Gln Lys Ser Leu Ser Leu Ser Pro Gly
210 215 220

Lys
225

<210> SEQ ID NO 202
<211> LENGTH: 225
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 202

Thr His Thr Cys Pro Pro Cys Pro Ala Pro Glu Leu Leu Gly Gly Pro
1 5 10 15

Ser Val Phe Leu Phe Pro Pro Lys Pro Lys Asp Thr Leu Met Ile Ser
20 25 30

Arg Thr Pro Glu Val Thr Cys Val Val Val Asp Val Ser His Glu Asp
35 40 45

Pro Glu Val Lys Phe Asn Trp Tyr Val Asp Gly Val Glu Val His Asn
50 55 60

Ala Lys Thr Lys Pro Arg Glu Glu Gln Tyr Asn Ser Thr Tyr Arg Val
65 70 75 80

Val Ser Val Leu Thr Val Leu His Gln Asp Trp Leu Asn Gly Lys Glu
85 90 95

Tyr Lys Cys Lys Val Ser Asn Lys Ala Leu Pro Ala Pro Ile Glu Lys
100 105 110

Thr Ile Ser Lys Ala Lys Gly Gln Pro Arg Glu Pro Gln Val Tyr Thr
115 120 125

Leu Pro Pro Ser Arg Glu Glu Met Thr Lys Asn Gln Val Ser Leu Tyr
130 135 140

Cys Leu Val Lys Gly Phe Tyr Pro Ser Asp Ile Ala Val Glu Trp Glu
145 150 155 160

Ser Asn Gly Gln Pro Glu Asn Asn Tyr Lys Thr Thr Pro Pro Val Leu
165 170 175

Asp Ser Asp Gly Ser Phe Phe Leu Tyr Ser Lys Leu Thr Val Asp Lys
180 185 190

Ser Arg Trp Gln Gln Gly Asn Val Phe Ser Cys Ser Val Met His Glu
195 200 205

Ala Leu His Asn His Tyr Thr Gln Lys Ser Leu Ser Leu Ser Pro Gly
210 215 220

Lys
225

<210> SEQ ID NO 203
<211> LENGTH: 225
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 203

Thr His Thr Cys Pro Pro Cys Pro Ala Pro Glu Leu Leu Gly Gly Pro
1 5 10 15

Ser Val Phe Leu Phe Pro Pro Lys Pro Lys Asp Thr Leu Met Ile Ser
20 25 30

Arg Thr Pro Glu Val Thr Cys Val Val Val Asp Val Ser His Glu Asp
35 40 45

Pro Glu Val Lys Phe Asn Trp Tyr Val Asp Gly Val Glu Val His Asn
50 55 60

Ala Lys Thr Lys Pro Arg Glu Glu Gln Tyr Asn Ser Thr Tyr Arg Val
65 70 75 80

Val Ser Val Leu Thr Val Leu His Gln Asp Trp Leu Asn Gly Lys Glu
85 90 95

Tyr Lys Cys Lys Val Ser Asn Lys Ala Leu Pro Ala Pro Ile Glu Lys
100 105 110

Thr Ile Ser Lys Ala Lys Gly Gln Pro Arg Glu Pro Gln Val Tyr Thr
115 120 125

Leu Pro Pro Ser Arg Glu Glu Met Thr Lys Asn Gln Val Ser Leu Thr

```
    130                 135                 140

Cys Leu Val Lys Gly Phe Tyr Pro Ser Asp Ile Ala Val Glu Trp Glu
145                 150                 155                 160

Ser Asn Gly Gln Pro Glu Asn Asn Tyr Lys Thr Thr Pro Pro Val Leu
                165                 170                 175

Asp Ser Asp Gly Ser Phe Phe Leu Thr Ser Lys Leu Thr Val Asp Lys
            180                 185                 190

Ser Arg Trp Gln Gln Gly Asn Val Phe Ser Cys Ser Val Met His Glu
        195                 200                 205

Ala Leu His Asn His Tyr Thr Gln Lys Ser Leu Ser Leu Ser Pro Gly
    210                 215                 220

Lys
225


<210> SEQ ID NO 204
<211> LENGTH: 225
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 204

Thr His Thr Cys Pro Pro Cys Pro Ala Pro Glu Leu Leu Gly Gly Pro
1               5                   10                  15

Ser Val Phe Leu Phe Pro Pro Lys Pro Lys Asp Thr Leu Met Ile Ser
            20                  25                  30

Arg Thr Pro Glu Val Thr Cys Val Val Val Asp Val Ser His Glu Asp
        35                  40                  45

Pro Glu Val Lys Phe Asn Trp Tyr Val Asp Gly Val Glu Val His Asn
    50                  55                  60

Ala Lys Thr Lys Pro Arg Glu Glu Gln Tyr Asn Ser Thr Tyr Arg Val
65                  70                  75                  80

Val Ser Val Leu Thr Val Leu His Gln Asp Trp Leu Asn Gly Lys Glu
                85                  90                  95

Tyr Lys Cys Lys Val Ser Asn Lys Ala Leu Pro Ala Pro Ile Glu Lys
            100                 105                 110

Thr Ile Ser Lys Ala Lys Gly Gln Pro Arg Glu Pro Gln Val Tyr Thr
        115                 120                 125

Leu Pro Pro Cys Arg Glu Glu Met Thr Lys Asn Gln Val Ser Leu Trp
    130                 135                 140

Cys Leu Val Lys Gly Phe Tyr Pro Ser Asp Ile Ala Val Glu Trp Glu
145                 150                 155                 160

Ser Asn Gly Gln Pro Glu Asn Asn Tyr Lys Thr Thr Pro Pro Val Leu
                165                 170                 175

Asp Ser Asp Gly Ser Phe Phe Leu Tyr Ser Lys Leu Thr Val Asp Lys
            180                 185                 190

Ser Arg Trp Gln Gln Gly Asn Val Phe Ser Cys Ser Val Met His Glu
        195                 200                 205

Ala Leu His Asn His Tyr Thr Gln Lys Ser Leu Ser Leu Ser Pro Gly
    210                 215                 220

Lys
225


<210> SEQ ID NO 205
<211> LENGTH: 225
```

<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 205

```
Thr His Thr Cys Pro Pro Cys Pro Ala Pro Glu Leu Leu Gly Gly Pro
1               5                   10                  15

Ser Val Phe Leu Phe Pro Pro Lys Pro Lys Asp Thr Leu Met Ile Ser
            20                  25                  30

Arg Thr Pro Glu Val Thr Cys Val Val Val Asp Val Ser His Glu Asp
        35                  40                  45

Pro Glu Val Lys Phe Asn Trp Tyr Val Asp Gly Val Glu Val His Asn
    50                  55                  60

Ala Lys Thr Lys Pro Arg Glu Glu Gln Tyr Asn Ser Thr Tyr Arg Val
65                  70                  75                  80

Val Ser Val Leu Thr Val Leu His Gln Asp Trp Leu Asn Gly Lys Glu
                85                  90                  95

Tyr Lys Cys Lys Val Ser Asn Lys Ala Leu Pro Ala Pro Ile Glu Lys
            100                 105                 110

Thr Ile Ser Lys Ala Lys Gly Gln Pro Arg Glu Pro Gln Val Cys Thr
        115                 120                 125

Leu Pro Pro Ser Arg Glu Glu Met Thr Lys Asn Gln Val Ser Leu Ser
    130                 135                 140

Cys Ala Val Lys Gly Phe Tyr Pro Ser Asp Ile Ala Val Glu Trp Glu
145                 150                 155                 160

Ser Asn Gly Gln Pro Glu Asn Asn Tyr Lys Thr Thr Pro Pro Val Leu
                165                 170                 175

Asp Ser Asp Gly Ser Phe Phe Leu Val Ser Lys Leu Thr Val Asp Lys
            180                 185                 190

Ser Arg Trp Gln Gln Gly Asn Val Phe Ser Cys Ser Val Met His Glu
        195                 200                 205

Ala Leu His Asn His Tyr Thr Gln Lys Ser Leu Ser Leu Ser Pro Gly
    210                 215                 220

Lys
225
```

<210> SEQ ID NO 206
<211> LENGTH: 228
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 206

```
Thr His Thr Cys Pro Pro Cys Pro Ala Pro Glu Leu Leu Gly Gly Pro
1               5                   10                  15

Ser Val Phe Leu Phe Pro Pro Lys Pro Lys Asp Thr Leu Met Ile Ser
            20                  25                  30

Arg Thr Pro Glu Val Thr Cys Val Val Val Asp Val Ser His Glu Asp
        35                  40                  45

Pro Glu Val Lys Phe Asn Trp Tyr Val Asp Gly Val Glu Val His Asn
    50                  55                  60

Ala Lys Thr Lys Pro Arg Glu Glu Gln Tyr Asn Ser Thr Tyr Arg Val
65                  70                  75                  80
```

```
Val Ser Val Leu Thr Val Leu His Gln Asp Trp Leu Asn Gly Lys Glu
                85                  90                  95

Tyr Lys Cys Lys Val Ser Asn Lys Ala Leu Pro Ala Pro Ile Glu Lys
            100                 105                 110

Thr Ile Ser Lys Ala Lys Gly Gln Pro Phe Arg Pro Glu Val His Leu
        115                 120                 125

Leu Pro Pro Ser Arg Glu Glu Met Thr Lys Asn Gln Val Ser Leu Thr
    130                 135                 140

Cys Leu Ala Arg Gly Phe Tyr Pro Lys Asp Ile Ala Val Glu Trp Glu
145                 150                 155                 160

Ser Asn Gly Gln Pro Glu Asn Asn Tyr Lys Thr Thr Pro Ser Arg Gln
                165                 170                 175

Glu Pro Ser Gln Gly Thr Thr Thr Phe Ala Val Thr Ser Lys Leu Thr
            180                 185                 190

Val Asp Lys Ser Arg Trp Gln Gln Gly Asn Val Phe Ser Cys Ser Val
        195                 200                 205

Met His Glu Ala Leu His Asn His Tyr Thr Gln Lys Thr Ile Ser Leu
    210                 215                 220

Ser Pro Gly Lys
225


<210> SEQ ID NO 207
<211> LENGTH: 228
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 207

Thr His Thr Cys Pro Pro Cys Pro Ala Pro Glu Leu Leu Gly Gly Pro
1               5                   10                  15

Ser Val Phe Leu Phe Pro Pro Lys Pro Lys Asp Thr Leu Met Ile Ser
            20                  25                  30

Arg Thr Pro Glu Val Thr Cys Val Val Val Asp Val Ser His Glu Asp
        35                  40                  45

Pro Glu Val Lys Phe Asn Trp Tyr Val Asp Gly Val Glu Val His Asn
    50                  55                  60

Ala Lys Thr Lys Pro Arg Glu Glu Gln Tyr Asn Ser Thr Tyr Arg Val
65                  70                  75                  80

Val Ser Val Leu Thr Val Leu His Gln Asp Trp Leu Asn Gly Lys Glu
                85                  90                  95

Tyr Lys Cys Lys Val Ser Asn Lys Ala Leu Pro Ala Pro Ile Glu Lys
            100                 105                 110

Thr Ile Ser Lys Ala Lys Gly Gln Pro Arg Glu Pro Gln Val Tyr Thr
        115                 120                 125

Leu Pro Pro Pro Ser Glu Glu Leu Ala Leu Asn Glu Leu Val Thr Leu
    130                 135                 140

Thr Cys Leu Val Lys Gly Phe Tyr Pro Ser Asp Ile Ala Val Glu Trp
145                 150                 155                 160

Glu Ser Asn Gly Gln Glu Leu Pro Arg Glu Lys Tyr Leu Thr Trp Ala
                165                 170                 175

Pro Val Leu Asp Ser Asp Gly Ser Phe Phe Leu Tyr Ser Ile Leu Arg
            180                 185                 190

Val Ala Ala Glu Asp Trp Lys Lys Gly Asp Thr Phe Ser Cys Ser Val
        195                 200                 205
```

Met His Glu Ala Leu His Asn His Tyr Thr Gln Lys Ser Leu Asp Arg
    210                 215                 220

Ser Pro Gly Lys
225

<210> SEQ ID NO 208
<211> LENGTH: 225
<212> TYPE: PRT
<213> ORGANISM: Homo sapiens

<400> SEQUENCE: 208

Thr His Thr Cys Pro Pro Cys Pro Ala Pro Glu Leu Leu Gly Gly Pro
1               5                   10                  15

Ser Val Phe Leu Phe Pro Pro Lys Pro Lys Asp Thr Leu Met Ile Ser
            20                  25                  30

Arg Thr Pro Glu Val Thr Cys Val Val Val Asp Val Ser His Glu Asp
        35                  40                  45

Pro Glu Val Lys Phe Asn Trp Tyr Val Asp Gly Val Glu Val His Asn
    50                  55                  60

Ala Lys Thr Lys Pro Arg Glu Glu Gln Tyr Asn Ser Thr Tyr Arg Val
65                  70                  75                  80

Val Ser Val Leu Thr Val Leu His Gln Asp Trp Leu Asn Gly Lys Glu
                85                  90                  95

Tyr Lys Cys Lys Val Ser Asn Lys Ala Leu Pro Ala Pro Ile Glu Lys
            100                 105                 110

Thr Ile Ser Lys Ala Lys Gly Gln Pro Arg Glu Pro Gln Val Tyr Thr
        115                 120                 125

Leu Pro Pro Ser Arg Glu Glu Met Thr Lys Asn Gln Val Ser Leu Thr
    130                 135                 140

Cys Leu Val Lys Gly Phe Tyr Pro Ser Asp Ile Ala Val Glu Trp Glu
145                 150                 155                 160

Ser Asn Gly Gln Pro Glu Asn Asn Tyr Lys Thr Thr Pro Pro Val Leu
                165                 170                 175

Asp Ser Asp Gly Ser Phe Phe Leu Tyr Ser Lys Leu Thr Val Asp Lys
            180                 185                 190

Ser Arg Trp Gln Gln Gly Asn Val Phe Ser Cys Ser Val Met His Glu
        195                 200                 205

Ala Leu His Asn His Tyr Thr Gln Lys Ser Leu Ser Leu Ser Pro Gly
    210                 215                 220

Lys
225

<210> SEQ ID NO 209
<211> LENGTH: 223
<212> TYPE: PRT
<213> ORGANISM: Homo sapiens

<400> SEQUENCE: 209

Val Glu Cys Pro Pro Cys Pro Ala Pro Pro Val Ala Gly Pro Ser Val
1               5                   10                  15

Phe Leu Phe Pro Pro Lys Pro Lys Asp Thr Leu Met Ile Ser Arg Thr
            20                  25                  30

Pro Glu Val Thr Cys Val Val Val Asp Val Ser His Glu Asp Pro Glu
        35                  40                  45

Val Gln Phe Asn Trp Tyr Val Asp Gly Val Glu Val His Asn Ala Lys
    50                  55                  60

Thr Lys Pro Arg Glu Glu Gln Phe Asn Ser Thr Phe Arg Val Val Ser
65 70 75 80

Val Leu Thr Val Val His Gln Asp Trp Leu Asn Gly Lys Glu Tyr Lys
85 90 95

Cys Lys Val Ser Asn Lys Gly Leu Pro Ala Pro Ile Glu Lys Thr Ile
100 105 110

Ser Lys Thr Lys Gly Gln Pro Arg Glu Pro Gln Val Tyr Thr Leu Pro
115 120 125

Pro Ser Arg Glu Glu Met Thr Lys Asn Gln Val Ser Leu Thr Cys Leu
130 135 140

Val Lys Gly Phe Tyr Pro Ser Asp Ile Ala Val Glu Trp Glu Ser Asn
145 150 155 160

Gly Gln Pro Glu Asn Asn Tyr Lys Thr Thr Pro Pro Met Leu Asp Ser
165 170 175

Asp Gly Ser Phe Phe Leu Tyr Ser Lys Leu Thr Val Asp Lys Ser Arg
180 185 190

Trp Gln Gln Gly Asn Val Phe Ser Cys Ser Val Met His Glu Ala Leu
195 200 205

His Asn His Tyr Thr Gln Lys Ser Leu Ser Leu Ser Pro Gly Lys
210 215 220

<210> SEQ ID NO 210
<211> LENGTH: 232
<212> TYPE: PRT
<213> ORGANISM: Homo sapiens

<400> SEQUENCE: 210

Glu Pro Lys Ser Cys Asp Thr Pro Pro Pro Cys Pro Arg Cys Pro Ala
1 5 10 15

Pro Glu Leu Leu Gly Gly Pro Ser Val Phe Leu Phe Pro Pro Lys Pro
20 25 30

Lys Asp Thr Leu Met Ile Ser Arg Thr Pro Glu Val Thr Cys Val Val
35 40 45

Val Asp Val Ser His Glu Asp Pro Glu Val Gln Phe Lys Trp Tyr Val
50 55 60

Asp Gly Val Glu Val His Asn Ala Lys Thr Lys Pro Arg Glu Glu Gln
65 70 75 80

Tyr Asn Ser Thr Phe Arg Val Val Ser Val Leu Thr Val Leu His Gln
85 90 95

Asp Trp Leu Asn Gly Lys Glu Tyr Lys Cys Lys Val Ser Asn Lys Ala
100 105 110

Leu Pro Ala Pro Ile Glu Lys Thr Ile Ser Lys Thr Lys Gly Gln Pro
115 120 125

Arg Glu Pro Gln Val Tyr Thr Leu Pro Pro Ser Arg Glu Glu Met Thr
130 135 140

Lys Asn Gln Val Ser Leu Thr Cys Leu Val Lys Gly Phe Tyr Pro Ser
145 150 155 160

Asp Ile Ala Val Glu Trp Glu Ser Ser Gly Gln Pro Glu Asn Asn Tyr
165 170 175

Asn Thr Thr Pro Pro Met Leu Asp Ser Asp Gly Ser Phe Phe Leu Tyr
180 185 190

Ser Lys Leu Thr Val Asp Lys Ser Arg Trp Gln Gln Gly Asn Ile Phe
195 200 205

Ser Cys Ser Val Met His Glu Ala Leu His Asn Arg Phe Thr Gln Lys

```
    210                 215                 220

Ser Leu Ser Leu Ser Pro Gly Lys
225                 230


<210> SEQ ID NO 211
<211> LENGTH: 279
<212> TYPE: PRT
<213> ORGANISM: Homo sapiens

<400> SEQUENCE: 211

Glu Leu Lys Thr Pro Leu Gly Asp Thr Thr His Thr Cys Pro Arg Cys
1               5                   10                  15

Pro Glu Pro Lys Ser Cys Asp Thr Pro Pro Pro Cys Pro Arg Cys Pro
            20                  25                  30

Glu Pro Lys Ser Cys Asp Thr Pro Pro Pro Cys Pro Arg Cys Pro Glu
        35                  40                  45

Pro Lys Ser Cys Asp Thr Pro Pro Pro Cys Pro Arg Cys Pro Ala Pro
    50                  55                  60

Glu Leu Leu Gly Gly Pro Ser Val Phe Leu Phe Pro Pro Lys Pro Lys
65                  70                  75                  80

Asp Thr Leu Met Ile Ser Arg Thr Pro Glu Val Thr Cys Val Val Val
                85                  90                  95

Asp Val Ser His Glu Asp Pro Glu Val Gln Phe Lys Trp Tyr Val Asp
            100                 105                 110

Gly Val Glu Val His Asn Ala Lys Thr Lys Pro Arg Glu Glu Gln Tyr
        115                 120                 125

Asn Ser Thr Phe Arg Val Val Ser Val Leu Thr Val Leu His Gln Asp
    130                 135                 140

Trp Leu Asn Gly Lys Glu Tyr Lys Cys Lys Val Ser Asn Lys Ala Leu
145                 150                 155                 160

Pro Ala Pro Ile Glu Lys Thr Ile Ser Lys Thr Lys Gly Gln Pro Arg
                165                 170                 175

Glu Pro Gln Val Tyr Thr Leu Pro Pro Ser Arg Glu Glu Met Thr Lys
            180                 185                 190

Asn Gln Val Ser Leu Thr Cys Leu Val Lys Gly Phe Tyr Pro Ser Asp
        195                 200                 205

Ile Ala Val Glu Trp Glu Ser Ser Gly Gln Pro Glu Asn Asn Tyr Asn
    210                 215                 220

Thr Thr Pro Pro Met Leu Asp Ser Asp Gly Ser Phe Phe Leu Tyr Ser
225                 230                 235                 240

Lys Leu Thr Val Asp Lys Ser Arg Trp Gln Gln Gly Asn Ile Phe Ser
                245                 250                 255

Cys Ser Val Met His Glu Ala Leu His Asn Arg Phe Thr Gln Lys Ser
            260                 265                 270

Leu Ser Leu Ser Pro Gly Lys
        275


<210> SEQ ID NO 212
<211> LENGTH: 229
<212> TYPE: PRT
<213> ORGANISM: Homo sapiens

<400> SEQUENCE: 212

Glu Ser Lys Tyr Gly Pro Pro Cys Pro Ser Cys Pro Ala Pro Glu Phe
1               5                   10                  15

Leu Gly Gly Pro Ser Val Phe Leu Phe Pro Pro Lys Pro Lys Asp Thr
```

```
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys
225


<210> SEQ ID NO 213
<211> LENGTH: 261
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 213

Thr His Thr Cys Pro Pro Cys Pro Ala Pro Glu Leu Leu Gly Gly Pro
1               5                   10                  15

Ser Val Phe Leu Phe Pro Pro Lys Pro Lys Asp Thr Leu Met Ile Ser
            20                  25                  30

Arg Thr Pro Glu Val Thr Cys Val Val Val Asp Val Ser His Glu Asp
        35                  40                  45

Pro Glu Val Lys Phe Asn Trp Tyr Val Asp Gly Val Glu Val His Asn
    50                  55                  60

Ala Lys Thr Lys Pro Arg Glu Glu Gln Tyr Asn Ser Thr Tyr Arg Val
65                  70                  75                  80

Val Ser Val Leu Thr Val Leu His Gln Asp Trp Leu Asn Gly Lys Glu
                85                  90                  95

Tyr Lys Cys Lys Val Ser Asn Lys Ala Leu Pro Ala Pro Ile Glu Lys
            100                 105                 110

Thr Ile Ser Lys Ala Lys Gly Gln Pro Arg Glu Pro Gln Val Tyr Thr
        115                 120                 125

Leu Pro Pro Ser Arg Glu Glu Met Thr Lys Asn Gln Val Ser Leu Thr
    130                 135                 140
```

```
Cys Leu Val Lys Gly Phe Tyr Pro Ser Asp Ile Ala Val Glu Trp Glu
145                 150                 155                 160

Ser Asn Gly Gln Pro Glu Asn Asn Tyr Lys Thr Thr Pro Pro Val Leu
                165                 170                 175

Asp Ser Asp Gly Ser Phe Phe Leu Tyr Ser Lys Leu Thr Val Asp Lys
            180                 185                 190

Ser Arg Trp Gln Gln Gly Asn Val Phe Ser Cys Ser Val Met His Glu
        195                 200                 205

Ala Leu His Asn His Tyr Thr Gln Lys Ser Leu Ser Leu Ser Pro Gly
    210                 215                 220

Lys Gly Gly Ser Ala Gln Leu Glu Lys Glu Leu Gln Ala Leu Glu Lys
225                 230                 235                 240

Glu Asn Ala Gln Leu Glu Trp Glu Leu Gln Ala Leu Glu Lys Glu Leu
                245                 250                 255

Ala Gln Gly Ala Thr
            260


<210> SEQ ID NO 214
<211> LENGTH: 261
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 214

Thr His Thr Cys Pro Pro Cys Pro Ala Pro Glu Leu Leu Gly Gly Pro
1               5                   10                  15

Ser Val Phe Leu Phe Pro Pro Lys Pro Lys Asp Thr Leu Met Ile Ser
            20                  25                  30

Arg Thr Pro Glu Val Thr Cys Val Val Val Asp Val Ser His Glu Asp
        35                  40                  45

Pro Glu Val Lys Phe Asn Trp Tyr Val Asp Gly Val Glu Val His Asn
    50                  55                  60

Ala Lys Thr Lys Pro Arg Glu Glu Gln Tyr Asn Ser Thr Tyr Arg Val
65                  70                  75                  80

Val Ser Val Leu Thr Val Leu His Gln Asp Trp Leu Asn Gly Lys Glu
                85                  90                  95

Tyr Lys Cys Lys Val Ser Asn Lys Ala Leu Pro Ala Pro Ile Glu Lys
            100                 105                 110

Thr Ile Ser Lys Ala Lys Gly Gln Pro Arg Glu Pro Gln Val Tyr Thr
        115                 120                 125

Leu Pro Pro Ser Arg Glu Glu Met Thr Lys Asn Gln Val Ser Leu Thr
    130                 135                 140

Cys Leu Val Lys Gly Phe Tyr Pro Ser Asp Ile Ala Val Glu Trp Glu
145                 150                 155                 160

Ser Asn Gly Gln Pro Glu Asn Asn Tyr Lys Thr Thr Pro Pro Val Leu
                165                 170                 175

Asp Ser Asp Gly Ser Phe Phe Leu Tyr Ser Lys Leu Thr Val Asp Lys
            180                 185                 190

Ser Arg Trp Gln Gln Gly Asn Val Phe Ser Cys Ser Val Met His Glu
        195                 200                 205

Ala Leu His Asn His Tyr Thr Gln Lys Ser Leu Ser Leu Ser Pro Gly
    210                 215                 220

Lys Gly Gly Ser Ala Gln Leu Lys Lys Lys Leu Gln Ala Leu Lys Lys
225                 230                 235                 240
```

```
Lys Asn Ala Gln Leu Lys Trp Lys Leu Gln Ala Leu Lys Lys Lys Leu
                245                 250                 255

Ala Gln Gly Ala Thr
            260
```

<210> SEQ ID NO 215

<400> SEQUENCE: 215

000

<210> SEQ ID NO 216

<400> SEQUENCE: 216

000

<210> SEQ ID NO 217

<400> SEQUENCE: 217

000

<210> SEQ ID NO 218

<400> SEQUENCE: 218

000

<210> SEQ ID NO 219

<400> SEQUENCE: 219

000

<210> SEQ ID NO 220

<400> SEQUENCE: 220

000

<210> SEQ ID NO 221

<400> SEQUENCE: 221

000

<210> SEQ ID NO 222

<400> SEQUENCE: 222

000

<210> SEQ ID NO 223

<400> SEQUENCE: 223

000

<210> SEQ ID NO 224

<400> SEQUENCE: 224

000

<210> SEQ ID NO 225

<400> SEQUENCE: 225

000

<210> SEQ ID NO 226

<400> SEQUENCE: 226

000

<210> SEQ ID NO 227

<400> SEQUENCE: 227

000

<210> SEQ ID NO 228

<400> SEQUENCE: 228

000

<210> SEQ ID NO 229

<400> SEQUENCE: 229

000

<210> SEQ ID NO 230

<400> SEQUENCE: 230

000

<210> SEQ ID NO 231

<400> SEQUENCE: 231

000

<210> SEQ ID NO 232

<400> SEQUENCE: 232

000

<210> SEQ ID NO 233

<400> SEQUENCE: 233

000

<210> SEQ ID NO 234

<400> SEQUENCE: 234

000

<210> SEQ ID NO 235

<400> SEQUENCE: 235

000

<210> SEQ ID NO 236

<400> SEQUENCE: 236

000

<210> SEQ ID NO 237

<400> SEQUENCE: 237

000

<210> SEQ ID NO 238

<400> SEQUENCE: 238

000

<210> SEQ ID NO 239

<400> SEQUENCE: 239

000

<210> SEQ ID NO 240

<400> SEQUENCE: 240

000

<210> SEQ ID NO 241

<400> SEQUENCE: 241

000

<210> SEQ ID NO 242

<400> SEQUENCE: 242

000

<210> SEQ ID NO 243

<400> SEQUENCE: 243

000

<210> SEQ ID NO 244

<400> SEQUENCE: 244

000

<210> SEQ ID NO 245

<400> SEQUENCE: 245

000

<210> SEQ ID NO 246

<400> SEQUENCE: 246

000

<210> SEQ ID NO 247

<400> SEQUENCE: 247

000

<210> SEQ ID NO 248

<400> SEQUENCE: 248

000

<210> SEQ ID NO 249

<400> SEQUENCE: 249

000

<210> SEQ ID NO 250

<400> SEQUENCE: 250

000

<210> SEQ ID NO 251

<400> SEQUENCE: 251

000

<210> SEQ ID NO 252

<400> SEQUENCE: 252

000

<210> SEQ ID NO 253

<400> SEQUENCE: 253

000

<210> SEQ ID NO 254

<400> SEQUENCE: 254

000

<210> SEQ ID NO 255

<400> SEQUENCE: 255

000

<210> SEQ ID NO 256

<400> SEQUENCE: 256

000

<210> SEQ ID NO 257

<400> SEQUENCE: 257

000

<210> SEQ ID NO 258

<400> SEQUENCE: 258

000

<210> SEQ ID NO 259

<400> SEQUENCE: 259

000

<210> SEQ ID NO 260

<400> SEQUENCE: 260

000

<210> SEQ ID NO 261

<400> SEQUENCE: 261

000

<210> SEQ ID NO 262

<400> SEQUENCE: 262

000

<210> SEQ ID NO 263

<400> SEQUENCE: 263

000

<210> SEQ ID NO 264

<400> SEQUENCE: 264

000

<210> SEQ ID NO 265

<400> SEQUENCE: 265

000

<210> SEQ ID NO 266

<400> SEQUENCE: 266

000

<210> SEQ ID NO 267

<400> SEQUENCE: 267

000

<210> SEQ ID NO 268

<400> SEQUENCE: 268

000

<210> SEQ ID NO 269

<400> SEQUENCE: 269

000

<210> SEQ ID NO 270

<400> SEQUENCE: 270

000

<210> SEQ ID NO 271

<400> SEQUENCE: 271

000

<210> SEQ ID NO 272

<400> SEQUENCE: 272

000

<210> SEQ ID NO 273

<400> SEQUENCE: 273

000

<210> SEQ ID NO 274

<400> SEQUENCE: 274

000

<210> SEQ ID NO 275

<400> SEQUENCE: 275

000

<210> SEQ ID NO 276

<400> SEQUENCE: 276

000

<210> SEQ ID NO 277

<400> SEQUENCE: 277

000

<210> SEQ ID NO 278

<400> SEQUENCE: 278

000

<210> SEQ ID NO 279

<400> SEQUENCE: 279

000

<210> SEQ ID NO 280

<400> SEQUENCE: 280

000

<210> SEQ ID NO 281

<400> SEQUENCE: 281

000

<210> SEQ ID NO 282

<400> SEQUENCE: 282

000

<210> SEQ ID NO 283

<400> SEQUENCE: 283

000

<210> SEQ ID NO 284

<400> SEQUENCE: 284

000

<210> SEQ ID NO 285

<400> SEQUENCE: 285

000

<210> SEQ ID NO 286

<400> SEQUENCE: 286

000

<210> SEQ ID NO 287

<400> SEQUENCE: 287

000

<210> SEQ ID NO 288

<400> SEQUENCE: 288

000

<210> SEQ ID NO 289

<400> SEQUENCE: 289

000

<210> SEQ ID NO 290

<400> SEQUENCE: 290

000

<210> SEQ ID NO 291

<400> SEQUENCE: 291

000

<210> SEQ ID NO 292

<400> SEQUENCE: 292

000

<210> SEQ ID NO 293

<400> SEQUENCE: 293

000

<210> SEQ ID NO 294

<400> SEQUENCE: 294

000

<210> SEQ ID NO 295

<400> SEQUENCE: 295

000

<210> SEQ ID NO 296

<400> SEQUENCE: 296

000

<210> SEQ ID NO 297

<400> SEQUENCE: 297

000

<210> SEQ ID NO 298

<400> SEQUENCE: 298

000

<210> SEQ ID NO 299

<400> SEQUENCE: 299

000

<210> SEQ ID NO 300

<400> SEQUENCE: 300

000

<210> SEQ ID NO 301
<211> LENGTH: 443
<212> TYPE: PRT
<213> ORGANISM: Homo sapiens

<400> SEQUENCE: 301

```
Met Leu Thr Asn Gly Lys Glu Gln Val Ile Lys Ser Cys Val Ser Leu
1               5                   10                  15

Pro Glu Leu Asn Ala Gln Val Phe Cys His Ser Ser Asn Asn Val Thr
            20                  25                  30

Lys Thr Glu Cys Cys Phe Thr Asp Phe Cys Asn Asn Ile Thr Leu His
        35                  40                  45

Leu Pro Thr Ala Ser Pro Asn Ala Pro Lys Leu Gly Pro Met Glu Leu
    50                  55                  60

Ala Ile Ile Ile Thr Val Pro Val Cys Leu Leu Ser Ile Ala Ala Met
65                  70                  75                  80
```

-continued

```
Leu Thr Val Trp Ala Cys Gln Gly Arg Gln Cys Ser Tyr Arg Lys Lys
                85                  90                  95

Lys Arg Pro Asn Val Glu Glu Pro Leu Ser Glu Cys Asn Leu Val Asn
            100                 105                 110

Ala Gly Lys Thr Leu Lys Asp Leu Ile Tyr Asp Val Thr Ala Ser Gly
        115                 120                 125

Ser Gly Ser Gly Leu Pro Leu Leu Val Gln Arg Thr Ile Ala Arg Thr
    130                 135                 140

Ile Val Leu Gln Glu Ile Val Gly Lys Gly Arg Phe Gly Glu Val Trp
145                 150                 155                 160

His Gly Arg Trp Cys Gly Glu Asp Val Ala Val Lys Ile Phe Ser Ser
                165                 170                 175

Arg Asp Glu Arg Ser Trp Phe Arg Glu Ala Glu Ile Tyr Gln Thr Val
            180                 185                 190

Met Leu Arg His Glu Asn Ile Leu Gly Phe Ile Ala Ala Asp Asn Lys
        195                 200                 205

Asp Asn Gly Thr Trp Thr Gln Leu Trp Leu Val Ser Glu Tyr His Glu
    210                 215                 220

Gln Gly Ser Leu Tyr Asp Tyr Leu Asn Arg Asn Ile Val Thr Val Ala
225                 230                 235                 240

Gly Met Ile Lys Leu Ala Leu Ser Ile Ala Ser Gly Leu Ala His Leu
                245                 250                 255

His Met Glu Ile Val Gly Thr Gln Gly Lys Pro Ala Ile Ala His Arg
            260                 265                 270

Asp Ile Lys Ser Lys Asn Ile Leu Val Lys Lys Cys Glu Thr Cys Ala
        275                 280                 285

Ile Ala Asp Leu Gly Leu Ala Val Lys His Asp Ser Ile Leu Asn Thr
    290                 295                 300

Ile Asp Ile Pro Gln Asn Pro Lys Val Gly Thr Lys Arg Tyr Met Ala
305                 310                 315                 320

Pro Glu Met Leu Asp Asp Thr Met Asn Val Asn Ile Phe Glu Ser Phe
                325                 330                 335

Lys Arg Ala Asp Ile Tyr Ser Val Gly Leu Val Tyr Trp Glu Ile Ala
            340                 345                 350

Arg Arg Cys Ser Val Gly Gly Ile Val Glu Glu Tyr Gln Leu Pro Tyr
        355                 360                 365

Tyr Asp Met Val Pro Ser Asp Pro Ser Ile Glu Glu Met Arg Lys Val
    370                 375                 380

Val Cys Asp Gln Lys Phe Arg Pro Ser Ile Pro Asn Gln Trp Gln Ser
385                 390                 395                 400

Cys Glu Ala Leu Arg Val Met Gly Arg Ile Met Arg Glu Cys Trp Tyr
                405                 410                 415

Ala Asn Gly Ala Ala Arg Leu Thr Ala Leu Arg Ile Lys Lys Thr Ile
            420                 425                 430

Ser Gln Leu Cys Val Lys Glu Asp Cys Lys Ala
        435                 440
```

<210> SEQ ID NO 302
<211> LENGTH: 63
<212> TYPE: PRT
<213> ORGANISM: Homo sapiens

<400> SEQUENCE: 302

```
Met Leu Thr Asn Gly Lys Glu Gln Val Ile Lys Ser Cys Val Ser Leu
1               5                   10                  15
```

Pro Glu Leu Asn Ala Gln Val Phe Cys His Ser Ser Asn Asn Val Thr
            20                  25                  30

Lys Thr Glu Cys Cys Phe Thr Asp Phe Cys Asn Asn Ile Thr Leu His
        35                  40                  45

Leu Pro Thr Ala Ser Pro Asn Ala Pro Lys Leu Gly Pro Met Glu
    50                  55                  60

<210> SEQ ID NO 303
<211> LENGTH: 1329
<212> TYPE: DNA
<213> ORGANISM: Homo sapiens

<400> SEQUENCE: 303
atgctaacca atggaaaaga gcaggtgatc aaatcctgtg tctcccttcc agaactgaat 60
gctcaagtct tctgtcatag ttccaacaat gttaccaaaa ccgaatgctg cttcacagat 120
ttttgcaaca acataacact gcaccttcca acagcatcac caaatgcccc aaaacttgga 180
cccatggagc tggccatcat tattactgtg cctgtttgcc tcctgtccat agctgcgatg 240
ctgacagtat gggcatgcca gggtcgacag tgctcctaca ggaagaaaaa gagaccaaat 300
gtggaggaac cactctctga gtgcaatctg gtaaatgctg gaaaaactct gaaagatctg 360
atttatgatg tgaccgcctc tggatctggc tctggtctac ctctgttggt tcaaaggaca 420
attgcaagga cgattgtgct tcaggaaata gtaggaaaag gtagatttgg tgaggtgtgg 480
catggaagat ggtgtgggga agatgtggct gtgaaaatat tctcctccag agatgaaaga 540
tcttggtttc gtgaggcaga aatttaccag acggtcatgc tgcgacatga aaacatcctt 600
ggtttcattg ctgctgacaa caaagataat ggaacttgga ctcaactttg gctggtatct 660
gaatatcatg aacagggctc cttatatgac tatttgaata gaaatatagt gaccgtggct 720
ggaatgatca agctggcgct ctcaattgct agtggtctgg cacaccttca tatggagatt 780
gttggtacac aaggtaaacc tgctattgct catcgagaca taaaatcaaa gaatatctta 840
gtgaaaaagt gtgaaacttg tgccatagcg gacttagggt tggctgtgaa gcatgattca 900
atactgaaca ctatcgacat acctcagaat cctaaagtgg gaaccaagag gtatatggct 960
cctgaaatgc ttgatgatac aatgaatgtg aatatctttg agtccttcaa acgagctgac 1020
atctattctg ttggtctggt ttactgggaa atagcccgga ggtgttcagt cggaggaatt 1080
gttgaggagt accaattgcc ttattatgac atggtgcctt cagatccctc gatagaggaa 1140
atgagaaagg ttgtttgtga ccagaagttt cgaccaagta tcccaaacca gtggcaaagt 1200
tgtgaagcac tccgagtcat ggggagaata atgcgtgagt gttggtatgc caacggagcg 1260
gcccgcctaa ctgctcttcg tattaagaag actatatctc aactttgtgt caaagaagac 1320
tgcaaagcc 1329

<210> SEQ ID NO 304
<211> LENGTH: 189
<212> TYPE: DNA
<213> ORGANISM: Homo sapiens

<400> SEQUENCE: 304
atgctaacca atggaaaaga gcaggtgatc aaatcctgtg tctcccttcc agaactgaat 60
gctcaagtct tctgtcatag ttccaacaat gttaccaaaa ccgaatgctg cttcacagat 120
ttttgcaaca acataacact gcaccttcca acagcatcac caaatgcccc aaaacttgga 180
cccatggag 189

<210> SEQ ID NO 305
<211> LENGTH: 413
<212> TYPE: PRT
<213> ORGANISM: Homo sapiens

<400> SEQUENCE: 305

```
Met Thr Arg Ala Leu Cys Ser Ala Leu Arg Gln Ala Leu Leu Leu Leu
1               5                   10                  15

Ala Ala Ala Ala Glu Leu Ser Pro Gly Leu Lys Cys Val Cys Leu Leu
            20                  25                  30

Cys Asp Ser Ser Asn Phe Thr Cys Gln Thr Glu Gly Ala Cys Trp Ala
        35                  40                  45

Ser Val Met Leu Thr Asn Gly Lys Glu Gln Val Ile Lys Ser Cys Val
    50                  55                  60

Ser Leu Pro Glu Leu Asn Ala Gln Val Phe Cys His Ser Ser Asn Asn
65                  70                  75                  80

Val Thr Lys Thr Glu Cys Cys Phe Thr Asp Phe Cys Asn Asn Ile Thr
                85                  90                  95

Leu His Leu Pro Thr Gly Leu Pro Leu Leu Val Gln Arg Thr Ile Ala
            100                 105                 110

Arg Thr Ile Val Leu Gln Glu Ile Val Gly Lys Gly Arg Phe Gly Glu
        115                 120                 125

Val Trp His Gly Arg Trp Cys Gly Glu Asp Val Ala Val Lys Ile Phe
    130                 135                 140

Ser Ser Arg Asp Glu Arg Ser Trp Phe Arg Glu Ala Glu Ile Tyr Gln
145                 150                 155                 160

Thr Val Met Leu Arg His Glu Asn Ile Leu Gly Phe Ile Ala Ala Asp
                165                 170                 175

Asn Lys Asp Asn Gly Thr Trp Thr Gln Leu Trp Leu Val Ser Glu Tyr
            180                 185                 190

His Glu Gln Gly Ser Leu Tyr Asp Tyr Leu Asn Arg Asn Ile Val Thr
        195                 200                 205

Val Ala Gly Met Ile Lys Leu Ala Leu Ser Ile Ala Ser Gly Leu Ala
    210                 215                 220

His Leu His Met Glu Ile Val Gly Thr Gln Gly Lys Pro Ala Ile Ala
225                 230                 235                 240

His Arg Asp Ile Lys Ser Lys Asn Ile Leu Val Lys Lys Cys Glu Thr
                245                 250                 255

Cys Ala Ile Ala Asp Leu Gly Leu Ala Val Lys His Asp Ser Ile Leu
            260                 265                 270

Asn Thr Ile Asp Ile Pro Gln Asn Pro Lys Val Gly Thr Lys Arg Tyr
        275                 280                 285

Met Ala Pro Glu Met Leu Asp Asp Thr Met Asn Val Asn Ile Phe Glu
    290                 295                 300

Ser Phe Lys Arg Ala Asp Ile Tyr Ser Val Gly Leu Val Tyr Trp Glu
305                 310                 315                 320

Ile Ala Arg Arg Cys Ser Val Gly Gly Ile Val Glu Glu Tyr Gln Leu
                325                 330                 335

Pro Tyr Tyr Asp Met Val Pro Ser Asp Pro Ser Ile Glu Glu Met Arg
            340                 345                 350

Lys Val Val Cys Asp Gln Lys Phe Arg Pro Ser Ile Pro Asn Gln Trp
        355                 360                 365

Gln Ser Cys Glu Ala Leu Arg Val Met Gly Arg Ile Met Arg Glu Cys
```

```
    370                 375                 380

Trp Tyr Ala Asn Gly Ala Ala Arg Leu Thr Ala Leu Arg Ile Lys Lys
385                 390                 395                 400

Thr Ile Ser Gln Leu Cys Val Lys Glu Asp Cys Lys Ala
                405                 410


<210> SEQ ID NO 306
<211> LENGTH: 393
<212> TYPE: PRT
<213> ORGANISM: Homo sapiens

<400> SEQUENCE: 306

Glu Leu Ser Pro Gly Leu Lys Cys Val Cys Leu Leu Cys Asp Ser Ser
1               5                   10                  15

Asn Phe Thr Cys Gln Thr Glu Gly Ala Cys Trp Ala Ser Val Met Leu
            20                  25                  30

Thr Asn Gly Lys Glu Gln Val Ile Lys Ser Cys Val Ser Leu Pro Glu
        35                  40                  45

Leu Asn Ala Gln Val Phe Cys His Ser Ser Asn Asn Val Thr Lys Thr
    50                  55                  60

Glu Cys Cys Phe Thr Asp Phe Cys Asn Asn Ile Thr Leu His Leu Pro
65                  70                  75                  80

Thr Gly Leu Pro Leu Leu Val Gln Arg Thr Ile Ala Arg Thr Ile Val
                85                  90                  95

Leu Gln Glu Ile Val Gly Lys Gly Arg Phe Gly Glu Val Trp His Gly
            100                 105                 110

Arg Trp Cys Gly Glu Asp Val Ala Val Lys Ile Phe Ser Ser Arg Asp
        115                 120                 125

Glu Arg Ser Trp Phe Arg Glu Ala Glu Ile Tyr Gln Thr Val Met Leu
    130                 135                 140

Arg His Glu Asn Ile Leu Gly Phe Ile Ala Ala Asp Asn Lys Asp Asn
145                 150                 155                 160

Gly Thr Trp Thr Gln Leu Trp Leu Val Ser Glu Tyr His Glu Gln Gly
                165                 170                 175

Ser Leu Tyr Asp Tyr Leu Asn Arg Asn Ile Val Thr Val Ala Gly Met
            180                 185                 190

Ile Lys Leu Ala Leu Ser Ile Ala Ser Gly Leu Ala His Leu His Met
        195                 200                 205

Glu Ile Val Gly Thr Gln Gly Lys Pro Ala Ile Ala His Arg Asp Ile
    210                 215                 220

Lys Ser Lys Asn Ile Leu Val Lys Lys Cys Glu Thr Cys Ala Ile Ala
225                 230                 235                 240

Asp Leu Gly Leu Ala Val Lys His Asp Ser Ile Leu Asn Thr Ile Asp
                245                 250                 255

Ile Pro Gln Asn Pro Lys Val Gly Thr Lys Arg Tyr Met Ala Pro Glu
            260                 265                 270

Met Leu Asp Asp Thr Met Asn Val Asn Ile Phe Glu Ser Phe Lys Arg
        275                 280                 285

Ala Asp Ile Tyr Ser Val Gly Leu Val Tyr Trp Glu Ile Ala Arg Arg
    290                 295                 300

Cys Ser Val Gly Gly Ile Val Glu Glu Tyr Gln Leu Pro Tyr Tyr Asp
305                 310                 315                 320

Met Val Pro Ser Asp Pro Ser Ile Glu Glu Met Arg Lys Val Val Cys
                325                 330                 335
```

```
Asp Gln Lys Phe Arg Pro Ser Ile Pro Asn Gln Trp Gln Ser Cys Glu
            340                 345                 350

Ala Leu Arg Val Met Gly Arg Ile Met Arg Glu Cys Trp Tyr Ala Asn
        355                 360                 365

Gly Ala Ala Arg Leu Thr Ala Leu Arg Ile Lys Lys Thr Ile Ser Gln
    370                 375                 380

Leu Cys Val Lys Glu Asp Cys Lys Ala
385                 390


<210> SEQ ID NO 307
<211> LENGTH: 1239
<212> TYPE: DNA
<213> ORGANISM: Homo sapiens

<400> SEQUENCE: 307

atgacccggg cgctctgctc agcgctccgc caggctctcc tgctgctcgc agcggccgcc      60

gagctctcgc caggactgaa gtgtgtatgt cttttgtgtg attcttcaaa ctttacctgc     120

caaacagaag gagcatgttg ggcatcagtc atgctaacca atggaaaaga gcaggtgatc     180

aaatcctgtg tctcccttcc agaactgaat gctcaagtct tctgtcatag ttccaacaat     240

gttaccaaaa ccgaatgctg cttcacagat tttgcaaca acataacact gcaccttcca      300

acaggtctac ctctgttggt tcaaaggaca attgcaagga cgattgtgct tcaggaaata     360

gtaggaaaag gtagatttgg tgaggtgtgg catggaagat ggtgtgggga agatgtggct     420

gtgaaaatat tctcctccag agatgaaaga tcttggtttc gtgaggcaga aatttaccag     480

acggtcatgc tgcgacatga aaacatcctt ggtttcattg ctgctgacaa caaagataat     540

ggaacttgga ctcaactttg gctggtatct gaatatcatg aacagggctc cttatatgac     600

tatttgaata gaaatatagt gaccgtggct ggaatgatca agctggcgct ctcaattgct     660

agtggtctgg cacaccttca tatggagatt gttggtacac aaggtaaacc tgctattgct     720

catcgagaca taaaatcaaa gaatatctta gtgaaaaagt gtgaaacttg tgccatagcg     780

gacttagggt tggctgtgaa gcatgattca atactgaaca ctatcgacat acctcagaat     840

cctaaagtgg gaaccaagag gtatatggct cctgaaatgc ttgatgatac aatgaatgtg     900

aatatctttg agtccttcaa acgagctgac atctattctg ttggtctggt ttactgggaa     960

atagcccgga ggtgttcagt cggaggaatt gttgaggagt accaattgcc ttattatgac    1020

atggtgcctt cagatccctc gatagaggaa atgagaaagg ttgtttgtga ccagaagttt    1080

cgaccaagta tcccaaacca gtggcaaagt tgtgaagcac tccgagtcat ggggagaata    1140

atgcgtgagt gttggtatgc caacggagcg gcccgcctaa ctgctcttcg tattaagaag    1200

actatatctc aactttgtgt caaagaagac tgcaaagcc                           1239


<210> SEQ ID NO 308
<211> LENGTH: 1179
<212> TYPE: DNA
<213> ORGANISM: Homo sapiens

<400> SEQUENCE: 308

gagctctcgc caggactgaa gtgtgtatgt cttttgtgtg attcttcaaa ctttacctgc      60

caaacagaag gagcatgttg ggcatcagtc atgctaacca atggaaaaga gcaggtgatc     120

aaatcctgtg tctcccttcc agaactgaat gctcaagtct tctgtcatag ttccaacaat     180

gttaccaaaa ccgaatgctg cttcacagat tttgcaaca acataacact gcaccttcca      240

acaggtctac ctctgttggt tcaaaggaca attgcaagga cgattgtgct tcaggaaata     300
```

```
gtaggaaaag gtagatttgg tgaggtgtgg catggaagat ggtgtgggga agatgtggct    360

gtgaaaatat tctcctccag agatgaaaga tcttggtttc gtgaggcaga aatttaccag    420

acggtcatgc tgcgacatga aaacatcctt ggtttcattg ctgctgacaa caaagataat    480

ggaacttgga ctcaactttg gctggtatct gaatatcatg aacagggctc cttatatgac    540

tatttgaata gaaatatagt gaccgtggct ggaatgatca agctggcgct ctcaattgct    600

agtggtctgg cacaccttca tatggagatt gttggtacac aaggtaaacc tgctattgct    660

catcgagaca taaaatcaaa gaatatctta gtgaaaaagt gtgaaacttg tgccatagcg    720

gacttagggt tggctgtgaa gcatgattca atactgaaca ctatcgacat acctcagaat    780

cctaaagtgg gaaccaagag gtatatggct cctgaaatgc ttgatgatac aatgaatgtg    840

aatatctttg agtccttcaa acgagctgac atctattctg ttggtctggt ttactgggaa    900

atagcccgga ggtgttcagt cggaggaatt gttgaggagt accaattgcc ttattatgac    960

atggtgcctt cagatccctc gatagaggaa atgagaaagg ttgtttgtga ccagaagttt   1020

cgaccaagta tcccaaacca gtggcaaagt tgtgaagcac tccgagtcat ggggagaata   1080

atgcgtgagt gttggtatgc caacggagcg gcccgcctaa ctgctcttcg tattaagaag   1140

actatatctc aactttgtgt caaagaagac tgcaaagcc                          1179
```

<210> SEQ ID NO 309
<211> LENGTH: 336
<212> TYPE: PRT
<213> ORGANISM: Homo sapiens

<400> SEQUENCE: 309

```
Met Thr Arg Ala Leu Cys Ser Ala Leu Arg Gln Ala Leu Leu Leu Leu
1               5                   10                  15

Ala Ala Ala Ala Glu Leu Ser Pro Gly Leu Lys Cys Val Cys Leu Leu
            20                  25                  30

Cys Asp Ser Ser Asn Phe Thr Cys Gln Thr Glu Gly Ala Cys Trp Ala
        35                  40                  45

Ser Val Met Leu Thr Asn Gly Lys Glu Gln Val Ile Lys Ser Cys Val
    50                  55                  60

Ser Leu Pro Glu Leu Asn Ala Gln Val Phe Cys His Ser Ser Asn Asn
65                  70                  75                  80

Val Thr Lys Thr Glu Cys Cys Phe Thr Asp Phe Cys Asn Asn Ile Thr
                85                  90                  95

Leu His Leu Pro Thr Asp Asn Gly Thr Trp Thr Gln Leu Trp Leu Val
            100                 105                 110

Ser Glu Tyr His Glu Gln Gly Ser Leu Tyr Asp Tyr Leu Asn Arg Asn
        115                 120                 125

Ile Val Thr Val Ala Gly Met Ile Lys Leu Ala Leu Ser Ile Ala Ser
    130                 135                 140

Gly Leu Ala His Leu His Met Glu Ile Val Gly Thr Gln Gly Lys Pro
145                 150                 155                 160

Ala Ile Ala His Arg Asp Ile Lys Ser Lys Asn Ile Leu Val Lys Lys
                165                 170                 175

Cys Glu Thr Cys Ala Ile Ala Asp Leu Gly Leu Ala Val Lys His Asp
            180                 185                 190

Ser Ile Leu Asn Thr Ile Asp Ile Pro Gln Asn Pro Lys Val Gly Thr
        195                 200                 205

Lys Arg Tyr Met Ala Pro Glu Met Leu Asp Asp Thr Met Asn Val Asn
```

```
    210                 215                 220

Ile Phe Glu Ser Phe Lys Arg Ala Asp Ile Tyr Ser Val Gly Leu Val
225                 230                 235                 240

Tyr Trp Glu Ile Ala Arg Arg Cys Ser Val Gly Gly Ile Val Glu Glu
                245                 250                 255

Tyr Gln Leu Pro Tyr Tyr Asp Met Val Pro Ser Asp Pro Ser Ile Glu
            260                 265                 270

Glu Met Arg Lys Val Val Cys Asp Gln Lys Phe Arg Pro Ser Ile Pro
        275                 280                 285

Asn Gln Trp Gln Ser Cys Glu Ala Leu Arg Val Met Gly Arg Ile Met
    290                 295                 300

Arg Glu Cys Trp Tyr Ala Asn Gly Ala Ala Arg Leu Thr Ala Leu Arg
305                 310                 315                 320

Ile Lys Lys Thr Ile Ser Gln Leu Cys Val Lys Glu Asp Cys Lys Ala
                325                 330                 335


<210> SEQ ID NO 310
<211> LENGTH: 316
<212> TYPE: PRT
<213> ORGANISM: Homo sapiens

<400> SEQUENCE: 310

Glu Leu Ser Pro Gly Leu Lys Cys Val Cys Leu Leu Cys Asp Ser Ser
1               5                   10                  15

Asn Phe Thr Cys Gln Thr Glu Gly Ala Cys Trp Ala Ser Val Met Leu
            20                  25                  30

Thr Asn Gly Lys Glu Gln Val Ile Lys Ser Cys Val Ser Leu Pro Glu
        35                  40                  45

Leu Asn Ala Gln Val Phe Cys His Ser Ser Asn Asn Val Thr Lys Thr
    50                  55                  60

Glu Cys Cys Phe Thr Asp Phe Cys Asn Asn Ile Thr Leu His Leu Pro
65                  70                  75                  80

Thr Asp Asn Gly Thr Trp Thr Gln Leu Trp Leu Val Ser Glu Tyr His
                85                  90                  95

Glu Gln Gly Ser Leu Tyr Asp Tyr Leu Asn Arg Asn Ile Val Thr Val
            100                 105                 110

Ala Gly Met Ile Lys Leu Ala Leu Ser Ile Ala Ser Gly Leu Ala His
        115                 120                 125

Leu His Met Glu Ile Val Gly Thr Gln Gly Lys Pro Ala Ile Ala His
    130                 135                 140

Arg Asp Ile Lys Ser Lys Asn Ile Leu Val Lys Lys Cys Glu Thr Cys
145                 150                 155                 160

Ala Ile Ala Asp Leu Gly Leu Ala Val Lys His Asp Ser Ile Leu Asn
                165                 170                 175

Thr Ile Asp Ile Pro Gln Asn Pro Lys Val Gly Thr Lys Arg Tyr Met
            180                 185                 190

Ala Pro Glu Met Leu Asp Asp Thr Met Asn Val Asn Ile Phe Glu Ser
        195                 200                 205

Phe Lys Arg Ala Asp Ile Tyr Ser Val Gly Leu Val Tyr Trp Glu Ile
    210                 215                 220

Ala Arg Arg Cys Ser Val Gly Gly Ile Val Glu Glu Tyr Gln Leu Pro
225                 230                 235                 240

Tyr Tyr Asp Met Val Pro Ser Asp Pro Ser Ile Glu Glu Met Arg Lys
                245                 250                 255
```

-continued

```
Val Val Cys Asp Gln Lys Phe Arg Pro Ser Ile Pro Asn Gln Trp Gln
            260                 265                 270

Ser Cys Glu Ala Leu Arg Val Met Gly Arg Ile Met Arg Glu Cys Trp
        275                 280                 285

Tyr Ala Asn Gly Ala Ala Arg Leu Thr Ala Leu Arg Ile Lys Lys Thr
    290                 295                 300

Ile Ser Gln Leu Cys Val Lys Glu Asp Cys Lys Ala
305                 310                 315


<210> SEQ ID NO 311
<211> LENGTH: 1011
<212> TYPE: DNA
<213> ORGANISM: Homo sapiens

<400> SEQUENCE: 311

atgacccggg cgctctgctc agcgctccgc caggctctcc tgctgctcgc agcggccgcc     60

gagctctcgc caggactgaa gtgtgtatgt cttttgtgtg attcttcaaa ctttacctgc    120

caaacagaag gagcatgttg ggcatcagtc atgctaacca atggaaaaga gcaggtgatc    180

aaatcctgtg tctcccttcc agaactgaat gctcaagtct tctgtcatag ttccaacaat    240

gttaccaaaa ccgaatgctg cttcacagat ttttgcaaca acataacact gcaccttcca    300

acagataatg gaacttggac tcaactttgg ctggtatctg aatatcatga acagggctcc    360

ttatatgact atttgaatag aaatatagtg accgtggctg gaatgatcaa gctggcgctc    420

tcaattgcta gtggtctggc acaccttcat atggagattg ttggtacaca aggtaaacct    480

gctattgctc atcgagacat aaaatcaaag aatatcttag tgaaaaagtg tgaaacttgt    540

gccatagcgg acttagggtt ggctgtgaag catgattcaa tactgaacac tatcgacata    600

cctcagaatc ctaaagtggg aaccaagagg tatatggctc ctgaaatgct tgatgataca    660

atgaatgtga atatctttga gtccttcaaa cgagctgaca tctattctgt tggtctggtt    720

tactgggaaa tagcccggag gtgttcagtc ggaggaattg ttgaggagta ccaattgcct    780

tattatgaca tggtgccttc agatccctcg atagaggaaa tgagaaaggt tgtttgtgac    840

cagaagtttc gaccaagtat cccaaaccag tggcaaagtt gtgaagcact ccgagtcatg    900

gggagaataa tgcgtgagtg ttggtatgcc aacggagcgg cccgcctaac tgctcttcgt    960

attaagaaga ctatatctca actttgtgtc aaagaagact gcaaagccta a            1011


<210> SEQ ID NO 312
<211> LENGTH: 951
<212> TYPE: DNA
<213> ORGANISM: Homo sapiens

<400> SEQUENCE: 312

gagctctcgc caggactgaa gtgtgtatgt cttttgtgtg attcttcaaa ctttacctgc     60

caaacagaag gagcatgttg ggcatcagtc atgctaacca atggaaaaga gcaggtgatc    120

aaatcctgtg tctcccttcc agaactgaat gctcaagtct tctgtcatag ttccaacaat    180

gttaccaaaa ccgaatgctg cttcacagat ttttgcaaca acataacact gcaccttcca    240

acagataatg gaacttggac tcaactttgg ctggtatctg aatatcatga acagggctcc    300

ttatatgact atttgaatag aaatatagtg accgtggctg gaatgatcaa gctggcgctc    360

tcaattgcta gtggtctggc acaccttcat atggagattg ttggtacaca aggtaaacct    420

gctattgctc atcgagacat aaaatcaaag aatatcttag tgaaaaagtg tgaaacttgt    480

gccatagcgg acttagggtt ggctgtgaag catgattcaa tactgaacac tatcgacata    540
```

```
cctcagaatc ctaaagtggg aaccaagagg tatatggctc ctgaaatgct tgatgataca    600

atgaatgtga atatctttga gtccttcaaa cgagctgaca tctattctgt tggtctggtt    660

tactgggaaa tagcccggag gtgttcagtc ggaggaattg ttgaggagta ccaattgcct    720

tattatgaca tggtgccttc agatccctcg atagaggaaa tgagaaaggt tgtttgtgac    780

cagaagtttc gaccaagtat cccaaaccag tggcaaagtt gtgaagcact ccgagtcatg    840

gggagaataa tgcgtgagtg ttggtatgcc aacggagcgg cccgcctaac tgctcttcgt    900

attaagaaga ctatatctca actttgtgtc aaagaagact gcaaagccta a             951
```

<210> SEQ ID NO 313
<211> LENGTH: 88
<212> TYPE: PRT
<213> ORGANISM: Homo sapiens

<400> SEQUENCE: 313

```
Leu Lys Cys Val Cys Leu Leu Cys Asp Ser Ser Asn Phe Thr Cys Gln
1               5                   10                  15

Thr Glu Gly Ala Cys Trp Ala Ser Val Met Leu Thr Asn Gly Lys Glu
            20                  25                  30

Gln Val Ile Lys Ser Cys Val Ser Leu Pro Glu Leu Asn Ala Gln Val
        35                  40                  45

Phe Cys His Ser Ser Asn Asn Val Thr Lys Thr Glu Cys Cys Phe Thr
    50                  55                  60

Asp Phe Cys Asn Asn Ile Thr Leu His Leu Pro Thr Ala Ser Pro Asn
65                  70                  75                  80

Ala Pro Lys Leu Gly Pro Met Glu
                85
```

<210> SEQ ID NO 314

<400> SEQUENCE: 314

000

<210> SEQ ID NO 315

<400> SEQUENCE: 315

000

<210> SEQ ID NO 316

<400> SEQUENCE: 316

000

<210> SEQ ID NO 317

<400> SEQUENCE: 317

000

<210> SEQ ID NO 318

<400> SEQUENCE: 318

000

<210> SEQ ID NO 319

<400> SEQUENCE: 319

000

<210> SEQ ID NO 320

<400> SEQUENCE: 320

000

<210> SEQ ID NO 321

<400> SEQUENCE: 321

000

<210> SEQ ID NO 322

<400> SEQUENCE: 322

000

<210> SEQ ID NO 323

<400> SEQUENCE: 323

000

<210> SEQ ID NO 324

<400> SEQUENCE: 324

000

<210> SEQ ID NO 325

<400> SEQUENCE: 325

000

<210> SEQ ID NO 326

<400> SEQUENCE: 326

000

<210> SEQ ID NO 327

<400> SEQUENCE: 327

000

<210> SEQ ID NO 328

<400> SEQUENCE: 328

000

<210> SEQ ID NO 329

<400> SEQUENCE: 329

000

<210> SEQ ID NO 330

<400> SEQUENCE: 330

000

<210> SEQ ID NO 331

<400> SEQUENCE: 331

000

<210> SEQ ID NO 332

<400> SEQUENCE: 332

000

<210> SEQ ID NO 333

<400> SEQUENCE: 333

000

<210> SEQ ID NO 334

<400> SEQUENCE: 334

000

<210> SEQ ID NO 335

<400> SEQUENCE: 335

000

<210> SEQ ID NO 336

<400> SEQUENCE: 336

000

<210> SEQ ID NO 337

<400> SEQUENCE: 337

000

<210> SEQ ID NO 338

<400> SEQUENCE: 338

000

<210> SEQ ID NO 339

<400> SEQUENCE: 339

000

<210> SEQ ID NO 340

<400> SEQUENCE: 340

000

<210> SEQ ID NO 341

<400> SEQUENCE: 341

000

<210> SEQ ID NO 342

<400> SEQUENCE: 342

000

<210> SEQ ID NO 343

<400> SEQUENCE: 343

000

<210> SEQ ID NO 344

<400> SEQUENCE: 344

000

<210> SEQ ID NO 345

<400> SEQUENCE: 345

000

<210> SEQ ID NO 346

<400> SEQUENCE: 346

000

<210> SEQ ID NO 347

<400> SEQUENCE: 347

000

<210> SEQ ID NO 348

<400> SEQUENCE: 348

000

<210> SEQ ID NO 349

<400> SEQUENCE: 349

000

<210> SEQ ID NO 350

<400> SEQUENCE: 350

000

<210> SEQ ID NO 351

<400> SEQUENCE: 351

000

<210> SEQ ID NO 352

<400> SEQUENCE: 352

000

<210> SEQ ID NO 353

<400> SEQUENCE: 353

000

<210> SEQ ID NO 354

<400> SEQUENCE: 354

000

<210> SEQ ID NO 355

<400> SEQUENCE: 355

000

<210> SEQ ID NO 356

<400> SEQUENCE: 356

000

<210> SEQ ID NO 357

<400> SEQUENCE: 357

000

<210> SEQ ID NO 358

<400> SEQUENCE: 358

000

<210> SEQ ID NO 359

<400> SEQUENCE: 359

000

<210> SEQ ID NO 360

<400> SEQUENCE: 360

000

<210> SEQ ID NO 361

<400> SEQUENCE: 361

000

<210> SEQ ID NO 362

<400> SEQUENCE: 362

000

<210> SEQ ID NO 363

<400> SEQUENCE: 363

000

<210> SEQ ID NO 364

<400> SEQUENCE: 364

000

<210> SEQ ID NO 365

<400> SEQUENCE: 365

000

<210> SEQ ID NO 366

<400> SEQUENCE: 366

000

<210> SEQ ID NO 367

<400> SEQUENCE: 367

000

<210> SEQ ID NO 368

<400> SEQUENCE: 368

000

<210> SEQ ID NO 369

<400> SEQUENCE: 369

000

<210> SEQ ID NO 370

<400> SEQUENCE: 370

000

<210> SEQ ID NO 371

<400> SEQUENCE: 371

000

<210> SEQ ID NO 372

<400> SEQUENCE: 372

000

<210> SEQ ID NO 373

<400> SEQUENCE: 373

000

<210> SEQ ID NO 374

<400> SEQUENCE: 374

000

<210> SEQ ID NO 375

<400> SEQUENCE: 375

000

<210> SEQ ID NO 376

<400> SEQUENCE: 376

000

<210> SEQ ID NO 377

<400> SEQUENCE: 377

000

<210> SEQ ID NO 378

<400> SEQUENCE: 378

000

<210> SEQ ID NO 379

<400> SEQUENCE: 379

000

<210> SEQ ID NO 380

<400> SEQUENCE: 380

000

<210> SEQ ID NO 381

<400> SEQUENCE: 381

000

<210> SEQ ID NO 382

<400> SEQUENCE: 382

000

<210> SEQ ID NO 383

<400> SEQUENCE: 383

000

<210> SEQ ID NO 384

<400> SEQUENCE: 384

000

<210> SEQ ID NO 385

<400> SEQUENCE: 385

000

<210> SEQ ID NO 386

<400> SEQUENCE: 386

000

<210> SEQ ID NO 387

<400> SEQUENCE: 387

000

<210> SEQ ID NO 388

<400> SEQUENCE: 388

000

<210> SEQ ID NO 389

<400> SEQUENCE: 389

000

<210> SEQ ID NO 390

<400> SEQUENCE: 390

000

<210> SEQ ID NO 391

<400> SEQUENCE: 391

000

<210> SEQ ID NO 392

<400> SEQUENCE: 392

000

<210> SEQ ID NO 393

<400> SEQUENCE: 393

000

<210> SEQ ID NO 394

<400> SEQUENCE: 394

000

<210> SEQ ID NO 395

<400> SEQUENCE: 395

000

<210> SEQ ID NO 396

<400> SEQUENCE: 396

000

<210> SEQ ID NO 397

<400> SEQUENCE: 397

000

<210> SEQ ID NO 398

<400> SEQUENCE: 398

000

<210> SEQ ID NO 399

<400> SEQUENCE: 399

000

<210> SEQ ID NO 400

<400> SEQUENCE: 400

000

<210> SEQ ID NO 401
<211> LENGTH: 369
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 401

```
Met Asp Ala Met Lys Arg Gly Leu Cys Cys Val Leu Leu Leu Cys Gly
1               5                   10                  15

Ala Val Phe Val Ser Pro Gly Ala Ala Ile Leu Gly Arg Ser Glu Thr
            20                  25                  30

Gln Glu Cys Leu Phe Phe Asn Ala Asn Trp Glu Lys Asp Arg Thr Asn
        35                  40                  45

Gln Thr Gly Val Glu Pro Cys Tyr Gly Asp Lys Asp Lys Arg Arg His
    50                  55                  60

Cys Phe Ala Thr Trp Lys Asn Ile Ser Gly Ser Ile Glu Ile Val Lys
65                  70                  75                  80

Gln Gly Cys Trp Leu Asp Asp Ile Asn Cys Tyr Asp Arg Thr Asp Cys
                85                  90                  95

Val Glu Lys Lys Asp Ser Pro Glu Val Tyr Phe Cys Cys Cys Glu Gly
            100                 105                 110

Asn Met Cys Asn Glu Lys Phe Ser Tyr Phe Pro Glu Met Glu Val Thr
        115                 120                 125

Gln Pro Thr Ser Asn Pro Val Thr Pro Lys Pro Pro Thr Gly Gly Gly
    130                 135                 140

Thr His Thr Cys Pro Pro Cys Pro Ala Pro Glu Leu Leu Gly Gly Pro
145                 150                 155                 160

Ser Val Phe Leu Phe Pro Pro Lys Pro Lys Asp Thr Leu Met Ile Ser
                165                 170                 175

Arg Thr Pro Glu Val Thr Cys Val Val Val Asp Val Ser His Glu Asp
            180                 185                 190

Pro Glu Val Lys Phe Asn Trp Tyr Val Asp Gly Val Glu Val His Asn
        195                 200                 205

Ala Lys Thr Lys Pro Arg Glu Glu Gln Tyr Asn Ser Thr Tyr Arg Val
    210                 215                 220

Val Ser Val Leu Thr Val Leu His Gln Asp Trp Leu Asn Gly Lys Glu
225                 230                 235                 240

Tyr Lys Cys Lys Val Ser Asn Lys Ala Leu Pro Ala Pro Ile Glu Lys
                245                 250                 255

Thr Ile Ser Lys Ala Lys Gly Gln Pro Arg Glu Pro Gln Val Tyr Thr
            260                 265                 270
```

```
Leu Pro Pro Cys Arg Glu Glu Met Thr Lys Asn Gln Val Ser Leu Trp
        275                 280                 285

Cys Leu Val Lys Gly Phe Tyr Pro Ser Asp Ile Ala Val Glu Trp Glu
    290                 295                 300

Ser Asn Gly Gln Pro Glu Asn Asn Tyr Lys Thr Thr Pro Pro Val Leu
305                 310                 315                 320

Asp Ser Asp Gly Ser Phe Phe Leu Tyr Ser Lys Leu Thr Val Asp Lys
                325                 330                 335

Ser Arg Trp Gln Gln Gly Asn Val Phe Ser Cys Ser Val Met His Glu
            340                 345                 350

Ala Leu His Asn His Tyr Thr Gln Lys Ser Leu Ser Leu Ser Pro Gly
        355                 360                 365

Lys


<210> SEQ ID NO 402
<211> LENGTH: 344
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 402

Ile Leu Gly Arg Ser Glu Thr Gln Glu Cys Leu Phe Phe Asn Ala Asn
1               5                   10                  15

Trp Glu Lys Asp Arg Thr Asn Gln Thr Gly Val Glu Pro Cys Tyr Gly
            20                  25                  30

Asp Lys Asp Lys Arg Arg His Cys Phe Ala Thr Trp Lys Asn Ile Ser
        35                  40                  45

Gly Ser Ile Glu Ile Val Lys Gln Gly Cys Trp Leu Asp Asp Ile Asn
    50                  55                  60

Cys Tyr Asp Arg Thr Asp Cys Val Glu Lys Lys Asp Ser Pro Glu Val
65                  70                  75                  80

Tyr Phe Cys Cys Cys Glu Gly Asn Met Cys Asn Glu Lys Phe Ser Tyr
                85                  90                  95

Phe Pro Glu Met Glu Val Thr Gln Pro Thr Ser Asn Pro Val Thr Pro
            100                 105                 110

Lys Pro Pro Thr Gly Gly Gly Thr His Thr Cys Pro Pro Cys Pro Ala
        115                 120                 125

Pro Glu Leu Leu Gly Gly Pro Ser Val Phe Leu Phe Pro Pro Lys Pro
    130                 135                 140

Lys Asp Thr Leu Met Ile Ser Arg Thr Pro Glu Val Thr Cys Val Val
145                 150                 155                 160

Val Asp Val Ser His Glu Asp Pro Glu Val Lys Phe Asn Trp Tyr Val
                165                 170                 175

Asp Gly Val Glu Val His Asn Ala Lys Thr Lys Pro Arg Glu Glu Gln
            180                 185                 190

Tyr Asn Ser Thr Tyr Arg Val Val Ser Val Leu Thr Val Leu His Gln
        195                 200                 205

Asp Trp Leu Asn Gly Lys Glu Tyr Lys Cys Lys Val Ser Asn Lys Ala
    210                 215                 220

Leu Pro Ala Pro Ile Glu Lys Thr Ile Ser Lys Ala Lys Gly Gln Pro
225                 230                 235                 240

Arg Glu Pro Gln Val Tyr Thr Leu Pro Pro Cys Arg Glu Glu Met Thr
                245                 250                 255
```

Lys Asn Gln Val Ser Leu Trp Cys Leu Val Lys Gly Phe Tyr Pro Ser
            260                 265                 270

Asp Ile Ala Val Glu Trp Glu Ser Asn Gly Gln Pro Glu Asn Asn Tyr
        275                 280                 285

Lys Thr Thr Pro Pro Val Leu Asp Ser Asp Gly Ser Phe Phe Leu Tyr
    290                 295                 300

Ser Lys Leu Thr Val Asp Lys Ser Arg Trp Gln Gln Gly Asn Val Phe
305                 310                 315                 320

Ser Cys Ser Val Met His Glu Ala Leu His Asn His Tyr Thr Gln Lys
                325                 330                 335

Ser Leu Ser Leu Ser Pro Gly Lys
            340

<210> SEQ ID NO 403
<211> LENGTH: 368
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 403

Met Asp Ala Met Lys Arg Gly Leu Cys Cys Val Leu Leu Leu Cys Gly
1               5                   10                  15

Ala Val Phe Val Ser Pro Gly Ala Ser Gly Arg Gly Glu Ala Glu Thr
            20                  25                  30

Arg Glu Cys Ile Tyr Tyr Asn Ala Asn Trp Glu Leu Glu Arg Thr Asn
        35                  40                  45

Gln Ser Gly Leu Glu Arg Cys Glu Gly Glu Gln Asp Lys Arg Leu His
    50                  55                  60

Cys Tyr Ala Ser Trp Arg Asn Ser Ser Gly Thr Ile Glu Leu Val Lys
65                  70                  75                  80

Lys Gly Cys Trp Leu Asp Asp Phe Asn Cys Tyr Asp Arg Gln Glu Cys
                85                  90                  95

Val Ala Thr Glu Glu Asn Pro Gln Val Tyr Phe Cys Cys Cys Glu Gly
            100                 105                 110

Asn Phe Cys Asn Glu Arg Phe Thr His Leu Pro Glu Ala Gly Gly Pro
        115                 120                 125

Glu Val Thr Tyr Glu Pro Pro Pro Thr Ala Pro Thr Gly Gly Gly Thr
    130                 135                 140

His Thr Cys Pro Pro Cys Pro Ala Pro Glu Leu Leu Gly Gly Pro Ser
145                 150                 155                 160

Val Phe Leu Phe Pro Pro Lys Pro Lys Asp Thr Leu Met Ile Ser Arg
                165                 170                 175

Thr Pro Glu Val Thr Cys Val Val Val Asp Val Ser His Glu Asp Pro
            180                 185                 190

Glu Val Lys Phe Asn Trp Tyr Val Asp Gly Val Glu Val His Asn Ala
        195                 200                 205

Lys Thr Lys Pro Arg Glu Glu Gln Tyr Asn Ser Thr Tyr Arg Val Val
    210                 215                 220

Ser Val Leu Thr Val Leu His Gln Asp Trp Leu Asn Gly Lys Glu Tyr
225                 230                 235                 240

Lys Cys Lys Val Ser Asn Lys Ala Leu Pro Ala Pro Ile Glu Lys Thr
                245                 250                 255

Ile Ser Lys Ala Lys Gly Gln Pro Arg Glu Pro Gln Val Tyr Thr Leu

```
            260                 265                 270

Pro Pro Cys Arg Glu Glu Met Thr Lys Asn Gln Val Ser Leu Trp Cys
        275                 280                 285

Leu Val Lys Gly Phe Tyr Pro Ser Asp Ile Ala Val Glu Trp Glu Ser
    290                 295                 300

Asn Gly Gln Pro Glu Asn Asn Tyr Lys Thr Thr Pro Pro Val Leu Asp
305                 310                 315                 320

Ser Asp Gly Ser Phe Phe Leu Tyr Ser Lys Leu Thr Val Asp Lys Ser
                325                 330                 335

Arg Trp Gln Gln Gly Asn Val Phe Ser Cys Ser Val Met His Glu Ala
            340                 345                 350

Leu His Asn His Tyr Thr Gln Lys Ser Leu Ser Leu Ser Pro Gly Lys
        355                 360                 365


<210> SEQ ID NO 404
<211> LENGTH: 343
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 404

Gly Arg Gly Glu Ala Glu Thr Arg Glu Cys Ile Tyr Tyr Asn Ala Asn
1               5                   10                  15

Trp Glu Leu Glu Arg Thr Asn Gln Ser Gly Leu Glu Arg Cys Glu Gly
            20                  25                  30

Glu Gln Asp Lys Arg Leu His Cys Tyr Ala Ser Trp Arg Asn Ser Ser
        35                  40                  45

Gly Thr Ile Glu Leu Val Lys Lys Gly Cys Trp Leu Asp Asp Phe Asn
    50                  55                  60

Cys Tyr Asp Arg Gln Glu Cys Val Ala Thr Glu Glu Asn Pro Gln Val
65                  70                  75                  80

Tyr Phe Cys Cys Cys Glu Gly Asn Phe Cys Asn Glu Arg Phe Thr His
                85                  90                  95

Leu Pro Glu Ala Gly Gly Pro Glu Val Thr Tyr Glu Pro Pro Pro Thr
            100                 105                 110

Ala Pro Thr Gly Gly Gly Thr His Thr Cys Pro Pro Cys Pro Ala Pro
        115                 120                 125

Glu Leu Leu Gly Gly Pro Ser Val Phe Leu Phe Pro Pro Lys Pro Lys
    130                 135                 140

Asp Thr Leu Met Ile Ser Arg Thr Pro Glu Val Thr Cys Val Val Val
145                 150                 155                 160

Asp Val Ser His Glu Asp Pro Glu Val Lys Phe Asn Trp Tyr Val Asp
                165                 170                 175

Gly Val Glu Val His Asn Ala Lys Thr Lys Pro Arg Glu Glu Gln Tyr
            180                 185                 190

Asn Ser Thr Tyr Arg Val Val Ser Val Leu Thr Val Leu His Gln Asp
        195                 200                 205

Trp Leu Asn Gly Lys Glu Tyr Lys Cys Lys Val Ser Asn Lys Ala Leu
    210                 215                 220

Pro Ala Pro Ile Glu Lys Thr Ile Ser Lys Ala Lys Gly Gln Pro Arg
225                 230                 235                 240

Glu Pro Gln Val Tyr Thr Leu Pro Pro Cys Arg Glu Glu Met Thr Lys
                245                 250                 255
```

```
Asn Gln Val Ser Leu Trp Cys Leu Val Lys Gly Phe Tyr Pro Ser Asp
            260                 265                 270

Ile Ala Val Glu Trp Glu Ser Asn Gly Gln Pro Glu Asn Asn Tyr Lys
        275                 280                 285

Thr Thr Pro Pro Val Leu Asp Ser Asp Gly Ser Phe Phe Leu Tyr Ser
    290                 295                 300

Lys Leu Thr Val Asp Lys Ser Arg Trp Gln Gln Gly Asn Val Phe Ser
305                 310                 315                 320

Cys Ser Val Met His Glu Ala Leu His Asn His Tyr Thr Gln Lys Ser
                325                 330                 335

Leu Ser Leu Ser Pro Gly Lys
            340


<210> SEQ ID NO 405
<211> LENGTH: 376
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 405

Met Asp Ala Met Lys Arg Gly Leu Cys Cys Val Leu Leu Leu Cys Gly
1               5                   10                  15

Ala Val Phe Val Ser Pro Gly Ala Ser Gln Asn Gln Glu Arg Leu Cys
            20                  25                  30

Ala Phe Lys Asp Pro Tyr Gln Gln Asp Leu Gly Ile Gly Glu Ser Arg
        35                  40                  45

Ile Ser His Glu Asn Gly Thr Ile Leu Cys Ser Lys Gly Ser Thr Cys
    50                  55                  60

Tyr Gly Leu Trp Glu Lys Ser Lys Gly Asp Ile Asn Leu Val Lys Gln
65                  70                  75                  80

Gly Cys Trp Ser His Ile Gly Asp Pro Gln Glu Cys His Tyr Glu Glu
                85                  90                  95

Cys Val Val Thr Thr Thr Pro Pro Ser Ile Gln Asn Gly Thr Tyr Arg
            100                 105                 110

Phe Cys Cys Cys Ser Thr Asp Leu Cys Asn Val Asn Phe Thr Glu Asn
        115                 120                 125

Phe Pro Pro Pro Asp Thr Thr Pro Leu Ser Pro Pro His Ser Phe Asn
    130                 135                 140

Arg Asp Glu Thr Gly Gly Gly Thr His Thr Cys Pro Pro Cys Pro Ala
145                 150                 155                 160

Pro Glu Leu Leu Gly Gly Pro Ser Val Phe Leu Phe Pro Pro Lys Pro
                165                 170                 175

Lys Asp Thr Leu Met Ile Ser Arg Thr Pro Glu Val Thr Cys Val Val
            180                 185                 190

Val Asp Val Ser His Glu Asp Pro Glu Val Lys Phe Asn Trp Tyr Val
        195                 200                 205

Asp Gly Val Glu Val His Asn Ala Lys Thr Lys Pro Arg Glu Glu Gln
    210                 215                 220

Tyr Asn Ser Thr Tyr Arg Val Val Ser Val Leu Thr Val Leu His Gln
225                 230                 235                 240

Asp Trp Leu Asn Gly Lys Glu Tyr Lys Cys Lys Val Ser Asn Lys Ala
                245                 250                 255

Leu Pro Ala Pro Ile Glu Lys Thr Ile Ser Lys Ala Lys Gly Gln Pro
            260                 265                 270
```

Arg Glu Pro Gln Val Tyr Thr Leu Pro Pro Cys Arg Glu Glu Met Thr
275 280 285

Lys Asn Gln Val Ser Leu Trp Cys Leu Val Lys Gly Phe Tyr Pro Ser
290 295 300

Asp Ile Ala Val Glu Trp Glu Ser Asn Gly Gln Pro Glu Asn Asn Tyr
305 310 315 320

Lys Thr Thr Pro Pro Val Leu Asp Ser Asp Gly Ser Phe Phe Leu Tyr
325 330 335

Ser Lys Leu Thr Val Asp Lys Ser Arg Trp Gln Gln Gly Asn Val Phe
340 345 350

Ser Cys Ser Val Met His Glu Ala Leu His Asn His Tyr Thr Gln Lys
355 360 365

Ser Leu Ser Leu Ser Pro Gly Lys
370 375

<210> SEQ ID NO 406
<211> LENGTH: 352
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 406

Ser Gln Asn Gln Glu Arg Leu Cys Ala Phe Lys Asp Pro Tyr Gln Gln
1 5 10 15

Asp Leu Gly Ile Gly Glu Ser Arg Ile Ser His Glu Asn Gly Thr Ile
20 25 30

Leu Cys Ser Lys Gly Ser Thr Cys Tyr Gly Leu Trp Glu Lys Ser Lys
35 40 45

Gly Asp Ile Asn Leu Val Lys Gln Gly Cys Trp Ser His Ile Gly Asp
50 55 60

Pro Gln Glu Cys His Tyr Glu Glu Cys Val Val Thr Thr Thr Pro Pro
65 70 75 80

Ser Ile Gln Asn Gly Thr Tyr Arg Phe Cys Cys Cys Ser Thr Asp Leu
85 90 95

Cys Asn Val Asn Phe Thr Glu Asn Phe Pro Pro Pro Asp Thr Thr Pro
100 105 110

Leu Ser Pro Pro His Ser Phe Asn Arg Asp Glu Thr Gly Gly Gly Thr
115 120 125

His Thr Cys Pro Pro Cys Pro Ala Pro Glu Leu Leu Gly Gly Pro Ser
130 135 140

Val Phe Leu Phe Pro Pro Lys Pro Lys Asp Thr Leu Met Ile Ser Arg
145 150 155 160

Thr Pro Glu Val Thr Cys Val Val Val Asp Val Ser His Glu Asp Pro
165 170 175

Glu Val Lys Phe Asn Trp Tyr Val Asp Gly Val Glu Val His Asn Ala
180 185 190

Lys Thr Lys Pro Arg Glu Glu Gln Tyr Asn Ser Thr Tyr Arg Val Val
195 200 205

Ser Val Leu Thr Val Leu His Gln Asp Trp Leu Asn Gly Lys Glu Tyr
210 215 220

Lys Cys Lys Val Ser Asn Lys Ala Leu Pro Ala Pro Ile Glu Lys Thr
225 230 235 240

Ile Ser Lys Ala Lys Gly Gln Pro Arg Glu Pro Gln Val Tyr Thr Leu

```
                245                 250                 255

Pro Pro Cys Arg Glu Glu Met Thr Lys Asn Gln Val Ser Leu Trp Cys
            260                 265                 270

Leu Val Lys Gly Phe Tyr Pro Ser Asp Ile Ala Val Glu Trp Glu Ser
        275                 280                 285

Asn Gly Gln Pro Glu Asn Asn Tyr Lys Thr Thr Pro Pro Val Leu Asp
    290                 295                 300

Ser Asp Gly Ser Phe Phe Leu Tyr Ser Lys Leu Thr Val Asp Lys Ser
305                 310                 315                 320

Arg Trp Gln Gln Gly Asn Val Phe Ser Cys Ser Val Met His Glu Ala
                325                 330                 335

Leu His Asn His Tyr Thr Gln Lys Ser Leu Ser Leu Ser Pro Gly Lys
            340                 345                 350


<210> SEQ ID NO 407
<211> LENGTH: 385
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 407

Met Asp Ala Met Lys Arg Gly Leu Cys Cys Val Leu Leu Leu Cys Gly
1               5                   10                  15

Ala Val Phe Val Ser Pro Gly Ala Pro Pro Asn Arg Arg Thr Cys Val
            20                  25                  30

Phe Phe Glu Ala Pro Gly Val Arg Gly Ser Thr Lys Thr Leu Gly Glu
        35                  40                  45

Leu Leu Asp Thr Gly Thr Glu Leu Pro Arg Ala Ile Arg Cys Leu Tyr
    50                  55                  60

Ser Arg Cys Cys Phe Gly Ile Trp Asn Leu Thr Gln Asp Arg Ala Gln
65                  70                  75                  80

Val Glu Met Gln Gly Cys Arg Asp Ser Asp Glu Pro Gly Cys Glu Ser
                85                  90                  95

Leu His Cys Asp Pro Ser Pro Arg Ala His Pro Ser Pro Gly Ser Thr
            100                 105                 110

Leu Phe Thr Cys Ser Cys Gly Thr Asp Phe Cys Asn Ala Asn Tyr Ser
        115                 120                 125

His Leu Pro Pro Pro Gly Ser Pro Gly Thr Pro Gly Ser Gln Gly Pro
    130                 135                 140

Gln Ala Ala Pro Gly Glu Ser Ile Trp Met Ala Leu Thr Gly Gly Gly
145                 150                 155                 160

Thr His Thr Cys Pro Pro Cys Pro Ala Pro Glu Leu Leu Gly Gly Pro
                165                 170                 175

Ser Val Phe Leu Phe Pro Pro Lys Pro Lys Asp Thr Leu Met Ile Ser
            180                 185                 190

Arg Thr Pro Glu Val Thr Cys Val Val Val Asp Val Ser His Glu Asp
        195                 200                 205

Pro Glu Val Lys Phe Asn Trp Tyr Val Asp Gly Val Glu Val His Asn
    210                 215                 220

Ala Lys Thr Lys Pro Arg Glu Glu Gln Tyr Asn Ser Thr Tyr Arg Val
225                 230                 235                 240

Val Ser Val Leu Thr Val Leu His Gln Asp Trp Leu Asn Gly Lys Glu
                245                 250                 255
```

```
Tyr Lys Cys Lys Val Ser Asn Lys Ala Leu Pro Ala Pro Ile Glu Lys
            260                 265                 270

Thr Ile Ser Lys Ala Lys Gly Gln Pro Arg Glu Pro Gln Val Tyr Thr
        275                 280                 285

Leu Pro Pro Cys Arg Glu Glu Met Thr Lys Asn Gln Val Ser Leu Trp
    290                 295                 300

Cys Leu Val Lys Gly Phe Tyr Pro Ser Asp Ile Ala Val Glu Trp Glu
305                 310                 315                 320

Ser Asn Gly Gln Pro Glu Asn Asn Tyr Lys Thr Thr Pro Pro Val Leu
                325                 330                 335

Asp Ser Asp Gly Ser Phe Phe Leu Tyr Ser Lys Leu Thr Val Asp Lys
            340                 345                 350

Ser Arg Trp Gln Gln Gly Asn Val Phe Ser Cys Ser Val Met His Glu
        355                 360                 365

Ala Leu His Asn His Tyr Thr Gln Lys Ser Leu Ser Leu Ser Pro Gly
    370                 375                 380

Lys
385


<210> SEQ ID NO 408
<211> LENGTH: 361
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 408

Pro Pro Asn Arg Arg Thr Cys Val Phe Phe Glu Ala Pro Gly Val Arg
1               5                   10                  15

Gly Ser Thr Lys Thr Leu Gly Glu Leu Leu Asp Thr Gly Thr Glu Leu
            20                  25                  30

Pro Arg Ala Ile Arg Cys Leu Tyr Ser Arg Cys Cys Phe Gly Ile Trp
        35                  40                  45

Asn Leu Thr Gln Asp Arg Ala Gln Val Glu Met Gln Gly Cys Arg Asp
    50                  55                  60

Ser Asp Glu Pro Gly Cys Glu Ser Leu His Cys Asp Pro Ser Pro Arg
65                  70                  75                  80

Ala His Pro Ser Pro Gly Ser Thr Leu Phe Thr Cys Ser Cys Gly Thr
                85                  90                  95

Asp Phe Cys Asn Ala Asn Tyr Ser His Leu Pro Pro Pro Gly Ser Pro
            100                 105                 110

Gly Thr Pro Gly Ser Gln Gly Pro Gln Ala Ala Pro Gly Glu Ser Ile
        115                 120                 125

Trp Met Ala Leu Thr Gly Gly Gly Thr His Thr Cys Pro Pro Cys Pro
    130                 135                 140

Ala Pro Glu Leu Leu Gly Gly Pro Ser Val Phe Leu Phe Pro Pro Lys
145                 150                 155                 160

Pro Lys Asp Thr Leu Met Ile Ser Arg Thr Pro Glu Val Thr Cys Val
                165                 170                 175

Val Val Asp Val Ser His Glu Asp Pro Glu Val Lys Phe Asn Trp Tyr
            180                 185                 190

Val Asp Gly Val Glu Val His Asn Ala Lys Thr Lys Pro Arg Glu Glu
        195                 200                 205

Gln Tyr Asn Ser Thr Tyr Arg Val Val Ser Val Leu Thr Val Leu His
    210                 215                 220
```

```
Gln Asp Trp Leu Asn Gly Lys Glu Tyr Lys Cys Lys Val Ser Asn Lys
225                 230                 235                 240

Ala Leu Pro Ala Pro Ile Glu Lys Thr Ile Ser Lys Ala Lys Gly Gln
                245                 250                 255

Pro Arg Glu Pro Gln Val Tyr Thr Leu Pro Pro Cys Arg Glu Glu Met
            260                 265                 270

Thr Lys Asn Gln Val Ser Leu Trp Cys Leu Val Lys Gly Phe Tyr Pro
        275                 280                 285

Ser Asp Ile Ala Val Glu Trp Glu Ser Asn Gly Gln Pro Glu Asn Asn
    290                 295                 300

Tyr Lys Thr Thr Pro Pro Val Leu Asp Ser Asp Gly Ser Phe Phe Leu
305                 310                 315                 320

Tyr Ser Lys Leu Thr Val Asp Lys Ser Arg Trp Gln Gln Gly Asn Val
                325                 330                 335

Phe Ser Cys Ser Val Met His Glu Ala Leu His Asn His Tyr Thr Gln
            340                 345                 350

Lys Ser Leu Ser Leu Ser Pro Gly Lys
        355                 360


<210> SEQ ID NO 409
<211> LENGTH: 390
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 409

Met Asp Ala Met Lys Arg Gly Leu Cys Cys Val Leu Leu Leu Cys Gly
1               5                   10                  15

Ala Val Phe Val Ser Pro Gly Ala Thr Ile Pro Pro His Val Gln Lys
            20                  25                  30

Ser Val Asn Asn Asp Met Ile Val Thr Asp Asn Asn Gly Ala Val Lys
        35                  40                  45

Phe Pro Gln Leu Cys Lys Phe Cys Asp Val Arg Phe Ser Thr Cys Asp
    50                  55                  60

Asn Gln Lys Ser Cys Met Ser Asn Cys Ser Ile Thr Ser Ile Cys Glu
65                  70                  75                  80

Lys Pro Gln Glu Val Cys Val Ala Val Trp Arg Lys Asn Asp Glu Asn
                85                  90                  95

Ile Thr Leu Glu Thr Val Cys His Asp Pro Lys Leu Pro Tyr His Asp
            100                 105                 110

Phe Ile Leu Glu Asp Ala Ala Ser Pro Lys Cys Ile Met Lys Glu Lys
        115                 120                 125

Lys Lys Pro Gly Glu Thr Phe Phe Met Cys Ser Cys Ser Ser Asp Glu
    130                 135                 140

Cys Asn Asp Asn Ile Ile Phe Ser Glu Glu Tyr Asn Thr Ser Asn Pro
145                 150                 155                 160

Asp Thr Gly Gly Gly Thr His Thr Cys Pro Pro Cys Pro Ala Pro Glu
                165                 170                 175

Leu Leu Gly Gly Pro Ser Val Phe Leu Phe Pro Pro Lys Pro Lys Asp
            180                 185                 190

Thr Leu Met Ile Ser Arg Thr Pro Glu Val Thr Cys Val Val Val Asp
        195                 200                 205

Val Ser His Glu Asp Pro Glu Val Lys Phe Asn Trp Tyr Val Asp Gly
```

```
    210                 215                 220

Val Glu Val His Asn Ala Lys Thr Lys Pro Arg Glu Glu Gln Tyr Asn
225                 230                 235                 240

Ser Thr Tyr Arg Val Val Ser Val Leu Thr Val Leu His Gln Asp Trp
                245                 250                 255

Leu Asn Gly Lys Glu Tyr Lys Cys Lys Val Ser Asn Lys Ala Leu Pro
            260                 265                 270

Ala Pro Ile Glu Lys Thr Ile Ser Lys Ala Lys Gly Gln Pro Arg Glu
        275                 280                 285

Pro Gln Val Tyr Thr Leu Pro Pro Cys Arg Glu Glu Met Thr Lys Asn
    290                 295                 300

Gln Val Ser Leu Trp Cys Leu Val Lys Gly Phe Tyr Pro Ser Asp Ile
305                 310                 315                 320

Ala Val Glu Trp Glu Ser Asn Gly Gln Pro Glu Asn Asn Tyr Lys Thr
                325                 330                 335

Thr Pro Pro Val Leu Asp Ser Asp Gly Ser Phe Phe Leu Tyr Ser Lys
            340                 345                 350

Leu Thr Val Asp Lys Ser Arg Trp Gln Gln Gly Asn Val Phe Ser Cys
        355                 360                 365

Ser Val Met His Glu Ala Leu His Asn His Tyr Thr Gln Lys Ser Leu
    370                 375                 380

Ser Leu Ser Pro Gly Lys
385                 390


<210> SEQ ID NO 410
<211> LENGTH: 366
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 410

Thr Ile Pro Pro His Val Gln Lys Ser Val Asn Asn Asp Met Ile Val
1               5                   10                  15

Thr Asp Asn Asn Gly Ala Val Lys Phe Pro Gln Leu Cys Lys Phe Cys
            20                  25                  30

Asp Val Arg Phe Ser Thr Cys Asp Asn Gln Lys Ser Cys Met Ser Asn
        35                  40                  45

Cys Ser Ile Thr Ser Ile Cys Glu Lys Pro Gln Glu Val Cys Val Ala
    50                  55                  60

Val Trp Arg Lys Asn Asp Glu Asn Ile Thr Leu Glu Thr Val Cys His
65                  70                  75                  80

Asp Pro Lys Leu Pro Tyr His Asp Phe Ile Leu Glu Asp Ala Ala Ser
                85                  90                  95

Pro Lys Cys Ile Met Lys Glu Lys Lys Lys Pro Gly Glu Thr Phe Phe
            100                 105                 110

Met Cys Ser Cys Ser Ser Asp Glu Cys Asn Asp Asn Ile Ile Phe Ser
        115                 120                 125

Glu Glu Tyr Asn Thr Ser Asn Pro Asp Thr Gly Gly Gly Thr His Thr
    130                 135                 140

Cys Pro Pro Cys Pro Ala Pro Glu Leu Leu Gly Gly Pro Ser Val Phe
145                 150                 155                 160

Leu Phe Pro Pro Lys Pro Lys Asp Thr Leu Met Ile Ser Arg Thr Pro
                165                 170                 175
```

```
Glu Val Thr Cys Val Val Val Asp Val Ser His Glu Asp Pro Glu Val
            180                 185                 190

Lys Phe Asn Trp Tyr Val Asp Gly Val Glu Val His Asn Ala Lys Thr
        195                 200                 205

Lys Pro Arg Glu Glu Gln Tyr Asn Ser Thr Tyr Arg Val Val Ser Val
    210                 215                 220

Leu Thr Val Leu His Gln Asp Trp Leu Asn Gly Lys Glu Tyr Lys Cys
225                 230                 235                 240

Lys Val Ser Asn Lys Ala Leu Pro Ala Pro Ile Glu Lys Thr Ile Ser
                245                 250                 255

Lys Ala Lys Gly Gln Pro Arg Glu Pro Gln Val Tyr Thr Leu Pro Pro
            260                 265                 270

Cys Arg Glu Glu Met Thr Lys Asn Gln Val Ser Leu Trp Cys Leu Val
        275                 280                 285

Lys Gly Phe Tyr Pro Ser Asp Ile Ala Val Glu Trp Glu Ser Asn Gly
    290                 295                 300

Gln Pro Glu Asn Asn Tyr Lys Thr Thr Pro Pro Val Leu Asp Ser Asp
305                 310                 315                 320

Gly Ser Phe Phe Leu Tyr Ser Lys Leu Thr Val Asp Lys Ser Arg Trp
                325                 330                 335

Gln Gln Gly Asn Val Phe Ser Cys Ser Val Met His Glu Ala Leu His
            340                 345                 350

Asn His Tyr Thr Gln Lys Ser Leu Ser Leu Ser Pro Gly Lys
        355                 360                 365


<210> SEQ ID NO 411
<211> LENGTH: 352
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 411

Met Asp Ala Met Lys Arg Gly Leu Cys Cys Val Leu Leu Leu Cys Gly
1               5                   10                  15

Ala Val Phe Val Ser Pro Gly Ala Asp Pro Val Lys Pro Ser Arg Gly
            20                  25                  30

Pro Leu Val Thr Cys Thr Cys Glu Ser Pro His Cys Lys Gly Pro Thr
        35                  40                  45

Cys Arg Gly Ala Trp Cys Thr Val Val Leu Val Arg Glu Glu Gly Arg
    50                  55                  60

His Pro Gln Glu His Arg Gly Cys Gly Asn Leu His Arg Glu Leu Cys
65                  70                  75                  80

Arg Gly Arg Pro Thr Glu Phe Val Asn His Tyr Cys Cys Asp Ser His
                85                  90                  95

Leu Cys Asn His Asn Val Ser Leu Val Leu Glu Ala Thr Gln Pro Pro
            100                 105                 110

Ser Glu Gln Pro Gly Thr Asp Gly Gln Leu Ala Thr Gly Gly Gly Thr
        115                 120                 125

His Thr Cys Pro Pro Cys Pro Ala Pro Glu Leu Leu Gly Gly Pro Ser
    130                 135                 140

Val Phe Leu Phe Pro Pro Lys Pro Lys Asp Thr Leu Met Ile Ser Arg
145                 150                 155                 160

Thr Pro Glu Val Thr Cys Val Val Val Asp Val Ser His Glu Asp Pro
                165                 170                 175
```

```
Glu Val Lys Phe Asn Trp Tyr Val Asp Gly Val Glu Val His Asn Ala
            180                 185                 190

Lys Thr Lys Pro Arg Glu Glu Gln Tyr Asn Ser Thr Tyr Arg Val Val
        195                 200                 205

Ser Val Leu Thr Val Leu His Gln Asp Trp Leu Asn Gly Lys Glu Tyr
    210                 215                 220

Lys Cys Lys Val Ser Asn Lys Ala Leu Pro Ala Pro Ile Glu Lys Thr
225                 230                 235                 240

Ile Ser Lys Ala Lys Gly Gln Pro Arg Glu Pro Gln Val Cys Thr Leu
                245                 250                 255

Pro Pro Ser Arg Glu Glu Met Thr Lys Asn Gln Val Ser Leu Ser Cys
            260                 265                 270

Ala Val Lys Gly Phe Tyr Pro Ser Asp Ile Ala Val Glu Trp Glu Ser
        275                 280                 285

Asn Gly Gln Pro Glu Asn Asn Tyr Lys Thr Thr Pro Pro Val Leu Asp
    290                 295                 300

Ser Asp Gly Ser Phe Phe Leu Val Ser Lys Leu Thr Val Asp Lys Ser
305                 310                 315                 320

Arg Trp Gln Gln Gly Asn Val Phe Ser Cys Ser Val Met His Glu Ala
                325                 330                 335

Leu His Asn His Tyr Thr Gln Lys Ser Leu Ser Leu Ser Pro Gly Lys
            340                 345                 350


<210> SEQ ID NO 412
<211> LENGTH: 328
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 412

Asp Pro Val Lys Pro Ser Arg Gly Pro Leu Val Thr Cys Thr Cys Glu
1               5                   10                  15

Ser Pro His Cys Lys Gly Pro Thr Cys Arg Gly Ala Trp Cys Thr Val
            20                  25                  30

Val Leu Val Arg Glu Glu Gly Arg His Pro Gln Glu His Arg Gly Cys
        35                  40                  45

Gly Asn Leu His Arg Glu Leu Cys Arg Gly Arg Pro Thr Glu Phe Val
    50                  55                  60

Asn His Tyr Cys Cys Asp Ser His Leu Cys Asn His Asn Val Ser Leu
65                  70                  75                  80

Val Leu Glu Ala Thr Gln Pro Pro Ser Glu Gln Pro Gly Thr Asp Gly
                85                  90                  95

Gln Leu Ala Thr Gly Gly Gly Thr His Thr Cys Pro Pro Cys Pro Ala
            100                 105                 110

Pro Glu Leu Leu Gly Gly Pro Ser Val Phe Leu Phe Pro Pro Lys Pro
        115                 120                 125

Lys Asp Thr Leu Met Ile Ser Arg Thr Pro Glu Val Thr Cys Val Val
    130                 135                 140

Val Asp Val Ser His Glu Asp Pro Glu Val Lys Phe Asn Trp Tyr Val
145                 150                 155                 160

Asp Gly Val Glu Val His Asn Ala Lys Thr Lys Pro Arg Glu Glu Gln
                165                 170                 175

Tyr Asn Ser Thr Tyr Arg Val Val Ser Val Leu Thr Val Leu His Gln
```

```
            180                 185                 190

Asp Trp Leu Asn Gly Lys Glu Tyr Lys Cys Lys Val Ser Asn Lys Ala
        195                 200                 205

Leu Pro Ala Pro Ile Glu Lys Thr Ile Ser Lys Ala Lys Gly Gln Pro
    210                 215                 220

Arg Glu Pro Gln Val Cys Thr Leu Pro Pro Ser Arg Glu Glu Met Thr
225                 230                 235                 240

Lys Asn Gln Val Ser Leu Ser Cys Ala Val Lys Gly Phe Tyr Pro Ser
                245                 250                 255

Asp Ile Ala Val Glu Trp Glu Ser Asn Gly Gln Pro Glu Asn Asn Tyr
            260                 265                 270

Lys Thr Thr Pro Pro Val Leu Asp Ser Asp Gly Ser Phe Phe Leu Val
        275                 280                 285

Ser Lys Leu Thr Val Asp Lys Ser Arg Trp Gln Gln Gly Asn Val Phe
    290                 295                 300

Ser Cys Ser Val Met His Glu Ala Leu His Asn His Tyr Thr Gln Lys
305                 310                 315                 320

Ser Leu Ser Leu Ser Pro Gly Lys
                325


<210> SEQ ID NO 413
<211> LENGTH: 356
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 413

Met Asp Ala Met Lys Arg Gly Leu Cys Cys Val Leu Leu Leu Cys Gly
1               5                   10                  15

Ala Val Phe Val Ser Pro Gly Ala Met Glu Asp Glu Lys Pro Lys Val
            20                  25                  30

Asn Pro Lys Leu Tyr Met Cys Val Cys Glu Gly Leu Ser Cys Gly Asn
        35                  40                  45

Glu Asp His Cys Glu Gly Gln Gln Cys Phe Ser Ser Leu Ser Ile Asn
    50                  55                  60

Asp Gly Phe His Val Tyr Gln Lys Gly Cys Phe Gln Val Tyr Glu Gln
65                  70                  75                  80

Gly Lys Met Thr Cys Lys Thr Pro Pro Ser Pro Gly Gln Ala Val Glu
                85                  90                  95

Cys Cys Gln Gly Asp Trp Cys Asn Arg Asn Ile Thr Ala Gln Leu Pro
            100                 105                 110

Thr Lys Gly Lys Ser Phe Pro Gly Thr Gln Asn Phe His Leu Glu Thr
        115                 120                 125

Gly Gly Gly Thr His Thr Cys Pro Pro Cys Pro Ala Pro Glu Leu Leu
    130                 135                 140

Gly Gly Pro Ser Val Phe Leu Phe Pro Pro Lys Pro Lys Asp Thr Leu
145                 150                 155                 160

Met Ile Ser Arg Thr Pro Glu Val Thr Cys Val Val Val Asp Val Ser
                165                 170                 175

His Glu Asp Pro Glu Val Lys Phe Asn Trp Tyr Val Asp Gly Val Glu
            180                 185                 190

Val His Asn Ala Lys Thr Lys Pro Arg Glu Glu Gln Tyr Asn Ser Thr
        195                 200                 205
```

-continued

```
Tyr Arg Val Val Ser Val Leu Thr Val Leu His Gln Asp Trp Leu Asn
    210                 215                 220

Gly Lys Glu Tyr Lys Cys Lys Val Ser Asn Lys Ala Leu Pro Ala Pro
225                 230                 235                 240

Ile Glu Lys Thr Ile Ser Lys Ala Lys Gly Gln Pro Arg Glu Pro Gln
                245                 250                 255

Val Cys Thr Leu Pro Pro Ser Arg Glu Glu Met Thr Lys Asn Gln Val
            260                 265                 270

Ser Leu Ser Cys Ala Val Lys Gly Phe Tyr Pro Ser Asp Ile Ala Val
        275                 280                 285

Glu Trp Glu Ser Asn Gly Gln Pro Glu Asn Asn Tyr Lys Thr Thr Pro
    290                 295                 300

Pro Val Leu Asp Ser Asp Gly Ser Phe Phe Leu Val Ser Lys Leu Thr
305                 310                 315                 320

Val Asp Lys Ser Arg Trp Gln Gln Gly Asn Val Phe Ser Cys Ser Val
                325                 330                 335

Met His Glu Ala Leu His Asn His Tyr Thr Gln Lys Ser Leu Ser Leu
            340                 345                 350

Ser Pro Gly Lys
        355


<210> SEQ ID NO 414
<211> LENGTH: 332
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 414

Met Glu Asp Glu Lys Pro Lys Val Asn Pro Lys Leu Tyr Met Cys Val
1               5                   10                  15

Cys Glu Gly Leu Ser Cys Gly Asn Glu Asp His Cys Glu Gly Gln Gln
            20                  25                  30

Cys Phe Ser Ser Leu Ser Ile Asn Asp Gly Phe His Val Tyr Gln Lys
        35                  40                  45

Gly Cys Phe Gln Val Tyr Glu Gln Gly Lys Met Thr Cys Lys Thr Pro
    50                  55                  60

Pro Ser Pro Gly Gln Ala Val Glu Cys Cys Gln Gly Asp Trp Cys Asn
65                  70                  75                  80

Arg Asn Ile Thr Ala Gln Leu Pro Thr Lys Gly Lys Ser Phe Pro Gly
                85                  90                  95

Thr Gln Asn Phe His Leu Glu Thr Gly Gly Gly Thr His Thr Cys Pro
            100                 105                 110

Pro Cys Pro Ala Pro Glu Leu Leu Gly Gly Pro Ser Val Phe Leu Phe
        115                 120                 125

Pro Pro Lys Pro Lys Asp Thr Leu Met Ile Ser Arg Thr Pro Glu Val
    130                 135                 140

Thr Cys Val Val Val Asp Val Ser His Glu Asp Pro Glu Val Lys Phe
145                 150                 155                 160

Asn Trp Tyr Val Asp Gly Val Glu Val His Asn Ala Lys Thr Lys Pro
                165                 170                 175

Arg Glu Glu Gln Tyr Asn Ser Thr Tyr Arg Val Val Ser Val Leu Thr
            180                 185                 190

Val Leu His Gln Asp Trp Leu Asn Gly Lys Glu Tyr Lys Cys Lys Val
        195                 200                 205
```

Ser Asn Lys Ala Leu Pro Ala Pro Ile Glu Lys Thr Ile Ser Lys Ala
    210                 215                 220

Lys Gly Gln Pro Arg Glu Pro Gln Val Cys Thr Leu Pro Pro Ser Arg
225                 230                 235                 240

Glu Glu Met Thr Lys Asn Gln Val Ser Leu Ser Cys Ala Val Lys Gly
                245                 250                 255

Phe Tyr Pro Ser Asp Ile Ala Val Glu Trp Glu Ser Asn Gly Gln Pro
            260                 265                 270

Glu Asn Asn Tyr Lys Thr Thr Pro Pro Val Leu Asp Ser Asp Gly Ser
        275                 280                 285

Phe Phe Leu Val Ser Lys Leu Thr Val Asp Lys Ser Arg Trp Gln Gln
    290                 295                 300

Gly Asn Val Phe Ser Cys Ser Val Met His Glu Ala Leu His Asn His
305                 310                 315                 320

Tyr Thr Gln Lys Ser Leu Ser Leu Ser Pro Gly Lys
                325                 330

<210> SEQ ID NO 415
<211> LENGTH: 382
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 415

Met Asp Ala Met Lys Arg Gly Leu Cys Cys Val Leu Leu Leu Cys Gly
1               5                   10                  15

Ala Val Phe Val Ser Pro Gly Ala Gln Asn Leu Asp Ser Met Leu His
            20                  25                  30

Gly Thr Gly Met Lys Ser Asp Ser Asp Gln Lys Lys Ser Glu Asn Gly
        35                  40                  45

Val Thr Leu Ala Pro Glu Asp Thr Leu Pro Phe Leu Lys Cys Tyr Cys
    50                  55                  60

Ser Gly His Cys Pro Asp Asp Ala Ile Asn Asn Thr Cys Ile Thr Asn
65                  70                  75                  80

Gly His Cys Phe Ala Ile Ile Glu Glu Asp Asp Gln Gly Glu Thr Thr
                85                  90                  95

Leu Ala Ser Gly Cys Met Lys Tyr Glu Gly Ser Asp Phe Gln Cys Lys
            100                 105                 110

Asp Ser Pro Lys Ala Gln Leu Arg Arg Thr Ile Glu Cys Cys Arg Thr
        115                 120                 125

Asn Leu Cys Asn Gln Tyr Leu Gln Pro Thr Leu Pro Pro Val Val Ile
    130                 135                 140

Gly Pro Phe Phe Asp Gly Ser Ile Arg Thr Gly Gly Gly Thr His Thr
145                 150                 155                 160

Cys Pro Pro Cys Pro Ala Pro Glu Leu Leu Gly Gly Pro Ser Val Phe
                165                 170                 175

Leu Phe Pro Pro Lys Pro Lys Asp Thr Leu Met Ile Ser Arg Thr Pro
            180                 185                 190

Glu Val Thr Cys Val Val Val Asp Val Ser His Glu Asp Pro Glu Val
        195                 200                 205

Lys Phe Asn Trp Tyr Val Asp Gly Val Glu Val His Asn Ala Lys Thr
    210                 215                 220

Lys Pro Arg Glu Glu Gln Tyr Asn Ser Thr Tyr Arg Val Val Ser Val

-continued

```
225                 230                 235                 240

Leu Thr Val Leu His Gln Asp Trp Leu Asn Gly Lys Glu Tyr Lys Cys
                245                 250                 255

Lys Val Ser Asn Lys Ala Leu Pro Ala Pro Ile Glu Lys Thr Ile Ser
            260                 265                 270

Lys Ala Lys Gly Gln Pro Arg Glu Pro Gln Val Cys Thr Leu Pro Pro
        275                 280                 285

Ser Arg Glu Glu Met Thr Lys Asn Gln Val Ser Leu Ser Cys Ala Val
    290                 295                 300

Lys Gly Phe Tyr Pro Ser Asp Ile Ala Val Glu Trp Glu Ser Asn Gly
305                 310                 315                 320

Gln Pro Glu Asn Asn Tyr Lys Thr Thr Pro Pro Val Leu Asp Ser Asp
                325                 330                 335

Gly Ser Phe Phe Leu Val Ser Lys Leu Thr Val Asp Lys Ser Arg Trp
            340                 345                 350

Gln Gln Gly Asn Val Phe Ser Cys Ser Val Met His Glu Ala Leu His
        355                 360                 365

Asn His Tyr Thr Gln Lys Ser Leu Ser Leu Ser Pro Gly Lys
    370                 375                 380


<210> SEQ ID NO 416
<211> LENGTH: 360
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 416

Gly Ala Gln Asn Leu Asp Ser Met Leu His Gly Thr Gly Met Lys Ser
1               5                   10                  15

Asp Ser Asp Gln Lys Lys Ser Glu Asn Gly Val Thr Leu Ala Pro Glu
            20                  25                  30

Asp Thr Leu Pro Phe Leu Lys Cys Tyr Cys Ser Gly His Cys Pro Asp
        35                  40                  45

Asp Ala Ile Asn Asn Thr Cys Ile Thr Asn Gly His Cys Phe Ala Ile
    50                  55                  60

Ile Glu Glu Asp Asp Gln Gly Glu Thr Thr Leu Ala Ser Gly Cys Met
65                  70                  75                  80

Lys Tyr Glu Gly Ser Asp Phe Gln Cys Lys Asp Ser Pro Lys Ala Gln
                85                  90                  95

Leu Arg Arg Thr Ile Glu Cys Cys Arg Thr Asn Leu Cys Asn Gln Tyr
            100                 105                 110

Leu Gln Pro Thr Leu Pro Pro Val Val Ile Gly Pro Phe Phe Asp Gly
        115                 120                 125

Ser Ile Arg Thr Gly Gly Gly Thr His Thr Cys Pro Pro Cys Pro Ala
    130                 135                 140

Pro Glu Leu Leu Gly Gly Pro Ser Val Phe Leu Phe Pro Pro Lys Pro
145                 150                 155                 160

Lys Asp Thr Leu Met Ile Ser Arg Thr Pro Glu Val Thr Cys Val Val
                165                 170                 175

Val Asp Val Ser His Glu Asp Pro Glu Val Lys Phe Asn Trp Tyr Val
            180                 185                 190

Asp Gly Val Glu Val His Asn Ala Lys Thr Lys Pro Arg Glu Glu Gln
        195                 200                 205
```

Tyr Asn Ser Thr Tyr Arg Val Val Ser Val Leu Thr Val Leu His Gln
    210                 215                 220

Asp Trp Leu Asn Gly Lys Glu Tyr Lys Cys Lys Val Ser Asn Lys Ala
225                 230                 235                 240

Leu Pro Ala Pro Ile Glu Lys Thr Ile Ser Lys Ala Lys Gly Gln Pro
                245                 250                 255

Arg Glu Pro Gln Val Cys Thr Leu Pro Pro Ser Arg Glu Glu Met Thr
            260                 265                 270

Lys Asn Gln Val Ser Leu Ser Cys Ala Val Lys Gly Phe Tyr Pro Ser
        275                 280                 285

Asp Ile Ala Val Glu Trp Glu Ser Asn Gly Gln Pro Glu Asn Asn Tyr
    290                 295                 300

Lys Thr Thr Pro Pro Val Leu Asp Ser Asp Gly Ser Phe Phe Leu Val
305                 310                 315                 320

Ser Lys Leu Thr Val Asp Lys Ser Arg Trp Gln Gln Gly Asn Val Phe
                325                 330                 335

Ser Cys Ser Val Met His Glu Ala Leu His Asn His Tyr Thr Gln Lys
            340                 345                 350

Ser Leu Ser Leu Ser Pro Gly Lys
        355                 360

<210> SEQ ID NO 417
<211> LENGTH: 356
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 417

Met Asp Ala Met Lys Arg Gly Leu Cys Cys Val Leu Leu Leu Cys Gly
1               5                   10                  15

Ala Val Phe Val Ser Pro Gly Ala Ser Gly Pro Arg Gly Val Gln Ala
            20                  25                  30

Leu Leu Cys Ala Cys Thr Ser Cys Leu Gln Ala Asn Tyr Thr Cys Glu
        35                  40                  45

Thr Asp Gly Ala Cys Met Val Ser Ile Phe Asn Leu Asp Gly Met Glu
    50                  55                  60

His His Val Arg Thr Cys Ile Pro Lys Val Glu Leu Val Pro Ala Gly
65                  70                  75                  80

Lys Pro Phe Tyr Cys Leu Ser Ser Glu Asp Leu Arg Asn Thr His Cys
                85                  90                  95

Cys Tyr Thr Asp Tyr Cys Asn Arg Ile Asp Leu Arg Val Pro Ser Gly
            100                 105                 110

His Leu Lys Glu Pro Glu His Pro Ser Met Trp Gly Pro Val Glu Thr
        115                 120                 125

Gly Gly Gly Thr His Thr Cys Pro Pro Cys Pro Ala Pro Glu Leu Leu
    130                 135                 140

Gly Gly Pro Ser Val Phe Leu Phe Pro Pro Lys Pro Lys Asp Thr Leu
145                 150                 155                 160

Met Ile Ser Arg Thr Pro Glu Val Thr Cys Val Val Val Asp Val Ser
                165                 170                 175

His Glu Asp Pro Glu Val Lys Phe Asn Trp Tyr Val Asp Gly Val Glu
            180                 185                 190

Val His Asn Ala Lys Thr Lys Pro Arg Glu Glu Gln Tyr Asn Ser Thr
        195                 200                 205

```
Tyr Arg Val Val Ser Val Leu Thr Val Leu His Gln Asp Trp Leu Asn
    210                 215                 220

Gly Lys Glu Tyr Lys Cys Lys Val Ser Asn Lys Ala Leu Pro Ala Pro
225                 230                 235                 240

Ile Glu Lys Thr Ile Ser Lys Ala Lys Gly Gln Pro Arg Glu Pro Gln
                245                 250                 255

Val Cys Thr Leu Pro Pro Ser Arg Glu Glu Met Thr Lys Asn Gln Val
            260                 265                 270

Ser Leu Ser Cys Ala Val Lys Gly Phe Tyr Pro Ser Asp Ile Ala Val
        275                 280                 285

Glu Trp Glu Ser Asn Gly Gln Pro Glu Asn Asn Tyr Lys Thr Thr Pro
    290                 295                 300

Pro Val Leu Asp Ser Asp Gly Ser Phe Phe Leu Val Ser Lys Leu Thr
305                 310                 315                 320

Val Asp Lys Ser Arg Trp Gln Gln Gly Asn Val Phe Ser Cys Ser Val
                325                 330                 335

Met His Glu Ala Leu His Asn His Tyr Thr Gln Lys Ser Leu Ser Leu
            340                 345                 350

Ser Pro Gly Lys
        355


<210> SEQ ID NO 418
<211> LENGTH: 332
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 418

Ser Gly Pro Arg Gly Val Gln Ala Leu Leu Cys Ala Cys Thr Ser Cys
1               5                   10                  15

Leu Gln Ala Asn Tyr Thr Cys Glu Thr Asp Gly Ala Cys Met Val Ser
            20                  25                  30

Ile Phe Asn Leu Asp Gly Met Glu His His Val Arg Thr Cys Ile Pro
        35                  40                  45

Lys Val Glu Leu Val Pro Ala Gly Lys Pro Phe Tyr Cys Leu Ser Ser
    50                  55                  60

Glu Asp Leu Arg Asn Thr His Cys Cys Tyr Thr Asp Tyr Cys Asn Arg
65                  70                  75                  80

Ile Asp Leu Arg Val Pro Ser Gly His Leu Lys Glu Pro Glu His Pro
                85                  90                  95

Ser Met Trp Gly Pro Val Glu Thr Gly Gly Gly Thr His Thr Cys Pro
            100                 105                 110

Pro Cys Pro Ala Pro Glu Leu Leu Gly Gly Pro Ser Val Phe Leu Phe
        115                 120                 125

Pro Pro Lys Pro Lys Asp Thr Leu Met Ile Ser Arg Thr Pro Glu Val
    130                 135                 140

Thr Cys Val Val Val Asp Val Ser His Glu Asp Pro Glu Val Lys Phe
145                 150                 155                 160

Asn Trp Tyr Val Asp Gly Val Glu Val His Asn Ala Lys Thr Lys Pro
                165                 170                 175

Arg Glu Glu Gln Tyr Asn Ser Thr Tyr Arg Val Val Ser Val Leu Thr
            180                 185                 190

Val Leu His Gln Asp Trp Leu Asn Gly Lys Glu Tyr Lys Cys Lys Val
```

```
        195                 200                 205

Ser Asn Lys Ala Leu Pro Ala Pro Ile Glu Lys Thr Ile Ser Lys Ala
    210                 215                 220

Lys Gly Gln Pro Arg Glu Pro Gln Val Cys Thr Leu Pro Pro Ser Arg
225                 230                 235                 240

Glu Glu Met Thr Lys Asn Gln Val Ser Leu Ser Cys Ala Val Lys Gly
                245                 250                 255

Phe Tyr Pro Ser Asp Ile Ala Val Glu Trp Glu Ser Asn Gly Gln Pro
            260                 265                 270

Glu Asn Asn Tyr Lys Thr Thr Pro Pro Val Leu Asp Ser Asp Gly Ser
        275                 280                 285

Phe Phe Leu Val Ser Lys Leu Thr Val Asp Lys Ser Arg Trp Gln Gln
    290                 295                 300

Gly Asn Val Phe Ser Cys Ser Val Met His Glu Ala Leu His Asn His
305                 310                 315                 320

Tyr Thr Gln Lys Ser Leu Ser Leu Ser Pro Gly Lys
                325                 330


<210> SEQ ID NO 419
<211> LENGTH: 353
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 419

Met Asp Ala Met Lys Arg Gly Leu Cys Cys Val Leu Leu Leu Cys Gly
1               5                   10                  15

Ala Val Phe Val Ser Pro Gly Ala Ala Leu Leu Pro Gly Ala Thr Ala
            20                  25                  30

Leu Gln Cys Phe Cys His Leu Cys Thr Lys Asp Asn Phe Thr Cys Val
        35                  40                  45

Thr Asp Gly Leu Cys Phe Val Ser Val Thr Glu Thr Thr Asp Lys Val
    50                  55                  60

Ile His Asn Ser Met Cys Ile Ala Glu Ile Asp Leu Ile Pro Arg Asp
65                  70                  75                  80

Arg Pro Phe Val Cys Ala Pro Ser Ser Lys Thr Gly Ser Val Thr Thr
                85                  90                  95

Thr Tyr Cys Cys Asn Gln Asp His Cys Asn Lys Ile Glu Leu Pro Thr
            100                 105                 110

Thr Val Lys Ser Ser Pro Gly Leu Gly Pro Val Glu Thr Gly Gly Gly
        115                 120                 125

Thr His Thr Cys Pro Pro Cys Pro Ala Pro Glu Leu Leu Gly Gly Pro
    130                 135                 140

Ser Val Phe Leu Phe Pro Pro Lys Pro Lys Asp Thr Leu Met Ile Ser
145                 150                 155                 160

Arg Thr Pro Glu Val Thr Cys Val Val Val Asp Val Ser His Glu Asp
                165                 170                 175

Pro Glu Val Lys Phe Asn Trp Tyr Val Asp Gly Val Glu Val His Asn
            180                 185                 190

Ala Lys Thr Lys Pro Arg Glu Glu Gln Tyr Asn Ser Thr Tyr Arg Val
        195                 200                 205

Val Ser Val Leu Thr Val Leu His Gln Asp Trp Leu Asn Gly Lys Glu
    210                 215                 220
```

-continued

Tyr Lys Cys Lys Val Ser Asn Lys Ala Leu Pro Ala Pro Ile Glu Lys
225 230 235 240

Thr Ile Ser Lys Ala Lys Gly Gln Pro Arg Glu Pro Gln Val Cys Thr
245 250 255

Leu Pro Pro Ser Arg Glu Glu Met Thr Lys Asn Gln Val Ser Leu Ser
260 265 270

Cys Ala Val Lys Gly Phe Tyr Pro Ser Asp Ile Ala Val Glu Trp Glu
275 280 285

Ser Asn Gly Gln Pro Glu Asn Asn Tyr Lys Thr Thr Pro Pro Val Leu
290 295 300

Asp Ser Asp Gly Ser Phe Phe Leu Val Ser Lys Leu Thr Val Asp Lys
305 310 315 320

Ser Arg Trp Gln Gln Gly Asn Val Phe Ser Cys Ser Val Met His Glu
325 330 335

Ala Leu His Asn His Tyr Thr Gln Lys Ser Leu Ser Leu Ser Pro Gly
340 345 350

Lys

<210> SEQ ID NO 420
<211> LENGTH: 329
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 420

Ala Leu Leu Pro Gly Ala Thr Ala Leu Gln Cys Phe Cys His Leu Cys
1 5 10 15

Thr Lys Asp Asn Phe Thr Cys Val Thr Asp Gly Leu Cys Phe Val Ser
20 25 30

Val Thr Glu Thr Thr Asp Lys Val Ile His Asn Ser Met Cys Ile Ala
35 40 45

Glu Ile Asp Leu Ile Pro Arg Asp Arg Pro Phe Val Cys Ala Pro Ser
50 55 60

Ser Lys Thr Gly Ser Val Thr Thr Thr Tyr Cys Cys Asn Gln Asp His
65 70 75 80

Cys Asn Lys Ile Glu Leu Pro Thr Thr Val Lys Ser Ser Pro Gly Leu
85 90 95

Gly Pro Val Glu Thr Gly Gly Gly Thr His Thr Cys Pro Pro Cys Pro
100 105 110

Ala Pro Glu Leu Leu Gly Gly Pro Ser Val Phe Leu Phe Pro Pro Lys
115 120 125

Pro Lys Asp Thr Leu Met Ile Ser Arg Thr Pro Glu Val Thr Cys Val
130 135 140

Val Val Asp Val Ser His Glu Asp Pro Glu Val Lys Phe Asn Trp Tyr
145 150 155 160

Val Asp Gly Val Glu Val His Asn Ala Lys Thr Lys Pro Arg Glu Glu
165 170 175

Gln Tyr Asn Ser Thr Tyr Arg Val Val Ser Val Leu Thr Val Leu His
180 185 190

Gln Asp Trp Leu Asn Gly Lys Glu Tyr Lys Cys Lys Val Ser Asn Lys
195 200 205

Ala Leu Pro Ala Pro Ile Glu Lys Thr Ile Ser Lys Ala Lys Gly Gln
210 215 220

Pro Arg Glu Pro Gln Val Cys Thr Leu Pro Pro Ser Arg Glu Glu Met
225 230 235 240

Thr Lys Asn Gln Val Ser Leu Ser Cys Ala Val Lys Gly Phe Tyr Pro
245 250 255

Ser Asp Ile Ala Val Glu Trp Glu Ser Asn Gly Gln Pro Glu Asn Asn
260 265 270

Tyr Lys Thr Thr Pro Pro Val Leu Asp Ser Asp Gly Ser Phe Phe Leu
275 280 285

Val Ser Lys Leu Thr Val Asp Lys Ser Arg Trp Gln Gln Gly Asn Val
290 295 300

Phe Ser Cys Ser Val Met His Glu Ala Leu His Asn His Tyr Thr Gln
305 310 315 320

Lys Ser Leu Ser Leu Ser Pro Gly Lys
325

<210> SEQ ID NO 421
<211> LENGTH: 366
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 421

Met Asp Ala Met Lys Arg Gly Leu Cys Cys Val Leu Leu Leu Cys Gly
1 5 10 15

Ala Val Phe Val Ser Pro Gly Ala Lys Lys Glu Asp Gly Glu Ser Thr
20 25 30

Ala Pro Thr Pro Arg Pro Lys Val Leu Arg Cys Lys Cys His His His
35 40 45

Cys Pro Glu Asp Ser Val Asn Asn Ile Cys Ser Thr Asp Gly Tyr Cys
50 55 60

Phe Thr Met Ile Glu Glu Asp Asp Ser Gly Leu Pro Val Val Thr Ser
65 70 75 80

Gly Cys Leu Gly Leu Glu Gly Ser Asp Phe Gln Cys Arg Asp Thr Pro
85 90 95

Ile Pro His Gln Arg Arg Ser Ile Glu Cys Cys Thr Glu Arg Asn Glu
100 105 110

Cys Asn Lys Asp Leu His Pro Thr Leu Pro Pro Leu Lys Asn Arg Asp
115 120 125

Phe Val Asp Gly Pro Ile His His Arg Thr Gly Gly Gly Thr His Thr
130 135 140

Cys Pro Pro Cys Pro Ala Pro Glu Leu Leu Gly Gly Pro Ser Val Phe
145 150 155 160

Leu Phe Pro Pro Lys Pro Lys Asp Thr Leu Met Ile Ser Arg Thr Pro
165 170 175

Glu Val Thr Cys Val Val Val Asp Val Ser His Glu Asp Pro Glu Val
180 185 190

Lys Phe Asn Trp Tyr Val Asp Gly Val Glu Val His Asn Ala Lys Thr
195 200 205

Lys Pro Arg Glu Glu Gln Tyr Asn Ser Thr Tyr Arg Val Val Ser Val
210 215 220

Leu Thr Val Leu His Gln Asp Trp Leu Asn Gly Lys Glu Tyr Lys Cys
225 230 235 240

Lys Val Ser Asn Lys Ala Leu Pro Ala Pro Ile Glu Lys Thr Ile Ser
245 250 255

Lys Ala Lys Gly Gln Pro Arg Glu Pro Gln Val Cys Thr Leu Pro Pro
260 265 270

Ser Arg Glu Glu Met Thr Lys Asn Gln Val Ser Leu Ser Cys Ala Val
275 280 285

Lys Gly Phe Tyr Pro Ser Asp Ile Ala Val Glu Trp Glu Ser Asn Gly
290 295 300

Gln Pro Glu Asn Asn Tyr Lys Thr Thr Pro Pro Val Leu Asp Ser Asp
305 310 315 320

Gly Ser Phe Phe Leu Val Ser Lys Leu Thr Val Asp Lys Ser Arg Trp
325 330 335

Gln Gln Gly Asn Val Phe Ser Cys Ser Val Met His Glu Ala Leu His
340 345 350

Asn His Tyr Thr Gln Lys Ser Leu Ser Leu Ser Pro Gly Lys
355 360 365

<210> SEQ ID NO 422
<211> LENGTH: 342
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 422

Lys Lys Glu Asp Gly Glu Ser Thr Ala Pro Thr Pro Arg Pro Lys Val
1 5 10 15

Leu Arg Cys Lys Cys His His His Cys Pro Glu Asp Ser Val Asn Asn
20 25 30

Ile Cys Ser Thr Asp Gly Tyr Cys Phe Thr Met Ile Glu Glu Asp Asp
35 40 45

Ser Gly Leu Pro Val Val Thr Ser Gly Cys Leu Gly Leu Glu Gly Ser
50 55 60

Asp Phe Gln Cys Arg Asp Thr Pro Ile Pro His Gln Arg Arg Ser Ile
65 70 75 80

Glu Cys Cys Thr Glu Arg Asn Glu Cys Asn Lys Asp Leu His Pro Thr
85 90 95

Leu Pro Pro Leu Lys Asn Arg Asp Phe Val Asp Gly Pro Ile His His
100 105 110

Arg Thr Gly Gly Gly Thr His Thr Cys Pro Pro Cys Pro Ala Pro Glu
115 120 125

Leu Leu Gly Gly Pro Ser Val Phe Leu Phe Pro Pro Lys Pro Lys Asp
130 135 140

Thr Leu Met Ile Ser Arg Thr Pro Glu Val Thr Cys Val Val Val Asp
145 150 155 160

Val Ser His Glu Asp Pro Glu Val Lys Phe Asn Trp Tyr Val Asp Gly
165 170 175

Val Glu Val His Asn Ala Lys Thr Lys Pro Arg Glu Glu Gln Tyr Asn
180 185 190

Ser Thr Tyr Arg Val Val Ser Val Leu Thr Val Leu His Gln Asp Trp
195 200 205

Leu Asn Gly Lys Glu Tyr Lys Cys Lys Val Ser Asn Lys Ala Leu Pro
210 215 220

Ala Pro Ile Glu Lys Thr Ile Ser Lys Ala Lys Gly Gln Pro Arg Glu
225 230 235 240

Pro Gln Val Cys Thr Leu Pro Pro Ser Arg Glu Glu Met Thr Lys Asn

-continued

```
                245                 250                 255

Gln Val Ser Leu Ser Cys Ala Val Lys Gly Phe Tyr Pro Ser Asp Ile
            260                 265                 270

Ala Val Glu Trp Glu Ser Asn Gly Gln Pro Glu Asn Asn Tyr Lys Thr
        275                 280                 285

Thr Pro Pro Val Leu Asp Ser Asp Gly Ser Phe Phe Leu Val Ser Lys
    290                 295                 300

Leu Thr Val Asp Lys Ser Arg Trp Gln Gln Gly Asn Val Phe Ser Cys
305                 310                 315                 320

Ser Val Met His Glu Ala Leu His Asn His Tyr Thr Gln Lys Ser Leu
                325                 330                 335

Ser Leu Ser Pro Gly Lys
            340


<210> SEQ ID NO 423
<211> LENGTH: 342
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 423

Met Asp Ala Met Lys Arg Gly Leu Cys Cys Val Leu Leu Leu Cys Gly
1               5                   10                  15

Ala Val Phe Val Ser Pro Gly Ala Gly Leu Lys Cys Val Cys Leu Leu
            20                  25                  30

Cys Asp Ser Ser Asn Phe Thr Cys Gln Thr Glu Gly Ala Cys Trp Ala
        35                  40                  45

Ser Val Met Leu Thr Asn Gly Lys Glu Gln Val Ile Lys Ser Cys Val
    50                  55                  60

Ser Leu Pro Glu Leu Asn Ala Gln Val Phe Cys His Ser Ser Asn Asn
65                  70                  75                  80

Val Thr Lys Thr Glu Cys Cys Phe Thr Asp Phe Cys Asn Asn Ile Thr
                85                  90                  95

Leu His Leu Pro Thr Ala Ser Pro Asn Ala Pro Lys Leu Gly Pro Met
            100                 105                 110

Glu Thr Gly Gly Gly Thr His Thr Cys Pro Pro Cys Pro Ala Pro Glu
        115                 120                 125

Leu Leu Gly Gly Pro Ser Val Phe Leu Phe Pro Pro Lys Pro Lys Asp
    130                 135                 140

Thr Leu Met Ile Ser Arg Thr Pro Glu Val Thr Cys Val Val Val Asp
145                 150                 155                 160

Val Ser His Glu Asp Pro Glu Val Lys Phe Asn Trp Tyr Val Asp Gly
                165                 170                 175

Val Glu Val His Asn Ala Lys Thr Lys Pro Arg Glu Glu Gln Tyr Asn
            180                 185                 190

Ser Thr Tyr Arg Val Val Ser Val Leu Thr Val Leu His Gln Asp Trp
        195                 200                 205

Leu Asn Gly Lys Glu Tyr Lys Cys Lys Val Ser Asn Lys Ala Leu Pro
    210                 215                 220

Ala Pro Ile Glu Lys Thr Ile Ser Lys Ala Lys Gly Gln Pro Arg Glu
225                 230                 235                 240

Pro Gln Val Cys Thr Leu Pro Pro Ser Arg Glu Glu Met Thr Lys Asn
                245                 250                 255
```

-continued

```
Gln Val Ser Leu Ser Cys Ala Val Lys Gly Phe Tyr Pro Ser Asp Ile
            260                 265                 270

Ala Val Glu Trp Glu Ser Asn Gly Gln Pro Glu Asn Asn Tyr Lys Thr
        275                 280                 285

Thr Pro Pro Val Leu Asp Ser Asp Gly Ser Phe Phe Leu Val Ser Lys
    290                 295                 300

Leu Thr Val Asp Lys Ser Arg Trp Gln Gln Gly Asn Val Phe Ser Cys
305                 310                 315                 320

Ser Val Met His Glu Ala Leu His Asn His Tyr Thr Gln Lys Ser Leu
                325                 330                 335

Ser Leu Ser Pro Gly Lys
            340


<210> SEQ ID NO 424
<211> LENGTH: 318
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 424

Gly Leu Lys Cys Val Cys Leu Leu Cys Asp Ser Ser Asn Phe Thr Cys
1               5                   10                  15

Gln Thr Glu Gly Ala Cys Trp Ala Ser Val Met Leu Thr Asn Gly Lys
            20                  25                  30

Glu Gln Val Ile Lys Ser Cys Val Ser Leu Pro Glu Leu Asn Ala Gln
        35                  40                  45

Val Phe Cys His Ser Ser Asn Asn Val Thr Lys Thr Glu Cys Cys Phe
    50                  55                  60

Thr Asp Phe Cys Asn Asn Ile Thr Leu His Leu Pro Thr Ala Ser Pro
65                  70                  75                  80

Asn Ala Pro Lys Leu Gly Pro Met Glu Thr Gly Gly Gly Thr His Thr
                85                  90                  95

Cys Pro Pro Cys Pro Ala Pro Glu Leu Leu Gly Gly Pro Ser Val Phe
            100                 105                 110

Leu Phe Pro Pro Lys Pro Lys Asp Thr Leu Met Ile Ser Arg Thr Pro
        115                 120                 125

Glu Val Thr Cys Val Val Val Asp Val Ser His Glu Asp Pro Glu Val
    130                 135                 140

Lys Phe Asn Trp Tyr Val Asp Gly Val Glu Val His Asn Ala Lys Thr
145                 150                 155                 160

Lys Pro Arg Glu Glu Gln Tyr Asn Ser Thr Tyr Arg Val Val Ser Val
                165                 170                 175

Leu Thr Val Leu His Gln Asp Trp Leu Asn Gly Lys Glu Tyr Lys Cys
            180                 185                 190

Lys Val Ser Asn Lys Ala Leu Pro Ala Pro Ile Glu Lys Thr Ile Ser
        195                 200                 205

Lys Ala Lys Gly Gln Pro Arg Glu Pro Gln Val Cys Thr Leu Pro Pro
    210                 215                 220

Ser Arg Glu Glu Met Thr Lys Asn Gln Val Ser Leu Ser Cys Ala Val
225                 230                 235                 240

Lys Gly Phe Tyr Pro Ser Asp Ile Ala Val Glu Trp Glu Ser Asn Gly
                245                 250                 255

Gln Pro Glu Asn Asn Tyr Lys Thr Thr Pro Pro Val Leu Asp Ser Asp
            260                 265                 270
```

Gly Ser Phe Phe Leu Val Ser Lys Leu Thr Val Asp Lys Ser Arg Trp
275 280 285

Gln Gln Gly Asn Val Phe Ser Cys Ser Val Met His Glu Ala Leu His
290 295 300

Asn His Tyr Thr Gln Lys Ser Leu Ser Leu Ser Pro Gly Lys
305 310 315

<210> SEQ ID NO 425
<211> LENGTH: 262
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 425

Met Asp Ala Met Lys Arg Gly Leu Cys Cys Val Leu Leu Leu Cys Gly
1 5 10 15

Ala Val Phe Val Ser Pro Gly Ala Ser Asn Thr Lys Val Asp Lys Arg
20 25 30

Val Thr Gly Gly Gly Thr His Thr Cys Pro Pro Cys Pro Ala Pro Glu
35 40 45

Leu Leu Gly Gly Pro Ser Val Phe Leu Phe Pro Pro Lys Pro Lys Asp
50 55 60

Thr Leu Met Ile Ser Arg Thr Pro Glu Val Thr Cys Val Val Val Asp
65 70 75 80

Val Ser His Glu Asp Pro Glu Val Lys Phe Asn Trp Tyr Val Asp Gly
85 90 95

Val Glu Val His Asn Ala Lys Thr Lys Pro Arg Glu Glu Gln Tyr Asn
100 105 110

Ser Thr Tyr Arg Val Val Ser Val Leu Thr Val Leu His Gln Asp Trp
115 120 125

Leu Asn Gly Lys Glu Tyr Lys Cys Lys Val Ser Asn Lys Ala Leu Pro
130 135 140

Ala Pro Ile Glu Lys Thr Ile Ser Lys Ala Lys Gly Gln Pro Arg Glu
145 150 155 160

Pro Gln Val Cys Thr Leu Pro Pro Ser Arg Glu Glu Met Thr Lys Asn
165 170 175

Gln Val Ser Leu Ser Cys Ala Val Lys Gly Phe Tyr Pro Ser Asp Ile
180 185 190

Ala Val Glu Trp Glu Ser Asn Gly Gln Pro Glu Asn Asn Tyr Lys Thr
195 200 205

Thr Pro Pro Val Leu Asp Ser Asp Gly Ser Phe Phe Leu Val Ser Lys
210 215 220

Leu Thr Val Asp Lys Ser Arg Trp Gln Gln Gly Asn Val Phe Ser Cys
225 230 235 240

Ser Val Met His Glu Ala Leu His Asn His Tyr Thr Gln Lys Ser Leu
245 250 255

Ser Leu Ser Pro Gly Lys
260

<210> SEQ ID NO 426
<211> LENGTH: 238
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 426

Ser Asn Thr Lys Val Asp Lys Arg Val Thr Gly Gly Gly Thr His Thr
1 5 10 15

Cys Pro Pro Cys Pro Ala Pro Glu Leu Leu Gly Gly Pro Ser Val Phe
20 25 30

Leu Phe Pro Pro Lys Pro Lys Asp Thr Leu Met Ile Ser Arg Thr Pro
35 40 45

Glu Val Thr Cys Val Val Val Asp Val Ser His Glu Asp Pro Glu Val
50 55 60

Lys Phe Asn Trp Tyr Val Asp Gly Val Glu Val His Asn Ala Lys Thr
65 70 75 80

Lys Pro Arg Glu Glu Gln Tyr Asn Ser Thr Tyr Arg Val Val Ser Val
85 90 95

Leu Thr Val Leu His Gln Asp Trp Leu Asn Gly Lys Glu Tyr Lys Cys
100 105 110

Lys Val Ser Asn Lys Ala Leu Pro Ala Pro Ile Glu Lys Thr Ile Ser
115 120 125

Lys Ala Lys Gly Gln Pro Arg Glu Pro Gln Val Cys Thr Leu Pro Pro
130 135 140

Ser Arg Glu Glu Met Thr Lys Asn Gln Val Ser Leu Ser Cys Ala Val
145 150 155 160

Lys Gly Phe Tyr Pro Ser Asp Ile Ala Val Glu Trp Glu Ser Asn Gly
165 170 175

Gln Pro Glu Asn Asn Tyr Lys Thr Thr Pro Pro Val Leu Asp Ser Asp
180 185 190

Gly Ser Phe Phe Leu Val Ser Lys Leu Thr Val Asp Lys Ser Arg Trp
195 200 205

Gln Gln Gly Asn Val Phe Ser Cys Ser Val Met His Glu Ala Leu His
210 215 220

Asn His Tyr Thr Gln Lys Ser Leu Ser Leu Ser Pro Gly Lys
225 230 235

<210> SEQ ID NO 427
<211> LENGTH: 262
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 427

Met Asp Ala Met Lys Arg Gly Leu Cys Cys Val Leu Leu Leu Cys Gly
1 5 10 15

Ala Val Phe Val Ser Pro Gly Ala Ser Asn Thr Lys Val Asp Lys Arg
20 25 30

Val Thr Gly Gly Gly Thr His Thr Cys Pro Pro Cys Pro Ala Pro Glu
35 40 45

Leu Leu Gly Gly Pro Ser Val Phe Leu Phe Pro Pro Lys Pro Lys Asp
50 55 60

Thr Leu Met Ile Ser Arg Thr Pro Glu Val Thr Cys Val Val Val Asp
65 70 75 80

Val Ser His Glu Asp Pro Glu Val Lys Phe Asn Trp Tyr Val Asp Gly
85 90 95

Val Glu Val His Asn Ala Lys Thr Lys Pro Arg Glu Glu Gln Tyr Asn 100 105 110

Ser Thr Tyr Arg Val Val Ser Val Leu Thr Val Leu His Gln Asp Trp
115 120 125

Leu Asn Gly Lys Glu Tyr Lys Cys Lys Val Ser Asn Lys Ala Leu Pro
130 135 140

Ala Pro Ile Glu Lys Thr Ile Ser Lys Ala Lys Gly Gln Pro Arg Glu
145 150 155 160

Pro Gln Val Tyr Thr Leu Pro Pro Cys Arg Glu Glu Met Thr Lys Asn
165 170 175

Gln Val Ser Leu Trp Cys Leu Val Lys Gly Phe Tyr Pro Ser Asp Ile
180 185 190

Ala Val Glu Trp Glu Ser Asn Gly Gln Pro Glu Asn Asn Tyr Lys Thr
195 200 205

Thr Pro Pro Val Leu Asp Ser Asp Gly Ser Phe Phe Leu Tyr Ser Lys
210 215 220

Leu Thr Val Asp Lys Ser Arg Trp Gln Gln Gly Asn Val Phe Ser Cys
225 230 235 240

Ser Val Met His Glu Ala Leu His Asn His Tyr Thr Gln Lys Ser Leu
245 250 255

Ser Leu Ser Pro Gly Lys
260

<210> SEQ ID NO 428
<211> LENGTH: 238
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 428

Ser Asn Thr Lys Val Asp Lys Arg Val Thr Gly Gly Gly Thr His Thr
1 5 10 15

Cys Pro Pro Cys Pro Ala Pro Glu Leu Leu Gly Gly Pro Ser Val Phe
20 25 30

Leu Phe Pro Pro Lys Pro Lys Asp Thr Leu Met Ile Ser Arg Thr Pro
35 40 45

Glu Val Thr Cys Val Val Val Asp Val Ser His Glu Asp Pro Glu Val
50 55 60

Lys Phe Asn Trp Tyr Val Asp Gly Val Glu Val His Asn Ala Lys Thr
65 70 75 80

Lys Pro Arg Glu Glu Gln Tyr Asn Ser Thr Tyr Arg Val Val Ser Val
85 90 95

Leu Thr Val Leu His Gln Asp Trp Leu Asn Gly Lys Glu Tyr Lys Cys
100 105 110

Lys Val Ser Asn Lys Ala Leu Pro Ala Pro Ile Glu Lys Thr Ile Ser
115 120 125

Lys Ala Lys Gly Gln Pro Arg Glu Pro Gln Val Tyr Thr Leu Pro Pro
130 135 140

Cys Arg Glu Glu Met Thr Lys Asn Gln Val Ser Leu Trp Cys Leu Val
145 150 155 160

Lys Gly Phe Tyr Pro Ser Asp Ile Ala Val Glu Trp Glu Ser Asn Gly
165 170 175

Gln Pro Glu Asn Asn Tyr Lys Thr Thr Pro Pro Val Leu Asp Ser Asp
180 185 190

-continued

```
Gly Ser Phe Phe Leu Tyr Ser Lys Leu Thr Val Asp Lys Ser Arg Trp
        195                 200                 205

Gln Gln Gly Asn Val Phe Ser Cys Ser Val Met His Glu Ala Leu His
    210                 215                 220

Asn His Tyr Thr Gln Lys Ser Leu Ser Leu Ser Pro Gly Lys
225                 230                 235


<210> SEQ ID NO 429

<400> SEQUENCE: 429

000


<210> SEQ ID NO 430

<400> SEQUENCE: 430

000


<210> SEQ ID NO 431

<400> SEQUENCE: 431

000


<210> SEQ ID NO 432

<400> SEQUENCE: 432

000


<210> SEQ ID NO 433

<400> SEQUENCE: 433

000


<210> SEQ ID NO 434

<400> SEQUENCE: 434

000


<210> SEQ ID NO 435

<400> SEQUENCE: 435

000


<210> SEQ ID NO 436

<400> SEQUENCE: 436

000


<210> SEQ ID NO 437

<400> SEQUENCE: 437

000


<210> SEQ ID NO 438

<400> SEQUENCE: 438

000
```

<210> SEQ ID NO 439

<400> SEQUENCE: 439

000

<210> SEQ ID NO 440

<400> SEQUENCE: 440

000

<210> SEQ ID NO 441

<400> SEQUENCE: 441

000

<210> SEQ ID NO 442

<400> SEQUENCE: 442

000

<210> SEQ ID NO 443

<400> SEQUENCE: 443

000

<210> SEQ ID NO 444

<400> SEQUENCE: 444

000

<210> SEQ ID NO 445

<400> SEQUENCE: 445

000

<210> SEQ ID NO 446

<400> SEQUENCE: 446

000

<210> SEQ ID NO 447

<400> SEQUENCE: 447

000

<210> SEQ ID NO 448

<400> SEQUENCE: 448

000

<210> SEQ ID NO 449

<400> SEQUENCE: 449

000

<210> SEQ ID NO 450

<400> SEQUENCE: 450

000

<210> SEQ ID NO 451

<400> SEQUENCE: 451

000

<210> SEQ ID NO 452

<400> SEQUENCE: 452

000

<210> SEQ ID NO 453

<400> SEQUENCE: 453

000

<210> SEQ ID NO 454

<400> SEQUENCE: 454

000

<210> SEQ ID NO 455

<400> SEQUENCE: 455

000

<210> SEQ ID NO 456

<400> SEQUENCE: 456

000

<210> SEQ ID NO 457

<400> SEQUENCE: 457

000

<210> SEQ ID NO 458

<400> SEQUENCE: 458

000

<210> SEQ ID NO 459

<400> SEQUENCE: 459

000

<210> SEQ ID NO 460

<400> SEQUENCE: 460

000

<210> SEQ ID NO 461

<400> SEQUENCE: 461

-continued

000

<210> SEQ ID NO 462
<400> SEQUENCE: 462
000

<210> SEQ ID NO 463
<400> SEQUENCE: 463
000

<210> SEQ ID NO 464
<400> SEQUENCE: 464
000

<210> SEQ ID NO 465
<400> SEQUENCE: 465
000

<210> SEQ ID NO 466
<400> SEQUENCE: 466
000

<210> SEQ ID NO 467
<400> SEQUENCE: 467
000

<210> SEQ ID NO 468
<400> SEQUENCE: 468
000

<210> SEQ ID NO 469
<400> SEQUENCE: 469
000

<210> SEQ ID NO 470
<400> SEQUENCE: 470
000

<210> SEQ ID NO 471
<400> SEQUENCE: 471
000

<210> SEQ ID NO 472
<400> SEQUENCE: 472
000

-continued

<210> SEQ ID NO 473

<400> SEQUENCE: 473

000

<210> SEQ ID NO 474

<400> SEQUENCE: 474

000

<210> SEQ ID NO 475

<400> SEQUENCE: 475

000

<210> SEQ ID NO 476

<400> SEQUENCE: 476

000

<210> SEQ ID NO 477

<400> SEQUENCE: 477

000

<210> SEQ ID NO 478

<400> SEQUENCE: 478

000

<210> SEQ ID NO 479

<400> SEQUENCE: 479

000

<210> SEQ ID NO 480

<400> SEQUENCE: 480

000

<210> SEQ ID NO 481

<400> SEQUENCE: 481

000

<210> SEQ ID NO 482

<400> SEQUENCE: 482

000

<210> SEQ ID NO 483

<400> SEQUENCE: 483

000

<210> SEQ ID NO 484

<400> SEQUENCE: 484

000

<210> SEQ ID NO 485

<400> SEQUENCE: 485

000

<210> SEQ ID NO 486

<400> SEQUENCE: 486

000

<210> SEQ ID NO 487

<400> SEQUENCE: 487

000

<210> SEQ ID NO 488

<400> SEQUENCE: 488

000

<210> SEQ ID NO 489

<400> SEQUENCE: 489

000

<210> SEQ ID NO 490

<400> SEQUENCE: 490

000

<210> SEQ ID NO 491

<400> SEQUENCE: 491

000

<210> SEQ ID NO 492

<400> SEQUENCE: 492

000

<210> SEQ ID NO 493

<400> SEQUENCE: 493

000

<210> SEQ ID NO 494

<400> SEQUENCE: 494

000

<210> SEQ ID NO 495

<400> SEQUENCE: 495

000

<210> SEQ ID NO 496

<400> SEQUENCE: 496

000

<210> SEQ ID NO 497

<400> SEQUENCE: 497

000

<210> SEQ ID NO 498

<400> SEQUENCE: 498

000

<210> SEQ ID NO 499

<400> SEQUENCE: 499

000

<210> SEQ ID NO 500
<211> LENGTH: 116
<212> TYPE: PRT
<213> ORGANISM: Homo sapiens

<400> SEQUENCE: 500

```
Ile Leu Gly Arg Ser Glu Thr Gln Glu Cys Leu Phe Phe Asn Ala Asn
1               5                   10                  15

Trp Glu Lys Asp Arg Thr Asn Gln Thr Gly Val Glu Pro Cys Tyr Gly
            20                  25                  30

Asp Lys Asp Lys Arg Arg His Cys Phe Ala Thr Trp Lys Asn Ile Ser
        35                  40                  45

Gly Ser Ile Glu Ile Val Lys Gln Gly Cys Trp Leu Asp Asp Ile Asn
    50                  55                  60

Cys Tyr Asp Arg Thr Asp Cys Val Glu Lys Lys Asp Ser Pro Glu Val
65                  70                  75                  80

Tyr Phe Cys Cys Cys Glu Gly Asn Met Cys Asn Glu Lys Phe Ser Tyr
                85                  90                  95

Phe Pro Glu Met Glu Val Thr Gln Pro Thr Ser Asn Pro Val Thr Pro
            100                 105                 110

Lys Pro Pro Thr
        115
```

<210> SEQ ID NO 501
<211> LENGTH: 150
<212> TYPE: PRT
<213> ORGANISM: Rattus sp.

<400> SEQUENCE: 501

```
Met Thr Ala Pro Trp Ala Ala Leu Ala Leu Leu Trp Gly Ser Leu Cys
1               5                   10                  15

Ala Gly Ser Gly Arg Gly Glu Ala Glu Thr Arg Glu Cys Ile Tyr Tyr
            20                  25                  30

Asn Ala Asn Trp Glu Leu Glu Arg Thr Asn Gln Ser Gly Leu Glu Arg
```

```
        35                  40                  45

Cys Glu Gly Glu Gln Asp Lys Arg Leu His Cys Tyr Ala Ser Trp Pro
    50                  55                  60

Asn Ser Ser Gly Thr Ile Glu Leu Val Lys Lys Gly Cys Trp Leu Asp
65                  70                  75                  80

Asp Phe Asn Cys Tyr Asp Arg Gln Glu Cys Val Ala Thr Glu Glu Asn
                85                  90                  95

Pro Gln Val Tyr Phe Cys Cys Cys Glu Gly Asn Phe Cys Asn Glu Arg
            100                 105                 110

Phe Thr His Leu Pro Glu Pro Gly Gly Pro Glu Val Thr Tyr Glu Pro
        115                 120                 125

Pro Pro Thr Ala Pro Thr Leu Leu Thr Val Leu Ala Tyr Ser Leu Leu
    130                 135                 140

Pro Ile Gly Gly Leu Ser
145                 150


<210> SEQ ID NO 502
<211> LENGTH: 150
<212> TYPE: PRT
<213> ORGANISM: Sus sp.

<400> SEQUENCE: 502

Met Thr Ala Pro Trp Ala Ala Leu Ala Leu Leu Trp Gly Ser Leu Cys
1               5                   10                  15

Val Gly Ser Gly Arg Gly Glu Ala Glu Thr Arg Glu Cys Ile Tyr Tyr
            20                  25                  30

Asn Ala Asn Trp Glu Leu Glu Arg Thr Asn Gln Ser Gly Leu Glu Arg
        35                  40                  45

Cys Glu Gly Glu Gln Asp Lys Arg Leu His Cys Tyr Ala Ser Trp Arg
    50                  55                  60

Asn Ser Ser Gly Thr Ile Glu Leu Val Lys Lys Gly Cys Trp Leu Asp
65                  70                  75                  80

Asp Phe Asn Cys Tyr Asp Arg Gln Glu Cys Val Ala Thr Glu Glu Asn
                85                  90                  95

Pro Gln Val Tyr Phe Cys Cys Cys Glu Gly Asn Phe Cys Asn Glu Arg
            100                 105                 110

Phe Thr His Leu Pro Glu Ala Gly Gly Pro Glu Val Thr Tyr Glu Pro
        115                 120                 125

Pro Pro Thr Ala Pro Thr Leu Leu Thr Val Leu Ala Tyr Ser Leu Leu
    130                 135                 140

Pro Ile Gly Gly Leu Ser
145                 150


<210> SEQ ID NO 503
<211> LENGTH: 150
<212> TYPE: PRT
<213> ORGANISM: Mus sp.

<400> SEQUENCE: 503

Met Thr Ala Pro Trp Ala Ala Leu Ala Leu Leu Trp Gly Ser Leu Cys
1               5                   10                  15

Ala Gly Ser Gly Arg Gly Glu Ala Glu Thr Arg Glu Cys Ile Tyr Tyr
            20                  25                  30

Asn Ala Asn Trp Glu Leu Glu Arg Thr Asn Gln Ser Gly Leu Glu Arg
        35                  40                  45

Cys Glu Gly Glu Gln Asp Lys Arg Leu His Cys Tyr Ala Ser Trp Arg
```

```
    50                  55                  60

Asn Ser Ser Gly Thr Ile Glu Leu Val Lys Lys Gly Cys Trp Leu Asp
65                  70                  75                  80

Asp Phe Asn Cys Tyr Asp Arg Gln Glu Cys Val Ala Thr Glu Glu Asn
                85                  90                  95

Pro Gln Val Tyr Phe Cys Cys Cys Glu Gly Asn Phe Cys Asn Glu Arg
            100                 105                 110

Phe Thr His Leu Pro Glu Pro Gly Gly Pro Glu Val Thr Tyr Glu Pro
        115                 120                 125

Pro Pro Thr Ala Pro Thr Leu Leu Thr Val Leu Ala Tyr Ser Leu Leu
    130                 135                 140

Pro Ile Gly Gly Leu Ser
145                 150


<210> SEQ ID NO 504
<211> LENGTH: 150
<212> TYPE: PRT
<213> ORGANISM: Homo sapiens

<400> SEQUENCE: 504

Met Thr Ala Pro Trp Val Ala Leu Ala Leu Leu Trp Gly Ser Leu Cys
1               5                   10                  15

Ala Gly Ser Gly Arg Gly Glu Ala Glu Thr Arg Glu Cys Ile Tyr Tyr
            20                  25                  30

Asn Ala Asn Trp Glu Leu Glu Arg Thr Asn Gln Ser Gly Leu Glu Arg
        35                  40                  45

Cys Glu Gly Glu Gln Asp Lys Arg Leu His Cys Tyr Ala Ser Trp Arg
    50                  55                  60

Asn Ser Ser Gly Thr Ile Glu Leu Val Lys Lys Gly Cys Trp Leu Asp
65                  70                  75                  80

Asp Phe Asn Cys Tyr Asp Arg Gln Glu Cys Val Ala Thr Glu Glu Asn
                85                  90                  95

Pro Gln Val Tyr Phe Cys Cys Cys Glu Gly Asn Phe Cys Asn Glu Arg
            100                 105                 110

Phe Thr His Leu Pro Glu Ala Gly Gly Pro Glu Val Thr Tyr Glu Pro
        115                 120                 125

Pro Pro Thr Ala Pro Thr Leu Leu Thr Val Leu Ala Tyr Ser Leu Leu
    130                 135                 140

Pro Ile Gly Gly Leu Ser
145                 150


<210> SEQ ID NO 505
<211> LENGTH: 150
<212> TYPE: PRT
<213> ORGANISM: Bos sp.

<400> SEQUENCE: 505

Met Thr Ala Pro Trp Ala Ala Leu Ala Leu Leu Trp Gly Ser Leu Cys
1               5                   10                  15

Ala Gly Ser Gly Arg Gly Glu Ala Glu Thr Arg Glu Cys Ile Tyr Tyr
            20                  25                  30

Asn Ala Asn Trp Glu Leu Glu Arg Thr Asn Gln Ser Gly Leu Glu Arg
        35                  40                  45

Cys Glu Gly Glu Arg Asp Lys Arg Leu His Cys Tyr Ala Ser Trp Arg
    50                  55                  60

Asn Ser Ser Gly Thr Ile Glu Leu Val Lys Lys Gly Cys Trp Leu Asp
```

```
65                  70                  75                  80

Asp Phe Asn Cys Tyr Asp Arg Gln Glu Cys Val Ala Thr Glu Glu Asn
                85                  90                  95

Pro Gln Val Tyr Phe Cys Cys Cys Glu Gly Asn Phe Cys Asn Glu Arg
            100                 105                 110

Phe Thr His Leu Pro Glu Ala Gly Gly Pro Glu Val Thr Tyr Glu Pro
        115                 120                 125

Pro Pro Thr Ala Pro Thr Leu Leu Thr Val Leu Ala Tyr Ser Leu Leu
    130                 135                 140

Pro Val Gly Gly Leu Ser
145                 150


<210> SEQ ID NO 506
<211> LENGTH: 150
<212> TYPE: PRT
<213> ORGANISM: Xenopus sp.

<400> SEQUENCE: 506

Met Gly Ala Ser Val Ala Leu Thr Phe Leu Leu Leu Leu Ala Thr Phe
1               5                   10                  15

Arg Ala Gly Ser Gly His Asp Glu Val Glu Thr Arg Glu Cys Ile Tyr
            20                  25                  30

Tyr Asn Ala Asn Trp Glu Leu Glu Lys Thr Asn Gln Ser Gly Val Glu
        35                  40                  45

Arg Leu Val Glu Gly Lys Lys Asp Lys Arg Leu His Cys Tyr Ala Ser
    50                  55                  60

Trp Arg Asn Asn Ser Gly Phe Ile Glu Leu Val Lys Lys Gly Cys Trp
65                  70                  75                  80

Leu Asp Asp Phe Asn Cys Tyr Asp Arg Gln Glu Cys Ile Ala Lys Glu
                85                  90                  95

Glu Asn Pro Gln Val Phe Phe Cys Cys Cys Glu Gly Asn Tyr Cys Asn
            100                 105                 110

Lys Lys Phe Thr His Leu Pro Glu Val Glu Thr Phe Asp Pro Lys Pro
        115                 120                 125

Gln Pro Ser Ala Ser Val Leu Asn Ile Leu Ile Tyr Ser Leu Leu Pro
    130                 135                 140

Ile Val Gly Leu Ser Met
145                 150


<210> SEQ ID NO 507
<211> LENGTH: 150
<212> TYPE: PRT
<213> ORGANISM: Homo sapiens

<400> SEQUENCE: 507

Met Gly Ala Ala Ala Lys Leu Ala Phe Ala Val Phe Leu Ile Ser Cys
1               5                   10                  15

Ser Ser Gly Ala Ile Leu Gly Arg Ser Glu Thr Gln Glu Cys Leu Phe
            20                  25                  30

Phe Asn Ala Asn Trp Glu Lys Asp Arg Thr Asn Gln Thr Gly Val Glu
        35                  40                  45

Pro Cys Tyr Gly Asp Lys Asp Lys Arg Arg His Cys Phe Ala Thr Trp
    50                  55                  60

Lys Asn Ile Ser Gly Ser Ile Glu Ile Val Lys Gln Gly Cys Trp Leu
65                  70                  75                  80

Asp Asp Ile Asn Cys Tyr Asp Arg Thr Asp Cys Val Glu Lys Lys Asp
```

-continued

```
                85                  90                  95

Ser Pro Glu Val Tyr Phe Cys Cys Cys Glu Gly Asn Met Cys Asn Glu
            100                 105                 110

Lys Phe Ser Tyr Phe Pro Glu Met Glu Val Thr Gln Pro Thr Ser Asn
        115                 120                 125

Pro Val Thr Pro Lys Pro Pro Tyr Tyr Asn Ile Leu Leu Tyr Ser Leu
    130                 135                 140

Val Pro Leu Met Leu Ile
145                 150


<210> SEQ ID NO 508
<211> LENGTH: 154
<212> TYPE: PRT
<213> ORGANISM: Artificial Sequence
<220> FEATURE:
<223> OTHER INFORMATION: Description of Artificial Sequence: Synthetic
      consensus sequence
<220> FEATURE:
<221> NAME/KEY: MOD_RES
<222> LOCATION: (8)..(8)
<223> OTHER INFORMATION: Thr, Ala or absent
<220> FEATURE:
<221> NAME/KEY: MOD_RES
<222> LOCATION: (121)..(121)
<223> OTHER INFORMATION: Pro, Ala, Val or Met

<400> SEQUENCE: 508

Met Thr Ala Pro Trp Ala Ala Xaa Leu Ala Leu Leu Trp Gly Ser Leu
1               5                   10                  15

Cys Ala Gly Ser Gly Arg Gly Glu Ala Glu Thr Arg Glu Cys Ile Tyr
            20                  25                  30

Tyr Asn Ala Asn Trp Glu Leu Glu Arg Thr Asn Gln Ser Gly Leu Glu
        35                  40                  45

Arg Leu Cys Glu Gly Glu Gln Asp Lys Arg Leu His Cys Tyr Ala Ser
    50                  55                  60

Trp Arg Asn Ser Ser Gly Thr Ile Glu Leu Val Lys Lys Gly Cys Trp
65                  70                  75                  80

Leu Asp Asp Phe Asn Cys Tyr Asp Arg Gln Glu Cys Val Ala Thr Glu
                85                  90                  95

Glu Asn Pro Gln Val Tyr Phe Cys Cys Cys Glu Gly Asn Phe Cys Asn
            100                 105                 110

Glu Arg Phe Thr His Leu Pro Glu Xaa Gly Gly Pro Glu Val Thr Tyr
        115                 120                 125

Glu Pro Lys Pro Pro Thr Ala Pro Thr Leu Leu Thr Val Leu Ala Tyr
    130                 135                 140

Ser Leu Leu Pro Ile Gly Gly Leu Ser Met
145                 150


<210> SEQ ID NO 509
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 509

His His His His His His
1               5


<210> SEQ ID NO 510
```

-continued

```
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 510

Gly Gly Gly Gly Ser
1               5
```